United States Patent
Evans et al.

(10) Patent No.: US 11,130,779 B2
(45) Date of Patent: *Sep. 28, 2021

(54) PPAR AGONISTS AND METHODS OF USE THEREOF

(71) Applicant: The Salk Institute for Biological Studies, La Jolla, CA (US)

(72) Inventors: Ronald M. Evans, La Jolla, CA (US); Michael Downes, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,830

(22) Filed: Dec. 17, 2019

(65) Prior Publication Data
US 2020/0216490 A1 Jul. 9, 2020

Related U.S. Application Data

(60) Continuation of application No. 16/022,578, filed on Jun. 28, 2018, now Pat. No. 10,550,149, which is a
(Continued)

(51) Int. Cl.
*C07D 405/12* (2006.01)
*C07K 5/062* (2006.01)
(Continued)

(52) U.S. Cl.
CPC ........ *C07K 5/06034* (2013.01); *C07C 233/73* (2013.01); *C07C 233/75* (2013.01); *C07C 233/87* (2013.01); *C07C 235/42* (2013.01); *C07C 235/48* (2013.01); *C07C 235/84* (2013.01); *C07C 237/32* (2013.01); *C07C 255/57* (2013.01); *C07C 259/06* (2013.01); *C07C 317/44* (2013.01); *C07D 205/04* (2013.01); *C07D 209/34* (2013.01); *C07D 213/40* (2013.01); *C07D 213/56* (2013.01); *C07D 213/64* (2013.01); *C07D 231/12* (2013.01); *C07D 271/12* (2013.01); *C07D 295/13* (2013.01); *C07D 295/155* (2013.01); *C07D 305/06* (2013.01); *C07D 307/54* (2013.01); *C07D 307/68* (2013.01); *C07D 307/81* (2013.01); *C07D 307/83* (2013.01); *C07D 309/04* (2013.01);
(Continued)

(58) Field of Classification Search
CPC .... A61K 31/44; A61K 31/381; A61K 31/416; A61K 31/4178; C07D 231/12; C07D 295/03; C07D 307/36; C07D 333/10; C07D 401/12; C07D 505/12; C07D 409/12; C07D 413/12; C07D 405/12
USPC ...... 514/235.5, 236.5, 237.8, 357, 406, 451; 544/124, 140, 146, 152, 178; 548/365.7, 548/377.1; 549/78, 498
See application file for complete search history.

(56) References Cited

U.S. PATENT DOCUMENTS 4,228,281 A 10/1980 Kainmuller
6,054,457 A 4/2000 Setoi
(Continued)

FOREIGN PATENT DOCUMENTS

AU 2007252020 11/2007
EP 1 553 075 7/2005
(Continued)

OTHER PUBLICATIONS

Arnold et al., "Inflammatory monocytes recruited after skeletal muscle injury switch into anti-inflammatory macrophages to support myogenesis," *Journal of Experimental Medicine* 204(5):1057-1069, May 14, 2007.
(Continued)

*Primary Examiner* — Jeffrey H Murray
(74) *Attorney, Agent, or Firm* — Klarquist Sparkman, LLP

(57) ABSTRACT

Provided herein are deuterated compounds and compositions useful in increasing PPARδ activity. The compounds have a formula

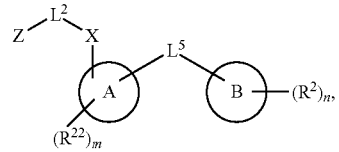

where $L^5$ comprises at least one deuterium. Exemplary species include

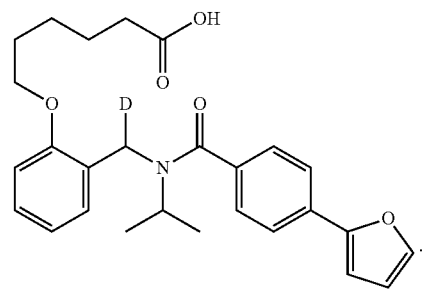

The compounds and compositions provided herein are useful for the treatment of PPARδ related diseases (e.g., muscular diseases, vascular disease, demyelinating disease, and metabolic diseases).

20 Claims, 25 Drawing Sheets

(9 of 25 Drawing Sheet(s) Filed in Color)

Related U.S. Application Data division of application No. 15/482,385, filed on Apr. 7, 2017, now Pat. No. 10,035,819, which is a continuation of application No. PCT/US2015/053674, filed on Oct. 2, 2015.

(60) Provisional application No. 62/061,547, filed on Oct. 8, 2014.

(51) Int. Cl.

| | |
|---|---|
| *C07D 309/04* | (2006.01) |
| *C07D 407/12* | (2006.01) |
| *C07D 271/12* | (2006.01) |
| *C07D 295/13* | (2006.01) |
| *C07D 213/40* | (2006.01) |
| *C07D 213/64* | (2006.01) |
| *C07D 307/68* | (2006.01) |
| *C07D 309/06* | (2006.01) |
| *C07D 231/12* | (2006.01) |
| *C07D 333/24* | (2006.01) |
| *C07D 401/04* | (2006.01) |
| *C07D 401/12* | (2006.01) |
| *C07D 405/04* | (2006.01) |
| *C07D 405/10* | (2006.01) |
| *C07D 409/12* | (2006.01) |
| *C07D 413/04* | (2006.01) |
| *C07D 413/12* | (2006.01) |
| *C07D 417/04* | (2006.01) |
| *C07D 417/10* | (2006.01) |
| *C07D 417/12* | (2006.01) |
| *C07C 233/87* | (2006.01) |
| *C07D 205/04* | (2006.01) |
| *C07D 209/34* | (2006.01) |
| *C07D 295/155* | (2006.01) |
| *C07D 213/56* | (2006.01) |
| *C07D 305/06* | (2006.01) |
| *C07D 307/54* | (2006.01) |
| *C07D 307/81* | (2006.01) |
| *C07D 307/83* | (2006.01) |
| *C07C 255/57* | (2006.01) |
| *C07C 259/06* | (2006.01) |
| *C07C 233/73* | (2006.01) |
| *C07C 235/42* | (2006.01) |
| *C07C 235/48* | (2006.01) |
| *C07C 235/84* | (2006.01) |
| *C07C 237/32* | (2006.01) |
| *C07C 317/44* | (2006.01) |
| *C07C 233/75* | (2006.01) |
| *C07D 333/38* | (2006.01) |

(52) U.S. Cl.
CPC ......... *C07D 309/06* (2013.01); *C07D 333/24* (2013.01); *C07D 333/38* (2013.01); *C07D 401/04* (2013.01); *C07D 401/12* (2013.01); *C07D 405/04* (2013.01); *C07D 405/10* (2013.01); *C07D 405/12* (2013.01); *C07D 407/12* (2013.01); *C07D 409/12* (2013.01); *C07D 413/04* (2013.01); *C07D 413/12* (2013.01); *C07D 417/04* (2013.01); *C07D 417/10* (2013.01); *C07D 417/12* (2013.01); *C07K 5/06026* (2013.01); *C07C 2601/02* (2017.05); *C07C 2601/08* (2017.05)

(56) References Cited

U.S. PATENT DOCUMENTS

| | | | |
|---|---|---|---|
| 7,655,641 | B2 | 2/2010 | Conner et al. |
| 9,938,234 | B2* | 4/2018 | Evans ............... A61K 31/341 |
| 10,035,819 | B2* | 7/2018 | Evans ............... C07D 413/04 |
| 2004/0214888 | A1 | 10/2004 | Matsuura et al. |
| 2005/0075378 | A1 | 4/2005 | Gossett et al. |
| 2006/0116410 | A1 | 6/2006 | Banner et al. |
| 2007/0065839 | A1 | 3/2007 | Okamoto |
| 2007/0082907 | A1 | 4/2007 | Canada et al. |
| 2007/0244094 | A1 | 10/2007 | Kuo et al. |
| 2009/0286974 | A1 | 11/2009 | Itai et al. |
| 2010/0063041 | A1 | 3/2010 | Moon et al. |

FOREIGN PATENT DOCUMENTS

| | | |
|---|---|---|
| EP | 2 014 652 | 1/2009 |
| EP | 2 128 138 | 12/2009 |
| WO | WO 2000/050391 | 8/2000 |
| WO | WO 2001/012612 | 2/2001 |
| WO | WO 2005/115383 | 12/2005 |
| WO | WO 2006/017055 | 2/2006 |
| WO | WO 2006/027135 | 3/2006 |
| WO | WO 2007/028424 | 3/2007 |
| WO | WO 2007/110237 | 10/2007 |
| WO | WO 2008/083330 | 7/2008 |
| WO | WO 2009/086526 | 7/2009 |
| WO | WO 2011/020001 | 2/2011 |
| WO | WO 2011/076786 | 6/2011 |
| WO | WO 2013/012614 | 1/2013 |
| WO | WO 2014/165827 | 10/2014 |
| WO | WO 2015/035171 | 3/2015 |
| WO | WO 2015/138969 | 9/2015 |

OTHER PUBLICATIONS

Bonala et al., "Peroxisome Proliferator-activated Receptor β/δ Induces Myogenesis by Modulating Myostatin Activity," *Journal of Biological Chemistry* 297(16):12935-12951, Apr. 13, 2012.

Bräuer et al., "Evolutionary Chemistry Approach Toward Finding Novel Inhibitors of Type 2 Diabetes Target Glucose-6-Phosphate Translocase," *Journal of Combinatorial Chemistry* 7:218-226, Feb. 19, 2005.

Chemical Abstracts Plus, Accession No. 2000:737780, STN entry date Oct. 19, 2000, and CAS Registry No. 312958-87-5.

Embler et al., "PPARdelta activation enhances skeletal muscle regeneration," http://eprints.cdlib.org/uc/item/3vg8k734, 2012, retrieved Dec. 8, 2015.

International Search Report dated Jul. 22, 2014, from International Application No. PCT/US2014/033088.

International Search Report dated Nov. 26, 2015, from International Application No. PCT/US2015/054477.

International Search Report dated Dec. 15, 2015, from International Application No. PCT/US2015/054475.

International Search Report dated Dec. 21, 2015, from International Application No. PCT/US2015/053674.

International Search Report dated Feb. 29, 2016, from International Application No. PCT/US2015/054473.

Jonker et al., "A PPARγ-FGF1 axis is required for adaptive adipose remodeling and metabolic homeostasis," *Nature* 485(7398):391-394, May 17, 2012.

Lee et al., "PPARδ regulates glucose metabolism and insulin sensitivity," *Proceedings of the National Academy of Sciences of the United States of America* 103(9):3444-3449, Feb. 28, 2006.

Luquet et al., "Peroxisome proliferator-activated receptor δ controls muscle development and oxidative capability," *The FASEB Journal* 17:2299-2301, Oct. 2, 2003.

Markert et al., "Exercise and Duchenne Muscular Dystrophy: Toward Evidence-Based Exercise Prescription," *Muscle & Nerve* 43:464-478, Mar. 14, 2011.

Menetrey et al., "Growth factors improve muscle healing in vivo," *The Journal of Bone & Joint Surgery* (BR) 82-B(1):131-137, Jan. 1, 2000.

(56) References Cited

OTHER PUBLICATIONS

Mitachi et al., "Synthesis and structure-activity relationship of disubstituted benzamides as a novel class of antimalarial agents," *Bioorganic & Medicinal Chemistry Letters* 22(14):4536-4539, Jul. 15, 2012.

Miura et al., "Pharmacological activation of PPARβ/δ stimulates utrophin A expression in skeletal muscle fibers and restores sarcolemmal integrity in mature *mdx* mice," *Human Molecular Genetics* 18(23):4640-4649, Dec. 1, 2009, published online Sep. 10, 2009.

Narkar et al., "AMPK and PPARδ agonists are exercise mimetics," *Cell* 134(3):405-415, Aug. 8, 2008.

Shefer et al., "Reduced Satellite Cell Numbers and Myogenic Capacity in Aging Can Be alleviated by Endurance Exercise," *PLoS ONE* 5(10):e13307:1-11, Oct. 12, 2010.

Wang et al., "Peroxisome-Proliferator-Activated Receptor δ Activates Fat Metabolism to Prevent Obesity," *Cell* 13:159-170, Apr. 18, 2003.

Wang et al., "Regulation of Muscle Fiber Type and Running Endurance by PPARδ," *PLoS Biology* 2(10):e294:1532-1539, Oct. 2004, published online Aug. 24, 2004.

Wang et al., Erratum: "Correction: Regulation of Muscle Fiber Type and Running Endurance by PPARδ," *PLoS Biology* 3(1):e61:0177, Jan. 18, 2005.

Warshawsky et al., "Synthesis and evaluation of aminomethyl dihydrocinnamates as a new class of PPAR ligands," *Bioorganic & Medicinal Chemistry* 16(24):6328-6333, Dec. 15, 2006.

\* cited by examiner 12 hours post injury 36 hrs post injury

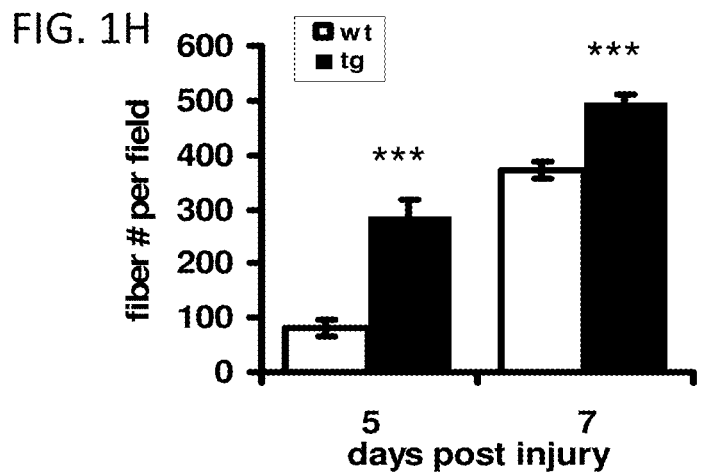
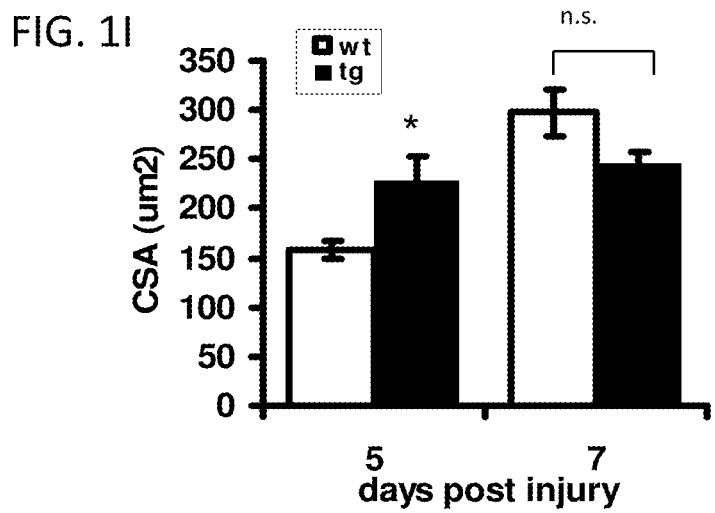
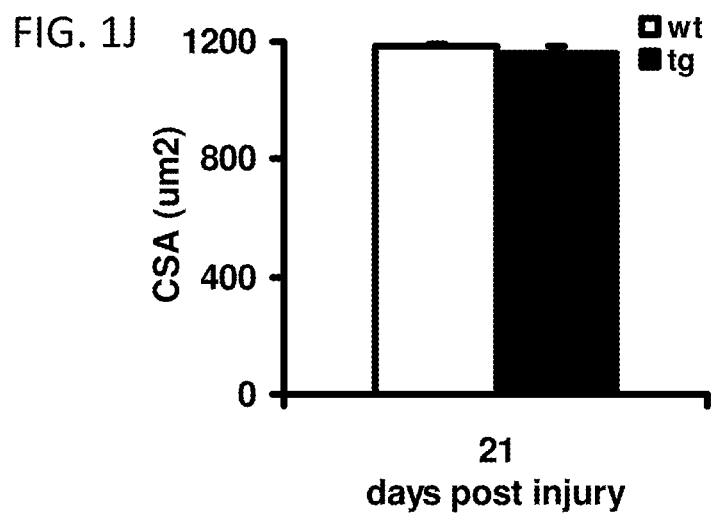

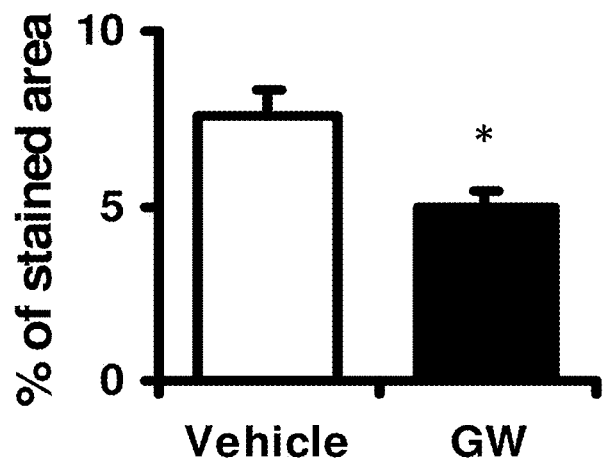
FIG. 5C
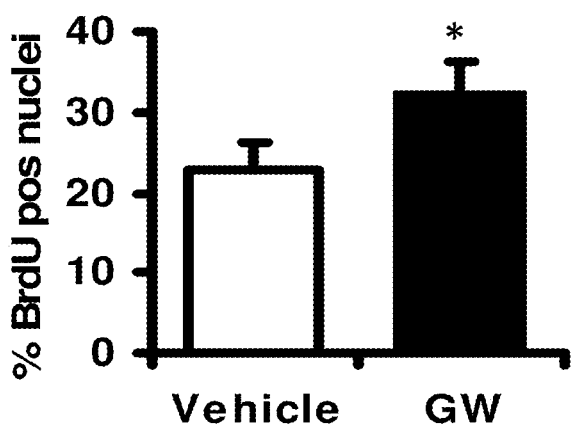
FIG. 5D
FIG. 5E
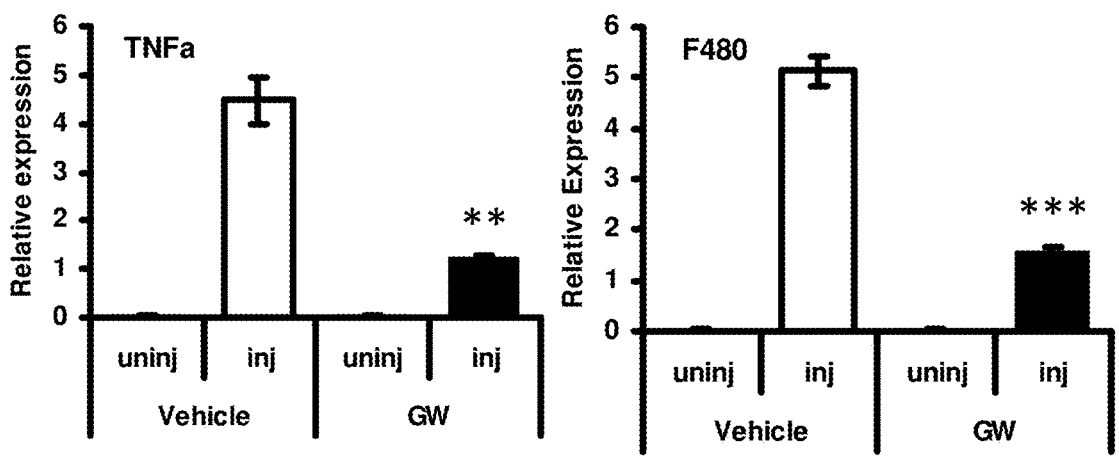

PPAR AGONISTS AND METHODS OF USE THEREOF

CROSS REFERENCE TO RELATED APPLICATIONS

This application is a continuation of U.S. patent application Ser. No. 16/022,578, filed on Jun. 28, 2018, which is a divisional of U.S. application Ser. No. 15/482,385, filed on Apr. 7, 2017, which is a continuation of International Application No. PCT/US2015/053674, filed on Oct. 2, 2015, which claims the benefit of the earlier filing date of U.S. Provisional Application No. 62/061,547, filed on Oct. 8, 2014, the contents of which are incorporated herein by reference in its entirety.

ACKNOWLEDGMENT OF GOVERNMENT SUPPORT

This invention was made with government support under DK057978-32 awarded by the National Institutes of Health. The government has certain rights in the invention.

FIELD

This application concerns agonists of peroxisome proliferator-activated receptors (PPAR), particularly PPAR delta (PPARδ), and methods for their use, such as to treat or prevent one or more PPARδ-related diseases.

BACKGROUND

Skeletal muscle is a mechanically and energetically active organ, supporting vital processes such as respiration and locomotion, and is a major site of glucose and lipid metabolism. Therefore, maintaining proper muscle mass and function is critical. Muscle incurs damage due to a variety of insults such as use, disuse, aging and pathology. While skeletal muscle does not undergo rapid turn-over under normal conditions, upon being damaged, it is capable of executing a robust regenerative response through mobilization of its resident progenitor cells, the satellite cells (Moss F P, Leblond C P, *Anat Rec* 170:421-436 (1970); Schultz E, Gibson M C, Champion T, *J Exp Zool* 206(3):451-6 (1978); Snow M H, *Cell Tissue Res* 186(3):535-40 (1978)). The self-renewal and differentiation capacity of the satellite cells have alluded to the archetypic "stemness," but their fate seems largely committed (Sinanan A C M, Buxton P G, Lewis M P, *Bio Cell* 98:203-214 (2006); Beauchamp J R et al., *J Cell Biol* 151:1221-1234 (2000); Starkey J D et al., *J Histochem Cytochem* 59(1):33-46 (2011)). In an adult, satellite cells comprise less than 5% of total nuclei on a myofiber; nevertheless, based on their proliferation kinetics and capacity, this is sufficient to regenerate an entire muscle (Schmalbruch H, Hellhammer U, *Anat Rec* 189:169-176 (1977); Kelly A M, *Dev Bio* 65(1): 1-10 (1978); Gibson M C, Schultz E, *Anat Rec* 202(3):329-337 (1982); Bischoff R in *Myology*, Vol 1, eds Engel A G, Franzini-Armstrong C (McGraw-Hill, Inc., New York), (1994); Zammit P S et al., *Exp Cell Res* 281:39-49 (2002)).

Upon injury, skeletal muscle responds to damage in three distinct but overlapping phases: degeneration; regeneration; and finally remodeling (Charge S B P, Rudnicki M A, *Physiol Rev* 84:209-238 (2004)). Immediately following the injury, inflammatory cells are recruited to the injury site to promote degeneration of the damaged tissue through necrosis and phagocytosis (Tidball J G, *Am J Physiol Regul Integr Comp Physio* 288:R345-353 (2005); McLennan I S, *J Anat* 188:17-28 (1996); Pimorady-Esfahani A, Grounds M D, McMenamin P G, *Muscle Nerve* 20:158-166 (1997); Vierck J et al., *Cell Bio Int* 24:263-272 (2000); Arnold L et al., *J Exp Med* 204(5):1057-1069 (2007)). The subsequent regenerative phase is characterized by mobilization of satellite cells, whereby the progenitor cells proliferate, differentiate and fuse to each other or to the existing fibers to regenerate the muscle (Zammit P S in Skeletal muscle repair and regeneration, eds Schiaffino S, Partridge T (Springer, Dordrecht (2008)). Finally, the contractile proteins are reassembled and function is restored during the remodeling phase.

SUMMARY

Provided herein, inter alia, are compounds and compositions comprising such compounds that are useful for increasing PPAR activity, particularly PPARδ activity. Also disclosed are methods of using the disclosed compositions for treating or preventing PPARδ related diseases (e.g., muscular diseases, demyelinating disease, vascular disease, and metabolic diseases).

Certain disclosed embodiments concern compounds having a formula

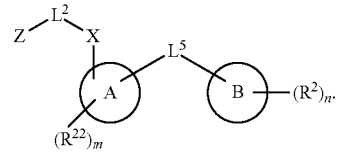

With reference to this formula, ring A may be selected from a cycloalkylene, heterocycloalkylene, arylene or heteroarylene; ring B is selected from aryl, heteroaryl, cycloalkyl, heterocycloalkyl, cycloalkylene, heterocycloalkylene, arylene or heteroarylene; each $R^2$ independently is selected from deuterium, halogen, aryl, heteroaryl, aliphatic, heteroaliphatic, cycloaliphatic, $NO_2$, OH, amino, amide, aminosulfonyl, carboxyl, carboxyl ester, alkylsulfonyl, $SO_3H$, or acyl; each $R^{22}$ independently is selected from deuterium, halogen, aryl, heteroaryl, aliphatic, heteroaliphatic, cycloaliphatic, $NO_2$, OH, amino, amide, aminosulfonyl, carboxyl, carboxyl ester, alkylsulfonyl, $SO_3H$, or acyl; n is from 0 to 5; m is from 0 to 4; X is O, $NR^{30}$, sulfonyl, or S; $R^{30}$ is selected from H or aliphatic, aryl, or cycloaliphatic; each $L^2$ is selected from a bond, aliphatic, heteroaliphatic, arylene, heteroarylene, cycloalkylene, heterocycloalkylene or —$CR^{23}R^{24}$—; $R^{23}$ and $R^{24}$ are each independently selected from H, deuterium, halogen, aliphatic, alkyl, —C(O)$OR^{25}$ or —C(O)$NR^{25}R^{26}$; $R^{25}$ and $R^{26}$ are each independently selected from hydrogen, aliphatic or alkyl; Z is selected from $R^1L^1C(O)$— or a carboxyl bioisostere; $L^1$ is a bond or —$NR^{30}$—; $R^1$ is hydrogen, aliphatic, —$OR^{1A}$, —$NR^{1A}R^{1B}$, —C(O)$R^{1A}$, —S(O)$_2R^{1A}$, —C(O)$OR^{1A}$, —S(O)$_2NR^{1A}R^{1B}$ or —C(O)$NR^{1A}R^{1B}$; $R^{1A}$, $R^{1B}$ are each independently selected from hydrogen or aliphatic, typically aliphatic, alkyl; $L^5$ is

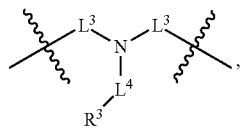

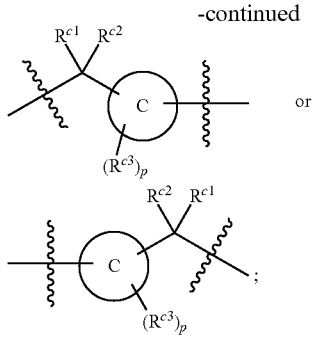 or

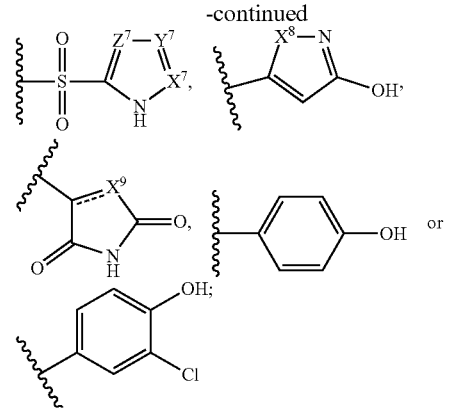

$R^{c1}$ and $R^{c2}$ are each independently H, D or alkyl; $R^{c3}$ is aliphatic or D; p is 0, 1 or 2; ring C is a 5- or 6-membered heterocyclyl or a 5- or 6-membered heteroaryl; each $L^3$ independently is selected from a bond, aliphatic, —C(O)—, alkylC(O)—, —C(O)alkyl-, or sulfonyl; $L^4$ is selected from a bond, aliphatic, heteroaliphatic, arylene, heteroarylene, cycloalkylene, heterocycloalkylene or —$CR^{23}R^{24}$; $R^3$ is selected from —OH, —$OR^{3A}$, —$NR^{3A}R^{3B}$, —$C(O)R^{3A}$, —$S(O)_2R^{3A}$, —$C(O)OR^{3A}$, —$S(O)_2NR^{3A}R^{3B}$, —$C(O)NR^{3A}R^{3B}$, aliphatic, heteroaliphatic, cycloalkyl, heterocycloalkyl, aryl, heteroaryl, or $R^3$ can be joined with an atom of ring B to form a fused ring system or may be joined with an atom of $L^3$ to form a heterocyclic ring system; and $R^{3A}$ and $R^{3B}$ are independently selected from hydrogen or aliphatic. Also with reference to this formula at least one of $L^3$, $L^4$ or $R^3$ comprises at least one deuterium and one $L^3$ is or comprises a —C(O)— adjacent to the nitrogen atom, or at least one of $R^{c1}$ and $R^{c2}$ is D.

In certain embodiments, ring A is selected from a $C_3$-$C_8$cycloalkylene, $C_2$-$C_5$heterocycloalkylene, $C_6$-$C_{10}$arylene or $C_1$-$C_{10}$heteroarylene, with particular examples having ring A being selected from phenyl, pyridine, cyclopentane, cyclohexane, pyrazole, thiophene or isothiazole. In certain embodiments, ring B is selected from $C_3$-$C_8$cycloalkylene, $C_2$-$C_8$heterocycloalkylene, $C_6$-$C_{10}$arylene or $C_1$-$C_{10}$heteroarylene. In particular examples, ring B is selected from phenyl, pyridine, thiophene, thiazole, pyrazole, oxazole, isoxazole, benzo[b]furan, indazole, piperidine, cyclohexane, piperidin-2-one, piperazine-2,5-dione or quinazolin-4(3H)-one.

Certain disclosed compounds include carboxyl biostere functionalities, such as

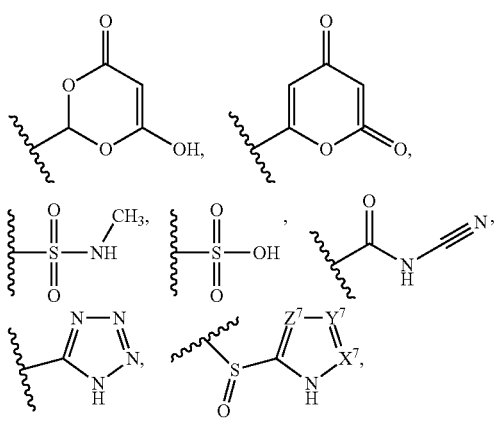

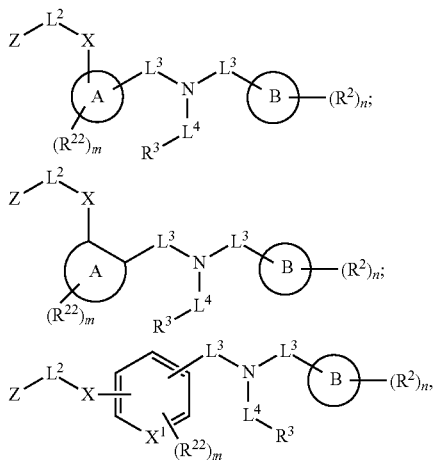

where $X^7$, $Y^7$, and $Z^7$ each independently is selected from N, $CH_2$ or CO; $X^8$ is selected from O, S or NMe; and $X^9$ is selected from O, N, NH, S, CH or $CH_2$.

More particular embodiments concern compounds having one or more of the following formulas:

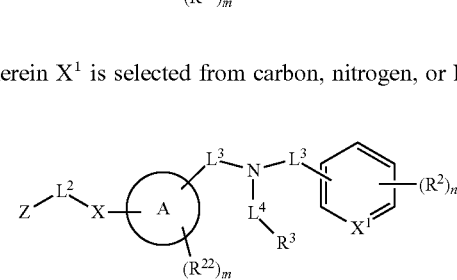

wherein $X^1$ is selected from carbon, nitrogen, or N-oxide;

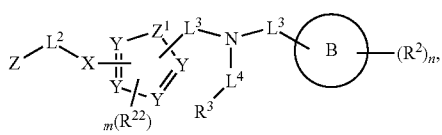

wherein $X^1$ is selected from carbon, nitrogen, or N-oxide;

wherein $Z^1$ is selected from carbon, oxygen, sulfur, or $NR^{30}$, and each Y independently is selected from carbon or nitrogen;

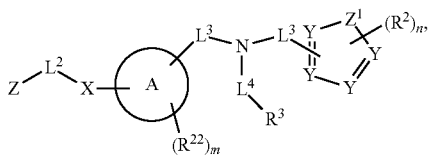

wherein $Z^1$ is selected from carbon, oxygen, sulfur, or $NR^{30}$, and each Y independently is selected from carbon or nitrogen;

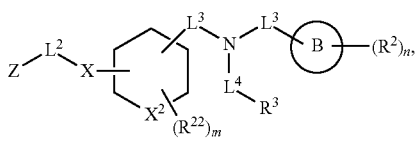

wherein $X^2$ is selected from a bond, carbon, oxygen, sulfur, or $NR^{30}$;

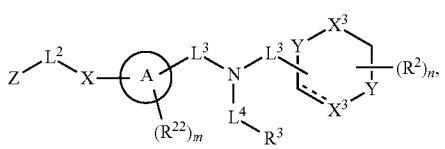

wherein each $X^3$ independently is selected from nitrogen, carbon, $NR^{30}$, or oxo, and each Y independently is selected from carbon or $NR^{30}$;

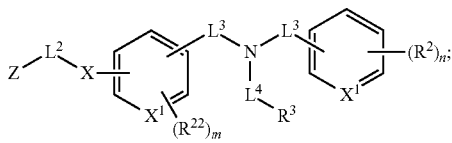

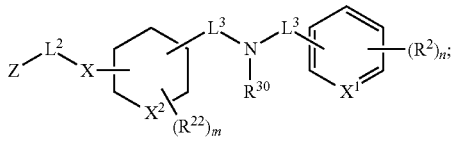

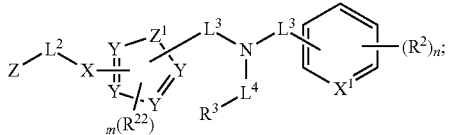

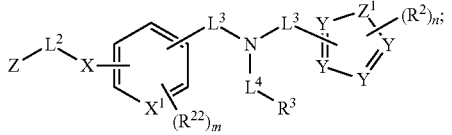

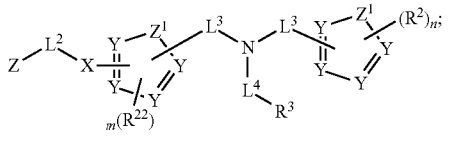

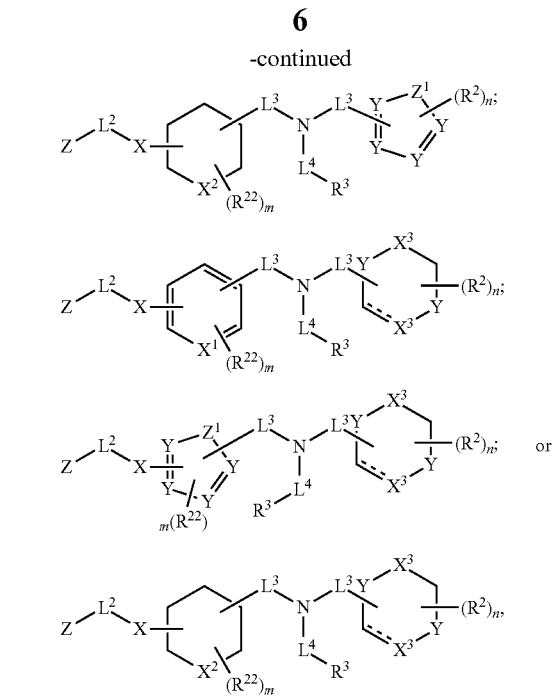

where each $X^1$, $X^2$, $X^3$, Y and $Z^1$ are as defined above.

In some embodiments of any of the prior compound formulas, -$L^3N(L^4R^3)L^3$- may be selected

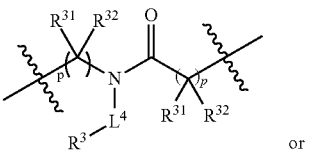

or

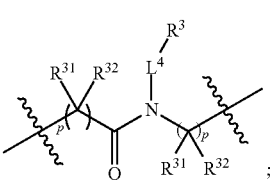

from each $R^{31}$ and $R^{32}$ is independently selected from deuterium, hydrogen, aliphatic, heteroaliphatic, or any one of $R^{31}$ and $R^{32}$ can be joined with an atom of $R^3$ to form a heterocyclic or heteroaryl ring system, or can be joined with an atom of ring B to form a fused ring system; each p independently is 0 to 5; and at least one $R^{31}$ or one $R^{32}$ is deuterium, or one of $L^4$ or $R^3$ comprises at least one deuterium. In certain embodiments, -$L^3N(L^4R^3)L^3$- is selected from

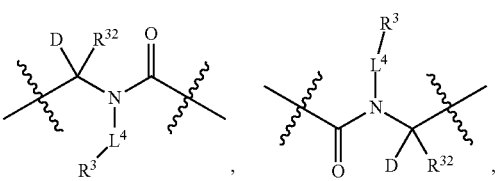

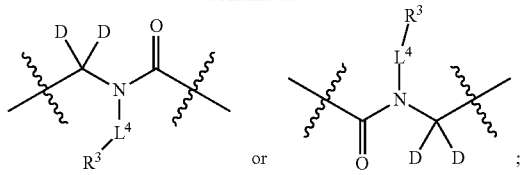

and $R^{32}$ is selected from deuterium, hydrogen, aliphatic or heteroaliphatic.

In other embodiments, of the prior compound formulas, -$L^4R^3$ is selected from

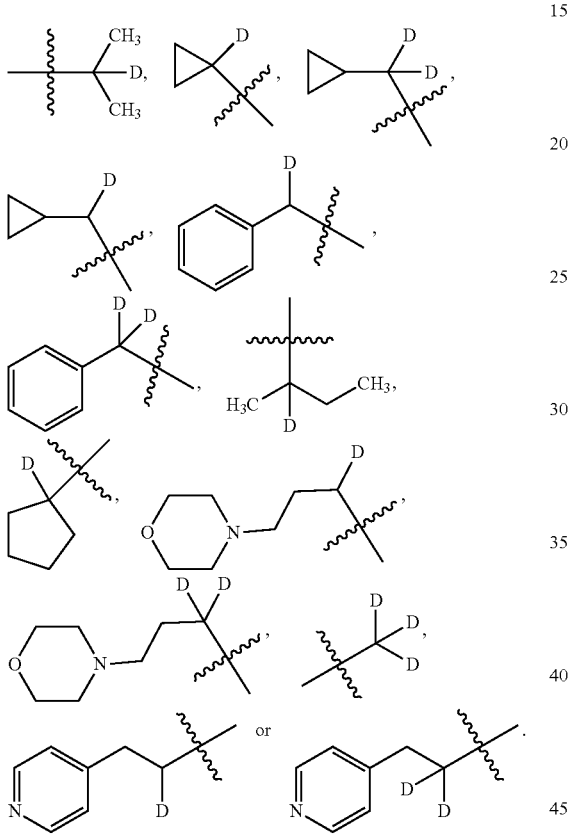

Also with reference to any of the prior compound formulas, in certain embodiments: $R^3$ may be selected from aliphatic, alkyl, heteroalkyl, cycloalkyl, heterocycloalkyl, aryl or heteroaryl; $L^2$, $L^3$ and $L^4$ each independently is a bond or alkylene; $L^4R^3$ is isopropyl; $R^2$ is furan-2-yl or furan-3-yl; $L^2$ may be selected from

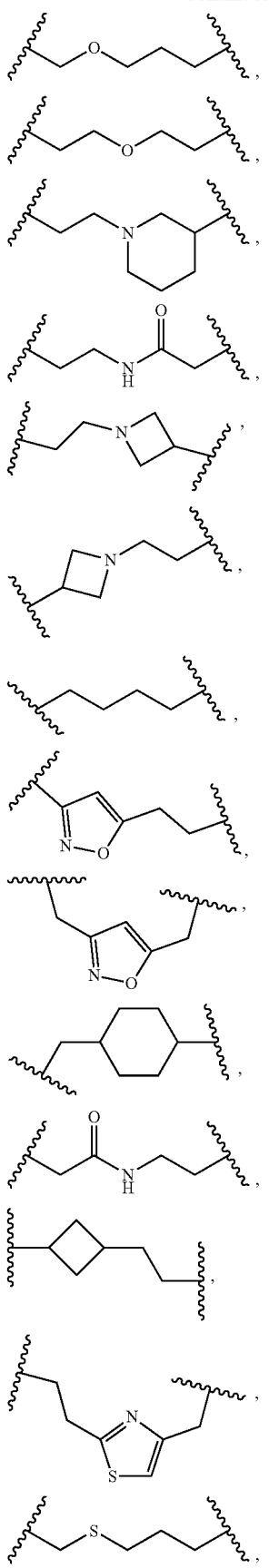

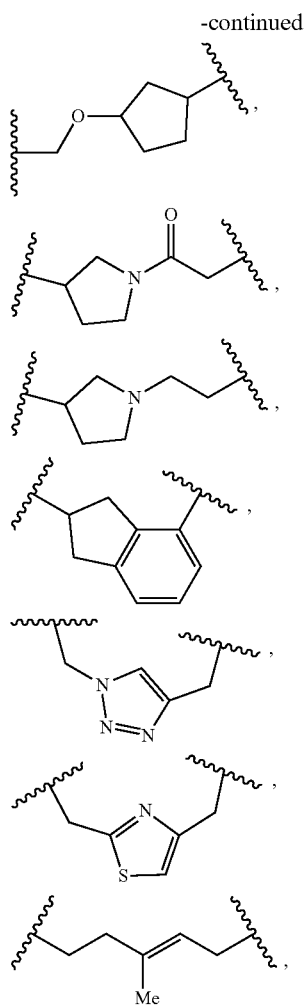

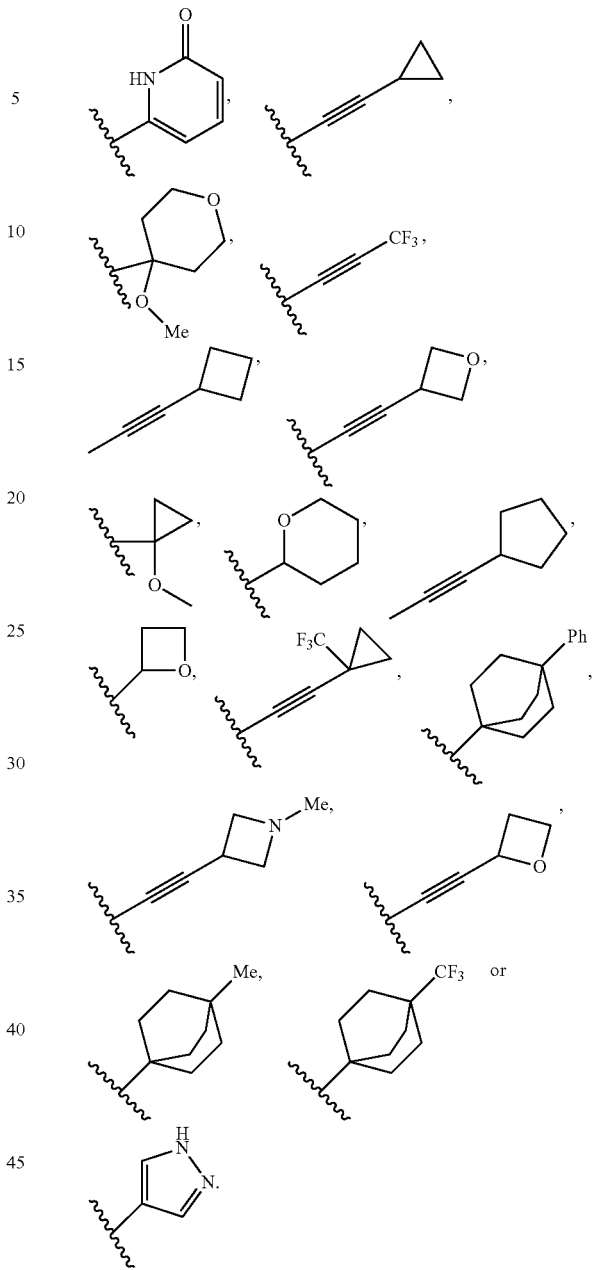

or halogenated, versions thereof, particularly fluorinated compounds; $R^{22}$ is selected from Cl, F, I, Br, alkyloxy, haloalkyloxy, cycloalkyloxy, cyano, haloalkyl, $CD_3$, $OCD_3$, aliphatic, alkyl, alkenyl, alkynyl, amino, heterocyclic, aryl, cycloaliphatic or heteroaryl, particularly Br, F, methyl, trifluoromethyl, cyano, methoxy, cyclopropyl or azetidine; $R^2$ is selected from Cl, F, I, Br, alkyloxy, haloalkyloxy, cycloalkyloxy, cyano, haloalkyl, $CD_3$, $OCD_3$, aliphatic, alkyl, alkenyl, alkynyl, amino, heterocyclic, aryl, cycloaliphatic or heteroaryl; n is from 2 to 4; two adjacent $R^2$ groups may form a fused ring system with ring B, with particular compounds having $R^2$ selected from bromo, fluoro, methyl, trifluoromethyl, methoxy, trifluoromethoxy, dimethylamino, acetyl, methanesulfonyl, cyano, cyclopropoxy, phenyl, furan-2-yl, furan-3-yl, thiophen-2-yl, thiophen-3-yl, 2-methoxyphenyl, 3-methoxyphenyl, 4-methoxyphenyl, 2-fluorophenyl, 3-fluorophenyl, 4-fluorophenyl, 2-trifluoromethylphenyl, 3-trifluoromethylphenyl, 4-trifluoromethylphenyl, 4-n-butylphenyl, 4-n-propylphenyl, 2-methylphenyl, 3-methylphenyl, 4-methylphenyl, 4-ethylphenyl, 2-ethylphenyl, 2,3-dimethylphenyl, 2,5-dimethylphenyl, 3,5-dimethylphenyl, 3-pyridyl, 4-pyridyl, naphthalen-1-yl, naphthalen-2-yl, (1,1'-biphenyl)-2-yl, pyrrolidin-1-yl, 3-(furan-3-yl)phenyl, In some embodiments, the compound has a formula

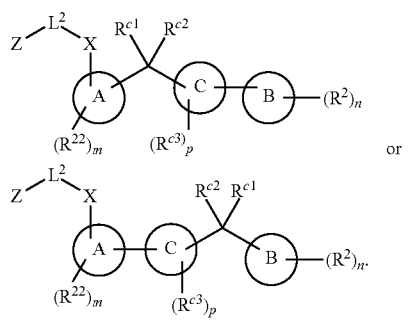

With reference to these formulas, $R^{c3}$ may be alkyl or $CX_3$, where X is halogen, such as with $CF_3$. In some embodiments, ring C is a 5-membered heterocycle, and may be selected from imidazole, pyrazole, pyrrole, triazole, tetrazole, thiazole, isothiazole, thiadiazole, oxazole, isoxazole, oxadiazole, imidazoline, pyrrolidine, thiazoline or oxazoline. In certain embodiments, the

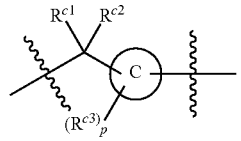

moiety or the

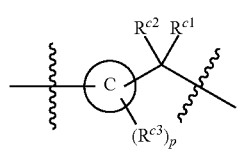

moiety is selected from

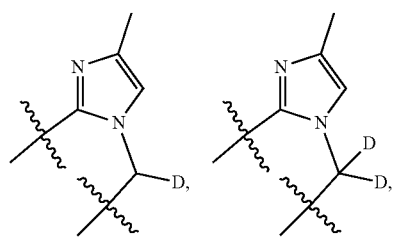

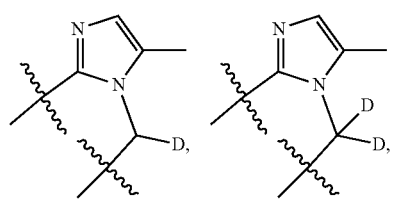

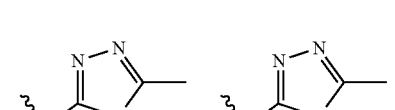

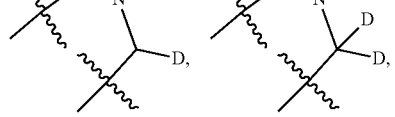

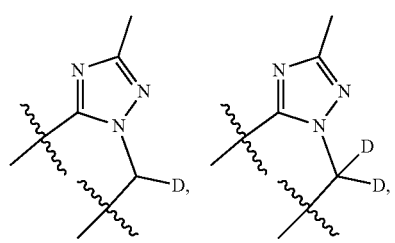

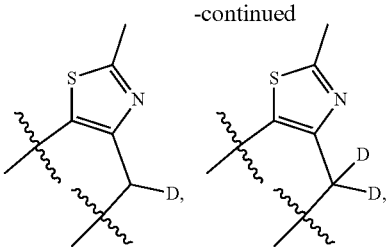

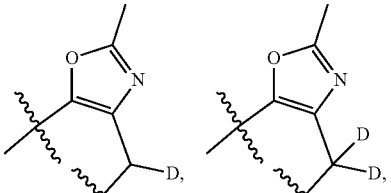

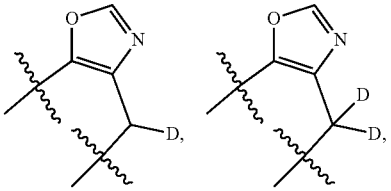

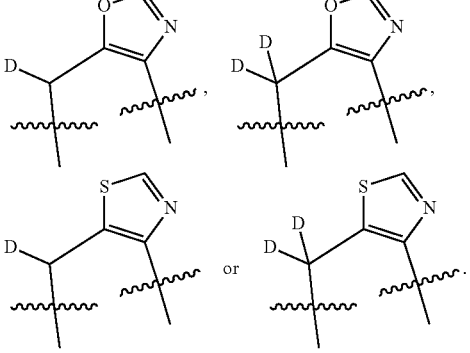

Pharmaceutical compositions also are disclosed. Particular embodiments comprise a pharmaceutically acceptable excipient and one or more of the disclosed compounds.

A method of activating PPARδ also is disclosed. For certain embodiments, the method comprises contacting a PPARδ protein with an effective amount of one or more disclosed compounds, or a pharmaceutical composition comprising one or more disclosed compounds, thereby activating the PPARδ protein. The PPARδ protein may be present in a subject, wherein contacting comprises administering the one or more compounds to the subject. Activating the PPARδ protein within the subject can increase or maintain muscle mass or muscle tone in the subject.

Another embodiment comprises treating a PPARδ-related disease or condition in a subject by administering to the subject in need thereof a therapeutically effective amount of one or more disclosed compounds, or a pharmaceutical composition comprising the compound(s). For certain embodiments, administering a deuterated compound(s), or composition comprising a deuterated compound(s), provides substantially superior biological efficacy. Additional information concerning deuteration effects is provided by "Analogs of Fexaramine and Methods of Making and Using," filed concurrently on Oct. 8, 2014, and listing Ronald Evans et al. as inventors. Each of these applications is incorporated herein by reference in its entirety. In certain embodiments, the PPARδ-related disease is a vascular disease; a muscular disease, such as a muscular dystrophy disease, with particular examples including Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, or Emery-Dreifuss muscular dystrophydemyelinating disease; a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome; a muscle structure disorder, such as Bethlem myopathy, central core disease, congenital fiber type disproportion, distal muscular dystrophy (MD), Duchenne & Becker M D, Emery-Dreifuss M D, facioscapulohumeral MD, hyaline body myopathy, limb-girdle MD, a muscle sodium channel disorder, myotonic chondrodystrophy, myotonic dystrophy, myotubular myopathy, nemaline body disease, oculopharyngeal MD, or stress urinary incontinence; a neuronal activation disorder, such as amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, or toxic myoneural disorder; a muscle fatigue disorder, such as chronic fatigue syndrome, diabetes type I or II, glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus; a mitochondrial disease, such as Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, or Pearson Syndrome; a beta oxidation disease, such as systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency or riboflavin-responsive disorders of β-oxidation (RR-MADD); a metabolic disease, such as hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes, type I or type II, hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, or pancreatitis; a cancer, such as a cancer of the colon, large intestine, skin, breast, prostate, ovary, or lung; a vascular disease, such as peripheral vascular insufficiency, peripheral vascular disease, intermittent claudication, peripheral vascular disease (PVD), peripheral artery disease (PAD), peripheral artery occlusive disease (PAOD), or peripheral obliterative arteriopathy; an ocular vascular disease, such as age-related macular degeneration (AMD), stargardt disease, hypertensive retinopathy, diabetic retinopathy, retinopathy, macular degeneration, retinal haemorrhage, or glaucoma; or a muscular eye disease, such as strabismus, progressive external ophthalmoplegia, esotropia, exotropia, a disorder of refraction and accommodation, hypermetropia, myopia, astigmatism, anisometropia, presbyopia, disorders of accommodation, or internal ophthalmoplegia.

For certain disclosed method embodiments, the subject is a sedentary or immobilized subject. In other embodiments, the subject can be an exercising subject.

For disclosed embodiments, administering may comprise intraarticular, intravenous, intramuscular, intratumoral, intradermal, intraperitoneal, subcutaneous, oral, topical, intrathecal, inhalational, transdermal, rectal administration, or any combination thereof. The one or more compounds are administered to the subject at an effective dose, such as a dose of from greater than 0 mg/kg, such as from about 1 mg/kg to about 20 mg/kg, or from about 2 mg/kg to about 10 mg/kg, with certain embodiments being administered at a dose of from about 2 mg/kg to about 5 mg/kg.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1C provides Evans Blue stains of transverse sections of tibialis anterior (TA) muscle of WT and TG animals 5 days after the injury. Damaged fibers are stained by dye.

FIG. 1D provides quantitation of the proportion of stained area over the total cross-sectional area (CSA) of TA 5 days after the injury (n=5; **$P<0.01$).

FIG. 1E provides quantification of Evans Blue stain at 12 hours after injury (n=3).

FIG. 1F provides quantification of Evans Blue stain at 36 hours after injury (n=3).

FIGS. 1G-1J illustrate VP16-PPARδ transgenic animals that exhibit accelerated muscle regeneration after acute injury. All error bars are SEM. *$P<0.05$; $P<0.01$; *$P<0.001$; n.s.=not significant.

FIG. 1G provides H&E stained transverse sections of injured tibialis anterior (TA) muscle from wildtype (WT) and transgenic (TG) animals. Images are representative from 3, 5 and 7 days after injury. Arrows=regenerating fibers with centralized nuclei. Arrowheads=hollowed remains of basal lamina. Asterisks=uninjured fibers.

FIG. 1H illustrates the average number of regenerating fibers per field.

FIG. 1I illustrates the average CSA of regenerating myofiber (n=5 for day 5; n=11 for day 7).

FIG. 1J illustrates the average CSA of regenerating myofiber, 21 days after injury (n=5).

FIG. 2A provides a GO classification of injury-specific upregulated genes in VP16-PPARδ (TG) compared to wildtype TA muscle (n=3).

FIG. 2B shows the relative expression of specific genes associated with regeneration in VP16-PPARδ (TG) compared to wildtype TA muscle.

FIG. 2C is a graph of relative expression versus days post injury, illustrating post injury temporal gene expression profiles of inflammatory marker CD68, measured by QPCR (n=5).

FIG. 2D is a graph of relative expression versus days post injury, illustrating post injury temporal gene expression profiles of a myogenic marker MyoD by Q-PCR (n=5).

FIG. 2E is a bar graph showing the Myh8 mRNA levels in control, uninjured and injured wildtype (WT) and VP16-PPARδ (TG) mice 5 days post injury (n>5).

FIG. 3A provides immunofluorescence staining for CD31 on transverse sections of uninjured tibialis anterior (TA) muscle from WT and TG animals.

FIG. 3B provides quantification of CD31 positive capillary numbers from uninjured tibialis anterior (TA) muscle from WT and TG animals (n=4).

FIG. 3C illustrates the FGF1a mRNA level in TA of WT and TG by QPCR (n=5).

FIG. 3D provides a Western blot showing increased FGF1 in the VP16-PPARδ (TG) mice compared to wildtype mice (GAPDH western blot included as a loading control).

FIG. 3E provides immunofluorescence staining for CD31 positive capillaries on transverse sections of TA from WT and TG animals 5 days after the injury (n=3).

FIG. 3F provides quantification for CD31 positive capillaries on transverse sections of TA, 5 days after the injury (n=3).

FIG. 3G shows the ligand-dependent induction of FGF1a by PPARδ. Results of luciferase reporter assays of the FGF1a promoter co-transfected with PPARδ with or without the ligand, GW501516.

FIG. 4A provides digital images of isolated myofibers from lateral gastrocnemius of 8-week-old nestin reporter mice with or without VP16-PPARδ transgene. The top panel shows the GFP fluorescence of nestin-positive satellite cells, the middle panel shows DAPI staining of all cell nuceli, and the overlay of the GFP fluorescence and DAPI staining is shown in the bottom panel.

FIG. 4B is a bar graph showing quantification of GFP+ satellite cells per unit length of myofiber in nestin-GFP mice (WT) and nestin-GFP mice crossed to the VP16-PPARδ mice, nestin-GFP; VP16-PPARδ mice (TG) (n=3).

FIG. 4C is a bar graph showing the proportion of BrdU positive nuclei at 0.5, 1 and 2 days after injury in nestin-GFP mice (WT) and nestin-GFP mice crossed to the VP16-PPARδ mice, nestin-GFP; VP16-PPARδ mice (TG) (n=5).

FIG. 4D is a bar graph showing VP16 mRNA levels in whole TA compared to isolated satellite cells (SC) from nestin-GFP mice (WT) and nestin-GFP mice crossed to the VP16-PPARδ mice, nestin-GFP; VP16-PPARδ mice (TG).

FIG. 4E is a bar graph showing PPARδ mRNA levels in whole TA compared to isolated satellite cells (SC) from nestin-GFP mice (WT) and nestin-GFP mice crossed to the VP16-PPARδ mice, nestin-GFP; VP16-PPARδ mice (TG).

FIGS. 5A-5E illustrate that acute pharmacological activation of PPARδ confers regenerative advantage. *P<0.05; P<0.01; *P<0.001. All error bars are SEM.

FIG. 5A is a series of bar graphs showing PPARδ target gene expression in TA after a 9 day treatment with either vehicle or the PPARδ ligand GW501516 (n=6).

FIG. 5B provides digital images of transverse TA sections from vehicle or GW501516 treated mice showing Evans Blue dye uptake 5 days after the injury.

FIG. 5C is a bar graph showing the proportions of Evans blue stained area (n=5) in the images of FIG. 5B.

FIG. 5D is a bar graph showing the percentage of BrdU positive nuclei 2 days after injury in transverse TA sections from vehicle or GW501516 treated mice (n=4).

FIG. 5E is a series of bar graphs showing relative gene expression of TNFα and F4/80 in TA muscle from vehicle or GW501516 treated mice 3 days after injury, as measured by QPCR (n=6). The gene expression levels in the uninjured, contralateral TA muscles are shown as the uninjured control.

FIG. 9A are graphs showing the bioavailability of MA-0089 at 3 mg/kg i.v. or 10 mg/kg p.o. in mice.

FIG. 9B are graphs showing the bioavailability of MA-0011 at 3 mg/kg i.v. or 10 mg/kg p.o. in mice.

FIG. 9C are graphs showing the bioavailability of MA-0089 at 3 mg/kg i.v. or 10 mg/kg p.o. in mice.

FIG. 9D are graphs showing the bioavailability of GW501516 at 3 mg/kg i.v. or 10 mg/kg p.o. in rats.

FIG. 9E are graphs showing the bioavailability of GW501516 at 3 mg/kg i.v. and 10 mg/kg p.o. in mice.

DETAILED DESCRIPTION

I. Terms

Figure 1A:
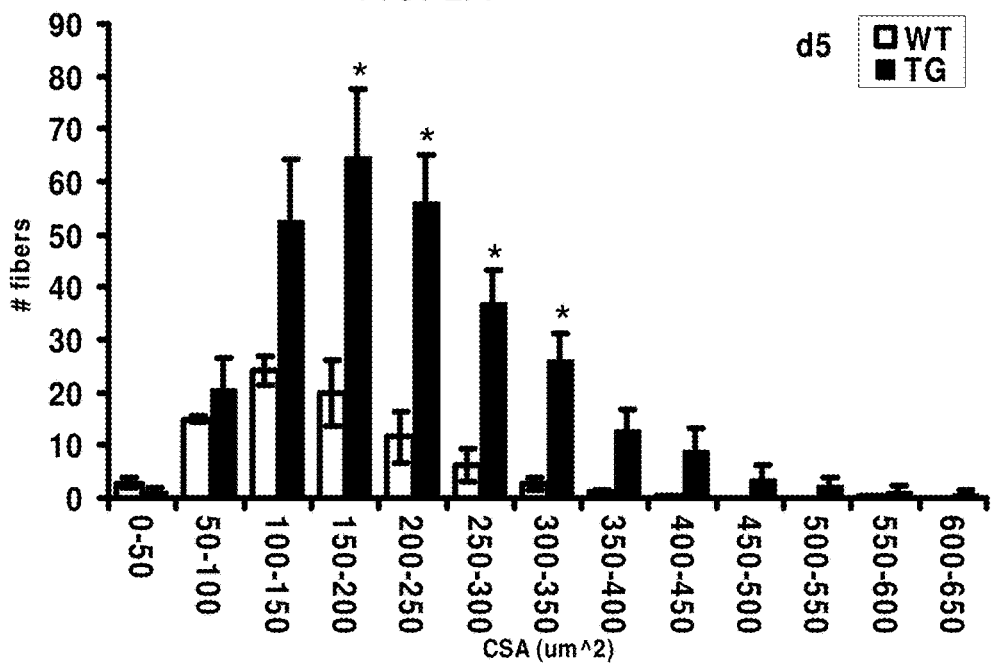
FIGS. 1A and 1B are bar graphs showing recovery of damaged muscle fibers after injury. The number of muscle fibers of a specified size (bined into 50 $\mu m^2$ area bins) is reported for wildtype (WT) and VP16-PPARδ (TG) mice 5 days (FIG. 1A) and 7 days (FIG. 1B) after injury. All error bars are SEM. *$P<0.05$; $P<0.01$; *$P<0.001$.
Figure 1B:
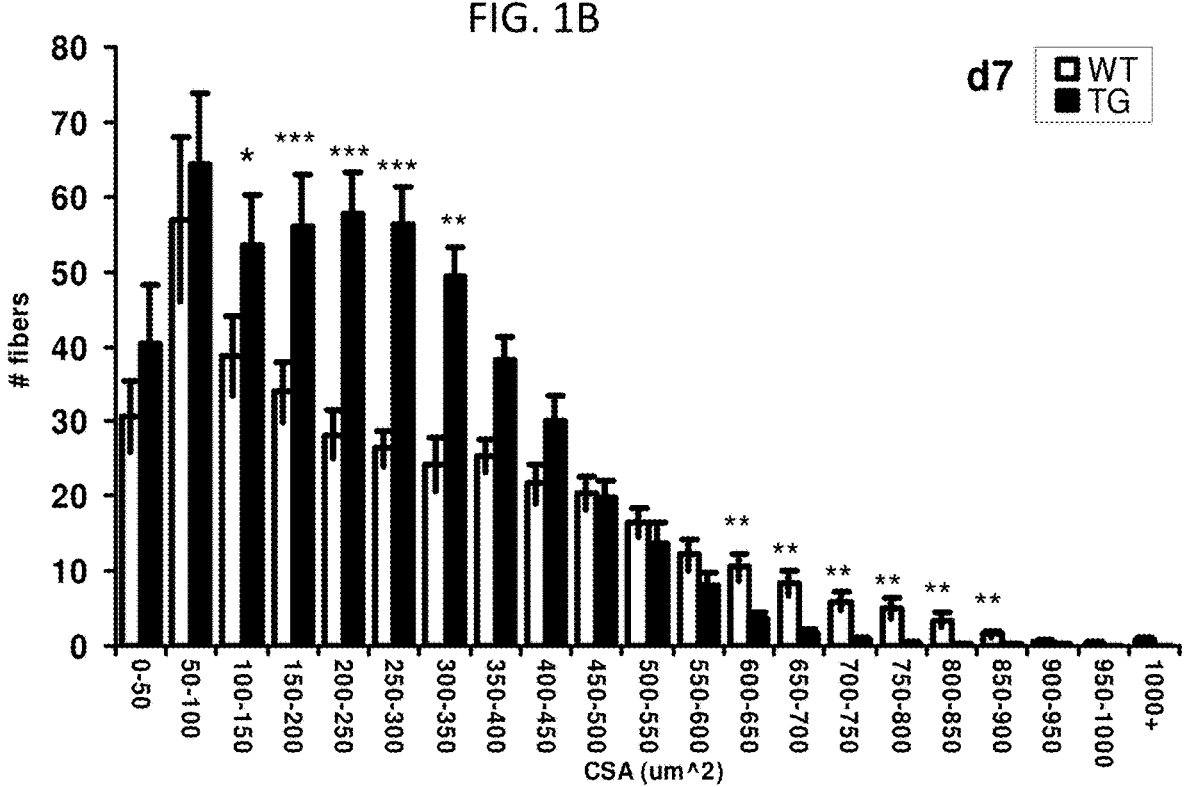

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a PPARδ agonist" includes single or plural PPARδ agonists and is considered equivalent to the phrase "comprising at least one PPARδ agonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as October 2014. All references, including patents and patent applications, and GenBank® Accession numbers cited herein, are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

The abbreviations used herein have their conventional meaning within the chemical and biological arts. The chemical structures and formulae set forth herein are constructed according to the standard rules of chemical valency known in the chemical arts.

All groups stated herein are understood to include both substituted and unsubstituted forms unless specifically stated otherwise, or context indicates otherwise. "Substituted" means that one or more hydrogen atoms of the specified group or moiety is each, independently of one another, replaced with the same or a different non-hydrogen substituent.

In some embodiments, exemplary substituent groups can include those listed below:

Substituents for aliphatic, heteroaliphatic, cycloaliphatic and/or heterocycloaliphatic moieties can be one or more of a variety of groups selected from, but not limited to, aliphatic, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, —OR', oxo, =NR', =N—OR', —NR'R", —SW, halogen, —SiR'R"R'", —OC(O)R, —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN, and —NO$_2$ in a number ranging from zero to (2 m'+1) or (2 m'-1), where m' is the total number of carbon atoms in such moiety. R', R", R'", and R"" each independently refer to hydrogen, aliphatic, heteroaliphatic, cycloaliphatic, heterocycloaliphatic, or aryl groups. In some embodiments, R', R", R', and R"" can independently refer to aliphatic, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, or heterocycloalkynyl groups. When a compound includes more than one R', R", R'", or R"" group, for example, each of the R', R", R'", or R"" groups can be independently selected relative to the remaining R', R", R'", and R"" group(s). In some embodiments, when R' and R" are attached to the same or an adjacent atom, such as a nitrogen atom, they can be combined to form a cyclic structure, such as a 4-, 5-, 6-, or 7-membered heterocyclic ring.

Substituents for aryl and heteroaryl groups may be selected from, for example: aliphatic, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, —OR', —NR'R", —SR', halogen, —SiR'R"R'", —OC(O)R, —C(O)R, —CO$_2$R', —CONR'R", —OC(O)NR'R", —NR"C(O)R, —NR'—C(O)NR"R", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of possible positions on the aromatic ring system; and where R', R", R'", and R"" are independently refer to hydrogen, aliphatic, heteroaliphatic, cycloaliphatic, heterocycloaliphatic, or aryl groups. In some embodiments, R', R", R'", and R"" can independently refer to alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, or heterocycloalkynyl groups. When a compound includes more than one R', R", R'", or R"" group, for example, each of the R', R", R'", or R"" groups can be independently selected relative to the remaining R', R", R'", and R"" group(s).

Two or more substituents may optionally be joined to form aryl, heteroaryl, cycloaliphatic, or heterocycloaliphatic groups. Such ring-forming substituents are typically, though not necessarily, attached to a cyclic base structure. In some embodiments, the ring-forming substituents are attached to adjacent members of the base structure. For example, two ring-forming substituents can attached to adjacent atoms of a cyclic base structure to create a fused ring structure. In other embodiments, the ring-forming substituents can be attached to a single atom of the base structure to create a spirocyclic structure. In yet another embodiment, the ring-forming substituents are attached to non-adjacent atoms of the base structure.

Unless otherwise stated, structures depicted herein are also meant to include all stereochemical forms of the structure; such as the R and S configurations for each asymmetric center, E and Z isomers for olefins, and/or the m and p configurations for each biaryl ring system. Therefore, single stereochemical isomers, as well as enantiomeric, diastereomeric, and atropisomeric mixtures of the present compounds are within the scope of the disclosure, as well as racemic mixtures. In some embodiments, the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon, are within the scope of this disclosure.

The compounds of the present disclosure may also contain unnatural proportions of atomic isotopes at one or more of atoms that constitute such compounds. For example, the compounds may be radiolabeled with radioactive isotopes, such as, for example, tritium ($^3$H), nitrogen ($N^{15}$), iodine-125 ($^{125}$I) or carbon-14 ($^{14}$C). All isotopic variations of the compounds of the present disclosure, whether radioactive or not, are encompassed within the scope of the present disclosure.

The terms "a," "an," or "a(n)," when used in reference to a group of substituents herein, mean at least one.

The symbol "  " denotes the point of attachment of a chemical moiety to the remainder of a molecule or chemical formula.

The term "alkyl," means, unless otherwise stated, a straight (i.e., unbranched), branched or cyclic saturated hydrocarbon chain, or combination thereof, and can include di- and multivalent moieties, having the number of carbon atoms designated (for example, $C_1$-$C_{10}$ includes alkyl groups comprising one to ten carbons). Examples of alkyl groups include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An "alkoxy" group is an alkyl group comprising at least one oxygen atom in the chain. Alkyl groups may also comprise one or more isotopic variants, such as deuterium atoms in place of one or more corresponding hydrogen atoms.

The term "aliphatic" refers to a hydrocarbon-based compound, or a moiety thereof, and can include alkanes, alkenes, alkynes, including cyclic versions thereof, (cycloaliphatic or cyclicaliphatic such as cycloalkyl, cycloalkenyl and cycloalkynyl) and further including straight- and/or branched-chain arrangements, and all stereo and positional isomers as well. Unless expressly stated otherwise, an aliphatic group contains at least one carbon atom. Aliphatic groups may also comprise one or more isotopic variants, such as deuterium atoms in place of one or more corresponding hydrogen atoms.

"Alkenyl" refers to straight chain or branched hydrocarbyl groups having from 2 to 10 carbon atoms, and in some embodiments 2 to 8 carbon atoms, and having at least 1 double bond. Such groups are exemplified, for example, bi-vinyl, allyl, and but-3-en-1-yl. Included within this term are the cis and trans isomers or mixtures of these isomers, unless otherwise specified. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the higher homologs and isomers. A person of ordinary skill in the art will understand that the olefin can be at any allowable position in an alkenyl chain. The term "alkenylene" refers to a divalent moiety derived from an alkenyl. Alkenyl groups may also comprise one or more isotopic variants, such as deuterium atoms in place of one or more corresponding hydrogen atoms.

"Alkynyl," by itself or as part of another substituent, refers to straight chain or branched hydrocarbyl groups having from 2 to 10 carbon atoms, and in some embodiments 2 to 8 carbon atoms, and having at least 1 site of triple bond unsaturation. Such groups are exemplified, for example, by ethynyl, 1-propynyl and 2-propynyl. The term "alkynylene" refers to a divalent moiety derived from an alkynyl. Example alkynyl groups include ethynyl, 1- and 3-propynyl, 3-butynyl, and higher homologs and isomers. Alkynyl groups may also comprise one or more isotopic variants, such as deuterium atoms in place of one or more corresponding hydrogen atoms.

The term "heteroaliphatic" refers to an aliphatic compound or group having at least one heteroatom. For example, in some embodiments, one or more carbon atoms has been replaced with an atom typically having at least one lone pair of electrons, such as O, N, P, S, and Si. Heteroaliphatic compounds or groups may be branched or unbranched, cyclic or acyclic, and can include "heterocycle," "heterocyclyl," "heterocycloaliphatic," or "heterocyclic" groups. Heteroaliphatic groups may also comprise one or more isotopic variants, such as deuterium atoms in place of one or more corresponding hydrogen atoms.

The term "heteroalkyl," by itself or in combination with another term, means, unless otherwise stated, a stable straight, branched or cyclic chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —Si(CH$_3$)$_3$, —O—CH$_3$, —O—CH$_2$—CH$_3$, and —CN. Up to two heteroatoms may be consecutive, such as, for example, —CH$_2$—NH—OCH$_3$. Heteroalkyl groups may also comprise one or more isotopic variants, such as deuterium atoms in place of one or more corresponding hydrogen atoms.

Similarly, the term "heteroalkylene," by itself or as part of another substituent, means, unless otherwise stated, at least a divalent moiety derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means at least a divalent moiety derived from a cycloalkyl and heterocycloalkyl, respectively. Cycloalkyl and heterocycloalkyl groups may also comprise one or more one or more isotopic variants, such as deuterium atoms in place of one or more corresponding hydrogen atoms.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl, including mixed halogen-bearing substituents comprising two different halogens. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "amino," refers to a chemical functional group —N($R^1$)$R^{11}$ where $R^1$ and $R^{11}$ are independently hydrogen, aliphatic, alkyl, heteroalkyl, haloalkyl, aliphatic, heteroaliphatic, aryl (such as phenyl or benzyl), heteroaryl, or other functionality. A "primary amino" group is —$NH_2$. The term "aminocarbonyl" refers to a chemical functional group —C(O)-amino, where amino is as defined herein. A primary aminocarbonyl is —$CONH_2$.

The term "cyano" refers to the chemical functional group —CN.

The term "carboxyl," "carboxylic acid" or "carboxy" refers to the chemical functional group —$CO_2H$.

The term "carboxyl ester," "carboxylic acid ester," or "carboxy ester" refers to the chemical functional group —$CO_2R$ where R is aliphatic, alkyl, heteroalkyl, haloalkyl, aliphatic, heteroaliphatic, aryl (such as phenyl or benzyl), heteroaryl, or other functionality.

The term "aminosulfonyl" refers to a chemical function group —$SO_2$-amino, where amino is as defined herein. A primary aminosulfonyl is —$SO_2NH_2$.

The term "acyl" means, unless otherwise stated, —C(O)R where R is a aliphatic, alkyl, cycloalkyl, heteroalkyl, heterocycloalkyl, aryl, or heteroaryl.

The term "aryl" means, unless otherwise stated, a polyunsaturated, aromatic moiety, such as an aromatic hydrocarbon substituent, which can be a single ring or multiple rings (e.g., from 1 to 5, typically 1 to 3, rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom, typically N, O, and S. For certain embodiments, heteroatoms, such as the nitrogen and sulfur atoms, are optionally oxidized, and the nitrogen atom(s) are optionally quaternized. Thus, the term "heteroaryl" includes fused ring heteroaryl groups (e.g., multiple rings fused together wherein at least one of the fused rings is a heteroaromatic ring). A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of a molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 4-benzoxadiazolyle, 5-benzoxodiazole, benzofuran, benzofuranone, benzothiophene, indole, indoline, indolinone 3-quinolyl, and 6-quinolyl. Substituents for each of the above noted aryl and heteroaryl ring systems are selected from the group of acceptable substituents described below. "Arylene" and a "heteroarylene," alone or as part of another substituent, mean at least a divalent moiety derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those moieties in which an aryl group is attached to an aliphatic or alkyl group (e.g., benzyl, phenethyl, pyridylmethyl and the like) including those aliphatic or alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "sulfonyl," as used herein, means a moiety having the formula —$S(O_2)$—R', where R' is an aliphatic, alkyl, aryl or heteroaryl, group as defined above. R' may have a specified number of carbons (e.g., "$C_1$-$C_4$ alkylsulfonyl").

The terms "carboxyl bioisosteric," or "carboxyl bioisostere" refer to a group with similar physical or chemical properties to a carboxyl group that produce broadly similar biological properties, but which may reduce toxicity or modify the activity of the compound, and may alter the metabolism of the compound. Exemplary carboxyl bioisosteres include, but are not limited to,

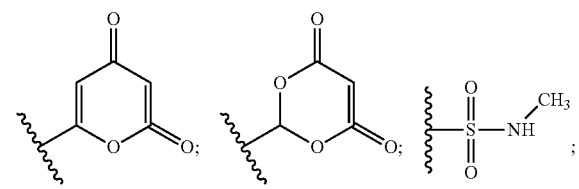

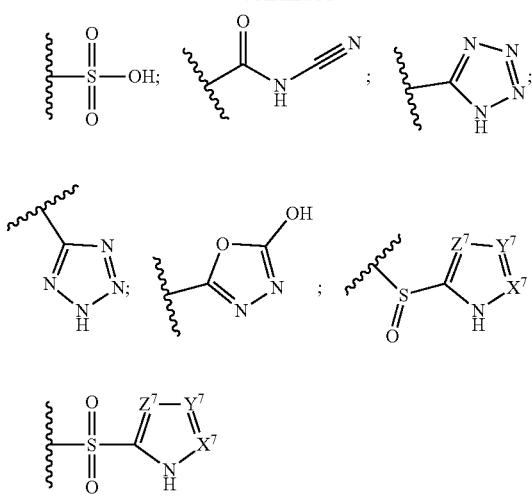
where $X^7$, $Y^7$, and $Z^7$ are each independently selected from N, $CH_2$ or CO;
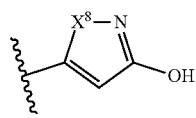
where $X^8$ is selected from O, S or NMe;
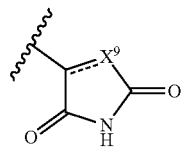
where $X^9$ is selected from O, N, S, CH or $CH_2$;
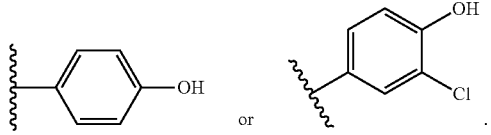 [SMILES: *c1ccc(O)cc1 ; *c1ccc(O)c(Cl)c1]
Additional carboxyl bioisosteric groups contemplated by the present disclosure include
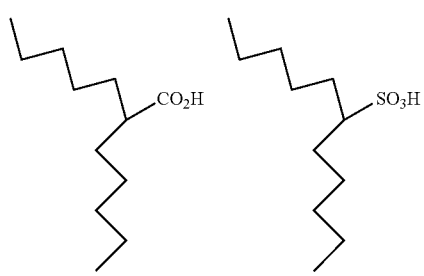
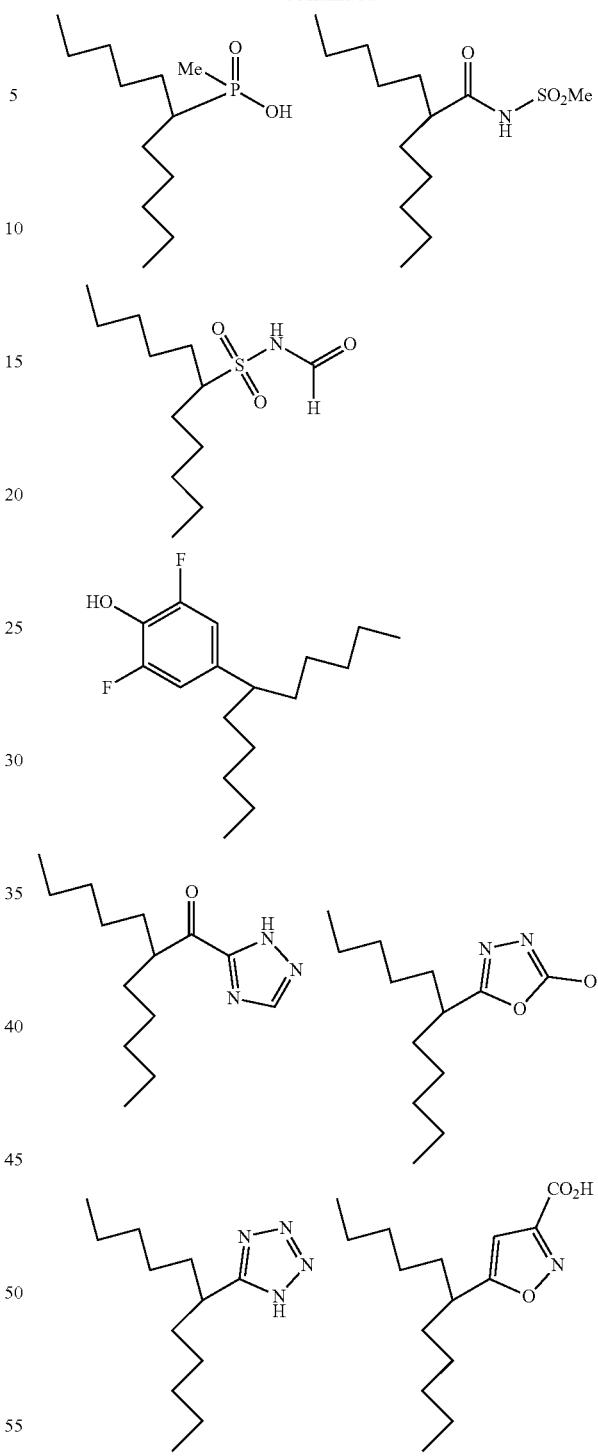

-continued

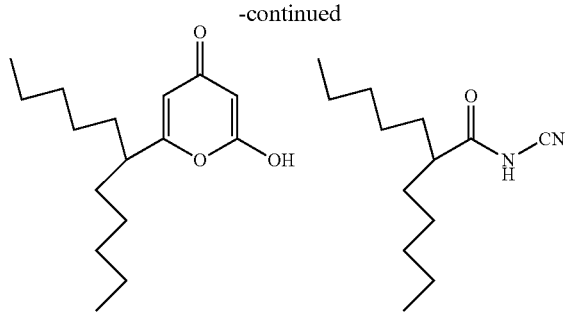

The term "pharmaceutically acceptable salts" is meant to include salts of active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable solvent. Examples of pharmaceutically acceptable base addition salts include, by way of example and without limitation, sodium salts, potassium salts, calcium salts, ammonium salts, organic amino salts, or magnesium salts, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids, like glucuronic or galactunoric acids and the like (see, for example, Berge et al., "Pharmaceutical Salts," *Journal of Pharmaceutical Science*, 1977, 66, 1-19). Certain specific compounds of the present disclosure contain both basic and acidic functionalities that allow the compounds to be converted into either base or acid addition salts.

Thus, the compounds provided herein can exist as salts with pharmaceutically acceptable acids. The present disclosure includes such salts. Examples of such salts include hydrohalides, such as hydrochlorides and hydrobromides, sulfates, methanesulfonates, nitrates, maleates, acetates, citrates, fumarates, tartrates (eg (+)-tartrates, (−)-tartrates or mixtures thereof including racemic mixtures), succinates, benzoates and salts with amino acids such as glutamic acid. These salts may be prepared by methods known to those of ordinary skill in the art.

The neutral forms of the compounds are in some examples regenerated by contacting the salt with a base or acid and isolating the parent compound in the conventional manner. The parent form of the compound may differ from the various salt forms in certain physical properties, such as solubility in polar solvents.

In addition to salt forms, the present disclosure includes compounds in a prodrug form. Prodrugs of the compounds described herein are those compounds that readily undergo chemical changes under physiological conditions to provide the compounds herein. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds provided herein can exist in unsolvated forms as well as solvated forms, including hydrated forms. In general, the solvated forms are equivalent to unsolvated forms and are encompassed within the scope of the present disclosure. Certain compounds provided herein can exist in multiple crystalline or amorphous forms. In general, all physical forms are equivalent for the uses contemplated by the present disclosure and are intended to be within the scope of the present disclosure.

The terms "administer," "administering," "administration," and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, The Pharmacological Basis of Therapeutics, current ed.; Pergamon; and Remington's, Pharmaceutical Sciences (current edition), Mack Publishing Co., Easton, Pa.

As used herein, the terms "co-administration," "administered in combination with," and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The term "effective amount" or "therapeutically effective amount" refers to the amount of an active agent (such as one or more compounds provided herein alone, in combination, or potentially in combination with other therapeutic agent(s)) sufficient to induce a desired biological result. That result may be amelioration or alleviation of the signs, symptoms, or causes of a disease, or any other desired alteration of a biological system. The term "therapeutically effective amount" is used herein to denote any amount of a therapeutic that causes an ameloriation, improvement and/or prevention in a disease condition. The amount can vary with the condition being treated, the stage of advancement of the condition, and the type and concentration of formulation applied. Appropriate amounts in any given instance will be readily apparent to those of ordinary skill in the art or capable of determination by routine experimentation.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a subject at risk of developing a particular disease, to a subject reporting one or more of the physiological symptoms of a disease, or to a subject at risk of reoccurrence of the disease. Preventing the disease can result in the delay or prevention of development of one or more clinical symptoms of the disease by administration of a protective composition prior to the induction of the disease; suppressing the disease, that is, causing the clinical symptoms of the disease not to develop by administration of a protective composition after the inductive event but prior to the clinical appearance or reappearance of the disease.

"Inhibiting" the disease refers to arresting the development of clinical symptoms by administration of a protective composition after their initial appearance; preventing re-occurring of the disease and/or relieving the disease, that is, causing the regression of clinical symptoms by administration of a protective composition after their initial appearance.

The terms "subject," "individual," or "patient," are used interchangeably. These terms refer to a biological entity, such as a vertebrate, including a mammal, for example a human. Mammals include, but are not limited to, murines, simians, humans, farm animals, sport animals, and pets. Tissues, cells and their progeny of a biological entity obtained in vitro or cultured in vitro are also encompassed. In some embodiments, the subject administered one or more of the compounds provided herein is a sedentary (such as one with no or irregular physical activity, for example one who sits or remains inactive for most of the day with little or no exercise) or immobilized subject (such as a subject confined to a wheelchair, hospital bed, and the like, or one who has a body part in a cast, such as a leg or arm). In other embodiments, the subject administered one or more of the compounds provided herein is an ambulatory or exercised subject, such as a subject in rehab potentially after surgery, or aged or obese subjects. In some embodiments, exercise can include low impact exercise, spanning from once or twice per day. Examples of low impact exercise can include swimming and light to moderate resistance training.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The term "preparation" is intended to include formulations of an active compound with another material, such as an encapsulating material as a carrier to provide a capsule. Similarly, cachets and lozenges are included. Tablets, powders, capsules, pills, cachets, and lozenges can be used as solid dosage forms suitable for oral administration.

The term "peroxisome proliferator-activated receptor delta (PPARδ)" refers to the PPARδ protein (or its coding or gene sequence), a member of a subfamily of nuclear hormone receptors. Ligands of PPARδ can promote myoblast proliferation after injury, such as injury to skeletal muscle. PPARδ (OMIM 600409) sequences are publically available, for example from GenBank® sequence database (e.g., accession numbers NP_001165289.1 (human, protein) NP 035275 (mouse, protein), NM_001171818 (human, nucleic acid) and NM_011145 (mouse, nucleic acid)).

II. Compounds

Disclosed herein are embodiments of a compound having general Formula 1

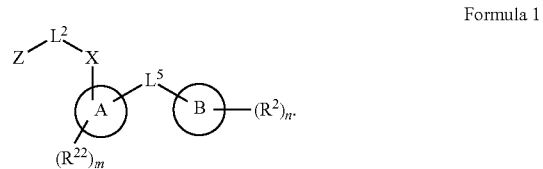

Formula 1

With respect to Formula 1, $L^5$ is

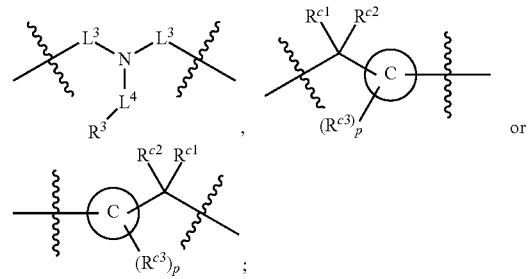

or

;

$R^{c1}$ and $R^{c2}$ are each independently H, D or alkyl, and at least one of $R^{c1}$ and $R^{c2}$ is D; $R^{c3}$ is aliphatic or D; p is 0, 1 or 2; ring C is a 5- or 6-membered heterocyclyl or a 5- or 6-membered heteroaryl; each $L^3$ independently is selected from a bond, aliphatic, —C(O)—, alkylC(O)—, —C(O) alkyl-, or sulfonyl, and at least one $L^3$ is or comprises a —C(O)— that forms an amide moiety with the nitrogen in Formula 1A; $L^4$ is selected from a bond, aliphatic, heteroaliphatic, arylene, heteroarylene, cycloalkylene, heterocycloalkylene or —CR$^{23}$R$^{24}$—; $R^3$ is selected from —OH, —OR$^{3A}$, —NR$^{3A}$R$^{3B}$, —C(O)R$^{3A}$, —S(O)$_2$R$^{3A}$, —C(O) OR$^{3A}$, —S(O)$_2$NR$^{3A}$R$^{3B}$, —C(O)NR$^{3A}$R$^{3B}$, aliphatic, heteroaliphatic, cycloalkyl, heterocycloalkyl, aryl, heteroaryl, or $R^3$ can be joined with an atom of ring A ring B to form a fused ring system or may be joined with an atom of $L^3$ to form a heterocyclic ring system; and at least one of $L^3$, $L^4$ or $R^3$ comprises at least one deuterium; and $R^{3A}$ and $R^{3B}$ are independently selected from hydrogen or aliphatic, typically alkyl.

Also with reference to Formula 1, ring A is selected from a cycloaliphatic, cycloalkylene, heterocycloalkylene, arylene or heteroarylene. Further with respect to ring A, in certain embodiments when ring A is phenyl, the L⁵ group and the X-L²-Z group typically are positioned ortho or para to each other. In further embodiments wherein ring A is phenyl, the L⁵ group and the X-L²-Z are not positioned meta to each other unless L⁵ forms a fused ring system with ring A. Exemplary ring A embodiments are illustrated below:

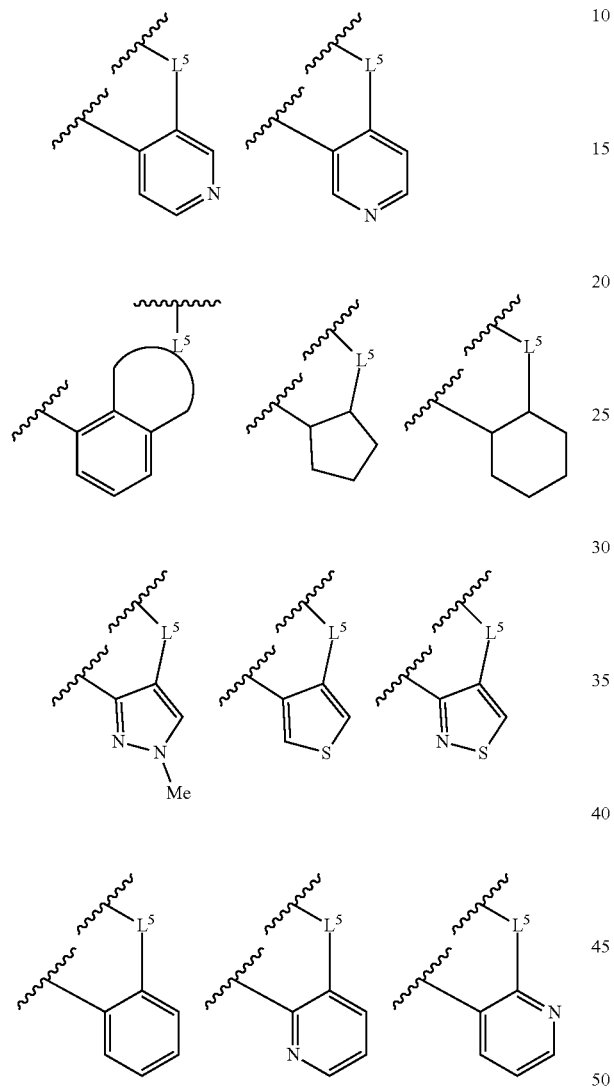

In an independent embodiment, ring A is selected from

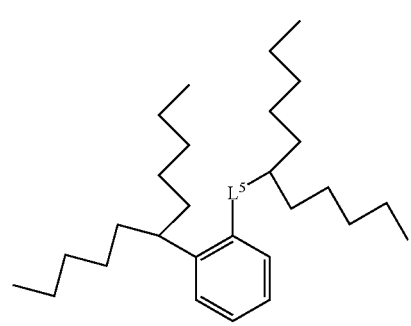

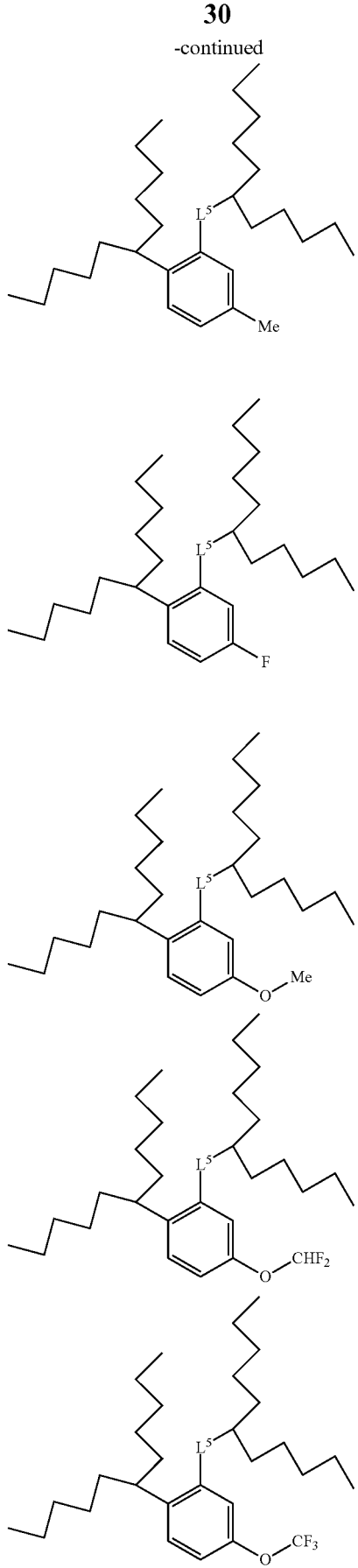

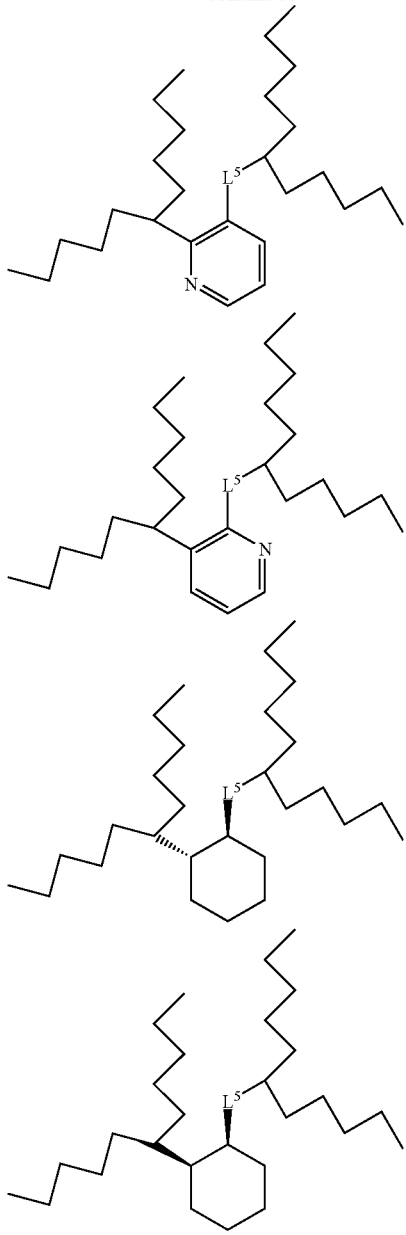
Ring B is selected from aryl, heteroaryl, cycloaliphatic, cycloalkyl, heterocycloalkyl, cycloalkylene, heterocycloalkylene, arylene or heteroarylene. Exemplary ring B embodiments are illustrated below:
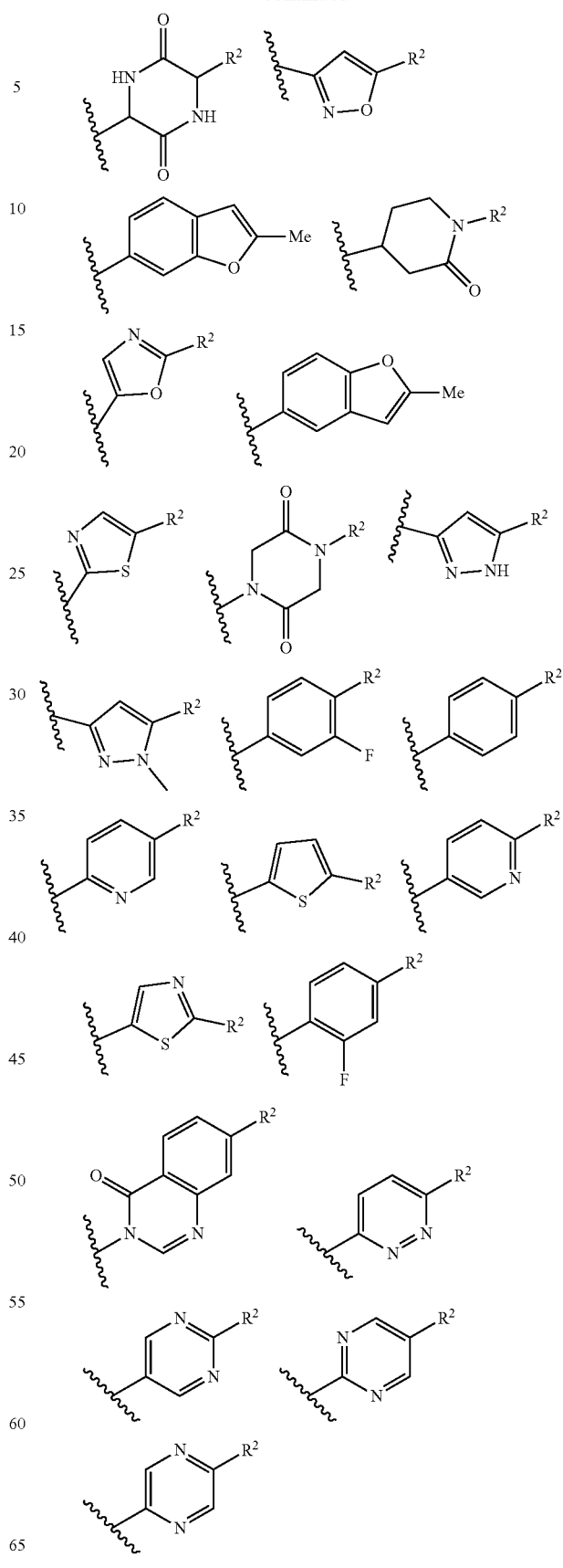

In an independent embodiment, ring B is selected from

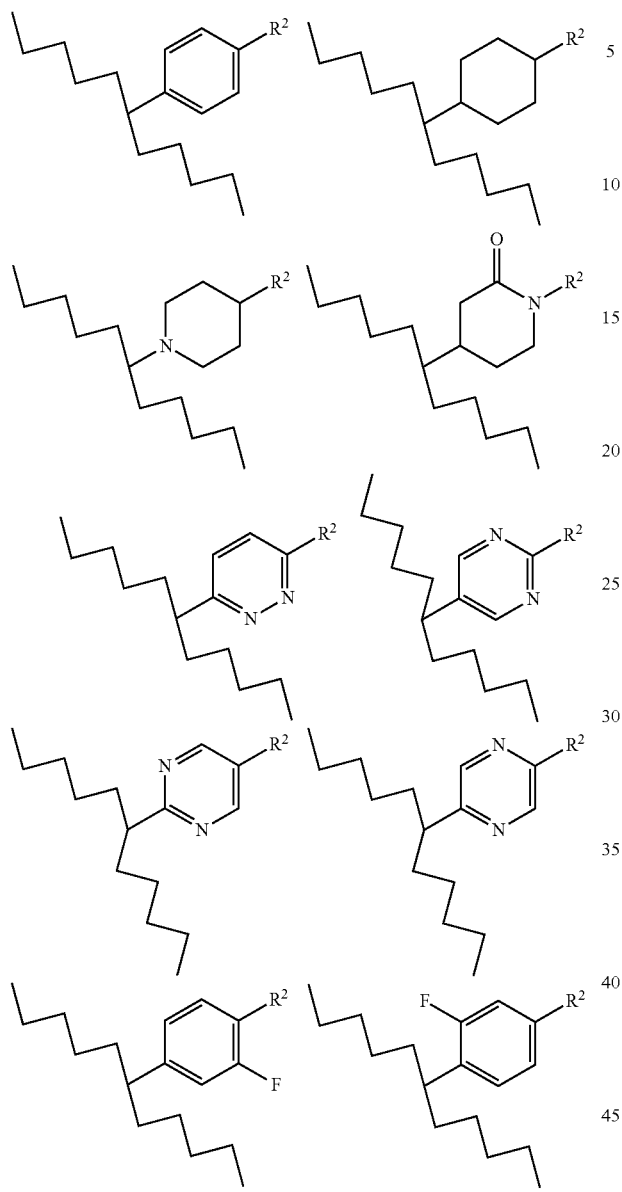

Each R² independently is selected from hydrogen, deuterium, halogen, aryl, heteroaryl, aliphatic, heteroaliphatic, cycloaliphatic, NO₂, OH, amino, amide, aminosulfonyl, carboxyl, carboxyl ester, alkylsulfonyl, SO₃H, or acyl.

In some embodiments R² may be halogen selected from Cl, F, I, Br; heteroaliphatic selected from alkyloxy (e.g., $O(CH_2)_{0-5}CH_3$), haloalkyloxy (e.g., $O(CH_2)_{0-5}CF_3$, $O(CH_2)_{0-5}CHF_2$), cycloalkyloxy (e.g., O-cyclopropyl, O-cyclobutyl, O-cyclopentyl, O-cyclohexyl), cyano, haloalkyl (e.g., $CF_3$), $CD_3$, $OCD_3$; aliphatic, selected from alkyl, alkenyl, alkynyl; amino selected from $N(R^{30})_2$ wherein each $R^{30}$ may be selected from hydrogen, aliphatic, aryl, or cycloaliphatic; heterocyclic selected from piperidinyl, piperazinyl, pyrrolidinyl, 4H-pyranyl, 4H-furanyl, 4H-thiophene, 4H-thiopyranyl, azetidinyl, oxetanyl, piperidinone, 4H-pyranone, 4H-furanone, 4H-pyrrolidone, 4H-thiopyranone, 4H-thiophenone, and any such groups comprising one or more sites of unsaturation; aryl selected from phenyl, naphthalene, anthracene, or phenanthracene; cycloaliphatic selected from cyclopropane, cyclobutane, cyclopentane, cyclohexane, cycloheptane, bicyclononane, bicycloheptane, and any such groups comprising one or more sites of unsaturation; heteroaryl selected from pyridinyl, furanyl, thiophene, pyrrole, oxazole, isoxazole, oxadiazole, thiazole, isothiazole, thiodiazole, diazole, triazole, or tetrazole. In some embodiments, at least two R² groups are present and adjacent to each other and join together to form a fused ring system with ring B. In such embodiments, each R² can be selected to form a fused heterocylic, cyclicaliphatic, heteroaryl, or aryl ring system. Exemplary R² groups are provided below:

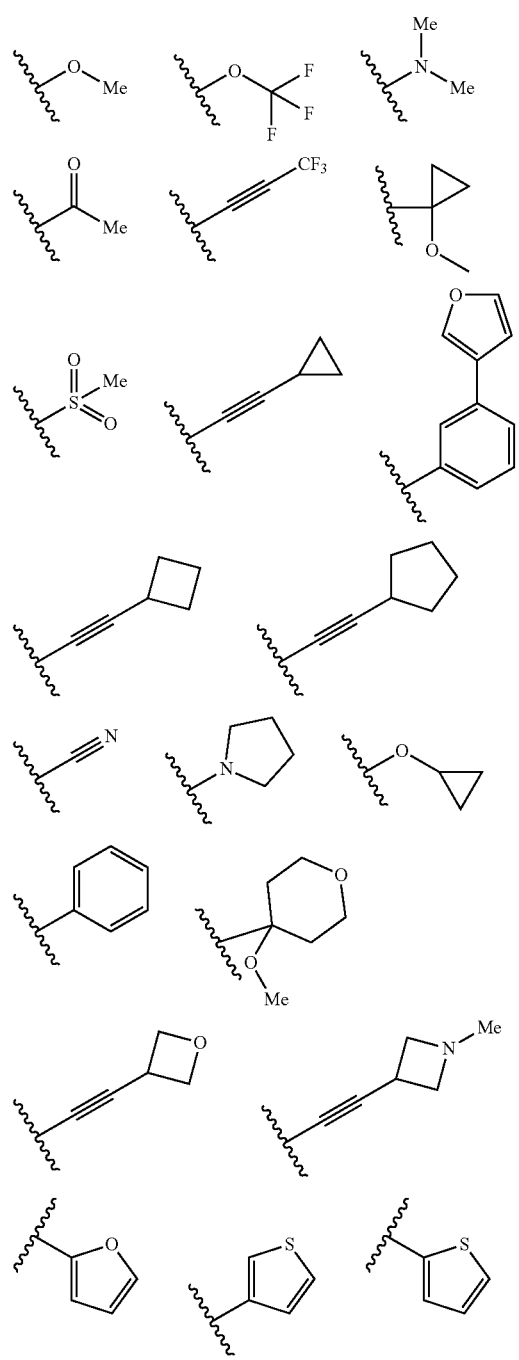

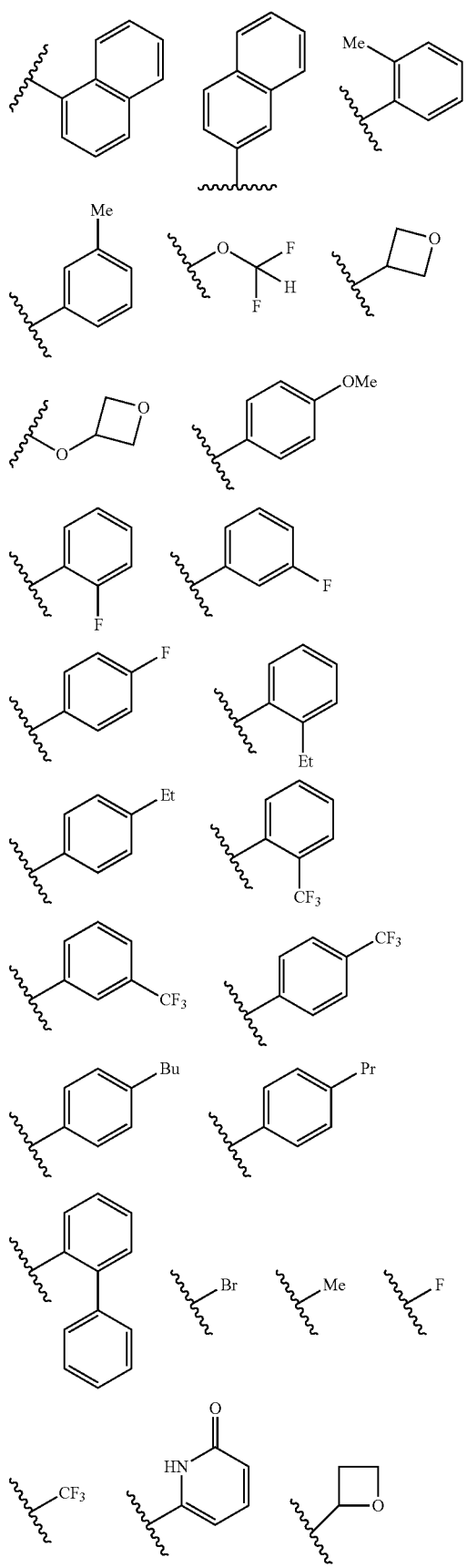
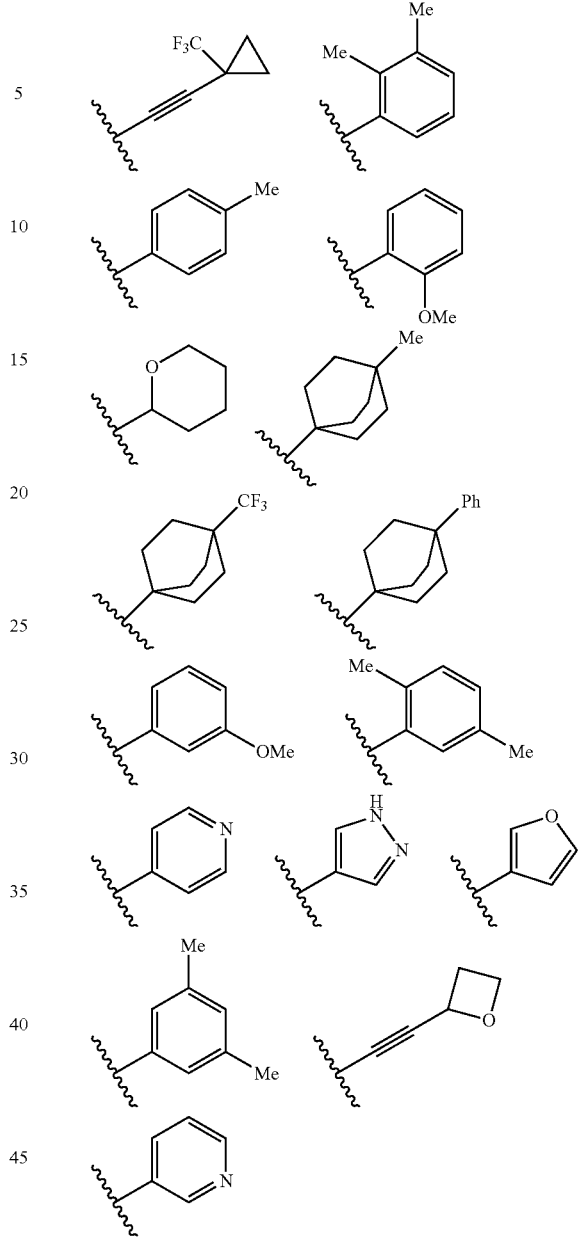

With continued reference to Formula 1:
n is from 0 to 5;
m is from 0 to 4;
each $R^{22}$ independently is selected from hydrogen, deuterium, halogen, aryl, heteroaryl, aliphatic, heteroaliphatic, cycloaliphatic, $NO_2$, OH, amino, amide, aminosulfonyl, carboxyl, carboxyl ester, alkylsulfonyl, $SO_3H$, or acyl. In some embodiments $R^{22}$ may be halogen selected from Cl, Fl, I, Br; heteroaliphatic selected from alkyloxy (e.g., $O(CH_2)_{0-5}CH_3$), haloalkyloxy (e.g., $O(CH_2)_{0-5}CF_3$, $O(CH_2)_{0-5}CHF_2$), cycloalkyloxy (e.g., O-cyclopropyl, O-cyclobutyl, O-cyclopentyl, O-cyclohexyl), cyano, haloalkyl (e.g., $CF_3$), $CD_3$, $OCD_3$; aliphatic, selected from alkyl, alkenyl, alkynyl; amino selected from $N(R^1R^{11})_2$ wherein each $R^{30}$ may be selected from hydrogen, aliphatic, aryl, or cycloaliphatic; heterocyclic selected from piperidinyl, piperazinyl, pyrrolidinyl, 4H-pyranyl, 4H-furanyl, 4H-thiophene, 4H-thiopyranyl, azetidinyl, oxetanyl, piperidinone, 4H-pyranone, 4H-furanone, 4H-pyrrolidone, 4H-thiopyranone, 4H-thiophenone, and any such groups comprising one or more sites of unsaturation; aryl selected from phenyl, naphthalene, anthracene, or phenanthracene; cycloaliphatic selected from cyclopropane, cyclobutane, cyclopentane, cyclohexane, cycloheptane, bicyclononane, bicycloheptane, and any such groups comprising one or more sites of unsaturation; heteroaryl, selected from pyridinyl, furanyl, thiophene, pyrrole, oxazole, isoxazole, oxadiazole, thiazole, isothiazole, thiodiazole, diazole, triazole, or tetrazole. Exemplary $R^{22}$ groups are provided below:

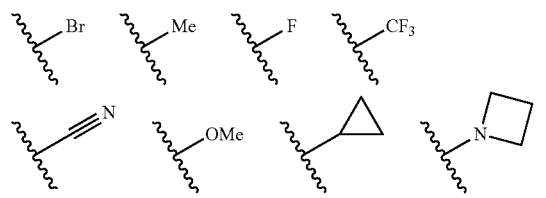

X is O, $NR^{30}$, sulfonyl, or S, where $R^{30}$ is selected from H or aliphatic, aryl, or cycloaliphatic.

Each $L^2$ is selected from a bond, aliphatic, heteroaliphatic, arylene, heteroarylene, cycloalkylene, heterocycloalkylene or —$CR^{23}R^{24}$—, wherein $R^{23}$ and $R^{24}$ each independently is selected from H, deuterium, halogen, aliphatic, alkyl, —C(O)$OR^{25}$ or —C(O)$NR^{25}R^{26}$, wherein $R^{25}$ and $R^{26}$ each independently is hydrogen or aliphatic, alkyl. Exemplary $L^2$ groups are provided below. In any of the embodiments disclosed herein for $L^2$, the $L^2$ group can be halogenated. In some embodiments, the $L^2$ group may be fluorinated.

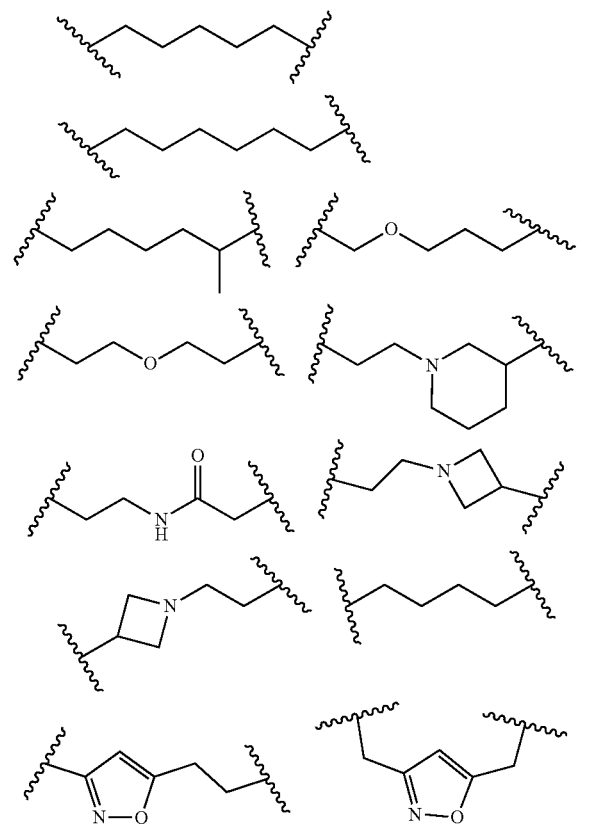

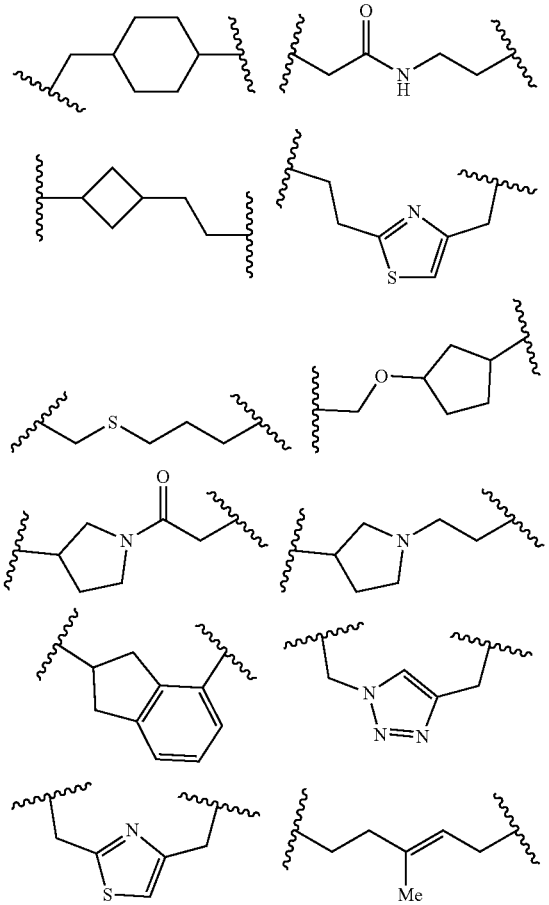

Z is selected from $R^1L^1C(O)$— or a carboxyl bioisostere, wherein $L^1$ is a bond or —$NR^{30}$—, and $R^1$ is hydrogen, aliphatic, —OR'—$NR^{1A}R^{1B}$, —C(O)$R^{1A}$, —S(O)$_2R^{1A}$, —C(O)$OR^{1A}$, —S(O)$_2NR^{1A}R^{1B}$ or —C(O)$NR^{1A}R^{1B}$, wherein $R^{1A}$, $R^{1B}$ each independently is hydrogen or aliphatic, alkyl, and $R^{30}$ is selected from H or aliphatic, aryl, or cycloaliphatic.

In some embodiments, Z is a carboxyl bioisostere, and in certain embodiments, Z is selected from

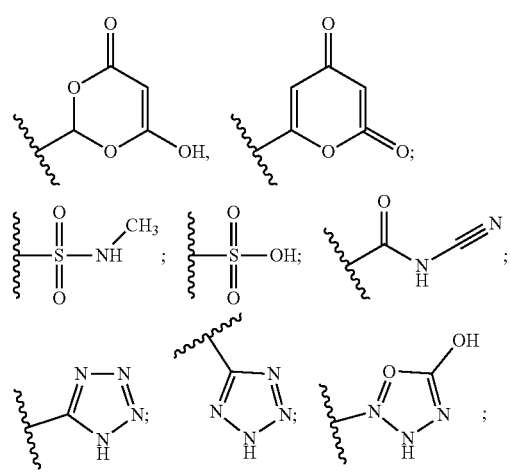

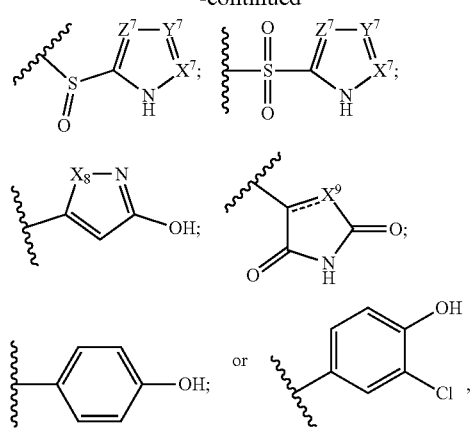
where $X^7$, $Y^7$, and $Z^7$ each independently is selected from N, $CH_2$ or CO; $X^8$ is selected from O, S or NMe; and $X^9$ is selected from O, N, NH, S, CH or $CH_2$.
In an independent embodiment, Z is selected from
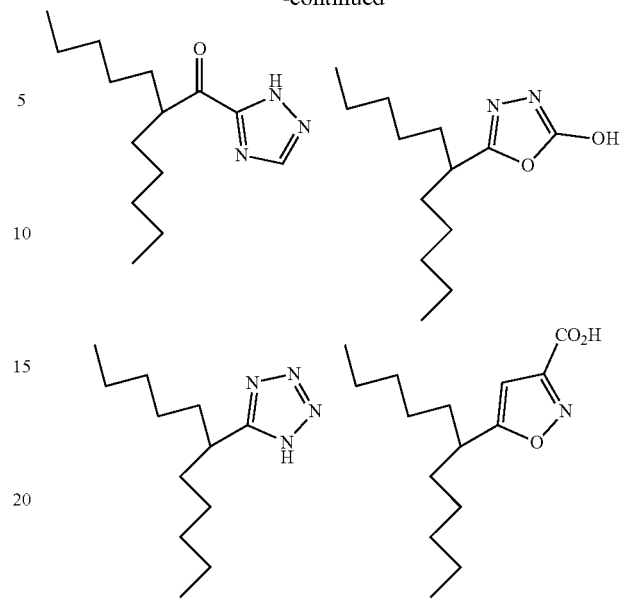
In some embodiments, $L^5$ is
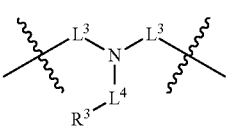
leading to compounds having a Formula 1A
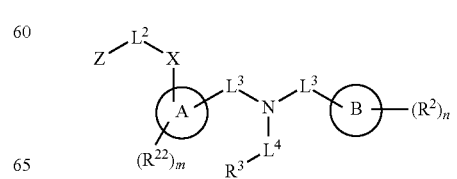
Formula 1A wherein $L^3$, $L^4$ and $R^3$ are as defined above with respect to Formula 1.

With respect to ring A, in some embodiments of Formula 1A, the $L^3$ group and the X-$L^2$-Z group are positioned ortho to each other, leading to compounds having Formula 2

Formula 2

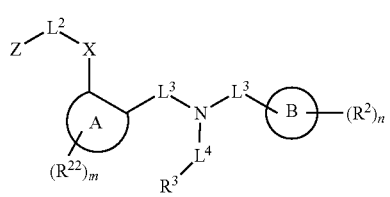

wherein rings A and B, X, $L^2$, Z, $R^2$, $R^{22}$, m, n, $L^3$, $L^4$ and $R^3$ are as recited above.

Also with reference to Formulas 1A and/or 2, the -$L^3$N($L^4R^3$)$L^3$- group may have any of the following formulas, which may be incorporated in any of the general formulas provided herein.

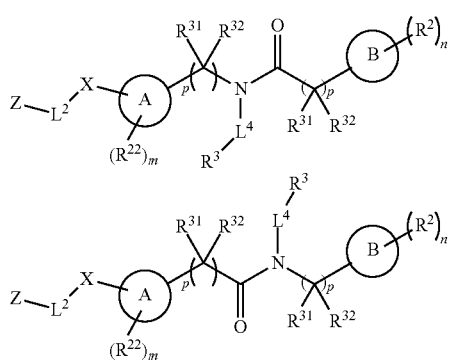

With reference to these embodiments, each $R^{31}$ and $R^{32}$ is independently selected from hydrogen, deuterium, aliphatic, heteroaliphatic, or any one of $R^{31}$ and $R^{32}$ may be joined with $R^3$ to form a ring, such as a four-, five-, six-, or seven-membered ring system, which may be saturated or unsaturated, or may be joined with an atom of ring B to form a fused ring system, such as a 5-6 fused ring system, a 6-6 fused ring system, or a 6-5 fused ring system; and each p independently is 0, 1, 2, 3, 4, or 5.

In particular embodiments of formulas 1A and/or 2, the -$L^3$N($L^4R^3$)$L^3$- group has one of the following formulas, which may be incorporated in any of formulas 1A to 20 provided herein

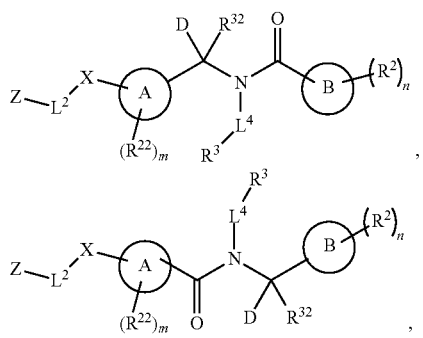

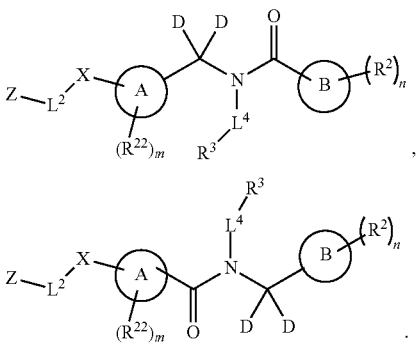

In other particular embodiments of Formulas 1A and/or 2, the -$L^3$N($L^4R^3$)$L^3$- group has one of the following formulas, which may be incorporated in any of the formulas provided herein

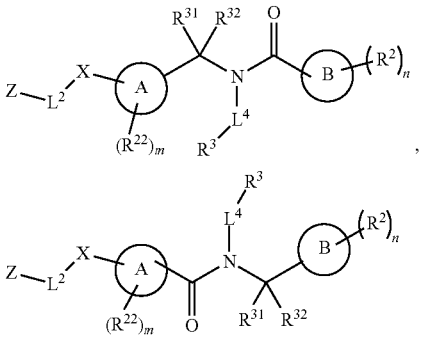

wherein $R^{31}$ and $R^{32}$ are as defined above, and the carbon in the -$L^4R^3$ moiety that is adjacent to the nitrogen is mono- or di-substituted with deuterium. In certain examples, the $L^4R^3$ group is selected from

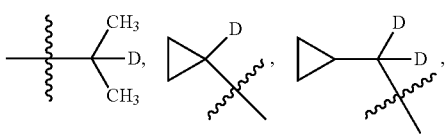

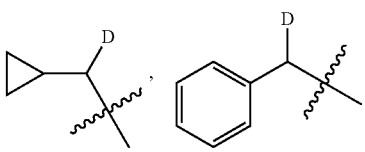

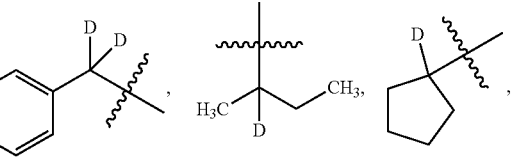

-continued

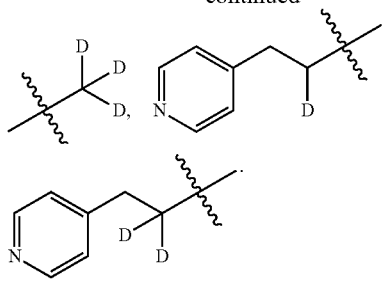

In some embodiments, disclosed compounds may have a Formula 3 or Formula 4, illustrated below.

Formula 3
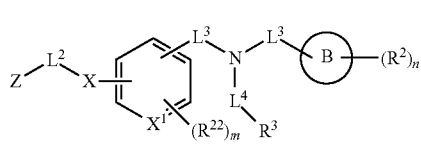

Formula 4
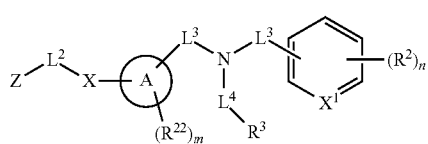

With reference to either one of Formulas 3 or 4, X, $L^2$, Z, $L^3$, ring B, ring A, $R^2$, $R^{22}$, m and n are as provided above. $X^1$ can be selected from carbon, nitrogen, or N-oxide.

In some embodiments, disclosed compounds may have a Formula 5 or Formula 6, illustrated below.

Formula 5
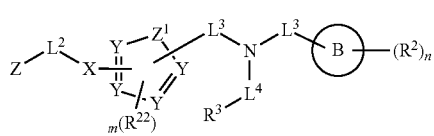

Formula 6
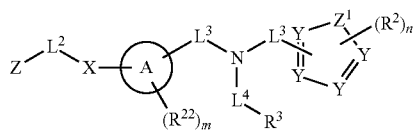

With reference to either one of Formulas 5 or 6, X, $L^2$, Z, $L^3$, ring B, ring A, $R^2$, $R^{22}$, m and n are as provided above; $Z^1$ may be selected from carbon, oxygen, sulfur, or $NR^{30}$; and each Y independently is carbon or nitrogen.

In some embodiments, disclosed compounds may have a Formula 7, illustrated below.

Formula 7
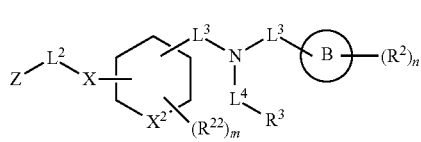

With reference to Formula 7, X, $L^2$, Z, $L^3$, ring B, ring A, $R^2$, $R^{22}$, m and n are as provided above; $X^2$ may be a bond, carbon, oxygen, sulfur, or $NR^{30}$.

In some embodiments, disclosed compounds may have a Formula 8, illustrated below.

Formula 8
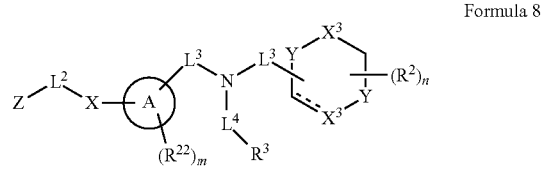

With reference to Formula 8, X, $L^2$, Z, $L^3$, ring B, ring A, $R^2$, $R^{22}$, m and n are as provided above; each $X^3$ independently may be nitrogen, carbon, $NR^{30}$, or oxo; each Y independently may be carbon or $NR^{30}$.

In yet other embodiments, disclosed compounds may have any one of Formulas 9-17, illustrated below.

Formula 9
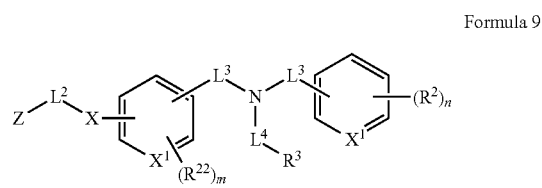

Formula 10
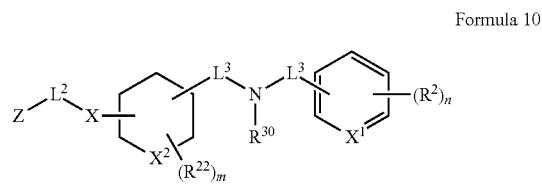

Formula 11
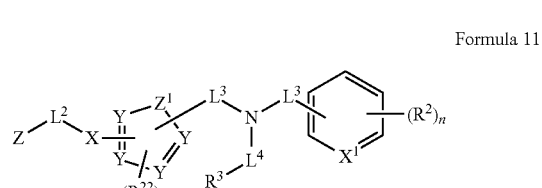

Formula 12
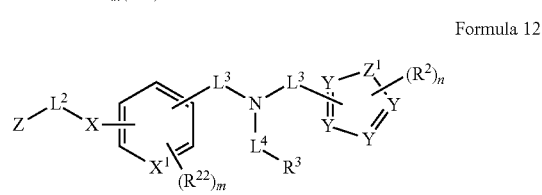

Formula 13
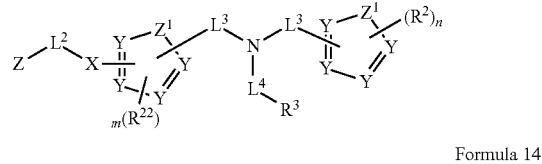

Formula 14
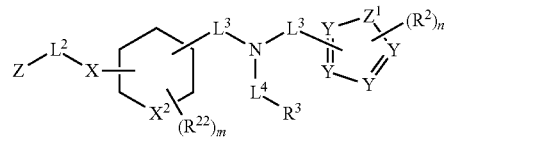

Formula 15

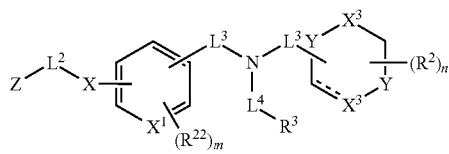

Formula 16

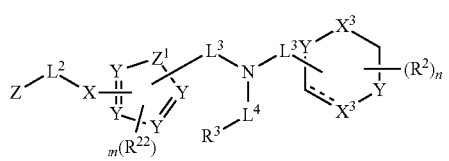

Formula 17

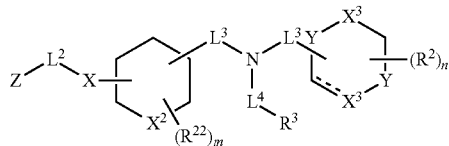

where each X, $X^1$, $X^2$, $X^3$, Z, $Z^1$, $L^2$, $L^3$, $L^4$, $R^2$, $R^3$, $R^{22}$, $R^{30}$, m and n are as previously defined, and Y is carbon or nitrogen for Formulas 12-14, and is carbon or $NR^{30}$ for Formulas 15-17.

In some embodiments, rings A and B are both phenyl, leading to compounds having Formula 18:

Formula 18

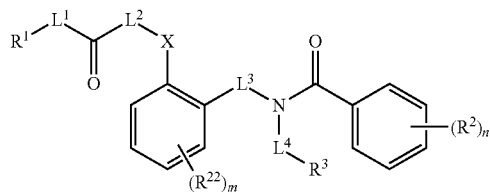

In certain embodiments, disclosed compounds can have Formula 19, illustrated below.

Formula 19

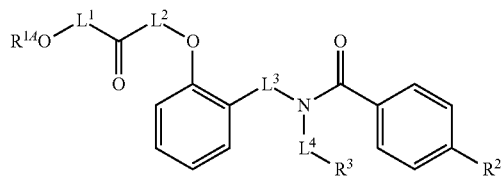

In certain embodiments of Formulas 18 and 19, $L^3$ is -CHD- or -CD$_2$-.

In some examples of compounds, rings A and B are six-membered rings, $R^1$ is —OR$^{14}$ and $R^2$ is para to the amide, leading to compounds with Formula 20:

Formula 20

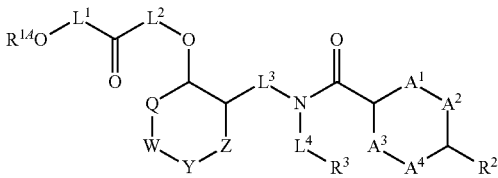

With respect to Formula 20, $R^{14}$ is hydrogen, aliphatic, or alkyl, $R^2$ is halogen, aryl or heteroaryl, $R^3$ is aliphatic, alkyl, heteroalkyl, cycloalkyl, heterocycloalkyl, aryl, heteroaryl, —NR$^{3A}$R$^{3B}$, —C(O)OR$^{3A}$, —S(O)$_2$NR$^{3A}$R$^{3B}$, or —C(O) NR$^{3A}$R$^{3B}$. R$^{3A}$ and R$^{3B}$ are independently hydrogen, aliphatic or alkyl. $L^1$ is a bond or —NR$^{30}$—, and $L^2$, $L^3$ and $L^4$ are independently a bond, alkylene, heteroalkylene, cycloalkylene, heterocycloalkylene or —CR$^9$R$^{10}$—, and at least one of $L^3$, $L^4$ and $R^3$ comprises at least one deuterium. $R^9$ and $R^{10}$ are independently hydrogen, D, F, aliphatic, alkyl or —C(O)R$^7$, wherein $R^7$ may be hydrogen, halogen, =O (oxo), —CF$_3$, —CN, —CCl$_3$, —COOH, —CH$_2$COOH, —OH, —SH, —SO$_2$Cl, —SO$_3$H, —SO$_2$NH$_2$, —NO$_2$, —NH$_2$, —NHNH$_2$, —NHC(O)NHNH$_2$, Q, W, Y, and Z are bonded by a single or double bond such that the resulting ring is aromatic. Q, W, Y, and Z are independently selected from CH, —CR$^{22}$ or N. $R^{22}$ is selected from D, F, Cl, aliphatic or alkyl, -CD$_3$, —CF$_3$, —OH, —OCH$_3$, —OCD$_3$ or —OCF$_3$. $A_1$, $A_2$, $A_3$, and $A_4$ are bonded by a single or double bond such that the resulting ring is aromatic. $A_1$, $A_2$, $A_3$, and $A_4$ are independently selected from —CR$^{27}$ or N. $R^{27}$ is selected from H, D, F, Cl, aliphatic or alkyl, -CD$_3$, —CF$_3$, —OH, —OCH$_3$, —OCD$_3$ or —OCF$_3$.

$R^{14}$ may be hydrogen or aliphatic, typically alkyl. In some embodiments, $R^{14}$ is $C_1$-$C_{20}$ (e.g., $C_1$-$C_6$) aliphatic or alkyl. In some embodiments, $R^{14}$ is $C_1$-$C_{10}$ aliphatic or alkyl. In some embodiments, $R^{14}$ is $C_2$ aliphatic or alkyl.

$R^3$ may be aliphatic, alkyl, cycloalkyl, heterocycloalkyl, aryl or heteroaryl. $R^3$ may be $C_1$-$C_{20}$ (e.g., $C_1$-$C_6$) aliphatic or alkyl, $C_3$-$C_8$ (e.g., $C_5$-$C_7$) cycloalkyl, 3 to 8-membered (e.g., 3 to 6-membered) heterocycloalkyl, $C_5$-$C_{10}$ (e.g., $C_5$-$C_6$) aryl, or 5 to 10-membered (e.g., 5 to 6-membered) heteroaryl. In some embodiments, $R^3$ is linear or branched $C_1$-$C_{20}$ (e.g., $C_1$-$C_6$) aliphatic or alkyl. In some embodiments, $R^3$ is linear aliphatic or alkyl. In other embodiments, $R^3$ is branched aliphatic or alkyl. In some embodiments, $R^3$ is $C_1$-$C_5$ aliphatic or alkyl. In other embodiments, $R^3$ is $C_4$ aliphatic or alkyl. In other embodiments, $R^3$ is $C_3$ aliphatic or alkyl. In some embodiments, $R^3$ is branched $C_1$-$C_5$ aliphatic or alkyl. In other embodiments, $R^3$ is branched $C_4$ aliphatic or alkyl. In other embodiments, $R^3$ is branched $C_3$ aliphatic or alkyl.

$R^3$ may be $C_3$-$C_8$ (e.g., $C_5$-$C_7$) cycloalkyl. In some embodiments, $R^3$ is 3- to 5-membered (i.e. $C_3$-$C_5$) cycloalkyl. In some embodiments, $R^3$ is 3-membered (i.e. $C_3$) cycloalkyl. In some embodiments, $R^3$ is 5-membered (i.e. $C_5$) cycloalkyl.

In other embodiments, $R^3$ is 3- to 8-membered (e.g., 3- to 6-membered) heterocycloalkyl. In some embodiments, $R^3$ is 5- to 6-membered heterocycloalkyl. In some embodiments, $R^3$ is 5-membered heterocycloalkyl. In other embodiments, $R^3$ is 6-membered heterocycloalkyl.

$R^3$ may be $C_5$-$C_{10}$ (e.g., $C_5$-$C_6$) aryl or 5- to 10-membered (e.g., 5- to 6-membered) heteroaryl. In some embodiments, $R^3$ is 5- to 6-membered aryl. In some embodiments, $R^3$ is 5-membered aryl. In other embodiments, $R^3$ is 6-membered aryl. Thus, in some embodiments, $R^3$ is phenyl. In some embodiments, $R^3$ is 5- to 6-membered heteroaryl. In some embodiments, $R^3$ is 5-membered heteroaryl. In other embodiments, $R^3$ is 6-membered heteroaryl.

$L^1$, $L^2$, $L^3$ and $L^4$ may be the same or different and may each independently be a bond, —$NR^{30}$—, —S(O)—, —S(O)$_2$NH—, —NHS(O)$_2$—, —C(O)O—, —OC(O)—C(O)—, —C(O)NH—, —NH—, —NHC(O)—, —O—, —S—, alkylene, heteroalkylene, cycloalkylene, heterocycloalkylene, arylene, or heteroarylene, and at least one of $L^3$ and $L^4$ comprises at least one deuterium. In some embodiments, $L^1$, $L^2$, $L^3$ and $L^4$ are independently a bond, —C(O)O—, —OC(O)—C(O)—, —C(O)NH—, —NH—, —NHC(O)—, —O—, —S—, alkylene, heteroalkylene, cycloalkylene, heterocykloalkylene, arylene, or heteroarylene.

As described above, $L^2$, $L^3$ and $L^4$ may be independently a bond or $C_1$-$C_{20}$ (e.g., $C_1$-$C_6$) alkylene. In some embodiments, $L^2$ is $C_1$-$C_5$ alkylene. In other embodiments, $L^2$ is $C_5$ alkylene. In some embodiments, $L^2$ is linear $C_5$ alkylene. In other embodiments, $L^2$ is branched $C_5$ alkylene.

As described above, $L^3$ and $L^4$ may be independently a bond or $C_1$-$C_{20}$ (e.g., $C_1$-$C_6$) alkylene. Thus, in some embodiments, $L^3$ and $L^4$ are independently a bond or $C_1$-$C_5$ alkylene. In some embodiments, $L^3$ is a bond or $C_1$-$C_5$ alkylene. In some embodiments, $L^3$ is methylene. In other embodiments, $L^4$ is a bond or $C_1$-$C_5$ alkylene. In some embodiments, $L^4$ is methylene, ethylene or propylene. In some embodiments, $L^4$ is methylene. In other embodiments, $L^4$ is ethylene. In other embodiments, $L^4$ is propylene.

In some embodiments of Formula 1, $L^5$ is

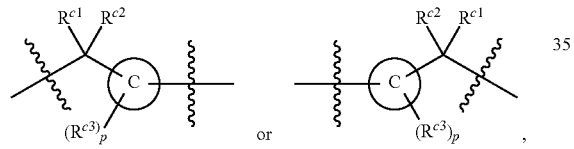

leading to compounds having Formulas 21 and 22 respectively

Formula 21
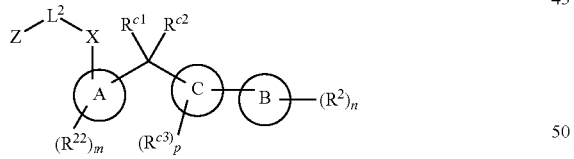

Formula 22
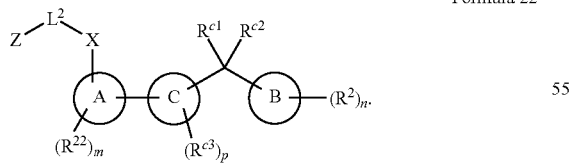

In some embodiments, of Formulas 21 and 22, $R^{c3}$ is alkyl or $CF_3$, and in certain embodiments, $R^{c3}$ is methyl. In some examples, p is 0 and in some other examples, p is 1.

Ring C may be a 5-membered heterocyclyl or a 5-membered heteroaryl, and in certain embodiments, ring C is a 5-membered heteroaryl. Ring C may be a nitrogen-containing heteroaryl or heterocyclyl, and in certain examples, ring C is selected from imidazole, pyrazole, pyrrole, triazole, tetrazole, thiazole, isothiazole, thiadiazole, oxazole, isoxazole, oxadiazole, imidazoline, pyrrolidine, thiazoline or oxazoline. In some embodiments, a point of connection to ring A or a point of connection to ring B, or both, is through one or more nitrogens in ring C. Exemplary

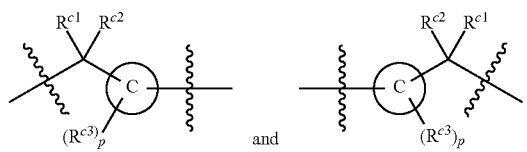

groups include, but are not limited to,

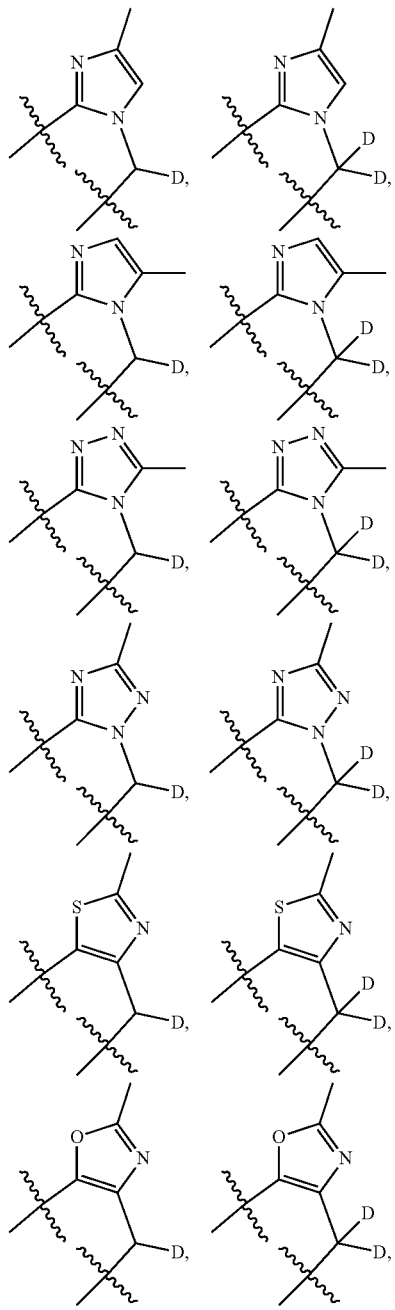

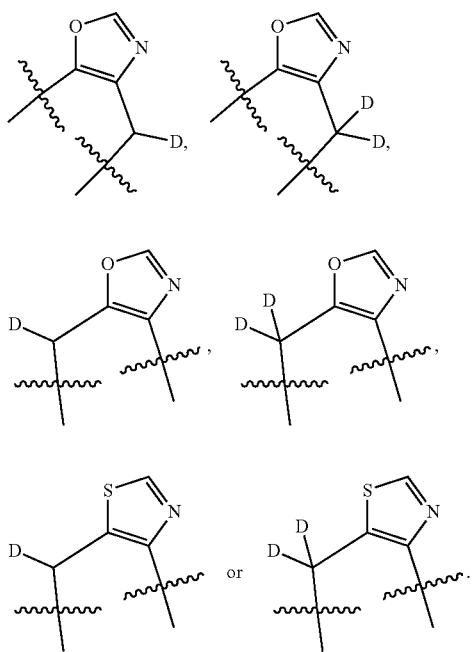

In certain embodiments of Formulas 21 and 22, the compounds have formulas selected from

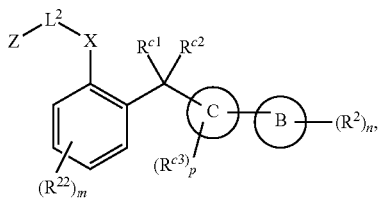

Formula 23

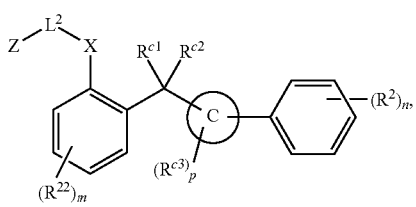

Formula 24

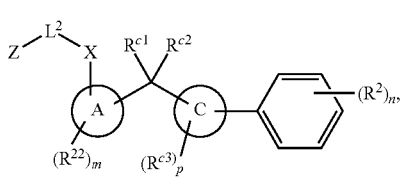

Formula 25

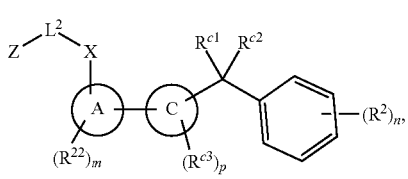

Formula 26

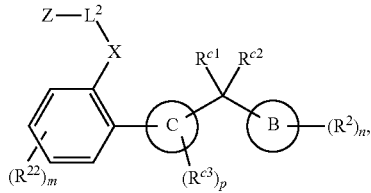

Formula 27

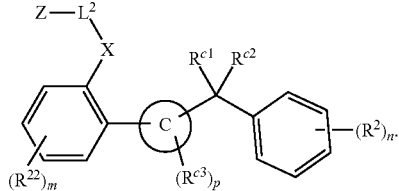

Formula 28

In certain particular embodiments of the any of the Formulas provided above, $R^{1A}$ is hydrogen, aliphatic, or alkyl. $R^2$ is halogen or furan, $R^3$, if present, is aliphatic, alkyl, heteroalkyl, cycloalkyl, heterocycloalkyl, aryl or heteroaryl. $L^1$ is a bond or —$NR^{30}$— and $L^2$, $L^3$ and $L^4$, if present, are independently a bond or alkylene, and at least one of $L^3$, $L^4$ and $R^3$, or at least one of $R^{c1}$ and $R^{c2}$, comprises at least one deuterium.

In some embodiments, the compound has the structure:

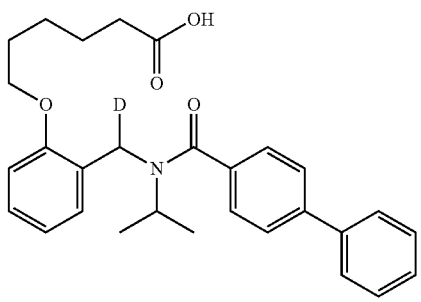

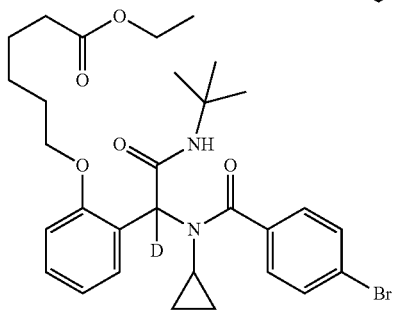

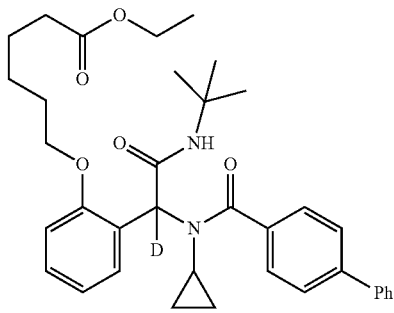

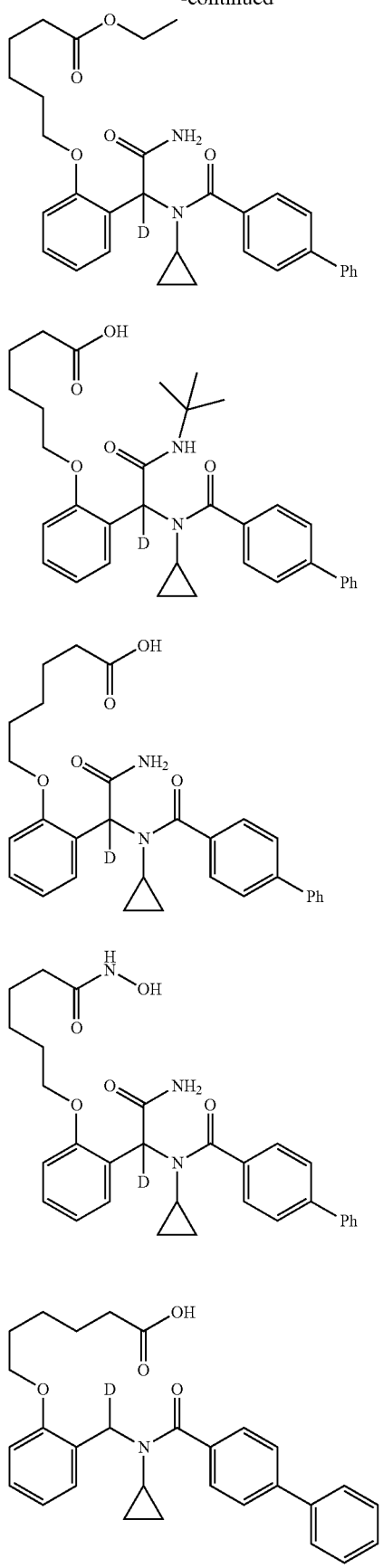

53
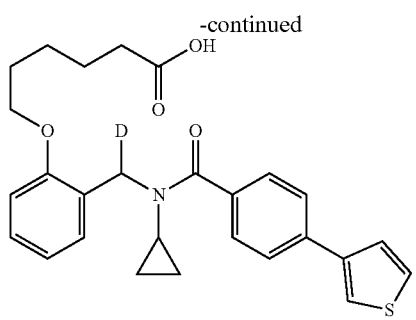
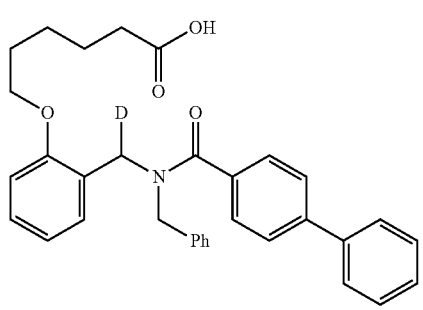
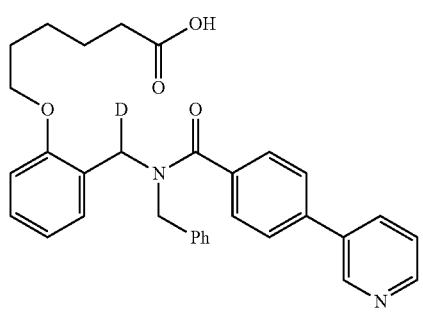
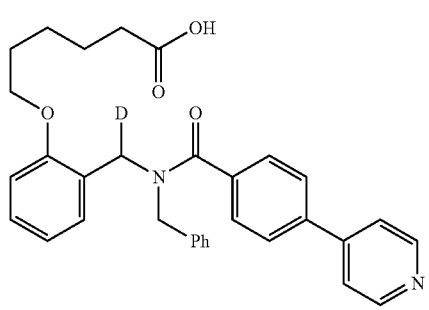
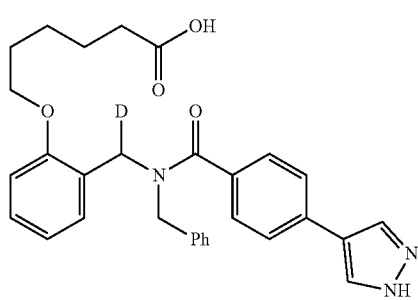
54
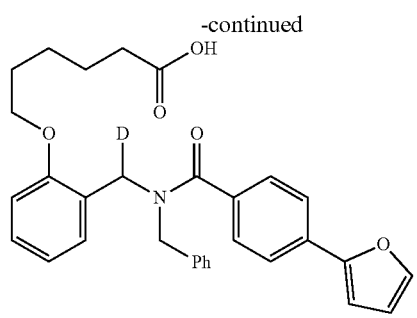
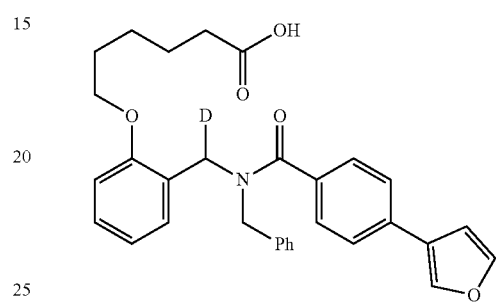
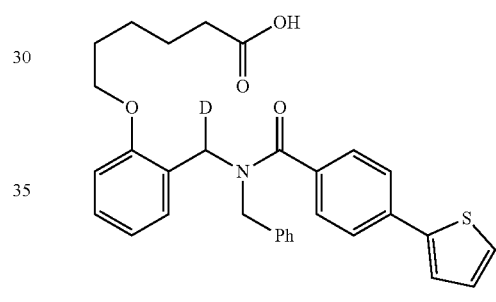
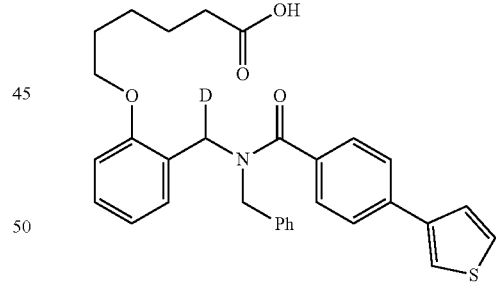
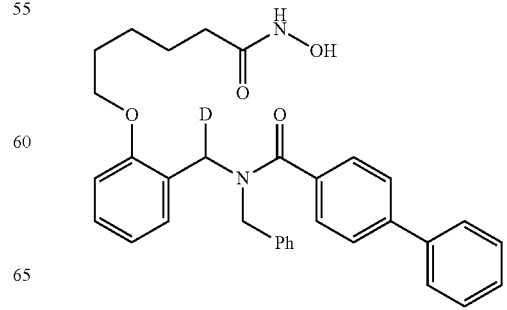

-continued
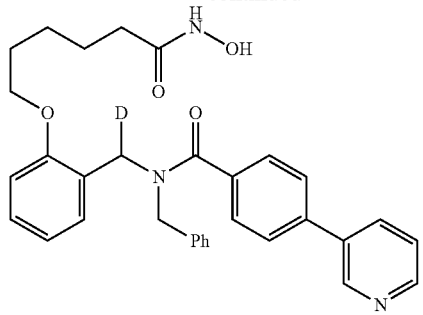
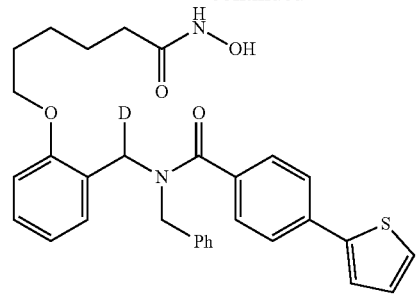
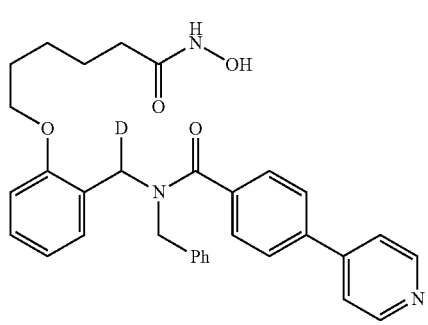
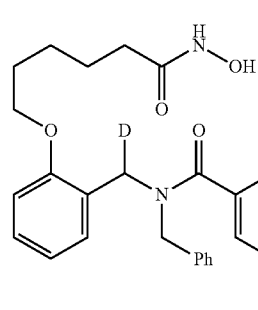
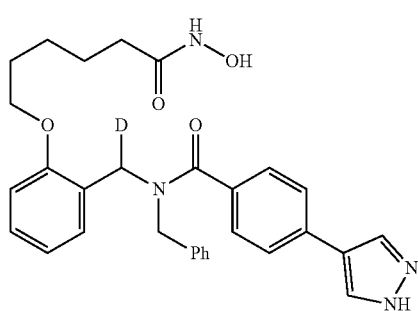
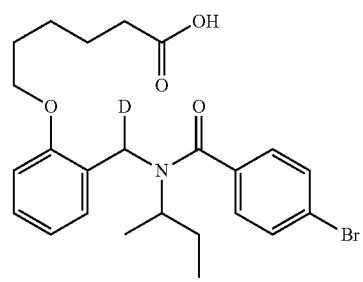
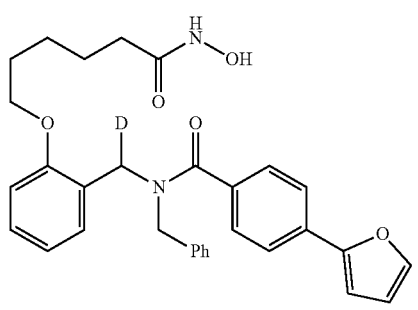
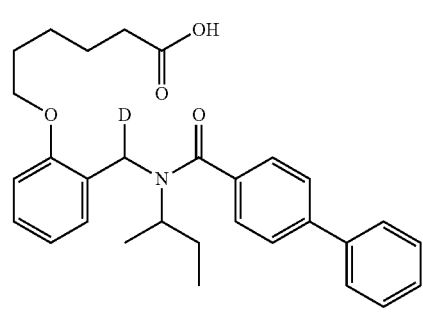
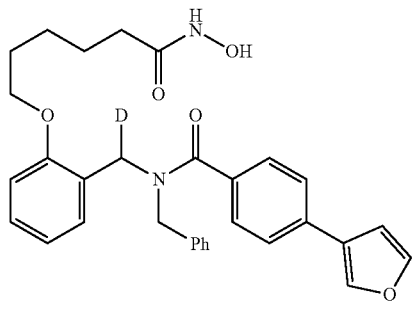
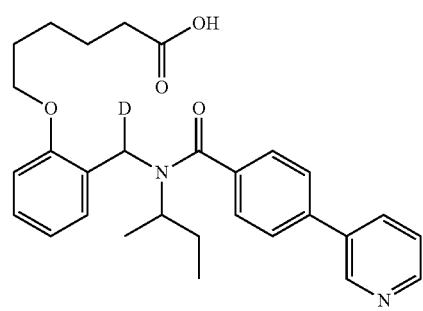

57
-continued
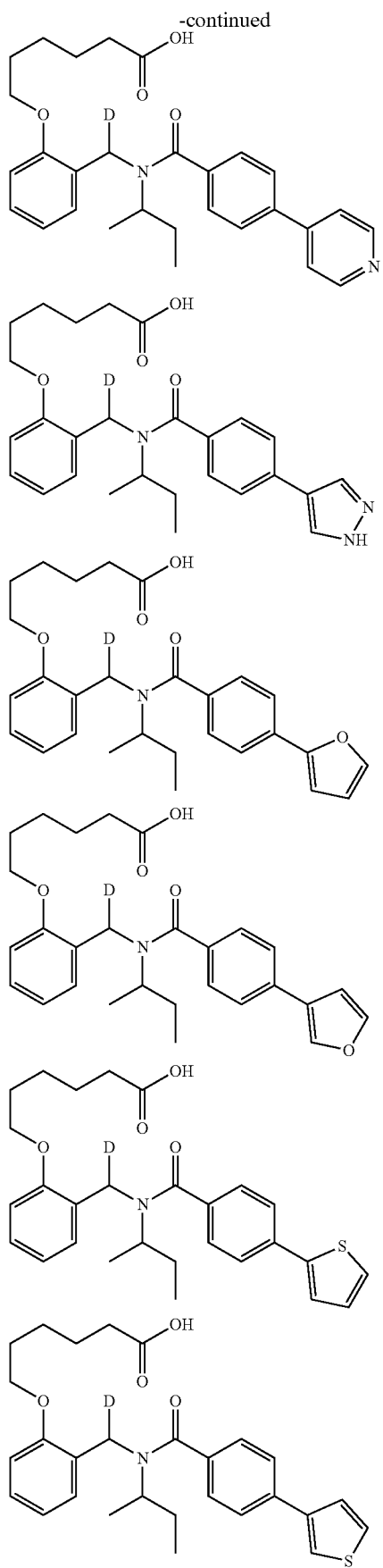
58
-continued
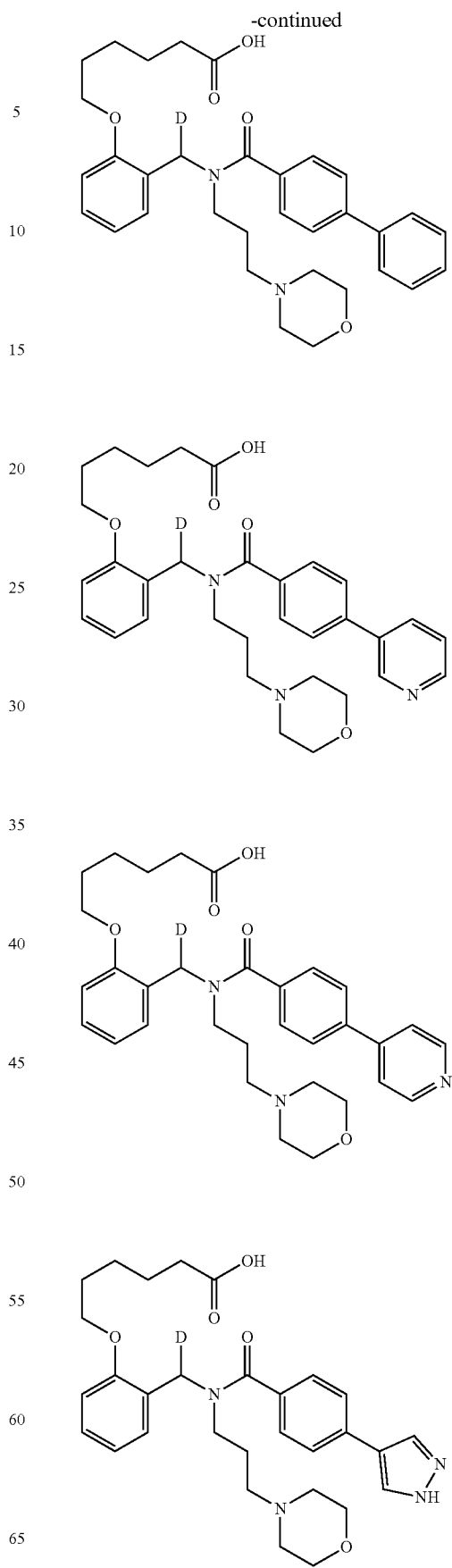

59
-continued
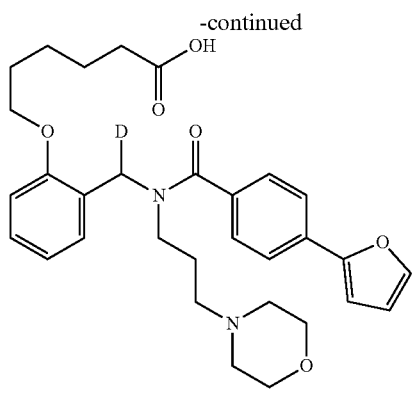
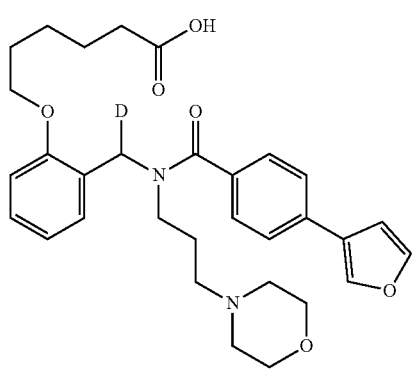
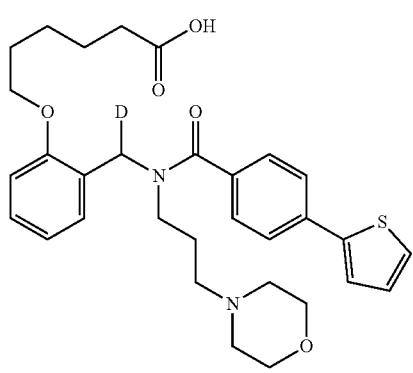
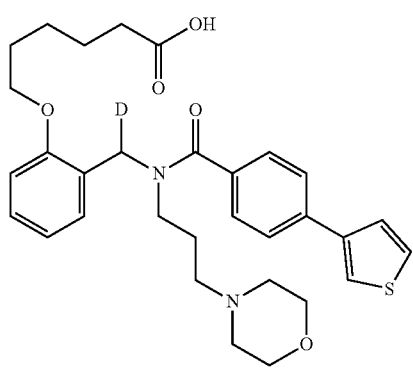
60
-continued
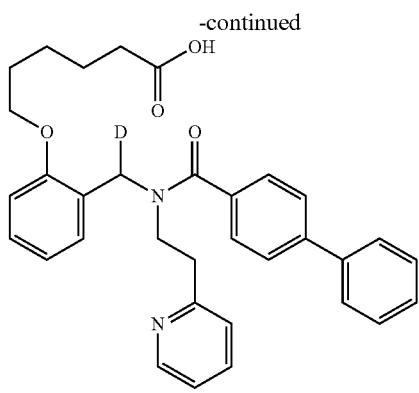
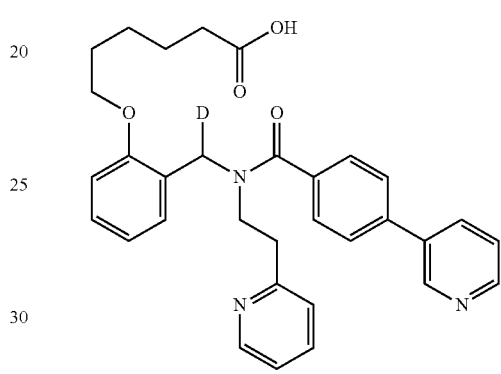
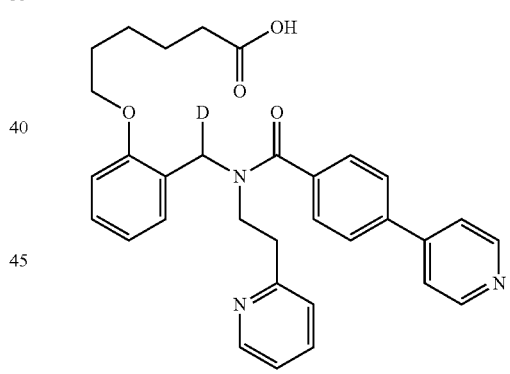
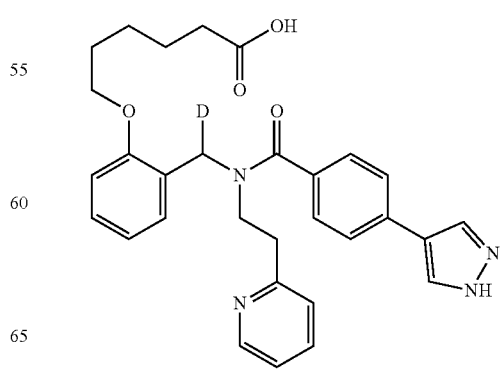

-continued
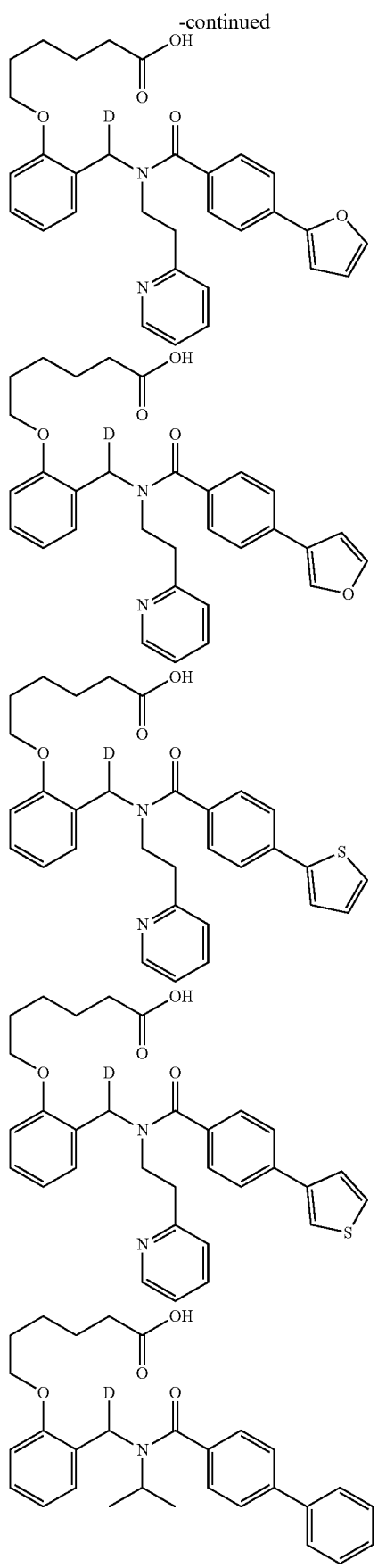
-continued
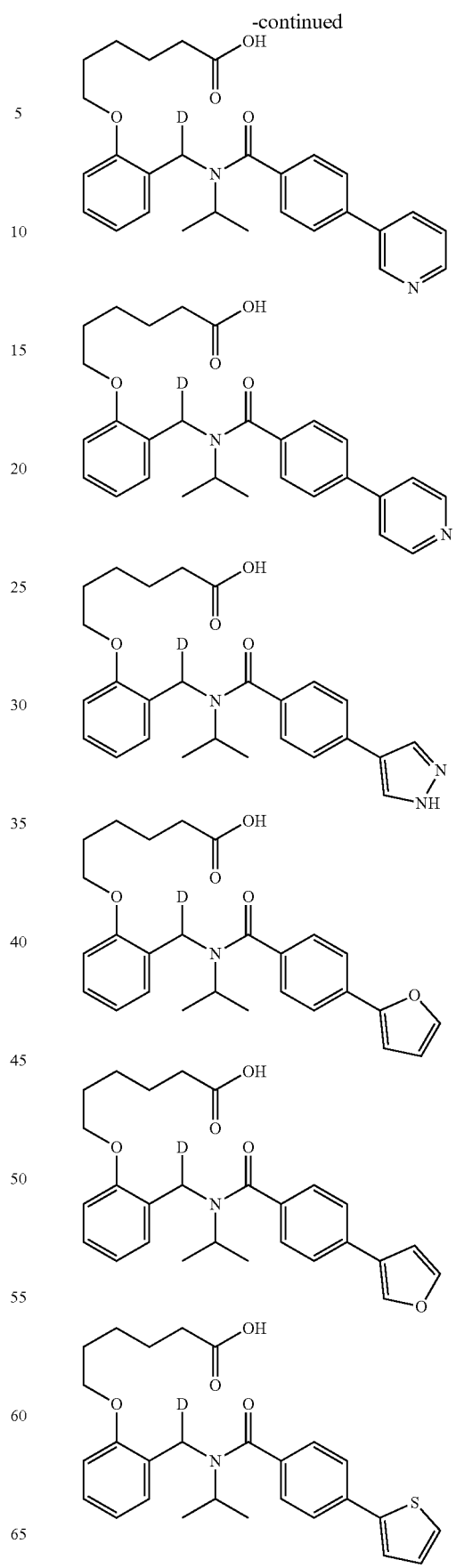

63
-continued
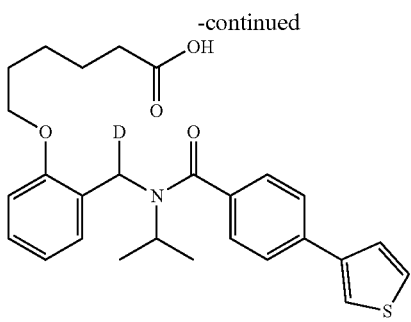
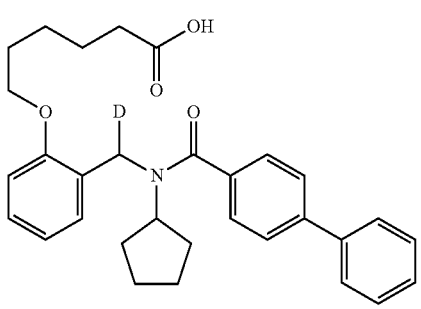
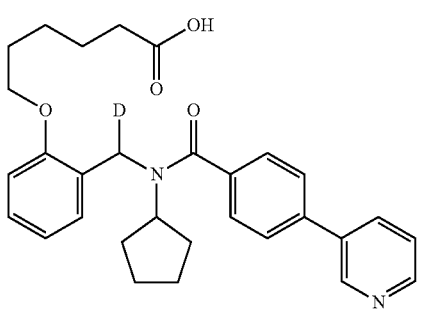
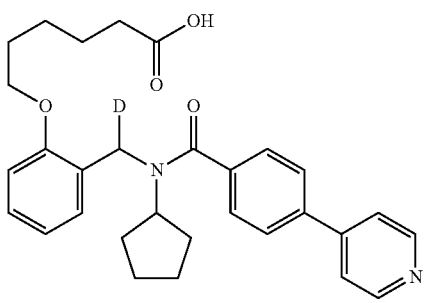
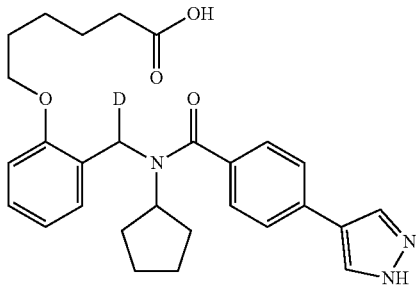
64
-continued
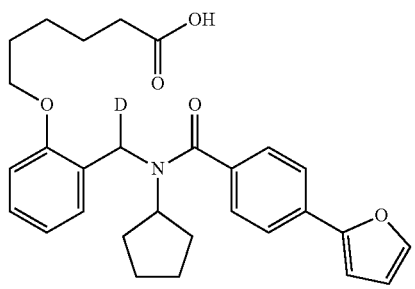
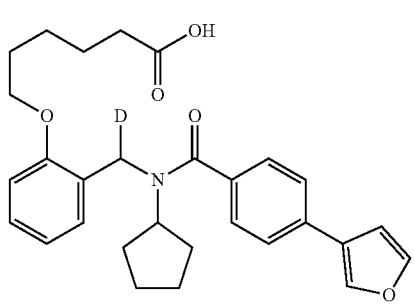
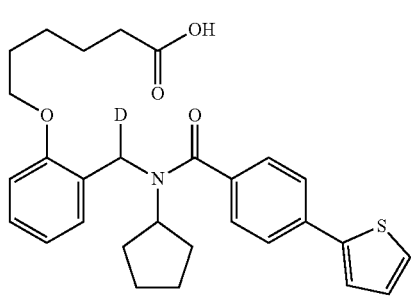
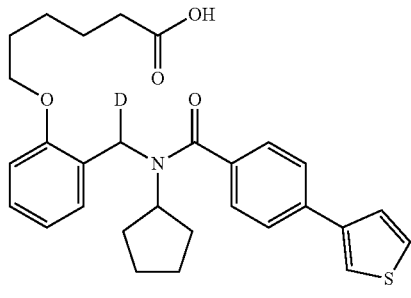
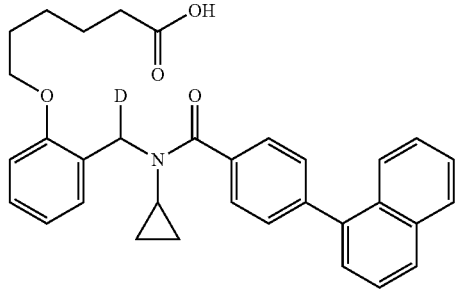

65
-continued
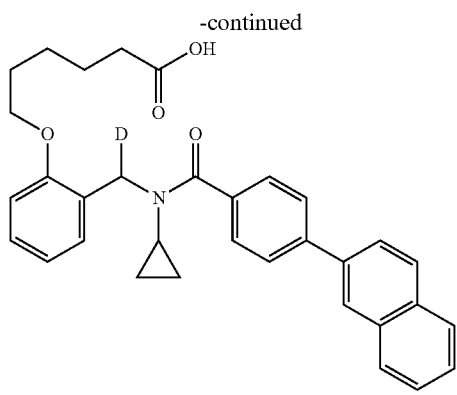
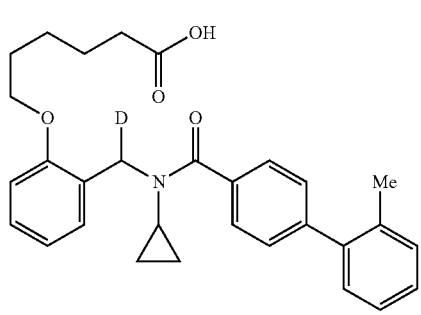
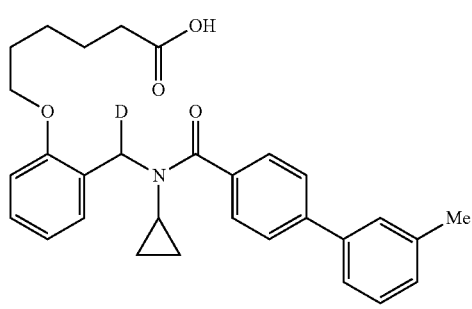
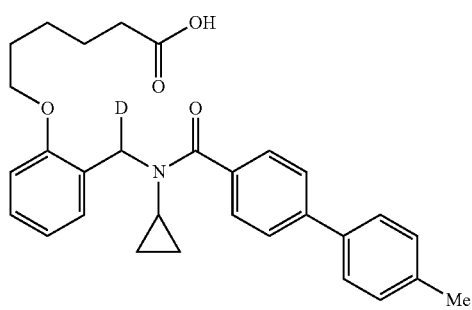
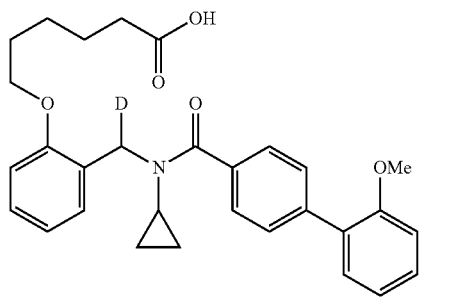
66
-continued
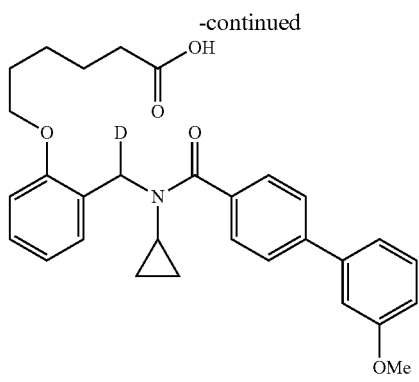
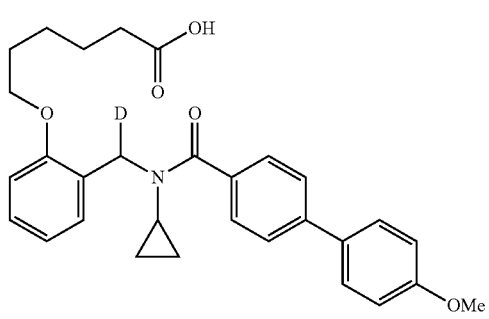
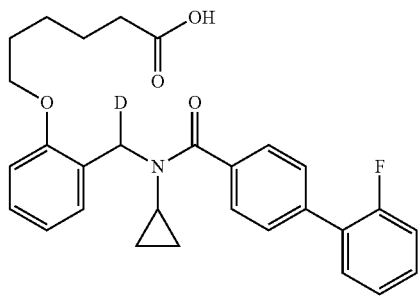
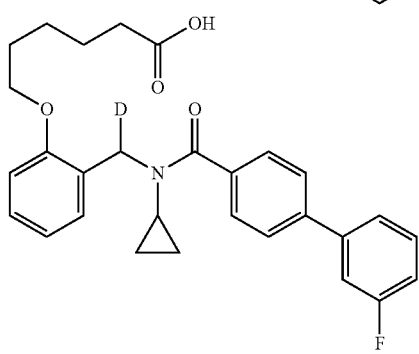
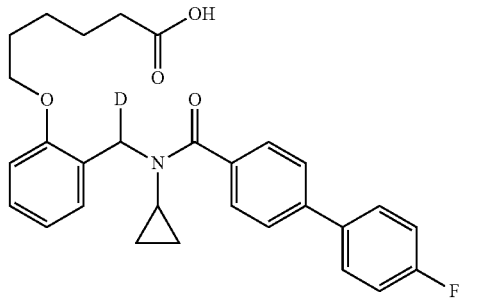

-continued
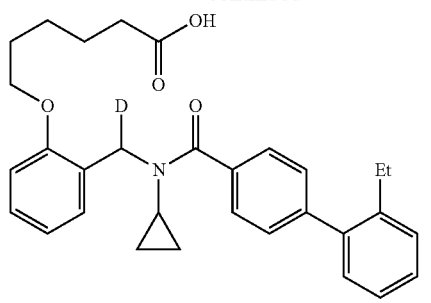
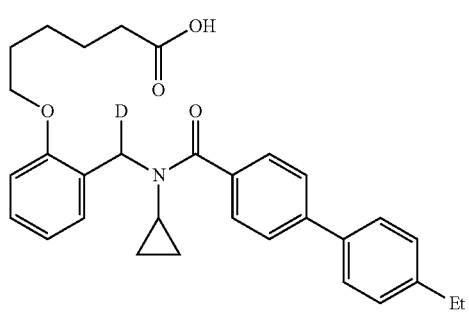
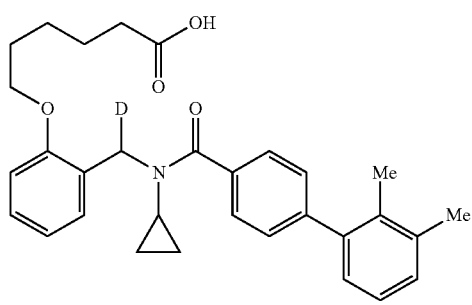
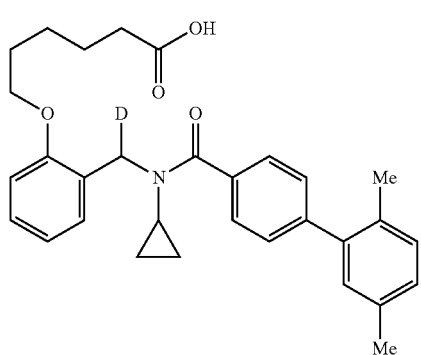
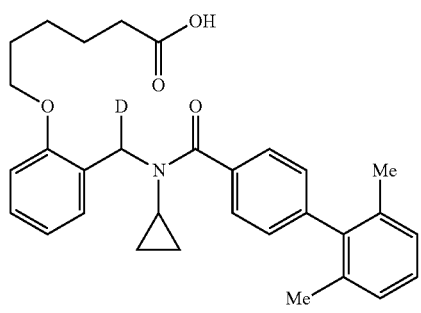
-continued
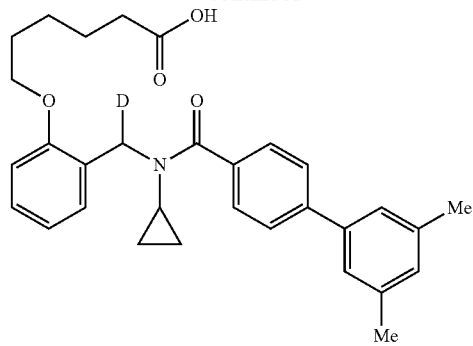
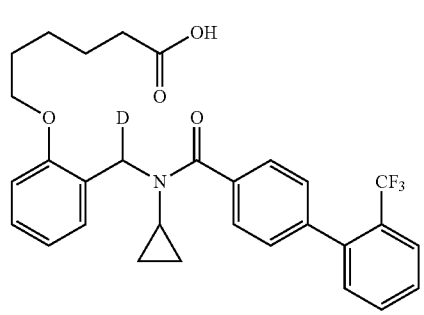
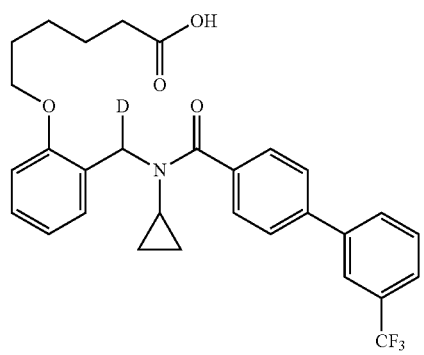
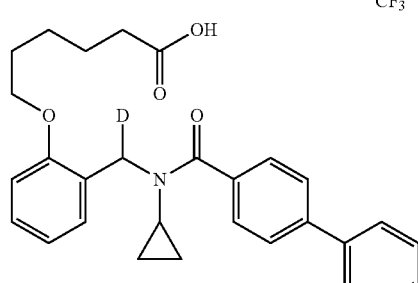
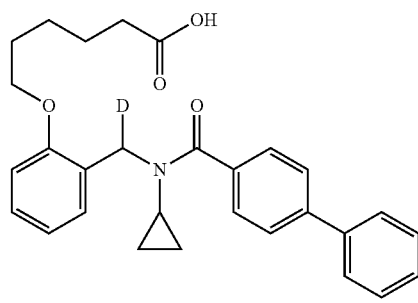

69
-continued
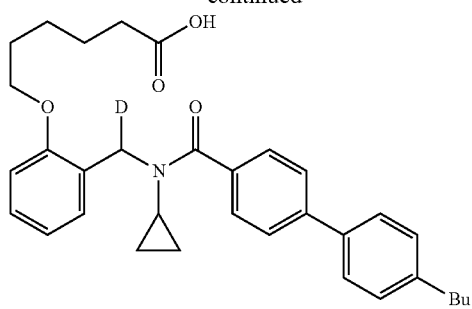
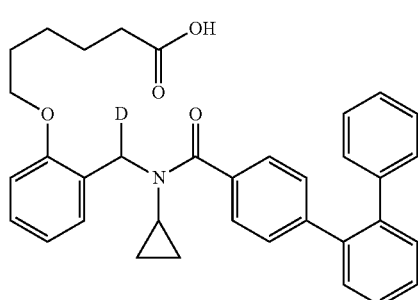
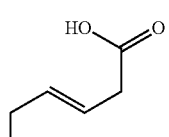
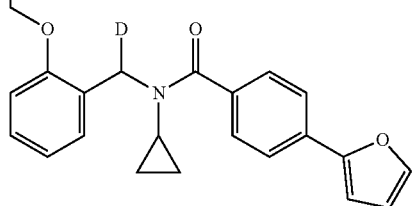
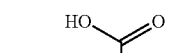
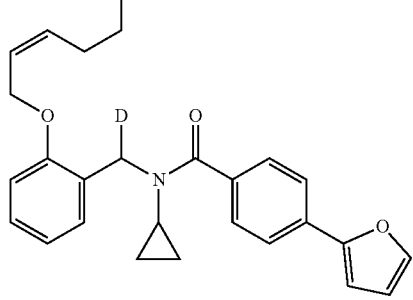
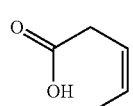
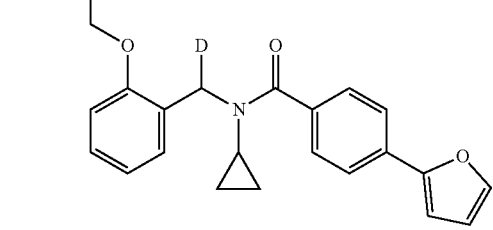
70
-continued
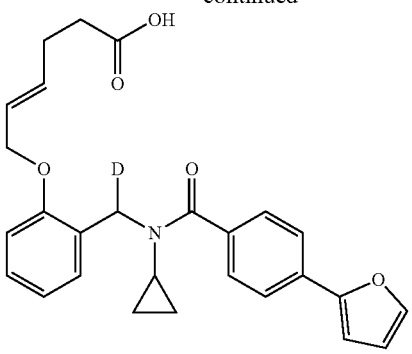
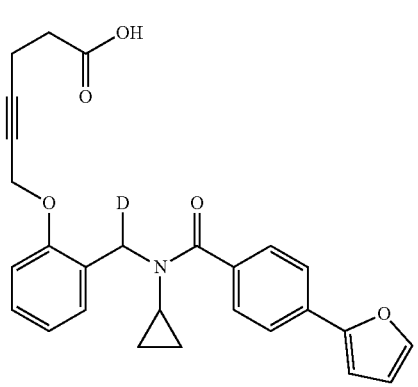
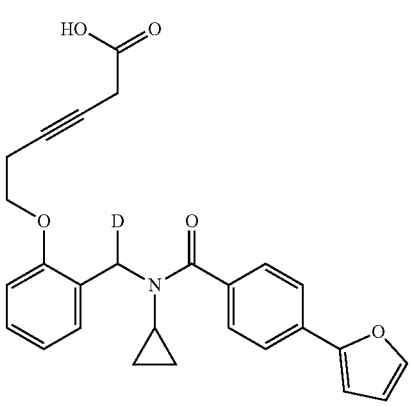
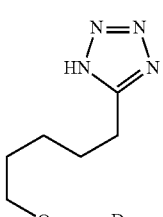
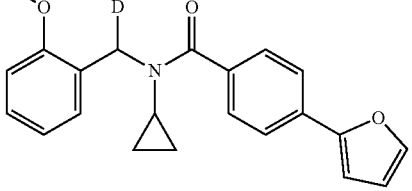

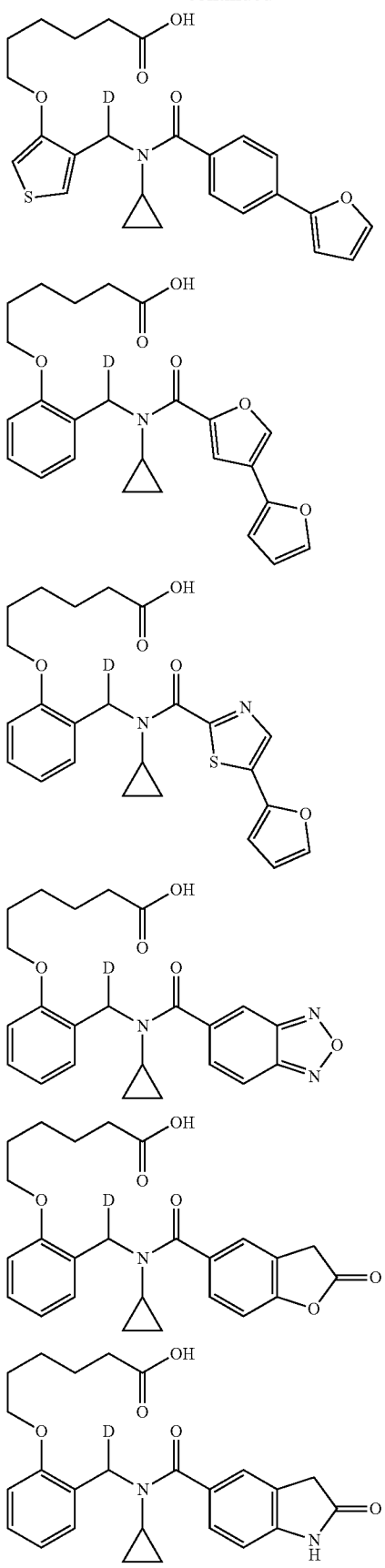
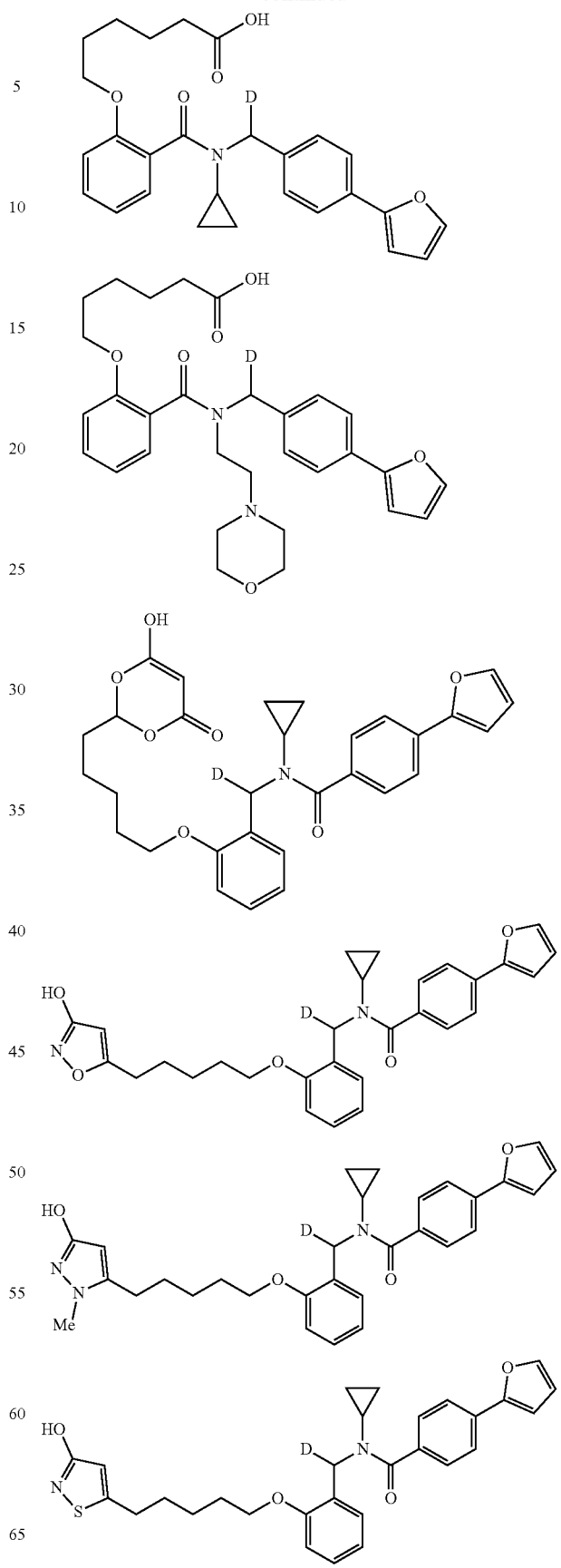

73
-continued
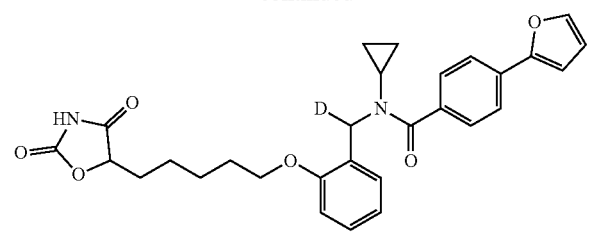
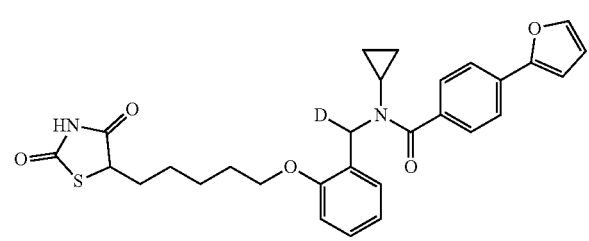
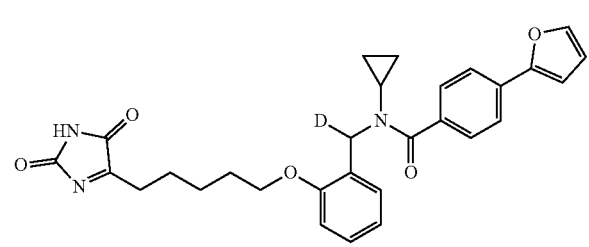
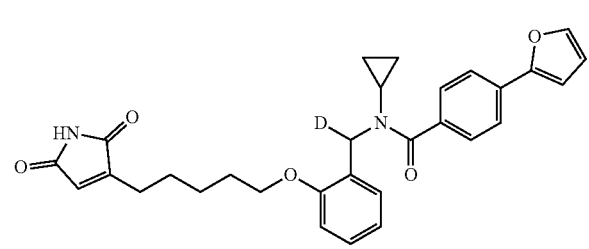
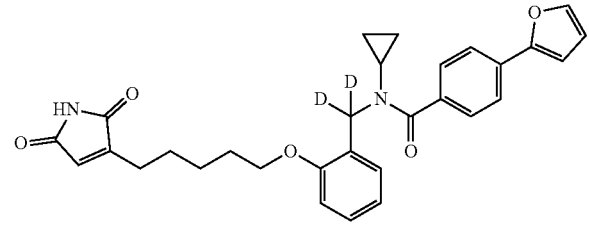
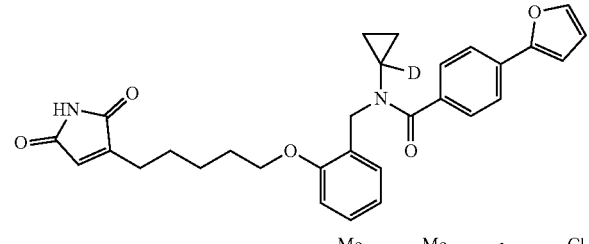
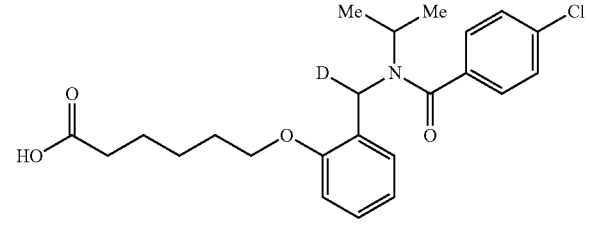
74
-continued
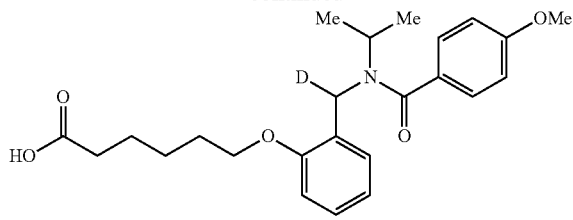
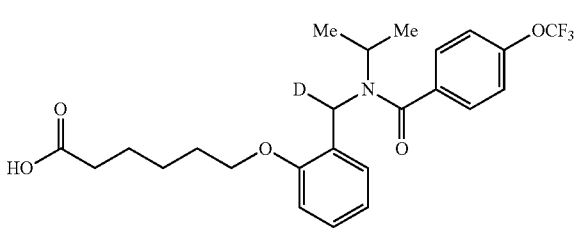
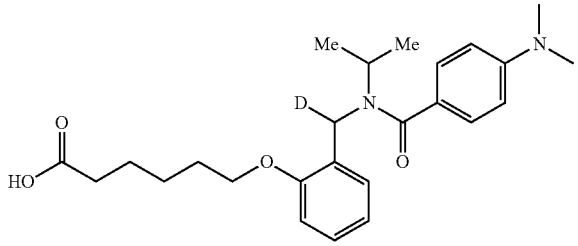
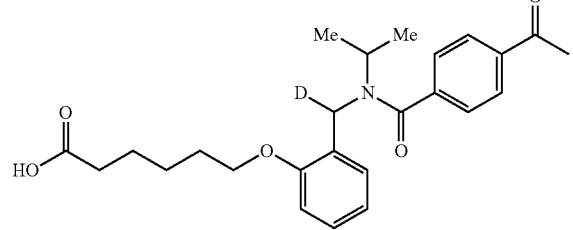
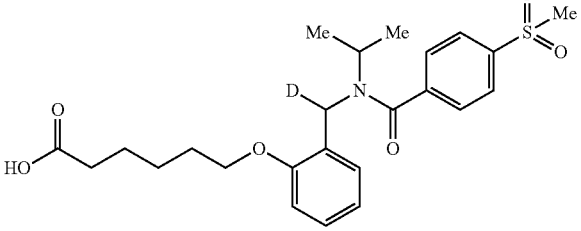
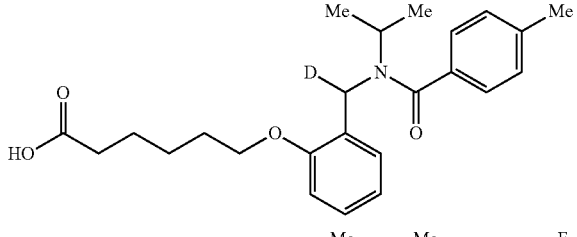
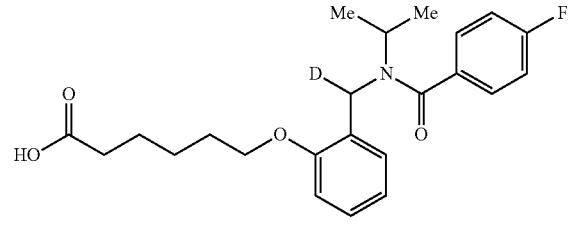

-continued
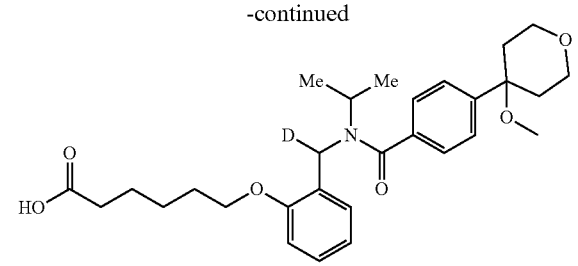
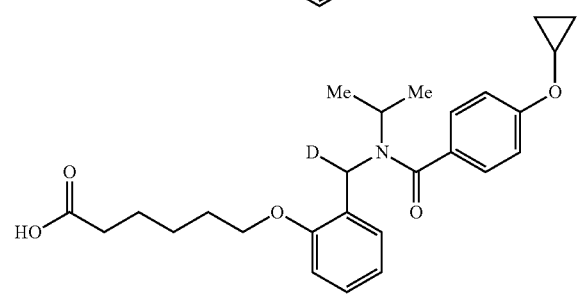
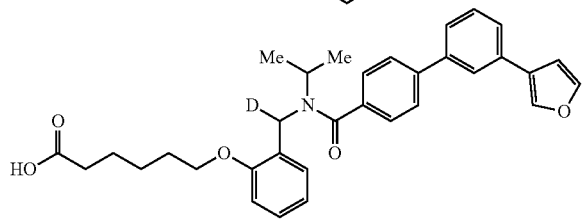
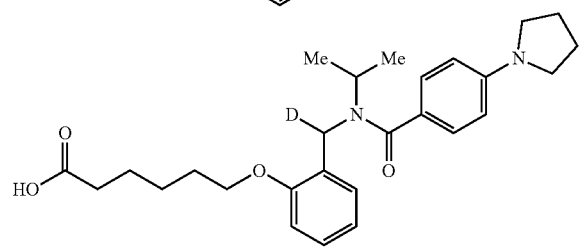
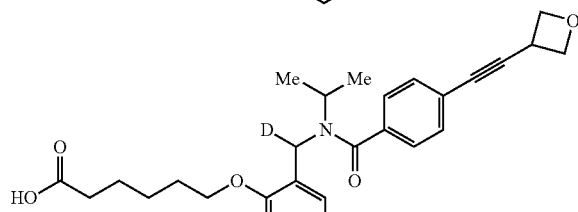
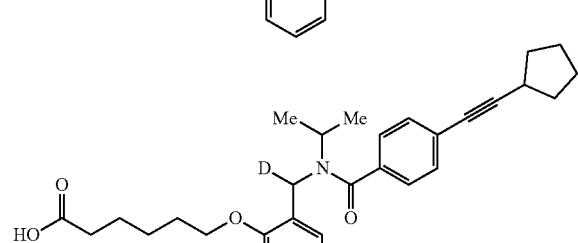
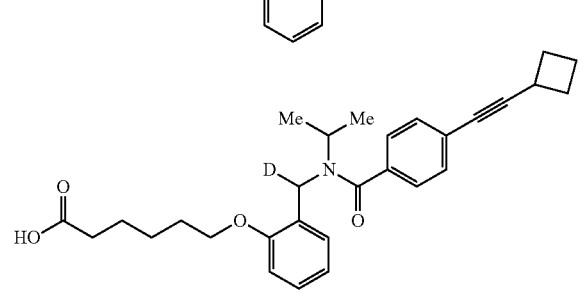
-continued
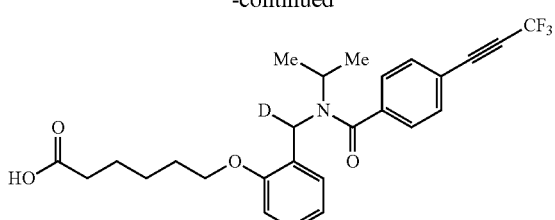
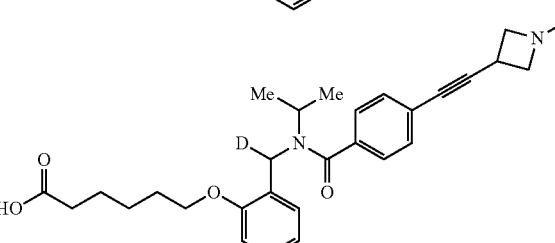
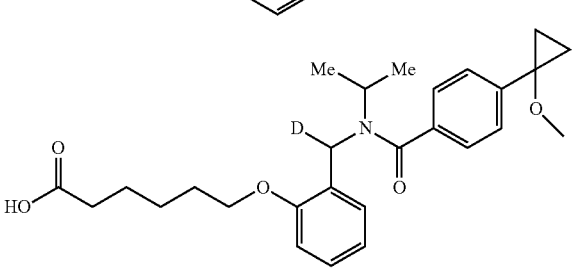
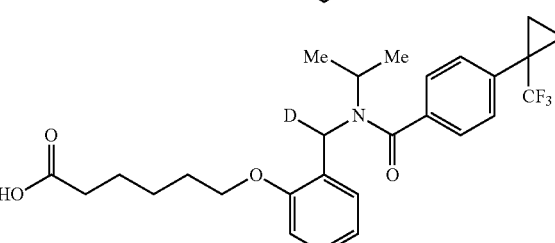
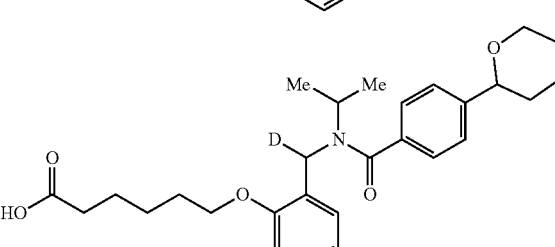
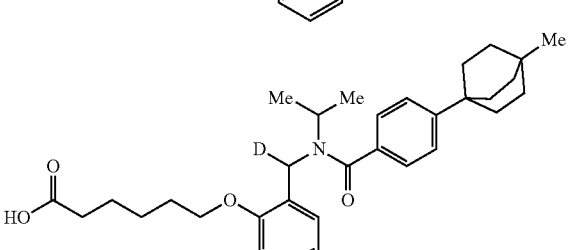
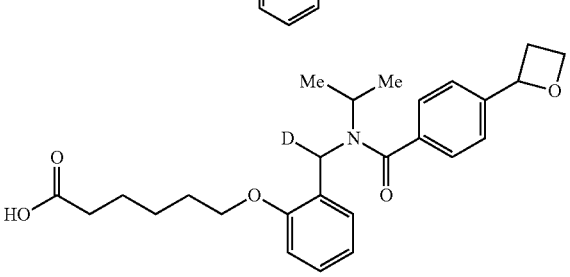

77
-continued
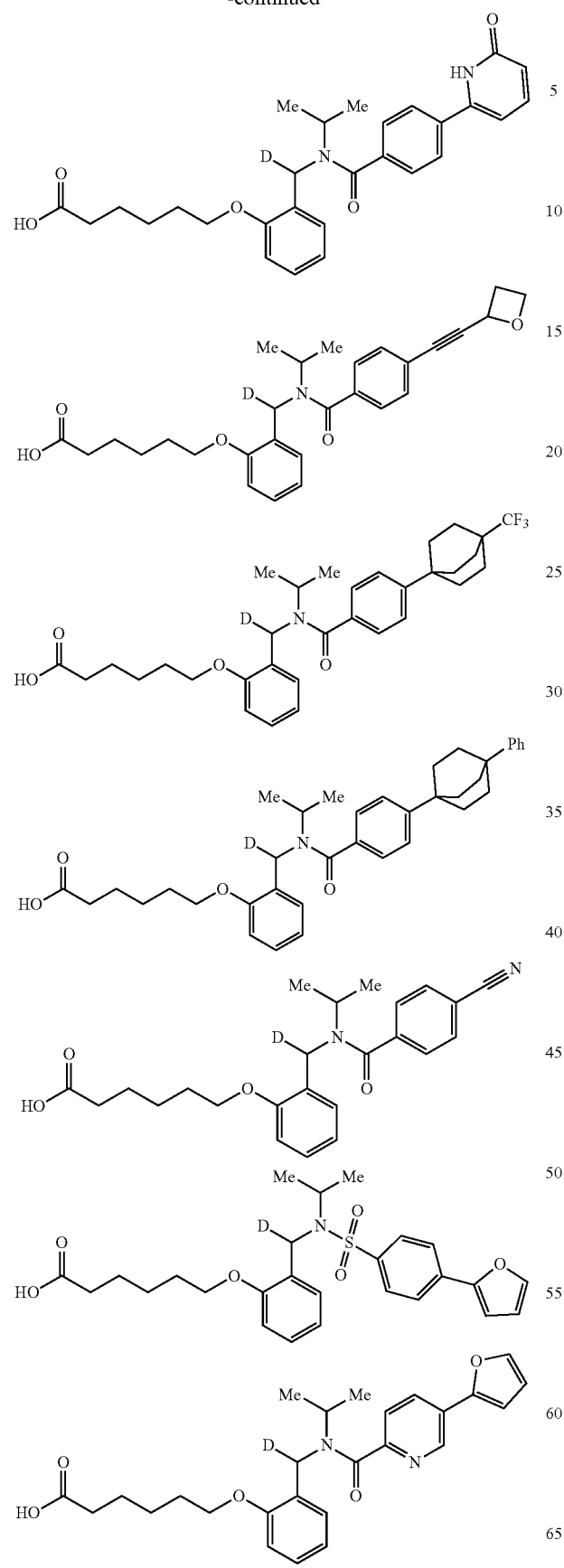
78
-continued
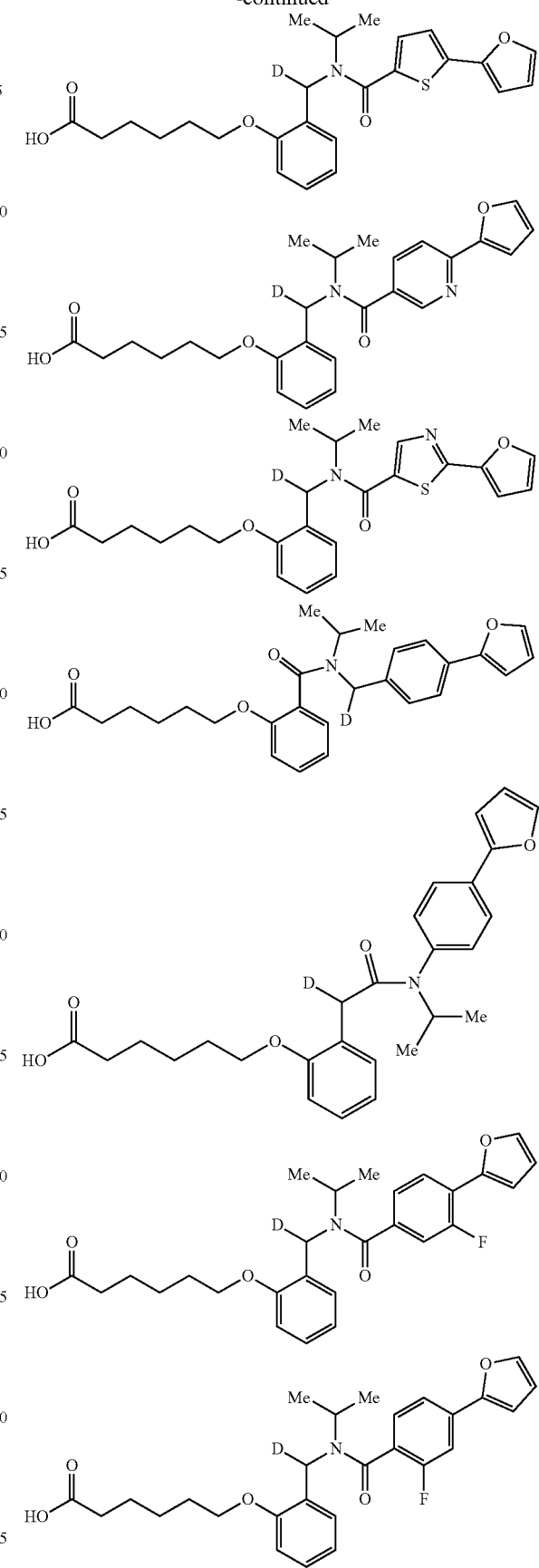

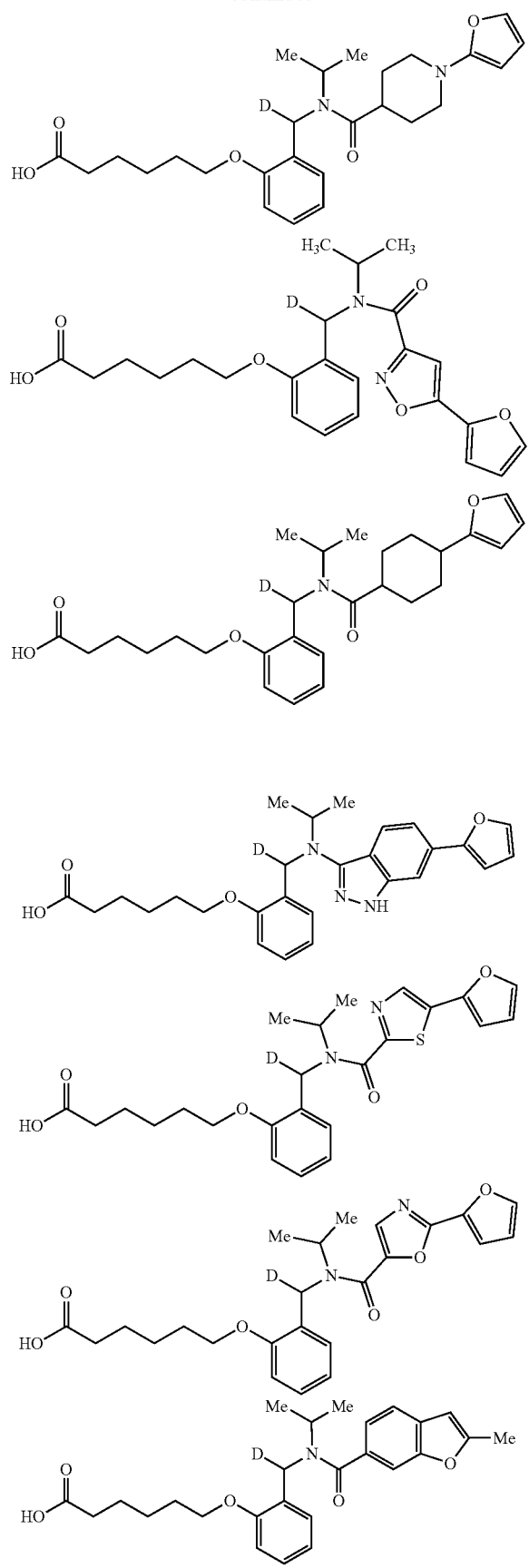
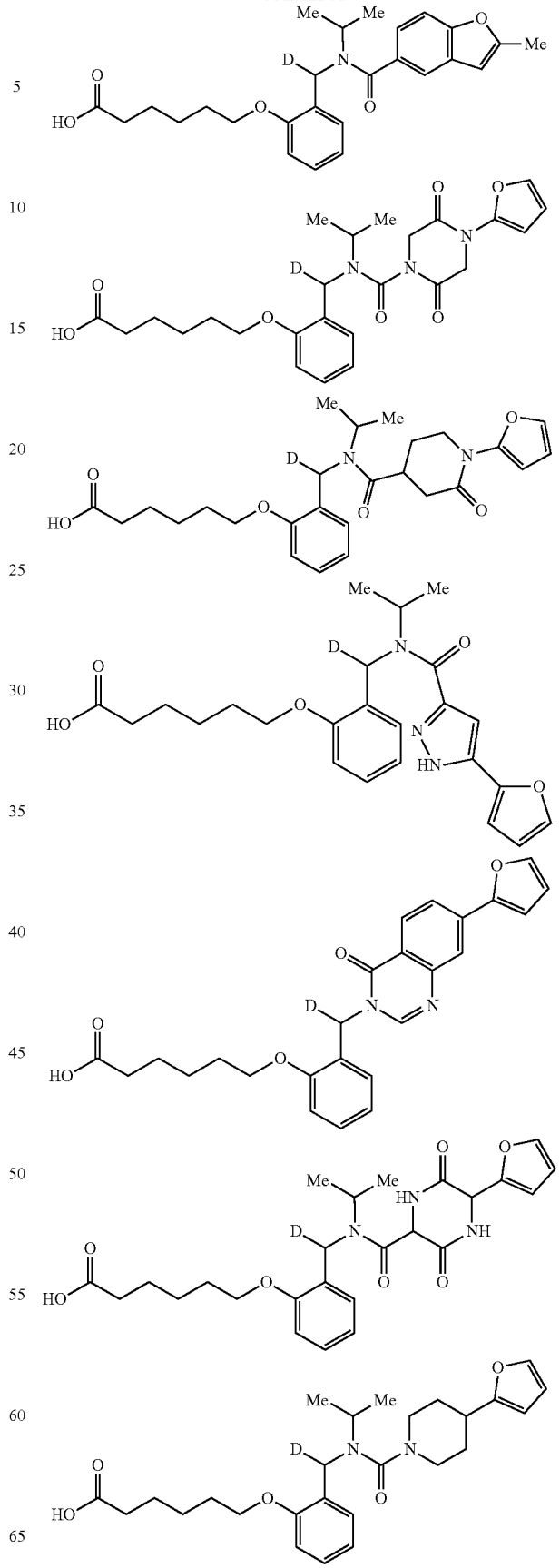

81
-continued
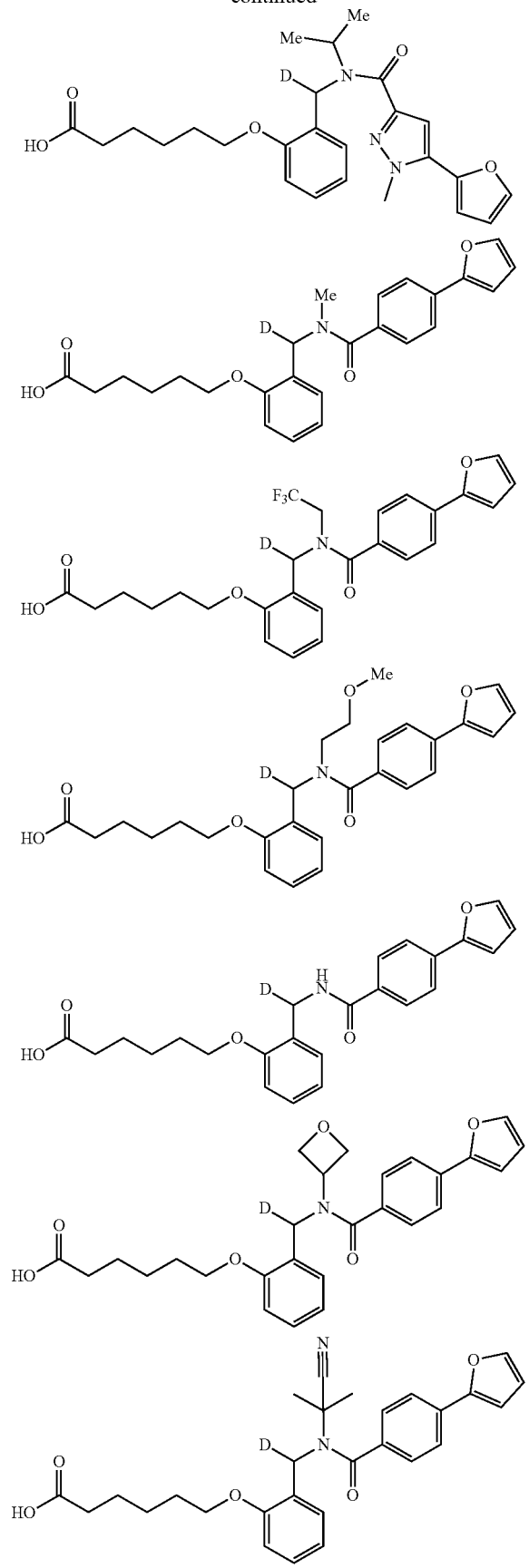
82
-continued
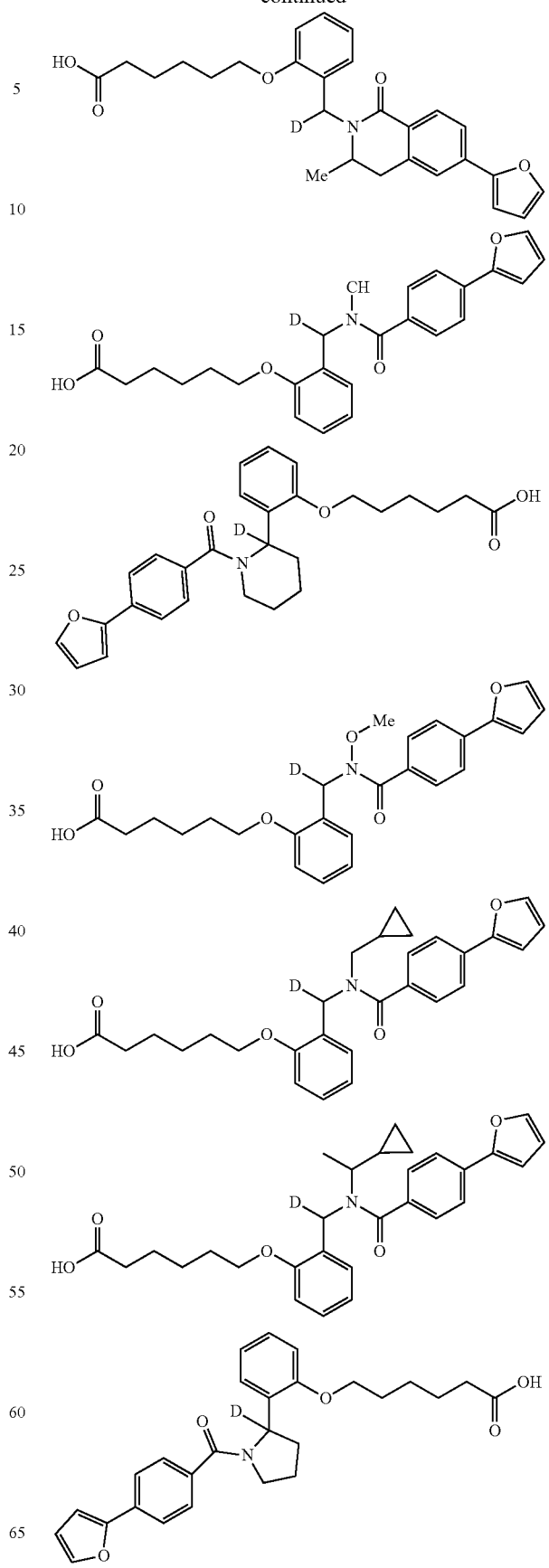

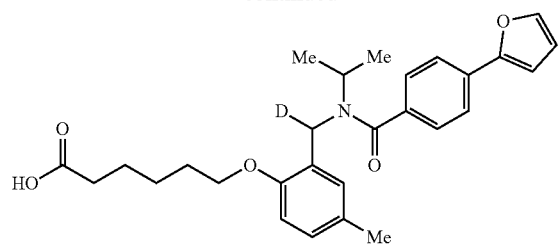
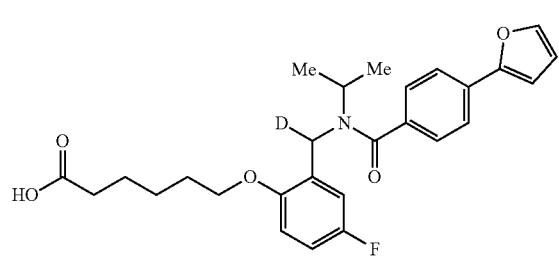
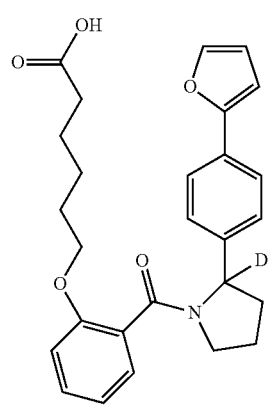
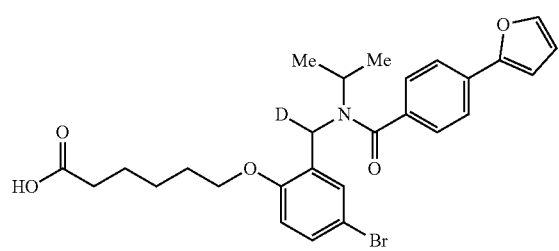
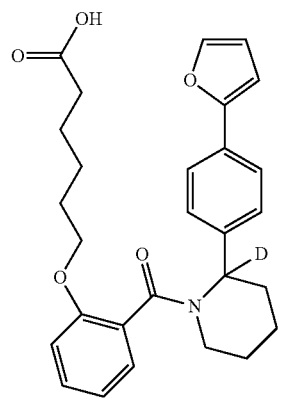
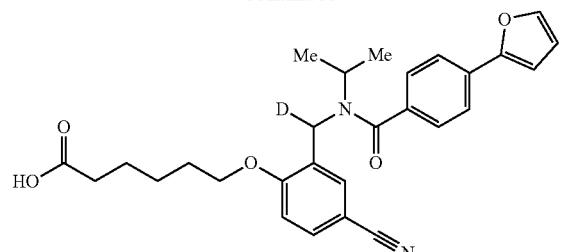
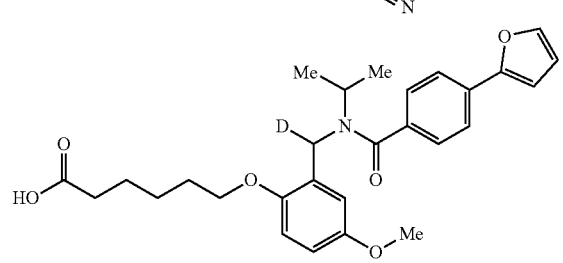
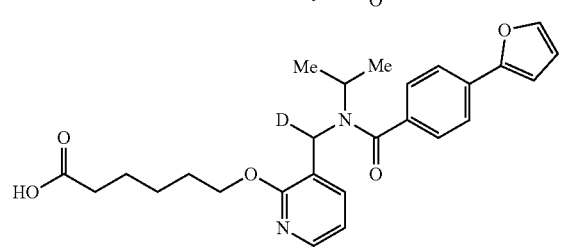
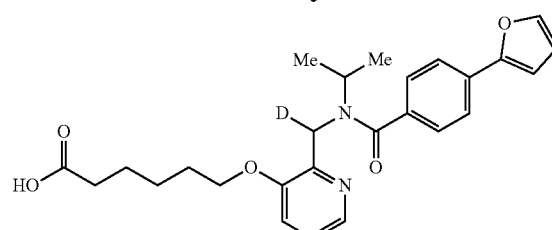
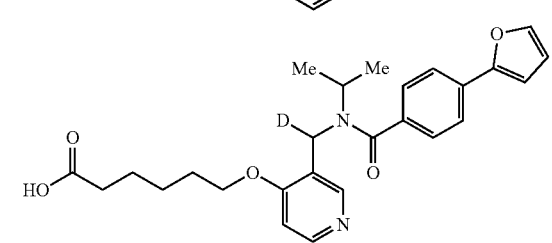
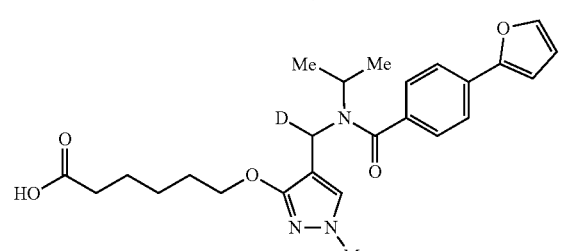
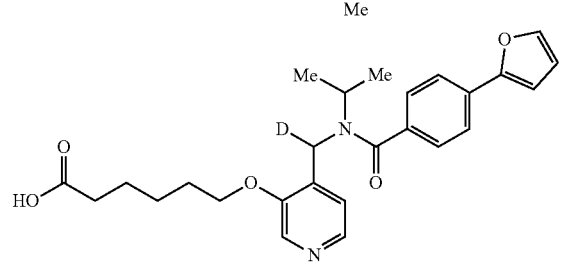

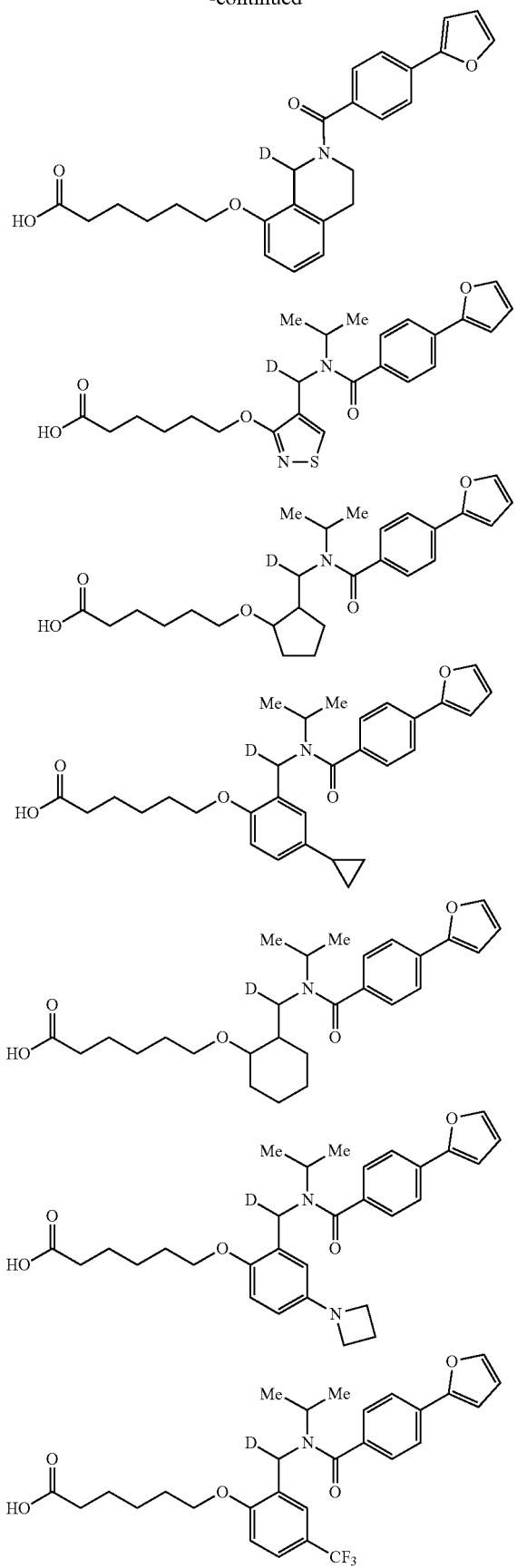
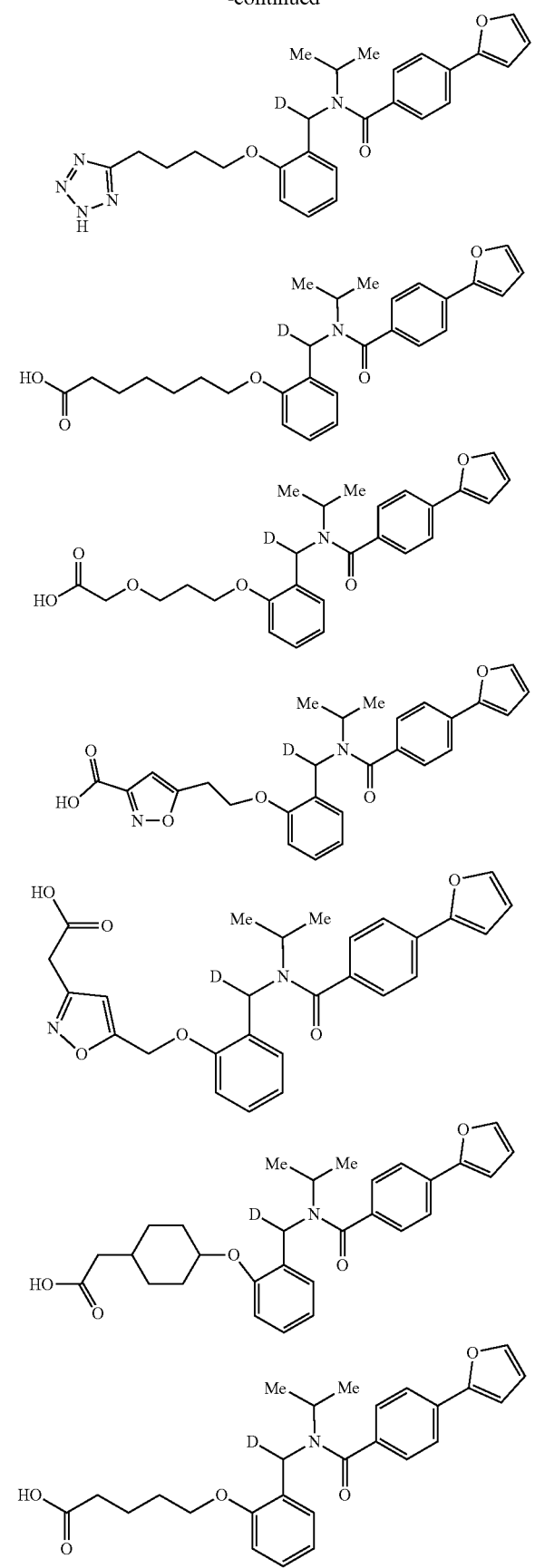

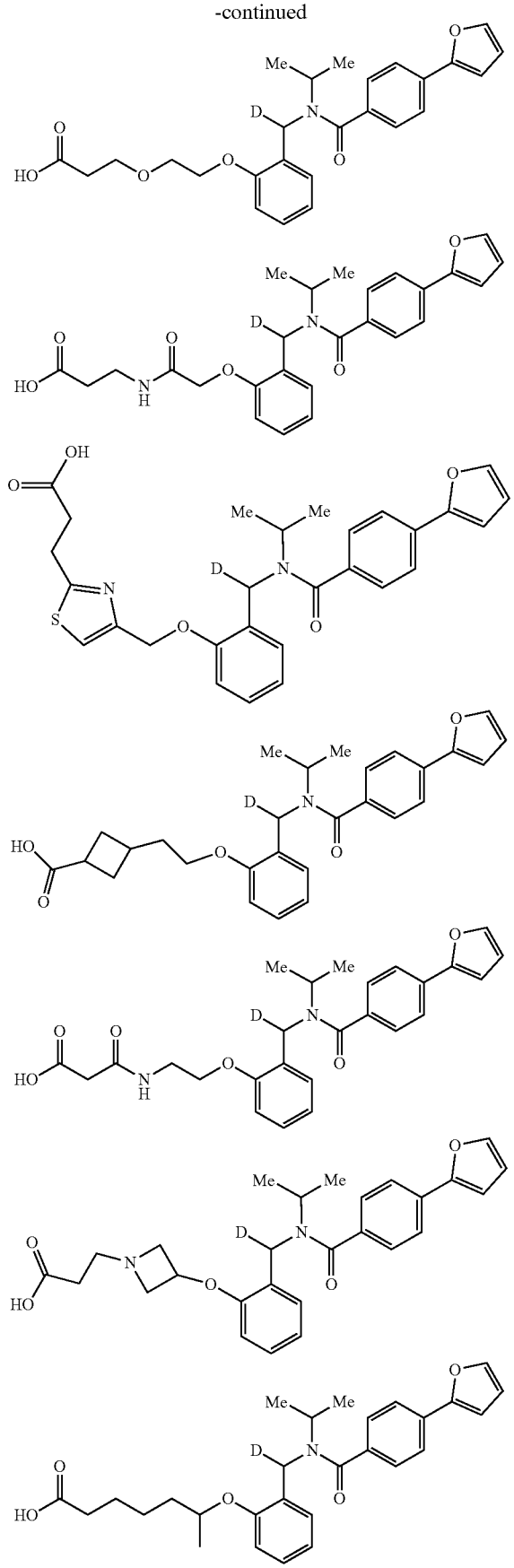
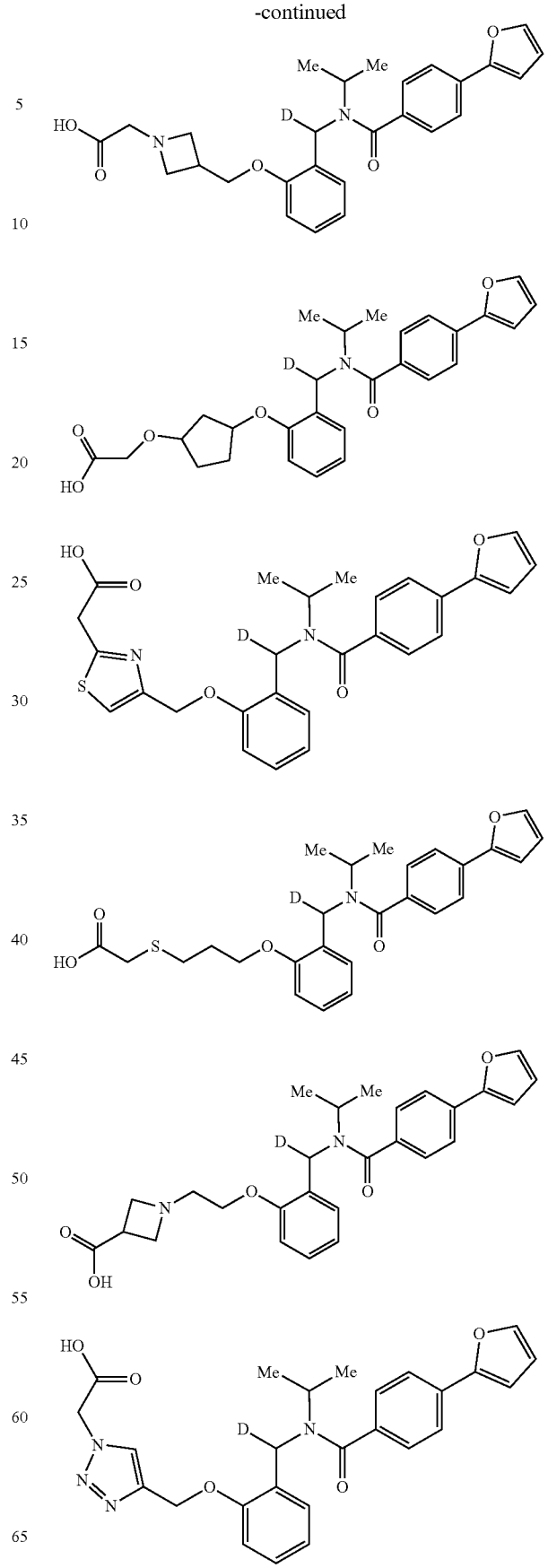

89
-continued
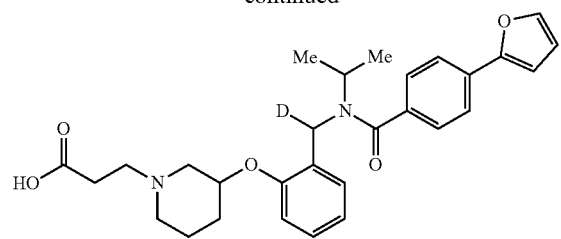
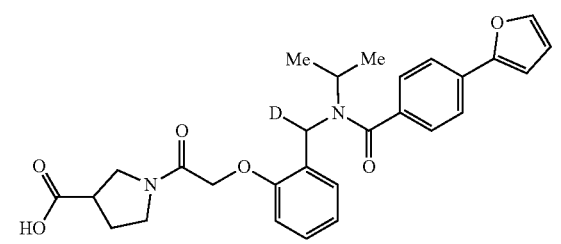
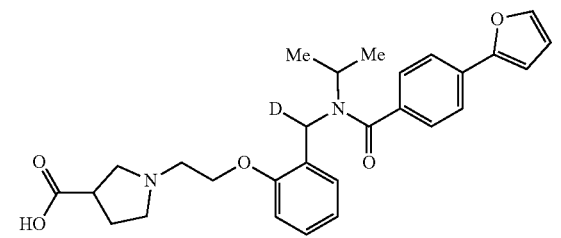
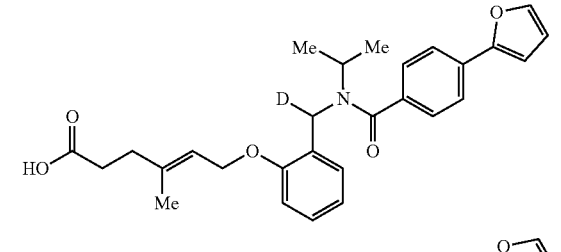
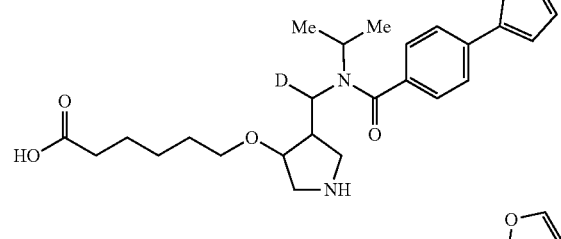
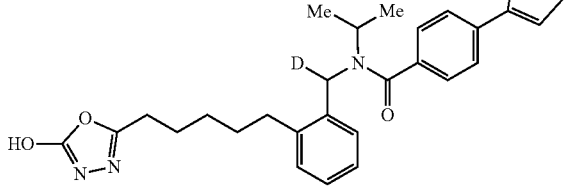
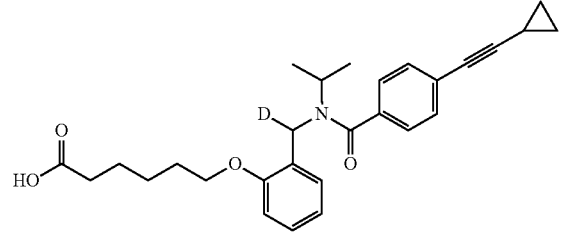
90
-continued
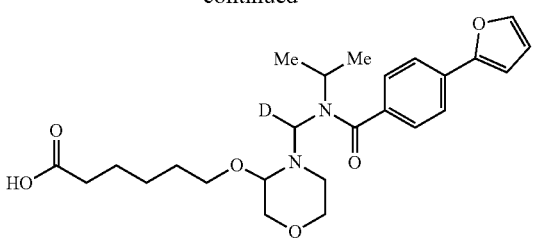
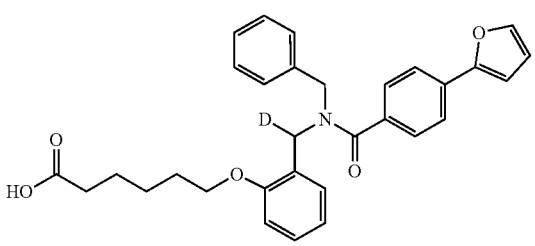
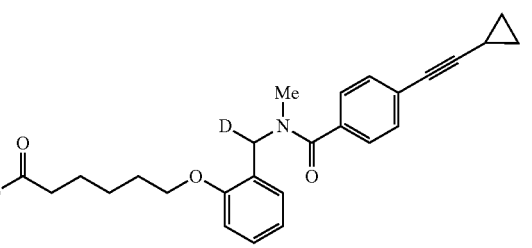
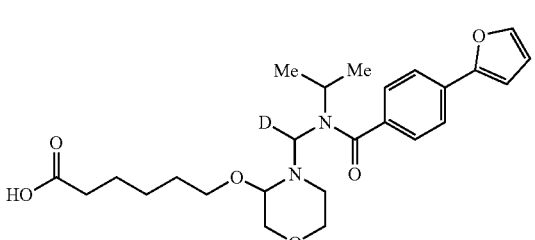
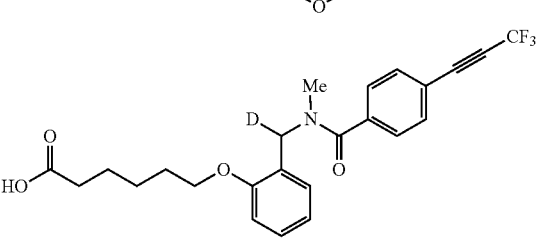
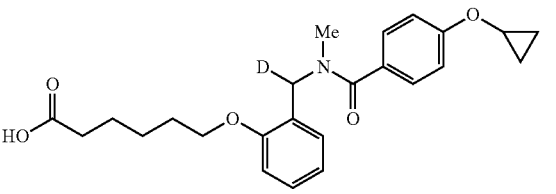
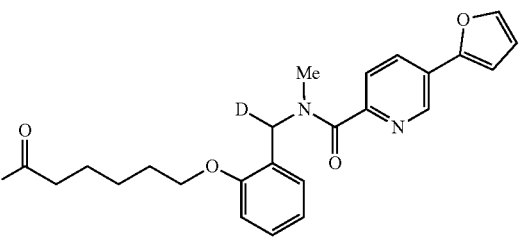

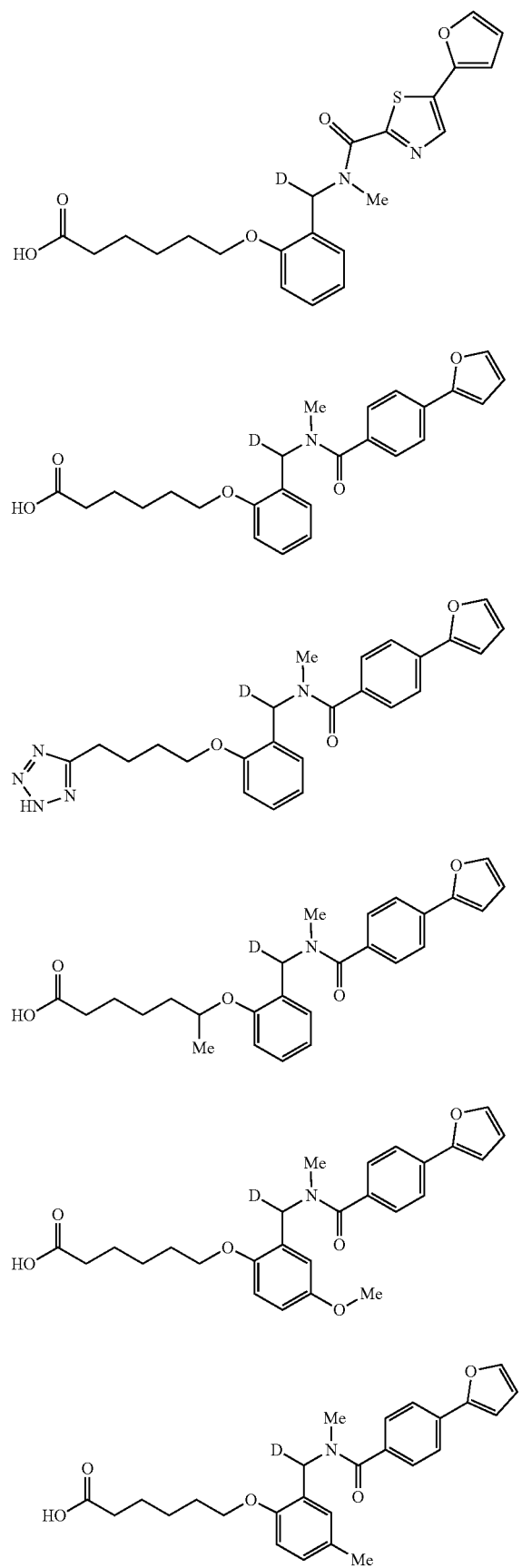
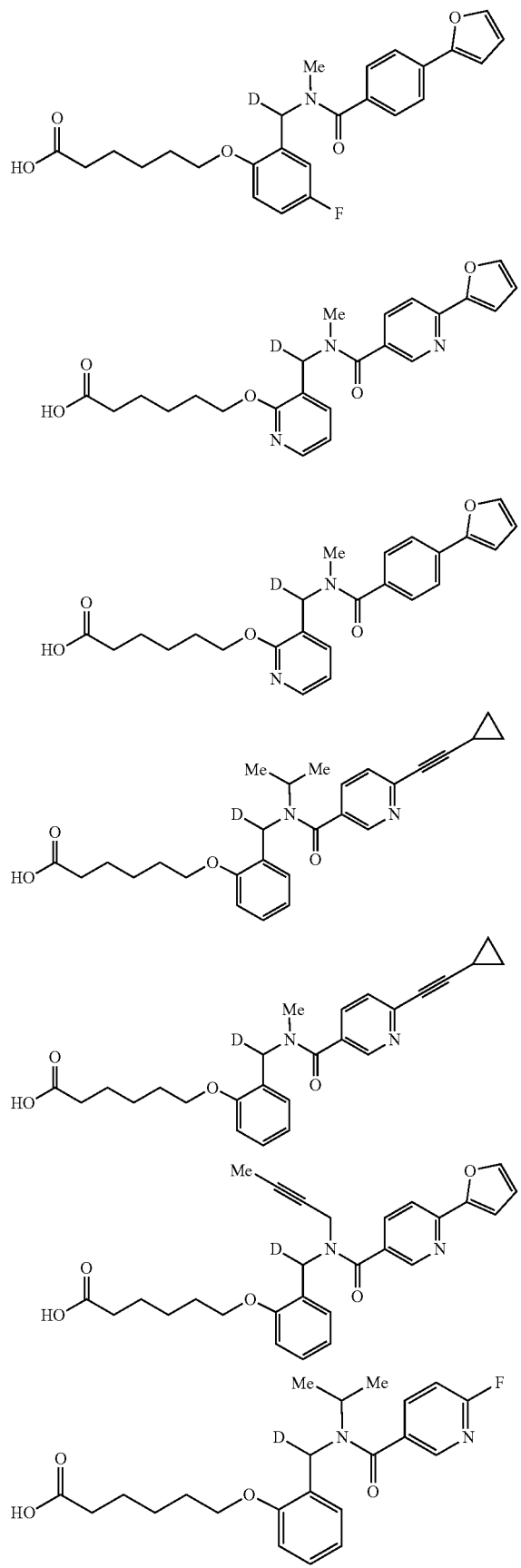

93
-continued
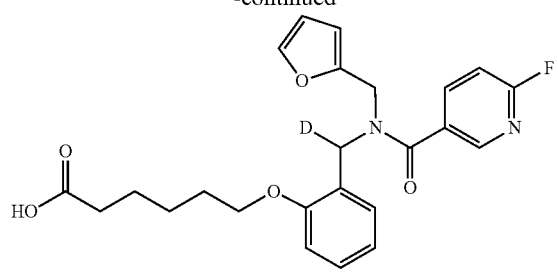
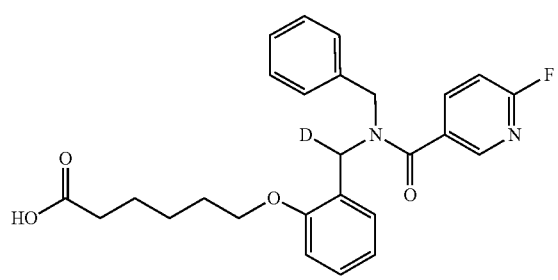
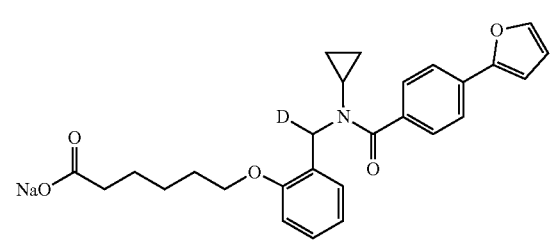
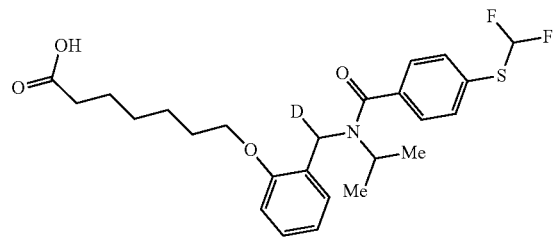
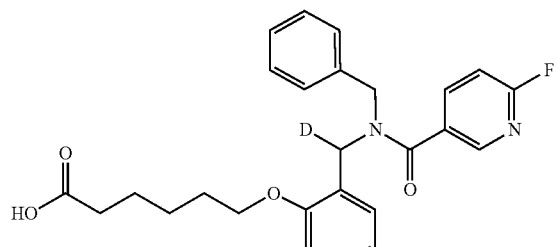
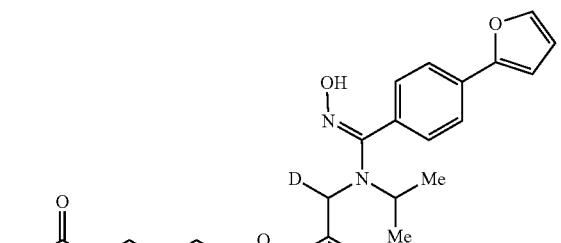
94
-continued
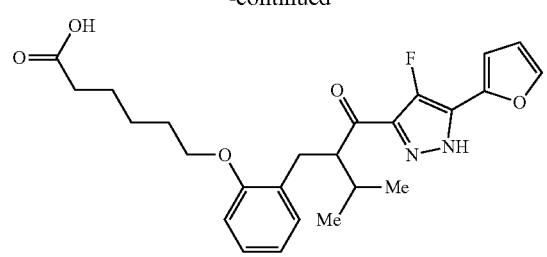
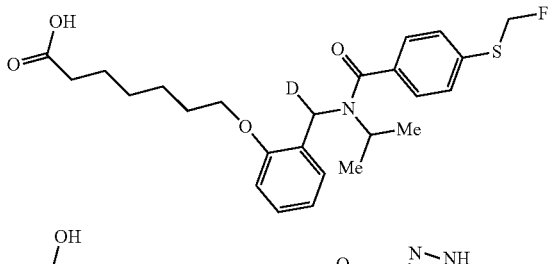
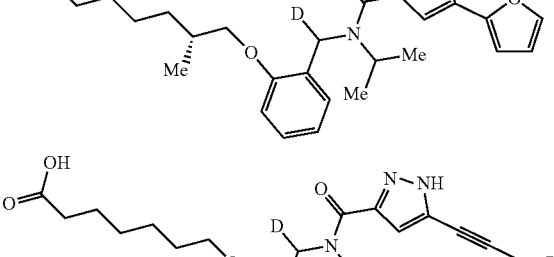
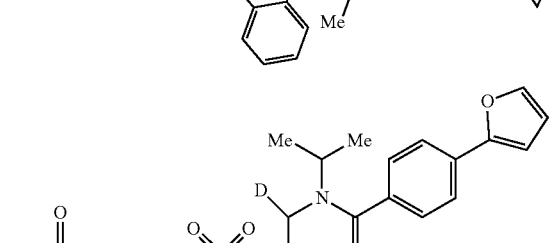
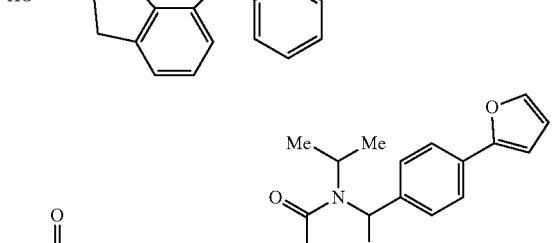
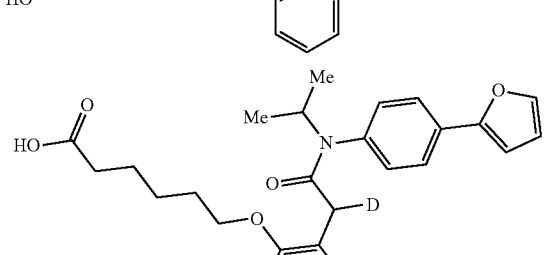

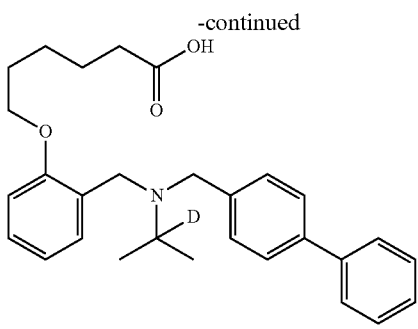
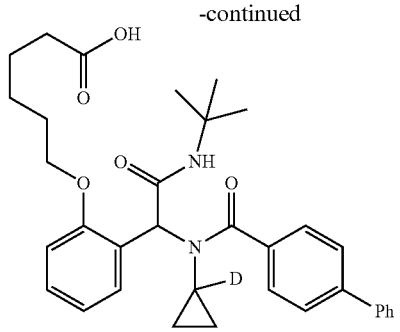
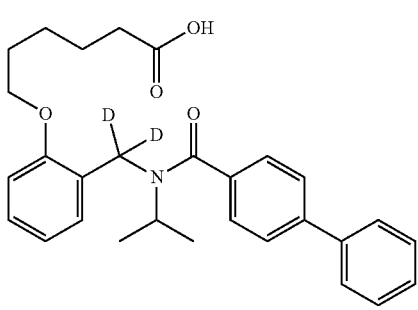
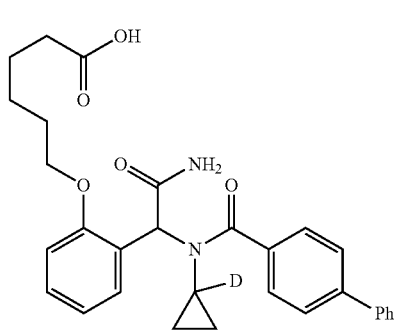
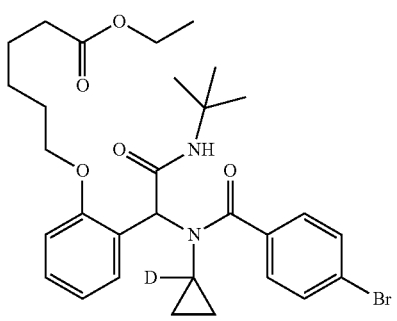
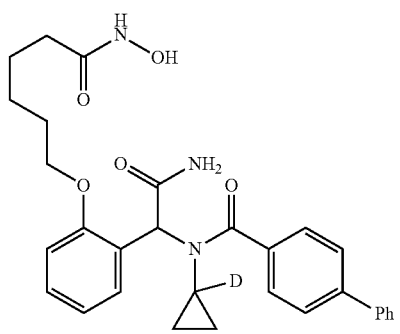
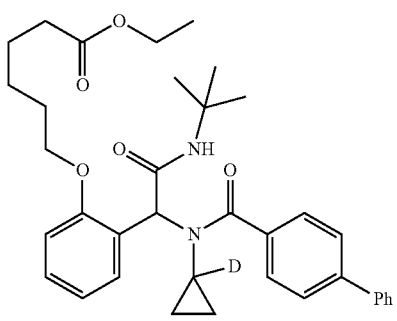
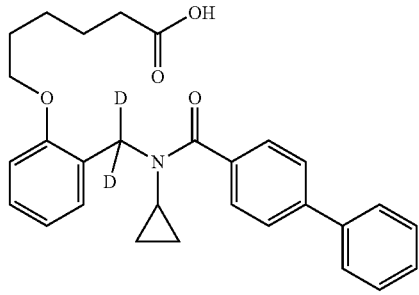
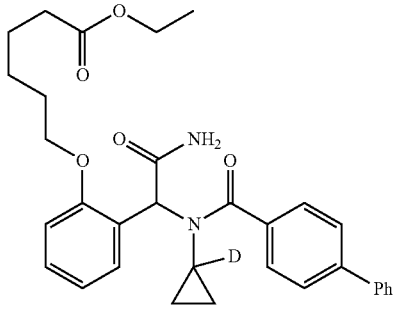
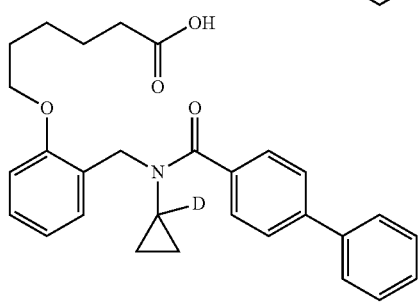

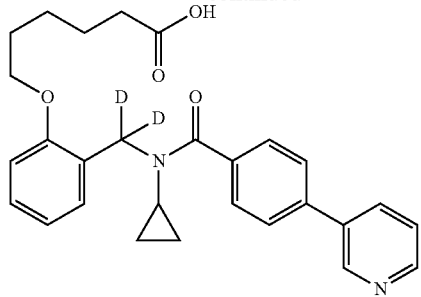
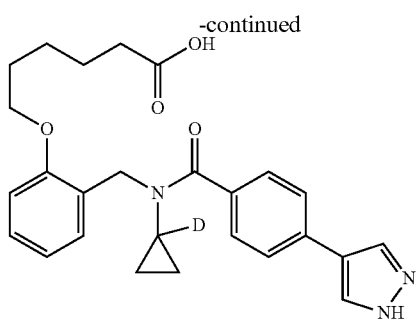
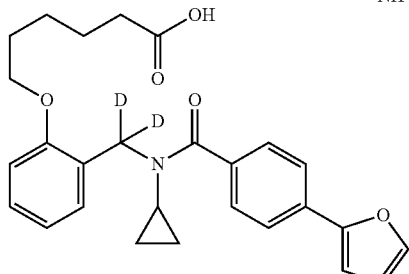
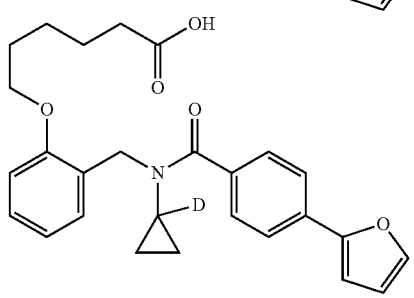
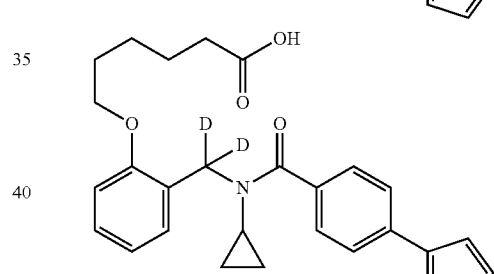
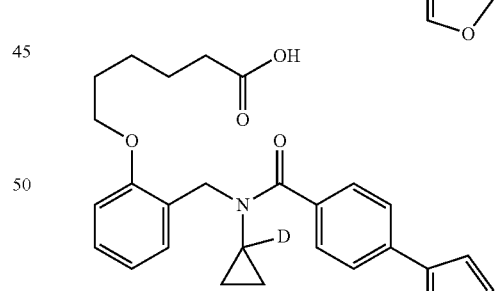
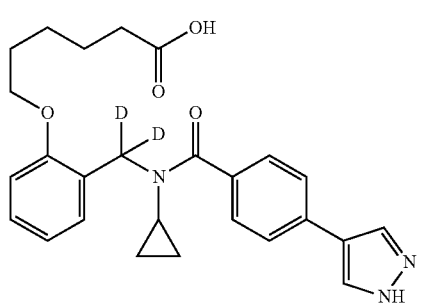

99
-continued
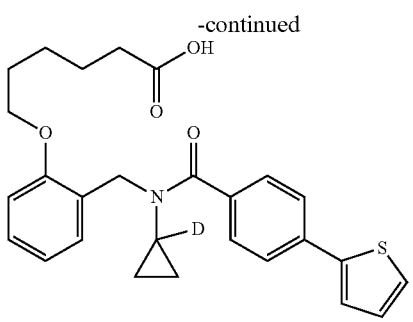
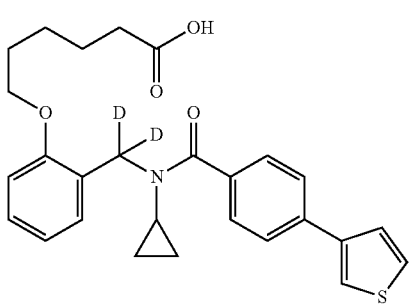
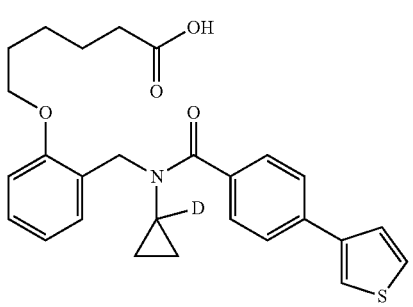
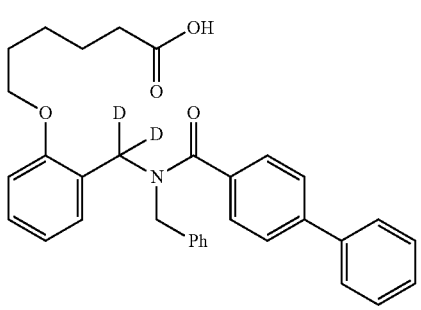
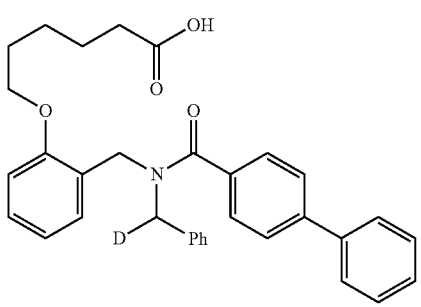
100
-continued
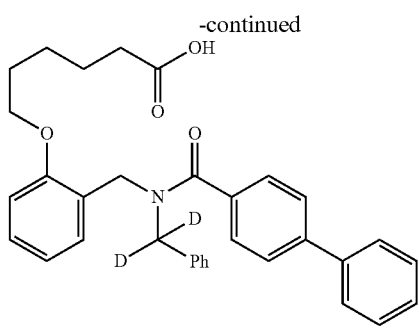
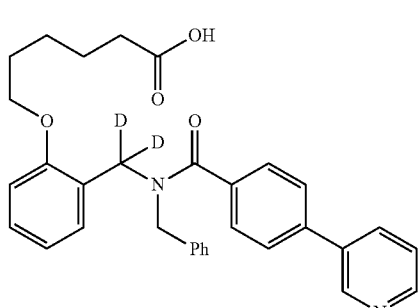
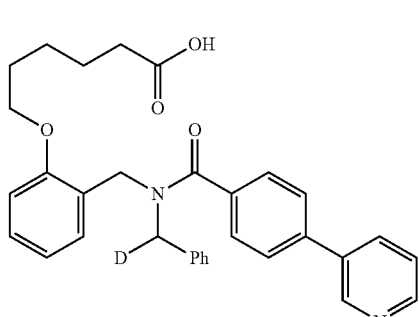
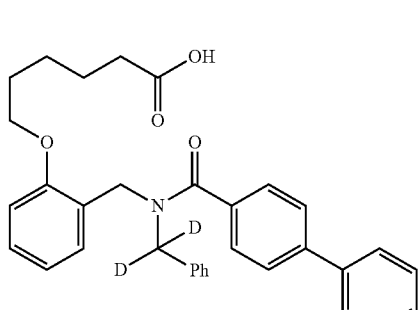
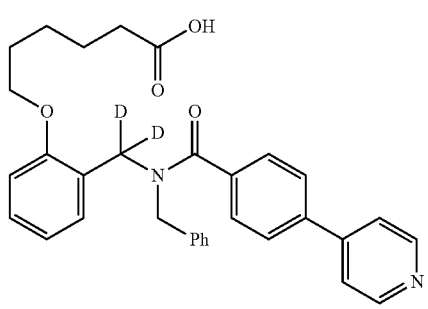

101
-continued
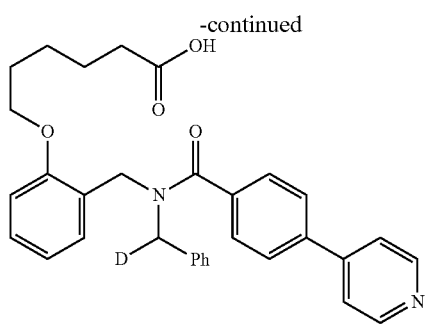
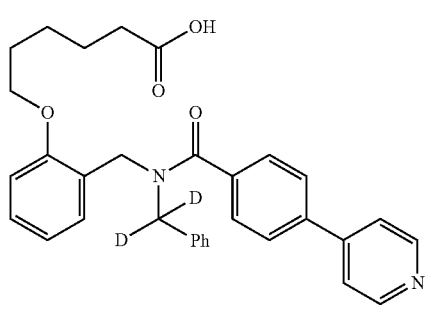
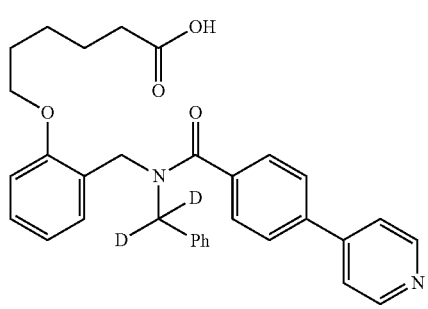
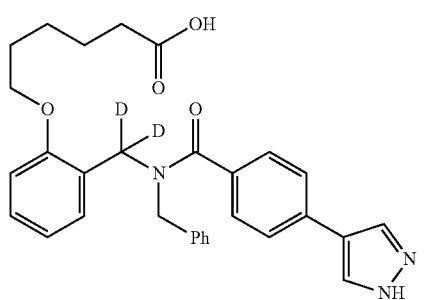
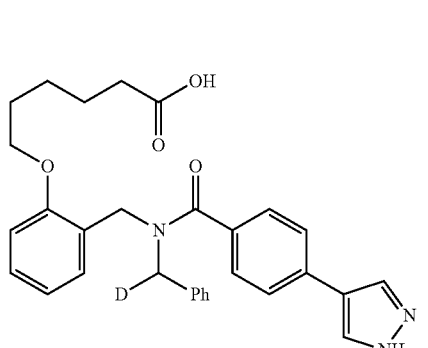
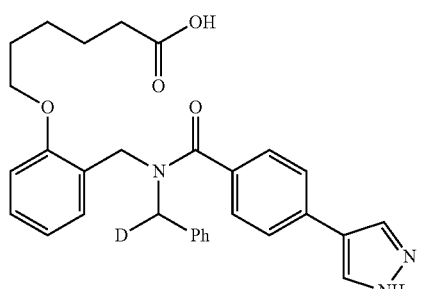
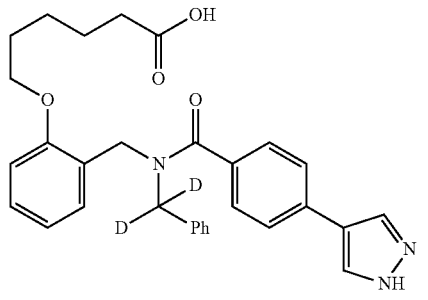
102
-continued
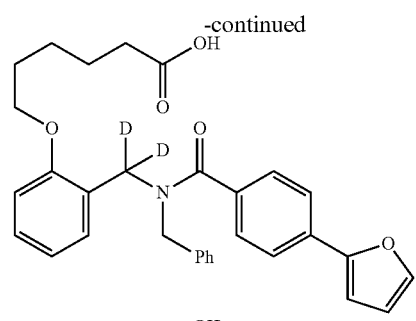
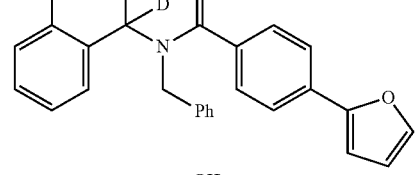
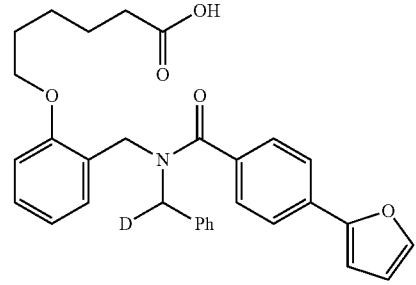
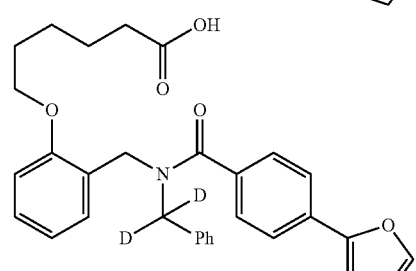
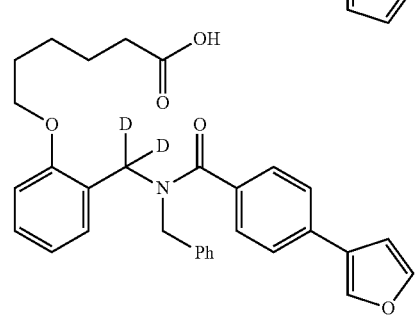
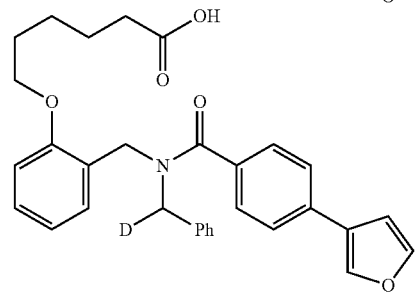
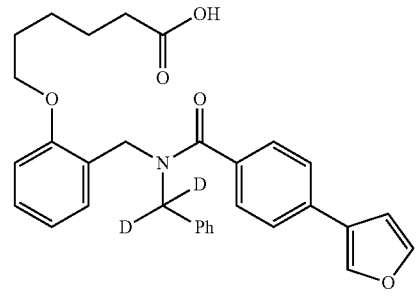

103
-continued
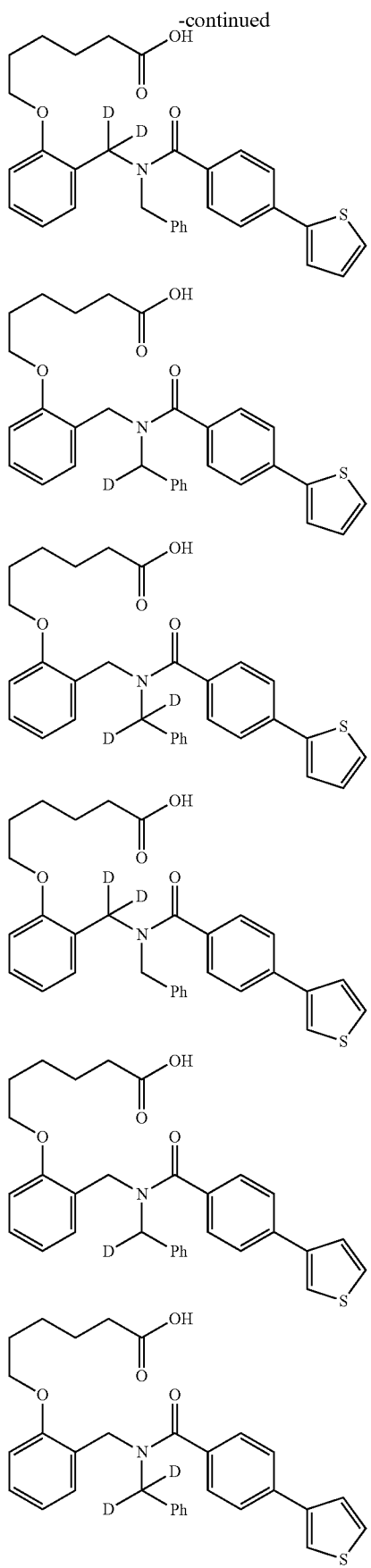
104
-continued
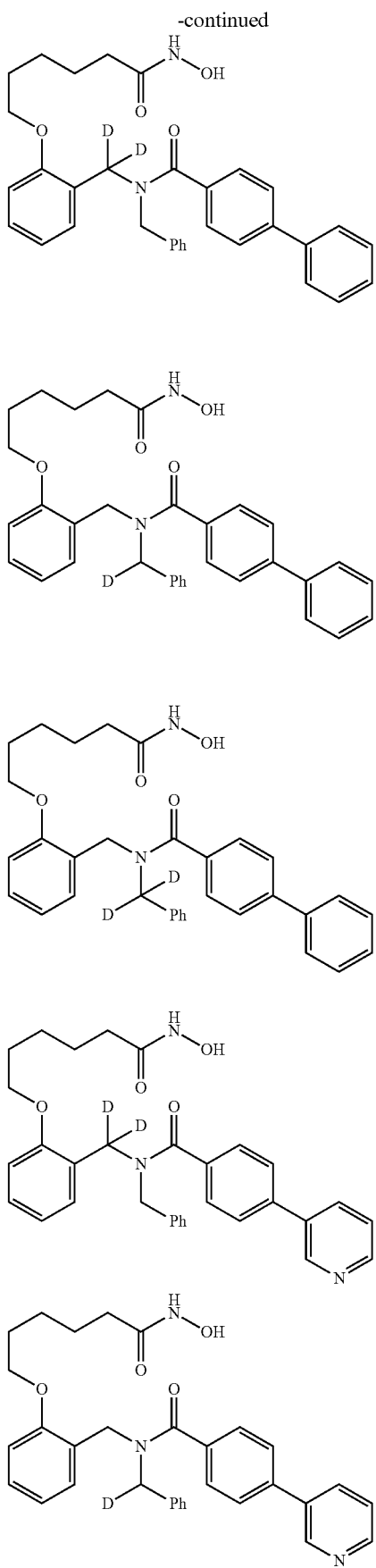

105
-continued
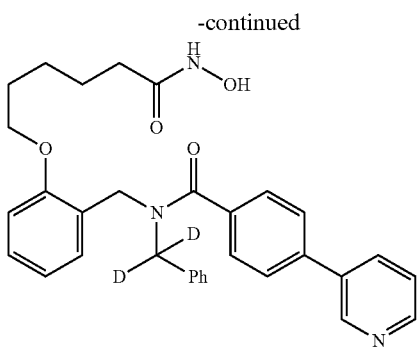
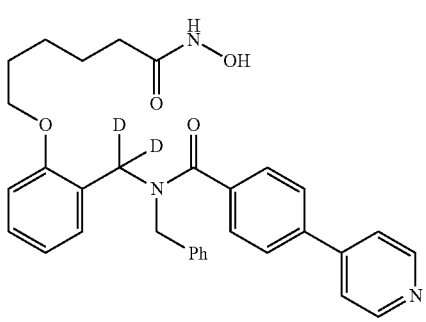
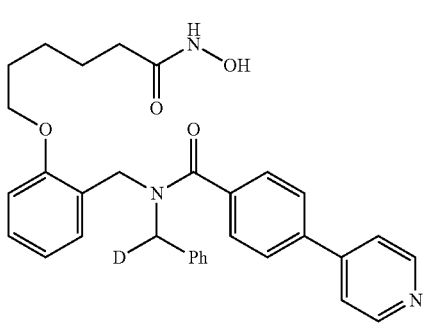
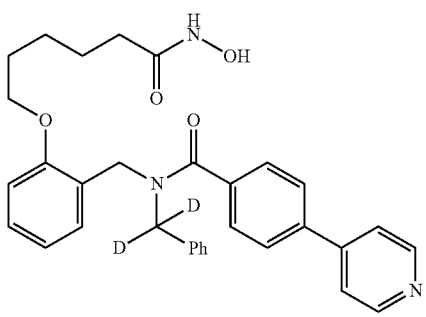
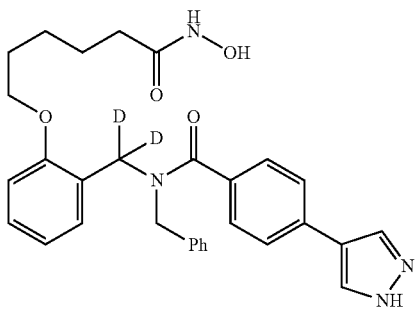
106
-continued

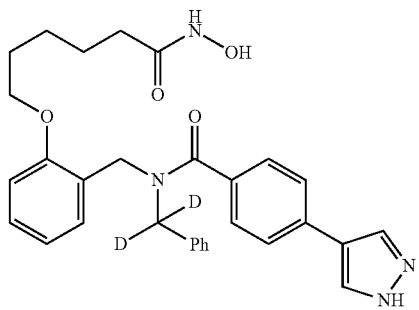
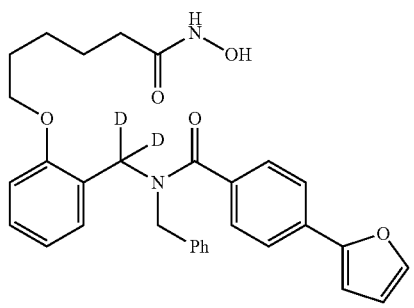
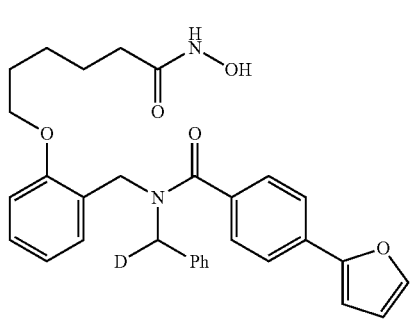
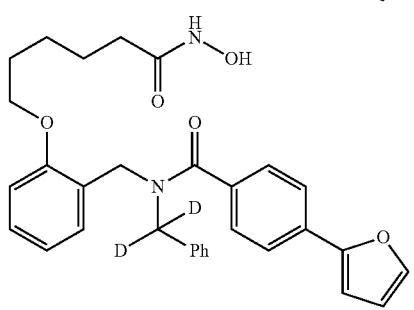

107
-continued
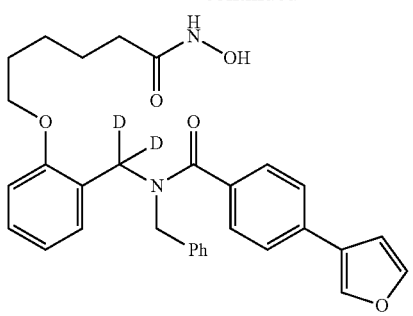
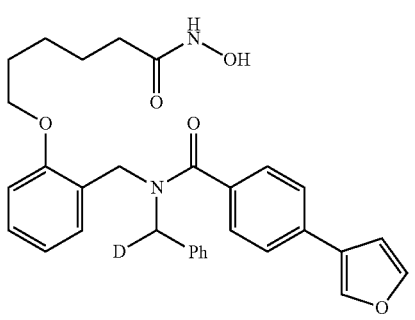
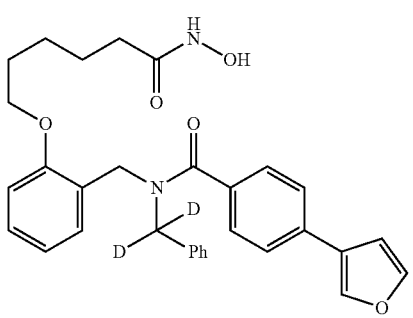
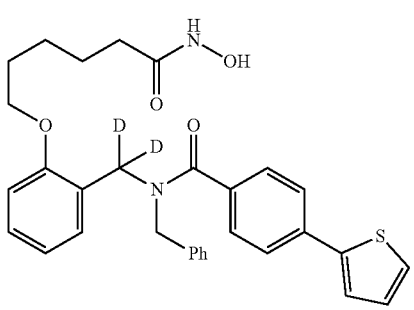
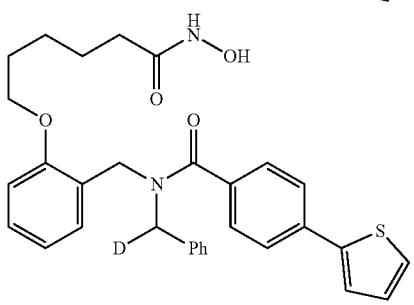
108
-continued
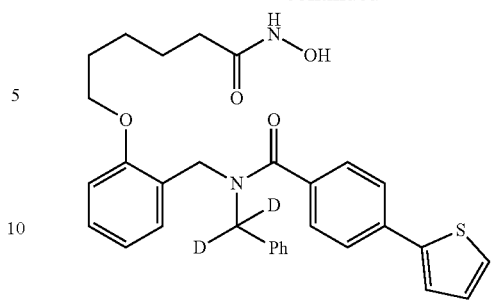
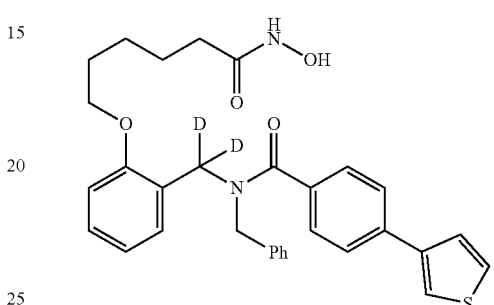
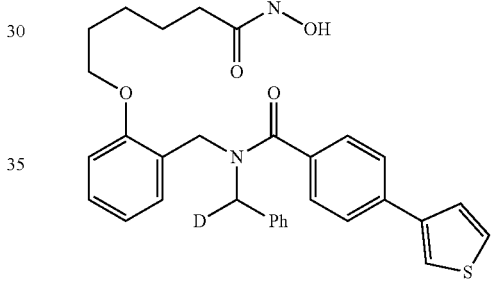
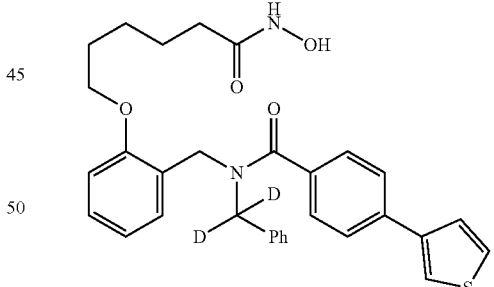
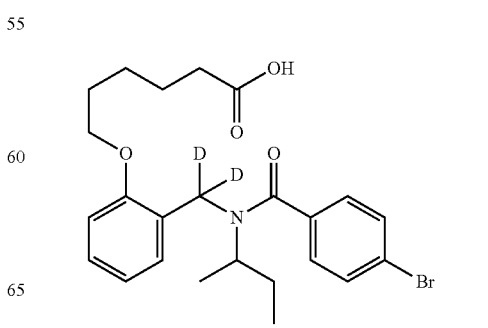

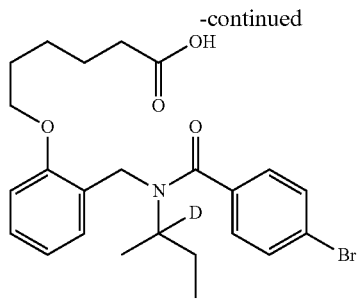
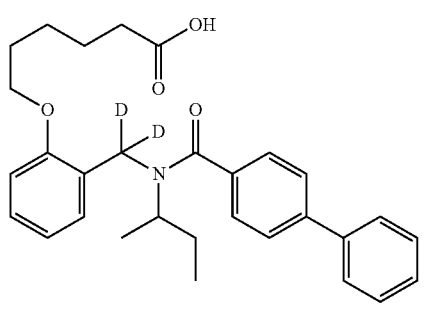
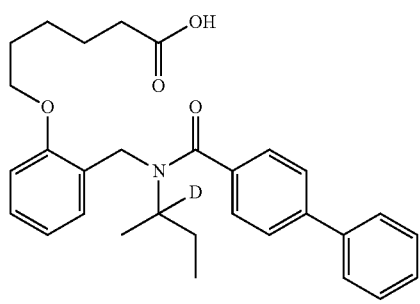
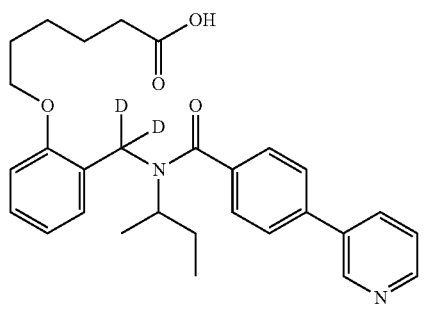
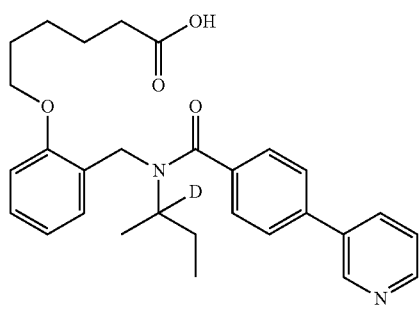
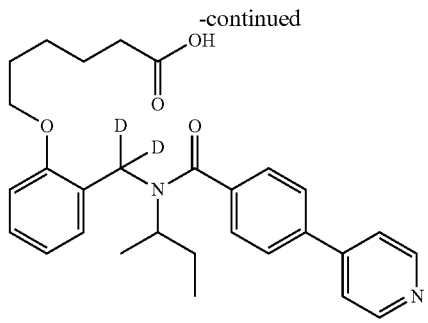
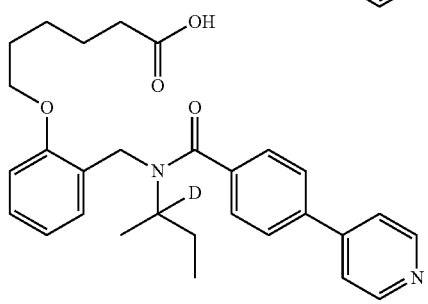
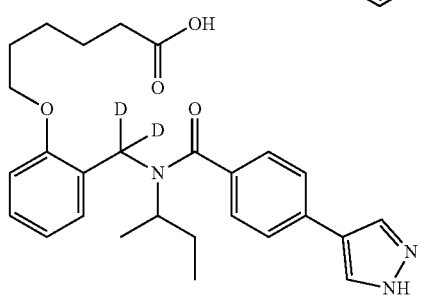
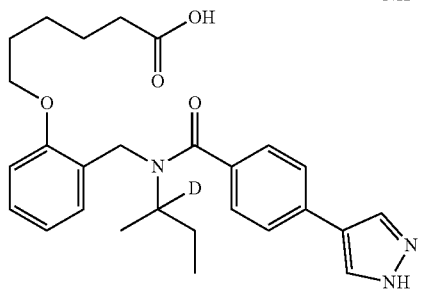
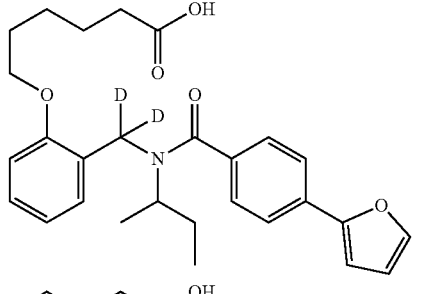
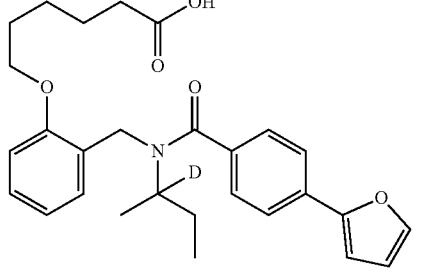

111
-continued
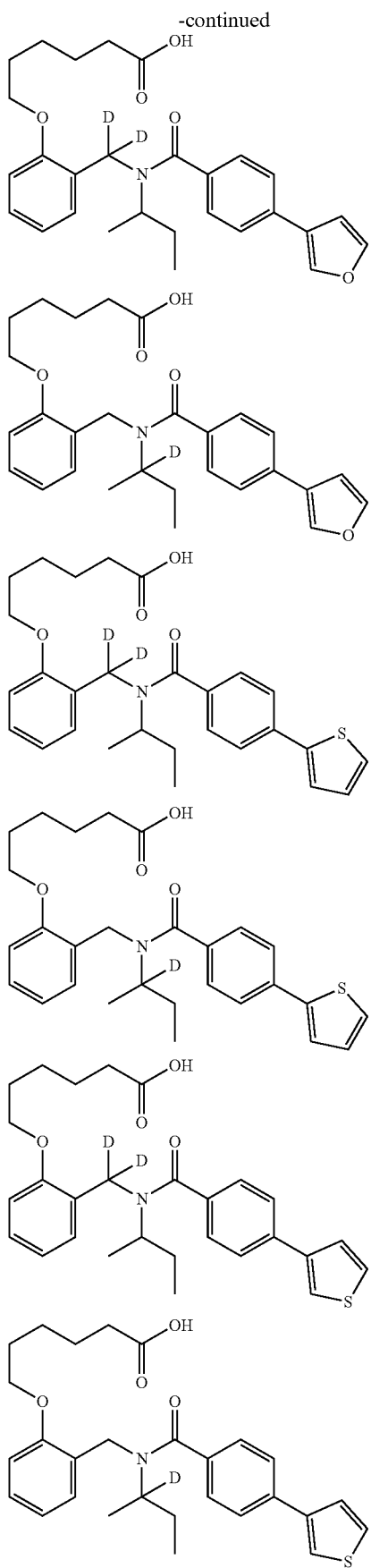
112
-continued
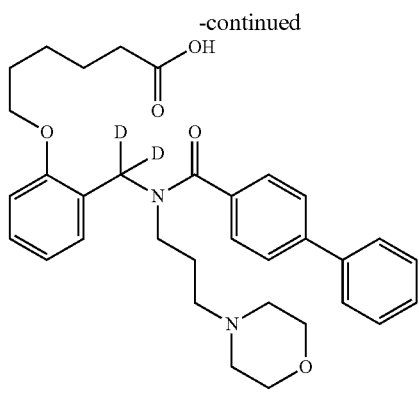
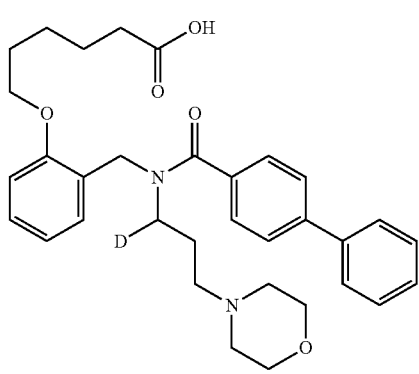
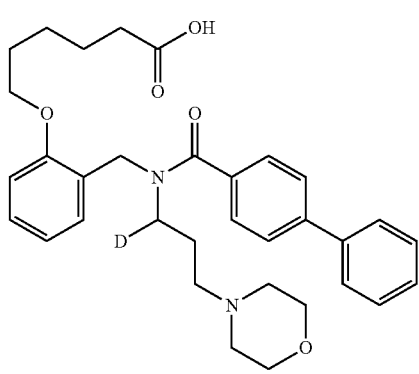

113
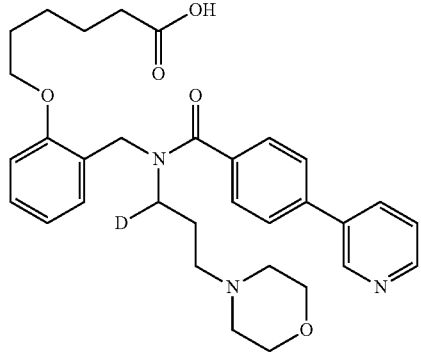
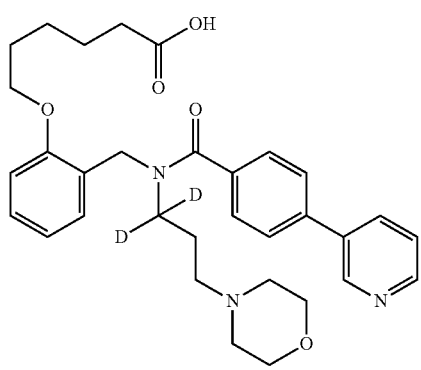
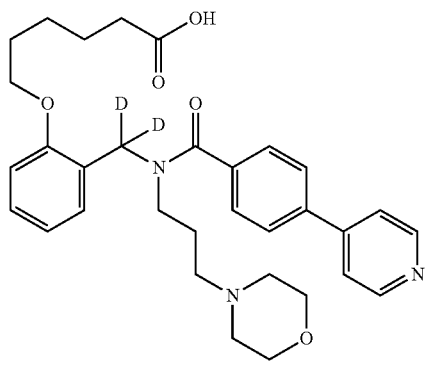
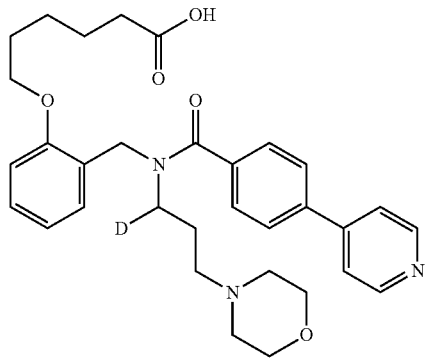
114
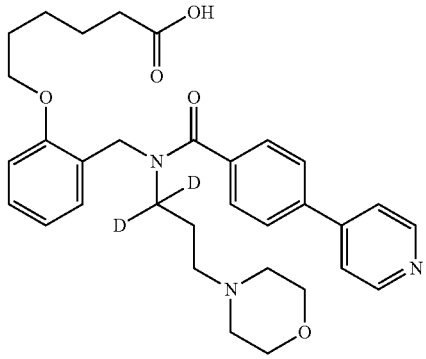
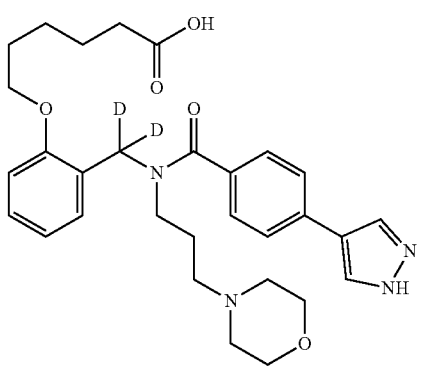
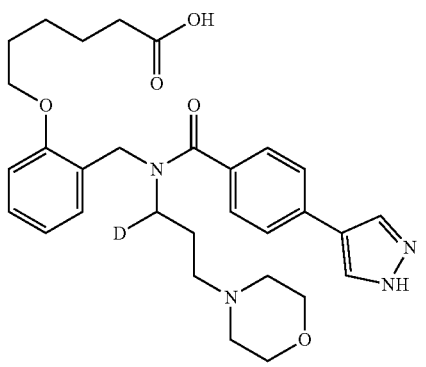
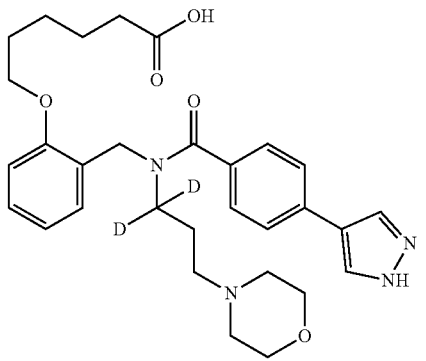

115
-continued
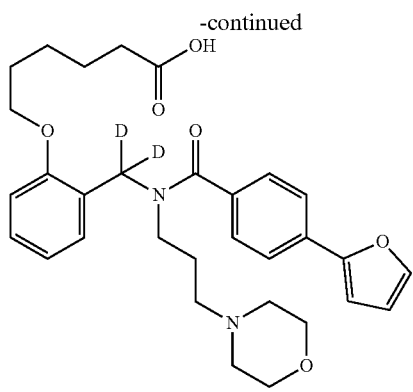
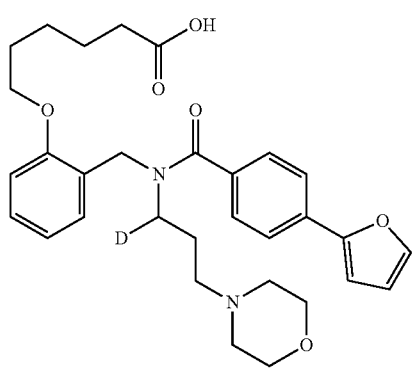
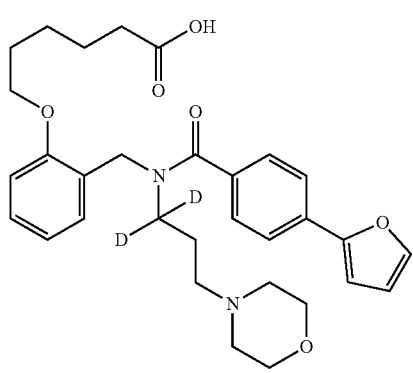
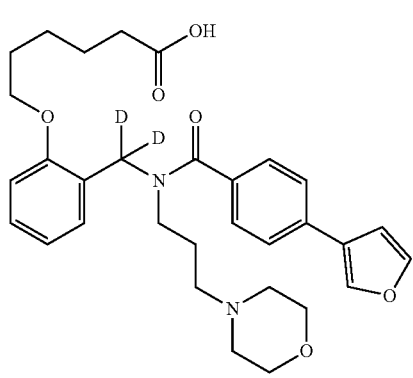
116
-continued
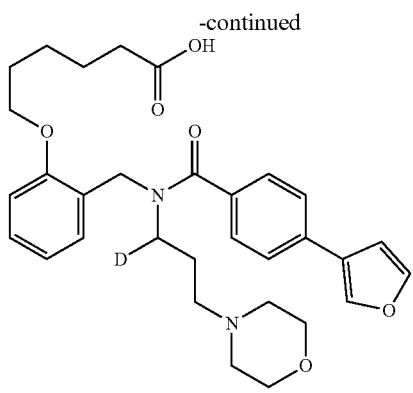
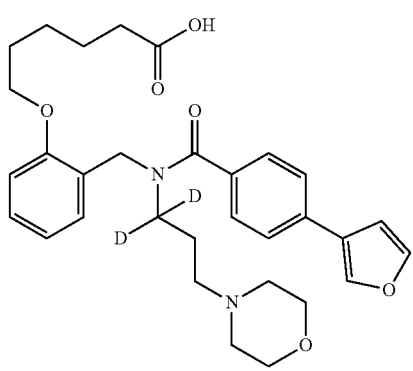
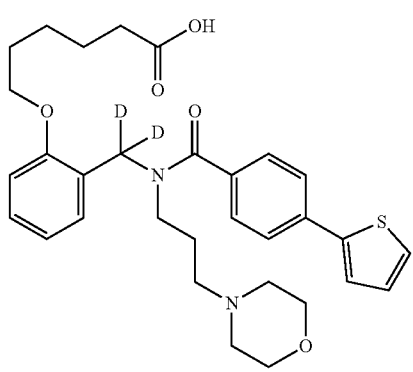
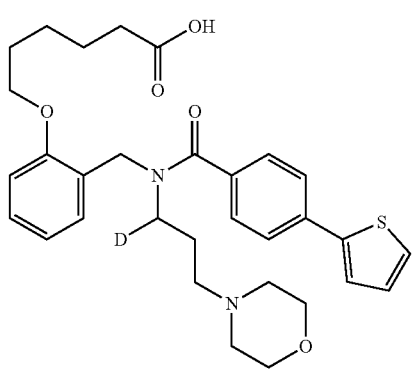

117
-continued
118
-continued
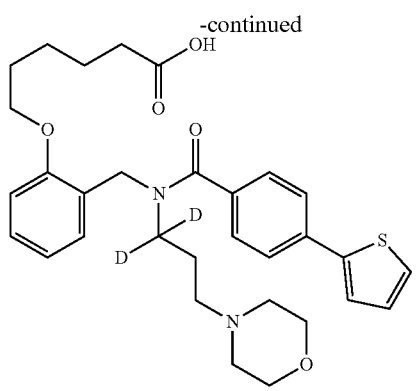
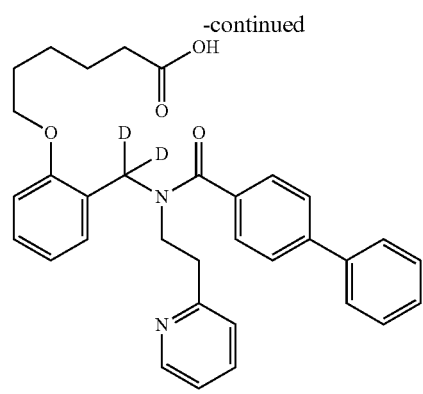
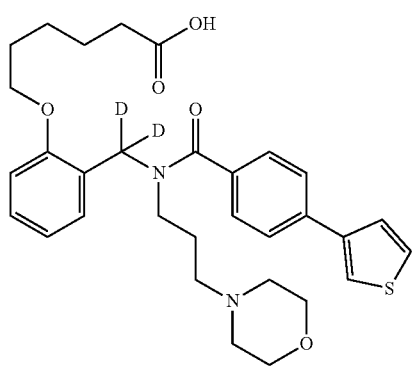
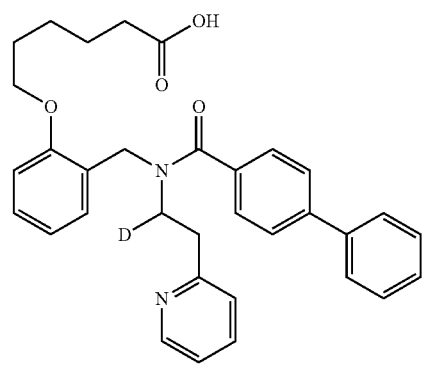
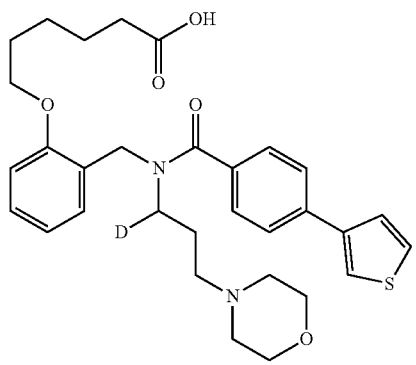
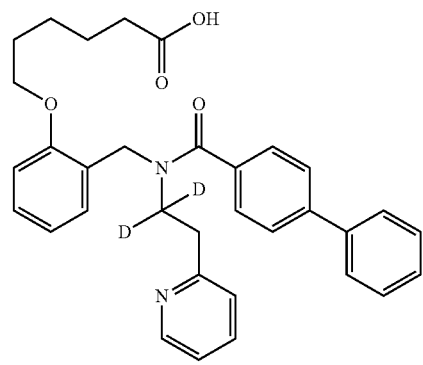
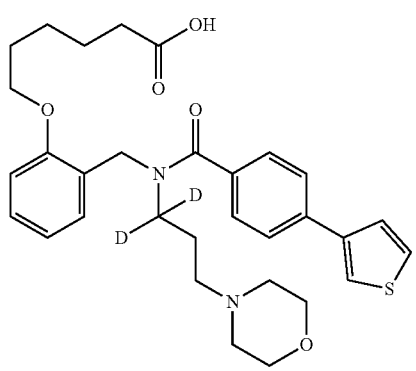
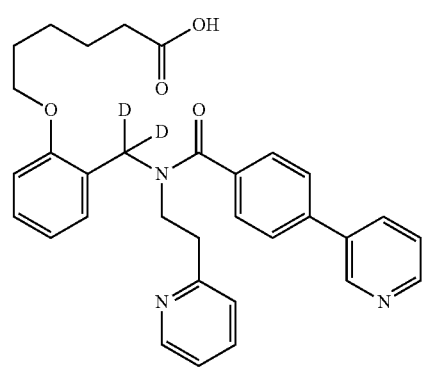

119
-continued
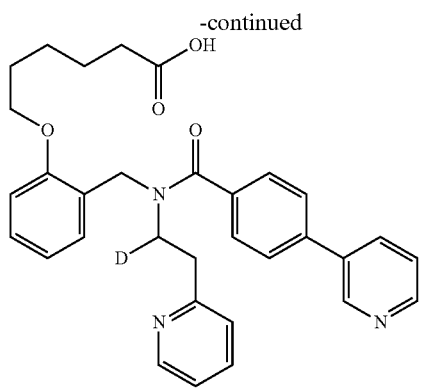
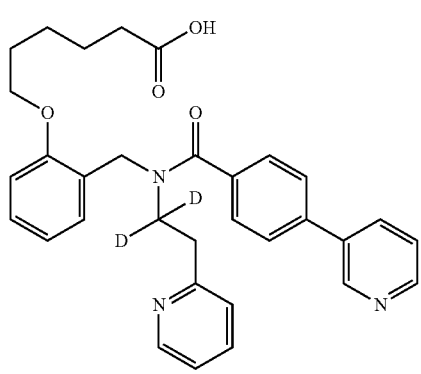
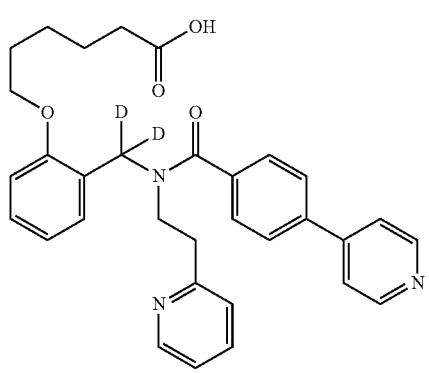
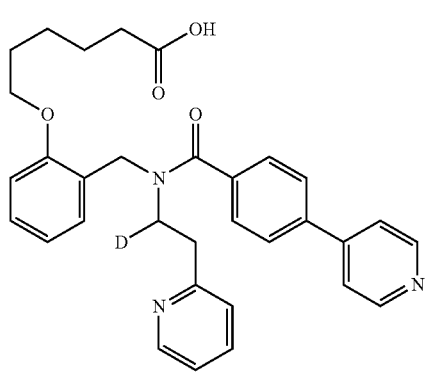
120
-continued
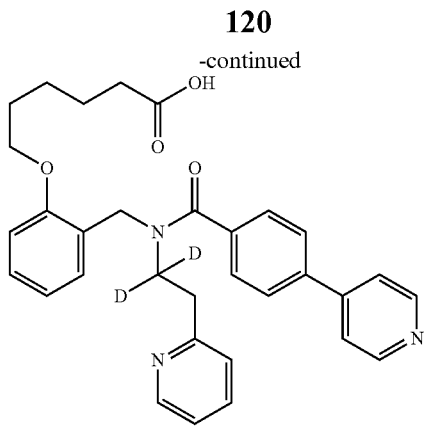
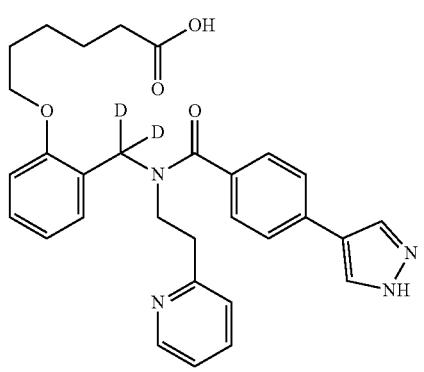
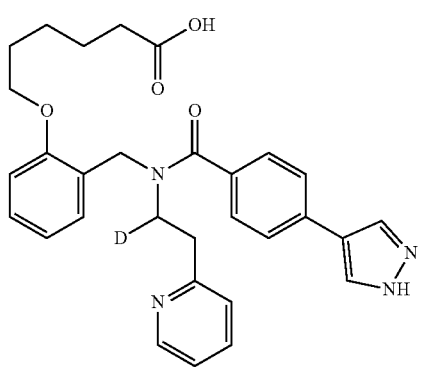
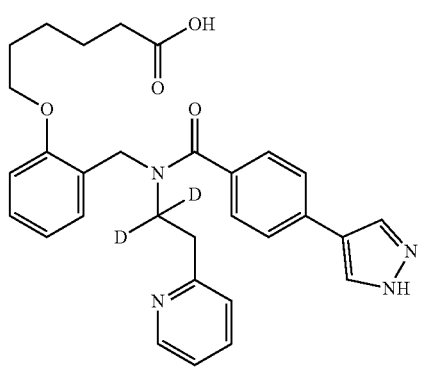

121
-continued
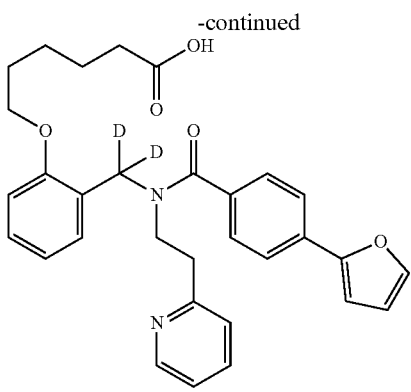
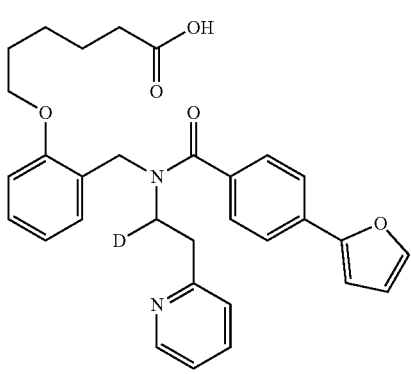
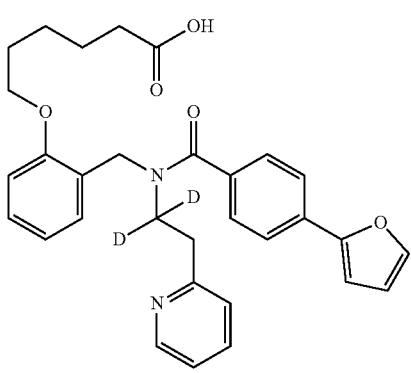
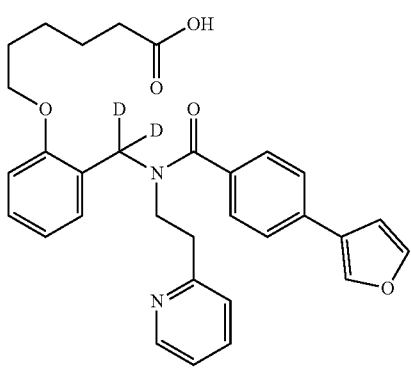
122
-continued
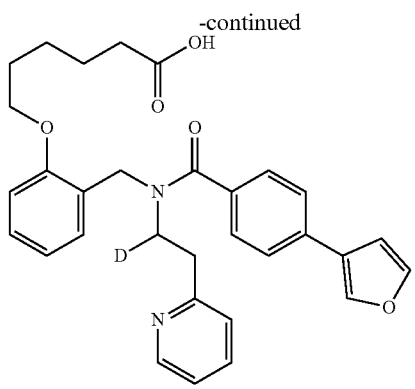
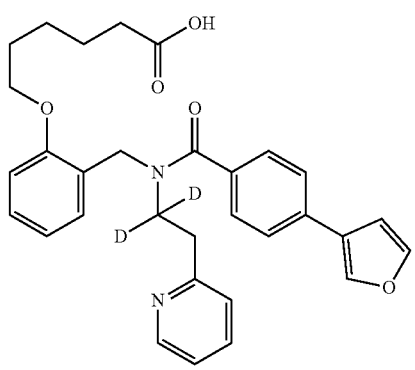
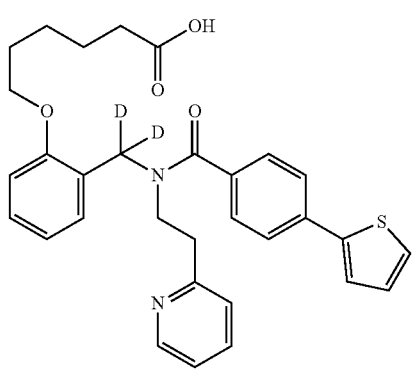
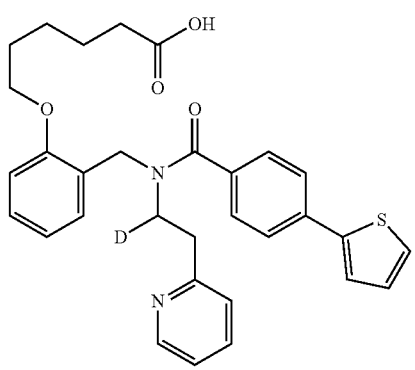

123
-continued
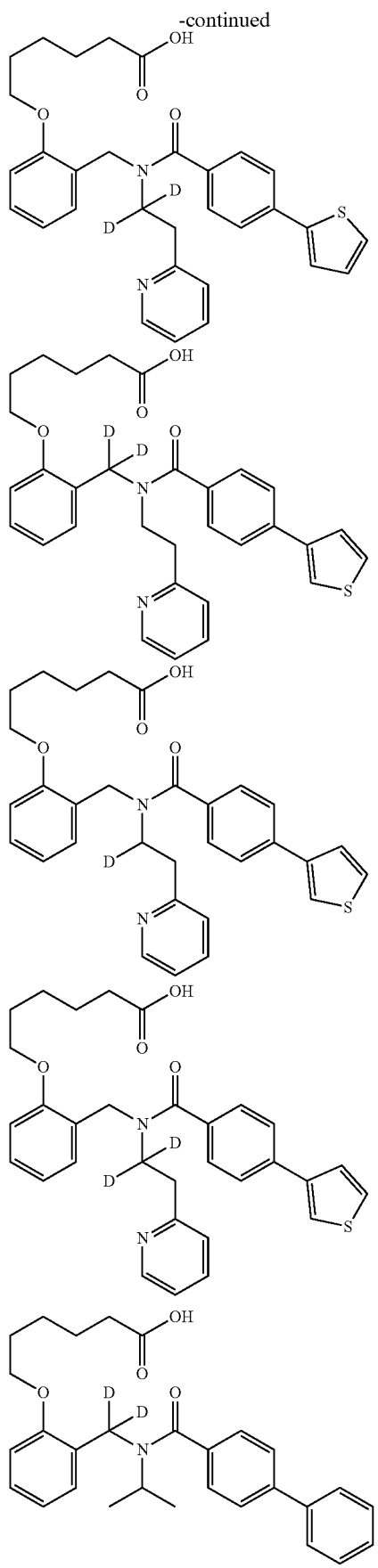
124
-continued
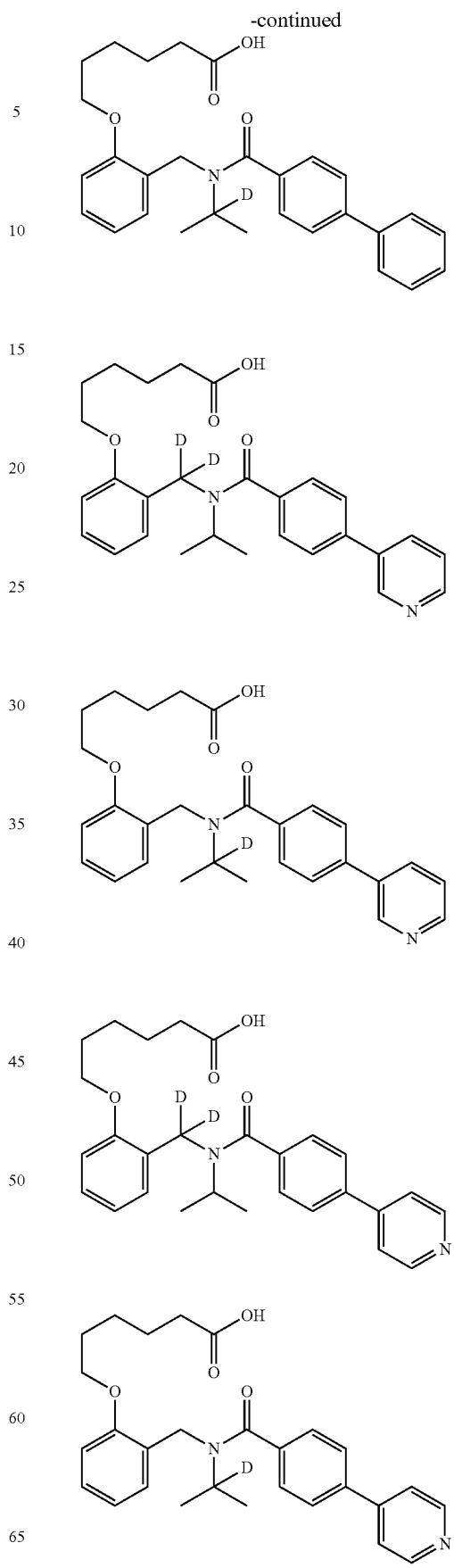

-continued
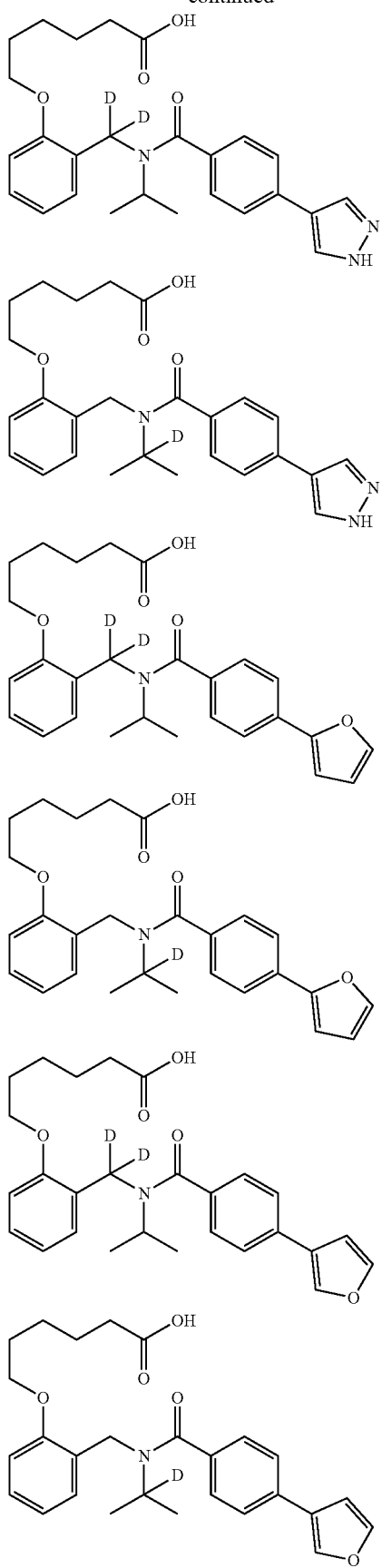
-continued
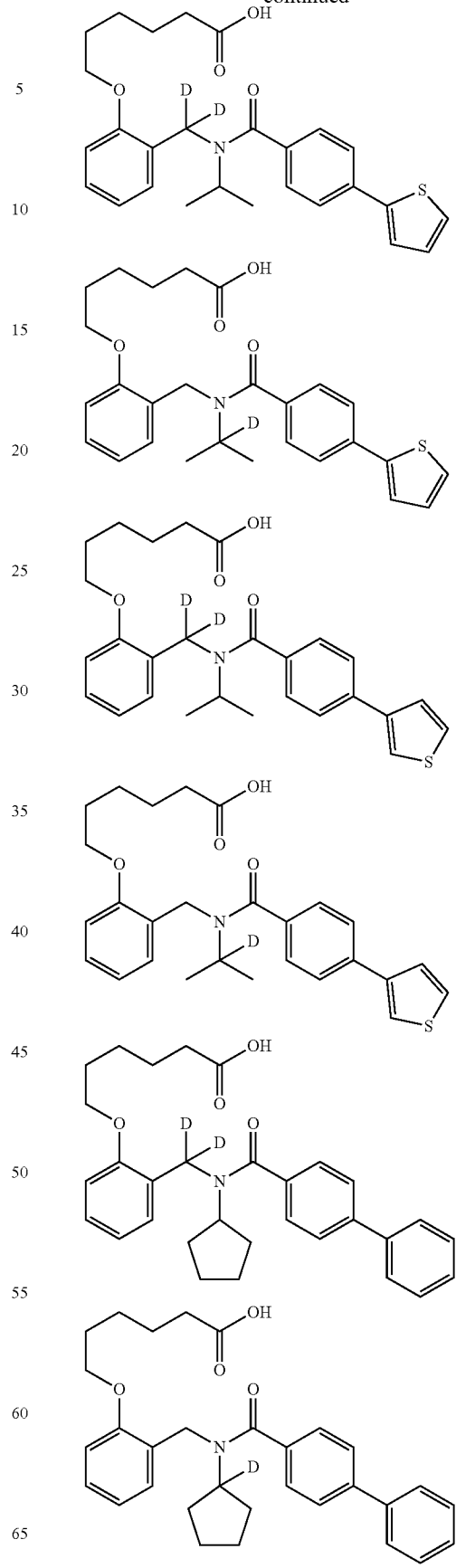

127
-continued
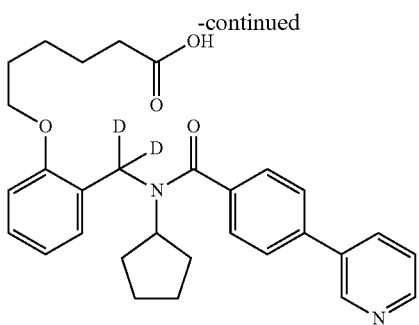
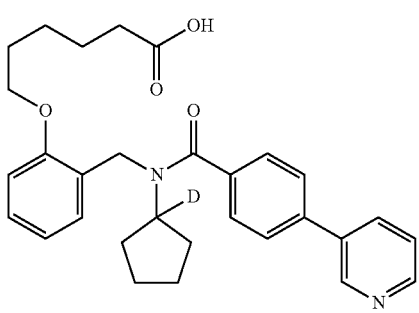
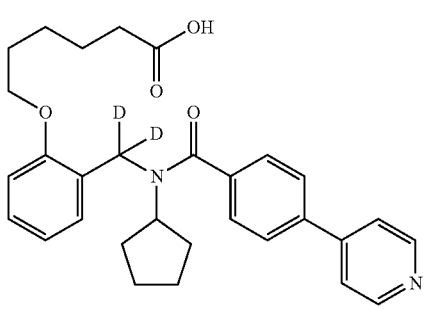
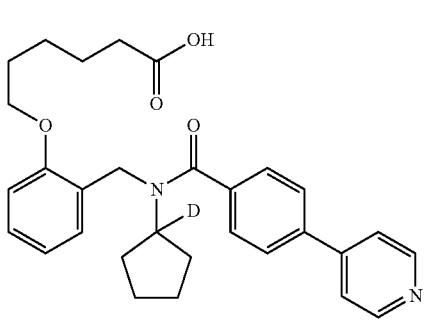
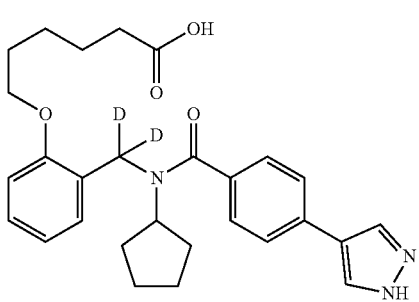
128
-continued
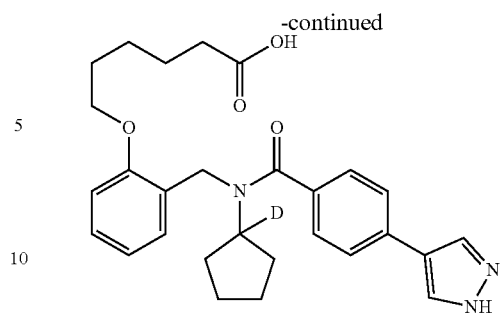
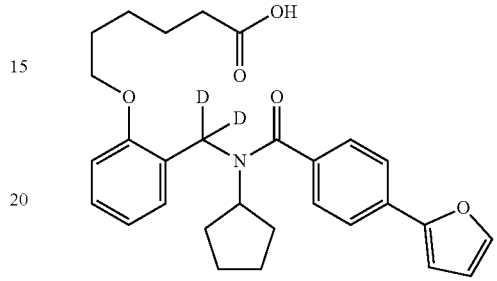
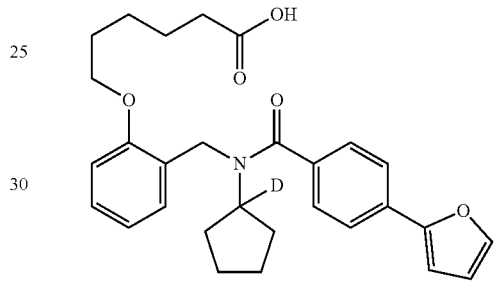

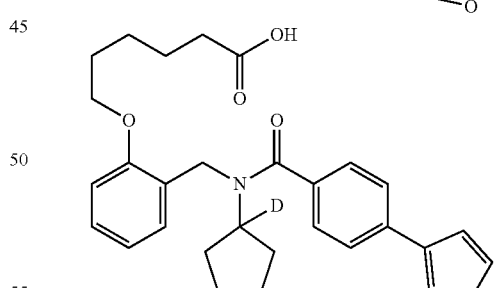
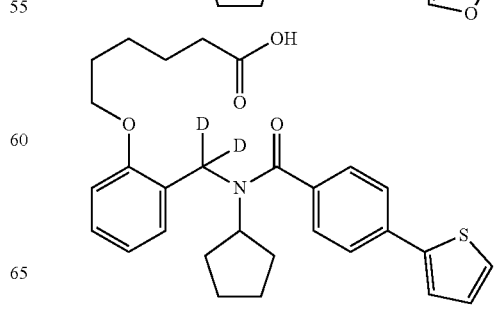

129
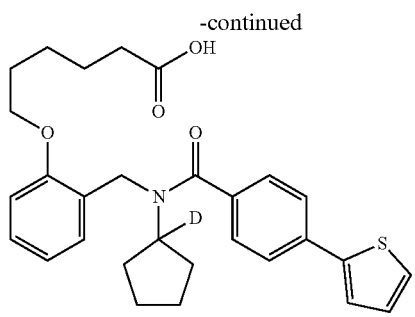
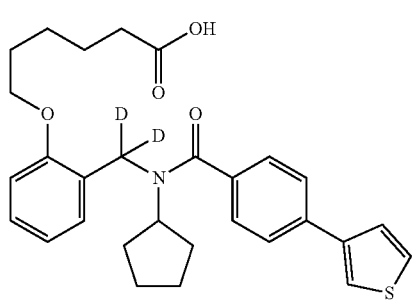
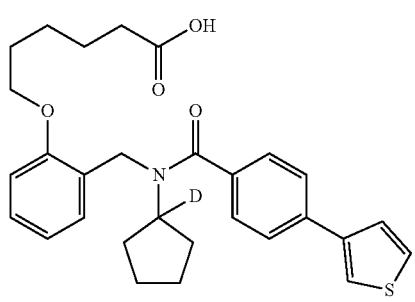
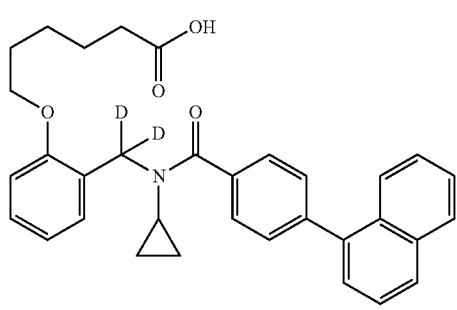
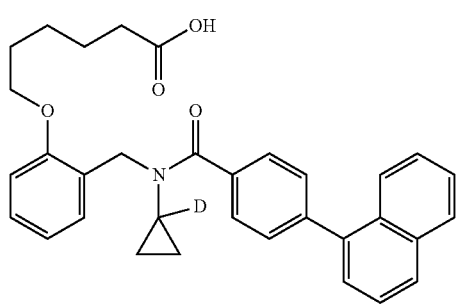
130
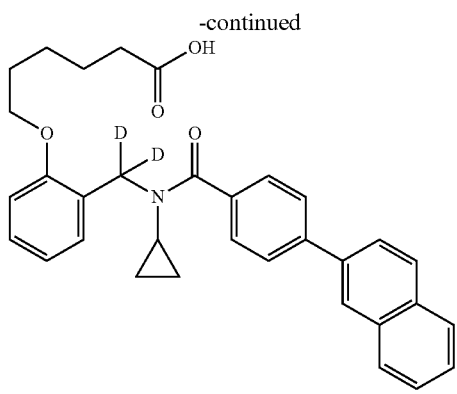
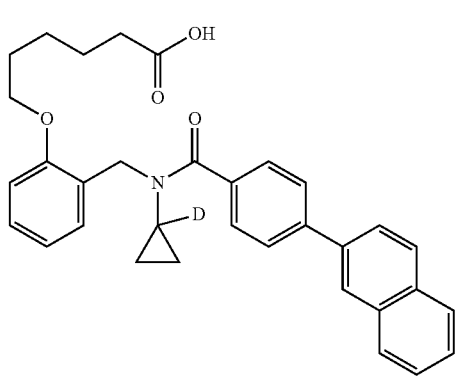
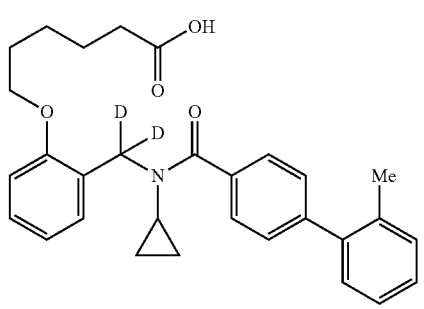
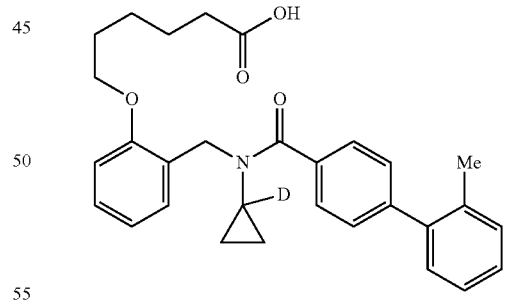
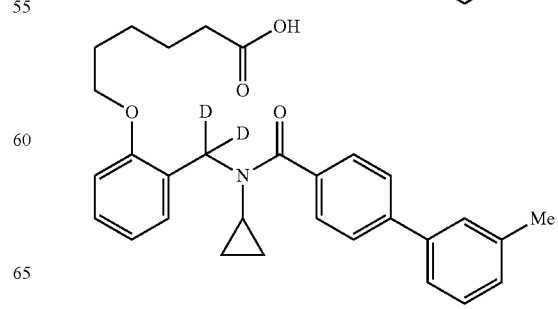

131
-continued
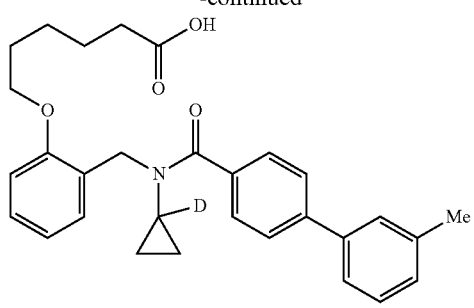
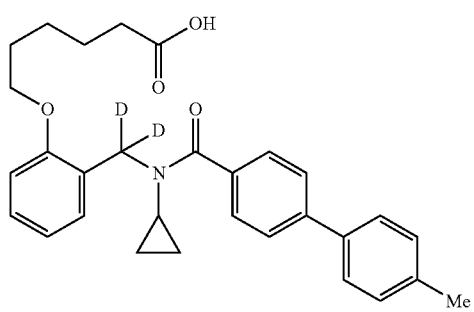
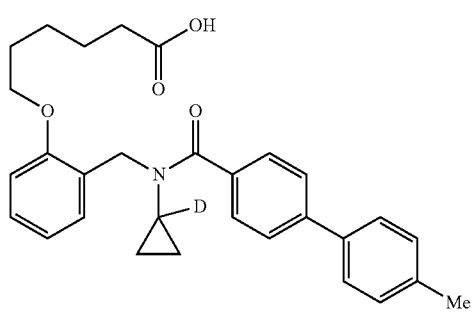
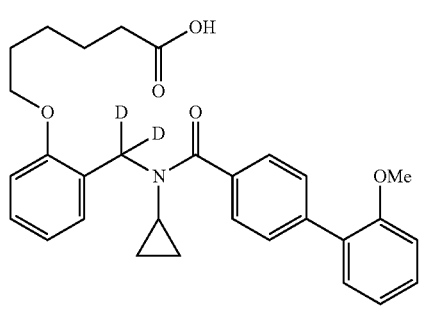
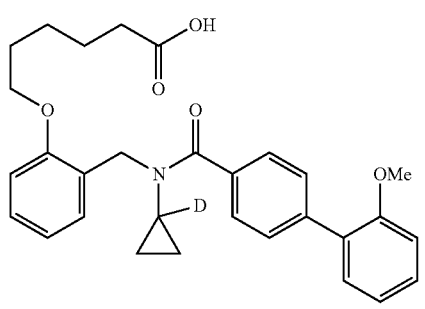
132
-continued
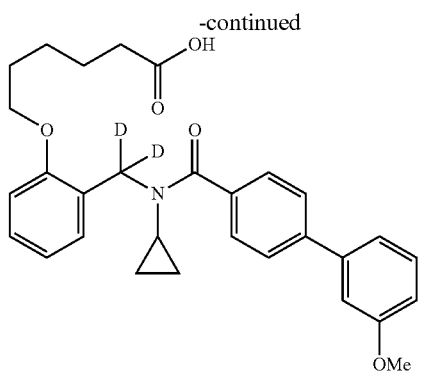
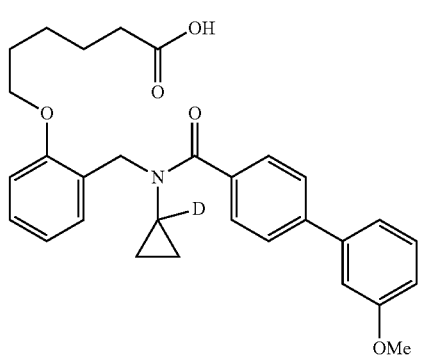
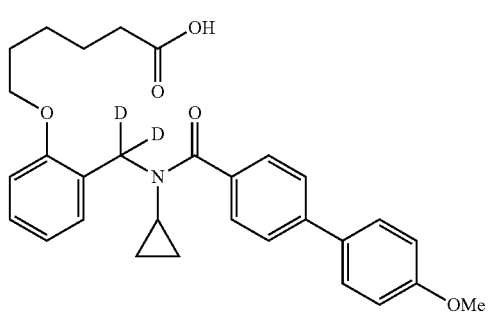
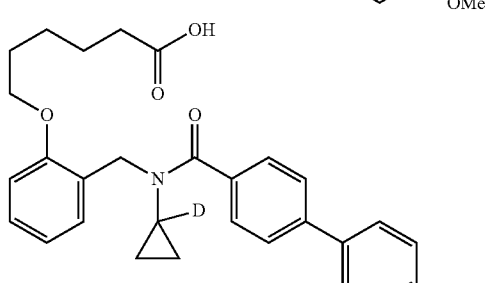
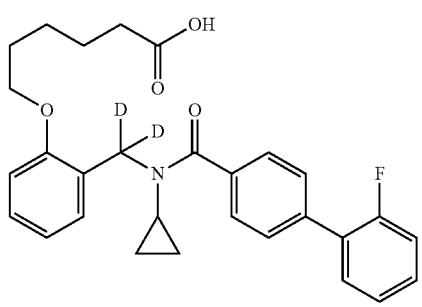

133
-continued

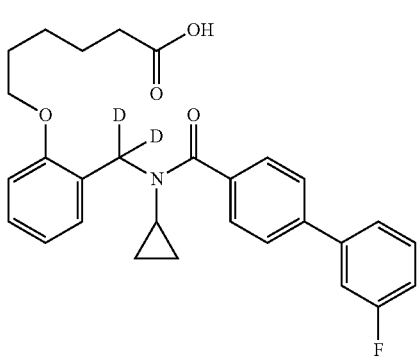
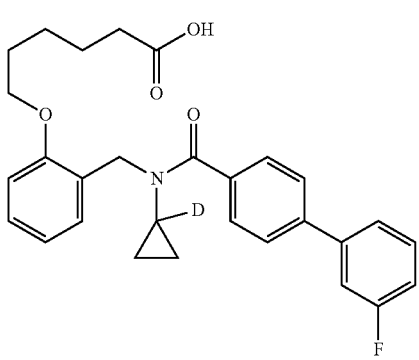
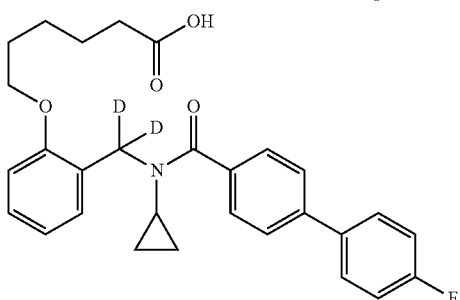
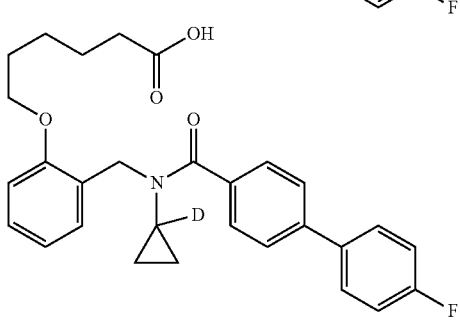
134
-continued
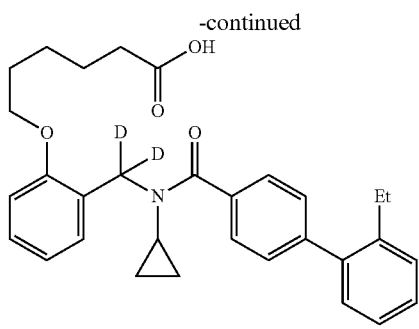
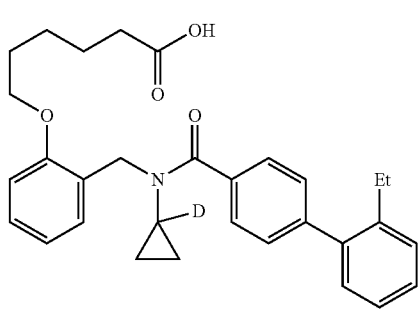
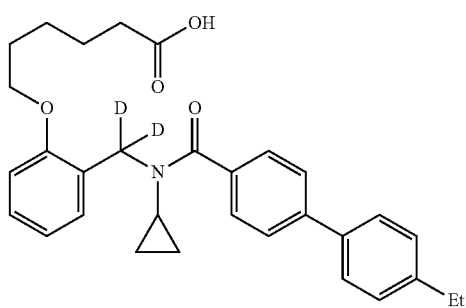
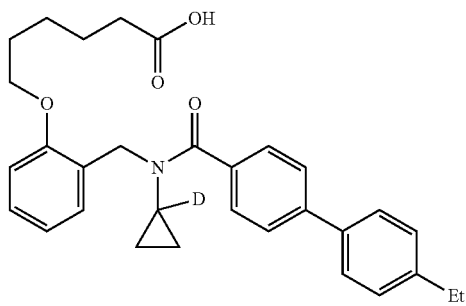
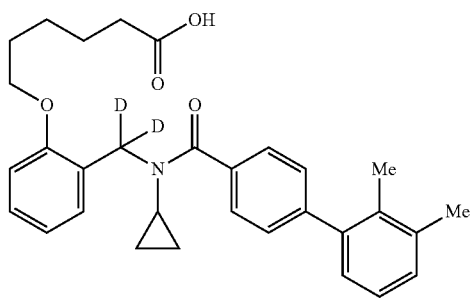

135
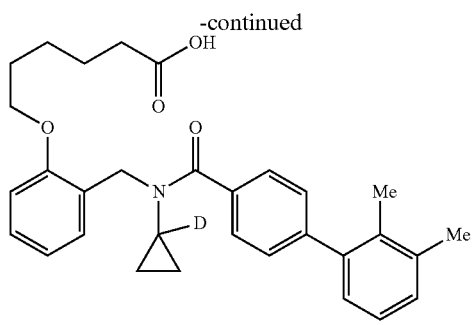
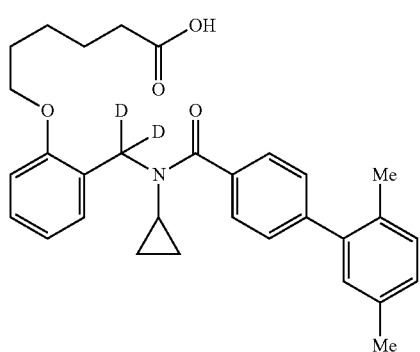
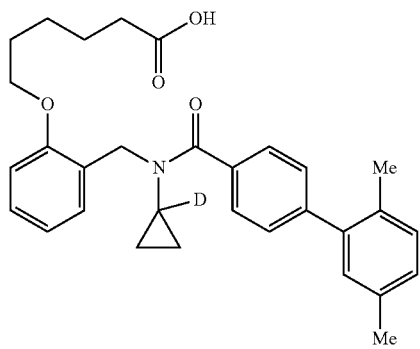
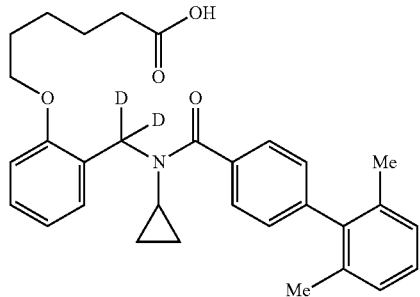
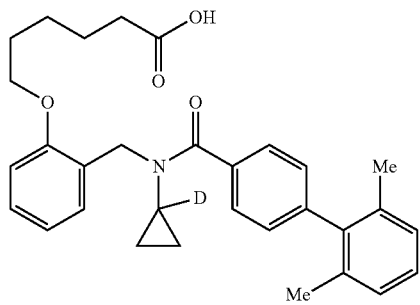
136
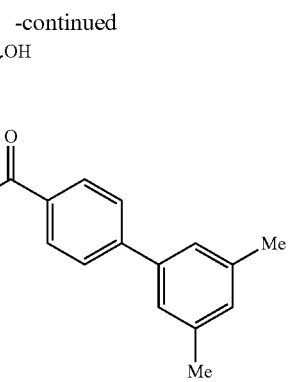
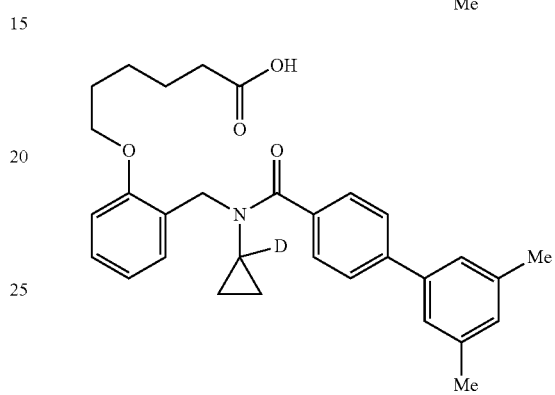
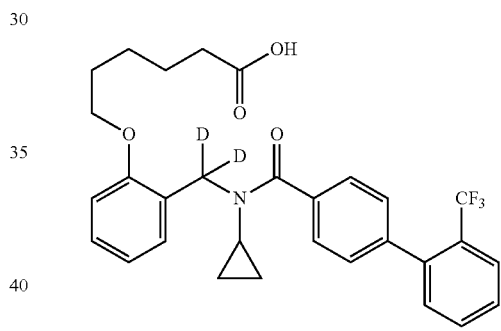
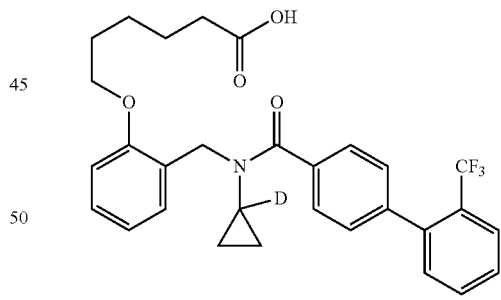
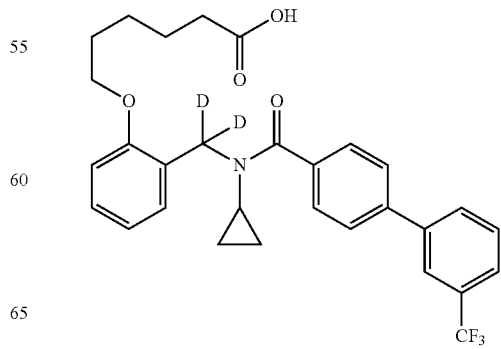

137
-continued
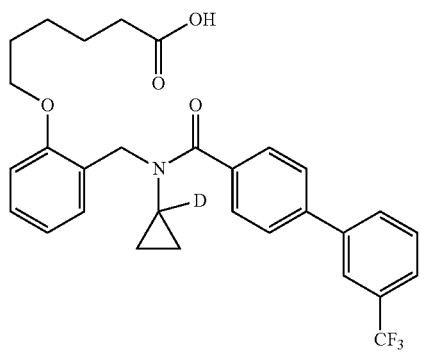
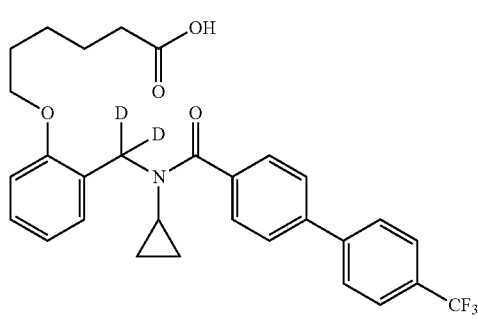
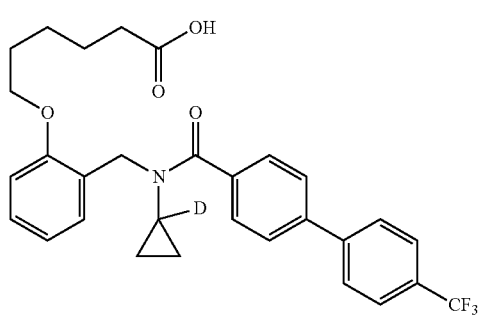
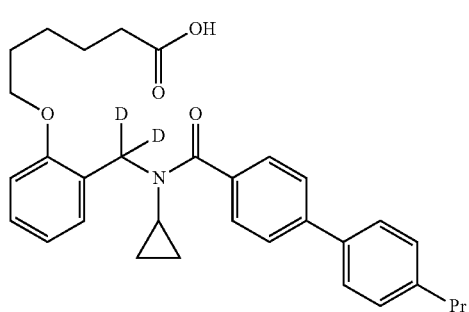
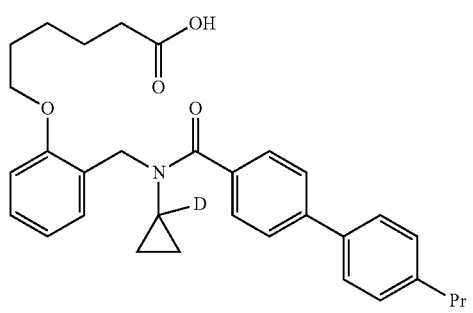
138
-continued
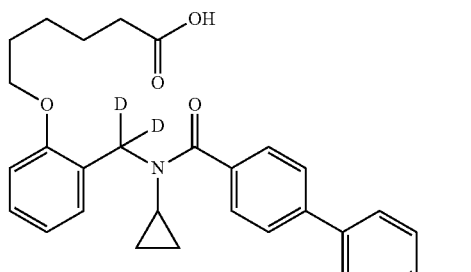
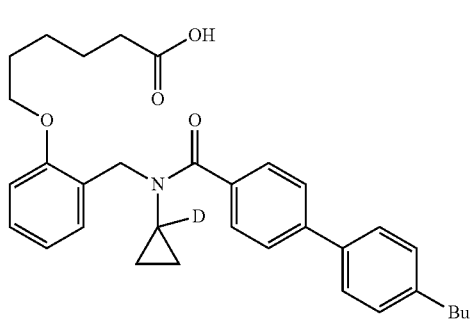
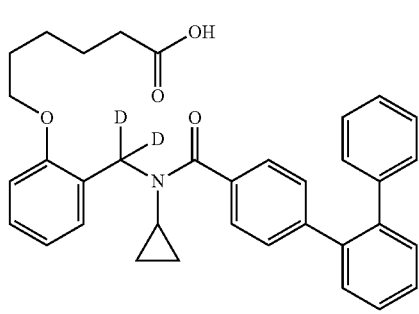
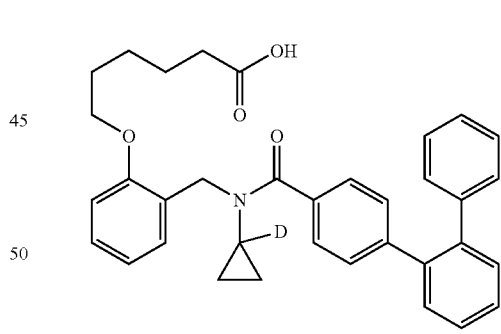
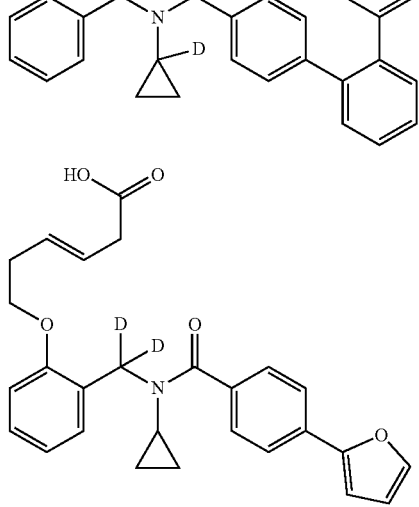

139
-continued
140
-continued
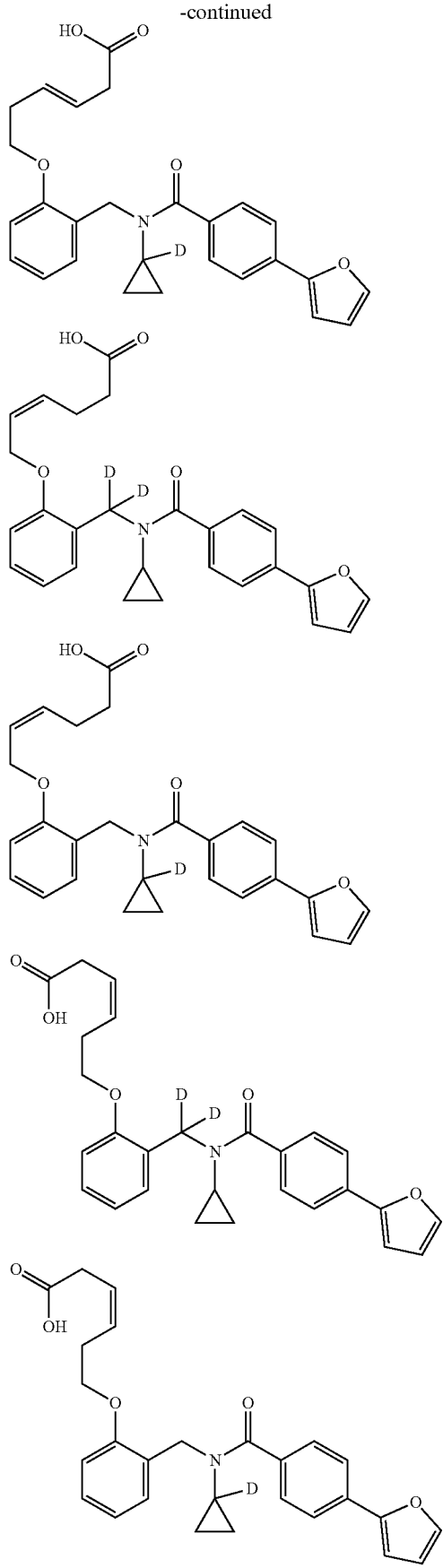
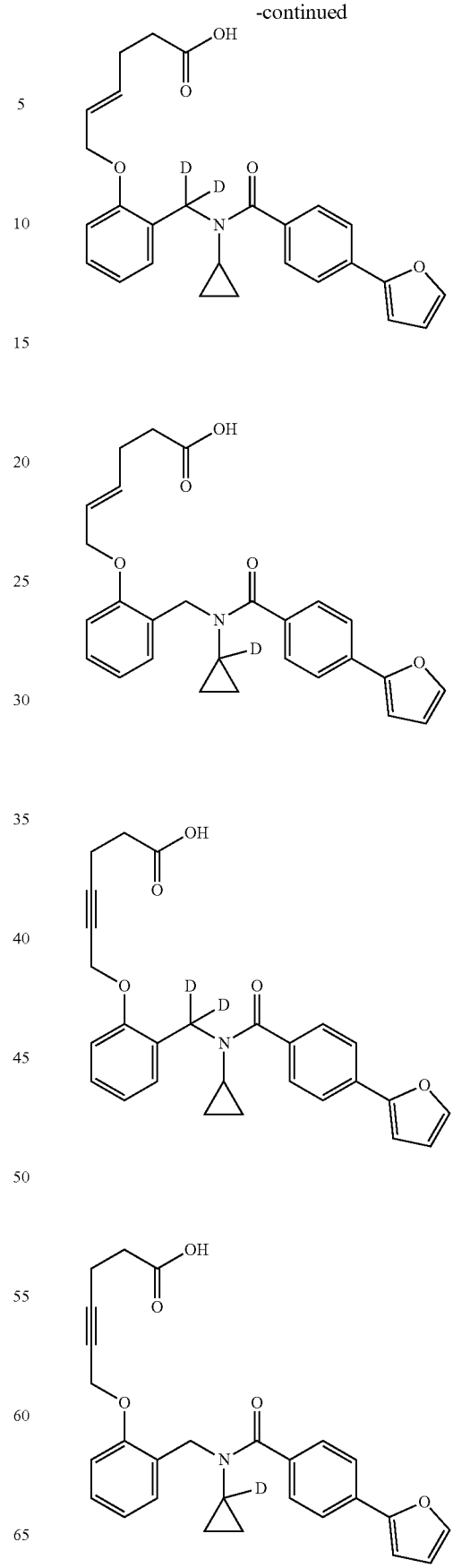

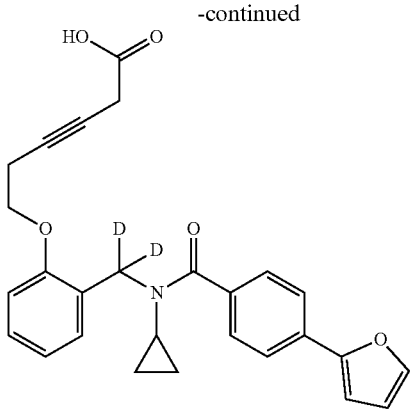
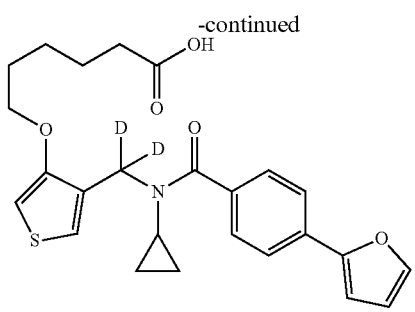
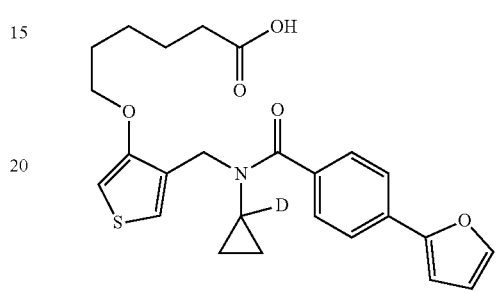
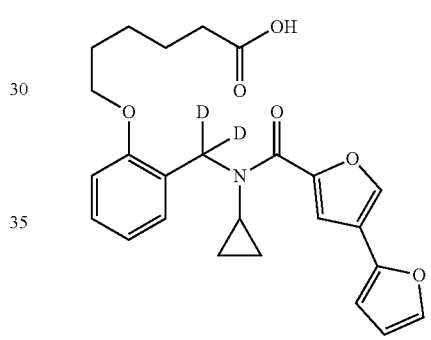
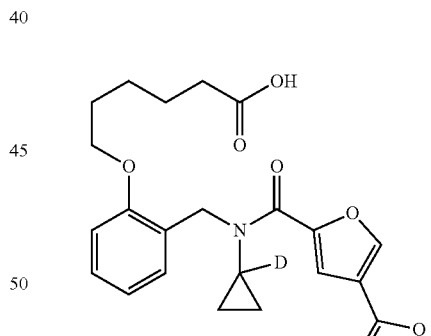
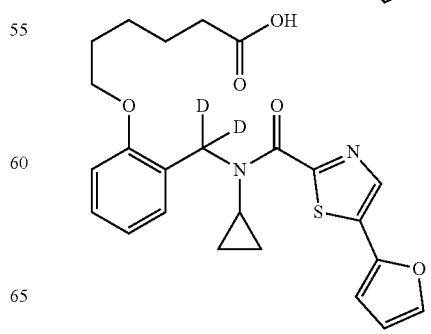

143
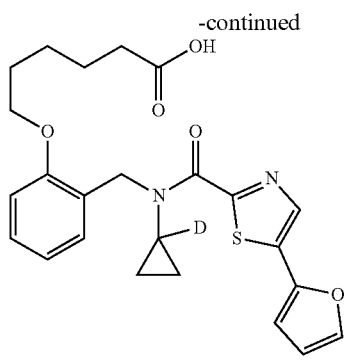
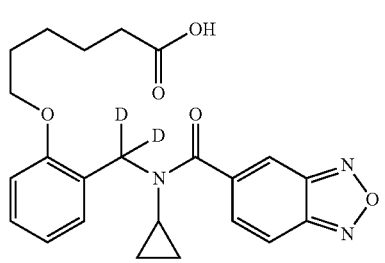
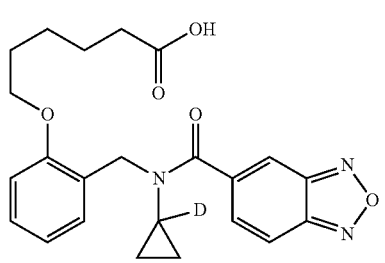
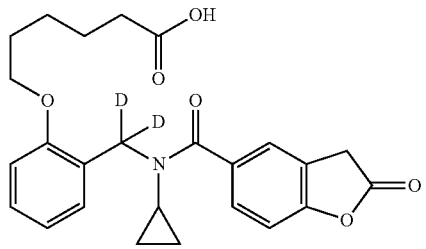
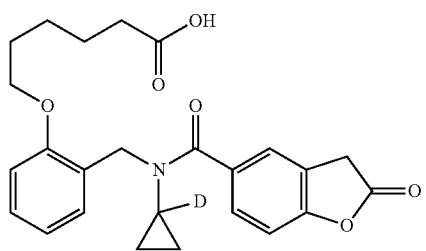
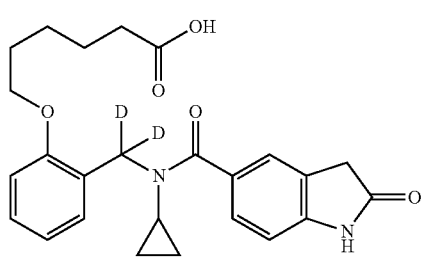
144
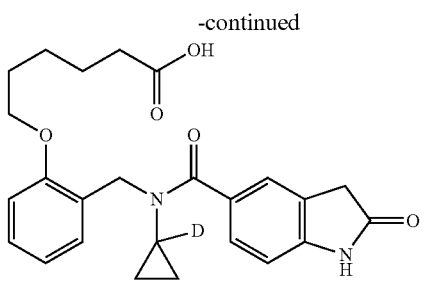
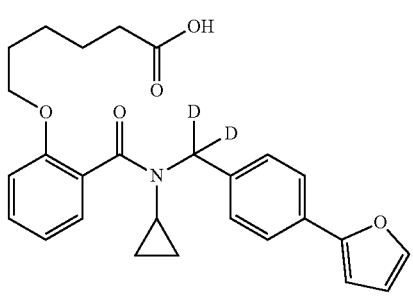
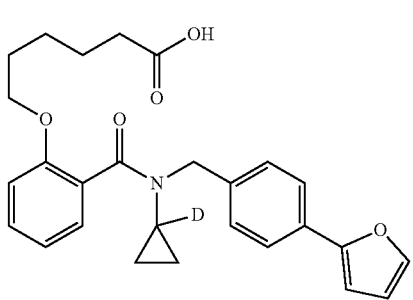
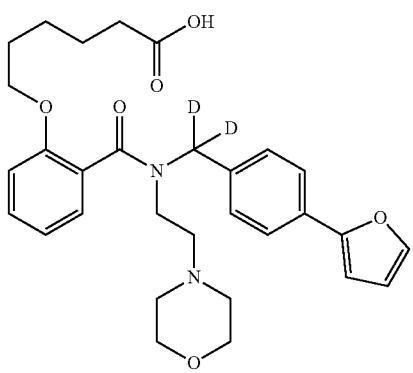
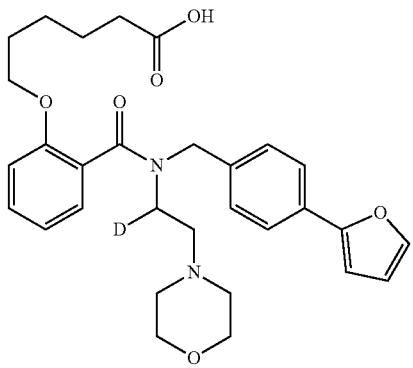

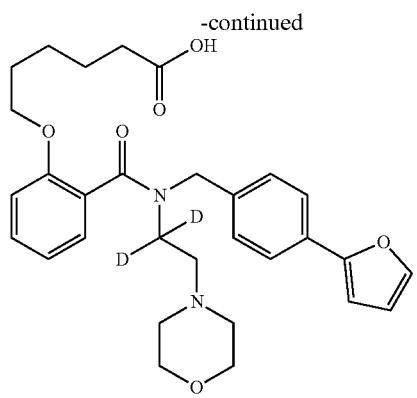
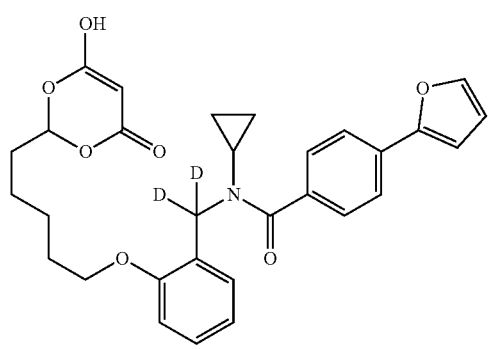
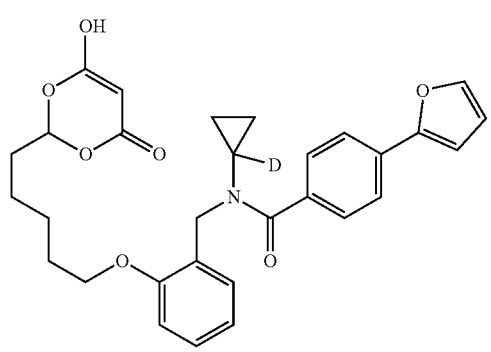
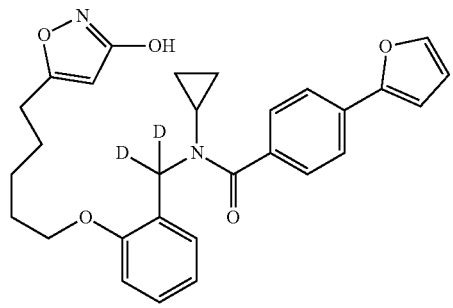
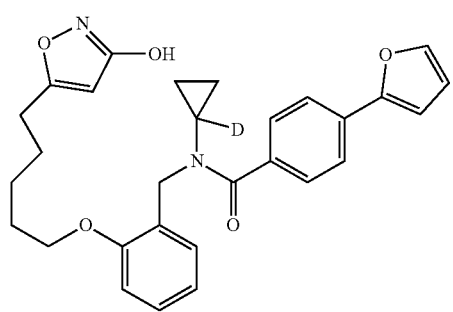
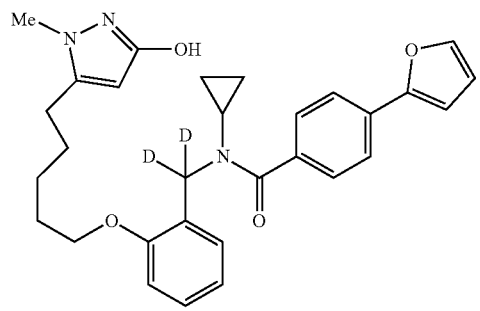
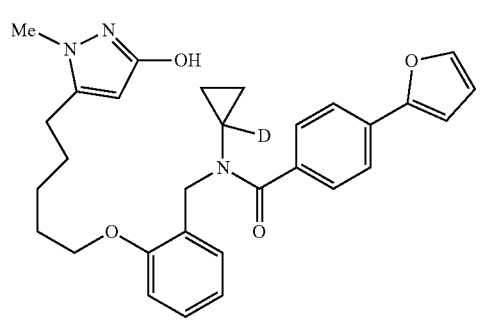
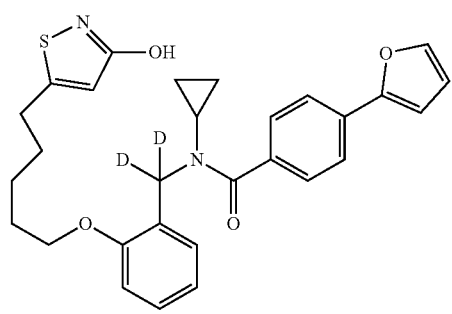
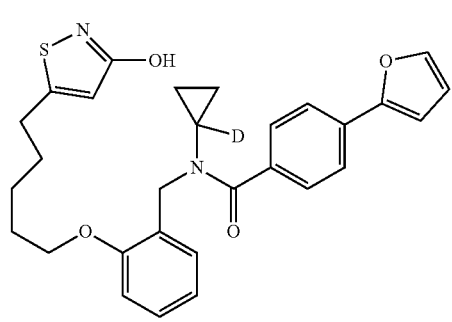
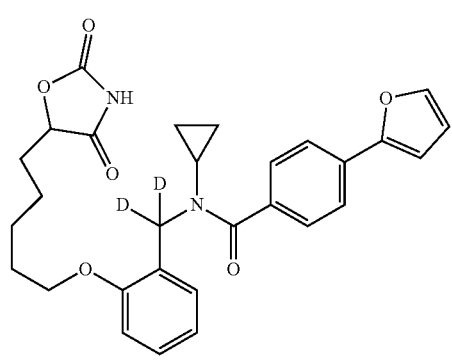

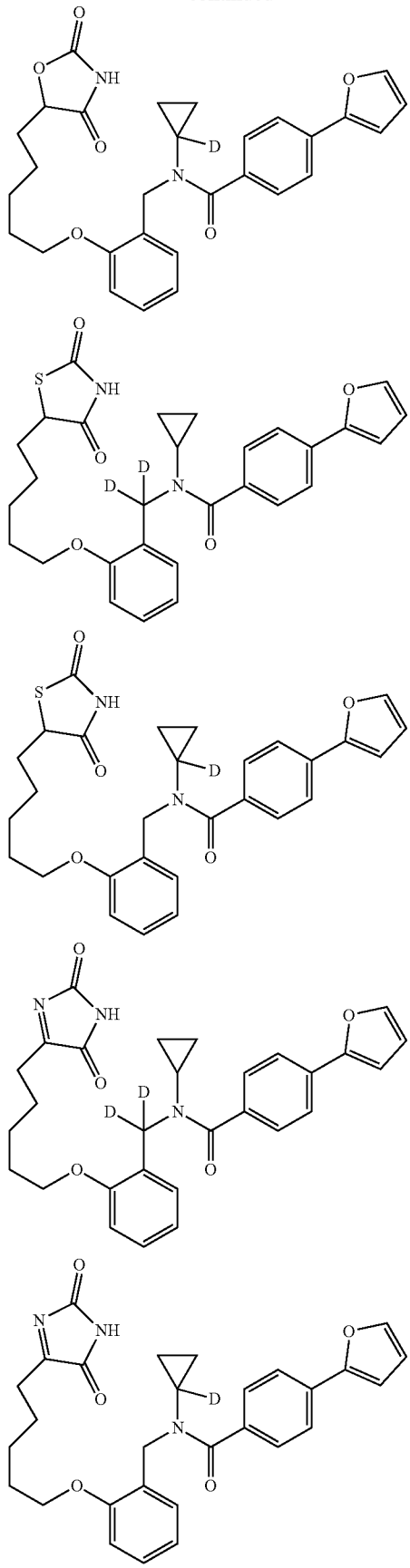
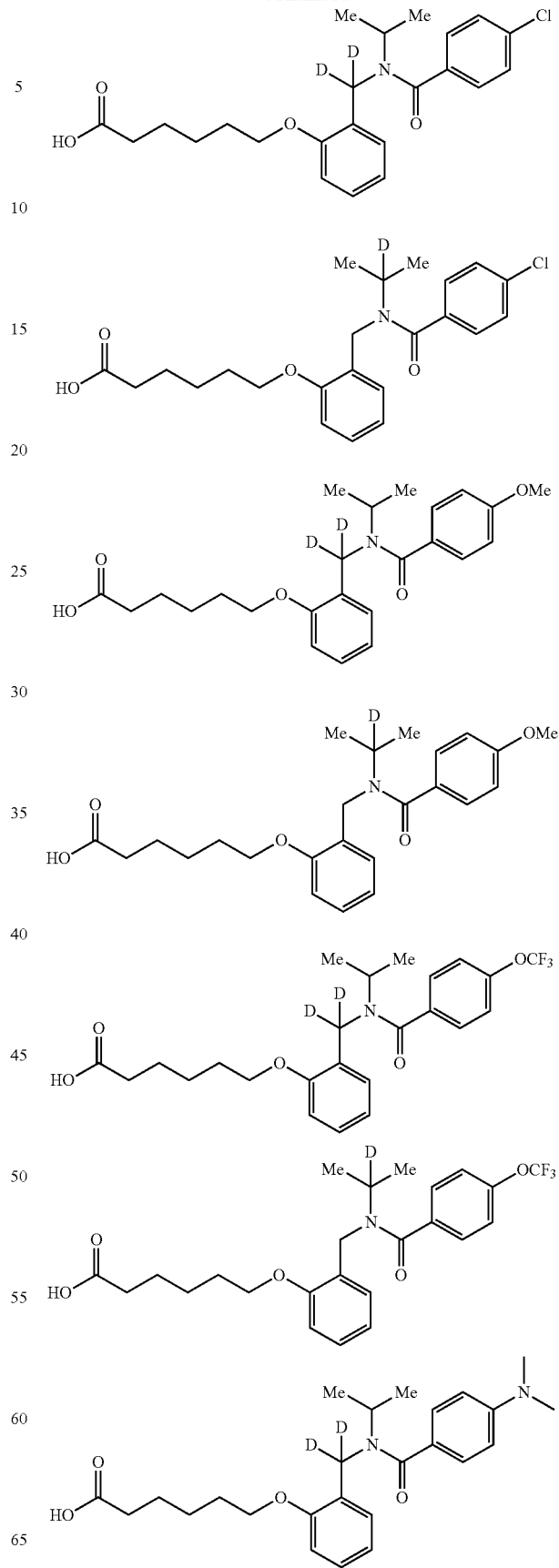

149
-continued
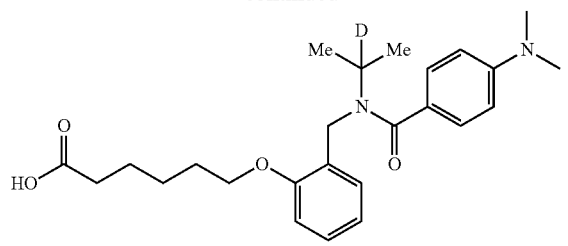
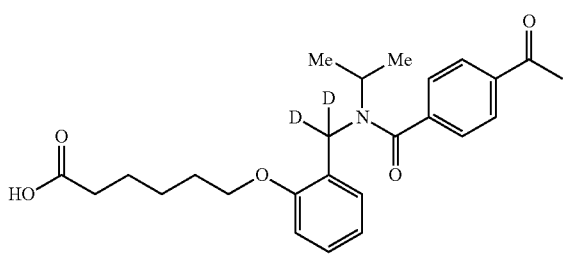
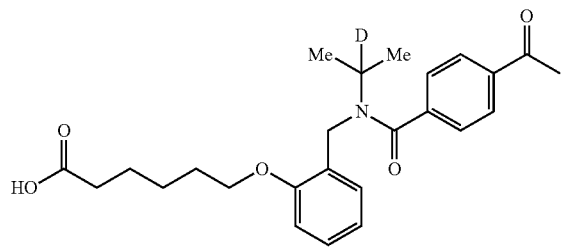
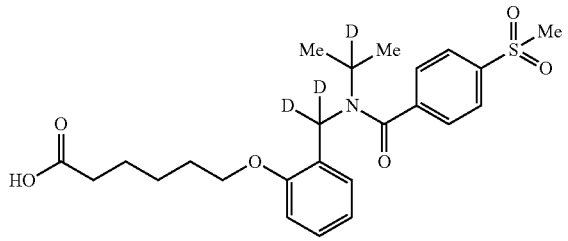
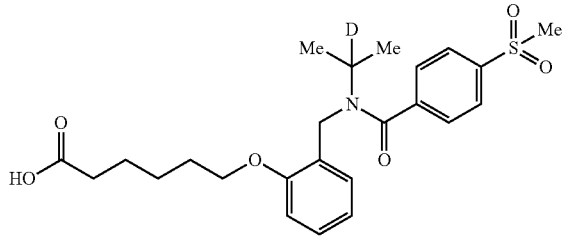
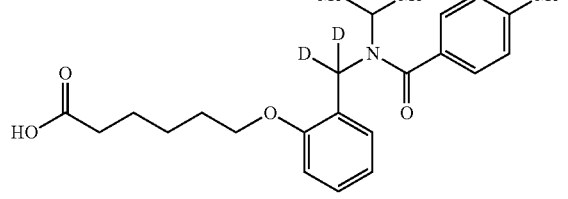
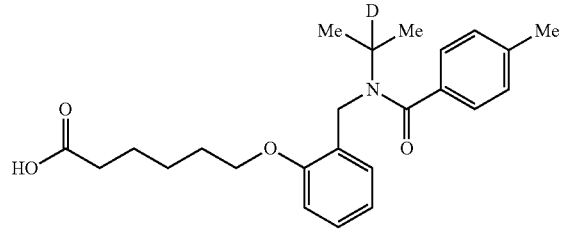
150
-continued
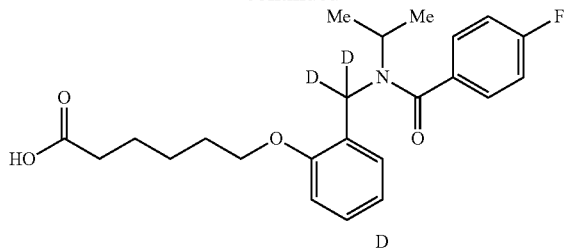
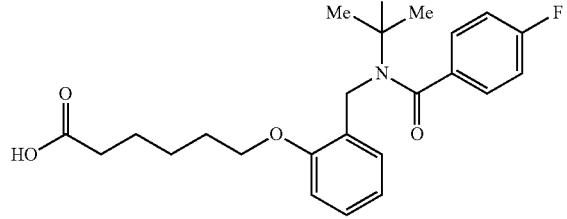
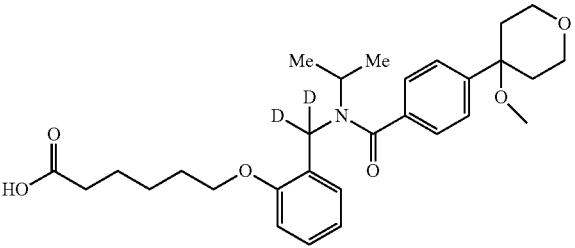
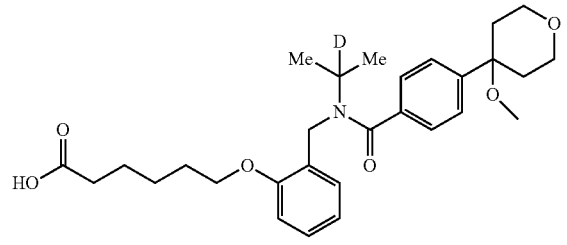
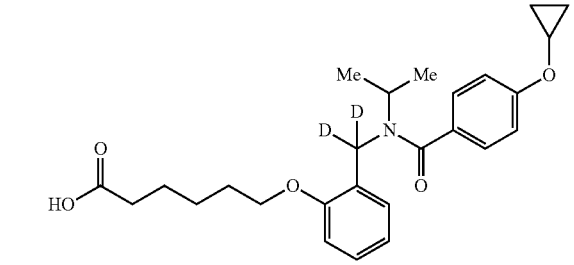
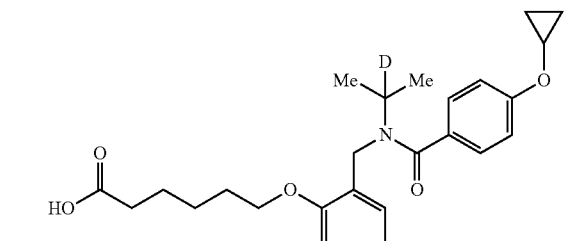
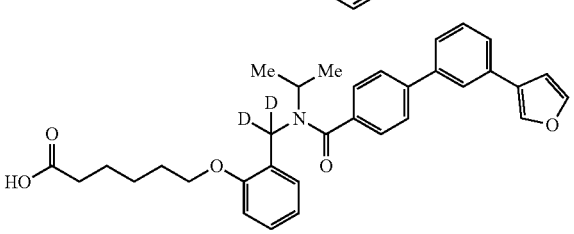

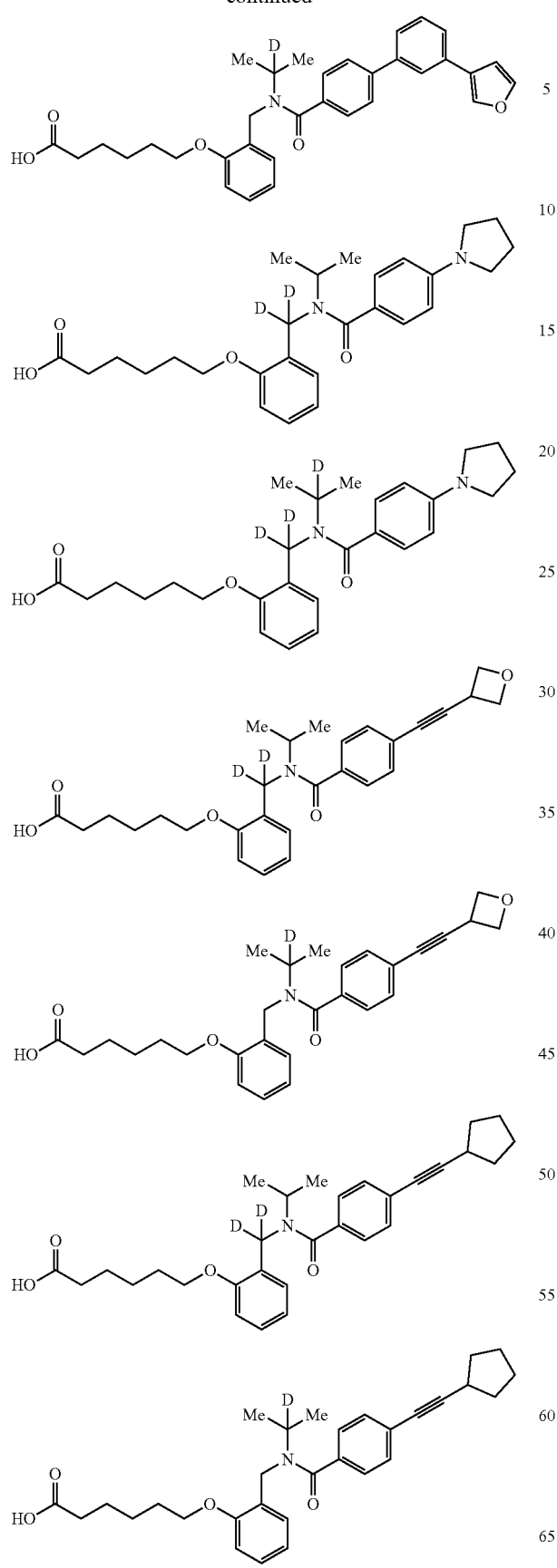
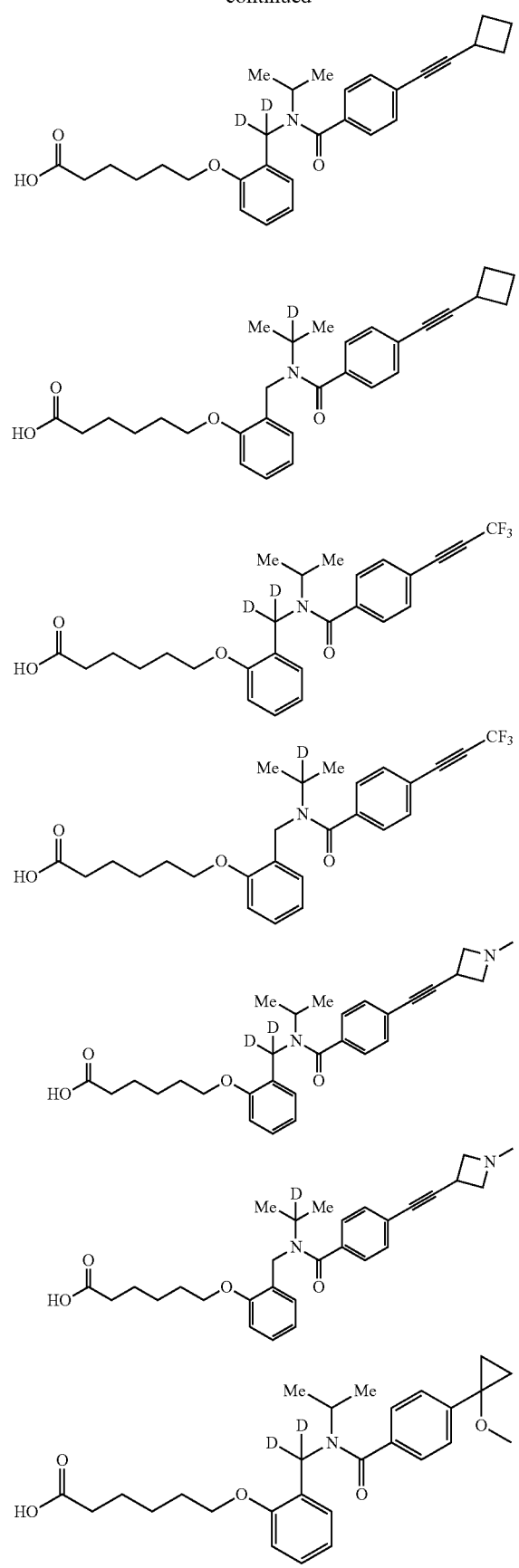

153
-continued
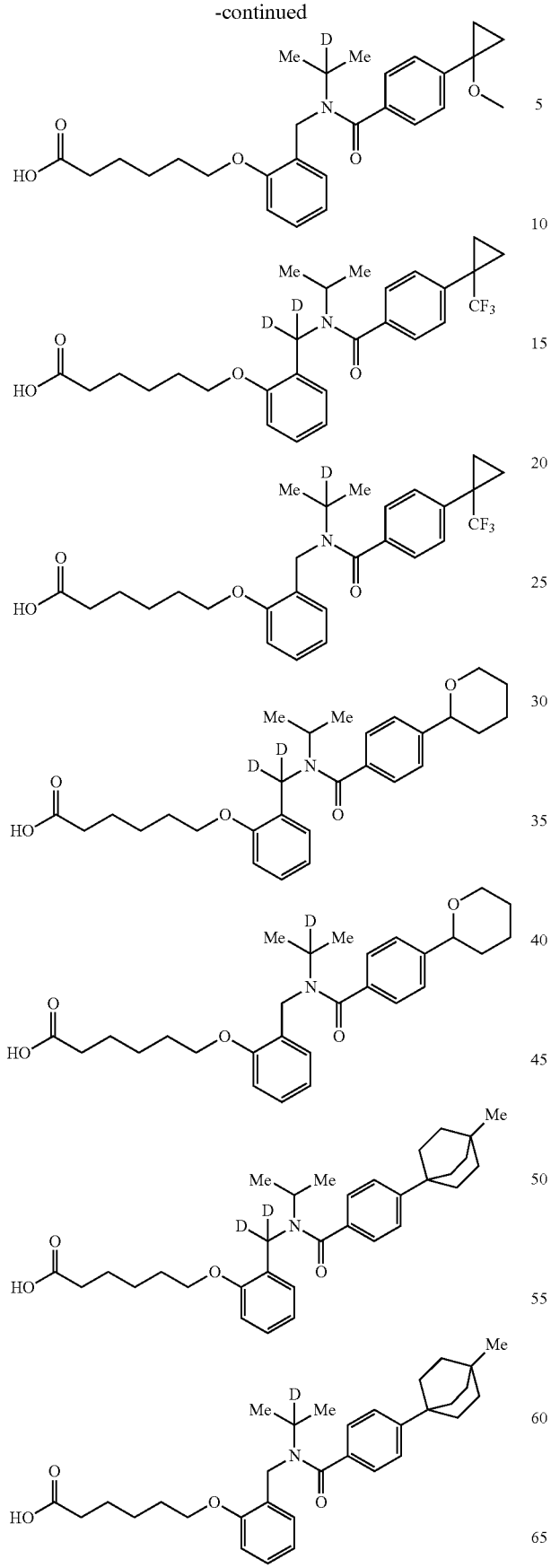
154
-continued
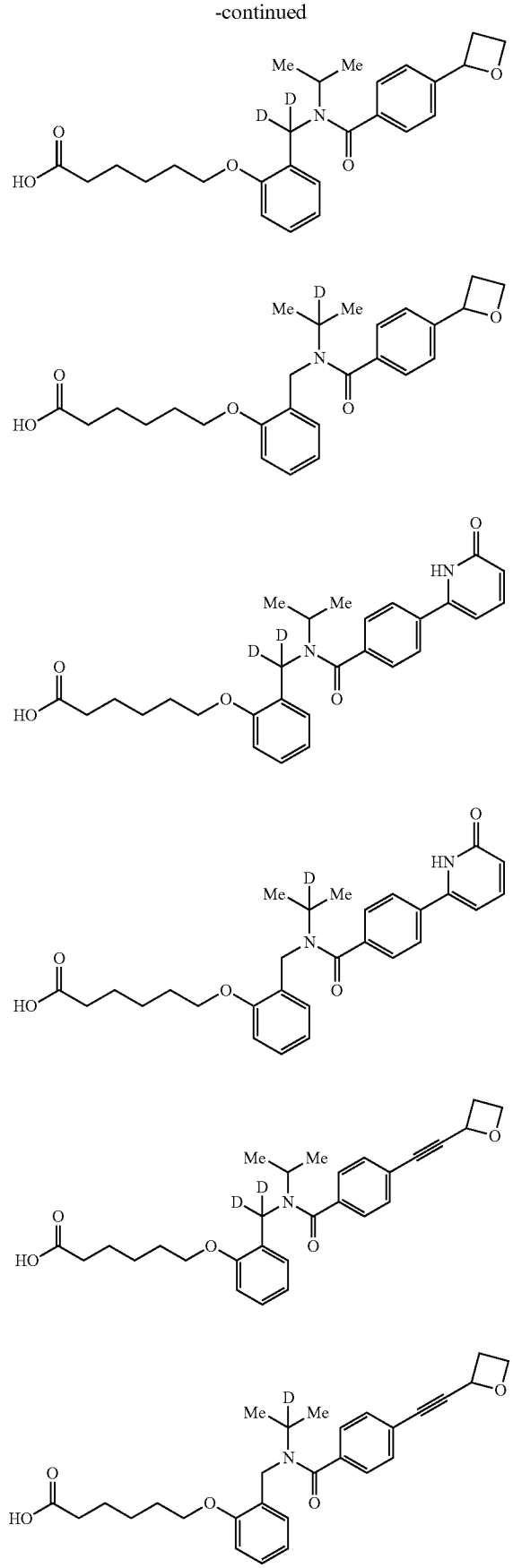

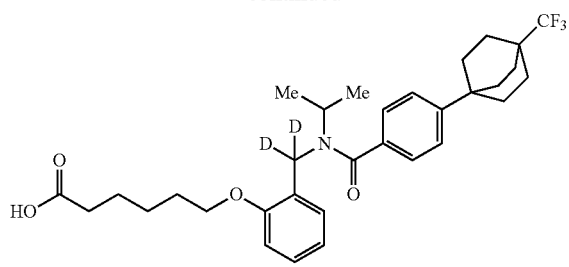
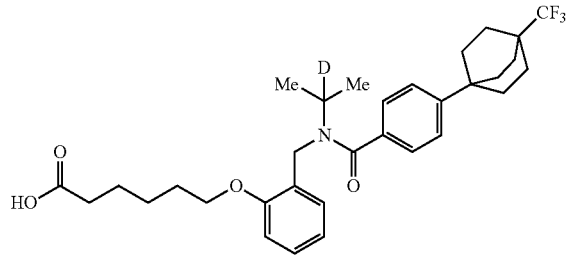
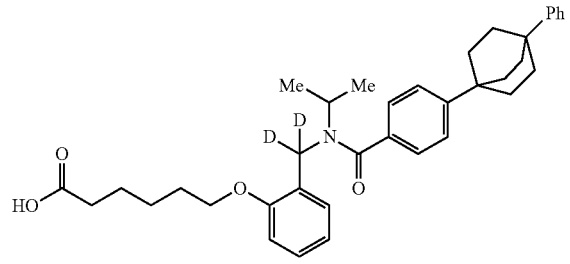
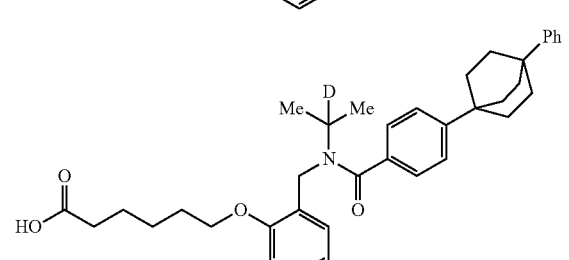
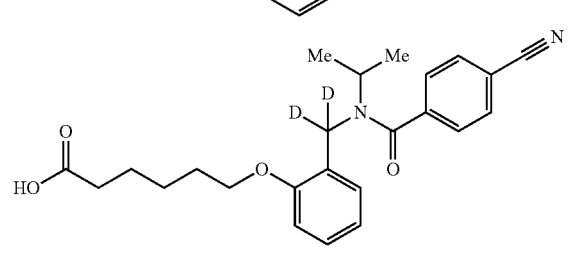
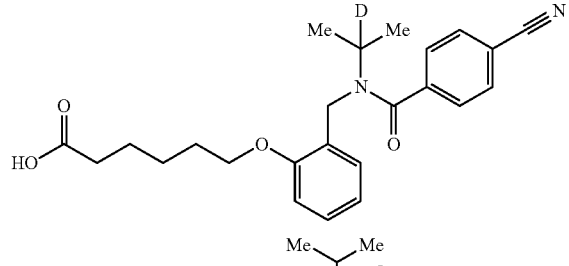
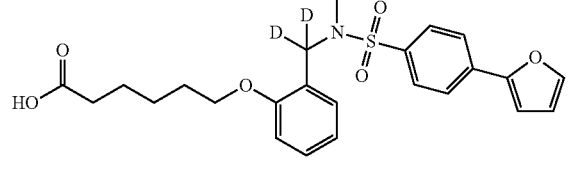
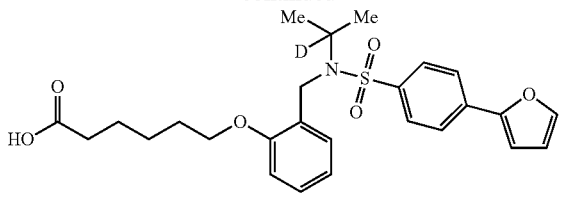
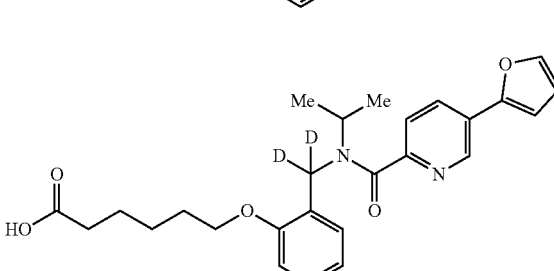
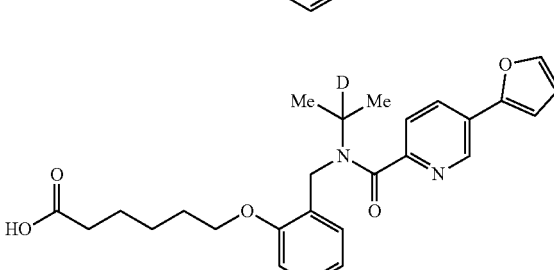
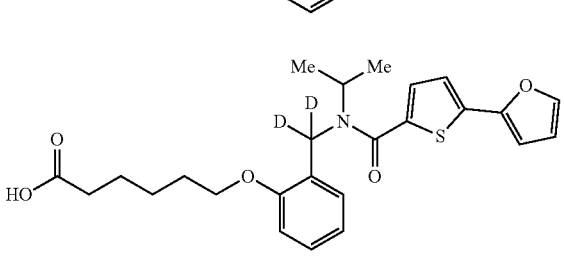
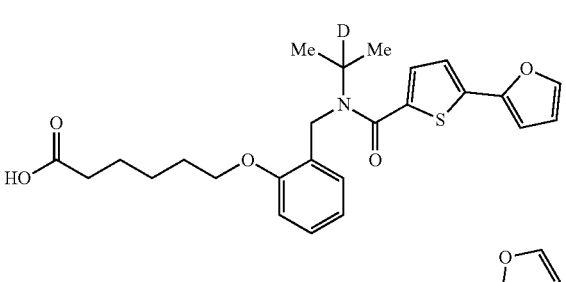
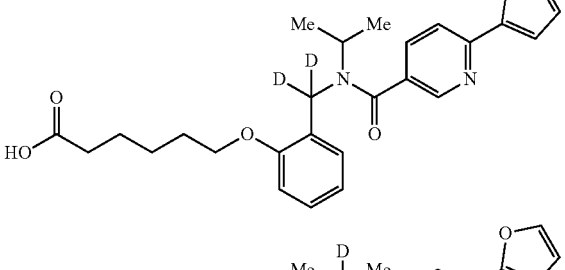
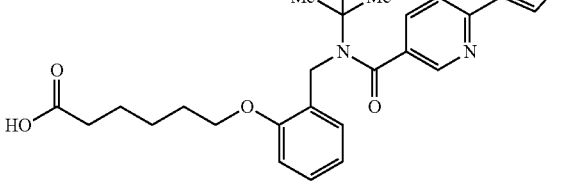

-continued
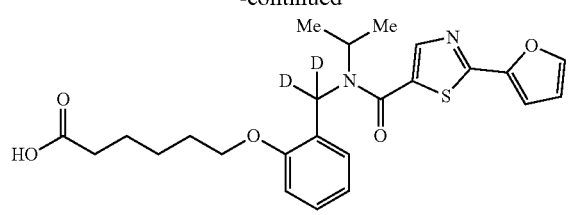
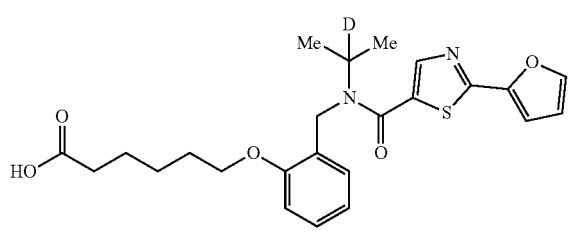
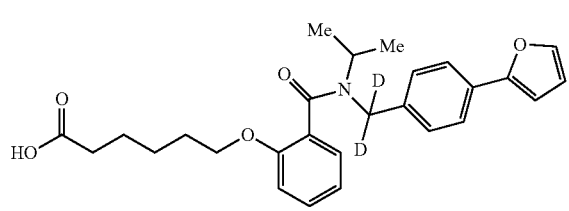
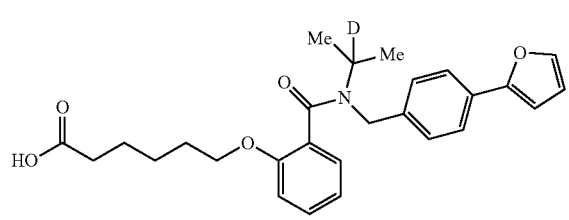
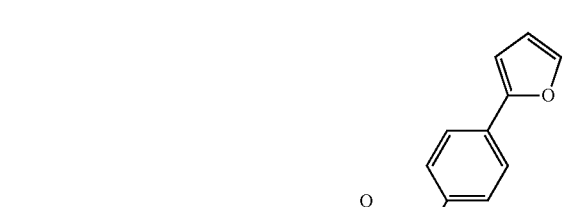
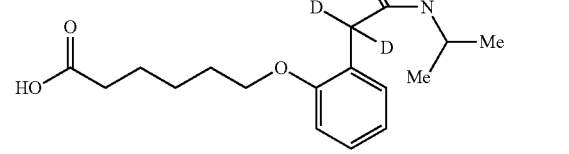
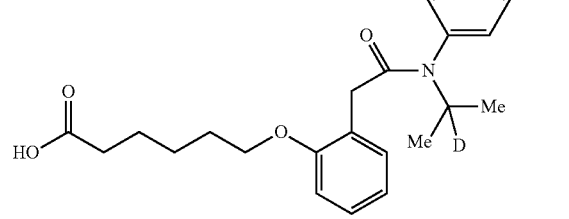
-continued
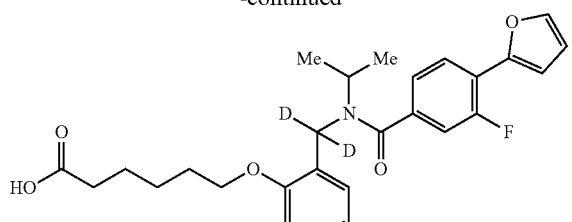
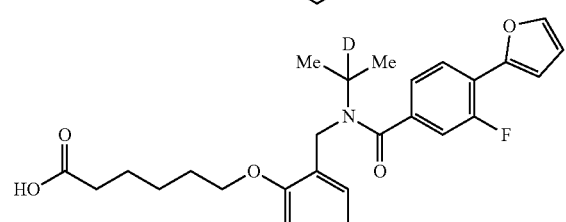
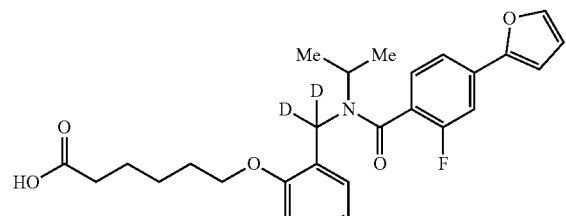
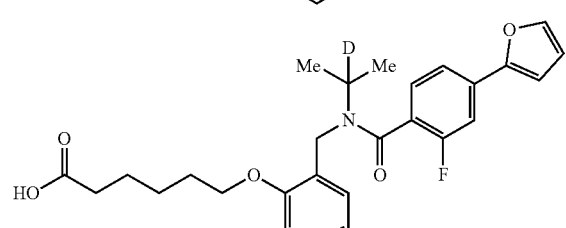
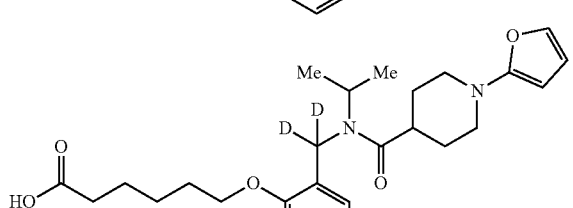
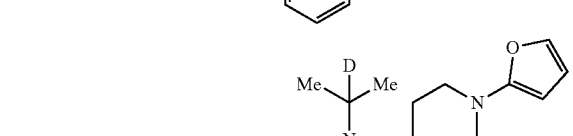
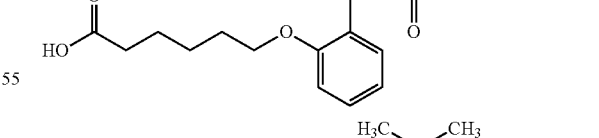
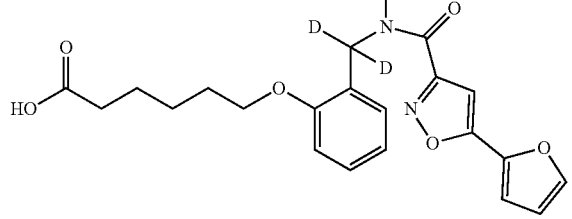

159
-continued
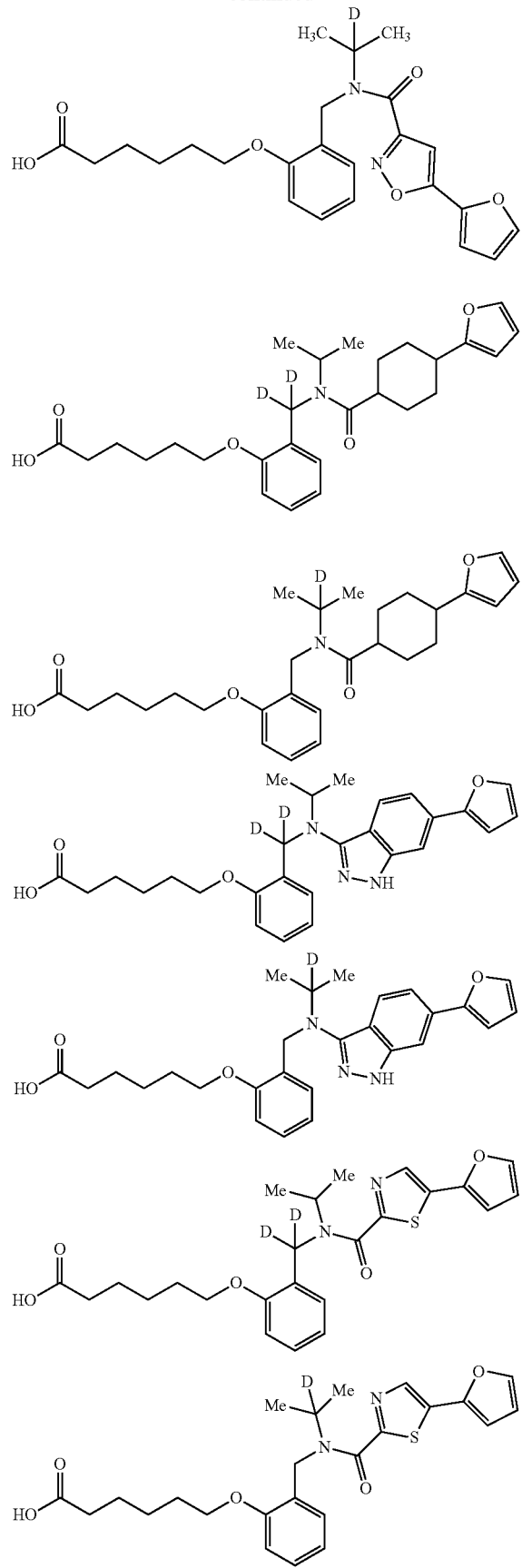
160
-continued
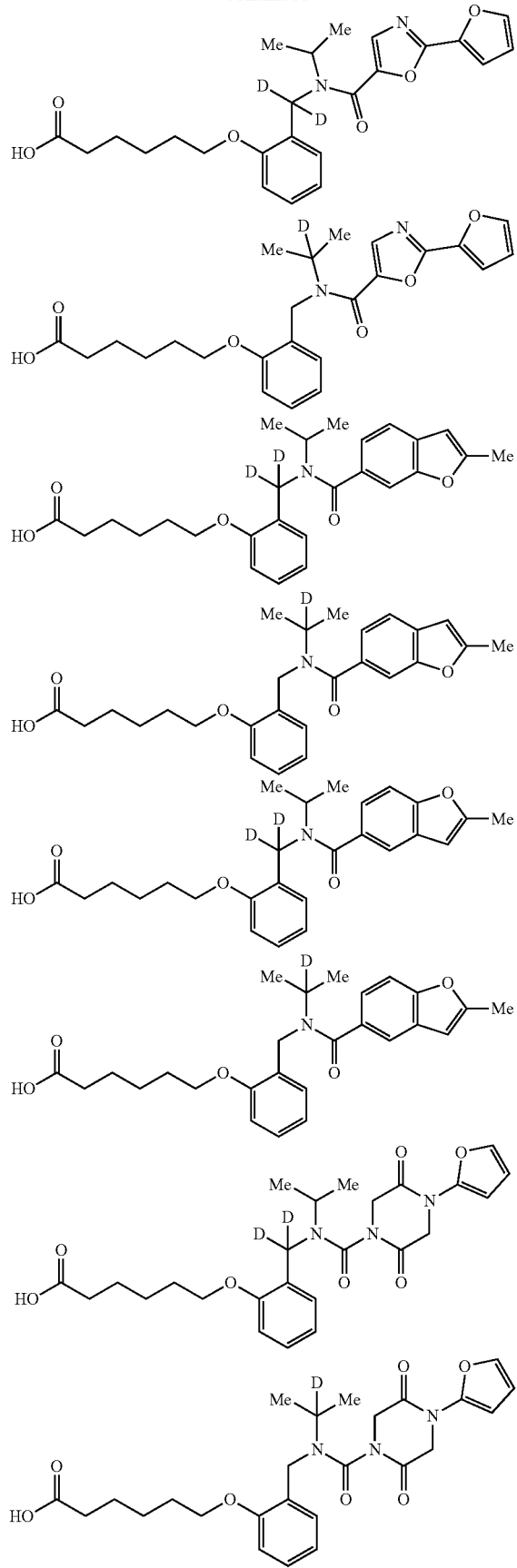

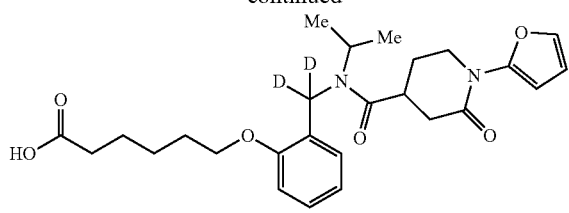
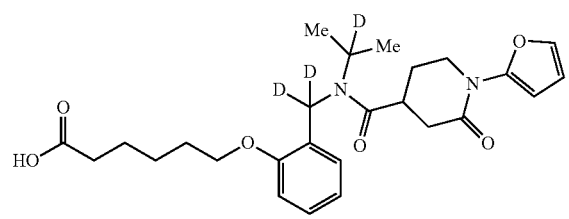
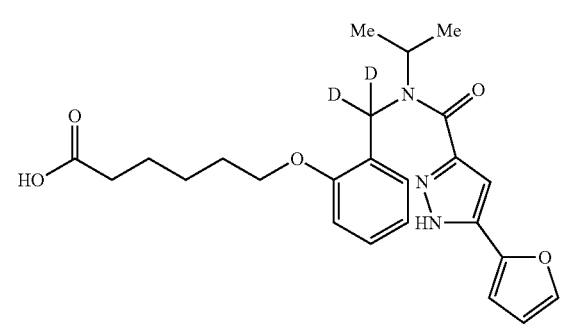
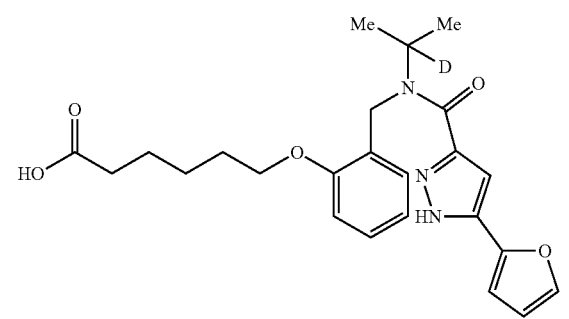
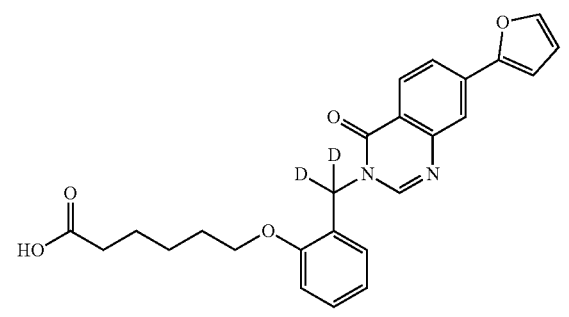
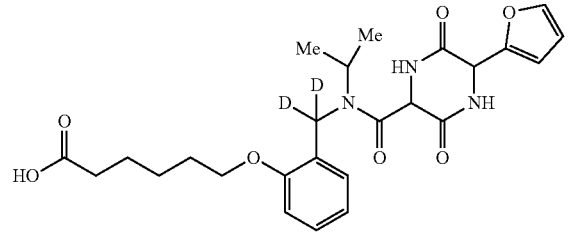
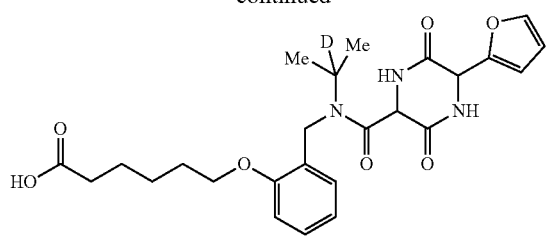
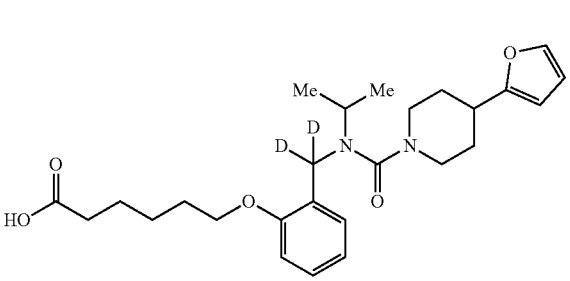
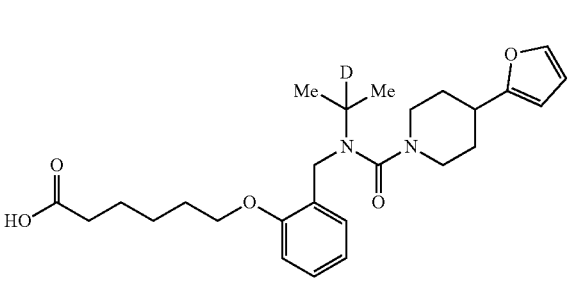
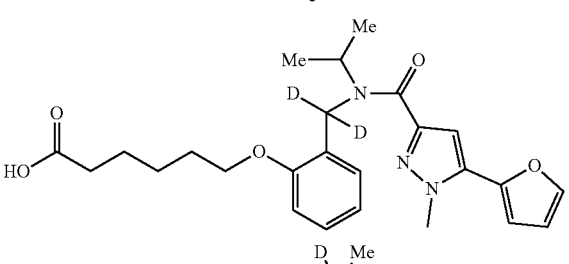
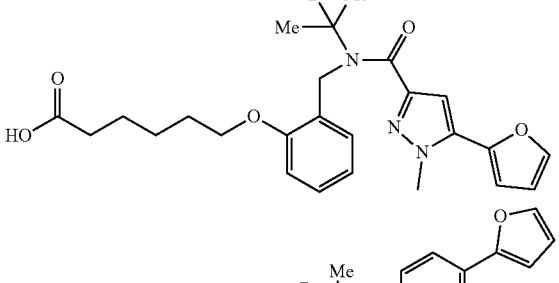
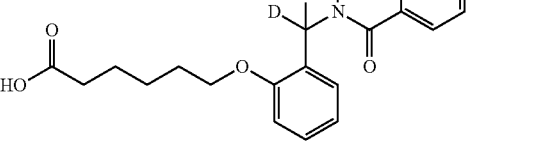
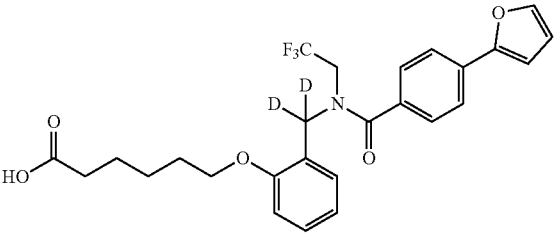

163
-continued
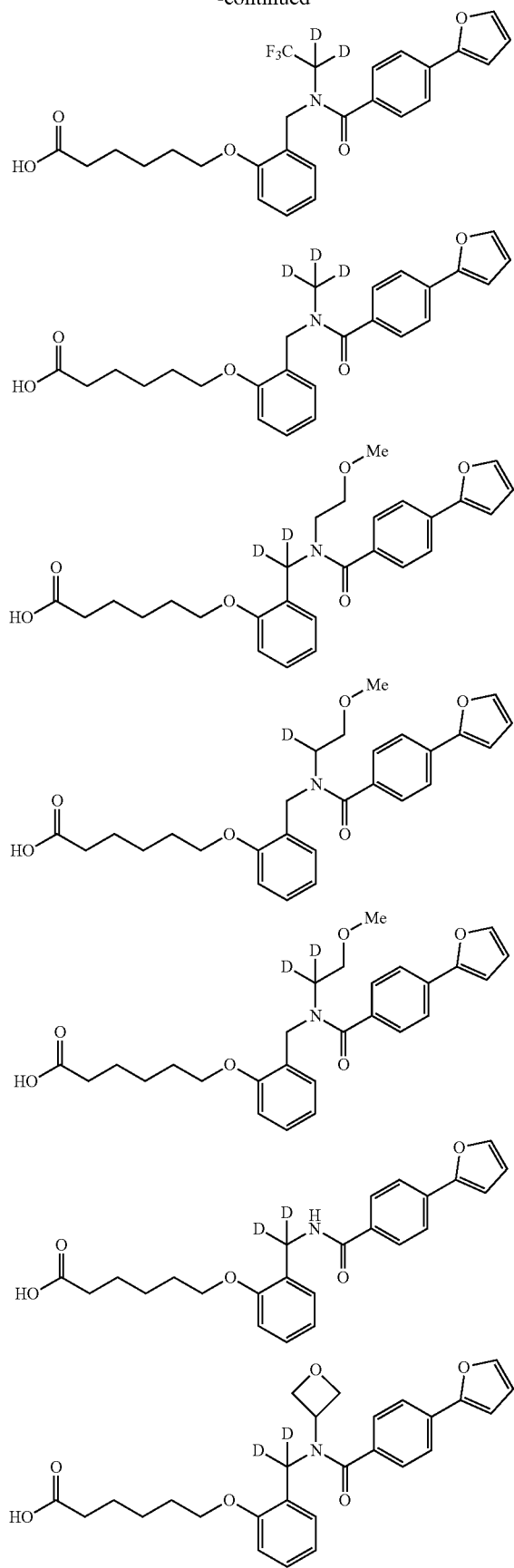
164
-continued
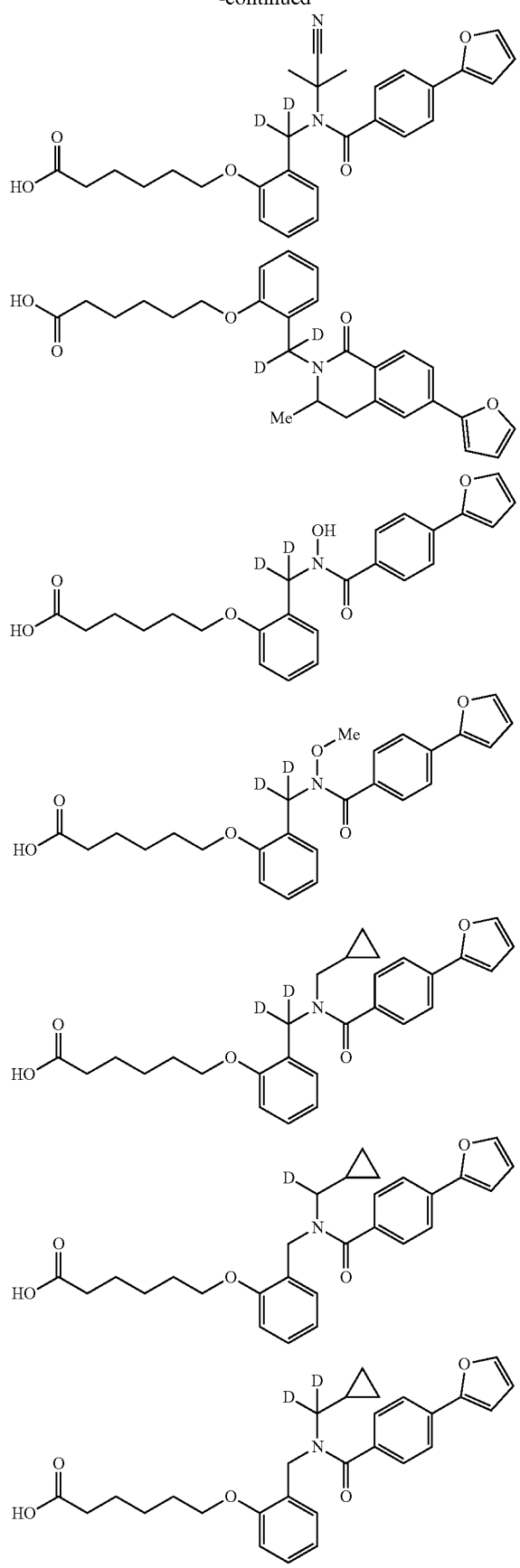

165
-continued
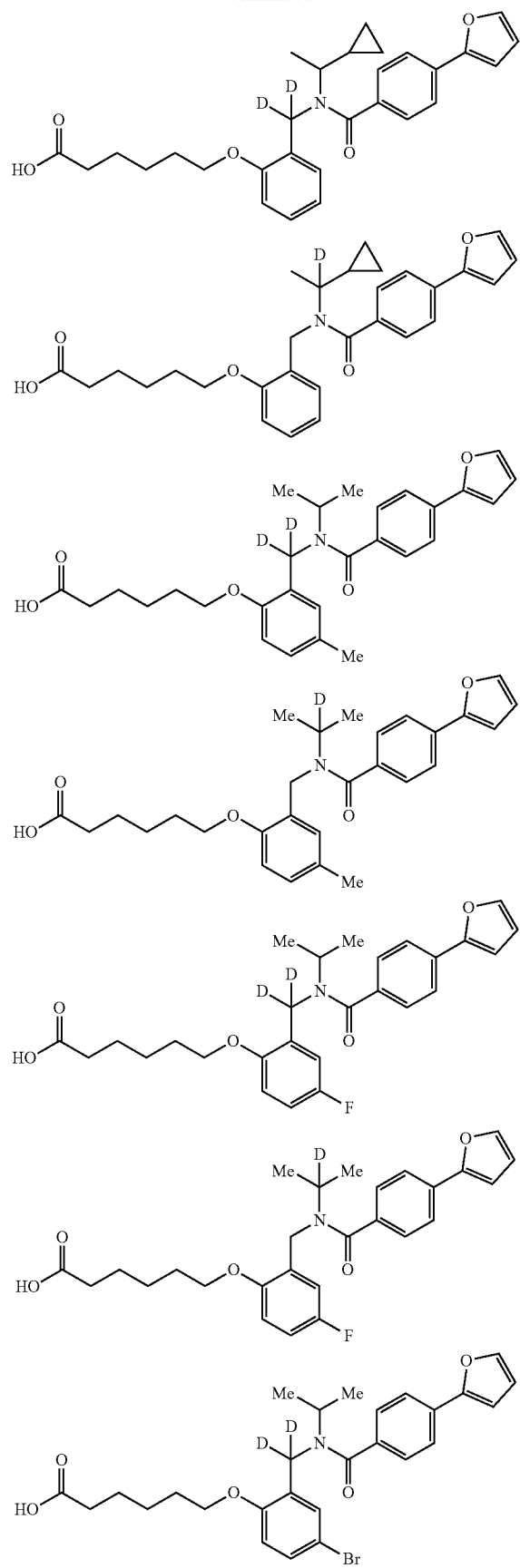
166
-continued
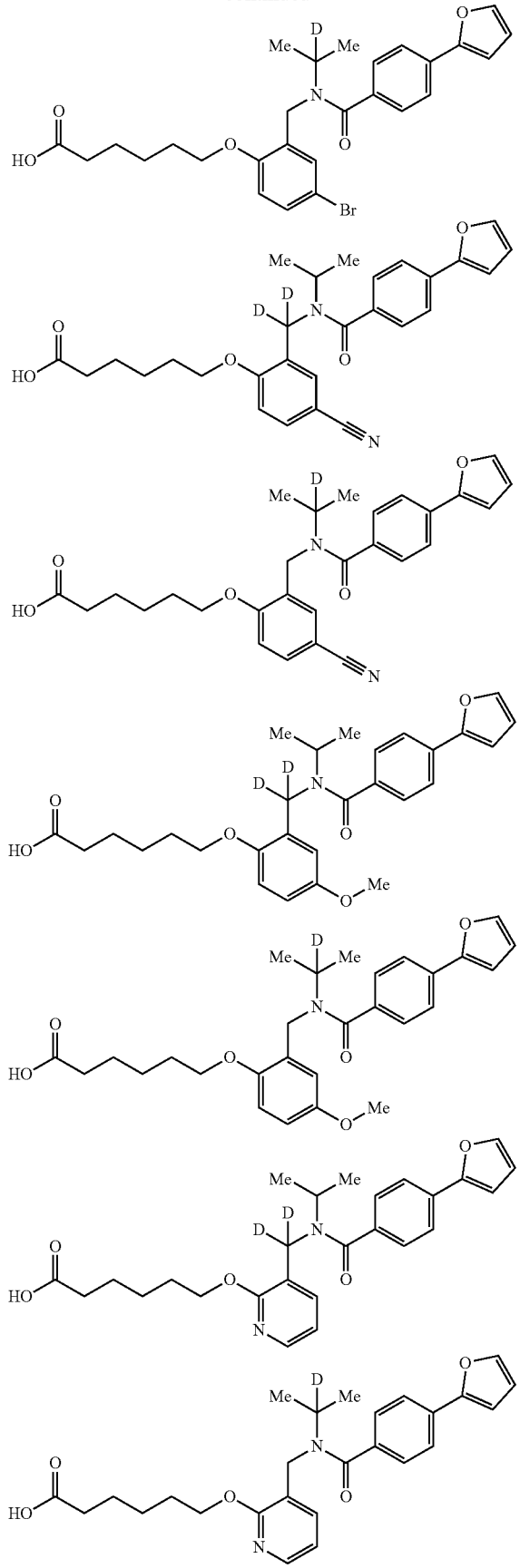

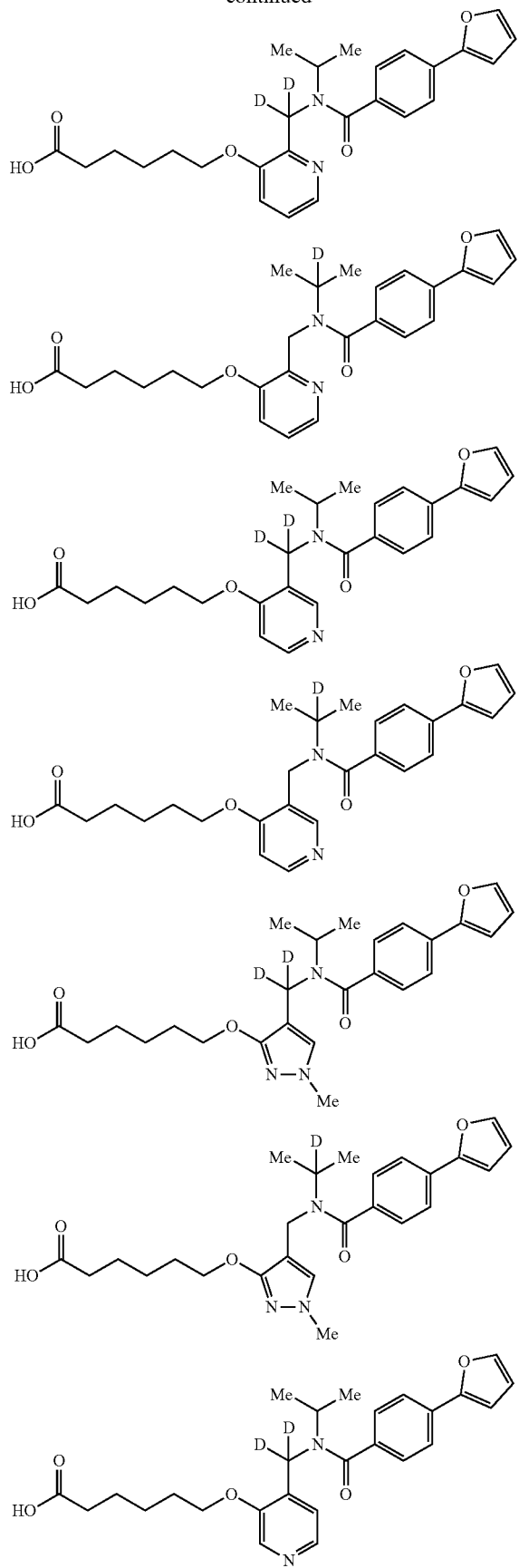
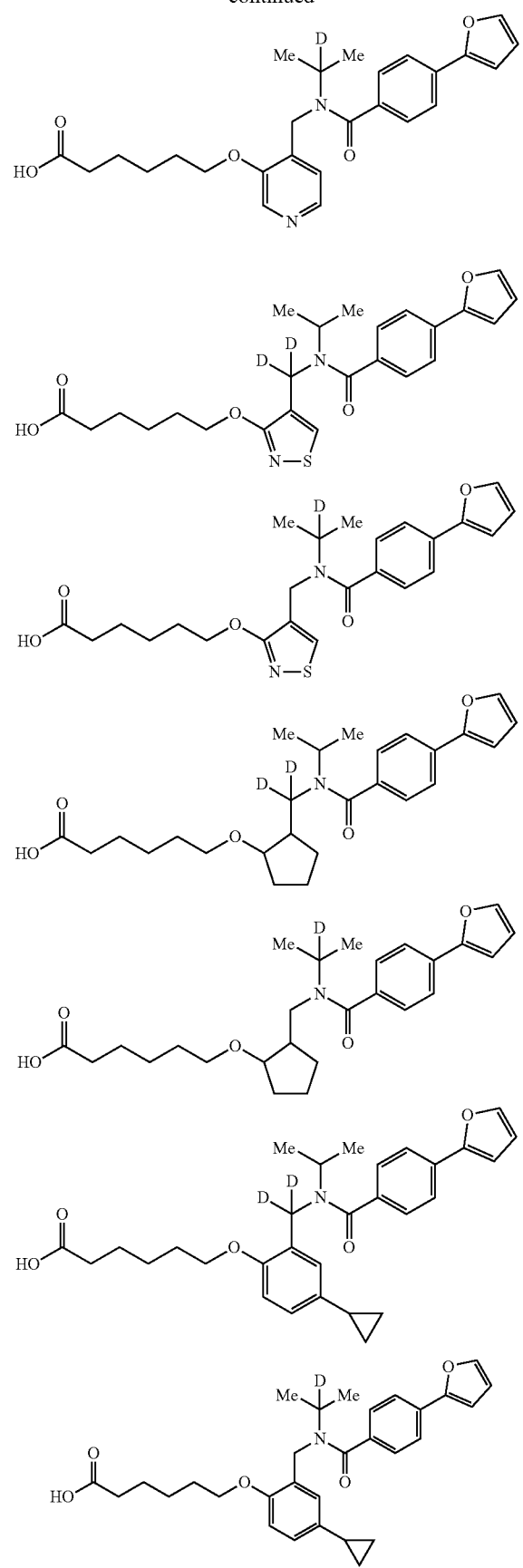

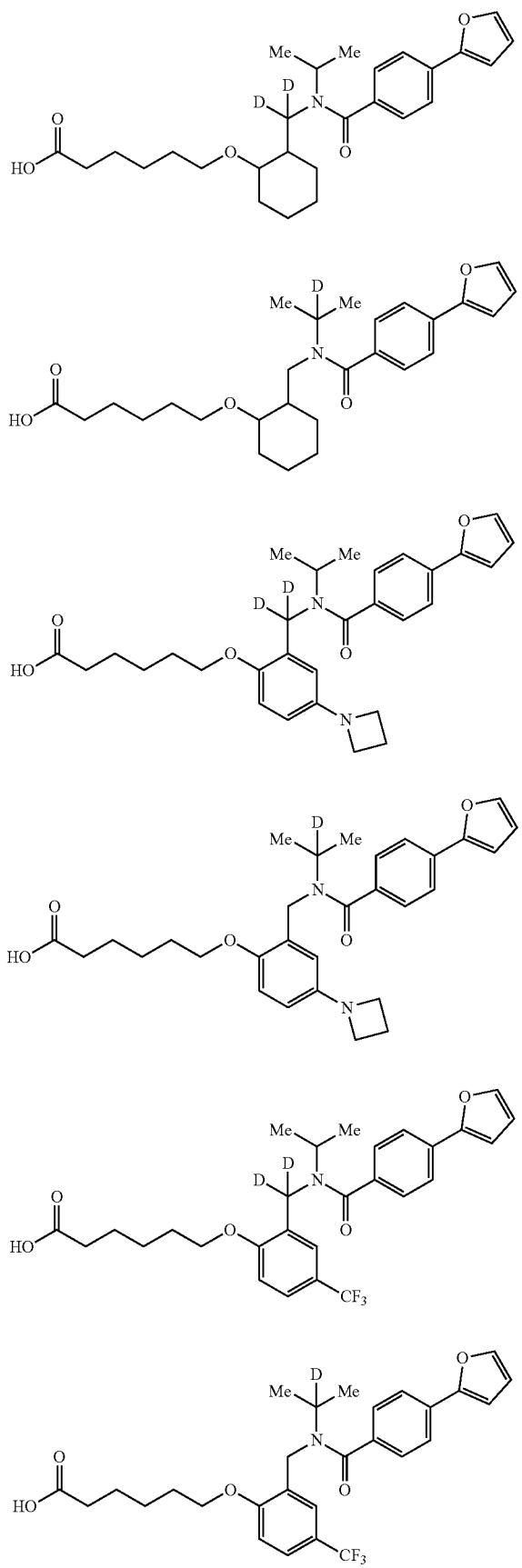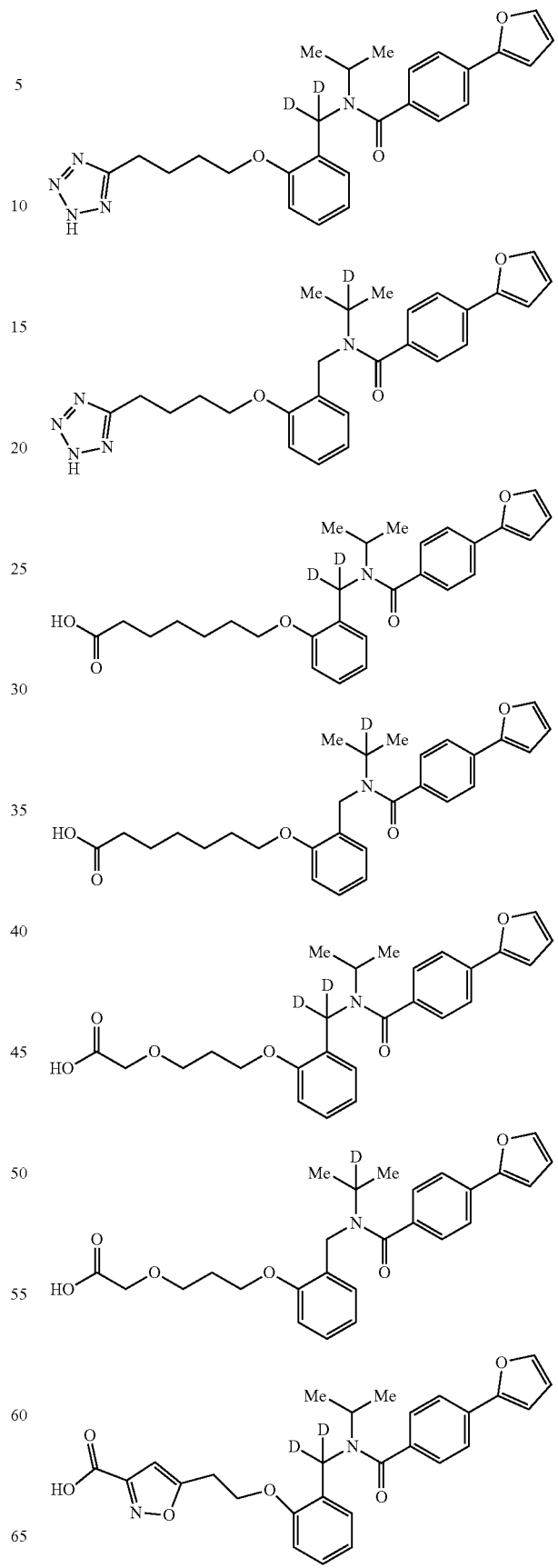

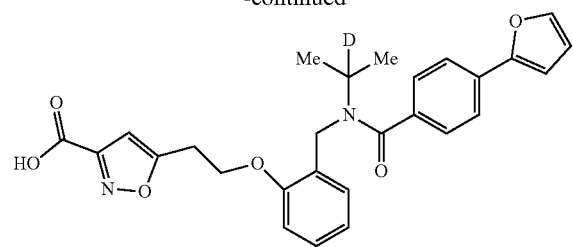
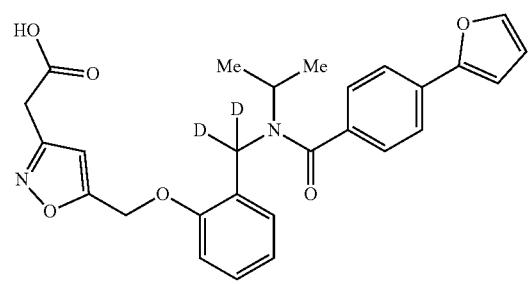
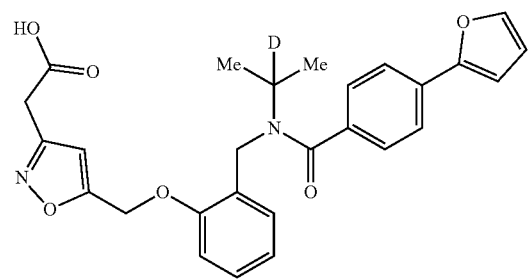
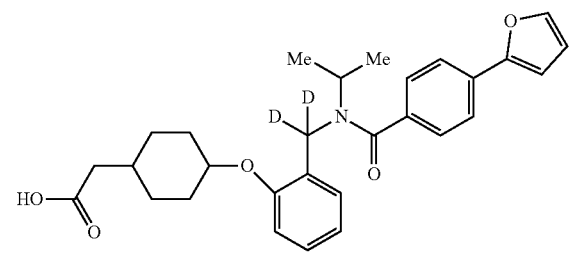
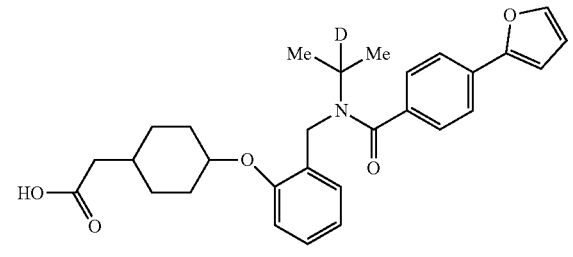
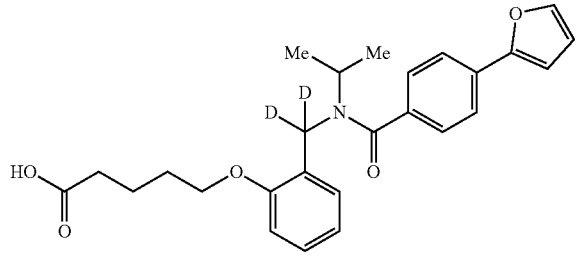
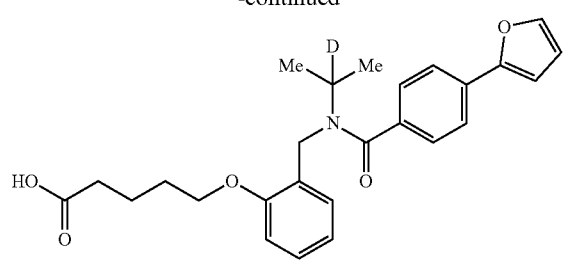
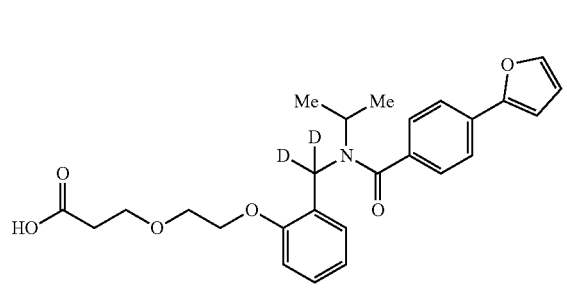 [SMILES: [2H]C([2H])(c1ccccc1OC1CCCN(CCC(=O)O)C1)N(C(=O)c1ccc(-c2ccco2)cc1)C(C)C]
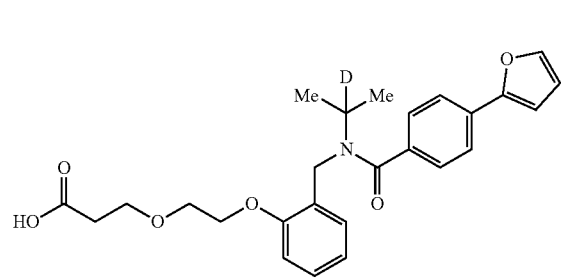
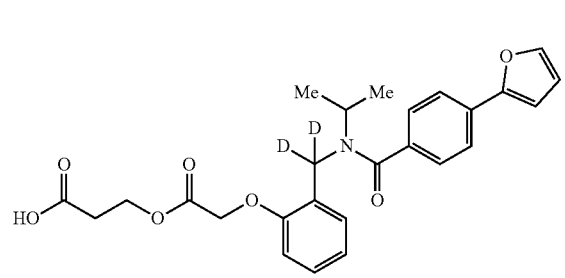
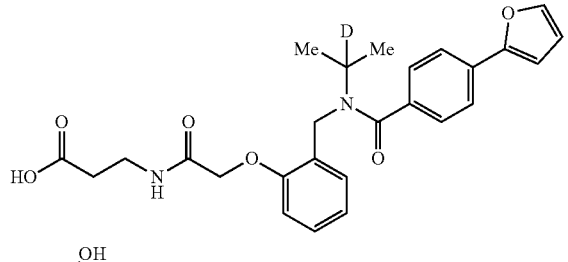
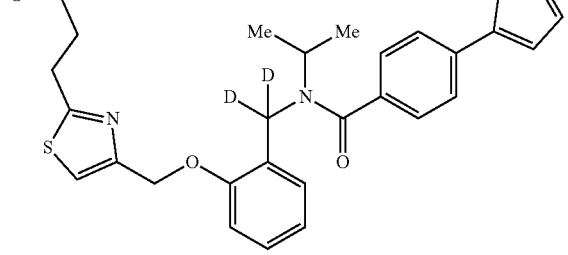

173
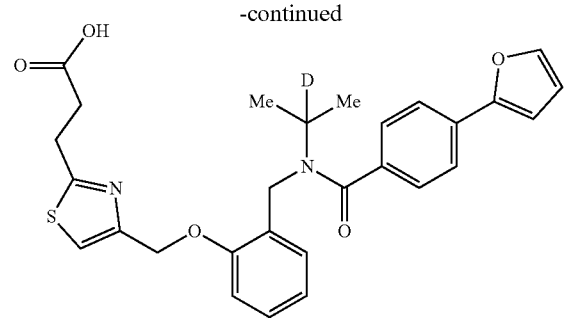
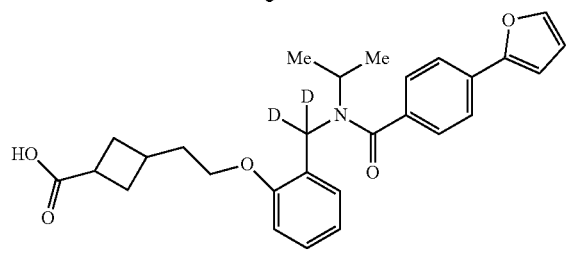
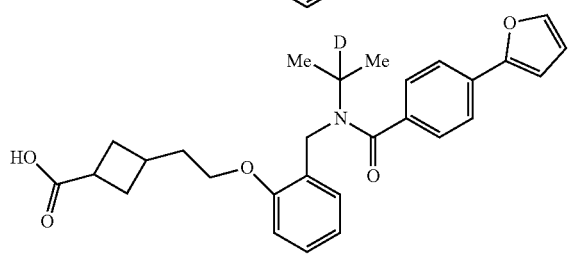
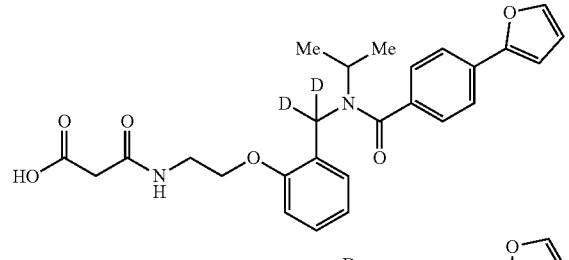
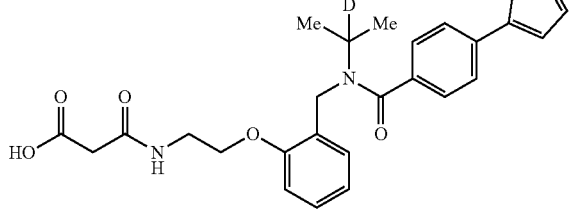
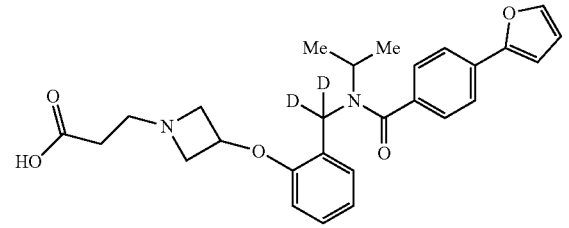
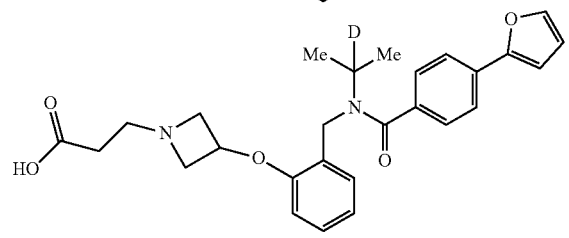
174
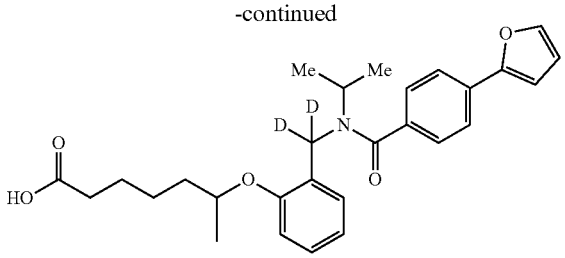
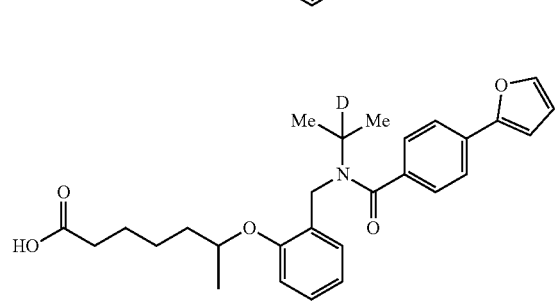
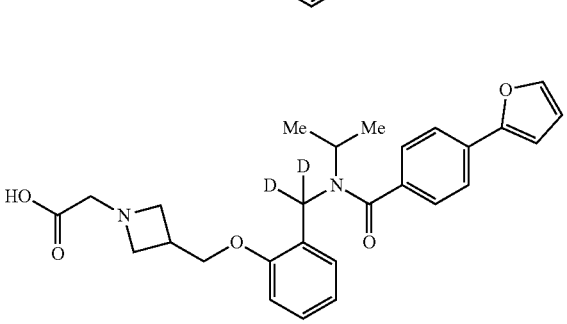
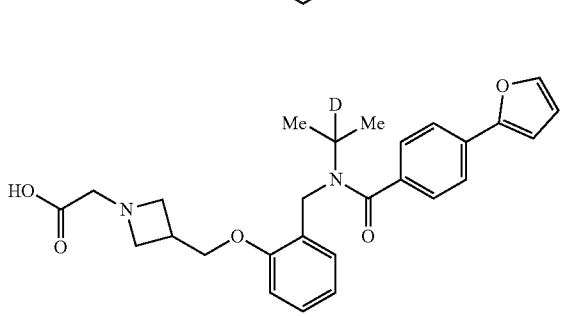
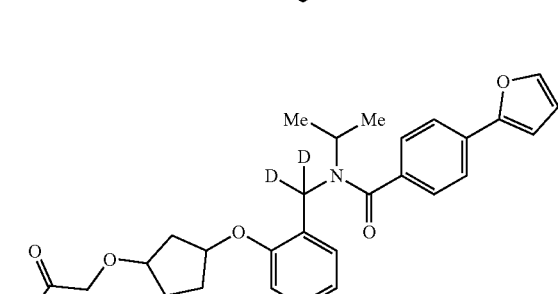
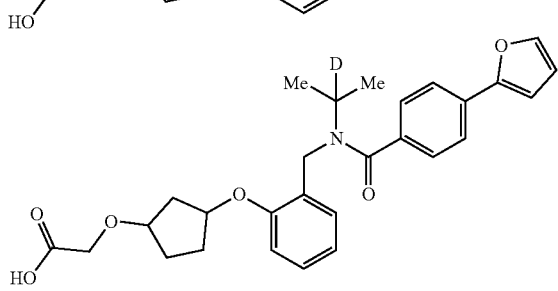

175
-continued
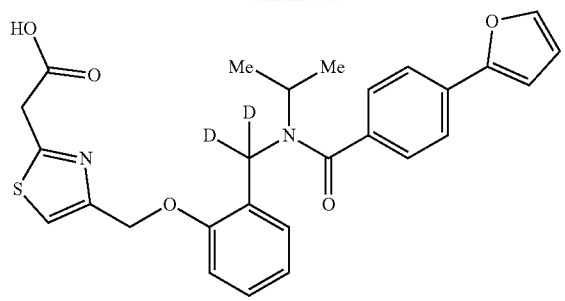
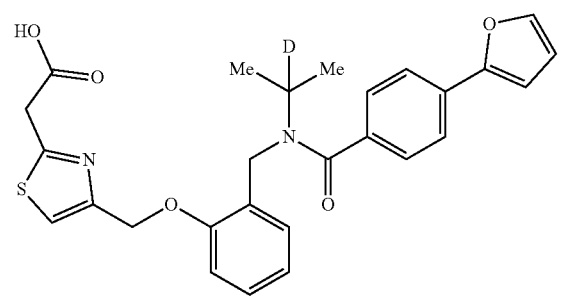
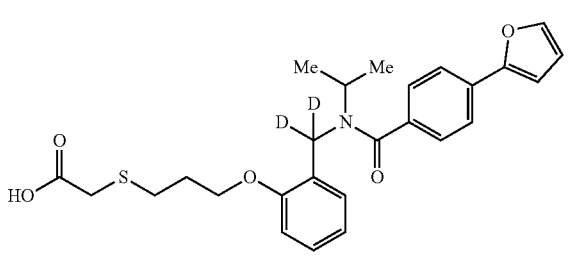
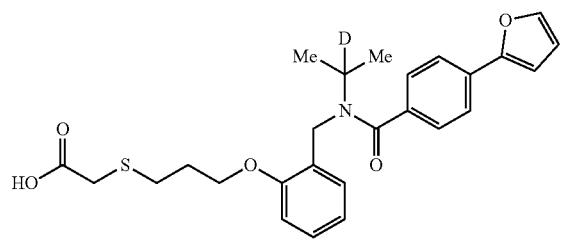
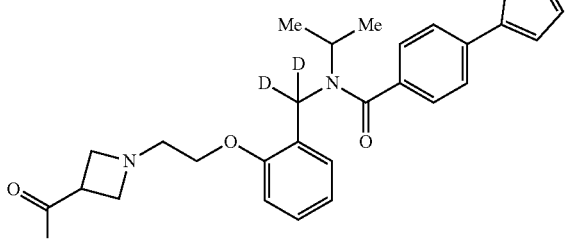
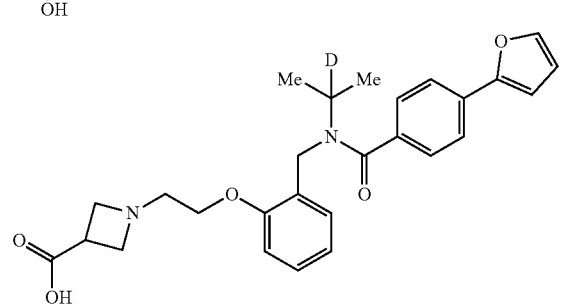
176
-continued
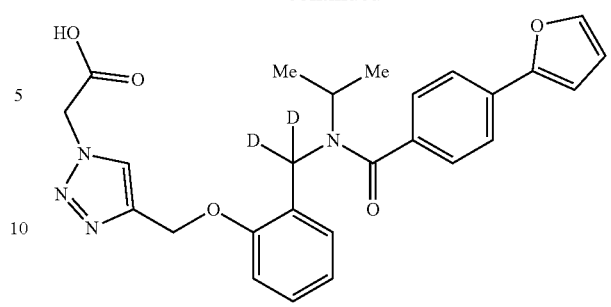
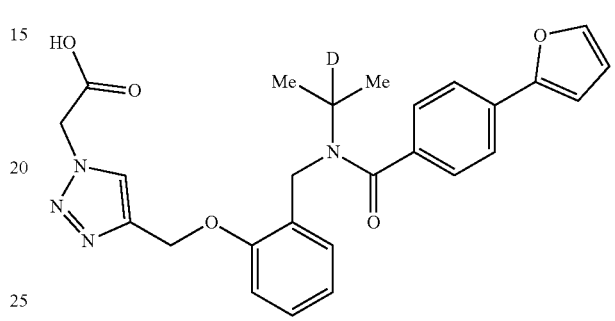
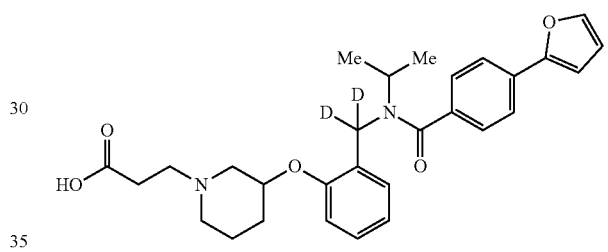
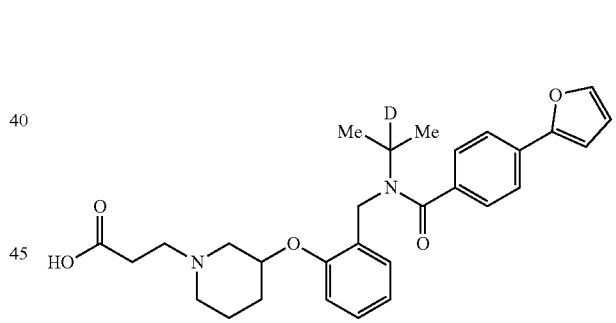
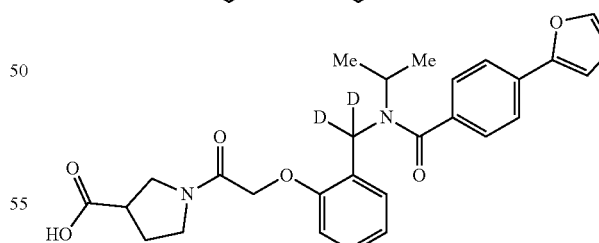
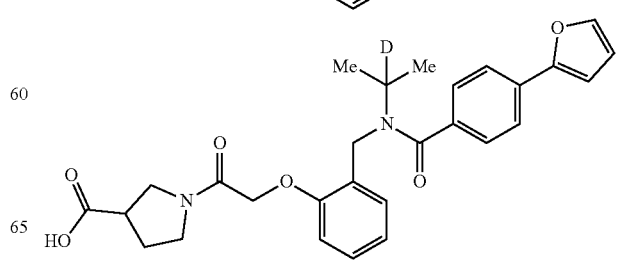

177
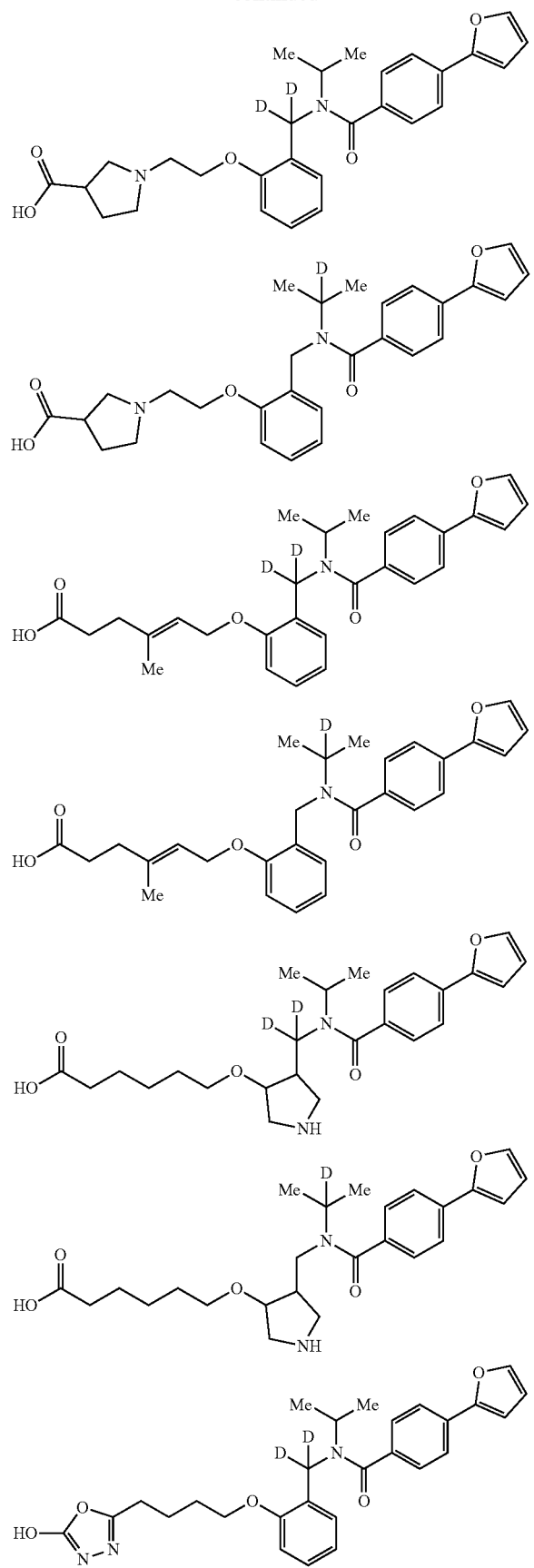
178
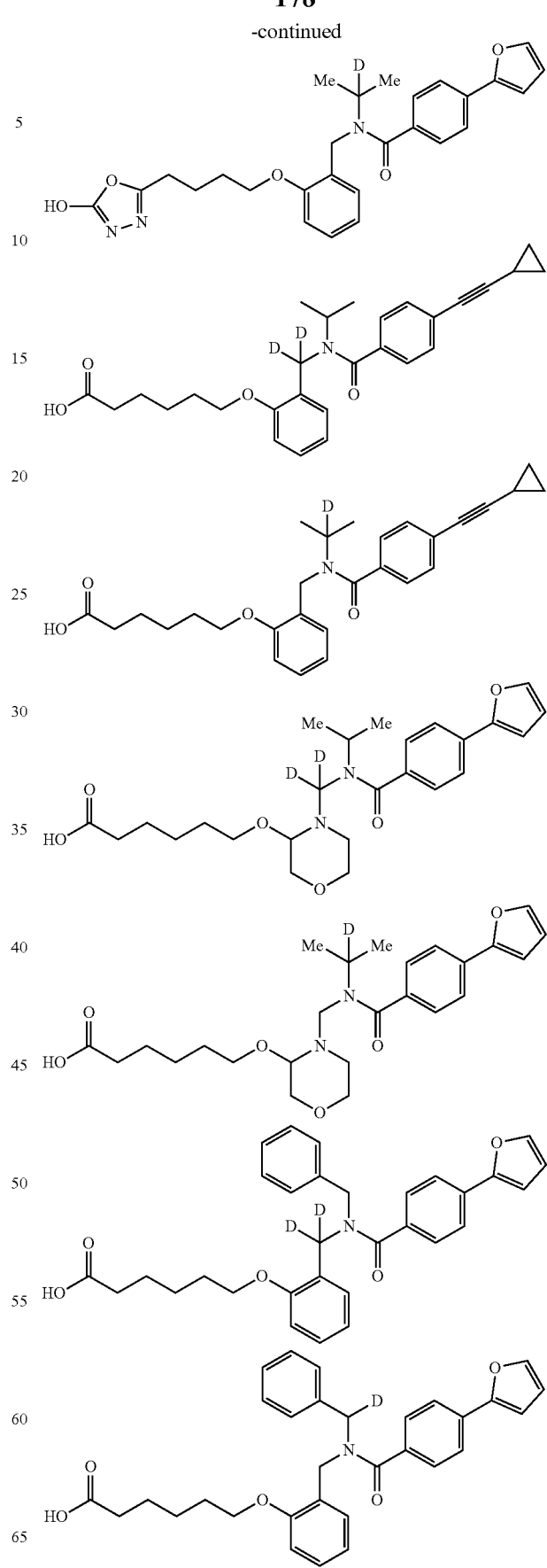

179
-continued
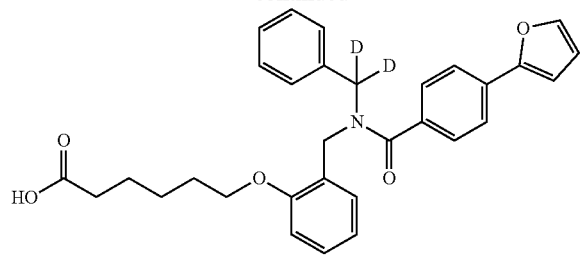
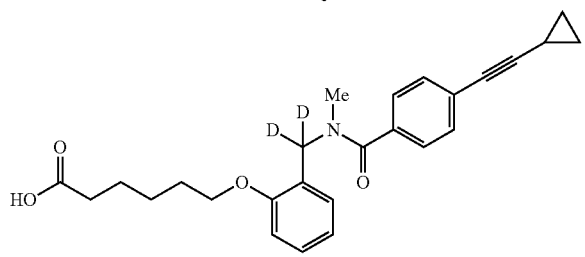
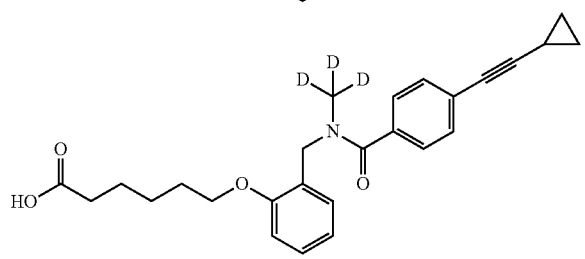
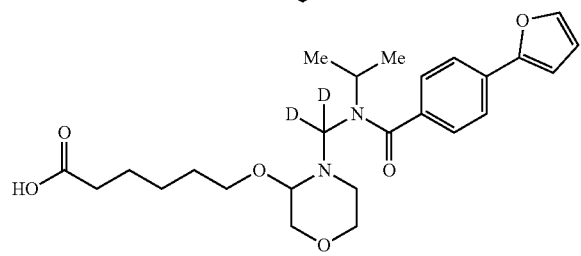
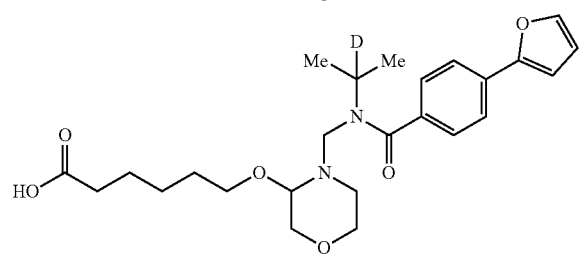
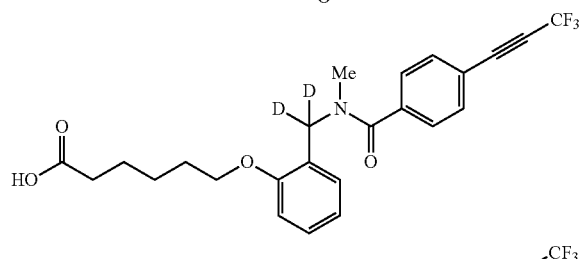
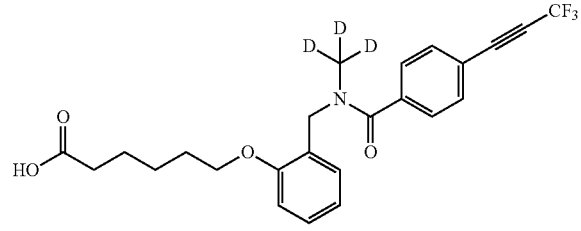
180
-continued
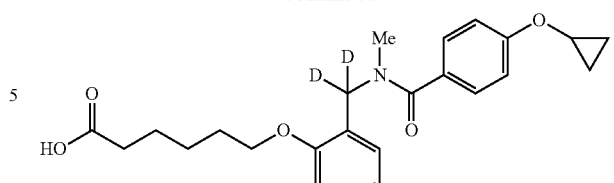
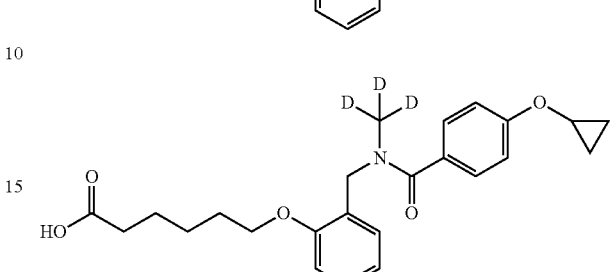
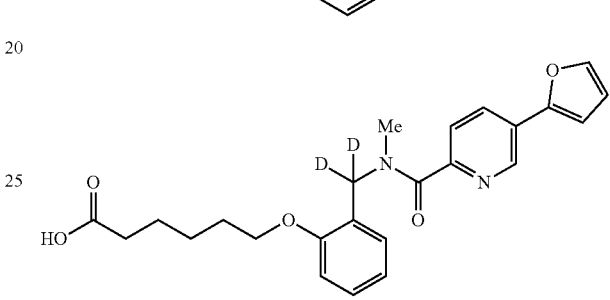
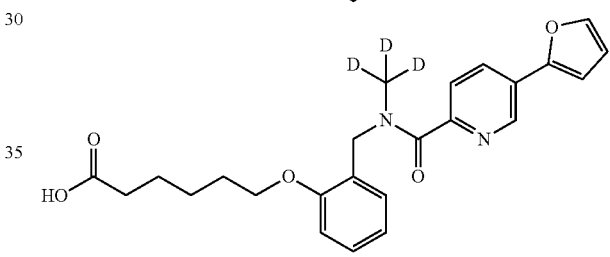
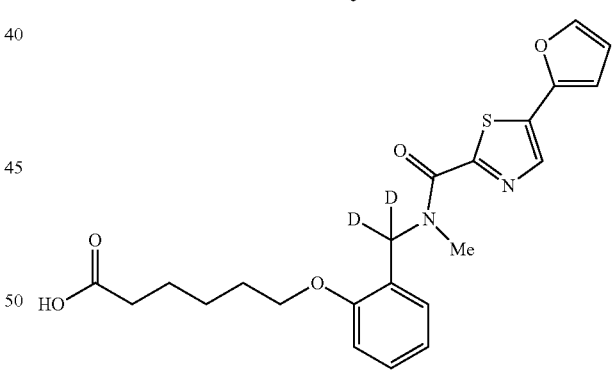
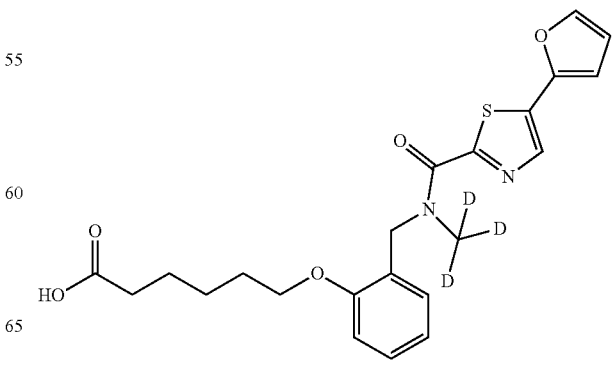

181
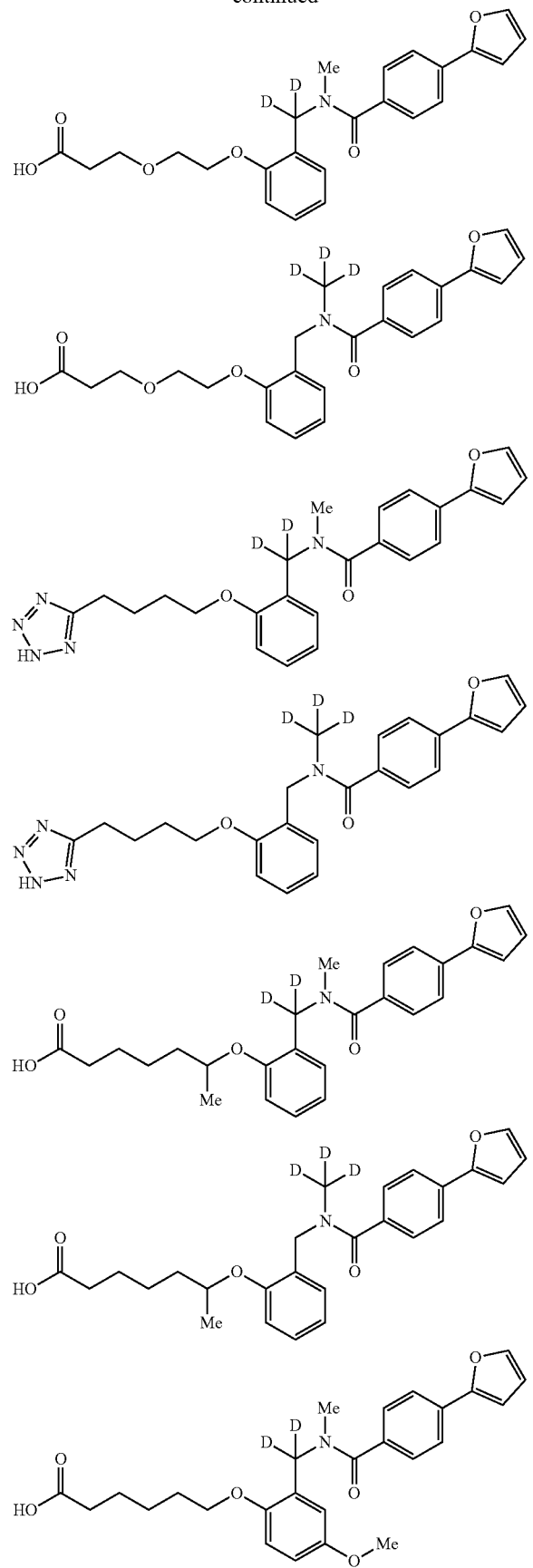
182
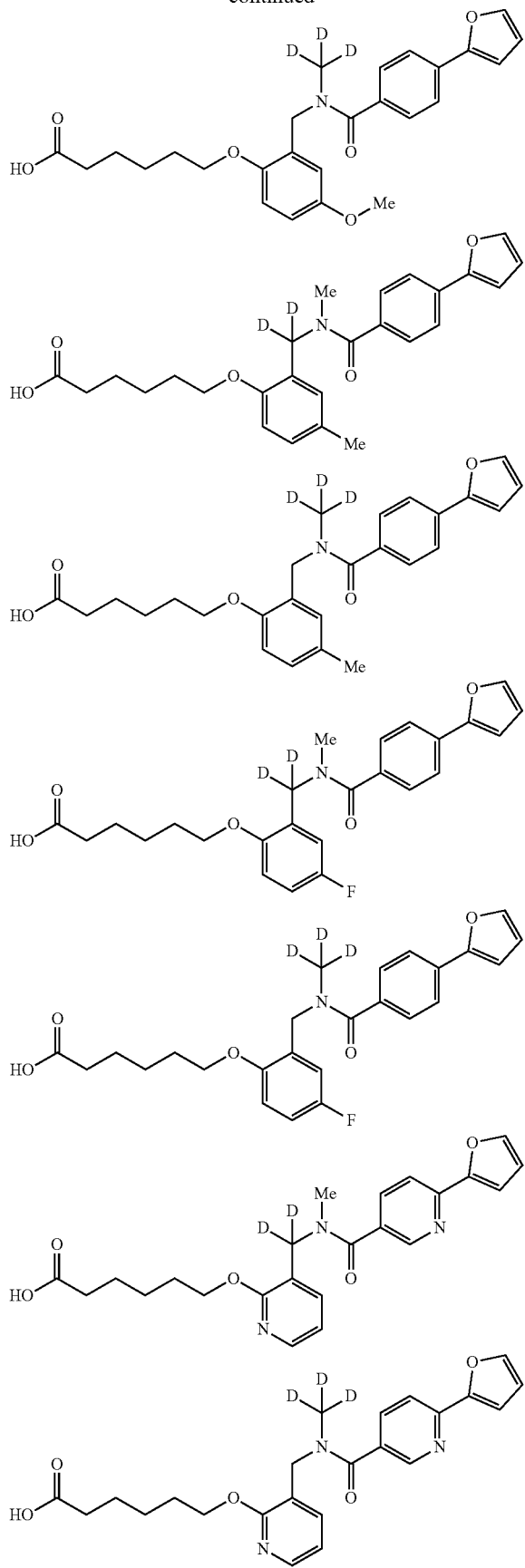

-continued
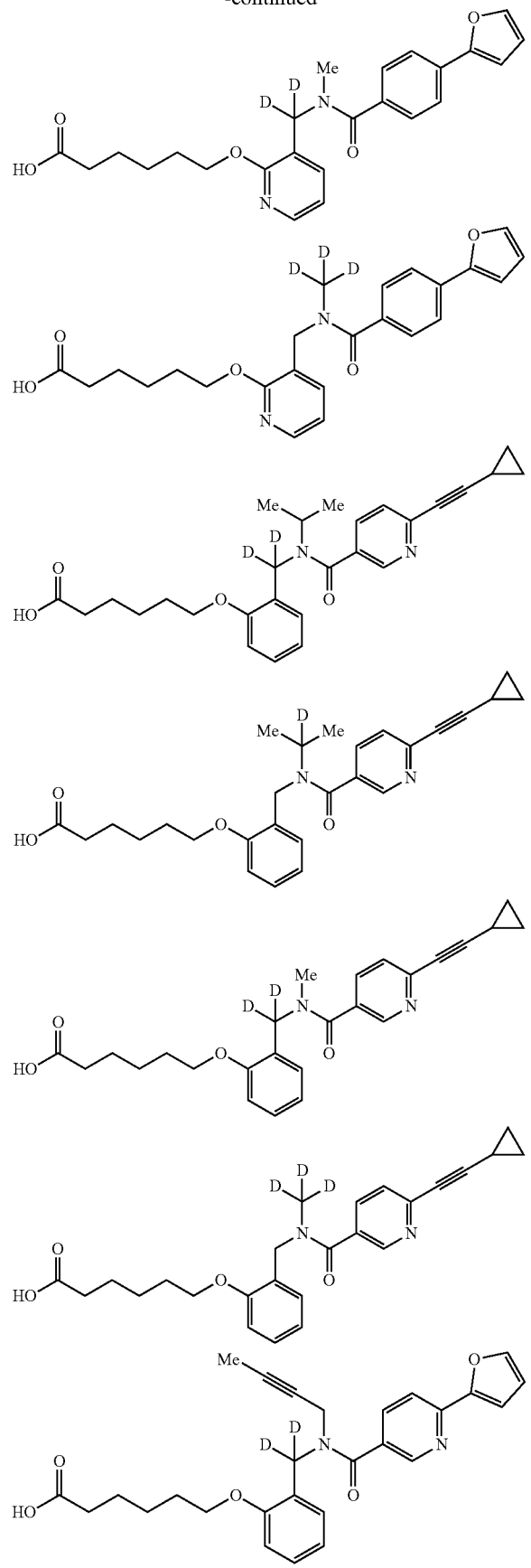
-continued
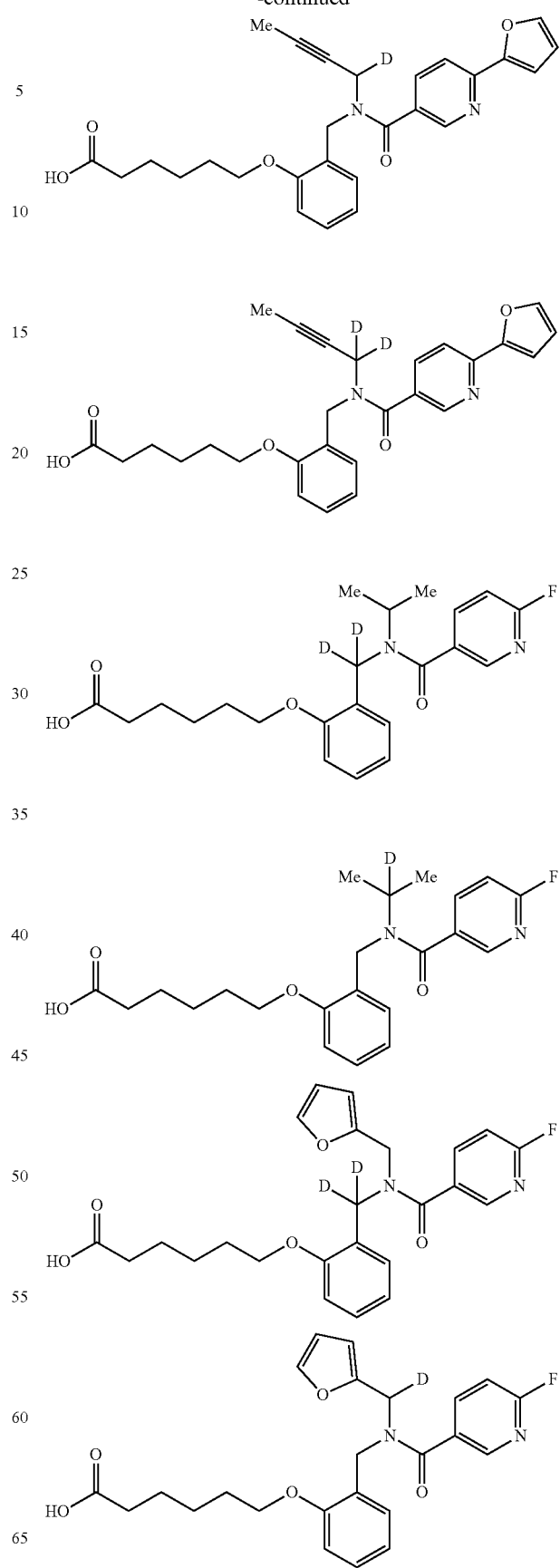

185
-continued
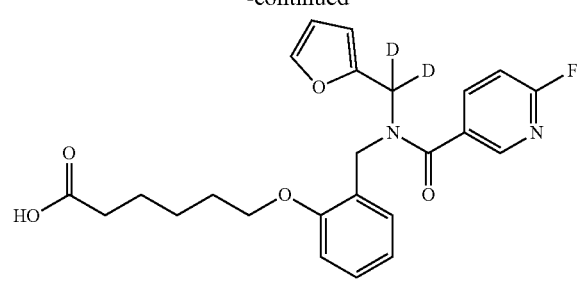
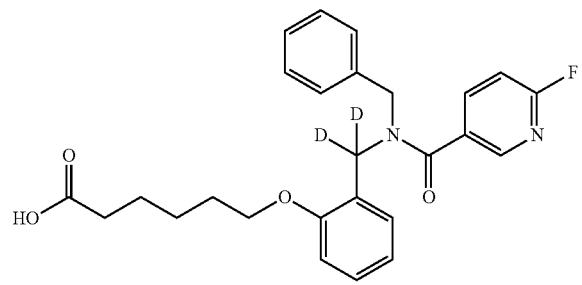
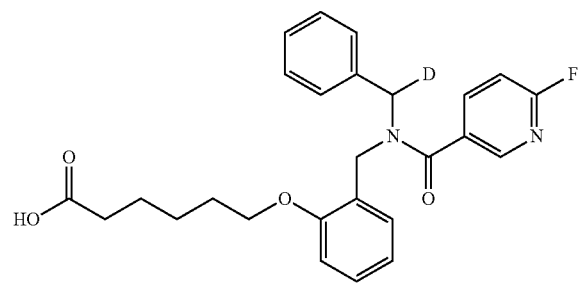
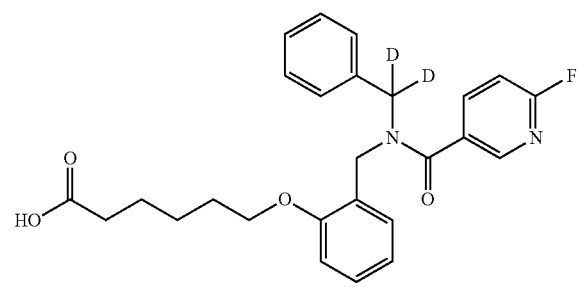
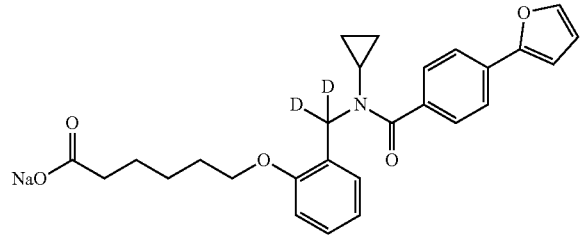
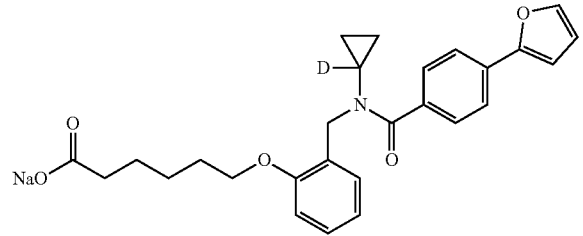
186
-continued
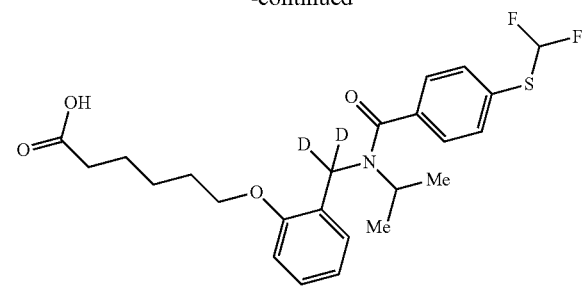
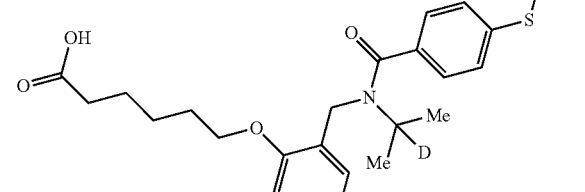
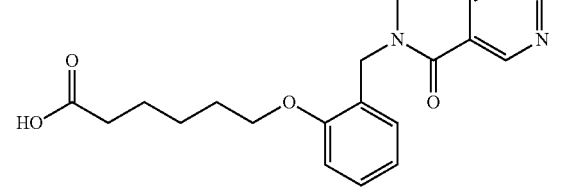
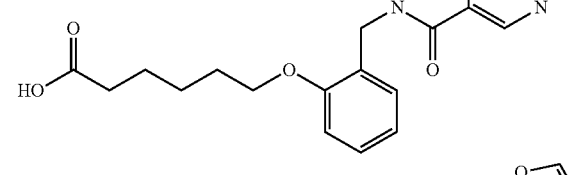
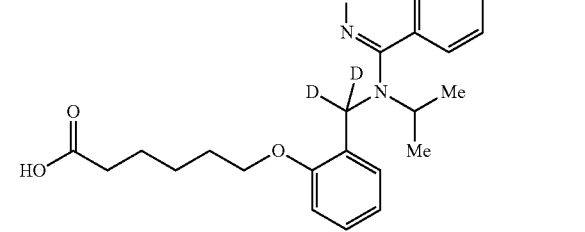

187
-continued
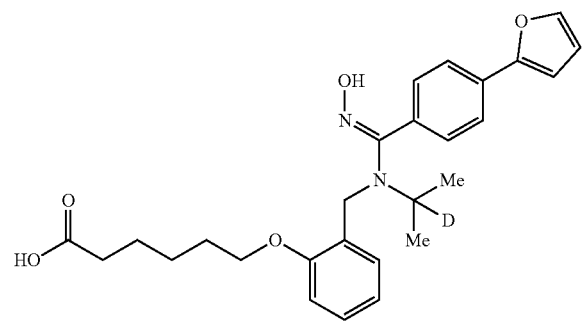
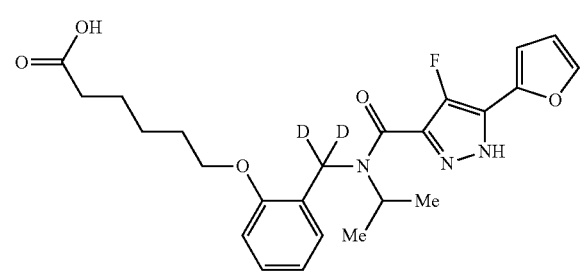
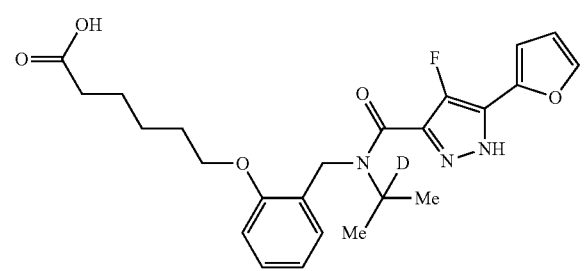
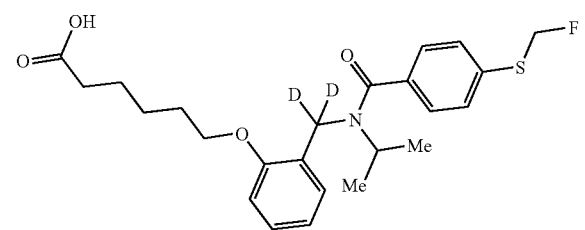
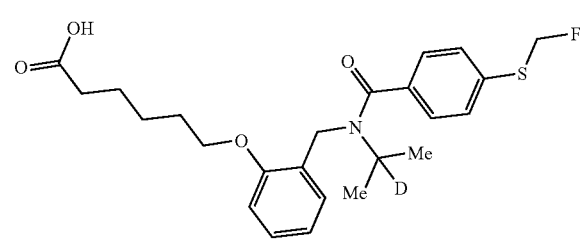
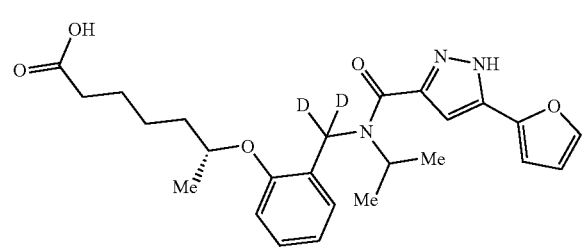
188
-continued
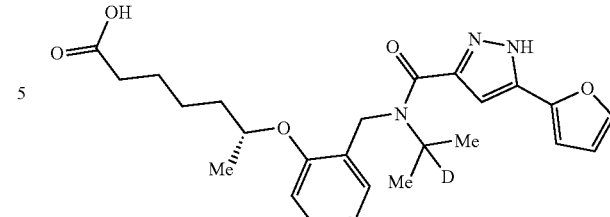
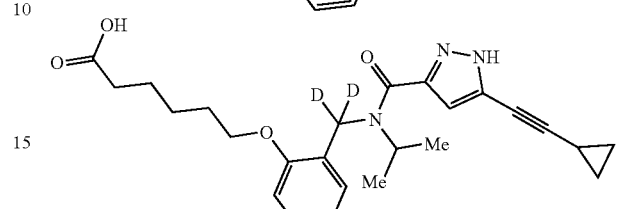
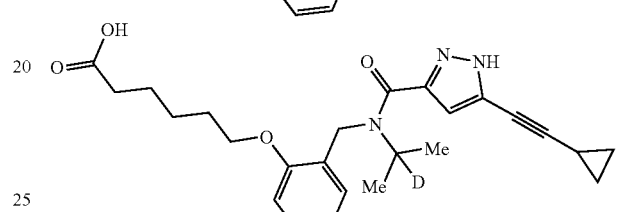
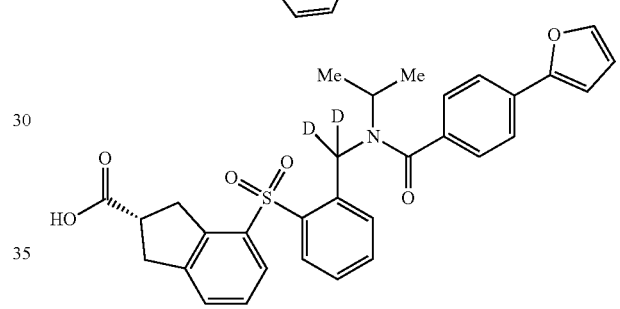
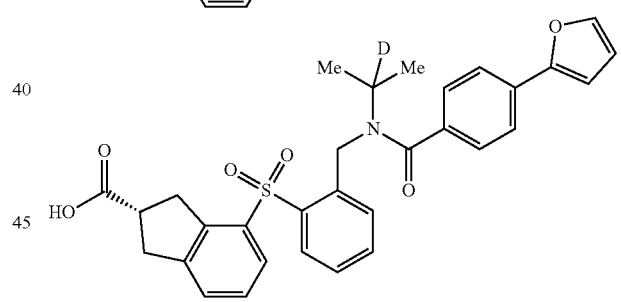
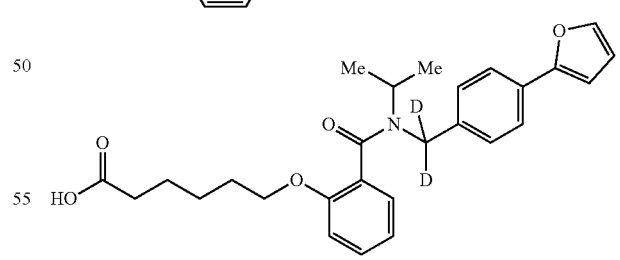
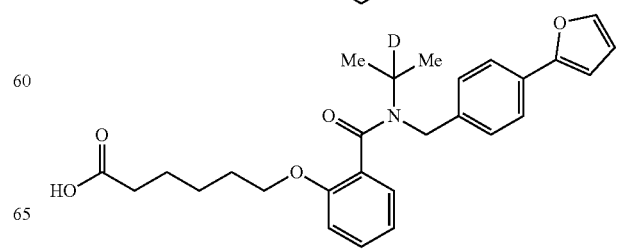

189
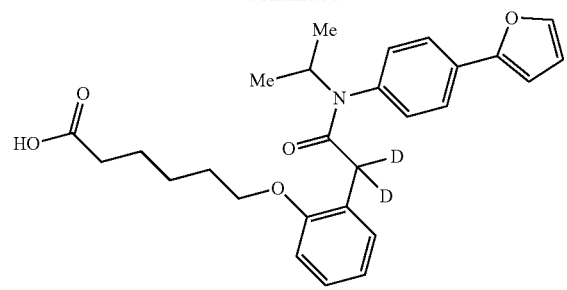
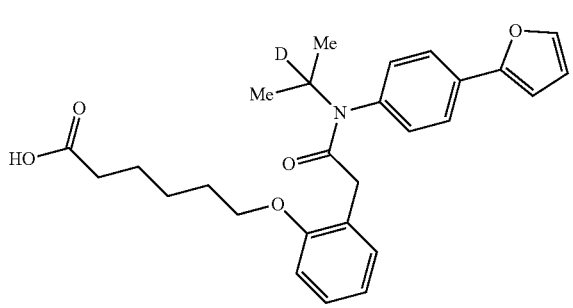
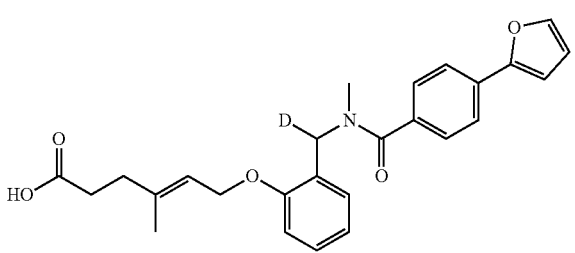
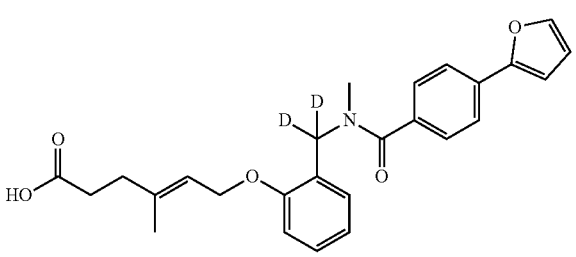
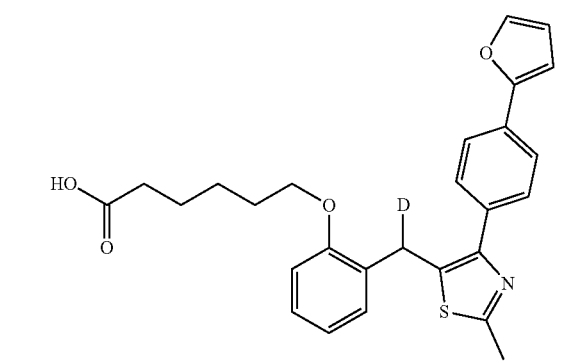
190
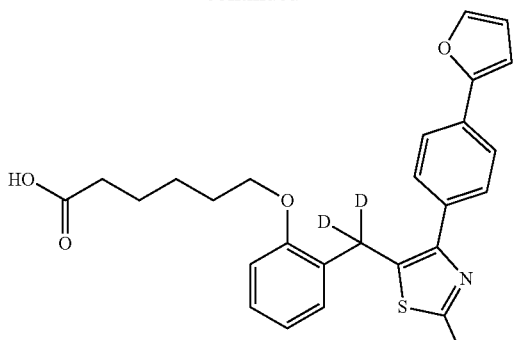
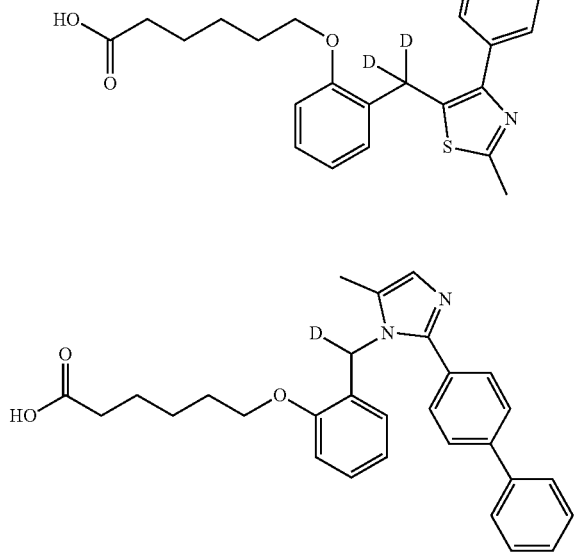
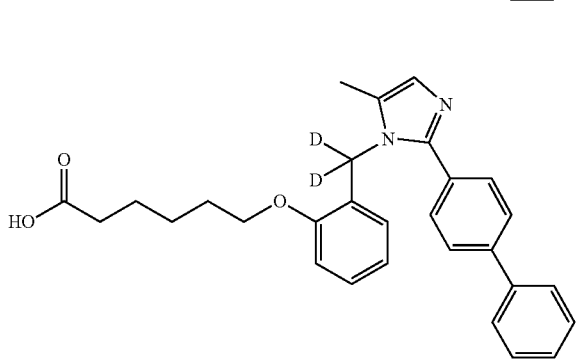
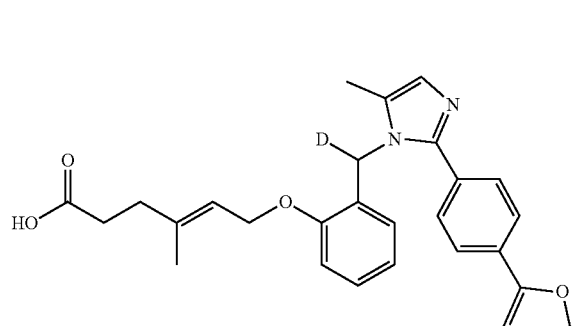
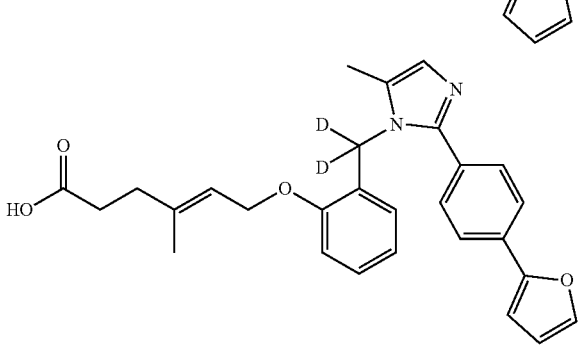

-continued

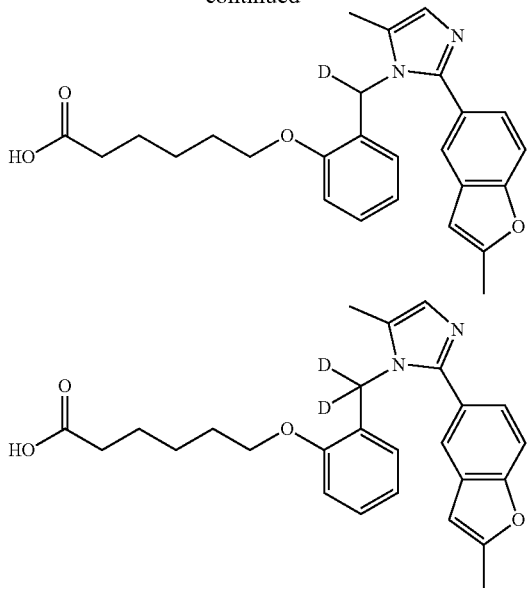

In some embodiments, the compound is selected from:
6-(2-((N-isopropyl-[1,1'-biphenyl]-4-carboxamido)methyl-d)phenoxy)hexanoic acid
ethyl 6-(2-(1-(4-bromo-N-cyclopropylbenzamido)-2-(tert-butylamino)-2-oxoethyl-1-d)phenoxy)hexanoate
ethyl 6-(2-(2-(tert-butylamino)-1-(N-cyclopropyl-[1,1'-biphenyl]-4-carboxamido)-2-oxoethyl-1-d)phenoxy)hexanoate
ethyl 6-(2-(2-amino-1-(N-cyclopropyl-[1,1'-biphenyl]-4-carboxamido)-2-oxoethyl-1-d)phenoxy)hexanoate
6-(2-(2-(tert-butylamino)-1-(N-cyclopropyl-[1,1'-biphenyl]-4-carboxamido)-2-oxoethyl-1-d)phenoxy)hexanoic acid
6-(2-(2-amino-1-(N-cyclopropyl-[1,1'-biphenyl]-4-carboxamido)-2-oxoethyl-1-d)phenoxy)hexanoic acid
N-(2-amino-1-(2-((6-(hydroxyamino)-6-oxohexyl)oxy)phenyl)-2-oxoethyl-1-d)-N-cyclopropyl-[1,1'-biphenyl]-4-carboxamide
6-(2-((N-cyclopropyl-[1,1'-biphenyl]-4-carboxamido)methyl-d)phenoxy)hexanoic acid
6-(2-((N-cyclopropyl-4-(pyridin-3-yl)benzamido)methyl-d)phenoxy)hexanoic acid
6-(2-((N-cyclopropyl-4-(pyridin-4-yl)benzamido)methyl-d)phenoxy)hexanoic acid
6-(2-((N-cyclopropyl-4-(1H-pyrazol-4-yl)benzamido)methyl-d)phenoxy)hexanoic acid
6-(2-((N-cyclopropyl-4-(furan-2-yl)benzamido)methyl-d)phenoxy)hexanoic acid
6-(2-((N-cyclopropyl-4-(furan-3-yl)benzamido)methyl-d)phenoxy)hexanoic acid
6-(2-((N-cyclopropyl-4-(thiophen-2-yl)benzamido)methyl-d)phenoxy)hexanoic acid
6-(2-((N-cyclopropyl-4-(thiophen-3-yl)benzamido)methyl-d)phenoxy)hexanoic acid
6-(2-((N-benzyl-[1,1'-biphenyl]-4-carboxamido)methyl-d)phenoxy)hexanoic acid
6-(2-((N-benzyl-4-(pyridin-3-yl)benzamido)methyl-d)phenoxy)hexanoic acid
6-(2-((N-benzyl-4-(pyridin-4-yl)benzamido)methyl-d)phenoxy)hexanoic acid
6-(2-((N-benzyl-4-(1H-pyrazol-4-yl)benzamido)methyl-d)phenoxy)hexanoic acid
6-(2-((N-benzyl-4-(furan-2-yl)benzamido)methyl-d)phenoxy)hexanoic acid
6-(2-((N-benzyl-4-(furan-3-yl)benzamido)methyl-d)phenoxy)hexanoic acid
6-(2-((N-benzyl-4-(thiophen-2-yl)benzamido)methyl-d)phenoxy)hexanoic acid
6-(2-((N-benzyl-4-(thiophen-3-yl)benzamido)methyl-d)phenoxy)hexanoic acid
N-benzyl-N-((2-((6-(hydroxyamino)-6-oxohexyl)oxy)phenyl)methyl-d)-[1,1'-biphenyl]-4-carboxamide
N-benzyl-N-((2-((6-(hydroxyamino)-6-oxohexyl)oxy)phenyl)methyl-d)-4-(pyridin-3-yl)benzamide
N-benzyl-N-((2-((6-(hydroxyamino)-6-oxohexyl)oxy)phenyl)methyl-d)-4-(pyridin-4-yl)benzamide
N-benzyl-N-((2-((6-(hydroxyamino)-6-oxohexyl)oxy)phenyl)methyl-d)-4-(1H-pyrazol-4-yl)benzamide
N-benzyl-4-(furan-2-yl)-N-((2-((6-(hydroxyamino)-6-oxohexyl)oxy)phenyl)methyl-d)benzamide
N-benzyl-4-(furan-3-yl)-N-((2-((6-(hydroxyamino)-6-oxohexyl)oxy)phenyl)methyl-d)benzamide
N-benzyl-N-((2-((6-(hydroxyamino)-6-oxohexyl)oxy)phenyl)methyl-d)-4-(thiophen-2-yl)benzamide
N-benzyl-N-((2-((6-(hydroxyamino)-6-oxohexyl)oxy)phenyl)methyl-d)-4-(thiophen-3-yl)benzamide
6-(2-((4-bromo-N-(sec-butyl)benzamido)methyl-d)phenoxy)hexanoic acid
6-(2-((N-(sec-butyl)[1,1'-biphenyl]-4-carboxamido)methyl-d)phenoxy)hexanoic acid
6-(2-((N-(sec-butyl)-4-(pyridin-3-yl)benzamido)methyl-d)phenoxy)hexanoic acid
6-(2-((N-(sec-butyl)-4-(pyridin-4-yl)benzamido)methyl-d)phenoxy)hexanoic acid
6-(2-((N-(sec-butyl)-4-(1H-pyrazol-4-yl)benzamido)methyl-d)phenoxy)hexanoic acid
6-(2-((N-(sec-butyl)-4-(furan-2-yl)benzamido)methyl-d)phenoxy)hexanoic acid
6-(2-((N-(sec-butyl)-4-(furan-3-yl)benzamido)methyl-d)phenoxy)hexanoic acid
6-(2-((N-(sec-butyl)-4-(thiophen-2-yl)benzamido)methyl-d)phenoxy)hexanoic acid
6-(2-((N-(sec-butyl)-4-(thiophen-3-yl)benzamido)methyl-d)phenoxy)hexanoic acid
6-(2-((N-(3-morpholinopropyl)-[1,1'-biphenyl]-4-carboxamido)methyl-d)phenoxy)hexanoic acid
6-(2-((N-(3-morpholinopropyl)-4-(pyridin-3-yl)benzamido)methyl-d)phenoxy)hexanoic acid
6-(2-((N-(3-morpholinopropyl)-4-(pyridin-4-yl)benzamido)methyl-d)phenoxy)hexanoic acid
6-(2-((N-(3-morpholinopropyl)-4-(1H-pyrazol-4-yl)benzamido)methyl-d)phenoxy)hexanoic acid
6-(2-((4-(furan-2-yl)-N-(3-morpholinopropyl)benzamido)methyl-d)phenoxy)hexanoic acid
6-(2-((4-(furan-3-yl)-N-(3-morpholinopropyl)benzamido)methyl-d)phenoxy)hexanoic acid
6-(2-((N-(3-morpholinopropyl)-4-(thiophen-2-yl)benzamido)methyl-d)phenoxy)hexanoic acid
6-(2-((N-(3-morpholinopropyl)-4-(thiophen-3-yl)benzamido)methyl-d)phenoxy)hexanoic acid
6-(2-((N-(2-(pyridin-2-yl)ethyl)-[1,1'-biphenyl]-4-carboxamido)methyl-d)phenoxy)hexanoic acid
6-(2-((N-(2-(pyridin-2-yl)ethyl)-4-(pyridin-3-yl)benzamido)methyl-d)phenoxy)hexanoic acid
6-(2-((N-(2-(pyridin-2-yl)ethyl)-4-(pyridin-4-yl)benzamido)methyl-d)phenoxy)hexanoic acid
6-(2-((4-(1H-pyrazol-4-yl)-N-(2-(pyridin-2-yl)ethyl)benzamido)methyl-d)phenoxy)hexanoic acid 6-(2-((4-(furan-2-yl)-N-(2-(pyridin-2-yl)ethyl)benzamido)methyl-d)phenoxy)hexanoic acid
6-(2-((4-(furan-3-yl)-N-(2-(pyridin-2-yl)ethyl)benzamido)methyl-d)phenoxy)hexanoic acid
6-(2-((N-(2-(pyridin-2-yl)ethyl)-4-(thiophen-2-yl)benzamido)methyl-d)phenoxy)hexanoic acid
6-(2-((N-(2-(pyridin-2-yl)ethyl)-4-(thiophen-3-yl)benzamido)methyl-d)phenoxy)hexanoic acid
6-(2-((N-isopropyl-[1,1'-biphenyl]-4-carboxamido)methyl-d)phenoxy)hexanoic acid
6-(2-((N-isopropyl-4-(pyridin-3-yl)benzamido)methyl-d)phenoxy)hexanoic acid
6-(2-((N-isopropyl-4-(pyridin-4-yl)benzamido)methyl-d)phenoxy)hexanoic acid
6-(2-((N-isopropyl-4-(1H-pyrazol-4-yl)benzamido)methyl-d)phenoxy)hexanoic acid
6-(2-((4-(furan-2-yl)-N-isopropylbenzamido)methyl-d)phenoxy)hexanoic acid
6-(2-((4-(furan-3-yl)-N-isopropylbenzamido)methyl-d)phenoxy)hexanoic acid
6-(2-((N-isopropyl-4-(thiophen-2-yl)benzamido)methyl-d)phenoxy)hexanoic acid
6-(2-((N-isopropyl-4-(thiophen-3-yl)benzamido)methyl-d)phenoxy)hexanoic acid
6-(2-((N-cyclopentyl-[1,1'-biphenyl]-4-carboxamido)methyl-d)phenoxy)hexanoic acid
6-(2-((N-cyclopentyl-4-(pyridin-3-yl)benzamido)methyl-d)phenoxy)hexanoic acid
6-(2-((N-cyclopentyl-4-(pyridin-4-yl)benzamido)methyl-d)phenoxy)hexanoic acid
6-(2-((N-cyclopentyl-4-(1H-pyrazol-4-yl)benzamido)methyl-d)phenoxy)hexanoic acid
6-(2-((N-cyclopentyl-4-(furan-2-yl)benzamido)methyl-d)phenoxy)hexanoic acid
6-(2-((N-cyclopentyl-4-(furan-3-yl)benzamido)methyl-d)phenoxy)hexanoic acid
6-(2-((N-cyclopentyl-4-(thiophen-2-yl)benzamido)methyl-d)phenoxy)hexanoic acid
6-(2-((N-cyclopentyl-4-(thiophen-3-yl)benzamido)methyl-d)phenoxy)hexanoic acid
6-(2-((N-cyclopropyl-4-(naphthalen-1-yl)benzamido)methyl-d)phenoxy)hexanoic acid
6-(2-((N-cyclopropyl-4-(naphthalen-2-yl)benzamido)methyl-d)phenoxy)hexanoic acid
6-(2-((N-cyclopropyl-2'-methyl-[1,1'-biphenyl]-4-carboxamido)methyl-d)phenoxy)hexanoic acid
6-(2-((N-cyclopropyl-3'-methyl-[1,1'-biphenyl]-4-carboxamido)methyl-d)phenoxy)hexanoic acid
6-(2-((N-cyclopropyl-4'-methyl-[1,1'-biphenyl]-4-carboxamido)methyl-d)phenoxy)hexanoic acid
6-(2-((N-cyclopropyl-2'-methoxy-[1,1'-biphenyl]-4-carboxamido)methyl-d)phenoxy)hexanoic acid
6-(2-((N-cyclopropyl-3'-methoxy-[1,1'-biphenyl]-4-carboxamido)methyl-d)phenoxy)hexanoic acid
6-(2-((N-cyclopropyl-4'-methoxy-[1,1'-biphenyl]-4-carboxamido)methyl-d)phenoxy)hexanoic acid
6-(2-((N-cyclopropyl-2'-fluoro-[1,1'-biphenyl]-4-carboxamido)methyl-d)phenoxy)hexanoic acid
6-(2-((N-cyclopropyl-3'-fluoro-[1,1'-biphenyl]-4-carboxamido)methyl-d)phenoxy)hexanoic acid
6-(2-((N-cyclopropyl-4'-fluoro-[1,1'-biphenyl]-4-carboxamido)methyl-d)phenoxy)hexanoic acid
6-(2-((N-cyclopropyl-2'-ethyl-[1,1'-biphenyl]-4-carboxamido)methyl-d)phenoxy)hexanoic acid
6-(2-((N-cyclopropyl-4'-ethyl-[1,1'-biphenyl]-4-carboxamido)methyl-d)phenoxy)hexanoic acid
6-(2-((N-cyclopropyl-2',3'-dimethyl-[1,1'-biphenyl]-4-carboxamido)methyl-d)phenoxy)hexanoic acid
6-(2-((N-cyclopropyl-2',5'-dimethyl-[1,1'-biphenyl]-4-carboxamido)methyl-d)phenoxy)hexanoic acid
6-(2-((N-cyclopropyl-2',6'-dimethyl-[1,1'-biphenyl]-4-carboxamido)methyl-d)phenoxy)hexanoic acid
6-(2-((N-cyclopropyl-3',5'-dimethyl-[1,1'-biphenyl]-4-carboxamido)methyl-d)phenoxy)hexanoic acid
6-(2-((N-cyclopropyl-2'-(trifluoromethyl)-[1,1'-biphenyl]-4-carboxamido)methyl-d)phenoxy)hexanoic acid
6-(2-((N-cyclopropyl-3'-(trifluoromethyl)-[1,1'-biphenyl]-4-carboxamido)methyl-d)phenoxy)hexanoic acid
6-(2-((N-cyclopropyl-4'-(trifluoromethyl)-[1,1'-biphenyl]-4-carboxamido)methyl-d)phenoxy)hexanoic acid
6-(2-((N-cyclopropyl-4'-propyl-[1,1'-biphenyl]-4-carboxamido)methyl-d)phenoxy)hexanoic acid
6-(2-((4'-butyl-N-cyclopropyl-[1,1'-biphenyl]-4-carboxamido)methyl-d)phenoxy)hexanoic acid
6-(2-((N-cyclopropyl-[1,1':2',1''-terphenyl]-4-carboxamido)methyl-d)phenoxy)hexanoic acid
(E)-6-(2-((N-cyclopropyl-4-(furan-2-yl)benzamido)methyl-d)phenoxy)hex-3-enoic acid
(Z)-6-(2-((N-cyclopropyl-4-(furan-2-yl)benzamido)methyl-d)phenoxy)hex-4-enoic acid
(Z)-6-(2-((N-cyclopropyl-4-(furan-2-yl)benzamido)methyl-d)phenoxy)hex-3-enoic acid
(E)-6-(2-((N-cyclopropyl-4-(furan-2-yl)benzamido)methyl-d)phenoxy)hex-4-enoic acid
6-(2-((N-cyclopropyl-4-(furan-2-yl)benzamido)methyl-d)phenoxy)hex-4-ynoic acid
6-(2-((N-cyclopropyl-4-(furan-2-yl)benzamido)methyl-d)phenoxy)hex-3-ynoic acid
N-((2-((5-(1H-tetrazol-5-yl)pentyl)oxy)phenyl)methyl-d)-N-cyclopropyl-4-(furan-2-yl)benzamide
6-((4-((N-cyclopropyl-4-(furan-2-yl)benzamido)methyl-d)thiophen-3-yl)oxy)hexanoic acid
6-(2-((N-cyclopropyl-[2,3'-bifuran]-5'-carboxamido)methyl-d)phenoxy)hexanoic acid
6-(2-((N-cyclopropyl-5-(furan-2-yl)thiazole-2-carboxamido)methyl-d)phenoxy)hexanoic acid
6-(2-((N-cyclopropylbenzo[c][1,2,5]oxadiazole-5-carboxamido)methyl-d)phenoxy)hexanoic acid
6-(2-((N-cyclopropyl-2-oxo-2,3-dihydrobenzofuran-5-carboxamido)methyl-d)phenoxy)hexanoic acid
6-(2-((N-cyclopropyl-2-oxoindoline-5-carboxamido)methyl-d)phenoxy)hexanoic acid
6-(2-(cyclopropyl((4-(furan-2-yl)phenyl)methyl-d)carbamoyl)phenoxy)hexanoic acid
6-(2-(((4-(furan-2-yl)phenyl)methyl-d)(2-morpholinoethyl)carbamoyl)phenoxy)hexanoic acid
N-cyclopropyl-4-(furan-2-yl)-N-((2-((5-(6-hydroxy-4-oxo-4H-1,3-dioxin-2-yl)pentyl)oxy)phenyl)methyl-d)benzamide
N-cyclopropyl-4-(furan-2-yl)-N-((2-((5-(3-hydroxyisoxazol-5-yl)pentyl)oxy)phenyl)methyl-d)benzamide
N-cyclopropyl-4-(furan-2-yl)-N-((2-((5-(3-hydroxy-1-methyl-1H-pyrazol-5-yl)pentyl)oxy)phenyl)methyl-d)benzamide
N-cyclopropyl-4-(furan-2-yl)-N-((2-((5-(3-hydroxyisothiazol-5-yl)pentyl)oxy)phenyl)methyl-d)benzamide
N-cyclopropyl-N-((2-((5-(2,4-dioxooxazolidin-5-yl)pentyl)oxy)phenyl)methyl-d)-4-(furan-2-yl)benzamide
N-cyclopropyl-N-((2-((5-(2,4-dioxothiazolidin-5-yl)pentyl)oxy)phenyl)methyl-d)-4-(furan-2-yl)benzamide
N-cyclopropyl-N-((2-((5-(2,5-dioxo-2,5-dihydro-1H-imidazol-4-yl)pentyl)oxy)phenyl)methyl-d)-4-(furan-2-yl)benzamide N-cyclopropyl-N-((2-((5-(2,5-dioxo-2,5-dihydro-1H-pyrrol-3-yl)pentyl)oxy)phenyl)methyl-d)-4-(furan-2-yl)benzamide
N-cyclopropyl-N-((2-((5-(2,5-dioxo-2,5-dihydro-1H-pyrrol-3-yl)pentyl)oxy)phenyl)methyl-d2)-4-(furan-2-yl)benzamide
N-(cyclopropyl-1-d)-N-(2-((5-(2,5-dioxo-2,5-dihydro-1H-pyrrol-3-yl)pentyl)oxy)benzyl)-4-(furan-2-yl)benzamide
6-(2-((4-chloro-N-isopropylbenzamido)methyl-d)phenoxy)hexanoic acid
6-(2-((N-isopropyl-4-methoxybenzamido)methyl-d)phenoxy)hexanoic acid
6-(2-((N-isopropyl-4-(trifluoromethoxy)benzamido)methyl-d)phenoxy)hexanoic acid
6-(2-((4-(dimethylamino)-N-isopropylbenzamido)methyl-d)phenoxy)hexanoic acid
6-(2-((4-acetyl-N-isopropylbenzamido)methyl-d)phenoxy)hexanoic acid
6-(2-((N-isopropyl-4-(methylsulfonyl)benzamido)methyl-d)phenoxy)hexanoic acid
6-(2-((N-isopropyl-4-methylbenzamido)methyl-d)phenoxy)hexanoic acid
6-(2-((4-fluoro-N-isopropylbenzamido)methyl-d)phenoxy)hexanoic acid
6-(2-((N-isopropyl-4-(4-methoxytetrahydro-2H-pyran-4-yl)benzamido)methyl-d)phenoxy)hexanoic acid
6-(2-((4-cyclopropoxy-N-isopropylbenzamido)methyl-d)phenoxy)hexanoic acid
6-(2-((3'-(furan-3-yl)-N-isopropyl-[1,1'-biphenyl]-4-carboxamido)methyl-d)phenoxy)hexanoic acid
6-(2-((N-isopropyl-4-(pyrrolidin-1-yl)benzamido)methyl-d)phenoxy)hexanoic acid
6-(2-((N-isopropyl-4-(oxetan-3-ylethynyl)benzamido)methyl-d)phenoxy)hexanoic acid
6-(2-((4-(cyclopentylethynyl)-N-isopropylbenzamido)methyl-d)phenoxy)hexanoic acid
6-(2-((4-(cyclobutylethynyl)-N-isopropylbenzamido)methyl-d)phenoxy)hexanoic acid
6-(2-((N-isopropyl-4-(3,3,3-trifluoroprop-1-yn-1-yl)benzamido)methyl-d)phenoxy)hexanoic acid
6-(2-((N-isopropyl-4-((1-methylazetidin-3-yl)ethynyl)benzamido)methyl-d)phenoxy)hexanoic acid
6-(2-((N-isopropyl-4-(1-methoxycyclopropyl)benzamido)methyl-d)phenoxy)hexanoic acid
6-(2-((N-isopropyl-4-(1-(trifluoromethyl)cyclopropyl)benzamido)methyl-d)phenoxy)hexanoic acid
6-(2-((N-isopropyl-4-(tetrahydro-2H-pyran-2-yl)benzamido)methyl-d)phenoxy)hexanoic acid
6-(2-((N-isopropyl-4-(4-methylbicyclo[2.2.2]octan-1-yl)benzamido)methyl-d)phenoxy)hexanoic acid
6-(2-((N-isopropyl-4-(oxetan-2-yl)benzamido)methyl-d)phenoxy)hexanoic acid
6-(2-((N-isopropyl-4-(6-oxo-1,6-dihydropyridin-2-yl)benzamido)methyl-d)phenoxy)hexanoic acid
6-(2-((N-isopropyl-4-(oxetan-2-ylethynyl)benzamido)methyl-d)phenoxy)hexanoic acid
6-(2-((N-isopropyl-4-(4-(trifluoromethyl)bicyclo[2.2.2]octan-1-yl)benzamido)methyl-d)phenoxy)hexanoic acid
6-(2-((N-isopropyl-4-(4-phenylbicyclo[2.2.2]octan-1-yl)benzamido)methyl-d)phenoxy)hexanoic acid
6-(2-((4-cyano-N-isopropylbenzamido)methyl-d)phenoxy)hexanoic acid
6-(2-((4-(furan-2-yl)-N-isopropylphenyl)sulfonamido)methyl-d)phenoxy)hexanoic acid
6-(2-((5-(furan-2-yl)-N-isopropylpicolinamido)methyl-d)phenoxy)hexanoic acid
6-(2-((5-(furan-2-yl)-N-isopropylthiophene-2-carboxamido)methyl-d)phenoxy)hexanoic acid
6-(2-((6-(furan-2-yl)-N-isopropylnicotinamido)methyl-d)phenoxy)hexanoic acid
6-(2-((2-(furan-2-yl)-N-isopropylthiazole-5-carboxamido)methyl-d)phenoxy)hexanoic acid
6-(2-(((4-(furan-2-yl)phenyl)methyl-d)(isopropyl)carbamoyl)phenoxy)hexanoic acid
6-(2-(2-((4-(furan-2-yl)phenyl)(isopropyl)amino)-2-oxoethyl-1-d)phenoxy)hexanoic acid
6-(2-((3-fluoro-4-(furan-2-yl)-N-isopropylbenzamido)methyl-d)phenoxy)hexanoic acid
6-(2-((2-fluoro-4-(furan-2-yl)-N-isopropylbenzamido)methyl-d)phenoxy)hexanoic acid
6-(2-((1-(furan-2-yl)-N-isopropylpiperidine-4-carboxamido)methyl-d)phenoxy)hexanoic acid
6-(2-((5-(furan-2-yl)-N-isopropylisoxazole-3-carboxamido)methyl-d)phenoxy)hexanoic acid
6-(2-((4-(furan-2-yl)-N-isopropylcyclohexane-1-carboxamido)methyl-d)phenoxy)hexanoic acid
6-(2-((6-(furan-2-yl)-1H-indazol-3-yl)(isopropyl)amino)methyl-d)phenoxy)hexanoic acid
6-(2-((5-(furan-2-yl)-N-isopropylthiazole-2-carboxamido)methyl-d)phenoxy)hexanoic acid
6-(2-((2-(furan-2-yl)-N-isopropyloxazole-5-carboxamido)methyl-d)phenoxy)hexanoic acid
6-(2-((N-isopropyl-2-methylbenzofuran-6-carboxamido)methyl-d)phenoxy)hexanoic acid
6-(2-((N-isopropyl-2-methylbenzofuran-5-carboxamido)methyl-d)phenoxy)hexanoic acid
6-(2-((4-(furan-2-yl)-N-isopropyl-2,5-dioxopiperazine-1-carboxamido)methyl-d)phenoxy)hexanoic acid
6-(2-((1-(furan-2-yl)-N-isopropyl-2-oxopiperidine-4-carboxamido)methyl-d)phenoxy)hexanoic acid
6-(2-((5-(furan-2-yl)-N-isopropyl-1H-pyrazole-3-carboxamido)methyl-d)phenoxy)hexanoic acid
6-(2-((7-(furan-2-yl)-4-oxoquinazolin-3(4H)-yl)methyl-d)phenoxy)hexanoic acid
6-(2-((5-(furan-2-yl)-N-isopropyl-3,6-dioxopiperazine-2-carboxamido)methyl-d)phenoxy)hexanoic acid
6-(2-((4-(furan-2-yl)-N-isopropylpiperidine-1-carboxamido)methyl-d)phenoxy)hexanoic acid
6-(2-((5-(furan-2-yl)-N-isopropyl-1-methyl-1H-pyrazole-3-carboxamido)methyl-d)phenoxy)hexanoic acid
6-(2-((4-(furan-2-yl)-N-methylbenzamido)methyl-d)phenoxy)hexanoic acid
6-(2-((4-(furan-2-yl)-N-(2,2,2-trifluoroethyl)benzamido)methyl-d)phenoxy)hexanoic acid
6-(2-((4-(furan-2-yl)-N-(2-methoxyethyl)benzamido)methyl-d)phenoxy)hexanoic acid
6-(2-((4-(furan-2-yl)benzamido)methyl-d)phenoxy)hexanoic acid
6-(2-((4-(furan-2-yl)-N-(oxetan-3-yl)benzamido)methyl-d)phenoxy)hexanoic acid
6-(2-((N-(2-cyanopropan-2-yl)-4-(furan-2-yl)benzamido)methyl-d)phenoxy)hexanoic acid
6-(2-((6-(furan-2-yl)-3-methyl-1-oxo-3,4-dihydroisoquinolin-2(1H)-yl)methyl-d)phenoxy)hexanoic acid
6-(2-((4-(furan-2-yl)-N-hydroxybenzamido)methyl-d)phenoxy)hexanoic acid
6-(2-(1-(4-(furan-2-yl)benzoyl)piperidin-2-yl-2-d)phenoxy)hexanoic acid
6-(2-((4-(furan-2-yl)-N-methoxybenzamido)methyl-d)phenoxy)hexanoic acid
6-(2-((N-(cyclopropylmethyl)-4-(furan-2-yl)benzamido)methyl-d)phenoxy)hexanoic acid 6-(2-((N-(1-cyclopropylethyl)-4-(furan-2-yl)benzamido)methyl-d)phenoxy)hexanoic acid
6-(2-(1-(4-(furan-2-yl)benzoyl)pyrrolidin-2-yl-2-d)phenoxy)hexanoic acid
6-(2-((4-(furan-2-yl)-N-isopropylbenzamido)methyl-d)-4-methylphenoxy)hexanoic acid
6-(4-fluoro-2-((4-(furan-2-yl)-N-isopropylbenzamido)methyl-d)phenoxy)hexanoic acid
6-(2-(2-(4-(furan-2-yl)phenyl)pyrrolidine-1-carbonyl-2-d)phenoxy)hexanoic acid
6-(4-bromo-2-((4-(furan-2-yl)-N-isopropylbenzamido)methyl-d)phenoxy)hexanoic acid
6-(2-(2-(4-(furan-2-yl)phenyl)piperidine-1-carbonyl-2-d)phenoxy)hexanoic acid
6-(4-cyano-2-((4-(furan-2-yl)-N-isopropylbenzamido)methyl-d)phenoxy)hexanoic acid
6-(2-((4-(furan-2-yl)-N-isopropylbenzamido)methyl-d)-4-methoxyphenoxy)hexanoic acid
6-((3-((4-(furan-2-yl)-N-isopropylbenzamido)methyl-d)pyridin-2-yl)oxy)hexanoic acid
6-((2-((4-(furan-2-yl)-N-isopropylbenzamido)methyl-d)pyridin-3-yl)oxy)hexanoic acid
6-((3-((4-(furan-2-yl)-N-isopropylbenzamido)methyl-d)pyridin-4-yl)oxy)hexanoic acid
6-((4-((4-(furan-2-yl)-N-isopropylbenzamido)methyl-d)-1-methyl-1H-pyrazol-3-yl)oxy)hexanoic acid
6-((4-((4-(furan-2-yl)-N-isopropylbenzamido)methyl-d)pyridin-3-yl)oxy)hexanoic acid
6-((2-(4-(furan-2-yl)benzoyl)-1,2,3,4-tetrahydroisoquinolin-8-yl-1-d)oxy)hexanoic acid
6-((4-((4-(furan-2-yl)-N-isopropylbenzamido)methyl-d)isothiazol-3-yl)oxy)hexanoic acid
6-((2-((4-(furan-2-yl)-N-isopropylbenzamido)methyl-d)cyclopentyl)oxy)hexanoic acid
6-(4-cyclopropyl-2-((4-(furan-2-yl)-N-isopropylbenzamido)methyl-d)phenoxy)hexanoic acid
6-((2-((4-(furan-2-yl)-N-isopropylbenzamido)methyl-d)cyclohexyl)oxy)hexanoic acid
6-(4-(azetidin-1-yl)-2-((4-(furan-2-yl)-N-isopropylbenzamido)methyl-d)phenoxy)hexanoic acid
6-(2-((4-(furan-2-yl)-N-isopropylbenzamido)methyl-d)-4-(trifluoromethyl)phenoxy)hexanoic acid
N-((2-(4-(2H-tetrazol-5-yl)butoxy)phenyl)methyl-d)-4-(furan-2-yl)-N-isopropylbenzamide
7-(2-((4-(furan-2-yl)-N-isopropylbenzamido)methyl-d)phenoxy)heptanoic acid
2-(3-(2-((4-(furan-2-yl)-N-isopropylbenzamido)methyl-d)phenoxy)propoxy)acetic acid
5-(2-(2-((4-(furan-2-yl)-N-isopropylbenzamido)methyl-d)phenoxy)ethyl)isoxazole-3-carboxylic acid
2-(5-((2-((4-(furan-2-yl)-N-isopropylbenzamido)methyl-d)phenoxy)methyl)isoxazol-3-yl)acetic acid
2-(4-(2-((4-(furan-2-yl)-N-isopropylbenzamido)methyl-d)phenoxy)cyclohexyl)acetic acid
5-(2-((4-(furan-2-yl)-N-isopropylbenzamido)methyl-d)phenoxy)pentanoic acid
3-(2-(2-((4-(furan-2-yl)-N-isopropylbenzamido)methyl-d)phenoxy)ethoxy)propanoic acid
3-(2-(2-((4-(furan-2-yl)-N-isopropylbenzamido)methyl-d)phenoxy)acetamido)propanoic acid
3-(4-((2-((4-(furan-2-yl)-N-isopropylbenzamido)methyl-d)phenoxy)methyl)thiazol-2-yl)propanoic acid
3-(2-(2-((4-(furan-2-yl)-N-isopropylbenzamido)methyl-d)phenoxy)ethyl)cyclobutane-1-carboxylic acid
3-((2-(2-((4-(furan-2-yl)-N-isopropylbenzamido)methyl-d)phenoxy)ethyl)amino)-3-oxopropanoic acid
3-(3-(2-((4-(furan-2-yl)-N-isopropylbenzamido)methyl-d)phenoxy)azetidin-1-yl)propanoic acid
6-(2-((4-(furan-2-yl)-N-isopropylbenzamido)methyl-d)phenoxy)heptanoic acid
2-(3-((2-((4-(furan-2-yl)-N-isopropylbenzamido)methyl-d)phenoxy)methyl)azetidin-1-yl)acetic acid
2-((3-(2-((4-(furan-2-yl)-N-isopropylbenzamido)methyl-d)phenoxy)cyclopentyl)oxy)acetic acid
2-(4-((2-((4-(furan-2-yl)-N-isopropylbenzamido)methyl-d)phenoxy)methyl)thiazol-2-yl)acetic acid
2-((3-(2-((4-(furan-2-yl)-N-isopropylbenzamido)methyl-d)phenoxy)propyl)thio)acetic acid
1-(2-(2-((4-(furan-2-yl)-N-isopropylbenzamido)methyl-d)phenoxy)ethyl)azetidine-3-carboxylic acid
2-(4-((2-((4-(furan-2-yl)-N-isopropylbenzamido)methyl-d)phenoxy)methyl)-1H-1,2,3-triazol-1-yl)acetic acid
3-(3-(2-((4-(furan-2-yl)-N-isopropylbenzamido)methyl-d)phenoxy)piperidin-1-yl)propanoic acid
1-(2-(2-((4-(furan-2-yl)-N-isopropylbenzamido)methyl-d)phenoxy)acetyl)pyrrolidine-3-carboxylic acid
1-(2-(2-((4-(furan-2-yl)-N-isopropylbenzamido)methyl-d)phenoxy)ethyl)pyrrolidine-3-carboxylic acid
(E)-6-(2-((4-(furan-2-yl)-N-isopropylbenzamido)methyl-d)phenoxy)-4-methylhex-4-enoic acid
6-((4-((4-(furan-2-yl)-N-isopropylbenzamido)methyl-d)pyrrolidin-3-yl)oxy)hexanoic acid
4-(furan-2-yl)-N-((2-(4-(5-hydroxy-1,3,4-oxadiazol-2-yl)butoxy)phenyl)methyl-d)-N-isopropylbenzamide
6-(2-((4-(cyclopropylethynyl)-N-isopropylbenzamido)methyl-d)phenoxy)hexanoic acid
6-((4-((4-(furan-2-yl)-N-isopropylbenzamido)methyl-d)morpholin-3-yl)oxy)hexanoic acid
6-(2-((N-benzyl-4-(furan-2-yl)benzamido)methyl-d)phenoxy)hexanoic acid
6-(2-((4-(cyclopropylethynyl)-N-methylbenzamido)methyl-d)phenoxy)hexanoic acid
6-((4-((4-(furan-2-yl)-N-isopropylbenzamido)methyl-d)morpholin-3-yl)oxy)hexanoic acid
6-(2-((N-methyl-4-(3,3,3-trifluoroprop-1-yn-1-yl)benzamido)methyl-d)phenoxy)hexanoic acid
6-(2-((4-cyclopropoxy-N-methylbenzamido)methyl-d)phenoxy)hexanoic acid
6-(2-((5-(furan-2-yl)-N-methylpicolinamido)methyl-d)phenoxy)hexanoic acid
6-(2-((5-(furan-2-yl)-N-methylthiazole-2-carboxamido)methyl-d)phenoxy)hexanoic acid
3-(2-(2-((4-(furan-2-yl)-N-methylbenzamido)methyl-d)phenoxy)ethoxy)propanoic acid
N-((2-(4-(2H-tetrazol-5-yl)butoxy)phenyl)methyl-d)-4-(furan-2-yl)-N-methylbenzamide
6-(2-((4-(furan-2-yl)-N-methylbenzamido)methyl-d)phenoxy)heptanoic acid
6-(2-((4-(furan-2-yl)-N-methylbenzamido)methyl-d)-4-methoxyphenoxy)hexanoic acid
6-(2-((4-(furan-2-yl)-N-methylbenzamido)methyl-d)-4-methylphenoxy)hexanoic acid
6-(4-fluoro-2-((4-(furan-2-yl)-N-methylbenzamido)methyl-d)phenoxy)hexanoic acid
6-((3-((6-(furan-2-yl)-N-methylnicotinamido)methyl-d)pyridin-2-yl)oxy)hexanoic acid
6-((3-((4-(furan-2-yl)-N-methylbenzamido)methyl-d)pyridin-2-yl)oxy)hexanoic acid
6-(2-((6-(cyclopropylethynyl)-N-isopropylnicotinamido)methyl-d)phenoxy)hexanoic acid
6-(2-((6-(cyclopropylethynyl)-N-methylnicotinamido)methyl-d)phenoxy)hexanoic acid 6-(2-((N-(but-2-yn-1-yl)-6-(furan-2-yl)nicotinamido)methyl-d)phenoxy)hexanoic acid 6-(2-((6-fluoro-N-isopropylnicotinamido)methyl-d)phenoxy)hexanoic acid 6-(2-((6-fluoro-N-(furan-2-ylmethyl)nicotinamido)methyl-d)phenoxy)hexanoic acid 6-(2-((N-benzyl-6-fluoronicotinamido)methyl-d)phenoxy)hexanoic acid sodium 6-(2-((N-cyclopropyl-4-(furan-2-yl)benzamido)methyl-d)phenoxy)hexanoate 6-(2-((4-((difluoromethyl)thio)-N-isopropylbenzamido)methyl-d)phenoxy)hexanoic acid 6-(2-((N-benzyl-6-fluoronicotinamido)methyl-d)phenoxy)hexanoic acid (E)-6-(2-((4-(furan-2-yl)-N'-hydroxy-N-isopropylbenzimidamido)methyl-d)phenoxy)hexanoic acid 6-(2-((4-fluoro-5-(furan-2-yl)-N-isopropyl-1H-pyrazole-3-carboxamido)methyl-d)phenoxy)hexanoic acid 6-(2-((4-((fluoromethyl)thio)-N-isopropylbenzamido)methyl-d)phenoxy)hexanoic acid (6R)-6-(2-((5-(furan-2-yl)-N-isopropyl-1H-pyrazole-3-carboxamido)methyl-d)phenoxy)heptanoic acid 6-(2-((5-(cyclopropylethynyl)-N-isopropyl-1H-pyrazole-3-carboxamido)methyl-d)phenoxy)hexanoic acid (2S)-4-((2-((4-(furan-2-yl)-N-isopropylbenzamido)methyl-d)phenyl)sulfonyl)-2,3-dihydro-1H-indene-2-carboxylic acid 6-(2-(((4-(furan-2-yl)phenyl)methyl-d)(isopropyl)carbamoyl)phenoxy)hexanoic acid 6-(2-(2-((4-(furan-2-yl)phenyl)(isopropyl)amino)-2-oxoethyl-1-d)phenoxy)hexanoic acid 6-(2-((N-(propan-2-yl-2-d)-[1,1'-biphenyl]-4-carboxamido)methyl)phenoxy)hexanoic acid 6-(2-((N-isopropyl-[1,1'-biphenyl]-4-carboxamido)methyl-d2)phenoxy)hexanoic acid ethyl 6-(2-(1-(4-bromo-N-(cyclopropyl-1-d)benzamido)-2-(tert-butylamino)-2-oxoethyl)phenoxy)hexanoate ethyl 6-(2-(2-(tert-butylamino)-1-(N-(cyclopropyl-1-d)-[1,1'-biphenyl]-4-carboxamido)-2-oxoethyl)phenoxy)hexanoate ethyl 6-(2-(2-amino-1-(N-(cyclopropyl-1-d)-[1,1'-biphenyl]-4-carboxamido)-2-oxoethyl)phenoxy)hexanoate 6-(2-(2-(tert-butylamino)-1-(N-(cyclopropyl-1-d)-[1,1'-biphenyl]-4-carboxamido)-2-oxoethyl)phenoxy)hexanoic acid 6-(2-(2-amino-1-(N-(cyclopropyl-1-d)-[1,1'-biphenyl]-4-carboxamido)-2-oxoethyl)phenoxy)hexanoic acid N-(2-amino-1-(2-((6-(hydroxyamino)-6-oxohexyl)oxy)phenyl)-2-oxoethyl)-N-(cyclopropyl-1-d)-[1,1'-biphenyl]-4-carboxamide 6-(2-((N-cyclopropyl-[1,1'-biphenyl]-4-carboxamido)methyl-d2)phenoxy)hexanoic acid 6-(2-((N-(cyclopropyl-1-d)-[1,1'-biphenyl]-4-carboxamido)methyl)phenoxy)hexanoic acid 6-(2-((N-cyclopropyl-4-(pyridin-3-yl)benzamido)methyl-d2)phenoxy)hexanoic acid 6-(2-((N-(cyclopropyl-1-d)-4-(pyridin-3-yl)benzamido)methyl)phenoxy)hexanoic acid 6-(2-((N-cyclopropyl-4-(pyridin-4-yl)benzamido)methyl-d2)phenoxy)hexanoic acid 6-(2-((N-(cyclopropyl-1-d)-4-(pyridin-4-yl)benzamido)methyl)phenoxy)hexanoic acid 6-(2-((N-cyclopropyl-4-(1H-pyrazol-4-yl)benzamido)methyl-d2)phenoxy)hexanoic acid 6-(2-((N-(cyclopropyl-1-d)-4-(1H-pyrazol-4-yl)benzamido)methyl)phenoxy)hexanoic acid 6-(2-((N-cyclopropyl-4-(furan-2-yl)benzamido)methyl-d2)phenoxy)hexanoic acid 6-(2-((N-(cyclopropyl-1-d)-4-(furan-2-yl)benzamido)methyl)phenoxy)hexanoic acid 6-(2-((N-cyclopropyl-4-(furan-3-yl)benzamido)methyl-d2)phenoxy)hexanoic acid 6-(2-((N-(cyclopropyl-1-d)-4-(furan-3-yl)benzamido)methyl)phenoxy)hexanoic acid 6-(2-((N-cyclopropyl-4-(thiophen-2-yl)benzamido)methyl-d2)phenoxy)hexanoic acid 6-(2-((N-(cyclopropyl-1-d)-4-(thiophen-2-yl)benzamido)methyl)phenoxy)hexanoic acid 6-(2-((N-cyclopropyl-4-(thiophen-3-yl)benzamido)methyl-d2)phenoxy)hexanoic acid 6-(2-((N-(cyclopropyl-1-d)-4-(thiophen-3-yl)benzamido)methyl)phenoxy)hexanoic acid 6-(2-((N-benzyl-[1,1'-biphenyl]-4-carboxamido)methyl-d2)phenoxy)hexanoic acid 6-(2-((N-(phenylmethyl-d)-[1,1'-biphenyl]-4-carboxamido)methyl)phenoxy)hexanoic acid 6-(2-((N-(phenylmethyl-d2)-[1,1'-biphenyl]-4-carboxamido)methyl)phenoxy)hexanoic acid 6-(2-((N-benzyl-4-(pyridin-3-yl)benzamido)methyl-d2)phenoxy)hexanoic acid 6-(2-((N-(phenylmethyl-d)-4-(pyridin-3-yl)benzamido)methyl)phenoxy)hexanoic acid 6-(2-((N-(phenylmethyl-d2)-4-(pyridin-3-yl)benzamido)methyl)phenoxy)hexanoic acid 6-(2-((N-benzyl-4-(pyridin-4-yl)benzamido)methyl-d2)phenoxy)hexanoic acid 6-(2-((N-(phenylmethyl-d)-4-(pyridin-4-yl)benzamido)methyl)phenoxy)hexanoic acid 6-(2-((N-(phenylmethyl-d2)-4-(pyridin-4-yl)benzamido)methyl)phenoxy)hexanoic acid 6-(2-((N-benzyl-4-(1H-pyrazol-4-yl)benzamido)methyl-d2)phenoxy)hexanoic acid 6-(2-((N-(phenylmethyl-d)-4-(1H-pyrazol-4-yl)benzamido)methyl)phenoxy)hexanoic acid 6-(2-((N-(phenylmethyl-d2)-4-(1H-pyrazol-4-yl)benzamido)methyl)phenoxy)hexanoic acid 6-(2-((N-benzyl-4-(furan-2-yl)benzamido)methyl-d2)phenoxy)hexanoic acid 6-(2-((4-(furan-2-yl)-N-(phenylmethyl-d)benzamido)methyl)phenoxy)hexanoic acid 6-(2-((4-(furan-2-yl)-N-(phenylmethyl-d2)benzamido)methyl)phenoxy)hexanoic acid 6-(2-((N-benzyl-4-(furan-3-yl)benzamido)methyl-d2)phenoxy)hexanoic acid 6-(2-((4-(furan-3-yl)-N-(phenylmethyl-d)benzamido)methyl)phenoxy)hexanoic acid 6-(2-((4-(furan-3-yl)-N-(phenylmethyl-d2)benzamido)methyl)phenoxy)hexanoic acid 6-(2-((N-benzyl-4-(thiophen-2-yl)benzamido)methyl-d2)phenoxy)hexanoic acid 6-(2-((N-(phenylmethyl-d)-4-(thiophen-2-yl)benzamido)methyl)phenoxy)hexanoic acid 6-(2-((N-(phenylmethyl-d2)-4-(thiophen-2-yl)benzamido)methyl)phenoxy)hexanoic acid 6-(2-((N-benzyl-4-(thiophen-3-yl)benzamido)methyl-d2)phenoxy)hexanoic acid 6-(2-((N-(phenylmethyl-d)-4-(thiophen-3-yl)benzamido)methyl)phenoxy)hexanoic acid 6-(2-((N-(phenylmethyl-d2)-4-(thiophen-3-yl)benzamido)methyl)phenoxy)hexanoic acid N-benzyl-N-((2-((6-(hydroxyamino)-6-oxohexyl)oxy)phenyl)methyl-d2)-[1,1'-biphenyl]-4-carboxamide N-(2-((6-(hydroxyamino)-6-oxohexyl)oxy)benzyl)-N-(phenylmethyl-d)-[1,1'-biphenyl]-4-carboxamide
N-(2-((6-(hydroxyamino)-6-oxohexyl)oxy)benzyl)-N-(phenylmethyl-d2)-[1,1'-biphenyl]-4-carboxamide
N-benzyl-N-((2-((6-(hydroxyamino)-6-oxohexyl)oxy)phenyl)methyl-d2)-4-(pyridin-3-yl)benzamide
N-(2-((6-(hydroxyamino)-6-oxohexyl)oxy)benzyl)-N-(phenylmethyl-d)-4-(pyridin-3-yl)benzamide
N-(2-((6-(hydroxyamino)-6-oxohexyl)oxy)benzyl)-N-(phenylmethyl-d2)-4-(pyridin-3-yl)benzamide
N-benzyl-N-((2-((6-(hydroxyamino)-6-oxohexyl)oxy)phenyl)methyl-d2)-4-(pyridin-4-yl)benzamide
N-(2-((6-(hydroxyamino)-6-oxohexyl)oxy)benzyl)-N-(phenylmethyl-d)-4-(pyridin-4-yl)benzamide
N-(2-((6-(hydroxyamino)-6-oxohexyl)oxy)benzyl)-N-(phenylmethyl-d2)-4-(pyridin-4-yl)benzamide
N-benzyl-N-((2-((6-(hydroxyamino)-6-oxohexyl)oxy)phenyl)methyl-d2)-4-(1H-pyrazol-4-yl)benzamide
N-(2-((6-(hydroxyamino)-6-oxohexyl)oxy)benzyl)-N-(phenylmethyl-d)-4-(1H-pyrazol-4-yl)benzamide
N-(2-((6-(hydroxyamino)-6-oxohexyl)oxy)benzyl)-N-(phenylmethyl-d2)-4-(1H-pyrazol-4-yl)benzamide
N-benzyl-4-(furan-2-yl)-N-((2-((6-(hydroxyamino)-6-oxohexyl)oxy)phenyl)methyl-d2)benzamide
4-(furan-2-yl)-N-(2-((6-(hydroxyamino)-6-oxohexyl)oxy)benzyl)-N-(phenylmethyl-d)benzamide
4-(furan-2-yl)-N-(2-((6-(hydroxyamino)-6-oxohexyl)oxy)benzyl)-N-(phenylmethyl-d2)benzamide
N-benzyl-4-(furan-3-yl)-N-((2-((6-(hydroxyamino)-6-oxohexyl)oxy)phenyl)methyl-d2)benzamide
4-(furan-3-yl)-N-(2-(hydroxyamino)-6-oxohexyl)oxy)benzyl)-N-(phenylmethyl-d)benzamide
4-(furan-3-yl)-N-(2-(hydroxyamino)-6-oxohexyl)oxy)benzyl)-N-(phenylmethyl-d2)benzamide
N-benzyl-N-((2-((6-(hydroxyamino)-6-oxohexyl)oxy)phenyl)methyl-d2)-4-(thiophen-2-yl)benzamide
N-(2-((6-(hydroxyamino)-6-oxohexyl)oxy)benzyl)-N-(phenylmethyl-d)-4-(thiophen-2-yl)benzamide
N-(2-((6-(hydroxyamino)-6-oxohexyl)oxy)benzyl)-N-(phenylmethyl-d2)-4-(thiophen-2-yl)benzamide
N-benzyl-N-((2-((6-(hydroxyamino)-6-oxohexyl)oxy)phenyl)methyl-d2)-4-(thiophen-3-yl)benzamide
N-(2-((6-(hydroxyamino)-6-oxohexyl)oxy)benzyl)-N-(phenylmethyl-d)-4-(thiophen-3-yl)benzamide
N-(2-((6-(hydroxyamino)-6-oxohexyl)oxy)benzyl)-N-(phenylmethyl-d2)-4-(thiophen-3-yl)benzamide
6-(2-((4-bromo-N-(sec-butyl)benzamido)methyl-d2)phenoxy)hexanoic acid
6-(2-((4-bromo-N-(butan-2-yl-2-d)benzamido)methyl)phenoxy)hexanoic acid
6-(2-((N-(sec-butyl)-[1,1'-biphenyl]-4-carboxamido)methyl-d2)phenoxy)hexanoic acid
6-(2-((N-(butan-2-yl-2-d)-[1,1'-biphenyl]-4-carboxamido)methyl)phenoxy)hexanoic acid
6-(2-((N-(sec-butyl)-4-(pyridin-3-yl)benzamido)methyl-d2)phenoxy)hexanoic acid
6-(2-((N-(butan-2-yl-2-d)-4-(pyridin-3-yl)benzamido)methyl)phenoxy)hexanoic acid
6-(2-((N-(sec-butyl)-4-(pyridin-4-yl)benzamido)methyl-d2)phenoxy)hexanoic acid
6-(2-((N-(butan-2-yl-2-d)-4-(pyridin-4-yl)benzamido)methyl)phenoxy)hexanoic acid
6-(2-((N-(sec-butyl)-4-(1H-pyrazol-4-yl)benzamido)methyl-d2)phenoxy)hexanoic acid
6-(2-((N-(butan-2-yl-2-d)-4-(1H-pyrazol-4-yl)benzamido)methyl)phenoxy)hexanoic acid
6-(2-((N-(sec-butyl)-4-(furan-2-yl)benzamido)methyl-d2)phenoxy)hexanoic acid
6-(2-((N-(butan-2-yl-2-d)-4-(furan-2-yl)benzamido)methyl)phenoxy)hexanoic acid
6-(2-((N-(sec-butyl)-4-(furan-3-yl)benzamido)methyl-d2)phenoxy)hexanoic acid
6-(2-((N-(butan-2-yl-2-d)-4-(furan-3-yl)benzamido)methyl)phenoxy)hexanoic acid
6-(2-((N-(sec-butyl)-4-(thiophen-2-yl)benzamido)methyl-d2)phenoxy)hexanoic acid
6-(2-((N-(butan-2-yl-2-d)-4-(thiophen-2-yl)benzamido)methyl)phenoxy)hexanoic acid
6-(2-((N-(sec-butyl)-4-(thiophen-3-yl)benzamido)methyl-d2)phenoxy)hexanoic acid
6-(2-((N-(butan-2-yl-2-d)-4-(thiophen-3-yl)benzamido)methyl)phenoxy)hexanoic acid
6-(2-((N-(3-morpholinopropyl)-[1,1'-biphenyl]-4-carboxamido)methyl-d2)phenoxy)hexanoic acid
6-(2-((N-(3-morpholinopropyl-1-d)-[1,1'-biphenyl]-4-carboxamido)methyl)phenoxy)hexanoic acid
6-(2-((N-(3-morpholinopropyl-1,1-d2)-[1,1'-biphenyl]-4-carboxamido)methyl)phenoxy)hexanoic acid
6-(2-((N-(3-morpholinopropyl)-4-(pyridin-3-yl)benzamido)methyl-d2)phenoxy)hexanoic acid
6-(2-((N-(3-morpholinopropyl-1-d)-4-(pyridin-3-yl)benzamido)methyl)phenoxy)hexanoic acid
6-(2-((N-(3-morpholinopropyl-1,1-d2)-4-(pyridin-3-yl)benzamido)methyl)phenoxy)hexanoic acid
6-(2-((N-(3-morpholinopropyl)-4-(pyridin-4-yl)benzamido)methyl-d2)phenoxy)hexanoic acid
6-(2-((N-(3-morpholinopropyl-1-d)-4-(pyridin-4-yl)benzamido)methyl)phenoxy)hexanoic acid
6-(2-((N-(3-morpholinopropyl-1,1-d2)-4-(pyridin-4-yl)benzamido)methyl)phenoxy)hexanoic acid
6-(2-((N-(3-morpholinopropyl)-4-(1H-pyrazol-4-yl)benzamido)methyl-d2)phenoxy)hexanoic acid
6-(2-((N-(3-morpholinopropyl-1-d)-4-(1H-pyrazol-4-yl)benzamido)methyl)phenoxy)hexanoic acid
6-(2-((N-(3-morpholinopropyl-1,1-d2)-4-(1H-pyrazol-4-yl)benzamido)methyl)phenoxy)hexanoic acid
6-(2-((4-(furan-2-yl)-N-(3-morpholinopropyl)benzamido)methyl-d2)phenoxy)hexanoic acid
6-(2-((4-(furan-2-yl)-N-(3-morpholinopropyl-1-d)benzamido)methyl)phenoxy)hexanoic acid
6-(2-((4-(furan-2-yl)-N-(3-morpholinopropyl-1,1-d2)benzamido)methyl)phenoxy)hexanoic acid
6-(2-((4-(furan-3-yl)-N-(3-morpholinopropyl)benzamido)methyl-d2)phenoxy)hexanoic acid
6-(2-((4-(furan-3-yl)-N-(3-morpholinopropyl-1-d)benzamido)methyl)phenoxy)hexanoic acid
6-(2-((4-(furan-3-yl)-N-(3-morpholinopropyl-1,1-d2)benzamido)methyl)phenoxy)hexanoic acid
6-(2-((N-(3-morpholinopropyl)-4-(thiophen-2-yl)benzamido)methyl-d2)phenoxy)hexanoic acid
6-(2-((N-(3-morpholinopropyl-1-d)-4-(thiophen-2-yl)benzamido)methyl)phenoxy)hexanoic acid
6-(2-((N-(3-morpholinopropyl-1,1-d2)-4-(thiophen-2-yl)benzamido)methyl)phenoxy)hexanoic acid
6-(2-((N-(3-morpholinopropyl)-4-(thiophen-3-yl)benzamido)methyl-d2)phenoxy)hexanoic acid
6-(2-((N-(3-morpholinopropyl-1-d)-4-(thiophen-3-yl)benzamido)methyl)phenoxy)hexanoic acid
6-(2-((N-(3-morpholinopropyl-1,1-d2)-4-(thiophen-3-yl)benzamido)methyl)phenoxy)hexanoic acid
6-(2-((N-(2-(pyridin-2-yl)ethyl)-[1,1'-biphenyl]-4-carboxamido)methyl-d2)phenoxy)hexanoic acid 6-(2-((N-(2-(pyridin-2-yl)ethyl-1-d)-[1,1'-biphenyl]-4-carboxamido)methyl)phenoxy)hexanoic acid
6-(2-((N-(2-(pyridin-2-yl)ethyl-1,1-d2)-[1,1'-biphenyl]-4-carboxamido)methyl)phenoxy)hexanoic acid
6-(2-((N-(2-(pyridin-2-yl)ethyl)-4-(pyridin-3-yl)benzamido)methyl-d2)phenoxy)hexanoic acid
6-(2-((N-(2-(pyridin-2-yl)ethyl-1-d)-4-(pyridin-3-yl)benzamido)methyl)phenoxy)hexanoic acid
6-(2-((N-(2-(pyridin-2-yl)ethyl-1,1-d2)-4-(pyridin-3-yl)benzamido)methyl)phenoxy)hexanoic acid
6-(2-((N-(2-(pyridin-2-yl)ethyl)-4-(pyridin-4-yl)benzamido)methyl-d2)phenoxy)hexanoic acid
6-(2-((N-(2-(pyridin-2-yl)ethyl-1-d)-4-(pyridin-4-yl)benzamido)methyl)phenoxy)hexanoic acid
6-(2-((N-(2-(pyridin-2-yl)ethyl-1,1-d2)-4-(pyridin-4-yl)benzamido)methyl)phenoxy)hexanoic acid
6-(2-((4-(1H-pyrazol-4-yl)-N-(2-(pyridin-2-yl)ethyl)benzamido)methyl-d2)phenoxy)hexanoic acid
6-(2-((4-(1H-pyrazol-4-yl)-N-(2-(pyridin-2-yl)ethyl-1-d)benzamido)methyl)phenoxy)hexanoic acid
6-(2-((4-(1H-pyrazol-4-yl)-N-(2-(pyridin-2-yl)ethyl-1,1-d2)benzamido)methyl)phenoxy)hexanoic acid
6-(2-((4-(furan-2-yl)-N-(2-(pyridin-2-yl)ethyl)benzamido)methyl-d2)phenoxy)hexanoic acid
6-(2-((4-(furan-2-yl)-N-(2-(pyridin-2-yl)ethyl-1-d)benzamido)methyl)phenoxy)hexanoic acid
6-(2-((4-(furan-2-yl)-N-(2-(pyridin-2-yl)ethyl-1,1-d2)benzamido)methyl)phenoxy)hexanoic acid
6-(2-((4-(furan-3-yl)-N-(2-(pyridin-2-yl)ethyl)benzamido)methyl-d2)phenoxy)hexanoic acid
6-(2-((4-(furan-3-yl)-N-(2-(pyridin-2-yl)ethyl-1-d)benzamido)methyl)phenoxy)hexanoic acid
6-(2-((4-(furan-3-yl)-N-(2-(pyridin-2-yl)ethyl-1,1-d2)benzamido)methyl)phenoxy)hexanoic acid
6-(2-((N-(2-(pyridin-2-yl)ethyl)-4-(thiophen-2-yl)benzamido)methyl-d2)phenoxy)hexanoic acid
6-(2-((N-(2-(pyridin-2-yl)ethyl-1-d)-4-(thiophen-2-yl)benzamido)methyl)phenoxy)hexanoic acid
6-(2-((N-(2-(pyridin-2-yl)ethyl-1,1-d2)-4-(thiophen-2-yl)benzamido)methyl)phenoxy)hexanoic acid
6-(2-((N-(2-(pyridin-2-yl)ethyl)-4-(thiophen-3-yl)benzamido)methyl-d2)phenoxy)hexanoic acid
6-(2-((N-(2-(pyridin-2-yl)ethyl-1-d)-4-(thiophen-3-yl)benzamido)methyl)phenoxy)hexanoic acid
6-(2-((N-(2-(pyridin-2-yl)ethyl-1,1-d2)-4-(thiophen-3-yl)benzamido)methyl)phenoxy)hexanoic acid
6-(2-((N-isopropyl-[1,1'-biphenyl]-4-carboxamido)methyl-d2)phenoxy)hexanoic acid
6-(2-((N-(propan-2-yl-2-d)-[1,1'-biphenyl]-4-carboxamido)methyl)phenoxy)hexanoic acid
6-(2-((N-isopropyl-4-(pyridin-3-yl)benzamido)methyl-d2)phenoxy)hexanoic acid
6-(2-((N-(propan-2-yl-2-d)-4-(pyridin-3-yl)benzamido)methyl)phenoxy)hexanoic acid
6-(2-((N-isopropyl-4-(pyridin-4-yl)benzamido)methyl-d2)phenoxy)hexanoic acid
6-(2-((N-(propan-2-yl-2-d)-4-(pyridin-4-yl)benzamido)methyl)phenoxy)hexanoic acid
6-(2-((N-isopropyl-4-(1H-pyrazol-4-yl)benzamido)methyl-d2)phenoxy)hexanoic acid
6-(2-((N-(propan-2-yl-2-d)-4-(1H-pyrazol-4-yl)benzamido)methyl)phenoxy)hexanoic acid
6-(2-((4-(furan-2-yl)-N-isopropylbenzamido)methyl-d2)phenoxy)hexanoic acid
6-(2-((4-(furan-2-yl)-N-(propan-2-yl-2-d)benzamido)methyl)phenoxy)hexanoic acid
6-(2-((4-(furan-3-yl)-N-isopropylbenzamido)methyl-d2)phenoxy)hexanoic acid
6-(2-((4-(furan-3-yl)-N-(propan-2-yl-2-d)benzamido)methyl)phenoxy)hexanoic acid
6-(2-((N-isopropyl-4-(thiophen-2-yl)benzamido)methyl-d2)phenoxy)hexanoic acid
6-(2-((N-(propan-2-yl-2-d)-4-(thiophen-2-yl)benzamido)methyl)phenoxy)hexanoic acid
6-(2-((N-isopropyl-4-(thiophen-3-yl)benzamido)methyl-d2)phenoxy)hexanoic acid
6-(2-((N-(propan-2-yl-2-d)-4-(thiophen-3-yl)benzamido)methyl)phenoxy)hexanoic acid
6-(2-((N-cyclopentyl-[1,1'-biphenyl]-4-carboxamido)methyl-d2)phenoxy)hexanoic acid
6-(2-((N-(cyclopentyl-1-d)-[1,1'-biphenyl]-4-carboxamido)methyl)phenoxy)hexanoic acid
6-(2-((N-cyclopentyl-4-(pyridin-3-yl)benzamido)methyl-d2)phenoxy)hexanoic acid
6-(2-((N-(cyclopentyl-1-d)-4-(pyridin-3-yl)benzamido)methyl)phenoxy)hexanoic acid
6-(2-((N-cyclopentyl-4-(pyridin-4-yl)benzamido)methyl-d2)phenoxy)hexanoic acid
6-(2-((N-(cyclopentyl-1-d)-4-(pyridin-4-yl)benzamido)methyl)phenoxy)hexanoic acid
6-(2-((N-cyclopentyl-4-(1H-pyrazol-4-yl)benzamido)methyl-d2)phenoxy)hexanoic acid
6-(2-((N-(cyclopentyl-1-d)-4-(1H-pyrazol-4-yl)benzamido)methyl)phenoxy)hexanoic acid
6-(2-((N-cyclopentyl-4-(furan-2-yl)benzamido)methyl-d2)phenoxy)hexanoic acid
6-(2-((N-(cyclopentyl-1-d)-4-(furan-2-yl)benzamido)methyl)phenoxy)hexanoic acid
6-(2-((N-cyclopentyl-4-(furan-3-yl)benzamido)methyl-d2)phenoxy)hexanoic acid
6-(2-((N-(cyclopentyl-1-d)-4-(furan-3-yl)benzamido)methyl)phenoxy)hexanoic acid
6-(2-((N-cyclopentyl-4-(thiophen-2-yl)benzamido)methyl-d2)phenoxy)hexanoic acid
6-(2-((N-(cyclopentyl-1-d)-4-(thiophen-2-yl)benzamido)methyl)phenoxy)hexanoic acid
6-(2-((N-cyclopentyl-4-(thiophen-3-yl)benzamido)methyl-d2)phenoxy)hexanoic acid
6-(2-((N-(cyclopentyl-1-d)-4-(thiophen-3-yl)benzamido)methyl)phenoxy)hexanoic acid
6-(2-((N-cyclopropyl-4-(naphthalen-1-yl)benzamido)methyl-d2)phenoxy)hexanoic acid
6-(2-((N-(cyclopropyl-1-d)-4-(naphthalen-1-yl)benzamido)methyl)phenoxy)hexanoic acid
6-(2-((N-cyclopropyl-4-(naphthalen-2-yl)benzamido)methyl-d2)phenoxy)hexanoic acid
6-(2-((N-(cyclopropyl-1-d)-4-(naphthalen-2-yl)benzamido)methyl)phenoxy)hexanoic acid
6-(2-((N-cyclopropyl-2'-methyl-[1,1'-biphenyl]-4-carboxamido)methyl-d2)phenoxy)hexanoic acid
6-(2-((N-(cyclopropyl-1-d)-2'-methyl-[1,1'-biphenyl]-4-carboxamido)methyl)phenoxy)hexanoic acid
6-(2-((N-cyclopropyl-3'-methyl-[1,1'-biphenyl]-4-carboxamido)methyl-d2)phenoxy)hexanoic acid
6-(2-((N-(cyclopropyl-1-d)-3'-methyl-[1,1'-biphenyl]-4-carboxamido)methyl)phenoxy)hexanoic acid
6-(2-((N-cyclopropyl-4'-methyl-[1,1'-biphenyl]-4-carboxamido)methyl-d2)phenoxy)hexanoic acid
6-(2-((N-(cyclopropyl-1-d)-4'-methyl-[1,1'-biphenyl]-4-carboxamido)methyl)phenoxy)hexanoic acid
6-(2-((N-cyclopropyl-2'-methoxy-[1,1'-biphenyl]-4-carboxamido)methyl-d2)phenoxy)hexanoic acid 6-(2-((N-(cyclopropyl-1-d)-2'-methoxy-[1,1'-biphenyl]-4-carboxamido)methyl)phenoxy)hexanoic acid 6-(2-((N-cyclopropyl-3'-methoxy-[1,1'-biphenyl]-4-carboxamido)methyl-d2)phenoxy)hexanoic acid 6-(2-((N-(cyclopropyl-1-d)-3'-methoxy-[1,1'-biphenyl]-4-carboxamido)methyl-d2)phenoxy)hexanoic acid 6-(2-((N-cyclopropyl-4'-methoxy-[1,1'-biphenyl]-4-carboxamido)methyl-d2)phenoxy)hexanoic acid 6-(2-((N-(cyclopropyl-1-d)-4'-methoxy-[1,1'-biphenyl]-4-carboxamido)methyl-d2)phenoxy)hexanoic acid 6-(2-((N-cyclopropyl-2'-fluoro-[1,1'-biphenyl]-4-carboxamido)methyl-d2)phenoxy)hexanoic acid 6-(2-((N-(cyclopropyl-1-d)-2'-fluoro-[1,1'-biphenyl]-4-carboxamido)methyl)phenoxy)hexanoic acid 6-(2-((N-cyclopropyl-3'-fluoro-[1,1'-biphenyl]-4-carboxamido)methyl-d2)phenoxy)hexanoic acid 6-(2-((N-(cyclopropyl-1-d)-3'-fluoro-[1,1'-biphenyl]-4-carboxamido)methyl)phenoxy)hexanoic acid 6-(2-((N-cyclopropyl-4'-fluoro-[1,1'-biphenyl]-4-carboxamido)methyl-d2)phenoxy)hexanoic acid 6-(2-((N-(cyclopropyl-1-d)-4'-fluoro-[1,1'-biphenyl]-4-carboxamido)methyl)phenoxy)hexanoic acid 6-(2-((N-cyclopropyl-2'-ethyl-[1,1'-biphenyl]-4-carboxamido)methyl-d2)phenoxy)hexanoic acid 6-(2-((N-(cyclopropyl-1-d)-2'-ethyl-[1,1'-biphenyl]-4-carboxamido)methyl)phenoxy)hexanoic acid 6-(2-((N-cyclopropyl-4'-ethyl-[1,1'-biphenyl]-4-carboxamido)methyl-d2)phenoxy)hexanoic acid 6-(2-((N-(cyclopropyl-1-d)-4'-ethyl-[1,1'-biphenyl]-4-carboxamido)methyl)phenoxy)hexanoic acid 6-(2-((N-cyclopropyl-2',3'-dimethyl-[1,1'-biphenyl]-4-carboxamido)methyl-d2)phenoxy)hexanoic acid 6-(2-((N-(cyclopropyl-1-d)-2',3'-dimethyl-[1,1'-biphenyl]-4-carboxamido)methyl)phenoxy)hexanoic acid 6-(2-((N-cyclopropyl-2',5'-dimethyl-[1,1'-biphenyl]-4-carboxamido)methyl-d2)phenoxy)hexanoic acid 6-(2-((N-(cyclopropyl-1-d)-2',5'-dimethyl-[1,1'-biphenyl]-4-carboxamido)methyl)phenoxy)hexanoic acid 6-(2-((N-cyclopropyl-2',6'-dimethyl-[1,1'-biphenyl]-4-carboxamido)methyl-d2)phenoxy)hexanoic acid 6-(2-((N-(cyclopropyl-1-d)-2',6'-dimethyl-[1,1'-biphenyl]-4-carboxamido)methyl)phenoxy)hexanoic acid 6-(2-((N-cyclopropyl-3',5'-dimethyl-[1,1'-biphenyl]-4-carboxamido)methyl-d2)phenoxy)hexanoic acid 6-(2-((N-(cyclopropyl-1-d)-3',5'-dimethyl-[1,1'-biphenyl]-4-carboxamido)methyl)phenoxy)hexanoic acid 6-(2-((N-cyclopropyl-2'-(trifluoromethyl)-[1,1'-biphenyl]-4-carboxamido)methyl-d2)phenoxy)hexanoic acid 6-(2-((N-(cyclopropyl-1-d)-2'-(trifluoromethyl)-[1,1'-biphenyl]-4-carboxamido)methyl)phenoxy)hexanoic acid 6-(2-((N-cyclopropyl-3'-(trifluoromethyl)-[1,1'-biphenyl]-4-carboxamido)methyl-d2)phenoxy)hexanoic acid 6-(2-((N-(cyclopropyl-1-d)-3'-(trifluoromethyl)-[1,1'-biphenyl]-4-carboxamido)methyl)phenoxy)hexanoic acid 6-(2-((N-cyclopropyl-4'-(trifluoromethyl)-[1,1'-biphenyl]-4-carboxamido)methyl-d2)phenoxy)hexanoic acid 6-(2-((N-(cyclopropyl-1-d)-4'-(trifluoromethyl)-[1,1'-biphenyl]-4-carboxamido)methyl)phenoxy)hexanoic acid 6-(2-((N-cyclopropyl-4'-propyl-[1,1'-biphenyl]-4-carboxamido)methyl-d2)phenoxy)hexanoic acid 6-(2-((N-(cyclopropyl-1-d)-4'-propyl-[1,1'-biphenyl]-4-carboxamido)methyl)phenoxy)hexanoic acid 6-(2-((4'-butyl-N-cyclopropyl-[1,1'-biphenyl]-4-carboxamido)methyl-d2)phenoxy)hexanoic acid 6-(2-((4'-butyl-N-(cyclopropyl-1-d)-[1,1'-biphenyl]-4-carboxamido)methyl)phenoxy)hexanoic acid 6-(2-((N-cyclopropyl-[1,1':2',1''-terphenyl]-4-carboxamido)methyl-d2)phenoxy)hexanoic acid 6-(2-((N-(cyclopropyl-1-d)-[1,1':2',1''-terphenyl]-4-carboxamido)methyl)phenoxy)hexanoic acid (E)-6-(2-((N-cyclopropyl-4-(furan-2-yl)benzamido)methyl-d2)phenoxy)hex-3-enoic acid (E)-6-(2-((N-(cyclopropyl-1-d)-4-(furan-2-yl)benzamido)methyl)phenoxy)hex-3-enoic acid (Z)-6-(2-((N-cyclopropyl-4-(furan-2-yl)benzamido)methyl-d2)phenoxy)hex-4-enoic acid (Z)-6-(2-((N-(cyclopropyl-1-d)-4-(furan-2-yl)benzamido)methyl)phenoxy)hex-4-enoic acid (Z)-6-(2-((N-cyclopropyl-4-(furan-2-yl)benzamido)methyl-d2)phenoxy)hex-3-enoic acid (Z)-6-(2-((N-(cyclopropyl-1-d)-4-(furan-2-yl)benzamido)methyl)phenoxy)hex-3-enoic acid (E)-6-(2-((N-cyclopropyl-4-(furan-2-yl)benzamido)methyl-d2)phenoxy)hex-4-enoic acid (E)-6-(2-((N-(cyclopropyl-1-d)-4-(furan-2-yl)benzamido)methyl)phenoxy)hex-4-enoic acid 6-(2-((N-cyclopropyl-4-(furan-2-yl)benzamido)methyl-d2)phenoxy)hex-4-ynoic acid 6-(2-((N-(cyclopropyl-1-d)-4-(furan-2-yl)benzamido)methyl)phenoxy)hex-4-ynoic acid 6-(2-((N-cyclopropyl-4-(furan-2-yl)benzamido)methyl-d2)phenoxy)hex-3-ynoic acid 6-(2-((N-(cyclopropyl-1-d)-4-(furan-2-yl)benzamido)methyl)phenoxy)hex-3-ynoic acid N-((2-((5-(1H-tetrazol-5-yl)pentyl)oxy)phenyl)methyl-d2)-N-cyclopropyl-4-(furan-2-yl)benzamide N-(2-((5-(1H-tetrazol-5-yl)pentyl)oxy)benzyl)-N-(cyclopropyl-1-d)-4-(furan-2-yl)benzamide 6-((4-((N-cyclopropyl-4-(furan-2-yl)benzamido)methyl-d2)thiophen-3-yl)oxy)hexanoic acid 6-((4-((N-(cyclopropyl-1-d)-4-(furan-2-yl)benzamido)methyl)thiophen-3-yl)oxy)hexanoic acid 6-(2-((N-cyclopropyl-[2,3'-bifuran]-5'-carboxamido)methyl-d2)phenoxy)hexanoic acid 6-(2-((N-(cyclopropyl-1-d)-[2,3'-bifuran]-5'-carboxamido)methyl)phenoxy)hexanoic acid 6-(2-((N-cyclopropyl-5-(furan-2-yl)thiazole-2-carboxamido)methyl-d2)phenoxy)hexanoic acid 6-(2-((N-(cyclopropyl-1-d)-5-(furan-2-yl)thiazole-2-carboxamido)methyl)phenoxy)hexanoic acid 6-(2-((N-cyclopropylbenzo[c][1,2,5]oxadiazole-5-carboxamido)methyl-d2)phenoxy)hexanoic acid 6-(2-((N-(cyclopropyl-1-d)benzo[c][1,2,5]oxadiazole-5-carboxamido)methyl)phenoxy)hexanoic acid 6-(2-((N-cyclopropyl-2-oxo-2,3-dihydrobenzofuran-5-carboxamido)methyl-d2)phenoxy)hexanoic acid 6-(2-((N-(cyclopropyl-1-d)-2-oxo-2,3-dihydrobenzofuran-5-carboxamido)methyl)phenoxy)hexanoic acid 6-(2-((N-cyclopropyl-2-oxoindoline-5-carboxamido)methyl-d2)phenoxy)hexanoic acid 6-(2-((N-(cyclopropyl-1-d)-2-oxoindoline-5-carboxamido)methyl)phenoxy)hexanoic acid 6-(2-(cyclopropyl((4-(furan-2-yl)phenyl)methyl-d2)carbamoyl)phenoxy)hexanoic acid 6-(2-((cyclopropyl-1-d)(4-(furan-2-yl)benzyl)carbamoyl)phenoxy)hexanoic acid 6-(2-((4-(furan-2-yl)phenyl)methyl-d2)(2-morpholinoethyl)carbamoyl)phenoxy)hexanoic acid 6-(2-((4-(furan-2-yl)benzyl)(2-morpholinoethyl-1-d)carbamoyl)phenoxy)hexanoic acid 6-(2-((4-(furan-2-yl)benzyl)(2-morpholinoethyl-1,1-d2)carbamoyl)phenoxy)hexanoic acid N-cyclopropyl-4-(furan-2-yl)-N-((2-((5-(6-hydroxy-4-oxo-4H-1,3-dioxin-2-yl)pentyl)oxy)phenyl)methyl-d2)benzamide N-(cyclopropyl-1-d)-4-(furan-2-yl)-N-(2-((5-(6-hydroxy-4-oxo-4H-1,3-dioxin-2-yl)pentyl)oxy)benzyl)benzamide N-cyclopropyl-4-(furan-2-yl)-N-((2-((5-(3-hydroxyisoxazol-5-yl)pentyl)oxy)phenyl)methyl-d2)benzamide N-(cyclopropyl-1-d)-4-(furan-2-yl)-N-(2-((5-(3-hydroxyisoxazol-5-yl)pentyl)oxy)benzyl)benzamide N-cyclopropyl-4-(furan-2-yl)-N-((2-((5-(3-hydroxy-1-methyl-1H-pyrazol-5-yl)pentyl)oxy)phenyl)methyl-d2)benzamide N-(cyclopropyl-1-d)-4-(furan-2-yl)-N-(2-((5-(3-hydroxy-1-methyl-1H-pyrazol-5-yl)pentyl)oxy)benzyl)benzamide N-cyclopropyl-4-(furan-2-yl)-N-((2-((5-(3-hydroxyisothiazol-5-yl)pentyl)oxy)phenyl)methyl-d2)benzamide N-(cyclopropyl-1-d)-4-(furan-2-yl)-N-(2-((5-(3-hydroxyisothiazol-5-yl)pentyl)oxy)benzyl)benzamide N-cyclopropyl-N-((2-((5-(2,4-dioxooxazolidin-5-yl)pentyl)oxy)phenyl)methyl-d2)-4-(furan-2-yl)benzamide N-(cyclopropyl-1-d)-N-(2-((5-(2,4-dioxooxazolidin-5-yl)pentyl)oxy)benzyl)-4-(furan-2-yl)benzamide N-cyclopropyl-N-((2-((5-(2,4-dioxothiazolidin-5-yl)pentyl)oxy)phenyl)methyl-d2)-4-(furan-2-yl)benzamide N-(cyclopropyl-1-d)-N-(2-((5-(2,4-dioxothiazolidin-5-yl)pentyl)oxy)benzyl)-4-(furan-2-yl)benzamide N-cyclopropyl-N-((2-((5-(2,5-dioxo-2,5-dihydro-1H-imidazol-4-yl)pentyl)oxy)phenyl)methyl-d2)-4-(furan-2-yl)benzamide N-(cyclopropyl-1-d)-N-(2-((5-(2,5-dioxo-2,5-dihydro-1H-imidazol-4-yl)pentyl)oxy)benzyl)-4-(furan-2-yl)benzamide 6-(2-((4-chloro-N-isopropylbenzamido)methyl-d2)phenoxy)hexanoic acid 6-(2-((4-chloro-N-(propan-2-yl-2-d)benzamido)methyl)phenoxy)hexanoic acid 6-(2-((N-isopropyl-4-methoxybenzamido)methyl-d2)phenoxy)hexanoic acid 6-(2-((4-methoxy-N-(propan-2-yl-2-d)benzamido)methyl)phenoxy)hexanoic acid 6-(2-((N-(propan-2-yl-2-d)-4-(trifluoromethoxy)benzamido)methyl)phenoxy)hexanoic acid 6-(2-((4-(dimethylamino)-N-isopropylbenzamido)methyl-d2)phenoxy)hexanoic acid 6-(2-((4-(dimethylamino)-N-(propan-2-yl-2-d)benzamido)methyl)phenoxy)hexanoic acid 6-(2-((4-acetyl-N-isopropylbenzamido)methyl-d2)phenoxy)hexanoic acid 6-(2-((4-acetyl-N-(propan-2-yl-2-d)benzamido)methyl)phenoxy)hexanoic acid 6-(2-((N-isopropyl-4-(methylsulfonyl)benzamido)methyl-d2)phenoxy)hexanoic acid 6-(2-((4-(methylsulfonyl)-N-(propan-2-yl-2-d)benzamido)methyl)phenoxy)hexanoic acid 6-(2-((N-isopropyl-4-methylbenzamido)methyl-d2)phenoxy)hexanoic acid 6-(2-((4-methyl-N-(propan-2-yl-2-d)benzamido)methyl)phenoxy)hexanoic acid 6-(2-((4-fluoro-N-isopropylbenzamido)methyl-d2)phenoxy)hexanoic acid 6-(2-((4-fluoro-N-(propan-2-yl-2-d)benzamido)methyl)phenoxy)hexanoic acid 6-(2-((N-isopropyl-4-(4-methoxytetrahydro-2H-pyran-4-yl)benzamido)methyl-d2)phenoxy)hexanoic acid 6-(2-((4-(4-methoxytetrahydro-2H-pyran-4-yl)-N-(propan-2-yl-2-d)benzamido)methyl)phenoxy)hexanoic acid 6-(2-((4-cyclopropoxy-N-isopropylbenzamido)methyl-d2)phenoxy)hexanoic acid 6-(2-((4-cyclopropoxy-N-(propan-2-yl-2-d)benzamido)methyl)phenoxy)hexanoic acid 6-(2-((3'-(furan-3-yl)-N-isopropyl-[1,1'-biphenyl]-4-carboxamido)methyl-d2)phenoxy)hexanoic acid 6-(2-((3'-(furan-3-yl)-N-(propan-2-yl-2-d)-[1,1'-biphenyl]-4-carboxamido)methyl)phenoxy)hexanoic acid 6-(2-((N-isopropyl-4-(pyrrolidin-1-yl)benzamido)methyl-d2)phenoxy)hexanoic acid 6-(2-((N-(propan-2-yl-2-d)-4-(pyrrolidin-1-yl)benzamido)methyl)phenoxy)hexanoic acid 6-(2-((N-isopropyl-4-(oxetan-3-ylethynyl)benzamido)methyl-d2)phenoxy)hexanoic acid 6-(2-((4-(oxetan-3-ylethynyl)-N-(propan-2-yl-2-d)benzamido)methyl)phenoxy)hexanoic acid 6-(2-((4-(cyclopentylethynyl)-N-isopropylbenzamido)methyl-d2)phenoxy)hexanoic acid 6-(2-((4-(cyclopentylethynyl)-N-(propan-2-yl-2-d)benzamido)methyl)phenoxy)hexanoic acid 6-(2-((4-(cyclobutylethynyl)-N-isopropylbenzamido)methyl-d2)phenoxy)hexanoic acid 6-(2-((4-(cyclobutylethynyl)-N-(propan-2-yl-2-d)benzamido)methyl)phenoxy)hexanoic acid 6-(2-((N-isopropyl-4-(3,3,3-trifluoroprop-1-yn-1-yl)benzamido)methyl-d2)phenoxy)hexanoic acid 6-(2-((N-(propan-2-yl-2-d)-4-(3,3,3-trifluoroprop-1-yn-1-yl)benzamido)methyl)phenoxy)hexanoic acid 6-(2-((N-isopropyl-4-((1-methylazetidin-3-yl)ethynyl)benzamido)methyl-d2)phenoxy)hexanoic acid 6-(2-((4-((1-methylazetidin-3-yl)ethynyl)-N-(propan-2-yl-2-d)benzamido)methyl)phenoxy)hexanoic acid 6-(2-((N-isopropyl-4-(1-methoxycyclopropyl)benzamido)methyl-d2)phenoxy)hexanoic acid 6-(2-((4-(1-methoxycyclopropyl)-N-(propan-2-yl-2-d)benzamido)methyl)phenoxy)hexanoic acid 6-(2-((N-isopropyl-4-(1-(trifluoromethyl)cyclopropyl)benzamido)methyl-d2)phenoxy)hexanoic acid 6-(2-((N-(propan-2-yl-2-d)-4-(1-(trifluoromethyl)cyclopropyl)benzamido)methyl)phenoxy)hexanoic acid 6-(2-((N-isopropyl-4-(tetrahydro-2H-pyran-2-yl)benzamido)methyl-d2)phenoxy)hexanoic acid 6-(2-((N-(propan-2-yl-2-d)-4-(tetrahydro-2H-pyran-2-yl)benzamido)methyl)phenoxy)hexanoic acid 6-(2-((N-isopropyl-4-(4-methylbicyclo[2.2.2]octan-1-yl)benzamido)methyl-d2)phenoxy)hexanoic acid 6-(2-((4-(4-methylbicyclo[2.2.2]octan-1-yl)-N-(propan-2-yl-2-d)benzamido)methyl)phenoxy)hexanoic acid 6-(2-((N-isopropyl-4-(oxetan-2-yl)benzamido)methyl-d2)phenoxy)hexanoic acid 6-(2-((4-(oxetan-2-yl)-N-(propan-2-yl-2-d)benzamido)methyl)phenoxy)hexanoic acid 6-(2-((N-isopropyl-4-(6-oxo-1,6-dihydropyridin-2-yl)benzamido)methyl-d2)phenoxy)hexanoic acid 6-(2-((4-(6-oxo-1,6-dihydropyridin-2-yl)-N-(propan-2-yl-2-d)benzamido)methyl)phenoxy)hexanoic acid 6-(2-((N-isopropyl-4-(oxetan-2-ylethynyl)benzamido)methyl-d2)phenoxy)hexanoic acid 6-(2-((4-(oxetan-2-ylethynyl)-N-(propan-2-yl-2-d)benzamido)methyl)phenoxy)hexanoic acid 6-(2-((N-isopropyl-4-(4-(trifluoromethyl)bicyclo[2.2.2]octan-1-yl)benzamido)methyl-d2)phenoxy)hexanoic acid 6-(2-((N-(propan-2-yl-2-d)-4-(4-(trifluoromethyl)bicyclo[2.2.2]octan-1-yl)benzamido)methyl)phenoxy)hexanoic acid 6-(2-((N-isopropyl-4-(4-phenylbicyclo[2.2.2]octan-1-yl)benzamido)methyl-d2)phenoxy)hexanoic acid 6-(2-((4-(4-phenylbicyclo[2.2.2]octan-1-yl)-N-(propan-2-yl-2-d)benzamido)methyl)phenoxy)hexanoic acid
6-(2-((4-cyano-N-isopropylbenzamido)methyl-d2)phenoxy)hexanoic acid
6-(2-((4-cyano-N-(propan-2-yl-2-d)benzamido)methyl)phenoxy)hexanoic acid
6-(2-((4-(furan-2-yl)-N-isopropylphenyl)sulfonamido)methyl-d2)phenoxy)hexanoic acid
6-(2-((4-(furan-2-yl)-N-(propan-2-yl-2-d)phenyl)sulfonamido)methyl)phenoxy)hexanoic acid
6-(2-((5-(furan-2-yl)-N-isopropylpicolinamido)methyl-d2)phenoxy)hexanoic acid
6-(2-((5-(furan-2-yl)-N-(propan-2-yl-2-d)picolinamido)methyl)phenoxy)hexanoic acid
6-(2-((5-(furan-2-yl)-N-isopropylthiophene-2-carboxamido)methyl-d2)phenoxy)hexanoic acid
6-(2-((5-(furan-2-yl)-N-(propan-2-yl-2-d)thiophene-2-carboxamido)methyl)phenoxy)hexanoic acid
6-(2-((6-(furan-2-yl)-N-isopropylnicotinamido)methyl-d2)phenoxy)hexanoic acid
6-(2-((6-(furan-2-yl)-N-(propan-2-yl-2-d)nicotinamido)methyl)phenoxy)hexanoic acid
6-(2-((2-(furan-2-yl)-N-isopropylthiazole-5-carboxamido)methyl-d2)phenoxy)hexanoic acid
6-(2-((2-(furan-2-yl)-N-(propan-2-yl-2-d)thiazole-5-carboxamido)methyl)phenoxy)hexanoic acid
6-(2-(((4-(furan-2-yl)phenyl)methyl-d2)(isopropyl)carbamoyl)phenoxy)hexanoic acid
6-(2-((4-(furan-2-yl)benzyl)(propan-2-yl-2-d)carbamoyl)phenoxy)hexanoic acid
6-(2-(2-((4-(furan-2-yl)phenyl)(isopropyl)amino)-2-oxoethyl-1,1-d2)phenoxy)hexanoic acid
6-(2-(2-((4-(furan-2-yl)phenyl)(propan-2-yl-2-d)amino)-2-oxoethyl)phenoxy)hexanoic acid
6-(2-((3-fluoro-4-(furan-2-yl)-N-isopropylbenzamido)methyl-d2)phenoxy)hexanoic acid
6-(2-((3-fluoro-4-(furan-2-yl)-N-(propan-2-yl-2-d)benzamido)methyl)phenoxy)hexanoic acid
6-(2-((2-fluoro-4-(furan-2-yl)-N-isopropylbenzamido)methyl-d2)phenoxy)hexanoic acid
6-(2-((2-fluoro-4-(furan-2-yl)-N-(propan-2-yl-2-d)benzamido)methyl)phenoxy)hexanoic acid
6-(2-((1-(furan-2-yl)-N-isopropylpiperidine-4-carboxamido)methyl-d2)phenoxy)hexanoic acid
6-(2-((1-(furan-2-yl)-N-(propan-2-yl-2-d)piperidine-4-carboxamido)methyl)phenoxy)hexanoic acid
6-(2-((5-(furan-2-yl)-N-isopropylisoxazole-3-carboxamido)methyl-d2)phenoxy)hexanoic acid
6-(2-((5-(furan-2-yl)-N-(propan-2-yl-2-d)isoxazole-3-carboxamido)methyl)phenoxy)hexanoic acid
6-(2-((4-(furan-2-yl)-N-isopropylcyclohexane-1-carboxamido)methyl-d2)phenoxy)hexanoic acid
6-(2-((4-(furan-2-yl)-N-(propan-2-yl-2-d)cyclohexane-1-carboxamido)methyl)phenoxy)hexanoic acid
6-(2-(((6-(furan-2-yl)-1H-indazol-3-yl)(isopropyl)amino)methyl-d2)phenoxy)hexanoic acid
6-(2-(((6-(furan-2-yl)-1H-indazol-3-yl)(propan-2-yl-2-d)amino)methyl)phenoxy)hexanoic acid
6-(2-((5-(furan-2-yl)-N-isopropylthiazole-2-carboxamido)methyl-d2)phenoxy)hexanoic acid
6-(2-((5-(furan-2-yl)-N-(propan-2-yl-2-d)thiazole-2-carboxamido)methyl)phenoxy)hexanoic acid
6-(2-((2-(furan-2-yl)-N-isopropyloxazole-5-carboxamido)methyl-d2)phenoxy)hexanoic acid
6-(2-((2-(furan-2-yl)-N-(propan-2-yl-2-d)oxazole-5-carboxamido)methyl)phenoxy)hexanoic acid
6-(2-((N-isopropyl-2-methylbenzofuran-6-carboxamido)methyl-d2)phenoxy)hexanoic acid
6-(2-((2-methyl-N-(propan-2-yl-2-d)benzofuran-6-carboxamido)methyl)phenoxy)hexanoic acid
6-(2-((N-isopropyl-2-methylbenzofuran-5-carboxamido)methyl-d2)phenoxy)hexanoic acid
6-(2-((2-methyl-N-(propan-2-yl-2-d)benzofuran-5-carboxamido)methyl)phenoxy)hexanoic acid
6-(2-((4-(furan-2-yl)-N-isopropyl-2,5-dioxopiperazine-1-carboxamido)methyl-d2)phenoxy)hexanoic acid
6-(2-(furan-2-yl)-2,5-dioxo-N-(propan-2-yl-2-d)piperazine-1-carboxamido)methyl)phenoxy)hexanoic acid
6-(2-((1-(furan-2-yl)-N-isopropyl-2-oxopiperidine-4-carboxamido)methyl-d2)phenoxy)hexanoic acid
6-(2-((1-(furan-2-yl)-2-oxo-N-(propan-2-yl-2-d)piperidine-4-carboxamido)methyl)phenoxy)hexanoic acid
6-(2-((5-(furan-2-yl)-N-isopropyl-1H-pyrazole-3-carboxamido)methyl-d2)phenoxy)hexanoic acid
6-(2-((5-(furan-2-yl)-N-(propan-2-yl-2-d)-1H-pyrazole-3-carboxamido)methyl)phenoxy)hexanoic acid
6-(2-((7-(furan-2-yl)-4-oxoquinazolin-3(4H)-yl)methyl-d2)phenoxy)hexanoic acid
6-(2-((5-(furan-2-yl)-N-isopropyl-3,6-dioxopiperazine-2-carboxamido)methyl-d2)phenoxy)hexanoic acid
6-(2-((5-(furan-2-yl)-3,6-dioxo-N-(propan-2-yl-2-d)piperazine-2-carboxamido)methyl)phenoxy)hexanoic acid
6-(2-((4-(furan-2-yl)-N-isopropylpiperidine-1-carboxamido)methyl-d2)phenoxy)hexanoic acid
6-(2-((4-(furan-2-yl)-N-(propan-2-yl-2-d)piperidine-1-carboxamido)methyl)phenoxy)hexanoic acid
6-(2-((5-(furan-2-yl)-N-isopropyl-1-methyl-1H-pyrazole-3-carboxamido)methyl-d2)phenoxy)hexanoic acid
6-(2-((5-(furan-2-yl)-1-methyl-N-(propan-2-yl-2-d)-1H-pyrazole-3-carboxamido)methyl)phenoxy)hexanoic acid
6-(2-((4-(furan-2-yl)-N-methylbenzamido)methyl-d2)phenoxy)hexanoic acid
6-(2-((4-(furan-2-yl)-N-(2,2,2-trifluoroethyl)benzamido)methyl-d2)phenoxy)hexanoic acid
6-(2-((4-(furan-2-yl)-N-(2,2,2-trifluoroethyl-1,1-d2)benzamido)methyl)phenoxy)hexanoic acid
6-(2-((4-(furan-2-yl)-N-(methyl-d3)benzamido)methyl)phenoxy)hexanoic acid
6-(2-((4-(furan-2-yl)-N-(2-methoxyethyl)benzamido)methyl-d2)phenoxy)hexanoic acid
6-(2-((4-(furan-2-yl)-N-(2-methoxyethyl-1-d)benzamido)methyl)phenoxy)hexanoic acid
6-(2-((4-(furan-2-yl)-N-(2-methoxyethyl-1,1-d2)benzamido)methyl)phenoxy)hexanoic acid
6-(2-((4-(furan-2-yl)benzamido)methyl-d2)phenoxy)hexanoic acid
6-(2-((4-(furan-2-yl)-N-(oxetan-3-yl)benzamido)methyl-d2)phenoxy)hexanoic acid
6-(2-((N-(2-cyanopropan-2-yl)-4-(furan-2-yl)benzamido)methyl-d2)phenoxy)hexanoic acid
6-(2-((6-(furan-2-yl)-3-methyl-1-oxo-3,4-dihydroisoquinolin-2(1H)-yl)methyl-d2)phenoxy)hexanoic acid
6-(2-((4-(furan-2-yl)-N-hydroxybenzamido)methyl-d2)phenoxy)hexanoic acid
6-(2-((4-(furan-2-yl)-N-methoxybenzamido)methyl-d2)phenoxy)hexanoic acid
6-(2-((N-(cyclopropylmethyl)-4-(furan-2-yl)benzamido)methyl-d2)phenoxy)hexanoic acid
6-(2-((N-(cyclopropylmethyl-d)-4-(furan-2-yl)benzamido)methyl)phenoxy)hexanoic acid
6-(2-((N-(cyclopropylmethyl-d2)-4-(furan-2-yl)benzamido)methyl)phenoxy)hexanoic acid 6-(2-((N-(1-cyclopropylethyl)-4-(furan-2-yl)benzamido)methyl-d2)phenoxy)hexanoic acid
6-(2-((N-(1-cyclopropylethyl-1-d)-4-(furan-2-yl)benzamido)methyl)phenoxy)hexanoic acid
6-(2-((4-(furan-2-yl)-N-isopropylbenzamido)methyl-d2)-4-methylphenoxy)hexanoic acid
6-(2-((4-(furan-2-yl)-N-(propan-2-yl-2-d)benzamido)methyl)-4-methylphenoxy)hexanoic acid
6-(4-fluoro-2-((4-(furan-2-yl)-N-isopropylbenzamido)methyl-d2)phenoxy)hexanoic acid
6-(4-fluoro-2-((4-(furan-2-yl)-N-(propan-2-yl-2-d)benzamido)methyl)phenoxy)hexanoic acid
6-(4-bromo-2-((4-(furan-2-yl)-N-isopropylbenzamido)methyl-d2)phenoxy)hexanoic acid
6-(4-bromo-2-((4-(furan-2-yl)-N-(propan-2-yl-2-d)benzamido)methyl)phenoxy)hexanoic acid
6-(4-cyano-2-((4-(furan-2-yl)-N-isopropylbenzamido)methyl-d2)phenoxy)hexanoic acid
6-(4-cyano-2-((4-(furan-2-yl)-N-(propan-2-yl-2-d)benzamido)methyl)phenoxy)hexanoic acid
6-(2-((4-(furan-2-yl)-N-isopropylbenzamido)methyl-d2)-4-methoxyphenoxy)hexanoic acid
6-(2-((4-(furan-2-yl)-N-(propan-2-yl-2-d)benzamido)methyl)-4-methoxyphenoxy)hexanoic acid
6-((3-((4-(furan-2-yl)-N-isopropylbenzamido)methyl-d2)pyridin-2-yl)oxy)hexanoic acid
6-((3-((4-(furan-2-yl)-N-(propan-2-yl-2-d)benzamido)methyl)pyridin-2-yl)oxy)hexanoic acid
6-((2-((4-(furan-2-yl)-N-isopropylbenzamido)methyl-d2)pyridin-3-yl)oxy)hexanoic acid
6-((2-((4-(furan-2-yl)-N-(propan-2-yl-2-d)benzamido)methyl)pyridin-3-yl)oxy)hexanoic acid
6-((3-((4-(furan-2-yl)-N-isopropylbenzamido)methyl-d2)pyridin-4-yl)oxy)hexanoic acid
6-((3-((4-(furan-2-yl)-N-(propan-2-yl-2-d)benzamido)methyl)pyridin-4-yl)oxy)hexanoic acid
6-((4-((4-(furan-2-yl)-N-isopropylbenzamido)methyl-d2)-1-methyl-1H-pyrazol-3-yl)oxy)hexanoic acid
6-((4-((4-(furan-2-yl)-N-(propan-2-yl-2-d)benzamido)methyl)-1-methyl-1H-pyrazol-3-yl)oxy)hexanoic acid
6-((4-((4-(furan-2-yl)-N-isopropylbenzamido)methyl-d2)pyridin-3-yl)oxy)hexanoic acid
6-((4-((4-(furan-2-yl)-N-(propan-2-yl-2-d)benzamido)methyl)pyridin-3-yl)oxy)hexanoic acid
6-((4-((4-(furan-2-yl)-N-isopropylbenzamido)methyl-d2)isothiazol-3-yl)oxy)hexanoic acid
6-((4-((4-(furan-2-yl)-N-(propan-2-yl-2-d)benzamido)methyl)isothiazol-3-yl)oxy)hexanoic acid
6-((2-((4-(furan-2-yl)-N-isopropylbenzamido)methyl-d2)cyclopentyl)oxy)hexanoic acid
6-((2-((4-(furan-2-yl)-N-(propan-2-yl-2-d)benzamido)methyl)cyclopentyl)oxy)hexanoic acid
6-(4-cyclopropyl-2-((4-(furan-2-yl)-N-isopropylbenzamido)methyl-d2)phenoxy)hexanoic acid
6-(4-cyclopropyl-2-((4-(furan-2-yl)-N-(propan-2-yl-2-d)benzamido)methyl)phenoxy)hexanoic acid
6-((2-((4-(furan-2-yl)-N-isopropylbenzamido)methyl-d2)cyclohexyl)oxy)hexanoic acid
6-((2-((4-(furan-2-yl)-N-(propan-2-yl-2-d)benzamido)methyl)cyclohexyl)oxy)hexanoic acid
6-(4-azetidin-1-yl)-2-((4-(furan-2-yl)-N-isopropylbenzamido)methyl-d2)phenoxy)hexanoic acid
6-(4-azetidin-1-yl)-2-((4-(furan-2-yl)-N-(propan-2-yl-2-d)benzamido)methyl)phenoxy)hexanoic acid
6-(2-((4-(furan-2-yl)-N-isopropylbenzamido)methyl-d2)-4-(trifluoromethyl)phenoxy)hexanoic acid
6-(2-((4-(furan-2-yl)-N-(propan-2-yl-2-d)benzamido)methyl)-4-(trifluoromethyl)phenoxy)hexanoic acid
N-((2-(4-(2H-tetrazol-5-yl)butoxy)phenyl)methyl-d2)-4-(furan-2-yl)-N-isopropylbenzamide
N-(2-(4-(2H-tetrazol-5-yl)butoxy)benzyl)-4-(furan-2-yl)-N-(propan-2-yl-2-d)benzamide
7-(2-((4-(furan-2-yl)-N-isopropylbenzamido)methyl-d2)phenoxy)heptanoic acid
7-(2-((4-(furan-2-yl)-N-(propan-2-yl-2-d)benzamido)methyl)phenoxy)heptanoic acid
2-(3-(2-((4-(furan-2-yl)-N-isopropylbenzamido)methyl-d2)phenoxy)propoxy)acetic acid
2-(3-(2-((4-(furan-2-yl)-N-(propan-2-yl-2-d)benzamido)methyl)phenoxy)propoxy)acetic acid
5-(2-(2-((4-(furan-2-yl)-N-isopropylbenzamido)methyl-d2)phenoxy)ethyl)isoxazole-3-carboxylic acid
5-(2-(2-((4-(furan-2-yl)-N-(propan-2-yl-2-d)benzamido)methyl)phenoxy)ethyl)isoxazole-3-carboxylic acid
2-(5-((2-((4-(furan-2-yl)-N-isopropylbenzamido)methyl-d2)phenoxy)methyl)isoxazol-3-yl)acetic acid
2-(5-((2-((4-(furan-2-yl)-N-(propan-2-yl-2-d)benzamido)methyl)phenoxy)methyl)isoxazol-3-yl)acetic acid
2-(4-(2-((4-(furan-2-yl)-N-isopropylbenzamido)methyl-d2)phenoxy)cyclohexyl)acetic acid
2-(4-(2-((4-(furan-2-yl)-N-(propan-2-yl-2-d)benzamido)methyl)phenoxy)cyclohexyl)acetic acid
5-(2-((4-(furan-2-yl)-N-isopropylbenzamido)methyl-d2)phenoxy)pentanoic acid
5-(2-((4-(furan-2-yl)-N-(propan-2-yl-2-d)benzamido)methyl)phenoxy)pentanoic acid
3-(2-(2-((4-(furan-2-yl)-N-isopropylbenzamido)methyl-d2)phenoxy)ethoxy)propanoic acid
3-(2-(2-((4-(furan-2-yl)-N-(propan-2-yl-2-d)benzamido)methyl)phenoxy)ethoxy)propanoic acid
3-(2-(2-((4-(furan-2-yl)-N-isopropylbenzamido)methyl-d2)phenoxy)acetamido)propanoic acid
3-(2-(2-((4-(furan-2-yl)-N-(propan-2-yl-2-d)benzamido)methyl)phenoxy)acetamido)propanoic acid
3-(4-((2-((4-(furan-2-yl)-N-isopropylbenzamido)methyl-d2)phenoxy)methyl)thiazol-2-yl)propanoic acid
3-(4-((2-((4-(furan-2-yl)-N-(propan-2-yl-2-d)benzamido)methyl)phenoxy)methyl)thiazol-2-yl)propanoic acid
3-(2-(2-((4-(furan-2-yl)-N-isopropylbenzamido)methyl-d2)phenoxy)ethyl)cyclobutane-1-carboxylic acid
3-(2-(2-((4-(furan-2-yl)-N-(propan-2-yl-2-d)benzamido)methyl)phenoxy)ethyl)cyclobutane-1-carboxylic acid
3-((2-(2-((4-(furan-2-yl)-N-isopropylbenzamido)methyl-d2)phenoxy)ethyl)amino)-3-oxopropanoic acid
3-((2-(2-((4-(furan-2-yl)-N-(propan-2-yl-2-d)benzamido)methyl)phenoxy)ethyl)amino)-3-oxopropanoic acid
3-(3-(2-((4-(furan-2-yl)-N-isopropylbenzamido)methyl-d2)phenoxy)azetidin-1-yl)propanoic acid
3-(3-(2-((4-(furan-2-yl)-N-(propan-2-yl-2-d)benzamido)methyl)phenoxy)azetidin-1-yl)propanoic acid
6-(2-((4-(furan-2-yl)-N-isopropylbenzamido)methyl-d2)phenoxy)heptanoic acid
6-(2-((4-(furan-2-yl)-N-(propan-2-yl-2-d)benzamido)methyl)phenoxy)heptanoic acid
2-(3-((2-((4-(furan-2-yl)-N-isopropylbenzamido)methyl-d2)phenoxy)methyl)azetidin-1-yl)acetic acid
2-(3-((2-((4-(furan-2-yl)-N-(propan-2-yl-2-d)benzamido)methyl)phenoxy)methyl)azetidin-1-yl)acetic acid
2-((3-(2-((4-(furan-2-yl)-N-isopropylbenzamido)methyl-d2)phenoxy)cyclopentyl)oxy)acetic acid
2-((3-(2-((4-(furan-2-yl)-N-(propan-2-yl-2-d)benzamido)methyl)phenoxy)cyclopentyl)oxy)acetic acid 2-(4-((2-((4-(furan-2-yl)-N-isopropylbenzamido)methyl-d2)phenoxy)methyl)thiazol-2-yl)acetic acid
2-(4-((2-((4-(furan-2-yl)-N-(propan-2-yl-2-d)benzamido)methyl)phenoxy)methyl)thiazol-2-yl)acetic acid
2-((3-(2-((4-(furan-2-yl)-N-isopropylbenzamido)methyl-d2)phenoxy)propyl)thio)acetic acid
2-((3-(2-((4-(furan-2-yl)-N-(propan-2-yl-2-d)benzamido)methyl)phenoxy)propyl)thio)acetic acid
1-(2-(2-((4-(furan-2-yl)-N-isopropylbenzamido)methyl-d2)phenoxy)ethyl)azetidine-3-carboxylic acid
1-(2-(2-((4-(furan-2-yl)-N-(propan-2-yl-2-d)benzamido)methyl)phenoxy)ethyl)azetidine-3-carboxylic acid
2-(4-((2-((4-(furan-2-yl)-N-isopropylbenzamido)methyl-d2)phenoxy)methyl)-1H-1,2,3-triazol-1-yl)acetic acid
2-(4-((2-((4-(furan-2-yl)-N-(propan-2-yl-2-d)benzamido)methyl)phenoxy)methyl)-1H-1,2,3-triazol-1-yl)acetic acid
3-(3-(2-((4-(furan-2-yl)-N-isopropylbenzamido)methyl-d2)phenoxy)piperidin-1-yl)propanoic acid
3-(3-(2-((4-(furan-2-yl)-N-(propan-2-yl-2-d)benzamido)methyl)phenoxy)piperidin-1-yl)propanoic acid
1-(2-(2-((4-(furan-2-yl)-N-isopropylbenzamido)methyl-d2)phenoxy)acetyl)pyrrolidine-3-carboxylic acid
1-(2-(2-((4-(furan-2-yl)-N-(propan-2-yl-2-d)benzamido)methyl)phenoxy)acetyl)pyrrolidine-3-carboxylic acid
1-(2-(2-((4-(furan-2-yl)-N-isopropylbenzamido)methyl-d2)phenoxy)ethyl)pyrrolidine-3-carboxylic acid
1-(2-(2-((4-(furan-2-yl)-N-(propan-2-yl-2-d)benzamido)methyl)phenoxy)ethyl)pyrrolidine-3-carboxylic acid
(E)-6-(2-((4-(furan-2-yl)-N-isopropylbenzamido)methyl-d2)phenoxy)-4-methylhex-4-enoic acid
(E)-6-(2-((4-(furan-2-yl)-N-(propan-2-yl-2-d)benzamido)methyl)phenoxy)-4-methylhex-4-enoic acid
6-((4-((4-(furan-2-yl)-N-isopropylbenzamido)methyl-d2)pyrrolidin-3-yl)oxy)hexanoic acid
6-((4-((4-(furan-2-yl)-N-(propan-2-yl-2-d)benzamido)methyl)pyrrolidin-3-yl)oxy)hexanoic acid
4-(furan-2-yl)-N-((2-(4-(5-hydroxy-1,3,4-oxadiazol-2-yl)butoxy)phenyl)methyl-d2)-N-isopropylbenzamide
4-(furan-2-yl)-N-(2-(4-(5-hydroxy-1,3,4-oxadiazol-2-yl)butoxy)benzyl)-N-(propan-2-yl-2-d)benzamide
6-(2-((4-(cyclopropylethynyl)-N-isopropylbenzamido)methyl-d2)phenoxy)hexanoic acid
6-(2-((4-(cyclopropylethynyl)-N-(propan-2-yl-2-d)benzamido)methyl)phenoxy)hexanoic acid
6-((4-((4-(furan-2-yl)-N-isopropylbenzamido)methyl-d2)morpholin-3-yl)oxy)hexanoic acid
6-((4-((4-(furan-2-yl)-N-(propan-2-yl-2-d)benzamido)methyl)morpholin-3-yl)oxy)hexanoic acid
6-(2-((N-benzyl-4-(furan-2-yl)benzamido)methyl-d2)phenoxy)hexanoic acid
6-(2-((4-(furan-2-yl)-N-(phenylmethyl-d)benzamido)methyl)phenoxy)hexanoic acid
6-(2-((4-(furan-2-yl)-N-(phenylmethyl-d2)benzamido)methyl)phenoxy)hexanoic acid
6-(2-((4-(cyclopropylethynyl)-N-methylbenzamido)methyl-d2)phenoxy)hexanoic acid
6-(2-((4-(cyclopropylethynyl)-N-(methyl-d3)benzamido)methyl)phenoxy)hexanoic acid
6-((4-((4-(furan-2-yl)-N-isopropylbenzamido)methyl-d2)morpholin-3-yl)oxy)hexanoic acid
6-((4-((4-(furan-2-yl)-N-(propan-2-yl-2-d)benzamido)methyl)morpholin-3-yl)oxy)hexanoic acid
6-(2-((N-methyl-4-(3,3,3-trifluoroprop-1-yn-1-yl)benzamido)methyl-d2)phenoxy)hexanoic acid
6-(2-((N-(methyl-d3)-4-(3,3,3-trifluoroprop-1-yn-1-yl)benzamido)methyl)phenoxy)hexanoic acid
6-(2-((4-cyclopropoxy-N-methylbenzamido)methyl-d2)phenoxy)hexanoic acid
6-(2-((4-cyclopropoxy-N-(methyl-d3)benzamido)methyl)phenoxy)hexanoic acid
6-(2-((5-(furan-2-yl)-N-methylpicolinamido)methyl-d2)phenoxy)hexanoic acid
6-(2-((5-(furan-2-yl)-N-(methyl-d3)picolinamido)methyl)phenoxy)hexanoic acid
6-(2-((5-(furan-2-yl)-N-methylthiazole-2-carboxamido)methyl-d2)phenoxy)hexanoic acid
6-(2-((5-(furan-2-yl)-N-(methyl-d3)thiazole-2-carboxamido)methyl)phenoxy)hexanoic acid
3-(2-(2-((4-(furan-2-yl)-N-methylbenzamido)methyl-d2)phenoxy)ethoxy)propanoic acid
3-(2-(2-((4-(furan-2-yl)-N-(methyl-d3)benzamido)methyl)phenoxy)ethoxy)propanoic acid
N-((2-(4-(2H-tetrazol-5-yl)butoxy)phenyl)methyl-d2)-4-(furan-2-yl)-N-methylbenzamide
N-(2-(4-(2H-tetrazol-5-yl)butoxy)benzyl)-4-(furan-2-yl)-N-(methyl-d3)benzamide
6-(2-((4-(furan-2-yl)-N-methylbenzamido)methyl-d2)phenoxy)heptanoic acid
6-(2-((4-(furan-2-yl)-N-(methyl-d3)benzamido)methyl)phenoxy)heptanoic acid
6-(2-((4-(furan-2-yl)-N-methylbenzamido)methyl-d2)-4-methoxyphenoxy)hexanoic acid
6-(2-((4-(furan-2-yl)-N-(methyl-d3)benzamido)methyl)-4-methoxyphenoxy)hexanoic acid
6-(2-((4-(furan-2-yl)-N-methylbenzamido)methyl-d2)-4-methylphenoxy)hexanoic acid
6-(2-((4-(furan-2-yl)-N-(methyl-d3)benzamido)methyl)-4-methylphenoxy)hexanoic acid
6-(4-fluoro-2-((4-(furan-2-yl)-N-methylbenzamido)methyl-d2)phenoxy)hexanoic acid
6-(4-fluoro-2-((4-(furan-2-yl)-N-(methyl-d3)benzamido)methyl)phenoxy)hexanoic acid
6-((3-((6-(furan-2-yl)-N-methylnicotinamido)methyl-d2)pyridin-2-yl)oxy)hexanoic acid
6-((3-((6-(furan-2-yl)-N-(methyl-d3)nicotinamido)methyl)pyridin-2-yl)oxy)hexanoic acid
6-((3-((4-(furan-2-yl)-N-methylbenzamido)methyl-d2)pyridin-2-yl)oxy)hexanoic acid
6-((3-((4-(furan-2-yl)-N-(methyl-d3)benzamido)methyl)pyridin-2-yl)oxy)hexanoic acid
6-(2-((6-(cyclopropylethynyl)-N-isopropylnicotinamido)methyl-d2)phenoxy)hexanoic acid
6-(2-((6-(cyclopropylethynyl)-N-(propan-2-yl-2-d)nicotinamido)methyl)phenoxy)hexanoic acid
6-(2-((6-(cyclopropylethynyl)-N-methylnicotinamido)methyl-d2)phenoxy)hexanoic acid
6-(2-((6-(cyclopropylethynyl)-N-(methyl-d3)nicotinamido)methyl)phenoxy)hexanoic acid
6-(2-((N-(but-2-yn-1-yl)-6-(furan-2-yl)nicotinamido)methyl-d2)phenoxy)hexanoic acid
6-(2-((N-(but-2-yn-1-yl-1-d)-6-(furan-2-yl)nicotinamido)methyl)phenoxy)hexanoic acid
6-(2-((N-(but-2-yn-1-yl-1,1-d2)-6-(furan-2-yl)nicotinamido)methyl)phenoxy)hexanoic acid
6-(2-((6-fluoro-N-isopropylnicotinamido)methyl-d2)phenoxy)hexanoic acid
6-(2-((6-fluoro-N-(propan-2-yl-2-d)nicotinamido)methyl)phenoxy)hexanoic acid
6-(2-((6-fluoro-N-(furan-2-ylmethyl)nicotinamido)methyl-d2)phenoxy)hexanoic acid
6-(2-((6-fluoro-N-(furan-2-ylmethyl-d)nicotinamido)methyl)phenoxy)hexanoic acid 6-(2-((6-fluoro-N-(furan-2-ylmethyl-d2)nicotinamido) methyl)phenoxy)hexanoic acid
6-(2-((N-benzyl-6-fluoronicotinamido)methyl-d2)phenoxy) hexanoic acid
6-(2-((6-fluoro-N-(phenylmethyl-d)nicotinamido)methyl) phenoxy)hexanoic acid
6-(2-((6-fluoro-N-(phenylmethyl-d2)nicotinamido)methyl) phenoxy)hexanoic acid
sodium 6-(2-((N-cyclopropyl-4-(furan-2-yl)benzamido) methyl-d2)phenoxy)hexanoate
sodium 6-(2-((N-(cyclopropyl-1-d)-4-(furan-2-yl)benzamido)methyl)phenoxy)hexanoate
6-(2-((4-((difluoromethyl)thio)-N-isopropylbenzamido) methyl-d2)phenoxy)hexanoic acid
6-(2-((4-((difluoromethyl)thio)-N-(propan-2-yl-2-d)benzamido)methyl)phenoxy)hexanoic acid
6-(2-((N-benzyl-6-fluoronicotinamido)methyl-d2)phenoxy) hexanoic acid
6-(2-((6-fluoro-N-(phenylmethyl-d)nicotinamido)methyl) phenoxy)hexanoic acid
6-(2-((6-fluoro-N-(phenylmethyl-d2)nicotinamido)methyl) phenoxy)hexanoic acid
(E)-6-(2-((4-(furan-2-yl)-N'-hydroxy-N-isopropylbenzimidamido)methyl-d2)phenoxy)hexanoic acid
(E)-6-(2-((4-(furan-2-yl)-N'-hydroxy-N-(propan-2-yl-2-d) benzimidamido)methyl)phenoxy)hexanoic acid
6-(2-((4-fluoro-5-(furan-2-yl)-N-isopropyl-1H-pyrazole-3-carboxamido)methyl-d2)phenoxy)hexanoic acid
6-(2-((4-fluoro-5-(furan-2-yl)-N-(propan-2-yl-2-d)-1H-pyrazole-3-carboxamido)methyl)phenoxy)hexanoic acid
6-(2-((4-((fluoromethyl)thio)-N-isopropylbenzamido) methyl-d2)phenoxy)hexanoic acid
6-(2-((4-((fluoromethyl)thio)-N-(propan-2-yl-2-d)benzamido)methyl)phenoxy)hexanoic acid
(R)-6-(2-((5-(furan-2-yl)-N-isopropyl-1H-pyrazole-3-carboxamido)methyl-d2)phenoxy)heptanoic acid
(R)-6-(2-((5-(furan-2-yl)-N-(propan-2-yl-2-d)-1H-pyrazole-3-carboxamido)methyl)phenoxy)heptanoic acid
6-(2-((5-(cyclopropylethynyl)-N-isopropyl-1H-pyrazole-3-carboxamido)methyl-d2)phenoxy)hexanoic acid
6-(2-((5-(cyclopropylethynyl)-N-(propan-2-yl-2-d)-1H-pyrazole-3-carboxamido)methyl)phenoxy)hexanoic acid
(S)-4-((2-((4-(furan-2-yl)-N-isopropylbenzamido)methyl-d2)phenyl)sulfonyl)-2,3-dihydro-1H-indene-2-carboxylic acid
(S)-4-((2-((4-(furan-2-yl)-N-(propan-2-yl-2-d)benzamido) methyl)phenyl)sulfonyl)-2,3-dihydro-1H-indene-2-carboxylic acid
6-(2-(((4-(furan-2-yl)phenyl)methyl-d2)(isopropyl)carbamoyl)phenoxy)hexanoic acid
6-(2-((4-(furan-2-yl)benzyl)(propan-2-yl-2-d)carbamoyl) phenoxy)hexanoic acid
6-(2-(2-((4-(furan-2-yl)phenyl)(isopropyl)amino)-2-oxoethyl-1,1-d2)phenoxy)hexanoic acid
6-(2-(2-((4-(furan-2-yl)phenyl)(propan-2-yl-2-d)amino)-2-oxoethyl)phenoxy)hexanoic acid
(E)-6-(2-((4-(furan-2-yl)-N-methylbenzamido)methyl-d) phenoxy)-4-methylhex-4-enoic acid
(E)-6-(2-((4-(furan-2-yl)-N-methylbenzamido)methyl-d2) phenoxy)-4-methylhex-4-enoic acid
6-(2-((4-(4-(furan-2-yl)phenyl)-2-methylthiazol-5-yl) methyl-d)phenoxy)hexanoic acid
6-(2-((4-(4-(furan-2-yl)phenyl)-2-methylthiazol-5-yl) methyl-d2)phenoxy)hexanoic acid
6-(2-((2-([1,1'-biphenyl]-4-yl)-5-methyl-1H-imidazol-1-yl) methyl-d)phenoxy)hexanoic acid 6-(2-((2-([1,1'-biphenyl]-4-yl)-5-methyl-1H-imidazol-1-yl) methyl-d2)phenoxy)hexanoic acid
(E)-6-(2-((2-(4-(furan-2-yl)phenyl)-5-methyl-1H-imidazol-1-yl)methyl-d)phenoxy)-4-methylhex-4-enoic acid
(E)-6-(2-((2-(4-(furan-2-yl)phenyl)-5-methyl-1H-imidazol-1-yl)methyl-d2)phenoxy)-4-methylhex-4-enoic acid
6-(2-((5-methyl-2-(2-methylbenzofuran-5-yl)-1H-imidazol-1-yl)methyl-d)phenoxy)hexanoic acid
6-(2-((5-methyl-2-(2-methylbenzofuran-5-yl)-1H-imidazol-1-yl)methyl-d2)phenoxy)hexanoic acid III. Method of Making the Compounds Disclosed compounds can be prepared to the carboxylic acid or hydroxamic acid at $L^1$ respectively, as exemplified below and as will be understood by a person of ordinary skill in the art of organic synthesis. For the preparation of the corresponding salts, an additional step would be performed. An exemplary synthesis may include the following 1" reaction step:

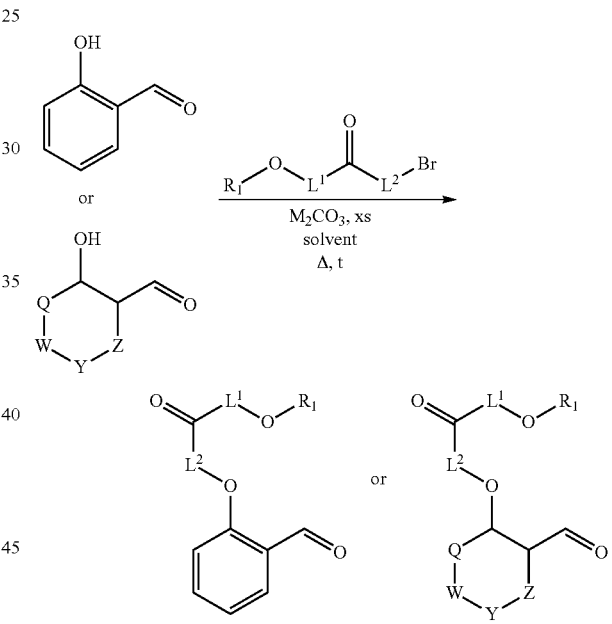

An alkylation reaction, specifically an etherification reaction, is performed where a hydroxyaryl or hydroxyheteroaryl moiety is reacted with an alkylating agent. For the hydroxyaryl or hydroxyheteroaryl moiety, the ring atoms are $CR^A$ or N; and $R^A$ is selected from H, D, F, Cl, lower aliphatic or alkyl, -CD$_3$, —CF$_3$, —OH, —OCH$_3$, —OCD$_3$ or —OCF$_3$. A suitable exemplary alkylating agent is an alkyl bromide $R_1$—O-$L^1$(CO)$L^2$-Br. The reactants are combined in the presence of a molar excess of a carbonate base (e.g. M=Na, K or Cs). The reaction is carried out in a polar aprotic solvent with a boiling point >100° C. such as DMF, DMA or DME. Typical reaction concentrations are 0.1 to 1.0M. Reactants are heated to >100° C., under ambient or elevated pressure, such as with microwave assisted organic synthesis (MAOS), for a period of time ranging from minutes to hours until both reactants are consumed. Exemplary aldehydes include:

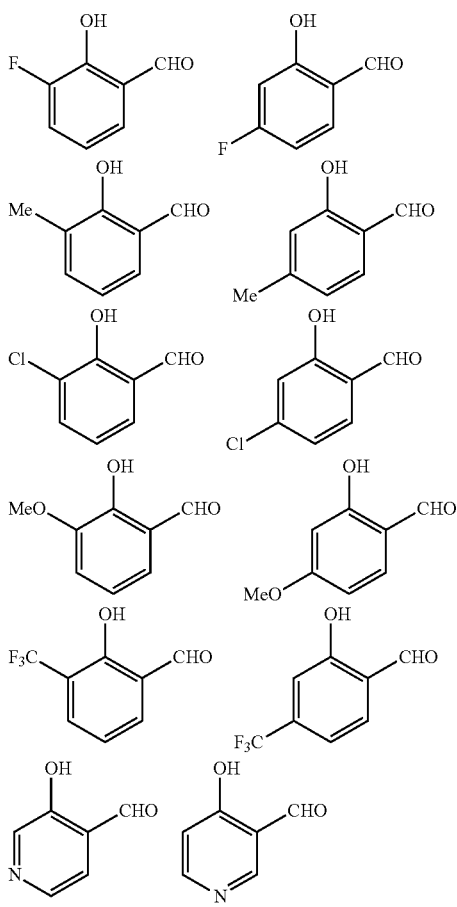

Exemplary linkers include:

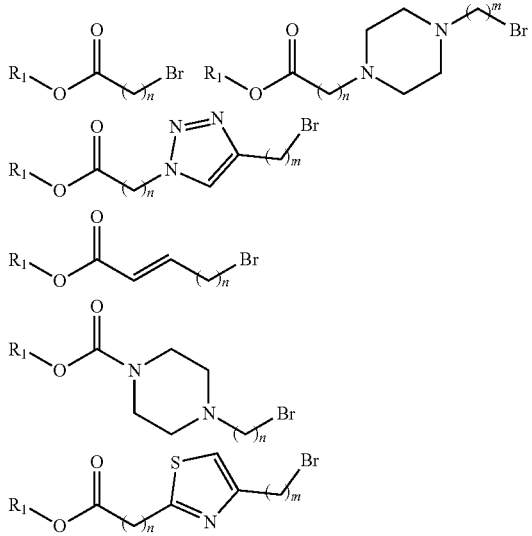

where m and n independently are selected from a range of 1-6 and $R^1$ (referred to herein as $R^{1A}$) is aliphatic, typically alkyl. Generally the distance between the bromide and the carbonyl carbon is 4-8 carbon-carbon bond lengths. Isolation, purification and characterization of the product aldehyde would be consistent with that typically practiced by one of ordinary skill in the art.

An exemplary 2$^{nd}$ step of the reaction process is provided below:

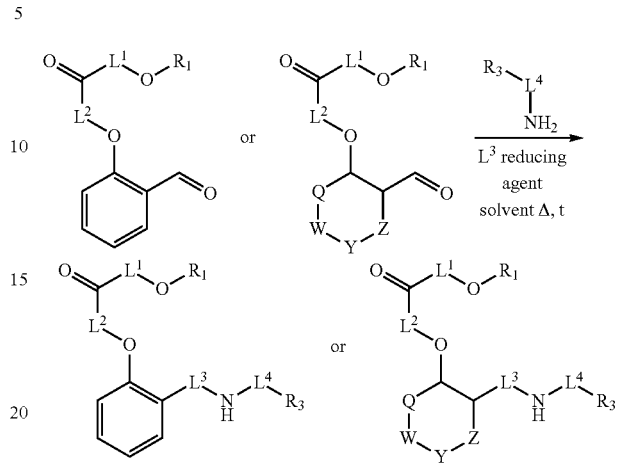

The 2$^{nd}$ reaction step is generally characterized as a reductive amination reaction of an aldehyde and primary amine, such as $R^3$-$L^4$-$NH_2$, where the reducing nucleophile is $L^3$. $L^3$ can be —H, -D, —$CH_3$, aliphatic, typically alkyl, and more typically lower alkyl. In certain embodiments, the $L^3$ reducing agent is a deuterated reducing agent such as, but not limited to, diborane-d6, sodium borodeuteride, sodium cyanoborodeuteride and deuterium. The reaction conditions are performed so that monoalkylation is the major product and over alkylation to the tertiary amine is suppressed. Reducing agents and co-solvent reaction additives are numerous, but readily known to those of ordinary skill in the art. Some exemplary primary amines comprising $R^3$ and $L^4$ functionalities include:

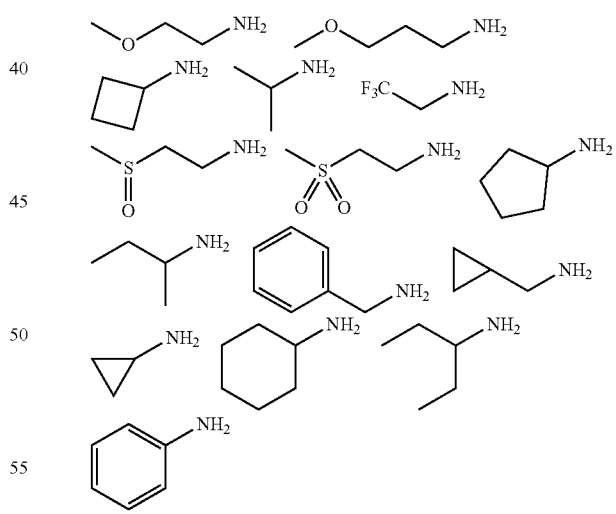

Solvents typically are chlorinated hydrocarbons, such as $CH_2Cl_2$, $CHCl_3$, or 1,2-dichloroethane. Reaction temperature and reaction time vary depending on the reaction temperature selected. As described above, MAOS versions of reductive amination exist.

The 3$^{rd}$ reaction step is generally characterized as a secondary amine acylation reaction. Exemplary acylating reagents include 4-bromobenzoyl or 4-bromoheteroaryoyl compounds. X typically is a leaving group, such as F, Cl, OTf, or similar favorable leaving group.

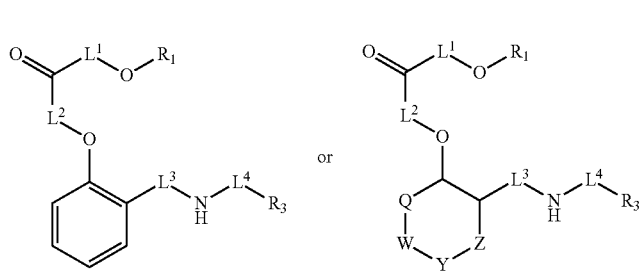

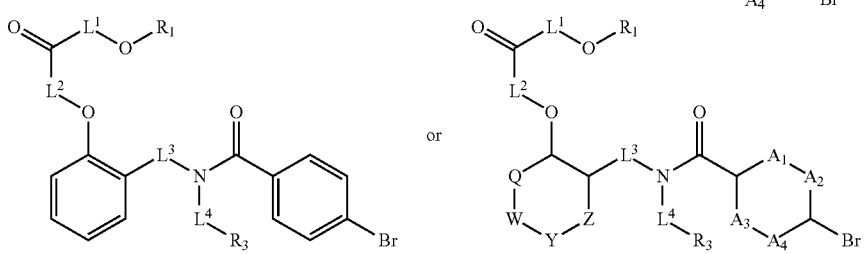

$A_1$, $A_2$, $A_3$, and $A_4$ are bonded by a single or double bond such that the resulting ring is aromatic; $A_1$, $A_2$, $A_3$, and $A_4$ are independently selected from —$CR^{12}$ or N; $R^{12}$ is selected from H, D, F, Cl, lower alkyl, —$CD_3$, —$CF_3$, —OH, —$OCH_3$, —$OCD_3$ or —$OCF_3$. Representative examples include:

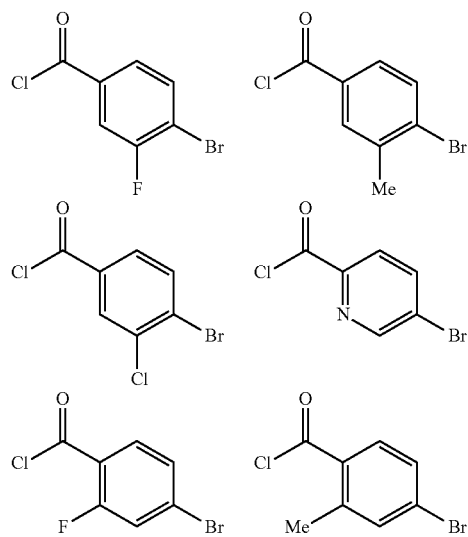

-continued

Typical reagent conditions include using a base, typically a non-nucleophillic base, or a hindered base having attenuated nucleophilicity, in excess molar amounts. Hindered amine bases, such as Hunig's base (N,N-diisopropylethylamine), would be a suitable choice, as will be recognized by a person of ordinary skill in the art. Solvents typically are chlorinated hydrocarbons, such as $CH_2Cl_2$, $CHCl_3$, or 1,2-dichloroethane. Reaction temperature and reaction time vary depending on the reaction temperature selected. As described above, MAOS versions of secondary amine acylation exist.

The 4$^{th}$ reaction step is generally characterized as a biaryl, aryl-heteroaryl or heteroaryl-heteroaryl coupling reaction mediated catalytically by a transition metal or transition metal complex.

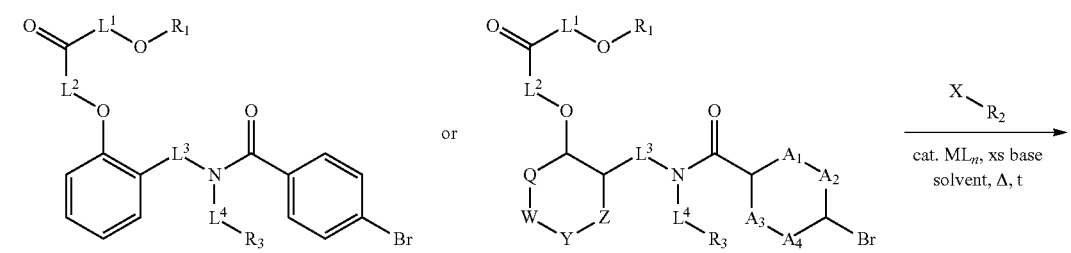

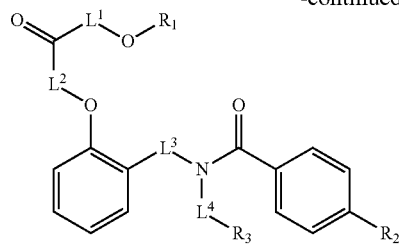
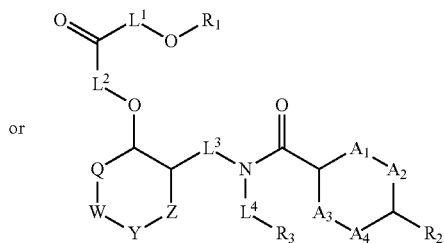

Numerous coupling reactions are known to those of ordinary skill in the art. In this embodiment, the coupling reaction could be the Suzuki-Miyaura cross-coupling where X is boronate —$B(OH)_2$, M is palladium, L is triphenylphosphine ($PPh_3$), and n is 4. With $Pd(PPh_3)_4$ as the catalyst, the cross-coupling reaction would be carried out in the presence of a base, such as a Na, K or Cs carbonate, in a ternary solvent system of DME, EtOH and Water. $R^2$ may be any aryl, aryl, heteroaryl, heteroaryl boronic acid, boronate ester or potassium trifluroboronate salt in this cross-coupling example. Exemplary $R^2$ moieties include:

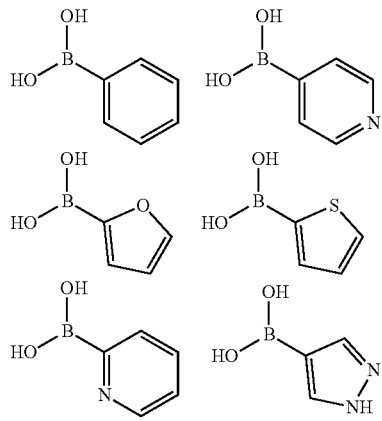

Reaction temperature and reaction time vary depending on the reaction temperature selected. As described above, MAOS versions of cross-coupling reactions exist.

The final step of this exemplary reaction sequence is saponification of $R^1$ where $L^1$ is a bond, thereby converting the carboxylic ester to the carboxylic acid. Where $L^1$ is nitrogen, $R^1$ is deprotected to the hydroxamic acid according to methods known to those of ordinary in the art. This reaction step is as follows:

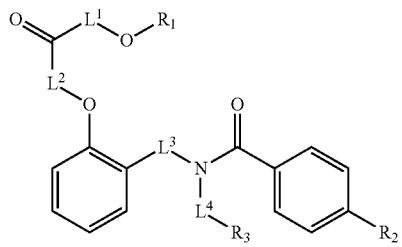
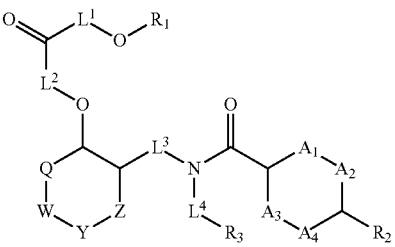
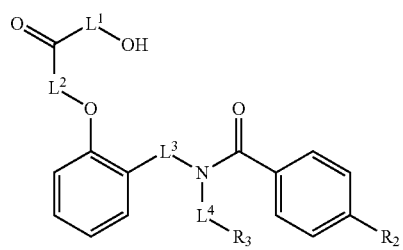
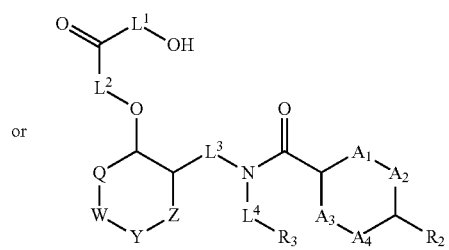

Typically the base is a hydroxide salt, such as Li, Na, K or Cs hydroxide. Suitable solvents include, but are not limited to, water, THF, alcohols, such as methanol, ethanol, propanol or isopropanol, DMF, DMSO, or any combination thereof. Reaction temperature and reaction time vary depending on the reaction temperature selected. As described above, MAOS versions of saponification reactions exist.

Additional formulation of these compounds include converting the carboxylic acid or hydroxamic acid versions to their complimentary pharmaceutically relevant salts. The various methods for salt formation are known to a person of ordinary skill in the art. An exemplary scheme is provided below.

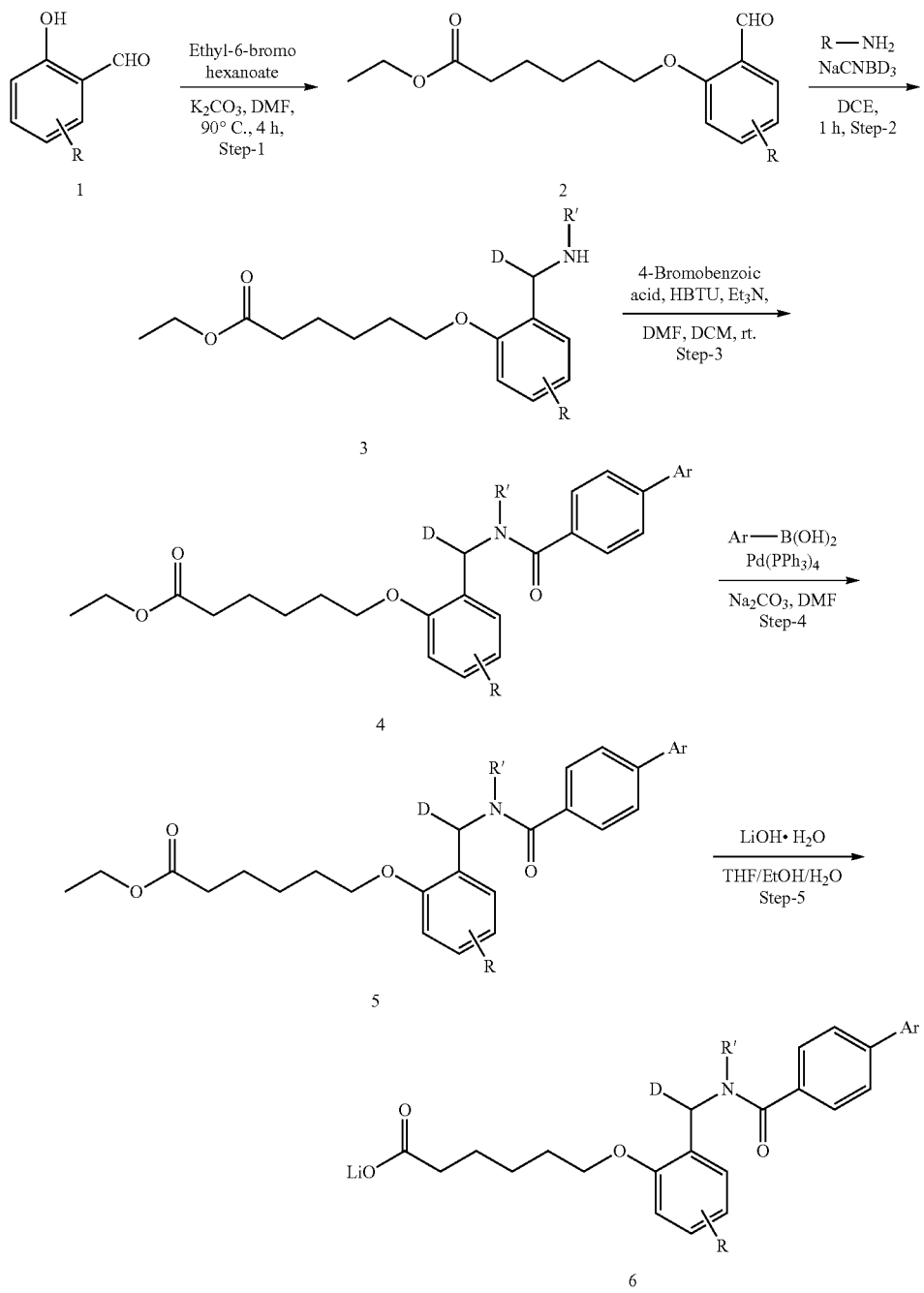

IV. Pharmaceutical Compositions and Administration

A. Additional Therapeutic Agents

Pharmaceutical compositions are disclosed that include one or more compounds provided herein (such as 1, 2, 3, 4 or 5 of such compounds), and typically at least one additional substance, such as an excipient, a known therapeutic other than those of the present disclosure, and combinations thereof. In some embodiments, the disclosed PPAR agonists can be used in combination with other agents known to have beneficial, additive or synergistic activity with the disclosed PPAR agonists. For example, disclosed compounds can be administered alone or in combination with: one or more other PPAR agonists, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (−)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds; further pharmacologically active substances which having favorable effects on metabolic disturbances or disorders frequently associated therewith, such as RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

Where cancer is being treated, one or more disclosed PPAR agonists can be used in combination with other agents for treating liquid, solid and/or metastatic tumors. Exemplary chemotherapeutic agents include agents that interfere with DNA replication, mitosis and chromosomal segregation, agents that disrupt the synthesis and fidelity of polynucleotide precursors, alkylating agents, antimetabolites, cytotoxic antibiotics, *vinca* alkaloids, tyrosine kinase inhibitors, metalloproteinase and COX-2 inhibitors, cyclophosphamide, cisplatin, docetaxel, paclitaxel, erlotinib, irinotecan, gemcitabine and cisplatin. Other particular examples of chemotherapeutic agents that can be used in combination with the disclosed compounds include alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide); microtubule binding agents (such as paclitaxel, docetaxel, vinblastine, vindesine, vinorelbine (navelbine) vincristine, the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof); anthracycline family members (for example, daunorubicin, doxorubicin, epirubicin, idarubicin, mitoxantrone, and valrubicin); antimetabolites, such as cytotoxic/antitumor antibiotics, bleomycin, rifampicin, hydroxyurea, and mitomycin; topoisomerase inhibitors, such as topotecan and irinotecan; photosensitizers, such as aminolevulinic acid, methyl aminolevulinate, porfimer sodium, and verteporfin, enzymes, enzyme inhibitors (such as camptothecin, etoposide, formestane, trichostatin and derivatives and analogs thereof), kinase inhibitors (such as imatinib, gefitinib, and erolitinib), gene regulators (such as raloxifene, 5-azacytidine, 5-aza-2'-deoxycytidine, tamoxifen, 4-hydroxytamoxifen, mifepristone and derivatives and analogs thereof); and other agents, such as alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, and tretinoin. In one example, the disclosed compounds are used in combination with a biologic for treating cancer (e.g., an antibody, such as a humanized antibody, which can be polyclonal, monoclonal, or chimeric, for example alemtuzumab, bevacizumab, cetuximab, gemtuzumab, rituximab, panitumumab, pertuzumab, or trastuzumab).

Orally effective hypoglycemic active ingredients that can be used in combination with one or more of the disclosed compounds include, for example, sulfonylureas, biguanides, meglitinides, oxadiazolidinediones, thiazolidinediones, glucosidase inhibitors, glucagon antagonists, GLP-1 agonists, DPP-IV inhibitors, potassium channel openers, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, and active ingredients which act on the ATP-dependent potassium channel of the beta cells.

In certain embodiments, disclosed compounds are administered in combination with substances which influence hepatic glucose production such as, for example, glycogen phosphorylase inhibitors; administered in combination with a biguanide such as, for example, metformin; administered in combination with a DPPIV inhibitor, such as (1-cyclopentyl-3-methyl-1-oxo-2-pentanammonium chloride), P-31/98, LAF237 (1-[2-[3-hydroxyadamant-1-ylamino)acetyl] pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate); administered in combination with an α-glucosidase inhibitor such as, for example, miglitol or acarbose; administered in combination with a bile acid reabsorption inhibitor; administered in combination with a polymeric bile acid adsorbent, such as, for example, cholestyramine or colesevelam; administered in combination with a cholesterol absorption inhibitor, such as ezetimibe, tiqueside, or pamaqueside; administered in combination with an LDL receptor inducer; administered in combination with a mixed PPAR alpha/gamma agonist such as, for example, Tesaglitazar, (S)-3-(4-[2-(4-methanesulfonyloxyphenyl)ethoxy]phenyl)-2-ethoxypropionic acid), or (N-[(4-methoxyphenoxy)carbonyl]-N-[[4-[2-(5-methyl-2-phenyl-4-oxazolyl)et-hoxy]phenyl]methyl]glycine); administered in combination with a fibrate such as, for example, fenofibrate, gemfibrozil, clofibrate, bezafibrate; administered in combination with nicotinic acid or niacin; administered in combination with a CETP inhibitor, such as torcetrapib; administered in combination with an ACAT inhibitor; administered in combination with an MTP inhibitor such as, for example, implitapide; administered in combination with an antioxidant; administered in combination with a lipoprotein lipase inhibitor; administered in combination with an ATP citrate lyase inhibitor; administered in combination with a squalene synthetase inhibitor; administered in combination with fenfluramine or dexfenfluramine; administered in combination with sibutramine; administered in combination with leptin.

In one embodiment, disclosed compounds may be administered in combination with dexamphetamine, amphetamine, mazindole or phentermine; and administered in combination with medicaments having an anti-inflammatory effect.

B. Excipients and Dosage Forms

The present disclosure provides pharmaceutical compositions that include a prophylactically or therapeutically effective amount of one or more disclosed compounds (such as 1, 2, 3, 4 or 5 disclosed compounds) in admixture with at least one pharmaceutically acceptable material, such as an excipient. Disclosed pharmaceutical compositions include a detectable amount of the PPAR agonist, such as greater than 0% to less than 100%, such as from 5% to 99%, or from about 50% to about 99%, or from 25% to about 99% by weight of the PPAR agonist of the present disclosure.

Disclosed compositions can be administered in any suitable dosage form, such as tablets, pills, capsules, powders, granules, sterile solutions or suspensions, metered aerosol or liquid sprays, drops, ampoules, auto-injector devices or suppositories. The compositions are intended for any suitable administration route, including oral, parenteral, intranasal, sublingual, rectal, transdermal, inhalation or insufflation. The compositions may be formulated by methods known by those of ordinary skill in the art, such as described in Remington's Pharmaceutical Sciences (15th ed., Mack Publishing Company, Easton, Pa., 1980).

The compositions can be administered for therapeutic or prophylactic treatments. In therapeutic applications, compositions are administered to a subject suffering from a disease (e.g., a PPARδ related disease) in a "therapeutically effective dose." Amounts effective for this use can depend upon the severity of the disease and the general state of the subject's health. Single or multiple administrations of the compositions can be administered depending on the dosage and frequency as required and tolerated by the subject. Also, the composition, shape, and type of dosage forms may vary depending on their use. For example, a dosage form used for acute treatment of a disease or disorder may contain larger amounts of the active ingredient than a dosage form used in the chronic treatment of the same disease or disorder. Similarly, a parenteral dosage form may contain smaller amounts of the active ingredient than an oral dosage form.

Oral dosage forms include, but are not limited to, tablets (including without limitation scored or coated tablets), pills, granules, lozenges, caplets, capsules, chewable tablets, powder packets, cachets, troches, wafers, aerosol sprays, mucosal patches, or liquids, such as syrups, elixirs, solutions or suspensions in an aqueous liquid, for example water or saline, a non-aqueous liquid, an oil-in-water emulsion, or a water-in-oil emulsion. Typical oral dosage forms may be prepared by combining the pharmaceutically acceptable PPAR agonist, potentially in a liquid, solid, granule or gelatin for and/or in a salt form, in admixture with at least one excipient including, but are not limited to, surface stabilizers, dispersion aids, binders, filling agents, lubricating agents, glidants, suspending agents, sweeteners, flavoring agents, preservatives, buffers, wetting agents, disintegrants, effervescent agents, humectants, controlled release agents, absorption accelerators, absorbents, plasticizers, lactose, sucrose, mannitol, sorbitol, calcium phosphates, corn starch, potato starch, cellulose, hydroxy propyl methyl cellulose, microcrystalline cellulose, gelatin, acacia, sodium alginate, alginic acid, tragacanth, guar gum, gelatin, colloidal silicon dioxide, talc, magnesium stearate, stearic acid, colorants, diluents, talc, calcium carbonate, kaslin, maltodextrin, polymethacrylates, moistening agents, preservatives, dyes, and any combination thereof.

Disintegrants facilitate producing tablets that disintegrate when exposed to an aqueous environment. The amount of disintegrant used varies based upon the type of formulation and mode of administration, and is readily determined by a person of ordinary skill in the art. Typical pharmaceutical compositions comprise from about 0.5 to about 15 weight percent of disintegrant, such as from about 1 to about 5 weight percent of disintegrant. Disintegrants include, but are not limited to, agar-agar, alginic acid, guar gum, calcium carbonate, microcrystalline cellulose, croscarmellose sodium, carboxymethylcellulose calcium, methylcellulose, crospovidone, polacrilin potassium, sodium starch glycolate, potato or tapioca starch, other starches, pre-gelatinized starch, clays, other algins, other celluloses, gums, and mixtures thereof.

Exemplary lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), sodium benzoate, sodium stearylfumarate, zinc stearate, ethyl oleate, ethyl laureate, agar, syloid silica gel, synthetic silica, and mixtures thereof. Lubricants typically are used in an amount of less than about 1 weight percent of the pharmaceutical compositions.

Disclosed PPAR agonists, and related forms, such as salts, can be administered as controlled- or delayed-release formulations. Controlled-release pharmaceutical products have a common goal of improving drug therapy over that achieved by their non-controlled release counterparts. These dosage forms can be used to provide slow or controlled-release of one or more active ingredients using, for example, alginic acid, aliphatic polyesters, bentonite, cellulose acetate, phthalate, carnuba wax, chitosan, ethylcellulose, guar gum, microcrystalline wax, paraffin, polymethacrylates, povidone, xanthan gum, yellow wax, carbomers, hydroxypropylcellulose, and hydroxypropylmethylcellulose.

Pharmaceutical compositions can also include large, slowly metabolized macromolecules such as proteins, polysaccharides, such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

The compositions provided herein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories. Exemplary suppositories include a suppository base, such as natural or synthetic triglycerides or paraffin hydrocarbons. Gelatin rectal capsules include a combination of the compound of choice with a base, including, for example, liquid triglycerides, polyethylene glycols, and paraffin hydrocarbons.

Topical dosage forms include, but are not limited to, creams, lotions, ointments, gels, shampoos, sprays, aerosols, solutions, emulsions, and other forms know to a person of ordinary skill in the art. Suitable formulations include, without limitation, solutions, suspensions, emulsions, creams, ointments, powders, liniments, and salves.

Transdermal and mucosal dosage forms can include, but are not limited to, ophthalmic solutions, patches, sprays, aerosols, creams, lotions, suppositories, ointments, gels, solutions, emulsions, or suspensions. Dosage forms suitable for treating mucosal tissues within the oral cavity can be formulated as mouthwashes, as oral gels, or as buccal patches.

The disclosed PPAR agonists can be formulated for parenteral administration, such as, for example, by intraarticular (in the joints), intravenous, intraarterial, intramuscular, intratumoral, intradermal, intraperitoneal, and subcutaneous routes. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared. Suitable materials for such administration include sterile water; saline solution; glucose solution; aqueous vehicles, such as sodium chloride Injection, Ringer's Injection, Dextrose Injection, Dextrose, Sodium Chloride Injection, Lactated Ringer's Injection; ethyl alcohol, polyethylene glycol, and propylene glycol; non-aqueous vehicles such as, but not limited to, corn oil, cottonseed oil, peanut oil, sesame oil, ethyl oleate, isopropyl myristate, and benzyl benzoate; aqueous and non-aqueous, isotonic sterile injection solutions, which can contain antioxidants, buffers, bacteriostats, and solutes that render the formulation isotonic with the blood of the intended recipient; and aqueous and non-aqueous sterile suspensions that can include suspending agents, solubilizers, thickening agents, stabilizers, and preservatives. In the practice of this disclosure, compositions can be administered, for example, by intravenous infusion, orally, topically, intraperitoneally, intravesically or intrathecally. In an independent embodiment, parenteral administration, oral administration, and/or intravenous administration are the methods of administration. The formulations of compounds can be presented in unit-dose or multi-dose sealed containers, such as ampules and vials.

The pharmaceutical preparation can be in unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

The combined administrations contemplate co-administration, using separate formulations or a single pharmaceutical formulation, and consecutive administration in either order, wherein, in some embodiments, there is a time period while both (or all) active agents simultaneously exert their biological activities.

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of one or more compounds disclosed herein can be administered in a single dose, twice daily, weekly, or in several doses, for example daily such as two, three or four times daily, or during a course of treatment. The disclosed PPAR agonists may be administered substantially continuously too, such as by using a transdermal delivery system. In a particular non-limiting example, treatment involves once daily dose or twice daily dose. However, a person of ordinary skill in the art would immediately recognize appropriate and/or equivalent doses looking at dosages of approved compositions for treating a PPARδ related disease using the disclosed PPAR agonists for guidance.

The pharmaceutical compositions that include one or more compounds disclosed herein can be formulated in unit dosage form, suitable for individual administration of precise dosages. In one non-limiting example, a unit dosage contains from about 1 mg to about 50 g of one or more compounds disclosed herein, such as about 10 mg to about 10 g, about 100 mg to about 10 g, about 100 mg to about 7 g, about 200 mg to about 10 g, or about 200 mg to about 5 g. In other examples, a therapeutically effective amount of one or more compounds disclosed herein is from about 0.01 mg/kg to about 500 mg/kg, for example, about 0.5 mg/kg to about 500 mg/kg, about 1 mg/kg to about 100 mg/kg, or about 1 mg/kg to about 50 mg/kg. In other examples, a therapeutically effective amount of one or more compounds disclosed herein is from about 1 mg/kg to about 20 mg/kg, such as about 2 mg/kg to about 5 mg/kg. In some embodiments, about 3 mg/kg or 10 mg/kg can be used.

V. Methods

Provided herein are methods of activating PPARδ. Such methods can include contacting a PPARδ protein with an effective amount of a compound or composition provided herein, thereby activating PPARδ. In some embodiments, the contacting is performed in vitro. In other embodiments, the contacting is performed within a subject, such as a human or other mammalian subject (such as a veterinary subject, for example a cat, dog, mouse, or rat), for example by administering a PPAR agonist disclosed herein to the subject. In some embodiments, the compound or composition is administered ton a healthy subject. In some embodiments, the subject is a sedentary or immobilized subject. In other embodiments, the subject is an exercising subject, such as one who exercises for at least 20 minutes, at least 30 minutes, at least 45 minutes, or at least 60 minutes, at least 2, at least 3, or at least 4 days per week. In some embodiments, a healthy subject is also an exercising subject.

In some examples, contacting a PPARδ protein in vitro or in vivo with an effective amount of one or more compounds or compositions provided herein, increases PPARδ activity by at least 10%, at least 20%, at least 30%, at least 40%, at least 50%, at least 60%, at least 70%, at least 80%, at least 90%, at least 95%, at least 100%, at least 200%, at least 300%, at least 400%, or even at least 500%, for example as compared to an amount of PPARδ activity in the absence of the compound/composition. Methods of measuring PPARδ activity are known, and specific examples are provided herein (e.g., measuring expression of PPARδ at the protein or nucleic acid level, measuring Beta oxidation levels, creatine kinase levels, pentose phosphate shunt in liver, blood glucose levels and methods provided in Wang et al., *PLos Biol.* 2(10):e294, 2004 and Lee et al., *PNAS* 103:3444-9, 2006).

In some embodiments, the subject recovers from acute injury following administration of the PPAR agonist.

In some embodiments, activating PPARδ within the subject by administration of a PPAR agonist disclosed herein (or composition containing the PPAR agonist) increases or maintains muscle mass or muscle tone (such as a skeletal or cardiac muscle) in the subject (such as in a healthy subject or a sedentary subject). For example, activating PPARδ within the subject can increase muscle mass, muscle tone, or both, in the subject. In some examples, administering an effective amount of one or more PPAR agonist compounds or compositions provided herein increases muscle mass, muscle tone, or both, by at least 10%, at least 20%, at least 30%, at least 40%, at least 50%, at least 60%, at least 70%, at least 80%, at least 90%, at least 95%, at least 100%, at least 200%, at least 300%, at least 400%, or even at least 500%, for example as compared to an amount of PPARδ activity in the absence of the compound/composition. Methods of measuring muscle mass and muscle tone are known, and specific examples are provided herein (e.g., see methods provided in WO 2009/086526).

In other embodiments, activating PPARδ within the subject (such as a healthy subject or a sedentary subject) maintains muscle mass, muscle tone, or both, in the subject. In some examples, administering an effective amount of one or more PPAR agonist compounds or compositions provided herein maintains muscle mass, muscle tone, or both, such that the amount of muscle mass, muscle tone or both, does not change by more than 1%, for example no more than 2%, no more than 3%, no more than 4%, no more than 5%, no more than 6%, no more than 7%, no more than 8%, no more than 9%, no more than 10%, or no more than 15%, for example as compared to an amount of muscle mass, muscle tone, or both in the absence of the compound/composition. Methods of measuring muscle mass and muscle tone are known, and specific examples are provided herein (e.g., see methods provided in WO 2009/086526).

Thus, the disclosed PPAR agonists and compositions containing such can be used to increase or maintain muscle mass or muscle tone (or both) in a subject. For example, the disclosed PPAR agonists and compositions containing such can be used to increase or maintain muscle mass or muscle tone (or both) in a subject following an injury, following a period of immobilization (for example confinement to a bed or wheelchair) or immobilization of a body part (for example immobilization of an appendage or joint due to a broken bone, joint replacement, tendon tear, surgery, and the like), which events can result in a loss of muscle mass and/or muscle tone. The method includes administering to the subject a therapeutically effective amount of one or more compounds provided herein. In some embodiments, the subject is a sedentary or immobilized subject. In other embodiments, the subject is an exercising subject.

Methods of treating or preventing a PPARδ-related disease or condition in a subject in need thereof are provided. The methods can include administering to the subject a therapeutically effective amount of one or more compounds or compositions provided herein. In some embodiments, the PPARδ-related disease is a vascular disease (such as a cardiovascular disease or any disease that would benefit from increasing vascularization in tissues exhibiting impaired or inadequate blood flow). In other embodiments, the PPARδ-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy. In some embodiments, the PPARδ-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In some embodiments, the PPARδ-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

Other PPARδ-related diseases that can be treated or prevented with the disclosed PPAR agonists (or compositions containing such compound), include but are not limited to one or more of the following diseases: (1) a muscle structure disorder, such as Bethlem myopathy, central core disease, congenital fiber type disproportion, distal muscular dystrophy (MD), Duchenne & Becker M D, Emery-Dreifuss M D, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence; (2) a neuronal activation disorder, such as amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, toxic myoneural disorder, (3) a muscle fatigue disorder such as chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, thyrotoxic myopathy, (4) a muscle mass disorder such as, cachexia, cartilage degeneration, cerebral palsy, compartment syndrome, critical illness myopathy, inclusion body myositis, muscular atrophy (disuse), sarcopenia, steroid myopathy, and systemic lupus erythematosus, (5) a mitochondrial disease such as, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome, (6) a beta oxidation disease such as, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, riboflavin-responsive disorders of β-oxidation (RR-MADD), (7) a metabolic disease such as, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis, (8) a cancer such as, cancer of the colon, large intestine, skin, breast, prostate, ovary, or lung; (9) a vascular disease such as peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy; (10) an ocular vascular disease such as, age-related macular degeneration (AMD), stargardt disease, hypertensive retinopathy, diabetic retinopathy, retinopathy, macular degeneration, retinal haemorrhage, or glaucoma; or (11) a muscular eye disease such as, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia. Thus, in some examples, the subject treated has or is at risk for developing one or more of these diseases.

VI. Working Examples

Skeletal muscle relies on the resident progenitor cells, the satellite cells, for postnatal growth and regeneration. Therefore, maintaining an adequate number and proper function of satellite cells is critical for muscle to appropriately response to damage. While endurance exercise promotes adaptive responses in the muscle, including an increase in the satellite cell number, it is not known whether transcriptionally directed "endurance exercise training" has similar effects. Here it is shown that mice harboring constitutively active PPARδ in skeletal muscle displayed an accelerated regenerative process in muscle after an acute injury. Gene expression analyses showed earlier resolution of the inflammatory response and induction of myogenic markers, indicating that PPARδ activation induces a temporal shift in the regenerative process. Notably, a significant increase in the number of satellite cells was found in mice with constitutively active PPARδ expressed in skeletal muscle, consistent with the observed increase in proliferating cell number after the injury. PPARδ activation induced the expression of FGF1, which is known to be involved in muscle development and regeneration. In particular, PPARδ up-regulates FGF1a isoform, which may be responsible for supporting cell proliferation and reestablishment of vasculature to augment the regenerative process. Furthermore, the restoration of fiber integrity was improved in wild-type mice after acute treatment with the PPARδ synthetic ligand, GW501516. Collectively, these findings allude to the therapeutic potential of PPARδ, to accelerate the recovery from acute muscle injury. GW501516 is 4-[({4-methyl-2-[4-(trifluoromethyl)phenyl]-1,3-thiazol-5-yl}methyl)sulfanyl]-2-methylphenoxy}acetic acid (also known as "GW501516," "GW-501,516," "GW1516," "GW" or GSK-516), and has a structure:

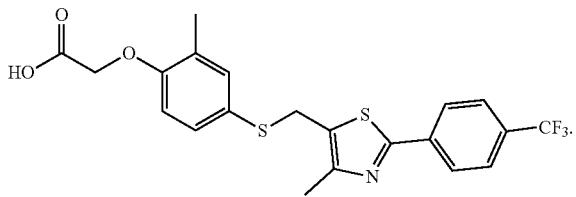 [SMILES: Cc1cc(SCc2sc(-c3ccc(C(F)(F)F)cc3)nc2C)ccc1OCC(=O)O]

Activation of peroxisome proliferator activated receptor δ (PPARδ) induces a fiber type switch toward a more oxidative phenotype, altering both metabolic and functional output of the muscle (Wang et al., *PLoS Biol* 2(10):e294. Erratum in: *PLoS Biol.* 2005 January; 3(1):e61 (2004); Luquet et al., *FASEB J* 17(15):2299-2301 (2003)). Specifically, PPARδ-mediated muscle remodeling translates into supernatural physical endurance, and protection against diet-induced obesity and symptoms of metabolic disorders that ensue (Wang et al., *PLoS Biol* 2(10):e294. Erratum in: *PLoS Biol.* 2005 January; 3(1):e61 (2004); Wang et al., *Cell* 113:159-170 (2003)). Furthermore, pharmacological activation of PPARδ and exercise training synergistically enhance oxidative fibers and running endurance (Narkar V A et al., *Cell* 134(3):405-415 (2008)). Exercise confers a myriad of healthful benefits to the body, including improvement of atrophic and disease conditions (Nicastro et al., *Braz J Med Biol Res* 44(11):1070-9 (2011); Markert et al., *Muscle Nerve* 43(4):464-78 (2011)). Recently, endurance exercise alone has been shown to improve ageing induced decrease in satellite cell number and their myogenic capacity (Shefer et al., *PLoS One* 5(10):e13307 (2010)).

It is demonstrated herein that both genetic and pharmacological activation of PPARδ promote muscle regeneration in an acute thermal injury mouse model. PPARδ activation during regeneration expedites resolution of inflammatory response and restoration of contractile proteins. Interestingly, acute pharmacological activation of PPARδ by oral administration of a synthetic ligand, GW501516, is sufficient to confer similar benefits during muscle regeneration after an acute injury. Based on these observations, a novel role of PPARδ during adult muscle regeneration and its use as a therapeutic target to enhance regenerative efficiency of skeletal muscle is provided.

Example 1

Experimental Procedures

A. Animals

VP16-PPARδ mice (Wang et al., *Cell* 113:159-170 (2003)) were bred to CB6F1 strain (Jackson Laboratories) and used as heterozygotes in experiments. The non-transgenic littermates served as controls. All experiments were performed when animals were 8 weeks of age. Nestin-GFP mice (Mignone et al., *J Comp Neurol* 469(3):311-324 (2004)) were kindly provided by Dr. Fred Gage at the Salk Institute for Biological Studies.

B. Freeze burn injury Tibialis anterior (TA) muscles were injured according to previously published methods with a few modifications (Brack et al., *Science* 317(5839):807-810 (2007)). A stainless steel 1 g weight (Mettler-Toledo) equilibrated to the temperature of dry ice was placed directly on the exposed TA for 10 seconds. Following the thermal injury, incision was closed using VetBond (3M). All injury procedures were performed on the left leg, and the right leg was used as control.

C. Histology

Animals were perfused with 15 mL of ice-cold PBS followed immediately by 20 mL of 10% saline buffered formalin. TA muscles were excised and immersed in 4% paraformaldehyde for at least 48 hours at 4° C. Tissues were dehydrated by exposure to a series of solutions with increasing percentage of ethanol. Dehydrated tissues were cleared in xylene and allowed for paraffin to permeate over night at 60° C. Tissues were then embedded in plastic molds.

Paraffin embedded tissue blocks were sectioned at 7 μm thick on Leica Jung 2500 Microtome. Sections were stained with hematoxylin and counter stained with 1% eosin. Slides were dried and mounted with Entellan mounting media (EMS). Three random non-overlapping fields were photographed for analysis. Regenerating fiber number was measured by counting the number of discernible muscle fibers with centralized myonuclei (Ge et al., *Am J Physiol Cell Physiol* 297(6):C1434-1444 (2009)). Regenerating fiber cross sectional area (CSA) was measured using Image J software.

D. Evans Blue dye staining

Injured animals were injected with Evans Blue dye according published protocol (Hamer et al., *J Anat* 200(Pt 1):69-79 (2002)). Sterile 1% w/v Evans Blue dye in PBS was intraperitoneally injected at 1% volume relative to the body mass of an animal. 7 hours after the injection, injured TA muscles were harvested and snap-frozen by isopentane quenching in liquid nitrogen. Frozen sections were cut in 10 μm thickness, fixed in ice-cold acetone, dipped in xylene and mounted with DPX. Proportion of the stained area over the total area was measured using ImageJ software.

E. BrdU Labeling 50 mg/kg body weight of BrdU (Sigma) was injected intraperitoneally as solution of 10 mg/mL BrdU in saline. TA muscles were harvested at 7 days after injury and processed for paraffin sections as described above. BrdU incorporation was visualized using the BrdU Labeling and Detection Kit I (Roche) and BrdU+ nuclei were counted and represented as a proportion of total nuclei in a field.

F. RT-QPCR

Whole or partial tissues were homogenized by Polytron probe homogenizer in Trizol reagent (Invitrogen). Total RNA was extracted from the homogenates according to the manufacturer's protocol. 1 μg of DNase-treated total RNA was reverse transcribed using Superscript II Reverse Transcriptase (Invitrogen) according to the manufacturer's instructions. cDNAs were diluted 1/40 with ddH$_2$O and used as templates in RT-QPCR reactions with SYBRGreenER qPCR SuperMix detection system (Invitrogen). Samples were prepared in technical triplicates and relative mRNA levels were calculated by using the standard curve methodology and normalized against GAPDH mRNA levels in the same samples.

G. Myofiber Isolation

Either whole or partial gastrocnemius muscle was digested in 2% collagenase I (Sigma) in DMEM with 10% FBS for 60 minutes at 37° C. Muscle tissue was further mechanically dispersed by triturating in a fire polished wide bore Pasteur pipet. Liberated fibers were washed in two changes of PBS with 10% FBS and finally mounted on glass slides with Vectashield mounting media (Vector Labs).

H. Isolation of satellite cells

Satellite cells were harvested from TA of 8 weeks old animals according to published protocols with some modifications (Day et al. (2007) Nestin-GFP reporter expression defines the quiescent state of skeletal muscle satellite cells. *Dev Biol* 304(1):246-259). Muscles were removed and washed briefly in DMEM on ice. They were then minced into a fine slurry with a razor blade on a 60 mm culture dish over ice. Minced muscles were transferred to one well of a 6-well plate containing 5 ml of 450 KPU/ml pronase in DMEM. The tissues were digested at 37° C./5% CO$_2$ for 60 minutes. After digestion, tissues were vigorously triturated 20 times through 10 ml serological pipet. Digested tissues were filtered through a 40 micron cell strainer and washed with an equal volume of DMEM with 20% horse serum. Cells were spun down at 1000 g for 10 minutes and resuspended in sorting buffer (DMEM with 10% FBS). Cells were separated from larger debris using a 20%/60% Percoll gradient (Yablonka-Reuveni Z et al. (1987) Isolation and clonal analysis of satellite cells from chicken pectoralis muscle. *Dev Bio* 119: 252-259). GFP positive cells were sorted on BD FACSAria II sorter.

Example 2

Muscle Specific Activation of PPARδ Confers Regenerative Advantage

While it has been shown that the majority of the metabolic genes are down regulated in injury, PPARδ expression was induced over 2 fold at 2 days after the injury (Warren et al. (2007) Mechanisms of skeletal muscle injury and repair revealed by gene expression studies in mouse models. *J Physiol.* 582.2: 825-841, FIG. 1A). This injury dependent up-regulation of PPARδ strongly suggested a possible role for PPARδ during the early part of the regenerative process.

Freeze burn injury was used to elicit the regenerative program, which has been shown to model the standard course of the regenerative response, including satellite cell activation (Karpati and Molnar. "Muscle fibre regeneration in human skeletal muscle diseases." In: Schiaffino S, Partridge T (eds). Skeletal muscle repair and regeneration. Springer, Dordrecht, 2008). Additionally, since the injury is directly applied to the surface of the muscle, it is highly localized and reproducible.

Using Evans Blue dye uptake as a marker of myofiber damage, fiber integrity was histologically assessed. The freeze burn injury does not incapacitate the animals and the damaged fibers restore original cross sectional area by 21 days after the injury (FIG. 1J).

Figure 1C:
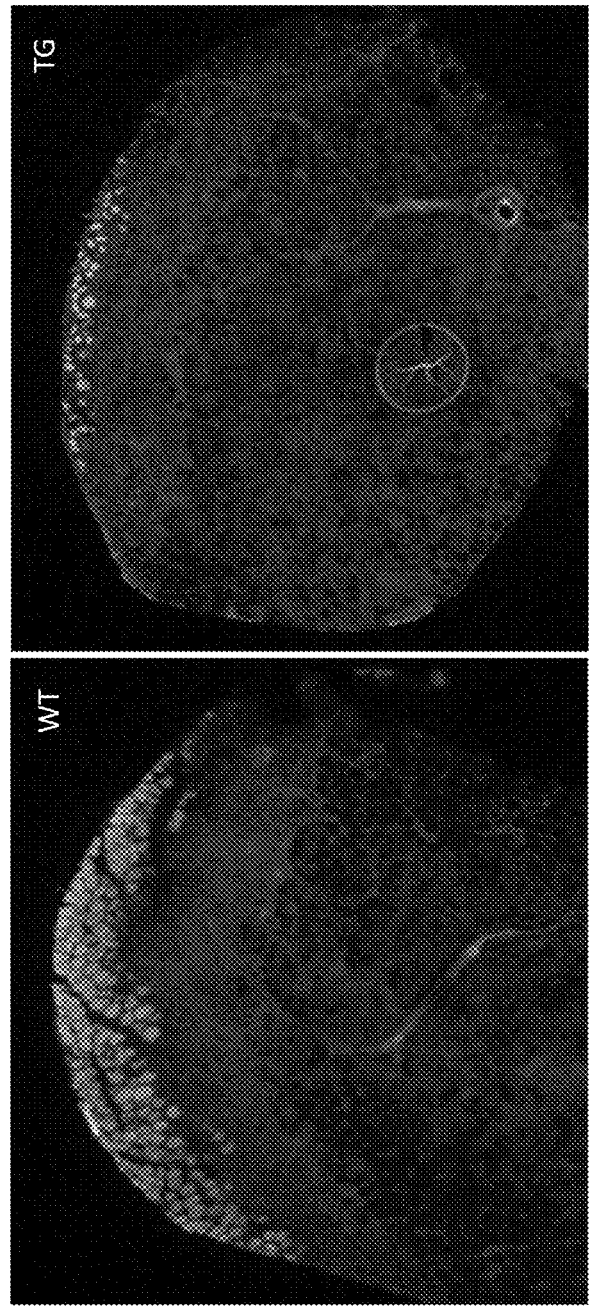
FIGS. 1C-1F show that VP16-PPARδ transgenic animals exhibit accelerated muscle regeneration after acute injury. All error bars are SEM.
Figure 1D:
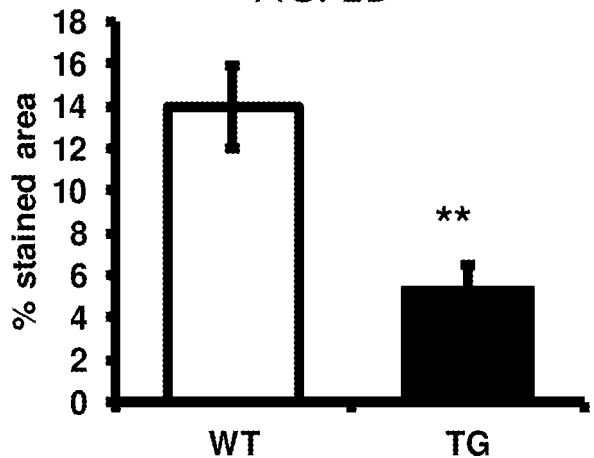
Figure 1E:
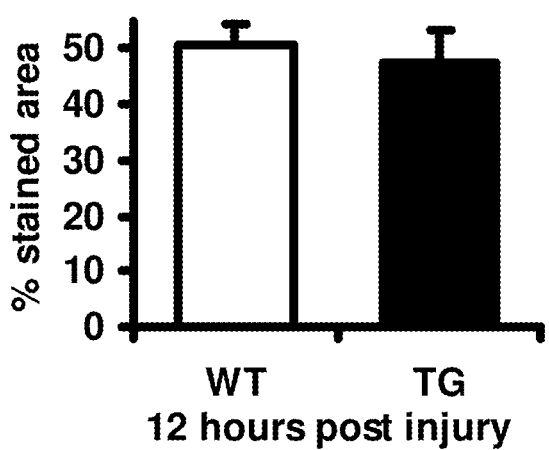
Figure 1F:
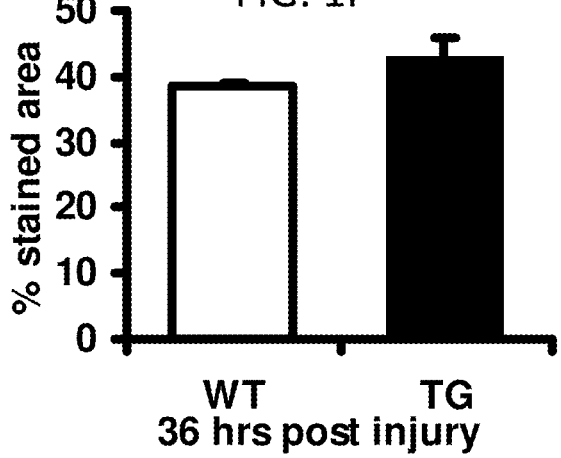

By comparing the proportion of stained fibers within the cross sectional area (CSA) of the injured muscle 5 days after the injury, the degree of damage was quantified. At 5 days after the injury, VP16-PPARδ (TG) animals show significantly less dye uptake, indicative of enhanced fiber regeneration, over the wildtype (WT) animals (FIGS. 1C and D). While 14% of the total CSA shows dye uptake in WT muscle, only 5% of the total CSA of TG muscle show dye uptake (n=8 WT; n=5 TG; p=0.001) (FIG. 1D). At 12 and 36 hours after the injury, however, both WT and TG animals showed similar proportions of stained area (50.6% and 47.4% (p=0.67), and 38.5% and 43.3% (p=0.23), respectively) (FIGS. 1E and 1F). Similar level of dye uptake shortly after the injury shows that both WT and TG animals initially sustain similar degree of damage from the injury and suggests that PPARδ activation does not confer protection from damage. Instead, the reduction in Evans Blue dye uptake observed 5 days after the injury suggests that the muscle specific PPARδ activation promotes restoration of fiber integrity after the injury.

Figure 1G:
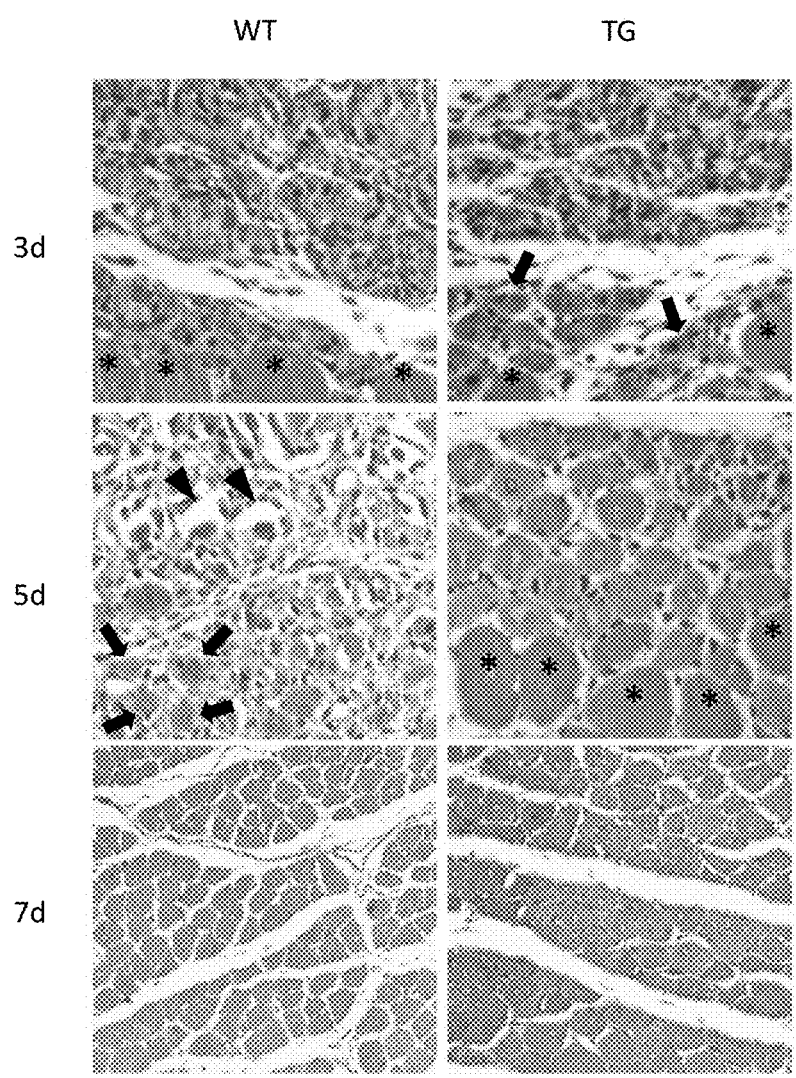

The morphological hallmarks of regenerating fibers were determined for a detailed analysis of the process. H&E stained transverse sections through the injured area were examined at 3, 5 and 7 days post injury. At 3 days after the injury, both WT and TG animals showed similar degrees of degeneration defined as necrosing fibers surrounded by infiltrating monocytes (FIG. 1G). No regenerating fibers, characterized by a small round shape and centralized nuclei, were discernible at 3 days in WT animals, but a notable few were seen in TG animals (arrows, FIG. 1G). By day 5 after the injury, obvious differences are seen. In WT animals, small regenerating fibers were visible but necrosing fibers and monocytes were still prevalent at the site of the injury (arrowheads, FIG. 1G). While in the TG animals, the injury site shows an orderly arrangement of small regenerating fibers. Quantification of regenerating fiber number and CSA reveals that by 5 days post injury, TG animals show significant regenerative advantage over their WT counterparts. Both CSA of the regenerating fibers and the number of regenerating fibers were significantly greater for TG animals at 43.5% (n=5 or 6; p<0.03) and 33.0% (n=11 or 12; p<0.001), respectively (FIGS. 1H and 1I). By day 7 post injury, the damage site appears architecturally similar between WT and TG animals, where both show a field of immature regenerating fibers without the infiltrating immune cells. However, quantification of the regenerating fibers revealed a regenerative advantage of the TG animals in the number of nascent regenerating fibers (FIG. 1H). At 21 days after the injury, both WT and TG animals have restored their fiber size and number to that of the uninjured level (FIG. 1J). These data demonstrate that the muscle specific activation of PPARδ bestows significant regenerative advantage, most prominently observed in the early stages of the regenerative process.

Example 3

PPARδ Activation Leads to Temporal Shift, Thus Increased Efficiency, of the Muscle Regenerative Process Skeletal muscle regeneration is an intricately orchestrated process involving a variety of cell types. For example, immune cells, both neutrophils and macrophages, are necessary for the proper progression of regenerative process (Zacks et al., Muscle Nerve 5:152-161 (1982); Grounds et al., Cell Tissue Res 250:563-569 (1987); Teixeira et al., Muscle Nerve 28(4):449-459 (2003); Summan et al., Am J Physiol Regul Integr Comp Physiol 290:R1488-R1495 (2006); Contreras-Shannon et al., Am J Physiol Cell Physiol 292:$C_{953}$-967 (2007); Segawa et al., Exp Cell Res 314(17): 3232-3244 (2008)). Additionally, various cytokines are necessary to promote chemotaxis of monocytes and also to directly regulate the activities of myogenic cells (Warren et al., Am J Physiol Cell Physiol 286(5):C1031-1036 (2004); Yahiaoui et al., J Physiol 586:3991-4004 (2008); Chazaud et al., JCB 163(5):1133-1143 (2003)). Therefore, the temporal expression profiles of genes associated with various aspects of the regenerative process were determined.

Figure 2A:
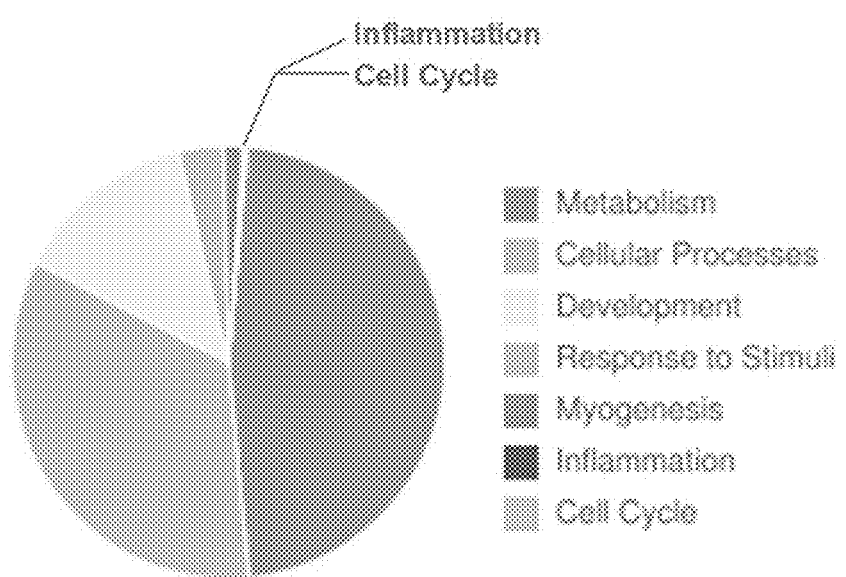
FIGS. 2A-E illustrate that PPARδ activation promotes a temporal shift of the gene expression profile associated with the regenerative process. *P<0.05. All error bars are SEM.
Figure 2B:
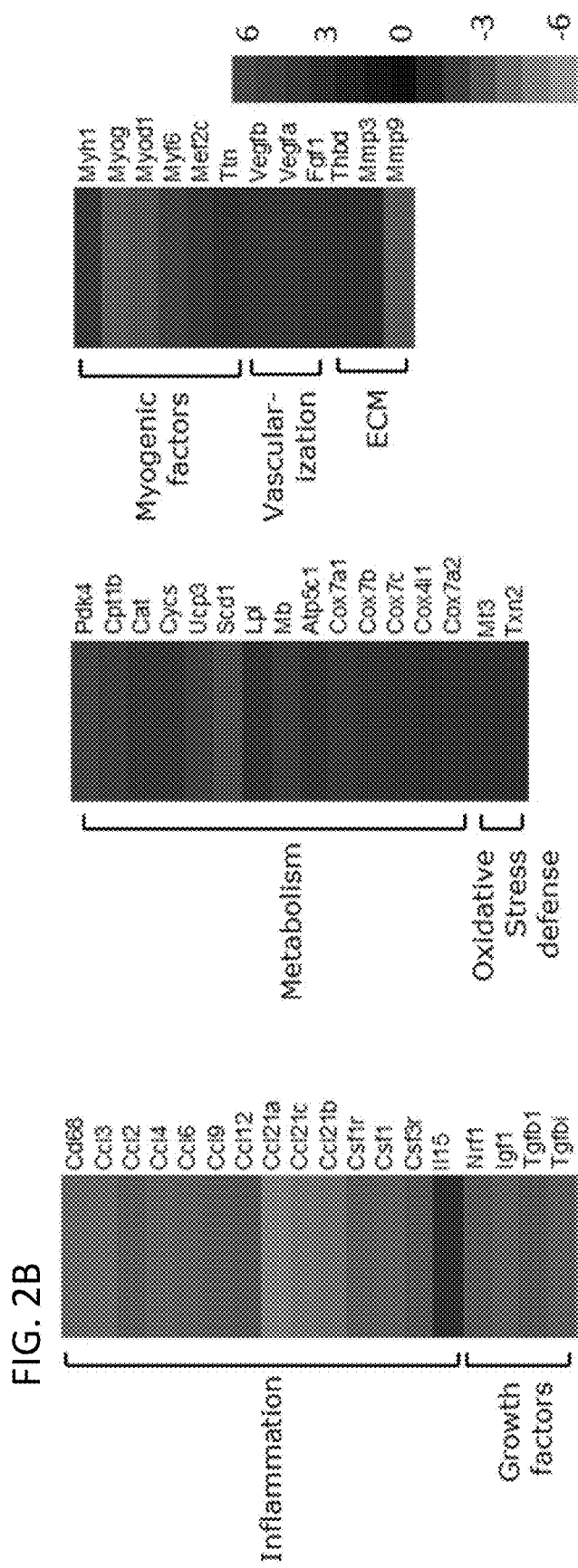

Global, injury-specific gene expression changes were identified in TA muscles by microarray. Comparing the gene expression profiles of injured TG and WT muscle 3 days post-injury, 3257 genes with altered expression were identified, of which 1375 were down regulated and 1882 were up regulated. Notably, genes involved in myogenesis and remodeling were robustly up-regulated by PPARδ activation while those involved in inflammatory response were down regulated in injured TG muscles (FIGS. 2A and B). Additionally, genes involved in developmental processes, angiogenesis and anti-apoptotic processes emerged from the analysis (FIG. 2A). Relative expressions of regeneration markers reveal down-regulation of early makers (inflammatory genes) and up-regulation of regenerative/remodeling genes (myogenic, vascularization, ECM genes) in TG animals 3 days post injury (FIG. 2B). Collectively, PPARδ activation appears to control a network of genes directly involved in myogenesis, as well as genes involved in remodeling and the repair processes after an injury.

Figure 2C:
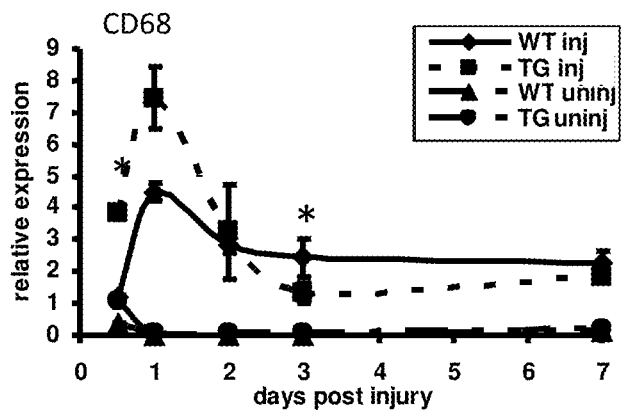
Figure 2D:
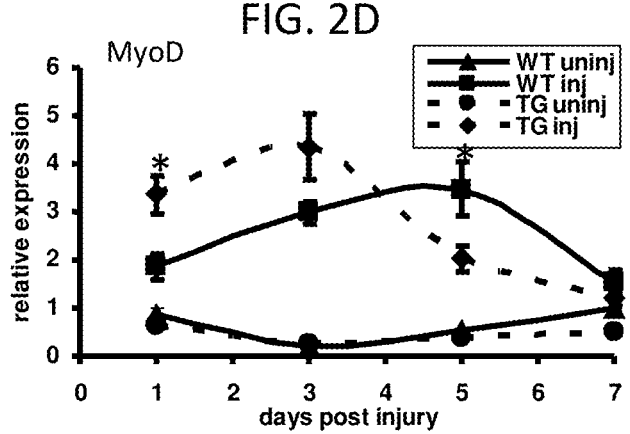
Figure 2E:
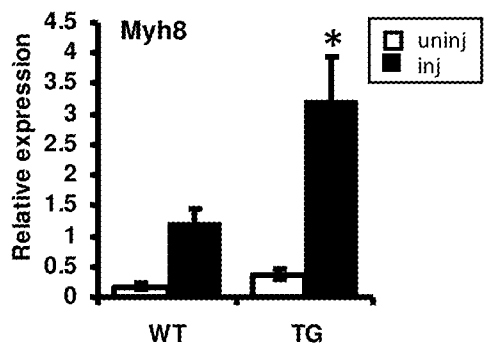

Underlying the phasic progression of the regenerative program is a temporally coordinated program of gene expression changes that affect a variety of contributing processes. In order to validate and temporally-expand the microarray data, expression of CD68 (an inflammation marker) and MyoD (a marker of myogenesis) were measured by Q-PCR at several time points over the 7 day period post injury (FIGS. 2C and 2D). A temporal shift in the expression patterns of regenerative markers for TG animals compared to their WT littermates was observed. TG animals showed a rapid, most robust induction of CD68, that was subsequently down regulated earlier than in the WT animals. Interestingly, inflammatory markers studied here peaked at similar levels between the two genotypes, which indicates that TG animals do not completely suppress their inflammatory responses. Instead, it appears that the TG animals resolve the inflammatory responses more efficiently, which is consistent with the accelerated restoration of muscle morphology observed. TG animals also show higher expression of perinatal myosin heavy chain gene, Myh8, at 7 days post injury, indicating more efficient reassembly of the contractile properties (FIG. 2E). PPARδ activation leads to a temporal shift in the expression patterns of regenerative markers, which together with the histology data, shows a role of PPARδ in increasing regenerative efficiency.

Example 4

PPARδ Directs Neo-Vascularization Via Regulation of FGF1

This example describes adaptive responses bestowed by PPARδ activation in the muscle which may contribute to the observed beneficial effects on regeneration.

Figure 3A:
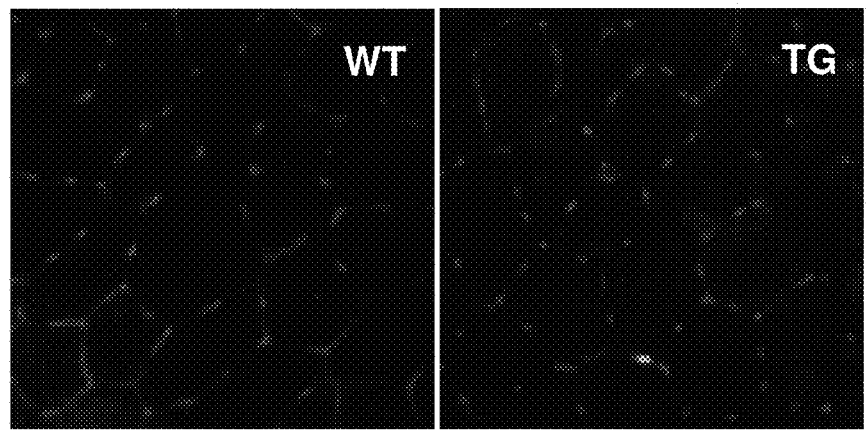
FIGS. 3A-3G illustrate that PPARδ promotes microvascularization through the regulation of FGF1a. *P<0.05; **P<0.01. All error bars are SEM.
Figure 3B:
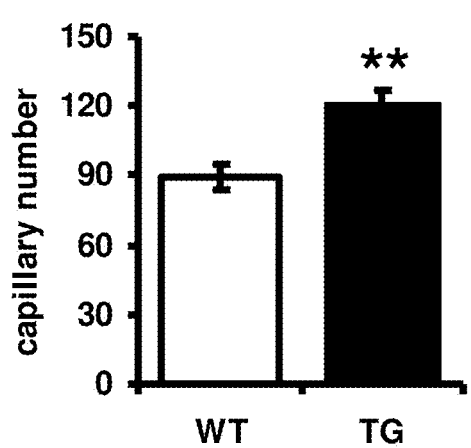
Figure 3C:
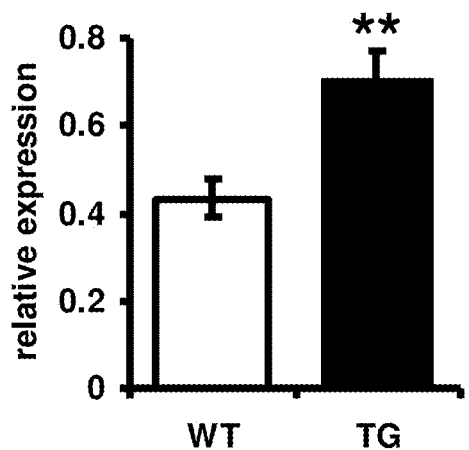
Figure 3D:
Figure 3E:
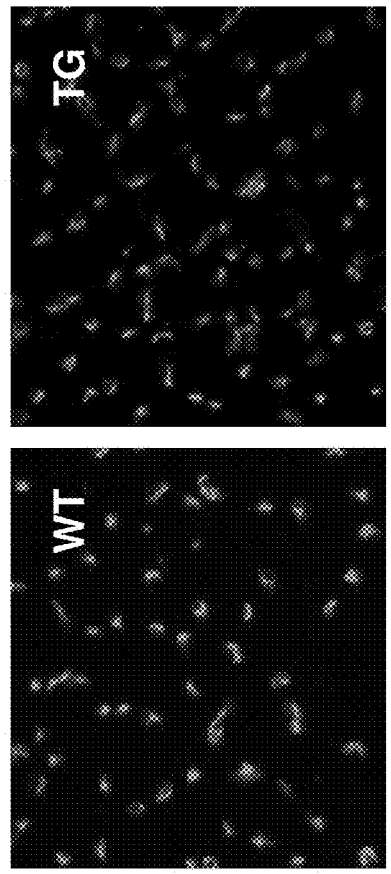
Figure 3G:
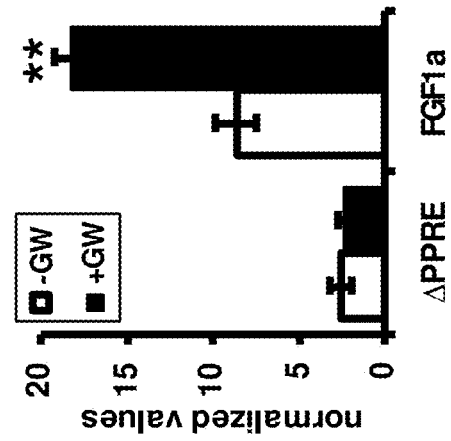
Figure 3F:
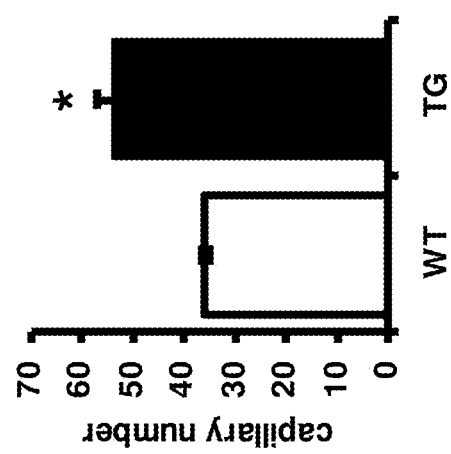

Increased vasculature is one of the hallmarks of oxidative myofibers, which facilitates introduction of immune cells and also supports increased number of satellite cells. TG animals show increased expression of FGF1 in TA muscle (FIG. 3D). Immunostaining transverse sections of uninjured TA from WT and TG animals revealed a 36% increase in the number of $CD_{31}$+ capillaries per field upon PPARδ activation (FIGS. 3A-B), as well as a significant increase in the expression of FGF1a. Furthermore, 5 days after injury, TG animals show increased expression of $CD_{31}$, which is indicative of increased vascularity (FIG. 3E-F). Notably, FGF1a is a direct PPARδ target gene, as demonstrated by the PPARδ response element (PPRE)-dependent activation with the PPARδ ligand, GW501516, in a luciferase reporter assay (FIG. 3G). FGF1 has been shown to be expressed in regenerating fibers in chronic disease models and has been implicated in myogenesis and regeneration (Oliver, Growth Factors. 1992; 7(2):97-106, 1992; Saito, 2000, Muscle Nerve. 23(4):490-7). In addition, FGF1 increasing the microvasculature in adipocytes and PPARδ has been shown to directly regulate the expression of FGF1a isoform (Jonker et al., Nature. 485(7398):391-4, 2012). Therefore, the increased vascularity induced by PPARδ may contribute to the accelerated regenerative process observed in VP16-PPARδ animals.

Example 5

PPARδ Activation Positively Regulates Quiescent Satellite Cell Number

One of the first events following the injury is the proliferation of muscle resident progenitors, the satellite cells. This example describes results showing that the regenerative advantage observed in TG animals could be due to altered satellite cell homeostasis.

Figure 4A:
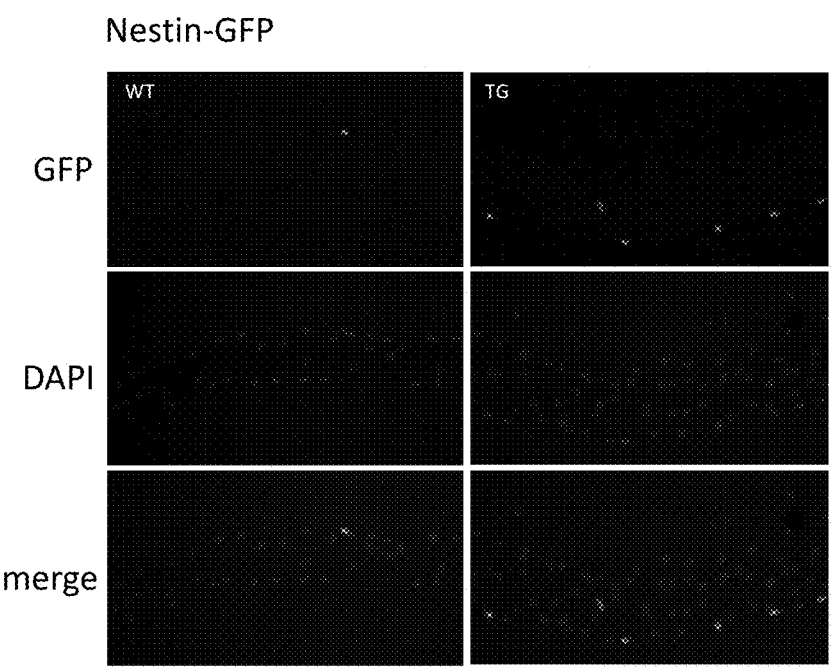
FIG. 4A-4E illustrate that the skeletal muscle specific activation of PPARδ increases the quiescent satellite cell pool. All error bars are SEM. *P<0.05; **P<0.01.
Figure 4B:
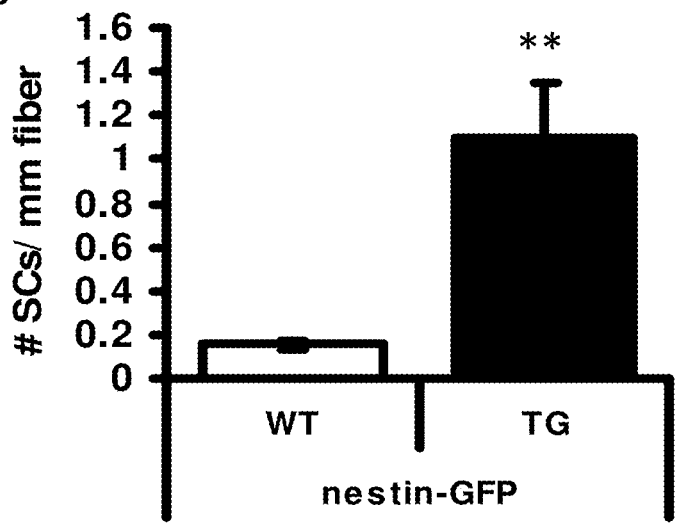

Nestin expression was used as a marker of satellite cells, and nestin-GFP; VP16-PPARδ double transgenic animals were used to genetically label quiescent satellite cells (SCs) in vivo (Mignone et al., *J Comp Neurol* 469(3):311-324 (2004); Day et al., *Dev Biol* 304(1):246-259 (2007)). Gastrocnemius muscles were enzymatically digested to liberate individual fibers, then mounted for quantification (FIG. 4A). While double transgenic animals averaged 1.01 SCs per mm of fiber length, GFP+ animals only had 0.15 SCs per mm, a 6.48 fold higher SC content on VP16-PPARδ muscle fiber (FIG. 4B).

Figure 4C:
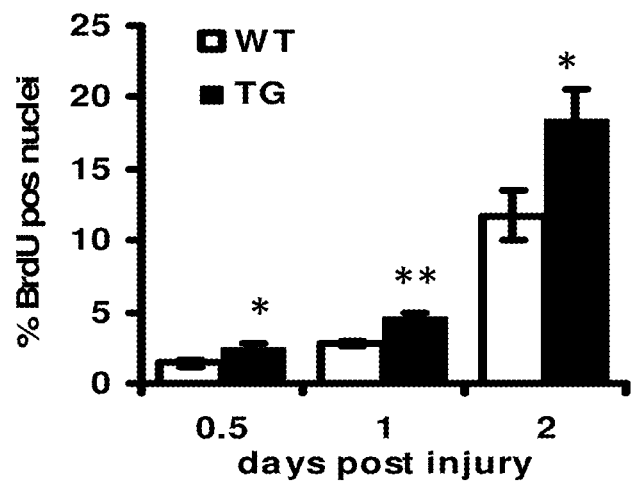
Figure 4D:
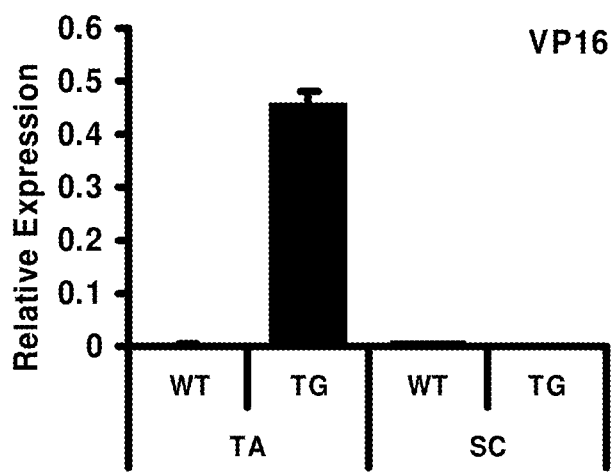
Figure 4E:
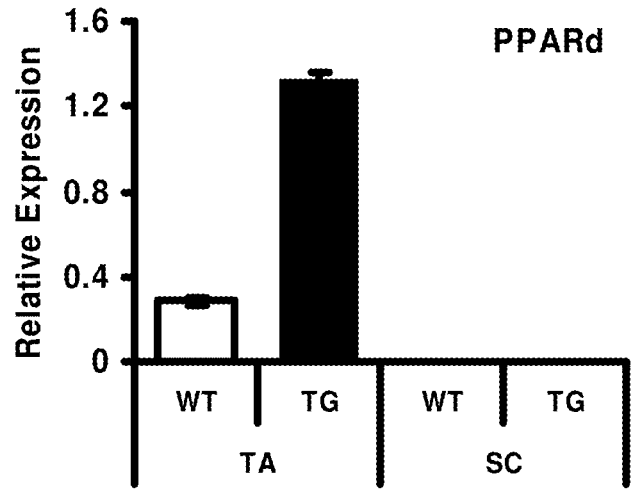

Satellite cell activity was measured as myoblast proliferation elicited by the freeze burn injury in vivo. After the freeze burn injury, BrdU was intraperitoneally injected at 12 hrs, 24 hrs and 2 days after the injury, and the muscles were harvested 7 days after the injury. The ratio of BrdU+ to total nuclei was calculated to determine the number of proliferating cells. TG animals showed 40-60% increase in the number of BrdU+ proliferating cells at all three injection times (FIG. 4C). These results are consistent with the PPARδ-induced increase in the number of quiescent satellite cells yielding higher numbers of fusion competent myoblasts, leading to the enhancement of regenerative capacity of the muscle. Interestingly, neither endogenous PPARδ, or the constitutively activate VP16-PPARδ, are significantly expressed in satellite cells (FIGS. 4D and E), indicating that the increase in satellite cell number in the TG muscle is an indirect consequence of PPARδ activation in muscle.

Example 6

Acute Pharmacological Activation of PPARδ Confers a Regenerative Advantage

Pharmacological activation of PPARδ has been shown to induce PPARδ target genes in fast-twitch hind limb muscles (Narkar et al., *Cell* 134(3):405-415 (2008)). To demonstrate that an acute pharmacological activation of PPARδ can modulate the regenerative process after injury, $C_{57}BL6J$ mice were treated with GW501516 (Sundai Chemicals, China) orally at 5 mg/kg for 4 days prior to, and 5 days after freeze burn injury to the TA muscle.

Figure 5A:
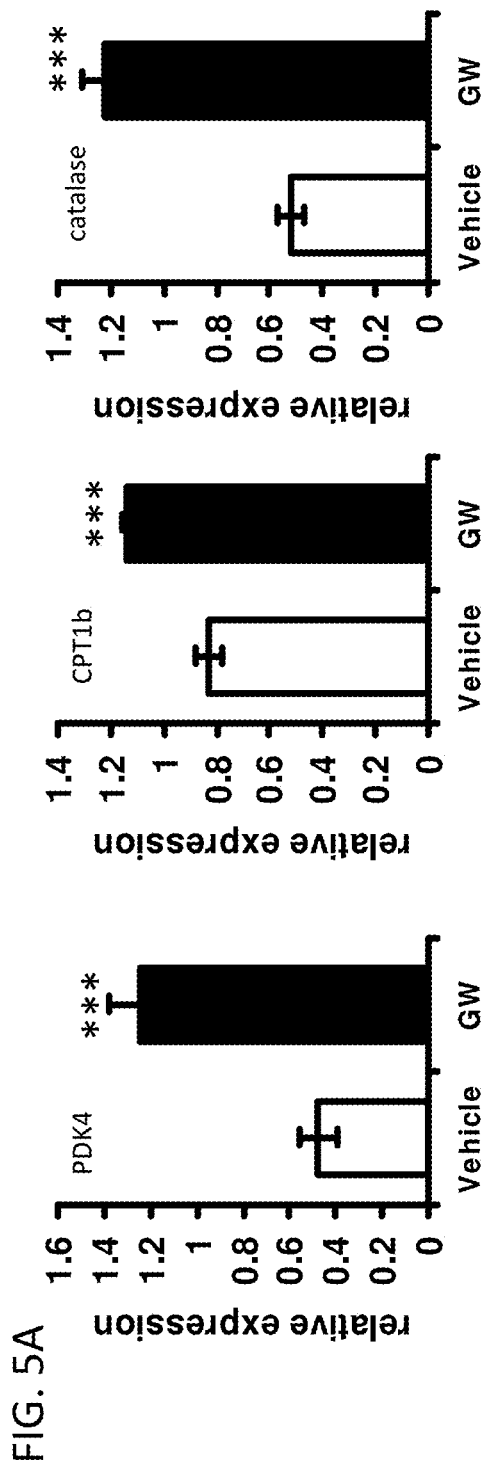
Figure 5B:
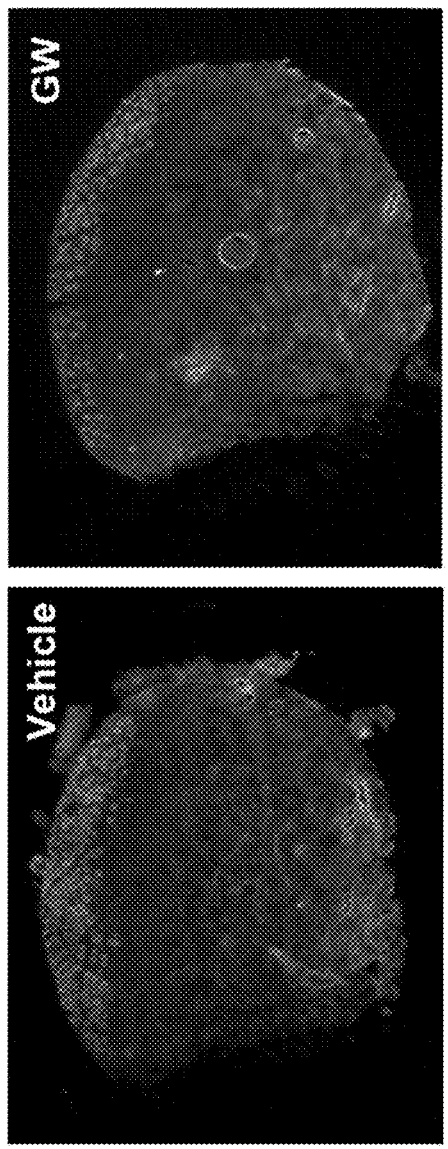

Up-regulation of known PPARδ target genes (PDK4, CPT1b, and catalase) in the TA muscle was confirmed by QPCR, attesting to the successful delivery and activity of the PPARδ ligand in the muscle (FIG. 5A). While vehicle treated animals showed Evans Blue dye uptake in 7.6% of the cross sectional area (CSA), only 4.9% of the muscle CSA was stained in the ligand treated animals (FIGS. 5B and 5C). Thus, PPARδ ligand-treated animals showed a 34.7% reduction in damaged muscle fibers 5 days after the injury, demonstrating that pharmacological activation of PPARδ enables accelerated restoration of myofiber integrity after injury.

Consistent with the PPARδ ligand conveying a regenerative advantage, BrdU injection at 48 hours after the injury showed a marked increase in proliferative cell number in the ligand treated muscle, supporting the notion that PPARδ activation promotes myoblast proliferation after injury (FIG. 5D). While the number of quiescent satellite cells was not significantly affected by either 9 days or 4 weeks of ligand treatment, satellite cells do not undergo rapid turnover. Thus, the duration of ligand treatment may have been insufficient to affect the numbers of these long-lived progenitor cells. Nonetheless, GW501516 treatment promoted myoblast proliferation in vivo after the injury, which may contribute to the accelerated regeneration after the injury.

The expression of inflammatory marker genes was measured after injury by QPCR. While the initial inflammatory responses at 12 hours after injury are similar with and without PPARδ ligand treatment, a significant reduction in both TNFα and the macrophage marker F4/80 expression was seen at 3 days post injury in PPARδ ligand treated muscle (FIG. 5E). These results are consistent with the known role of PPARδ as an anti-inflammatory regulator, and corroborate the beneficial findings observed in the VP16-PPARδ genetic model.

Example 7

Muscle Specific Activation of PPARδ is Protective Against Exercise-Induced Injury WT and TG mice were acclimated to moderate treadmill running (10 m/min for 15 min) every other day for 1 week. After acclimation, the speed was gradually increased to 15 m/min and then maintained constant until exhaustion (week 0). Subsequently, mice were subjected to 4 weeks (5 days/week) of exercise training on a treadmill inclined at 5 degree incline, with progressively increasing intensity and time. At the end of the training protocol (week 5), mice were run to exhaustions and serum samples were taken for the measurement of creatine kinase levels.

Figure 6:
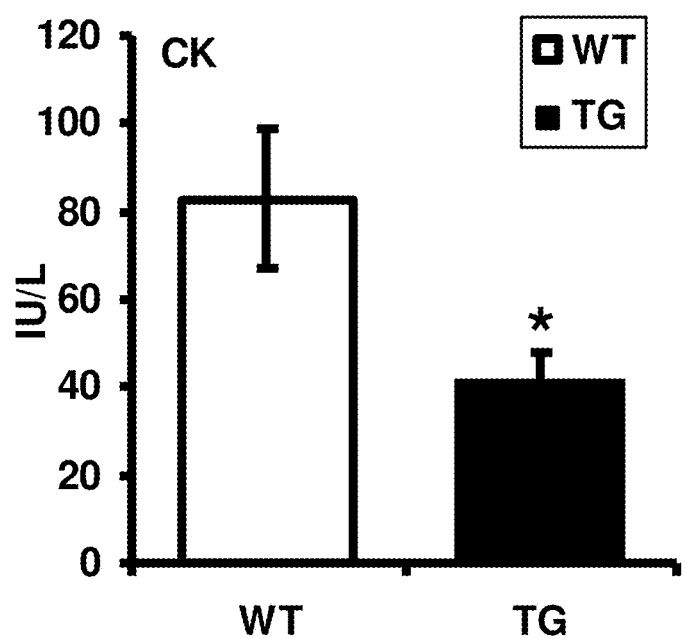
FIG. 6 is a bar graph showing serum creatine kinase levels in wildtype (WT) and VP16-PPARδ (TG) transgenic animals after treadmill running to exhaustion.

WT and VP16-PPARδ (TG) mice were run to exhaustion, and their serum creatine kinase (CK) levels we measured by ELISA. The levels of CK in the TG mice were significantly lower than those in WT mice, indicative of reduced exercise-induced muscle damage (FIG. 6).

Example 8

Muscle Specific Activation of PPARδ Enhances Recovery after Injury

This example describes adaptive responses bestowed by PPARδ activation in the muscle which may contribute to the observed beneficial effects on regeneration.

Figure 7A:
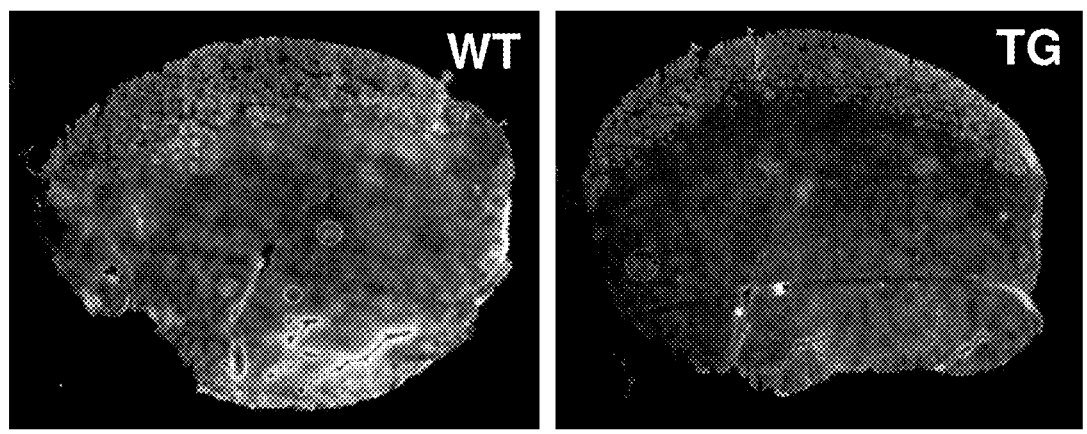
FIG. 7A shows transverse sections of TA of wildtype (WT) and VP16-PPARδ (TG) animals 3 days after the injury. Staining of damaged fibers by Evans Blue.
Figure 7B:
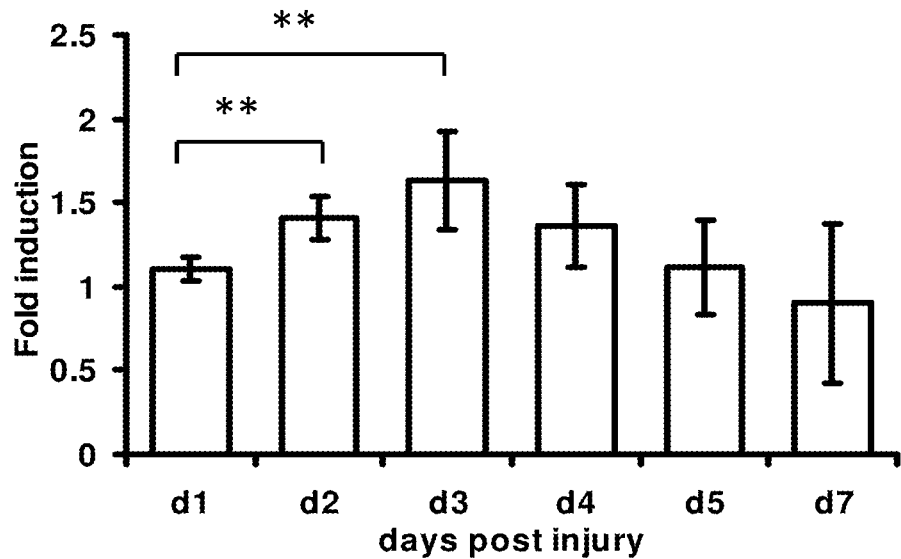
FIG. 7B shows the time course of injury-dependent induction of PPARδ by QPCR (n=5).
Figure 7C:
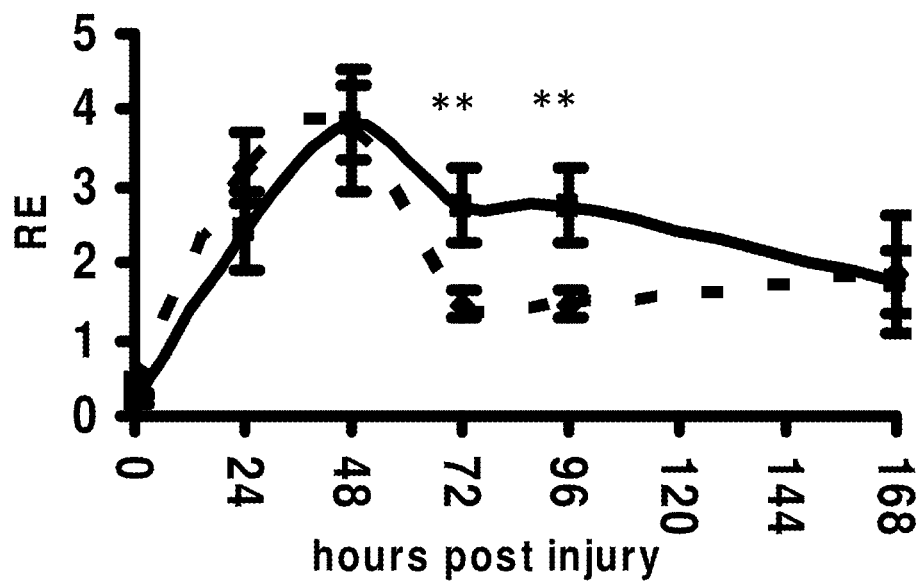
FIG. 7C shows post injury temporal gene expression profile of the inflammatory marker TNFα in wildtype (WT, solid line) and VP16-PPARδ (TG, dashed line) after injury.
Figure 7D:
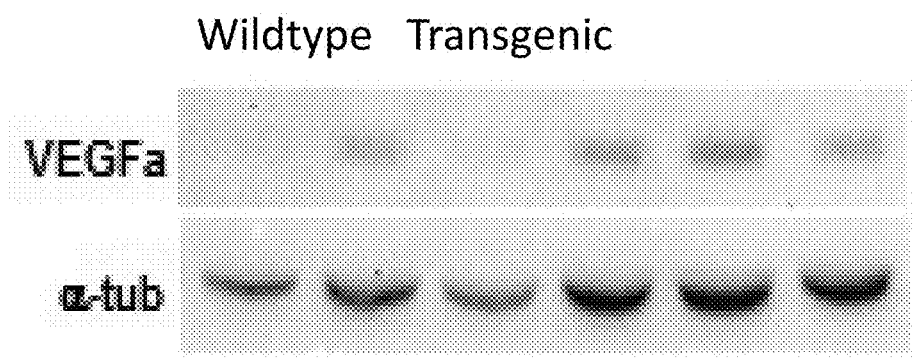
FIG. 7D shows induction of VEGFα in TA muscle, as measured by Western Blot, in VP16-PPARδ (TG) compared to wildtype mice.
Figure 7E:
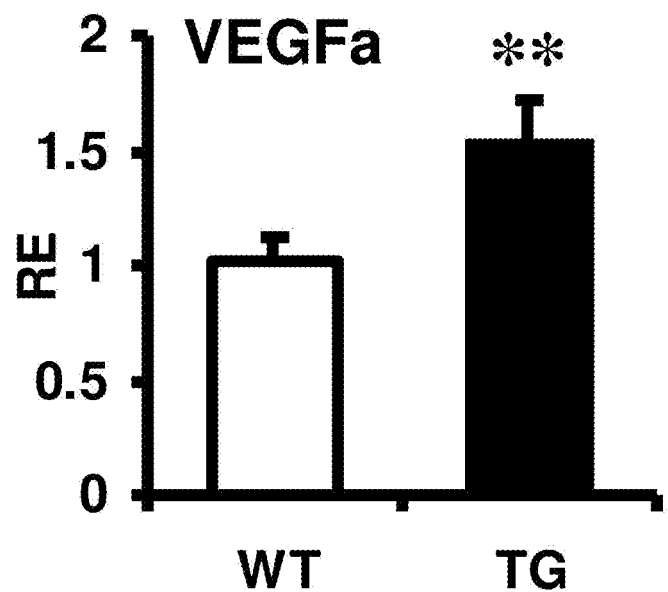
FIG. 7E shows quantification of VEGFα from a Western Blot.

Evans Blue staining of transverse sections of injured TA from WT and TG animals revealed decreased staining in TG muscle at 3 days post injury, consistent with PPARδ activation being beneficial for muscle repair (FIG. 7A). Supporting this notion, endogenous PPARδ is transiently increased in the TA muscle after freeze burn injury (FIG. 7B). Furthermore, the temporal expression profile of the inflammatory marker TNFα in wildtype (WT, solid line) and VP16-PPARδ (TG, dashed line) after injury was altered, suggesting a more rapid resolution of the inflammatory response in TG muscle (FIG. 7C). Increased vasculature is one of the hallmarks of oxidative myofibers, which facilitates introduction of immune cells and also supports increased number of satellite cells. TG animals show increased expression of VEGFα at both the mRNA and protein levels in TA muscle (FIG. 7D-E).

Example 9

Enhanced Notch Signaling in VP16-PPARδ Muscle

Figures 8A, 8B:
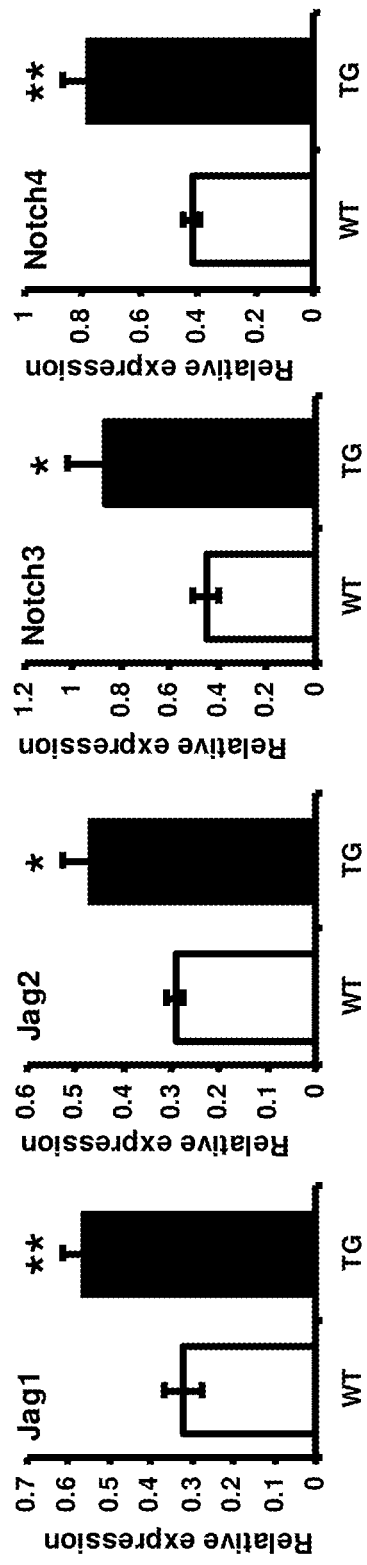
FIG. 8A provides the increase in expression, shown as fold change, of genes involved in the Notch pathway in tibialis anterior (TA) muscle from VP16-PPARδ (TG) compared to wildtype (WT) mice, as determined by microarray analysis (n=3).
FIG. 8B provides graphs of gene expression of Notch pathway components in tibialis anterior (TA) muscle from 2 months old VP16-PPARδ (TG) and wildtype (WT) mice, as determined by QPCR (n=5).
Figure 8C:
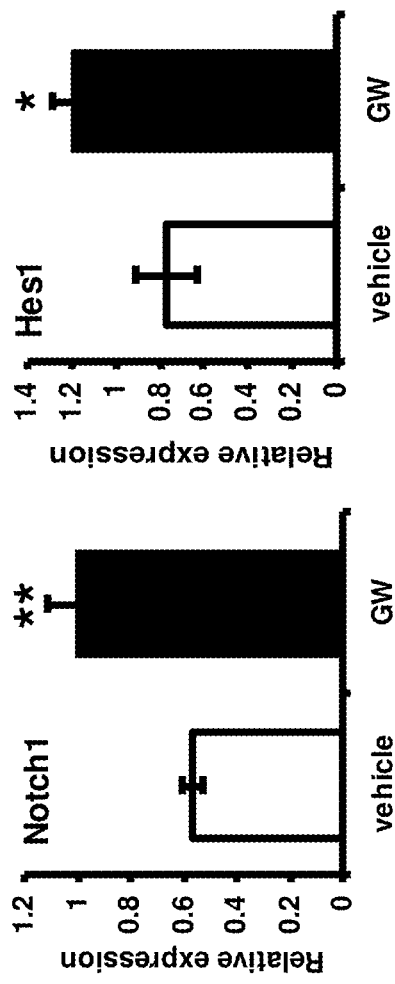
FIG. 8C provides graphs of gene expression of Notch pathway components in mice after 9 days of treatment with vehicle or the PPARδ ligand GW501516, as measured by QPCR (n=6).
Figure 8D:
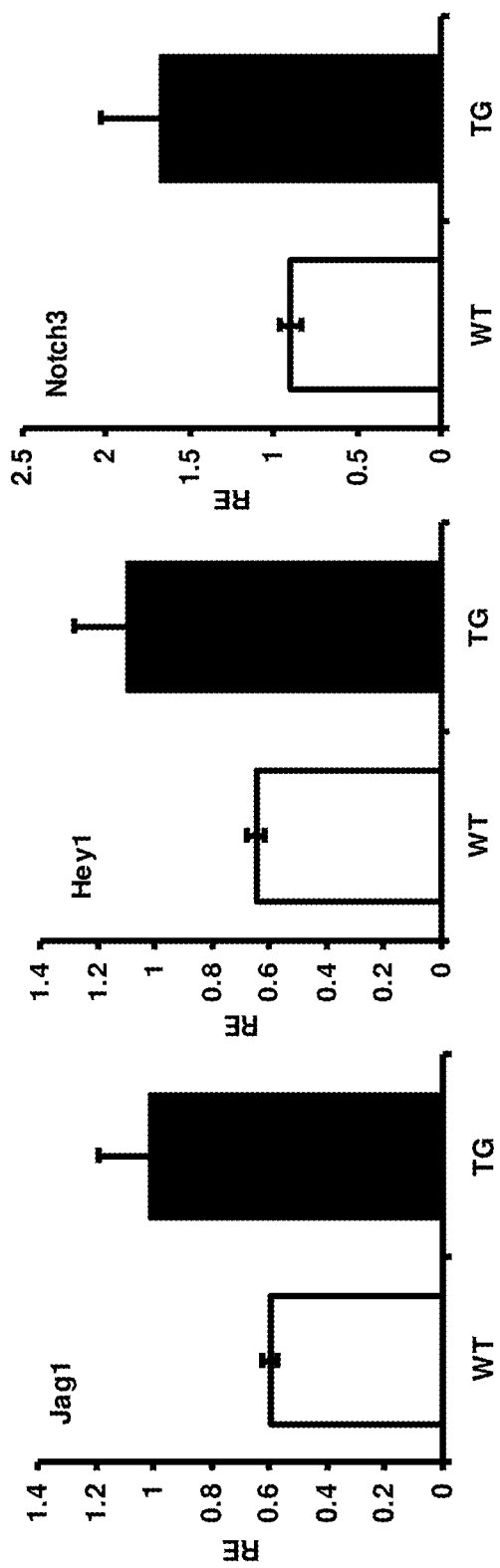
FIG. 8D provides graphs of gene expression of Notch pathway components in tibialis anterior (TA) muscle from 12 months old VP16-PPARδ (TG) and wildtype (WT) mice, as determined by QPCR (n=3).

Notch signaling is critical for skeletal muscle myogenesis and has important roles in maintaining the muscle stem cell pool and preventing premature muscle differentiation. To investigate whether constitutive PPARδ activation affects the Notch signaling pathway, we compared the expression of selected genes in the pathway in TA muscle from WT and VP16-PPARδ transgenic (TG) mice. Microarray analyses identified the upregulation of multiple genes in the Notch pathway in TG muscle (FIG. 8A). The PPARδ-induced increase in expression of Jag1, Jag2, Notch3 and Notch4 were confirmed in TA muscle from 2 month old mice by QPCR (FIG. 8B). Consistent with the notion that PPARδ activates the Notch pathway, increases in Notch1 and Hes1 expression were seen in mice after pharmacological activation via a 9 day treatment with the PPARδ ligand, GW501516 (FIG. 8C). Furthermore, examination of 12 month old TG mice revealed increased expression of Jag 1, Hey1, and Notch3, consistent with the sustained activation of the Notch pathway in VP16-PPARδ mice (FIG. 8D).

Example 10

Pharmacokinetics of PPARδ Ligands

Figure 9A:
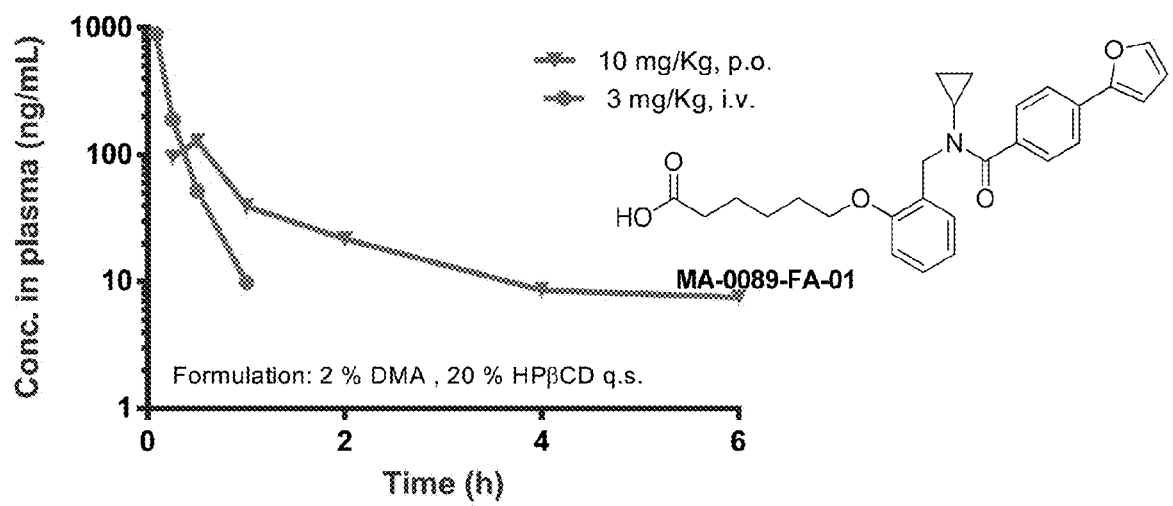
FIGS. 9A-9E are graphs showing pharmacokinetic data for several compounds at 3 mg/kg i.v. or 10 mg/kg p.o.
Figure 9B:
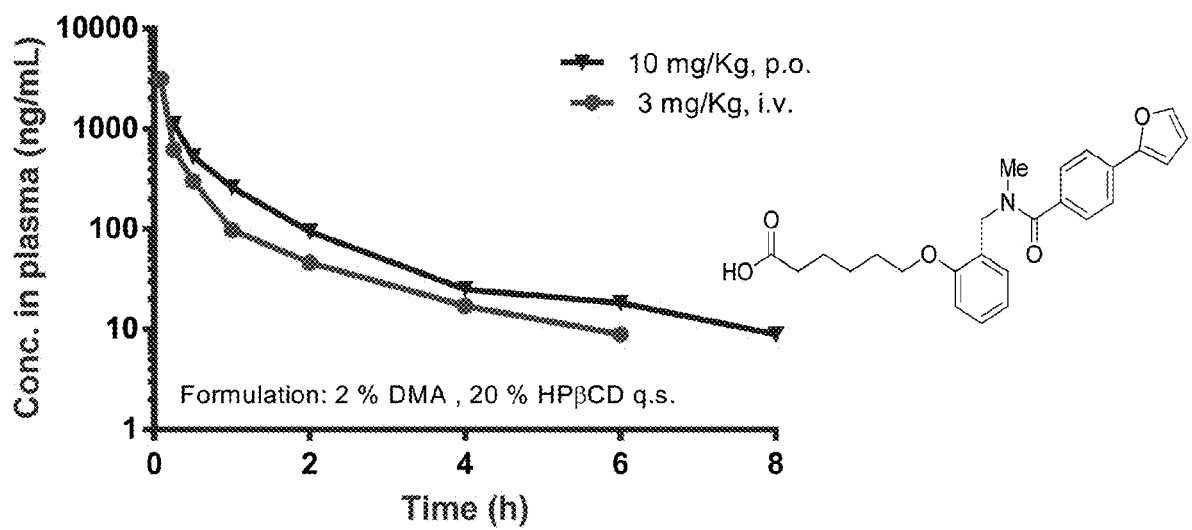
Figure 9C:
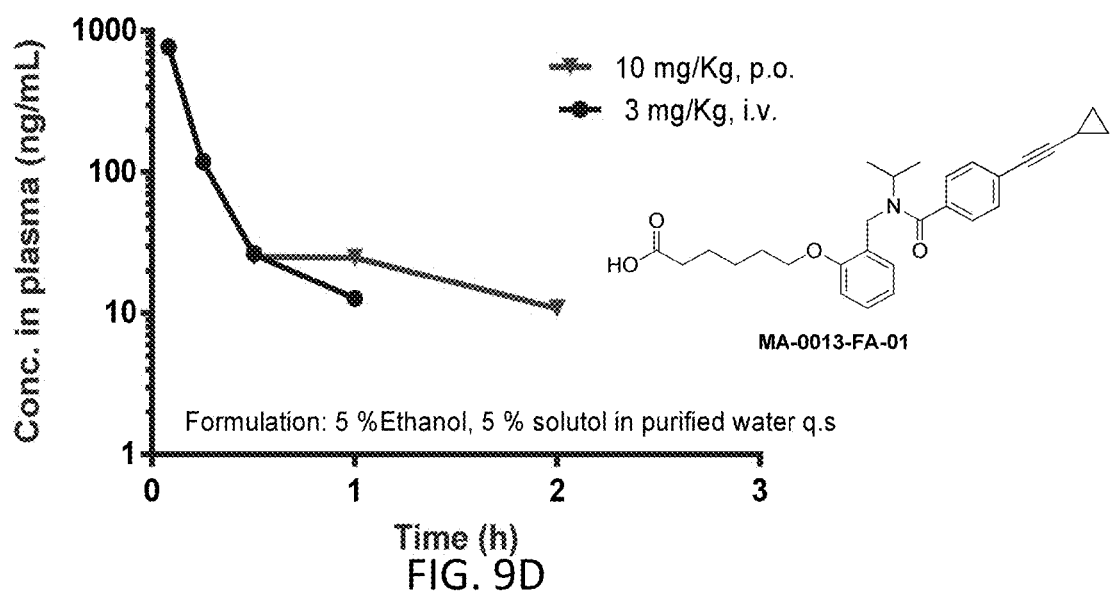
Figure 9D:
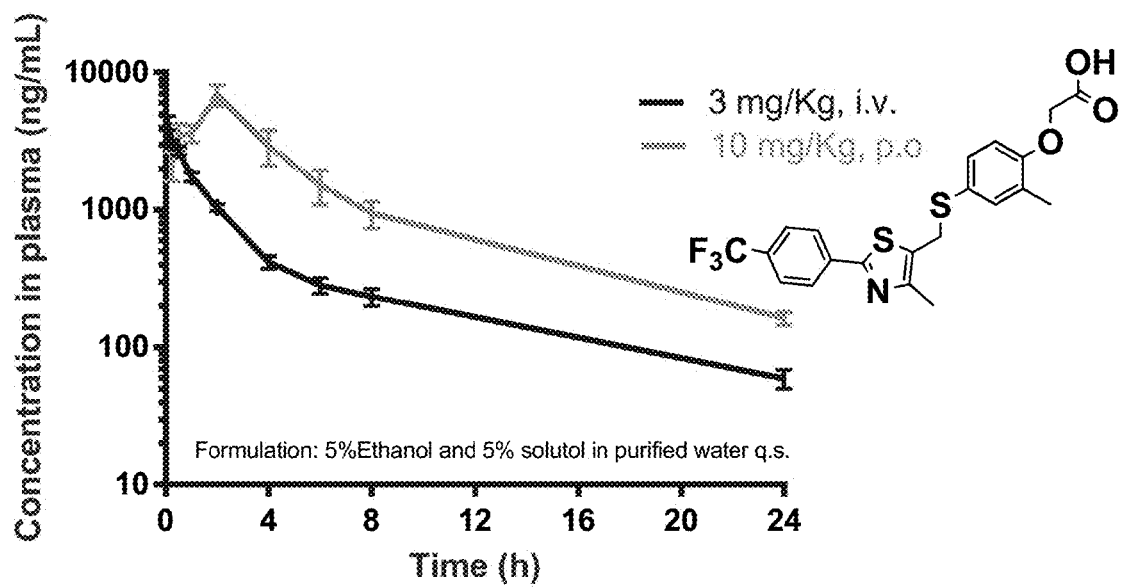
Figure 9E:
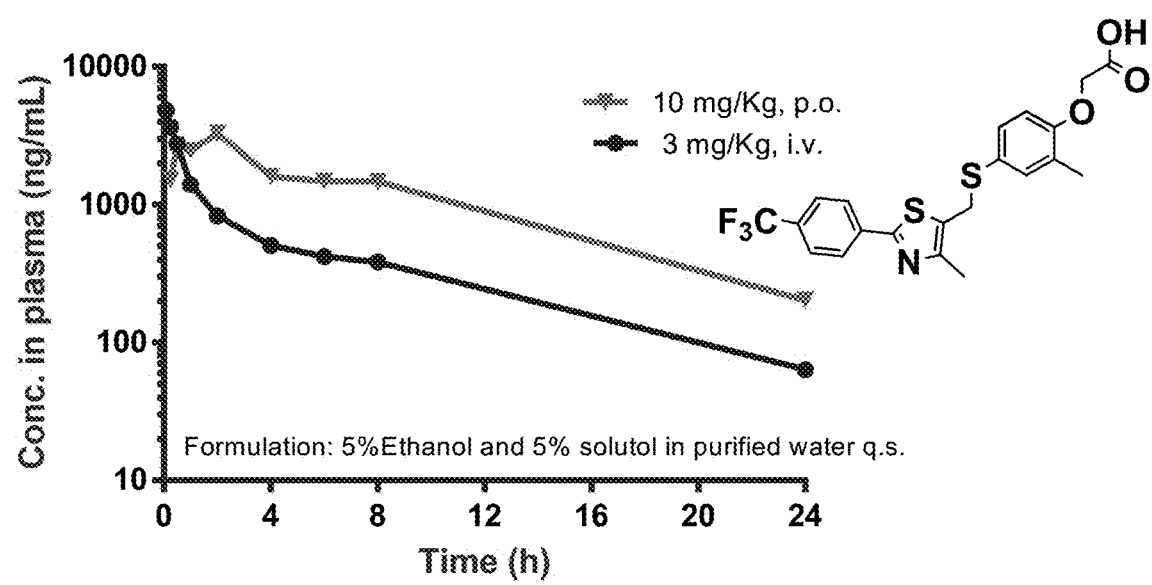

The oral bioavailability and serum half lives of PPARδ ligands were compared in mice. The pharmacokinetics of PPARδ ligands delivered orally (10 mg/kg p.o.) and intravenously (3 mg·kg i.v.) were determined by mass spectrometry. The circulating serum levels of novel PPARδ ligands (FIGS. 9A, B, C, E) at indicated times after drug delivery, as compared with GW501516 (FIG. 9D).

In summary, PPARδ activation expedites skeletal muscle regeneration following an acute thermal injury. VP16-PPARδ transgenic animals showed increased satellite cell proliferation at the early phase of the regenerative process, which subsequently translated into increased CSA and number of nascent regenerating fibers. Most interestingly, muscle specific over expression of PPARδ seems to increase the resident satellite cell pool. Increased satellite cell population on a muscle fiber seems to contribute to the accelerated resolution of the injury. These findings unveil a novel role for PPARδ in the maintenance of skeletal muscle; as a potential therapeutic target for accelerated restoration of muscle mass after an acute injury and other atrophic conditions.

Notably, PPARδ activation seems to promote rapid emergence of nascent fibers after the injury. There being no evidence of hyperplasia at 21 days after the injury when the regenerative process is essentially complete, it is concluded that the additional nascent fibers efficiently fuse with each other to restore mature fibers (Karpati G, Molnar M J in Skeletal muscle repair and regeneration, eds Schiaffino S, Partridge T (Springer, Dordrecht), (2008)). While IGF-1 and myostatin seem to rely on fiber hypertrophy to augment regenerative progress, PPARδ seems to employ a unique way to promote regeneration (Menetrey et al., *J Bone Joiny Surg Br* 82(1):131-7 (2000); Wagner et al., *Ann Neurol* 52(6): 832-6 (2002); Bogdanovich et al., *Nature* 420(6914): 418-21 (2002)). Underlying this difference may be the increased number of quiescent satellite cells. Higher number of progenitor cells leads to the increase in post injury proliferating cells and consequent increase in the number of nascent fibers. While various growth factors and chemokines, including IGF-1 and myostatin, have been shown to enhance proliferation of satellite cells and promote regeneration, it is unclear whether any of them positively regulate the number of quiescent satellite cells (Husmann I et al., *Cytokine Growth Factor Rev* 7(3):249-258 (1996); McCroskery et al., *J Cell Biol* 162(6):1135-1147 (2003); Musaro et al., *Nat Genet* 27:195-200 (2001); Amthor et al., *PNAS* 106(18):7479-84 (2009)). The findings shown herein indicate a novel role of PPARδ as a positive regulator of satellite cell pool. Interestingly, since rapid cell proliferation was not observed under normal conditions, PPARδ mediated satellite cell expansion is transient and tightly regulated, most likely elicited by external stimuli, such as signals for postnatal growth and injury. In an adult muscle, satellite cell number is finite, diminishing detrimentally in disease state and aging. It is of great therapeutic benefit if PPARδ activation can bestow infinite abundance of satellite cell population throughout the life of an organism.

While enhancement in regenerative capacity was observed in both genetic and pharmacological models, the inherent differences in the experimental parameters is acknowledged. Orally administered GW501516 was delivered systemically, presumably activating PPARδ in a variety of organs and cell types in the animal. However, in VP16-PPARδ animals, activation of the PPARδ receptors is limited to the mature muscle fibers. Additionally, genetic background of the animals may affect the efficiency of regeneration after an injury (Grounds and McGeachie, *Cell Tissue Res* 255(2):385-391 (1989); Roberts et al., *J Anat* 191:585-594 (1997)). Extramuscular effects of PPARδ agonist administration may require further investigation when considering clinical use of GW501516 to augment muscle injury treatment. Recently, pharmacological activation of PPARδ has been shown to improve sarcolemmal integrity in mdx mice (Miura et al., *Hum Mol Genet* 18(23):4640-4649 (2009)).

The results herein expand previous understandings of the role of PPARδ in muscle physiology. It is shown herein that PPARδ not only controls running endurance and metabolic parameters in the muscle, but also its regenerative program. PPARδ activation affects multiple facets of the regenerative program, exerting comprehensive but transient effects to expedite the progress. In view of these findings, PPARδ may be pharmacologically targeted to enhance the regenerative capacity of the muscle after injury and possibly other degenerative conditions where satellite cell function is compromised. For example, PPARδ activation can be used to treat other degenerative conditions such as aging induced satellite cell dysfunction and ensuing sarcopenia.

Example 11

PPARδ Activity Screen

Cell Culture and Transfection: CV-1 cells were grown in DMEM+10% charcoal stripped FCS. Cells were seeded into 384-well plates the day before transfection to give a confluency of 50-80% at transfection. A total of 0.8 g DNA containing 0.64 micrograms pCMX-PPARDelta LBD, 0.1 micrograms pCMX.beta.Gal, 0.08 micrograms pGLMH2004 reporter and 0.02 micrograms pCMX empty vector was transfected per well using FuGene transfection reagent according to the manufacturer's instructions (Roche). Cells were allowed to express protein for 48 h followed by addition of compound.

Plasmids: Human PPARδ was used to PCR amplify the PPARδ LBD. The amplified cDNA ligand binding domain (LBD) of PPARδ isoform was (PPARδ amino acid 128 to C-terminus) and fused to the DNA binding domain (DBD) of the yeast transcription factor GAL4 by subcloning fragments in frame into the vector pCMX GAL (Sadowski et al. (1992), Gene 118, 137) generating the plasmids pCMX-PPARDelta LBD. Ensuing fusions were verified by sequencing. The pCMXMH2004 luciferase reporter contains multiple copies of the GAL4 DNA response element under a minimal eukaryotic promoter (Hollenberg and Evans, (1988) Multiple and cooperative trans-activation domains of the human glucocorticoid receptor Cell 55, 899). pCMXβGal was generated.

Compounds: All compounds were dissolved in DMSO and diluted 1:1000 upon addition to the cells. Compounds were tested in quadruple in concentrations ranging from 0.001 to 100 µM. Cells were treated with compound for 24 h followed by luciferase assay. Each compound was tested in at least two separate experiments.

Luciferase assay: Medium including test compound was aspirated and washed with PBS. 50 µl PBS including 1 mM Mg++ and Ca++ were then added to each well. The luciferase assay was performed using the LucLite kit according to the manufacturer's instructions (Packard Instruments). Light emission was quantified by counting on a Perkin Elmer Envision reader. To measure β-galactosidase activity 25 µl supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods: The activity of a compound is calculated as fold induction compared to an untreated sample. For each compound the efficacy (maximal activity) is given as a relative activity compared to GW501516, a PPARδ agonist. The $EC_{50}$ is the concentration giving 50% of maximal observed activity. $EC_{50}$ values were calculated via non-linear regression using GraphPad PRISM (GraphPad Software, San Diego, Calif.).

Example 12

Synthetic Preparation of Compound Embodiments

Abbreviations rt room temperature
EDCI.HCl 1-ethyl-3-(3-dimethylaminopropyl)carbodiimide hydrochloride
HBTU O-benzotriazole-N,N,N',N'-tetramethyluronium hexafluorophosphate
HOBt 1-hydroxybenzotriazole

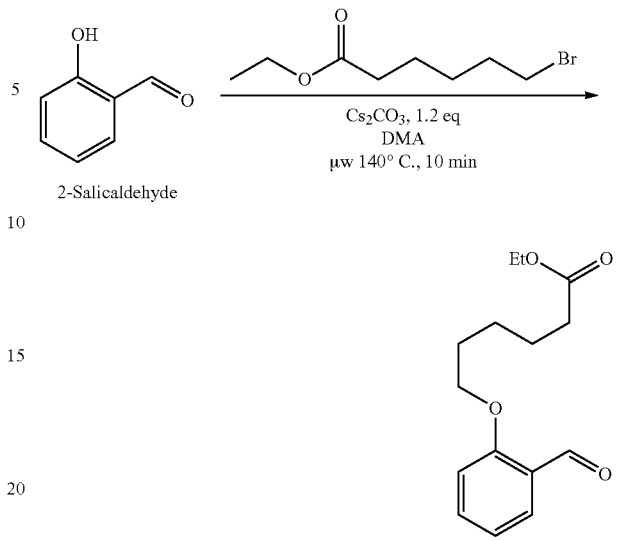

Reaction Step 1—Aryl Etherification

| Material | Source | Mol. Wt. | Density | Equiv | mmol | Amount |
|---|---|---|---|---|---|---|
| Ethyl-bromo-hexanoate | Sigma-Aldrich | 223.12 | 1.258 | 1.0 | 10.0 | 1.77 mL |
| Salicylaldehyde | Sigma-Aldrich | 122.12 | 1.166 | 1.0 | 10.0 | 1.05 mL |
| Cesium carbonate | Sigma-Aldrich | 325.82 | — | 1.2 | 12.0 | 3.91 g |
| DMA (solvent) | Sigma-Aldrich | — | — | — | — | 17.18 mL |
| Ethyl 6-(2-formyl-phenoxy)hexanoate | Product | 264.32 | — | (1.0) | (10.0) | (2.64 g) |

Reactions were carried out in a Biotage Initiator 60 Microwave Reactor, employing the 20 mL process-scale reactor vials. Thirteen (13) identical reactions at the 10 mmol scale were setup in parallel and processed in serial, as follows:

All three (3) reagents and reaction solvent were added to the MW vial in the following sequence; (1) ethyl-bromo-hexanoate (1.77 mL), (2) salicylaldehyde (1.05 mL), (3) cesium carbonate ($Cs_2CO_3$) (3.91 g) and (4) reaction solvent DMA (17.18 mL). Care was taken to dispense the N—N-dimethylacetamide (DMA) solvent in such a manner so as to wash down the vial walls of reactant or solid base. To each vial was added a magnetic stir bar and fitted with a crimp seal cap and adapter collar. The reactions were than process in the MW Reactor for 10 minutes (at temperature) at 140° C. with mixing. Following standard ramp up, fixed hold time at temperature and cool down, samples were kept sealed at ambient temperature until the entire lot was processed.

The reaction mixtures were combined and transferred to a 2 L separatory funnel. Vial contents were washed with ethyl acetate (EtOAc), and a total EtOAc layer of about 800 mL was added. To this was added 800 mL of 1.0 N NaOH solution, and the two layers were vigorously shaken and mixed and then separated. The NaOH aqueous layer was back-extracted 3×250 mL with EtOAc, and all the organic layers were combined (about 750 mL) and washed with 800 mL of 1.0 M citric acid solution. The citric acid layer was again back extracted with EtOAc (3×250 mL), and the organic layers were again combined (about 1.5 L) and washed (3×500 mL) with brine (saturated NaCl), dried over sodium sulfate ($Na_2SO_4$) and concentrated to dryness in vacuo. Silica gel TLC (3:1 Hexanes-EtOAc) $R_f$=0.34 (product), $R_f$=0.45, 0.25 (trace impurities). Theoretical yield=13× 2.64 g or 34.32 g (130 mmol). Isolation and Observed yield=33.30 g, (33.30 g/34.32 g×100)=97%. NMR ($^1H$, $^{13}C$, COSY) and LCMS (ESI+/−) conform to structure.

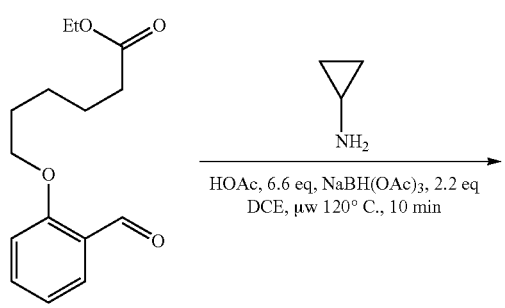

Reaction Step 2-Reductive Amination

| Material | Source | Mol. Wt. | Density | Equiv. | mmol | Amount |
|---|---|---|---|---|---|---|
| Ethyl 6-(2-formyl-phenoxy)hexanoate | Reaction1 Product | 264.32 | — | 1.0 | 10.0 | 2.6557 g |
| Cyclopropylamine | Sigma-Aldrich | 57.09 | 0.814 | 1.1 | 11.0 | 769 µL |
| Acetic acid, gl. | Sigma-Aldrich | 60.04 | 1.04 | 6.6 | 66.0 | 3.81 mL |
| NaBH(OAc)$_3$ | Sigma-Aldrich | 211.94 | — | 2.2 | 22.0 | 4.67 g |
| DCE (solvent) | Sigma-Aldrich | — | — | — | — | 10.0 mL |
| Ethyl 6-(2-((cyclo-propylamino)methyl)phenoxy)hexanoate | Product | 304.42 | — | (1.0) | (10.0) | (3.04 g) |

Reactions were carried out in a Biotage Initiator 60 Microwave Reactor, employing the 20 mL process-scale reactor vials. Twelve (12) identical reactions at the 10 mmol scale were setup in parallel and processed in serial, as follows:

All four (4) reagents and reaction solvent were added to the MW vial in the following sequence; (1) Ethyl 6-(2-formylphenoxy)hexanoate (about 2.66 g), (2) cyclopropylamine (769 µL), (3) acetic acid (AcOH) (3.81 mL) and 50% of the reaction solvent 1,2-dichloroethane (DCE), (4) sodium triacetoxyborohydride (4.67 g) and (5) the remaining 5 mL portion of DCE. Care was taken to dispense the DCE solvent in such a manner so as to wash down the vial walls of reactant or solid reducing agent. To each vial was added a magnetic stir bar and fitted with a crimp seal cap and adapter collar. The reactions were than process in the MW Reactor for 10 minutes (at temperature) at 120° C. with mixing. Following standard ramp up, fixed hold time at temperature and cool down, samples were kept sealed at ambient temperature until the entire lot was processed.

The reaction mixtures were combined and transferred to a 2 L separatory funnel. Vial contents were washed with ethyl acetate (EtOAc), and a total EtOAc layer of about 1 L was added. To this was added 800 mL of saturated NaHCO$_3$ solution, and the two layers were vigorously shaken and mixed and then separated, this extraction was performed an additional 2 times (3×800 mL in total). The organic EtOAc layer was then washed with brine (1×800 mL). The combined bicarb and brine aqueous layers were then back-extracted 1×200 mL with EtOAc, and all the organic layers were combined (about 1.4 L) and dried over sodium sulfate (Na$_2$SO$_4$) and concentrated to dryness in vacuo.

Observed crude yield=36.21 g of crude product. Three (3) spots by silica gel TLC (95:5 DCM-MeOH), R$_f$=0.17 (product), R$_f$=0.22 (tertiary amine by-product), R$_f$=0.08 (unk). Purified by silica gel chromatography, Biotage SP4, 65i column with samplet cartridge. A total of 3-columns were run, about 12 g of crude loaded into the samplet in MeOH and dried in vacuo. Elution program was as follows: 1 CV @ 99% DCM-1% MeOH, then 10 CV @ gradient 99→90% DCM and 1→10% MeOH, and 2 CV @ 90% DCM-10% MeOH. Fractions were combined, concentrated and dried under vacuum. Theoretical yield=12×3.04 g or 36.53 g (120 mmol). Isolation and Observed yield=29.28 g, (29.28 g/36.53 g×100)=80.2%. NMR $^{13}$C, COSY) and LCMS (ESI+/−) conform to structure.

Reaction Step 3-Aryl amide formation

| Material | Source | Mol. Wt. | Density | Equiv. | Mmol | Amount |
|---|---|---|---|---|---|---|
| Ethyl 6-(2-((cyclo-propylamino)methyl)phenoxy)hexanoate | Reaction2 Product | 304.42 | — | 1.0 | 4.42 | 1.35 g |
| 4-bromo-benzoyl chloride | Lancaster | 219.47 | — | 1.1 | 4.86 | 1.067 g |
| DIEA (Hunig's base) | Sigma-Aldrich | 129.25 | 0.742 | 2.2 | 9.72 | 933 μL |
| DCE (solvent) | Sigma-Aldrich | — | — | — | — | 15.0 mL |
| Ethyl 6-(2-((4-bromo-N-cyclopropylbenzamido)methyl)phenoxy) hexanoate | Product | 488.41 | — | (1.0) | (4.42) | (2.16 g) |

Reactions were carried out in a Biotage Initiator 60 Microwave Reactor, employing the 20 mL process-scale reactor vials. Twenty (20) identical reactions at the 4.42 mmol scale were setup in parallel and processed in serial, as follows:

All three (3) reagents and reaction solvent were added to the MW vial in the following sequence; (1) Ethyl 6-(2-((cyclo-propylamino)methyl) phenoxy)hexanoate (about 1.35 g), (2) 4-bromobenzoyl chloride (4-BrBzCl)(1.067 g), (3) DIEA (933 μL), (3.81 mL) and 50% of the reaction solvent 1,2-dichloroethane (DCE), and (4) the remaining 7.5 mL portion of DCE. Care was taken to dispense the DCE solvent in such a manner so as to wash down the vial walls of solid 4-BrBzCl. To each vial was added a magnetic stir bar and fitted with a crimp seal cap and adapter collar. The reactions were than process in the MW Reactor for 10 minutes (at temperature) at 75° C. with mixing. Following standard ramp up, fixed hold time at temperature and cool down, samples were kept sealed at ambient temperature until the entire lot was processed.

The reaction mixtures were combined and transferred to a 2 L separatory funnel. Vial contents were washed with ethyl acetate (EtOAc), and a total EtOAc layer of about 1 L was added. To this was added 800 mL of saturated $NaHCO_3$ solution, and the two layers were vigorously shaken and mixed and then separated, this extraction was performed one additional time (2×800 mL in total). The organic EtOAc layer was then washed with brine (2×800 mL). The combined bicarb and brine aqueous layers were then back-extracted 1×200 mL with EtOAc, and all the organic layers were combined (about 1.4 L) and dried over sodium sulfate ($Na_2SO_4$) and concentrated to dryness in vacuo.

Observed crude yield=45.3 g of crude product which was an oily semi-solid. Three (3) spots by silica gel TLC (2:1 Hexanes-EtOAc), $R_f$=0.42 (product), $R_f$=0.50, 0.17 (by-products). Purified by silica gel chromatography, Biotage SP4, 65i column with samplet cartridge. A total of 4-columns were run, about 11 g of crude loaded into the samplet in MeOH and dried in vacuo. Elution program was as follows: 1 CV @ 92% Hex-8% EtOAc, then 10 CV @ gradient 92→34% DCM and 8→66% EtOAc, and 2 CV @ 34% Hex-66% EtOAc. Fractions were combined, concentrated and dried under vacuum. Theoretical yield=20×2.16 g or 43.2 g (88.4 mmol). Isolation and Observed yield=23.02 g, (23.02 g/43.2 g×100)=53.3% (yields ranging from 50-80% have been obtained depending on the batch of 4-BrBzCl and the degree to which this reaction is carried out under anhydrous conditions). NMR ($^1H$, $^{13}C$, COSY) and LCMS (ESI+/−) conform to structure.

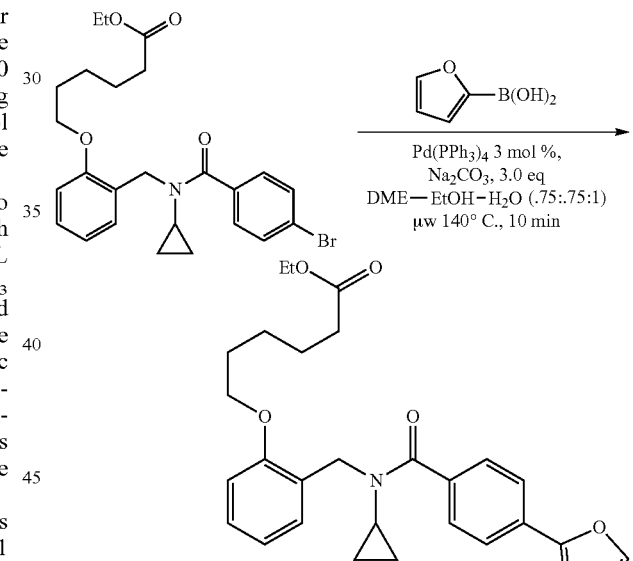

Reaction Step 4—Suzuki coupling

| Material | Source | Mol. Wt. | Density | Equiv. | mmol | Amount |
|---|---|---|---|---|---|---|
| Ethyl 6-(2-((4-bromo-N-cyclopropylbenzamido)methyl)phenoxy) hexanoate | Reaction3 Product | 488.41 | — | 1.0 | 4.09 | 2.00 g |
| Furan-2-boronic acid | Alfa Aesar | 111.89 | — | 1.25 | 5.11 | 572 mg |
| Pd(PPh₃)₄ | Sigma-Aldrich | 1155.58 | — | 0.03 | 0.123 | 141.8 mg |
| 2.0M Na₃CO₃ aq. | Sigma-Aldrich | — | — | 3.0 | 12.3 | 6.135 mL |
| DME (solvent) | Sigma-Aldrich | — | — | — | — | 4.6 mL |
| EtOH, 95% (co-solvent) | Sigma-Aldrich | — | — | — | — | 4.6 mL |
| Ethyl 6-(2-((N-cyclopropyl-4-(furan-2-yl)benzamido)methyl)phenoxy) hexanoate | Product | 475.61 | — | (1.0) | (4.09) | (1.95 g) |

Reactions were carried out in a Biotage Initiator 60 Microwave Reactor, employing the 20 mL process-scale reactor vials. Eleven (11) identical reactions at the 4.09 mmol scale were setup in parallel and processed in serial, as follows:

All four (4) reagents and reaction co-solvents were added to the MW vial in the following sequence; (1) Ethyl 6-(2-((4-bromo-N-cyclopropylbenzamido)methyl)phenoxy) hexanoate (about 2 g), (2) Furan-2-boronic acid (572 mg), (3) Pd(PPh$_3$)$_4$ (141.8 mg), (4) 2.0 M sodium carbonate solution (6.135 mL), followed by the co-solvents 95% EtOH and DME (1,2-dimethoxyethane). Care was taken to dispense the DME solvent in such a manner so as to wash down the vial walls of solid catalyst. To each vial was added a magnetic stir bar and fitted with a crimp seal cap and adapter collar. The reactions were than process in the MW Reactor for 10 minutes (at temperature) at 140° C. with mixing. Following standard ramp up, fixed hold time at temperature and cool down, samples were kept sealed at ambient temperature until the entire lot was processed. Note, depending on the age of the tetrakis Pd catalyst (fresh when red, darkens to brown with age) the microwave reaction temperature may need to be increased and the reaction time lengthened. It has been observed that a trace side product increases with reaction temp/time and corresponds to the saponified ester, which is the next and final synthetic step. This ester hydrolysis should be expected given the excess base in the presence of water and ethanol as co-solvents. Therefore the ethyl ester is not isolate.

The crude reaction mixtures were individually opens and poured out onto a 800 mL sintered filtration funnel (medium porosity) fitted with a 2 L side arm Erlenmeyer flask attached to house vacuum. The funnel was charged with a 2-3" bed of flash grade silica gel (Silicycle, 60 Å, 40-63 µm, F60 silica gel). A second layer (about 1-2") of diatomaceous earth filter aid (Celite 545) was packed on top of the silica gel, to produce a binary dry column vacuum chromatography (DCVC) system. A typical CV was about 100 mL, and each reaction mixture was eluted with 1CV of chromatography grade THF. The column was washed with 4CV of THF until no reaction product(s) were visible by TLC. The THF mixture was concentrated to produce about 25 g of viscous oil isolated, that was then taken directly onto the next step. Theoretical yield=11×1.95 g or 21.45 g (45.0 mmol). NMR ($^1$H, $^{13}$C, COSY) and LCMS (ESI+/−) conform to structure.

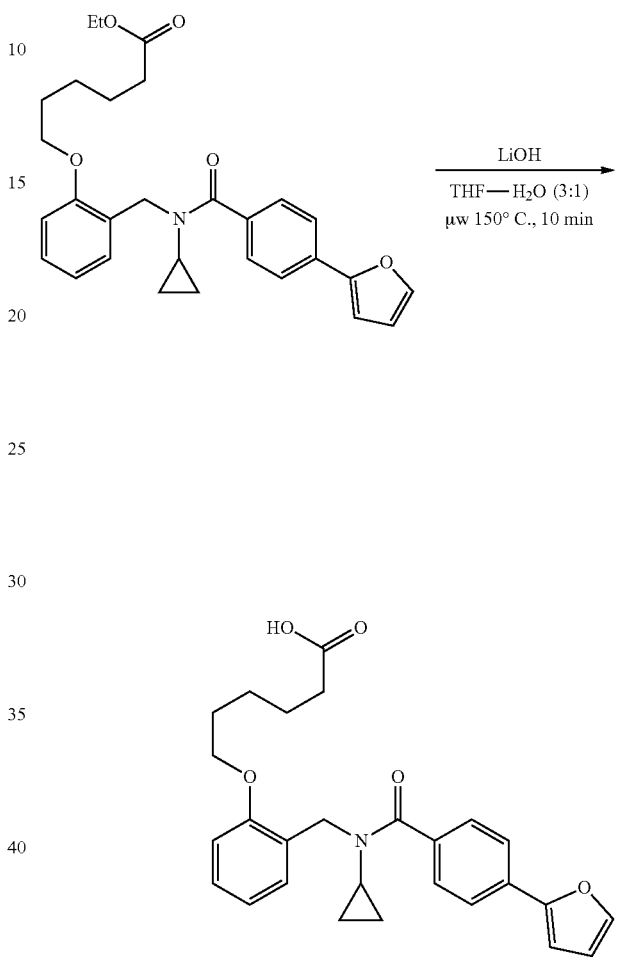

Reaction Step 5—Saponification

| Material | Source | Mol. Wt. | Density | Equiv. | Mmol | Amount |
|---|---|---|---|---|---|---|
| Ethyl 6-(2-((N-cyclopropyl-4-(furan-2-yl)benzamido)methyl)phenoxy) hexanoate | Reaction4 Product | 475.61 | — | 1.0 | 2.045 | 972.4 mg |
| LiOH•H$_2$O | Sigma-Aldrich | 41.96 | — | 4.89 | 10 | 420 mg |
| THF (solvent) | Sigma-Aldrich | — | — | — | — | 15 mL |
| H$_2$O (co-solvent) | Sigma-Aldrich | — | — | — | — | 5 mL |
| 6-(2-((N-cyclopropyl-4-(furan-2-yl)benzamido)methyl)phenoxy)hexanoic acid | Product | 447.52 | — | (1.0) | (2.045) | (915.2 mg) |

Reactions were carried out in a Biotage Initiator 60 Microwave Reactor, employing the 20 mL process-scale reactor vials. Twenty-two (22) identical reactions at the 2.045 mmol scale were setup in parallel and processed in serial, as follows:

All two (2) reagents and reaction co-solvents were added to the MW vial in the following sequence; (1) crude ethyl 6-(2-((N-cyclopropyl-4-(furan-2-yl)benzamido) methyl) phenoxy) hexanoate was dissolved to a volume of 33 mL, 15 mL per reaction vial, and (2) LiOH (hydrate) as a 2 M solution in water, 5 mL per reaction vial. To each vial was added a magnetic stir bar and fitted with a crimp seal cap and adapter collar. The reactions were than process in the MW Reactor for 10 minutes (at temperature) at 150° C. with mixing. Following standard ramp up, fixed hold time at temperature and cool down, samples were kept sealed at ambient temperature until the entire lot was processed.

The crude reaction mixtures were individually opens and poured out onto a 800 mL sintered filtration funnel (medium porosity) fitted with a 2 L side arm Erlenmeyer flask attached to house vacuum. The funnel was charged with a 2-3" bed of flash grade silica gel (Silicycle, 60 Å, 40-63 μm, F60 silica gel). A second layer (about 1-2") of diatomaceous earth filter aid (Celite 545) was packed on top of the silica gel, to produce a binary dry column vacuum chromatography system. The dry column was acid washed (acidified with either 1M citric acid or 1N HCl) with 2×1 L of acid solution. A typical CV was about 100 mL, and each reaction mixture was eluted with 1 CV of 1:1 DCM-THF. The column was washed with 4 CV of 1:1 DCM-THF until no reaction product(s) were visible by TLC. The DCM-THF mixture was concentrated to produce about 21 g of viscous oil. This crude product exhibited impurities with $R_f$ values close to that of the desired material. Flash chromatography used four (4) Biotage 65i columns on Biotage SP4, loading about 5 g crude. Theoretical yield=22×915.2 mg or 20.13 g (45.0 mmol). Isolation and Observed yield=11.54 g, (11.54 g/20.13 g×100)=57.3%. NMR $^{13}$C, COSY) and LCMS (ESI+/−) conform to structure.

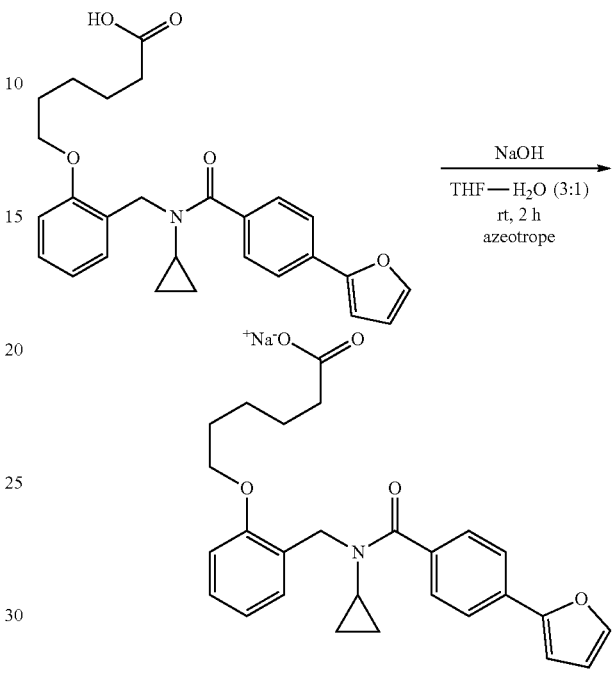

Reaction Step 6—Salt formation

| Material | Source | Mol. Wt. | Density | Equiv. | mmol | Amount |
|---|---|---|---|---|---|---|
| 6-(2-((N-cyclopropyl-4-(furan-2-yl)benzamido) methyl)phenoxy)hexanoic acid | Reaction5 Product | 447.52 | — | 1.0 | 25.78 | 11.54 g |
| NaOH | Sigma-Aldrich | 40.00 | — | 1.1 | 28.36 | 1.135 g |
| THF (solvent) | Sigma-Aldrich | — | — | — | — | 75 mL |
| H$_2$O (co-solvent) | Sigma-Aldrich | — | — | — | — | 25 mL |
| Sodium 6-(2-((N-cyclopropyl-4-(furan-2-yl)benzamido) methyl)phenoxy) hexanoate | Product | 469.50 | — | (1.0) | (25.78) | (12.10 g) |

6-(2-((N-cyclopropyl-4-(furan-2-yl)benzamido) methyl) phenoxy)hexanoic acid was dissolved in 75 mL of THF and cooled to 0° C. NaOH (1.135 g) was dissolved in 25 mL water, and added dropwise to the stirring THF solution. After the addition was complete the reaction color was very dark (grayish-black), the ice bath was removed and the reaction as allowed to warm to room temperature and continue to stir an additional 2 hours. The crude reaction mixture was then concentrated and the water was azeotroped away by charging the flask with about 100 mL portions of MeCN (20 times). The solution salt still was not crashing out or precipitating, so the crude salt was places on high vacuum overnight. A white crystalline solid appeared, and was triturated with fresh portions of MeCN, filtered and dried overnight once again to yield a 10.0 g portion (excluding additional material for secondary crystallization from the mother liquor). Theoretical yield=12.1 g (25.78 mmol). Observed yield=10.0 g, (10.0 g/12.1 g×100)=82.6%. NMR ($^1$H, $^{13}$C, COSY) and LCMS (ESI+/−) conform to structure.

TABLE 1

| ID | Formula | MW Calc. | MW Obser. | EC$_{50}$ nM | Structure |
|---|---|---|---|---|---|
| 1 | C$_{29}$H$_{33}$NO$_4$ | 459.58 | 458.2 [M − H]− | 42 | 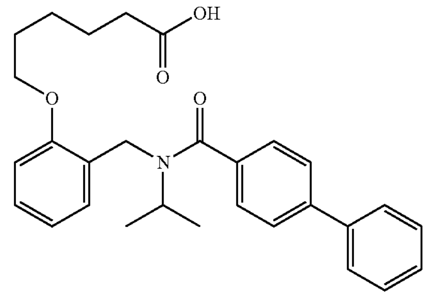 [SMILES: CC(C)N(Cc1ccccc1OCCCCCC(=O)O)C(=O)c1ccc(-c2ccccc2)cc1] |
| 2 | C$_{30}$H$_{39}$BrN$_2$O$_5$ | 587.55 | 587.2/ 589.2 [M + H]+ | | 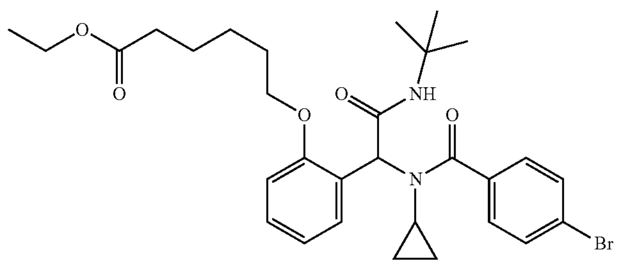 [SMILES: CCOC(=O)CCCCCOc1ccccc1C(C(=O)NC(C)(C)C)N(C(=O)c1ccc(Br)cc1)C1CC1] |
| 3 | C$_{36}$H$_{44}$N$_2$O$_5$ | 584.74 | 585.3 [M + H]+ | | 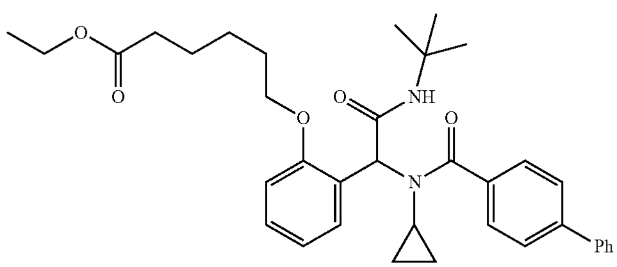 [SMILES: CCOC(=O)CCCCCOc1ccccc1C(C(=O)NC(C)(C)C)N(C(=O)c1ccc(-c2ccccc2)cc1)C1CC1] |
| 4 | C$_{32}$H$_{36}$N$_2$O$_5$ | 528.64 | 529.3 [M + H]+ | | 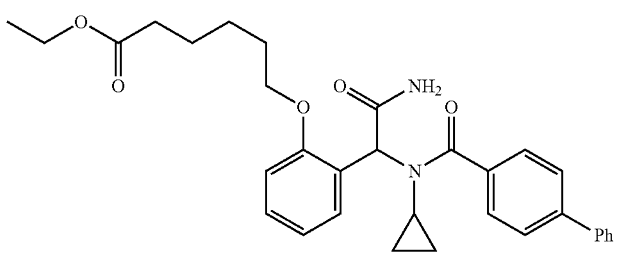 [SMILES: CCOC(=O)CCCCCOc1ccccc1C(C(N)=O)N(C(=O)c1ccc(-c2ccccc2)cc1)C1CC1] |
| 5 | C$_{34}$H$_{40}$N$_2$O$_5$ | 556.69 | 555.3 [M − H]− | | 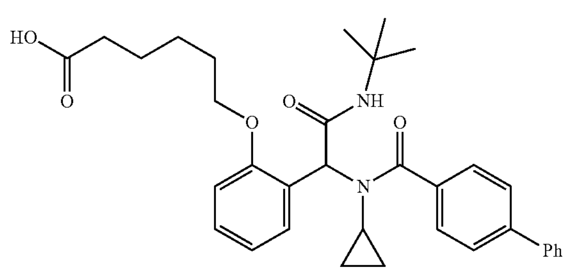 [SMILES: CC(C)(C)NC(=O)C(c1ccccc1OCCCCCC(=O)O)N(C(=O)c1ccc(-c2ccccc2)cc1)C1CC1] |

TABLE 1-continued
| ID | Formula | MW Calc. | MW Obser. | EC₅₀ nM | Structure |
|----|---------|----------|-----------|---------|-----------|
| 6 | $C_{30}H_{32}N_2O_5$ | 500.59 | 499.2 [M − H]− | | 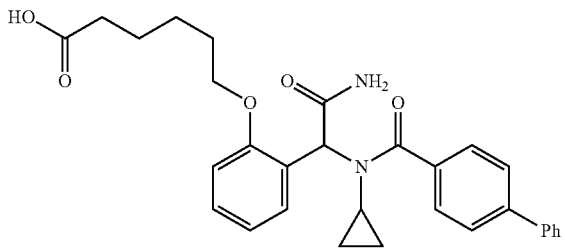 [SMILES: NC(=O)C(c1ccccc1OCCCCCC(=O)O)N(C(=O)c1ccc(-c2ccccc2)cc1)C1CC1] |
| 7 | $C_{30}H_{33}N_3O_5$ | 515.6 | 514.2 [M − H]− | | 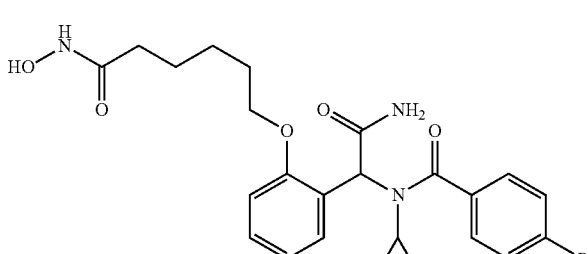 |
| 8 | $C_{29}H_{31}NO_4$ | 457.56 | 456.2 [M − H]− | 115 | 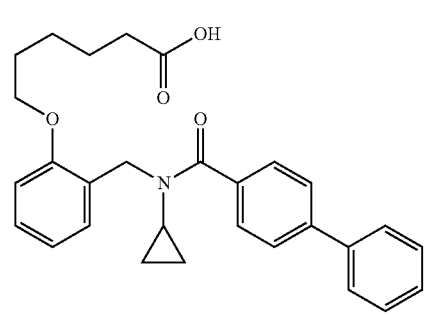 [SMILES: O=C(O)CCCCCOc1ccccc1CN(C(=O)c1ccc(-c2ccccc2)cc1)C1CC1] |
| 9 | $C_{28}H_{30}N_2O_4$ | 458.55 | 457.2 [M − H]− | 1960 | 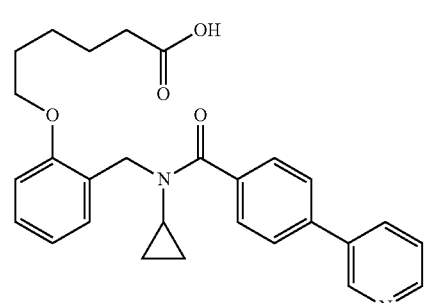 |
| 10 | $C_{28}H_{30}N_2O_4$ | 458.55 | 457.2 [M − H]− | | 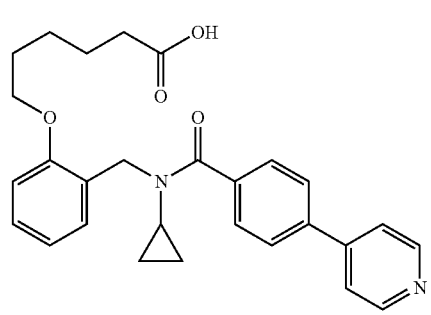 [SMILES: O=C(O)CCCCCOc1ccccc1CN(C(=O)c1ccc(-c2ccncc2)cc1)C1CC1] |

TABLE 1-continued
| ID | Formula | MW Calc. | MW Obser. | EC$_{50}$ nM | Structure |
|---|---|---|---|---|---|
| 11 | C$_{26}$H$_{29}$N$_3$O$_4$ | 447.53 | 446.2 [M − H]− | 2120 | 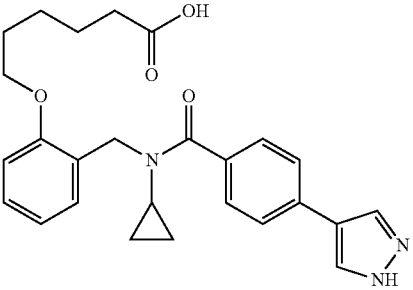 [SMILES: O=C(O)CCCCCOc1ccccc1CN(C(=O)c1ccc(-c2cn[nH]c2)cc1)C1CC1] |
| 12 | C$_{27}$H$_{29}$NO$_5$ | 447.52 | 446.2 [M − H]− | 19.6 | 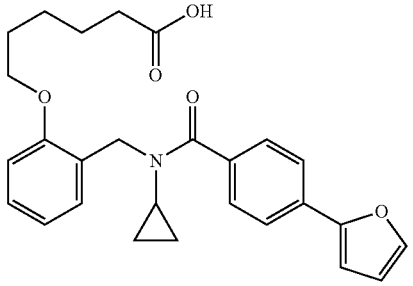 [SMILES: O=C(O)CCCCCOc1ccccc1CN(C(=O)c1ccc(-c2ccco2)cc1)C1CC1] |
| 13 | C$_{27}$H$_{29}$NO$_5$ | 447.52 | 446.2 [M − H]− | 215 | 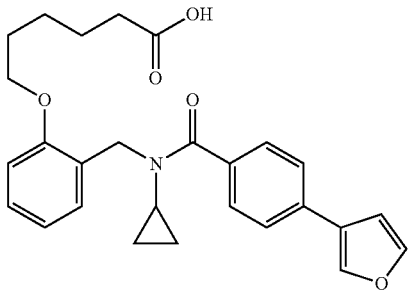 [SMILES: O=C(O)CCCCCOc1ccccc1CN(C(=O)c1ccc(-c2ccoc2)cc1)C1CC1] |
| 14 | C$_{27}$H$_{29}$NO$_4$S | 463.59 | 462.2 [M − H]− | 1800 | 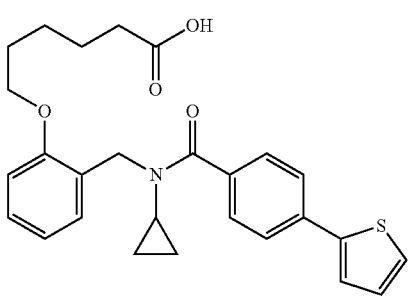 [SMILES: O=C(O)CCCCCOc1ccccc1CN(C(=O)c1ccc(-c2cccs2)cc1)C1CC1] |
| 15 | C$_{27}$H$_{29}$NO$_4$S | 463.59 | 462.2 [M − H]− | 58.4 | 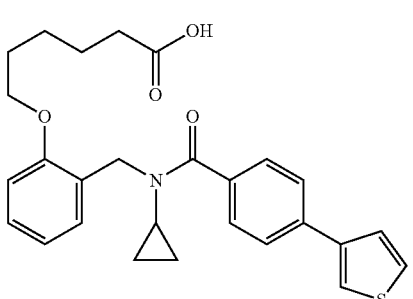 |

TABLE 1-continued

| ID | Formula | MW Calc. | MW Obser. | EC$_{50}$ nM | Structure |
|---|---|---|---|---|---|
| 16 | C$_{33}$H$_{33}$NO$_4$ | 507.62 | 506.2 [M − H]− | | 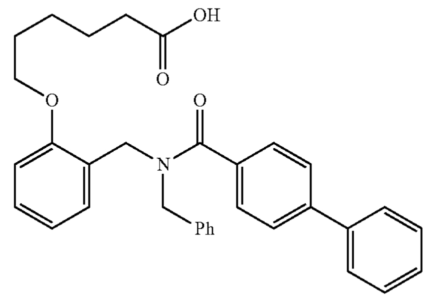 [SMILES: O=C(O)CCCCCOc1ccccc1CN(Cc1ccccc1)C(=O)c1ccc(-c2ccccc2)cc1] |
| 17 | C$_{32}$H$_{32}$N$_2$O$_4$ | 508.61 | 507.2 [M − H]− | | 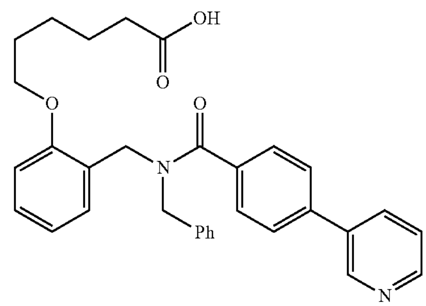 [SMILES: O=C(O)CCCCCOc1ccccc1CN(Cc1ccccc1)C(=O)c1ccc(-c2cccnc2)cc1] |
| 18 | C$_{32}$H$_{32}$N$_2$O$_4$ | 508.61 | 507.2 [M − H]− | | 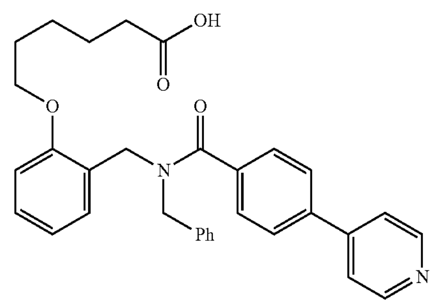 [SMILES: O=C(O)CCCCCOc1ccccc1CN(Cc1ccccc1)C(=O)c1ccc(-c2ccncc2)cc1] |
| 19 | C$_{30}$H$_{31}$N$_3$O$_4$ | 497.58 | 496.2 [M − H]− | | 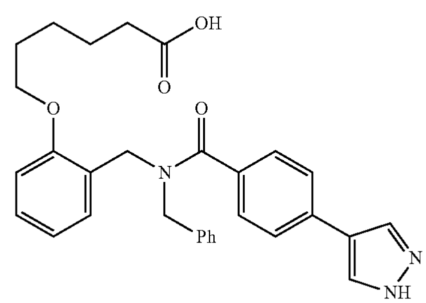 [SMILES: O=C(O)CCCCCOc1ccccc1CN(Cc1ccccc1)C(=O)c1ccc(-c2cn[nH]c2)cc1] |
| 20 | C$_{31}$H$_{31}$NO$_5$ | 497.58 | 496.2 [M − H]− | | 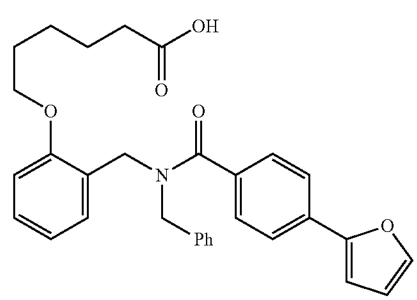 [SMILES: O=C(O)CCCCCOc1ccccc1CN(Cc1ccccc1)C(=O)c1ccc(-c2ccco2)cc1] |

TABLE 1-continued
| ID | Formula | MW Calc. | MW Obser. | EC$_{50}$ nM | Structure |
|---|---|---|---|---|---|
| 21 | C$_{31}$H$_{31}$NO$_5$ | 497.58 | 496.2 [M − H]− | | 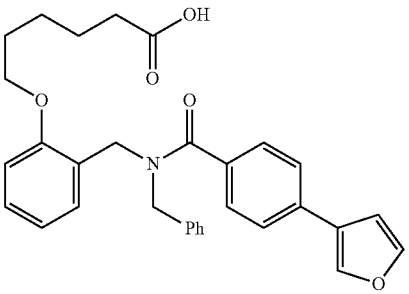 [SMILES: O=C(O)CCCCCOc1ccccc1CN(Cc1ccccc1)C(=O)c1ccc(-c2ccoc2)cc1] |
| 22 | C$_{31}$H$_{31}$NO$_4$S | 513.65 | 512.2 [M − H]− | | 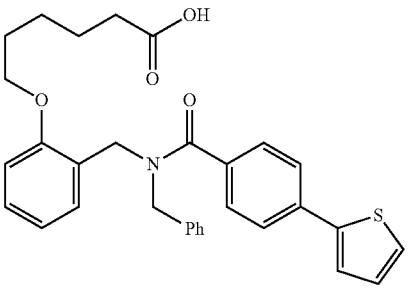 |
| 23 | C$_{31}$H$_{31}$NO$_4$S | 513.65 | 512.2 [M − H]− | | 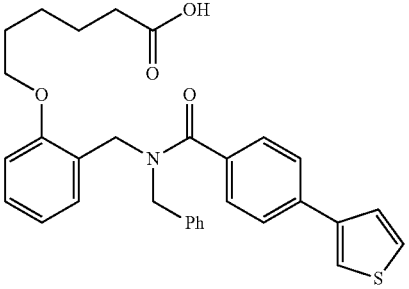 |
| 24 | C$_{33}$H$_{34}$N$_2$O$_4$ | 522.63 | 521.2 [M − H]− | | 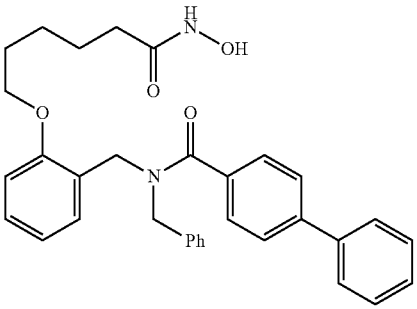 [SMILES: O=C(CCCCCOc1ccccc1CN(Cc1ccccc1)C(=O)c1ccc(-c2ccccc2)cc1)NO] |
| 25 | C$_{32}$H$_{33}$N$_3$O$_4$ | 523.62 | 522.2 [M − H]− | | 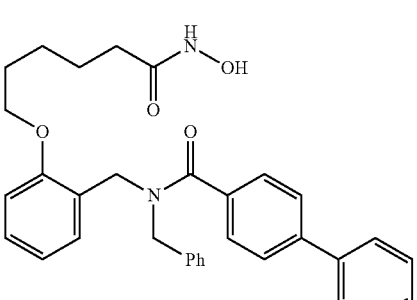 |

TABLE 1-continued
| ID | Formula | MW Calc. | MW Obser. | EC$_{50}$ nM | Structure |
|----|---------|----------|-----------|--------------|-----------|
| 26 | C$_{32}$H$_{33}$N$_3$O$_4$ | 523.62 | 522.2 [M − H]− | | 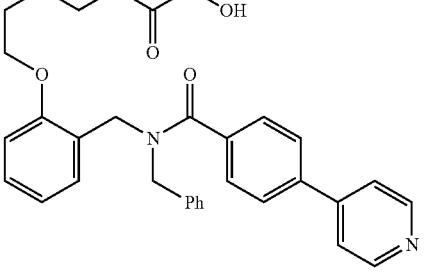 |
| 27 | C$_{30}$H$_{32}$N$_4$O$_4$ | 512.6 | 511.2 [M − H]− | | 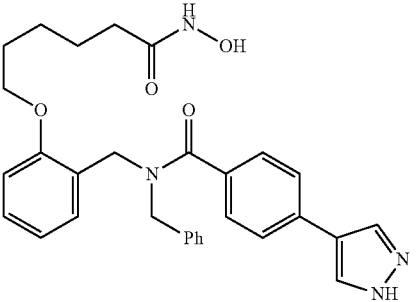 [SMILES: O=C(CCCCCOc1ccccc1CN(Cc1ccccc1)C(=O)c1ccc(-c2cn[nH]c2)cc1)NO] |
| 28 | C$_{31}$H$_{32}$N$_2$O$_5$ | 512.6 | 511.2 [M − H]− | | 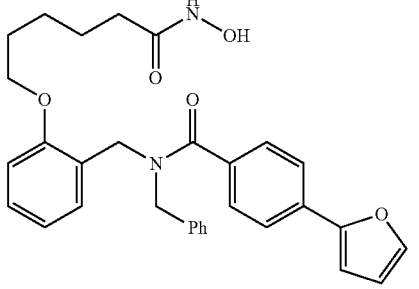 |
| 29 | C$_{31}$H$_{32}$N$_2$O$_5$ | 512.6 | 511.2 [M − H]− | | 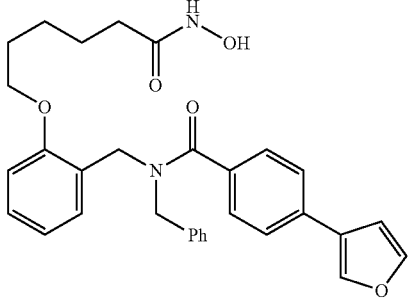 [SMILES: O=C(CCCCCOc1ccccc1CN(Cc1ccccc1)C(=O)c1ccc(-c2ccoc2)cc1)NO] |
| 30 | C$_{31}$H$_{32}$N$_2$O$_4$S | 528.66 | 527.2 [M − H]− | | 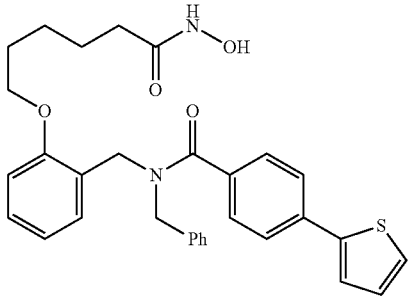 [SMILES: O=C(CCCCCOc1ccccc1CN(Cc1ccccc1)C(=O)c1ccc(-c2cccs2)cc1)NO] |

TABLE 1-continued
| ID | Formula | MW Calc. | MW Obser. | EC₅₀ nM | Structure |
|---|---|---|---|---|---|
| 31 | $C_{31}H_{32}N_2O_4S$ | 528.66 | 527.2 [M − H]− | | 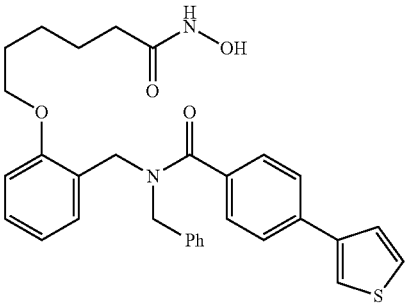 |
| 32 | $C_{24}H_{30}BrNO_4$ | 476.4 | 476.1/ 474.1 [M − H]− | 611 | 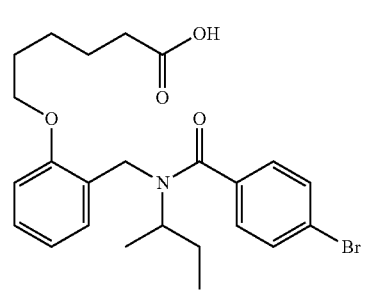 [SMILES: CCC(C)N(Cc1ccccc1OCCCCCC(=O)O)C(=O)c1ccc(Br)cc1] |
| 33 | $C_{30}H_{35}NO_4$ | 473.6 | 472.3 [M − H]− | 954 | 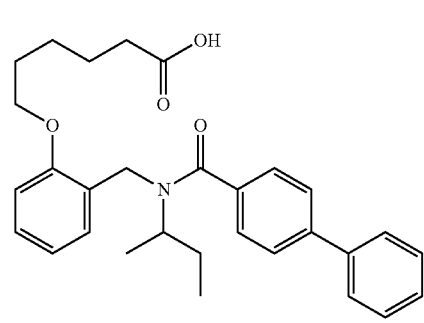 [SMILES: CCC(C)N(Cc1ccccc1OCCCCCC(=O)O)C(=O)c1ccc(-c2ccccc2)cc1] |
| 34 | $C_{29}H_{34}N_2O_4$ | 474.59 | 473.2 [M − H]− | 5140 | 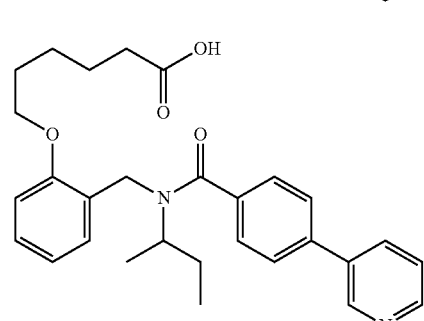 |
| 35 | $C_{29}H_{34}N_2O_4$ | 474.59 | 473.2 [M − H]− | 6400 | 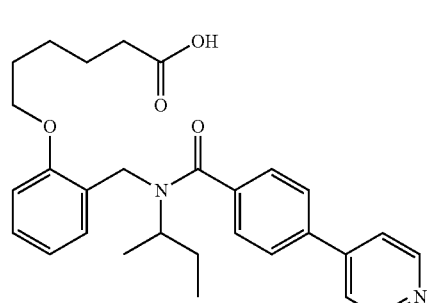 |

TABLE 1-continued

| ID | Formula | MW Calc. | MW Obser. | EC$_{50}$ nM | Structure |
|----|---------|----------|-----------|--------------|-----------|
| 36 | C$_{27}$H$_{33}$N$_3$O$_4$ | 463.57 | 462.2 [M − H]− | 15400 | 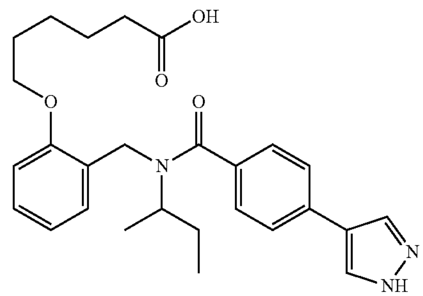 [SMILES: CCC(C)N(Cc1ccccc1OCCCCCC(=O)O)C(=O)c1ccc(-c2cn[nH]c2)cc1] |
| 37 | C$_{28}$H$_{33}$NO$_5$ | 463.57 | 462.2 [M − H]− | 41 | 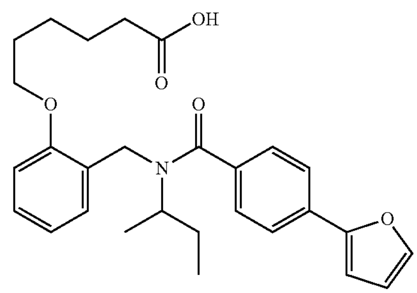 |
| 38 | C$_{28}$H$_{33}$NO$_5$ | 463.57 | 462.2 [M − H]− | 290 | 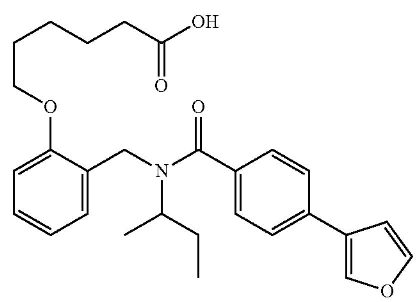 [SMILES: CCC(C)N(Cc1ccccc1OCCCCCC(=O)O)C(=O)c1ccc(-c2ccoc2)cc1] |
| 39 | C$_{28}$H$_{33}$NO$_4$S | 479.63 | 478.2 [M − H]− | 2100 | 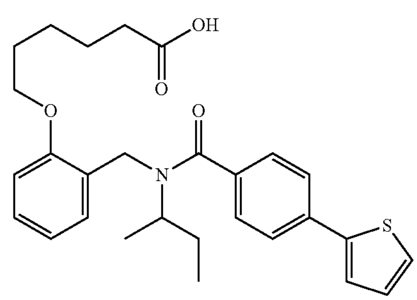 [SMILES: CCC(C)N(Cc1ccccc1OCCCCCC(=O)O)C(=O)c1ccc(-c2cccs2)cc1] |
| 40 | C$_{28}$H$_{33}$NO$_4$S | 479.63 | 478.2 [M − H]− | 179 | 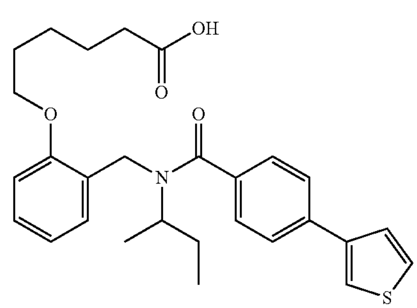 [SMILES: CCC(C)N(Cc1ccccc1OCCCCCC(=O)O)C(=O)c1ccc(-c2ccsc2)cc1] |

TABLE 1-continued
| ID | Formula | MW Calc. | MW Obser. | EC$_{50}$ nM | Structure |
|----|---------|----------|-----------|--------------|-----------|
| 41 | C$_{33}$H$_{40}$N$_2$O$_5$ | 544.68 | 543.3 [M − H]− | | 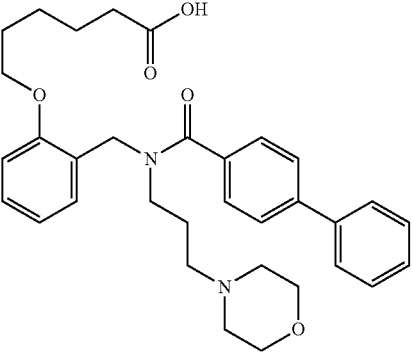 [SMILES: O=C(O)CCCCCOc1ccccc1CN(CCCN1CCOCC1)C(=O)c1ccc(-c2ccccc2)cc1] |
| 42 | C$_{32}$H$_{39}$N$_3$O$_5$ | 545.67 | 544.3 [M − H]− | | 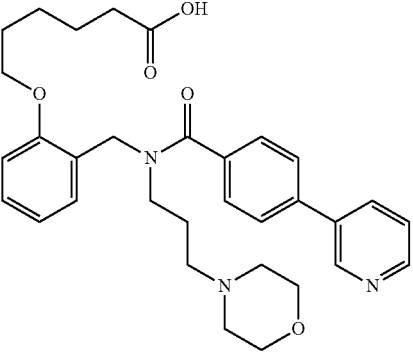 [SMILES: O=C(O)CCCCCOc1ccccc1CN(CCCN1CCOCC1)C(=O)c1ccc(-c2cccnc2)cc1] |
| 43 | C$_{32}$H$_{39}$N$_3$O$_5$ | 545.67 | 544.3 [M − H]− | | 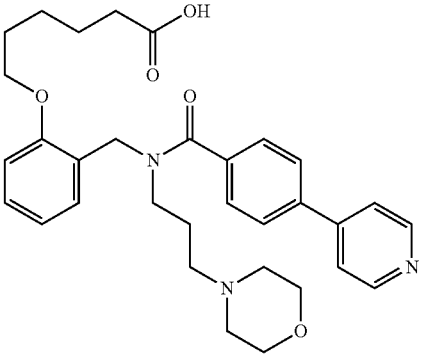 [SMILES: O=C(O)CCCCCOc1ccccc1CN(CCCN1CCOCC1)C(=O)c1ccc(-c2ccncc2)cc1] |
| 44 | C$_{30}$H$_{38}$N$_4$O$_5$ | 534.65 | 533.3 [M − H]− | | 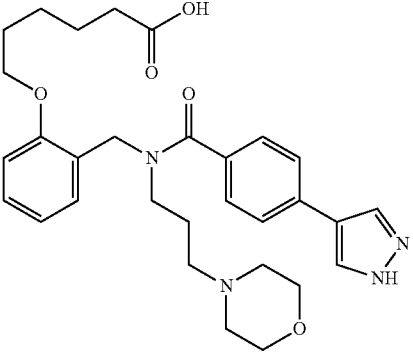 [SMILES: O=C(O)CCCCCOc1ccccc1CN(CCCN1CCOCC1)C(=O)c1ccc(-c2cn[nH]c2)cc1] |

TABLE 1-continued

| ID | Formula | MW Calc. | MW Obser. | EC$_{50}$ nM | Structure |
|---|---|---|---|---|---|
| 45 | C$_{31}$H$_{38}$N$_2$O$_6$ | 534.64 | 533.3 [M − H]− | | 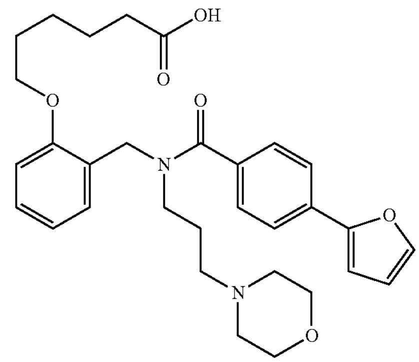 [SMILES: O=C(O)CCCCCOc1ccccc1CN(CCCN1CCOCC1)C(=O)c1ccc(-c2ccco2)cc1] |
| 46 | C$_{31}$H$_{38}$N$_2$O$_6$ | 534.64 | 533.3 [M − H]− | | 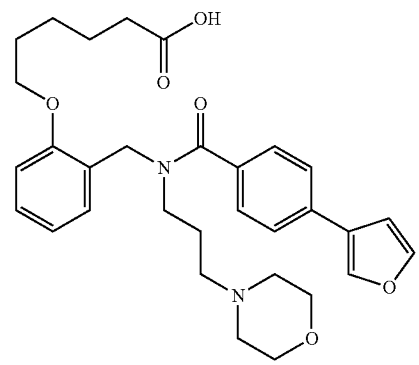 [SMILES: O=C(O)CCCCCOc1ccccc1CN(CCCN1CCOCC1)C(=O)c1ccc(-c2ccoc2)cc1] |
| 47 | C$_{31}$H$_{38}$N$_2$O$_5$S | 550.71 | 549.2 [M − H]− | | 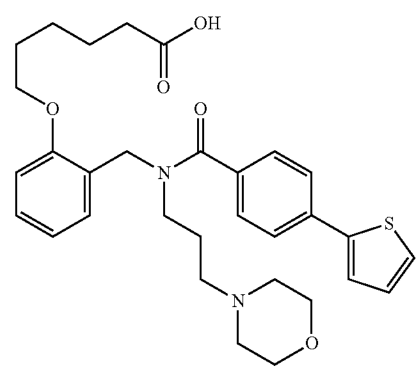 |
| 48 | C$_{31}$H$_{38}$N$_2$O$_5$S | 550.71 | 549.2 [M − H]− | | 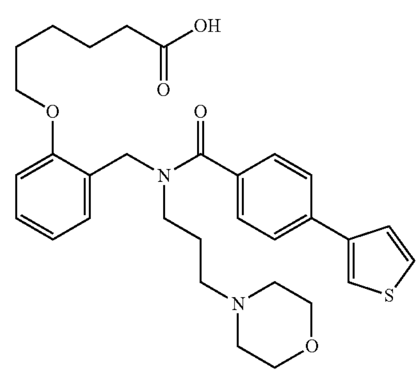 [SMILES: O=C(O)CCCCCOc1ccccc1CN(CCCN1CCOCC1)C(=O)c1ccc(-c2ccsc2)cc1] |

TABLE 1-continued

| ID | Formula | MW Calc. | MW Obser. | EC$_{50}$ nM | Structure |
|---|---|---|---|---|---|
| 49 | C$_{33}$H$_{34}$N$_2$O$_4$ | 522.63 | 521.2 [M − H]− | | 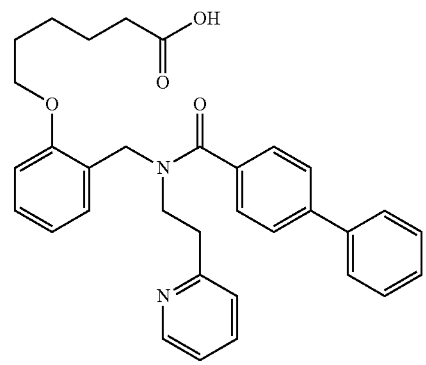 [SMILES: O=C(O)CCCCCOc1ccccc1CN(CCc1ccccn1)C(=O)c1ccc(-c2ccccc2)cc1] |
| 50 | C$_{32}$H$_{33}$N$_3$O$_4$ | 523.62 | 522.2 [M − H]− | | 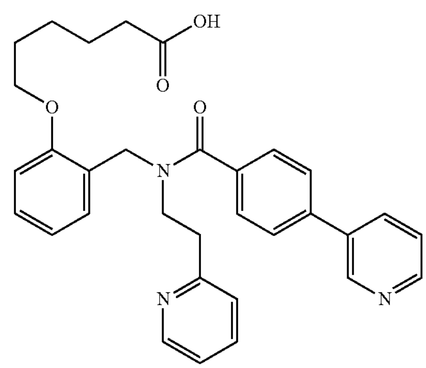 [SMILES: O=C(O)CCCCCOc1ccccc1CN(CCc1ccccn1)C(=O)c1ccc(-c2cccnc2)cc1] |
| 51 | C$_{32}$H$_{33}$N$_3$O$_4$ | 523.62 | 522.2 [M − H]− | | 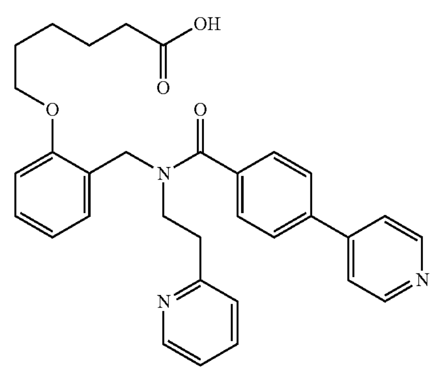 [SMILES: O=C(O)CCCCCOc1ccccc1CN(CCc1ccccn1)C(=O)c1ccc(-c2ccncc2)cc1] |
| 52 | C$_{30}$H$_{32}$N$_4$O$_4$ | 512.6 | 511.2 [M − H]− | | 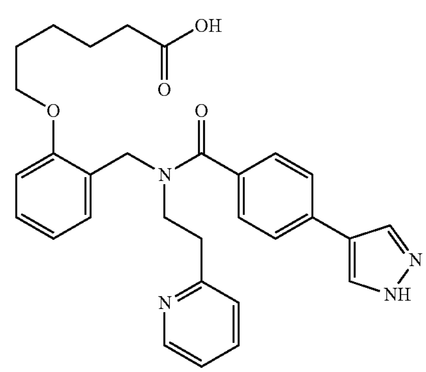 [SMILES: O=C(O)CCCCCOc1ccccc1CN(CCc1ccccn1)C(=O)c1ccc(-c2cn[nH]c2)cc1] |

TABLE 1-continued
| ID | Formula | MW Calc. | MW Obser. | EC$_{50}$ nM | Structure |
|----|---------|----------|-----------|--------------|-----------|
| 53 | C$_{31}$H$_{32}$N$_2$O$_5$ | 512.6 | 511.2 [M − H]− | | 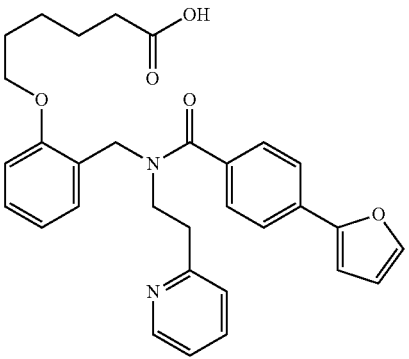 [SMILES: O=C(O)CCCCCOc1ccccc1CN(CCc1ccccn1)C(=O)c1ccc(-c2ccco2)cc1] |
| 54 | C$_{31}$H$_{32}$N$_2$O$_5$ | 512.6 | 511.2 [M − H]− | | 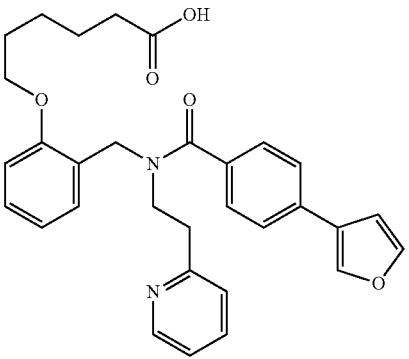 [SMILES: O=C(O)CCCCCOc1ccccc1CN(CCc1ccccn1)C(=O)c1ccc(-c2ccoc2)cc1] |
| 55 | C$_{31}$H$_{32}$N$_2$O$_4$S | 528.66 | 527.2 [M − H]− | | 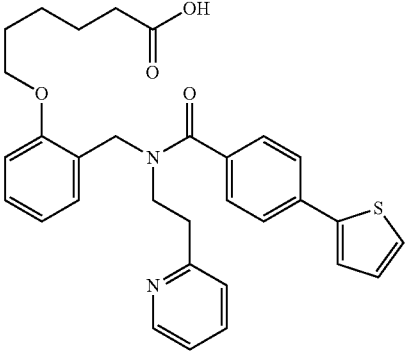 |
| 56 | C$_{31}$H$_{32}$N$_2$O$_4$S | 528.66 | 527.2 [M − H]− | | 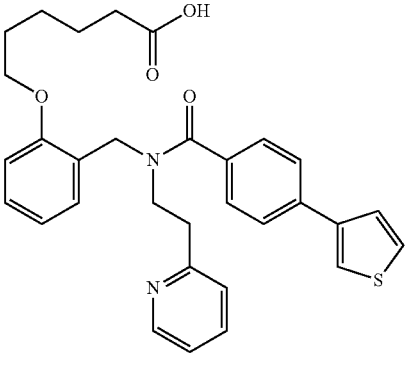 [SMILES: O=C(O)CCCCCOc1ccccc1CN(CCc1ccccn1)C(=O)c1ccc(-c2ccsc2)cc1] |

TABLE 1-continued
| ID | Formula | MW Calc. | MW Obser. | EC$_{50}$ nM | Structure |
|---|---|---|---|---|---|
| 57 | C$_{29}$H$_{33}$NO$_4$ | 459.58 | 458.2 [M − H]− | 60 | 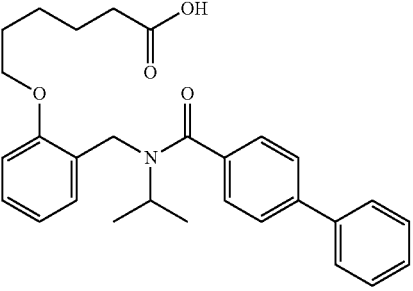 [SMILES: CC(C)N(Cc1ccccc1OCCCCCC(=O)O)C(=O)c1ccc(-c2ccccc2)cc1] |
| 58 | C$_{28}$H$_{32}$N$_2$O$_4$ | 460.56 | 459.2 [M − H]− | 1240 | 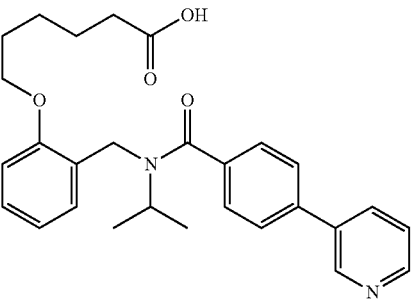 [SMILES: CC(C)N(Cc1ccccc1OCCCCCC(=O)O)C(=O)c1ccc(-c2cccnc2)cc1] |
| 59 | C$_{28}$H$_{32}$N$_2$O$_4$ | 460.56 | 459.2 [M − H]− | 2860 | 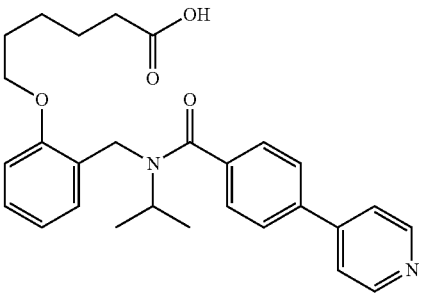 [SMILES: CC(C)N(Cc1ccccc1OCCCCCC(=O)O)C(=O)c1ccc(-c2ccncc2)cc1] |
| 60 | C$_{26}$H$_{31}$N$_3$O$_4$ | 449.54 | 448.2 [M − H]− | 710 | 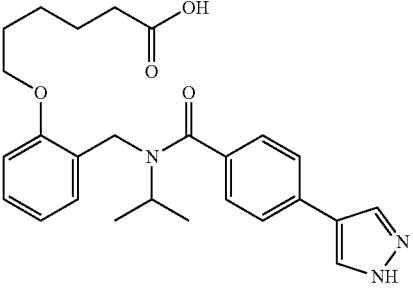 [SMILES: CC(C)N(Cc1ccccc1OCCCCCC(=O)O)C(=O)c1ccc(-c2cn[nH]c2)cc1] |
| 61 | C$_{27}$H$_{31}$NO$_5$ | 449.54 | 448.2 [M − H]− | 9.0 | 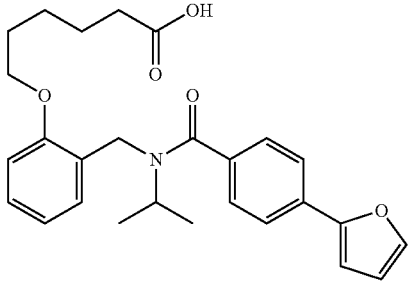 |

TABLE 1-continued

| ID | Formula | MW Calc. | MW Obser. | EC$_{50}$ nM | Structure |
|---|---|---|---|---|---|
| 62 | C$_{27}$H$_{31}$NO$_5$ | 449.54 | 448.2 [M − H]− | 61 | 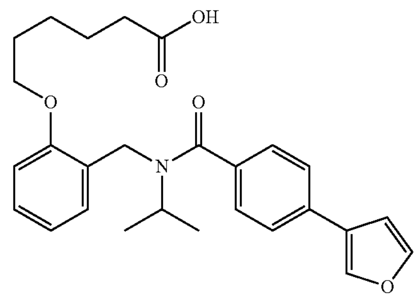 |
| 63 | C$_{27}$H$_{31}$NO$_4$S | 465.6 | 464.2 [M − H]− | ND | 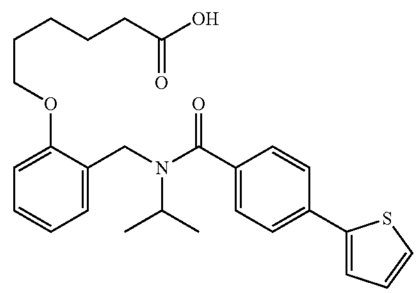 [SMILES: CC(C)N(Cc1ccccc1OCCCCCC(=O)O)C(=O)c1ccc(-c2ccco2)cc1] |
| 64 | C$_{27}$H$_{31}$NO$_4$S | 465.6 | 464.2 [M − H]− | 17.2 | 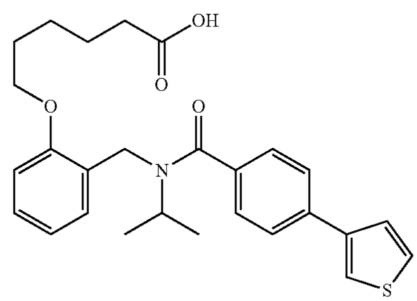 [SMILES: CC(C)N(Cc1ccccc1OCCCCCC(=O)O)C(=O)c1ccc(-c2ccoc2)cc1] |
| 65 | C$_{31}$H$_{35}$NO$_4$ | 485.61 | 484.3 [M − H]− | 405 | 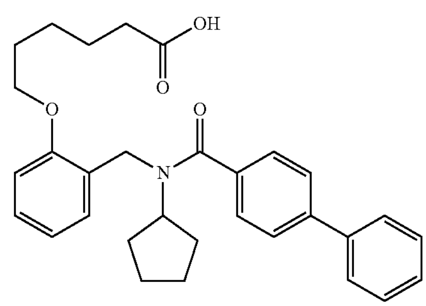 [SMILES: O=C(O)CCCCCOc1ccccc1CN(C(=O)c1ccc(-c2ccccc2)cc1)C1CCCC1] |
| 66 | C$_{30}$H$_{34}$N$_2$O$_4$ | 486.6 | 485.2 [M − H]− | 786 | 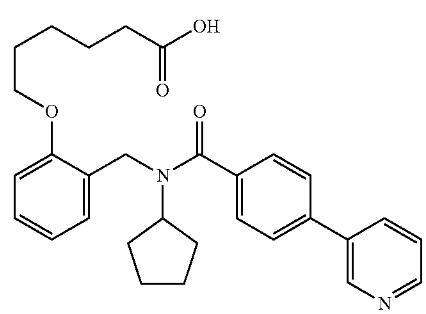 [SMILES: O=C(O)CCCCCOc1ccccc1CN(C(=O)c1ccc(-c2cccnc2)cc1)C1CCCC1] |

TABLE 1-continued
| ID | Formula | MW Calc. | MW Obser. | EC$_{50}$ nM | Structure |
|---|---|---|---|---|---|
| 67 | C$_{30}$H$_{34}$N$_2$O$_4$ | 486.6 | 485.2 [M − H]− | 1490 | 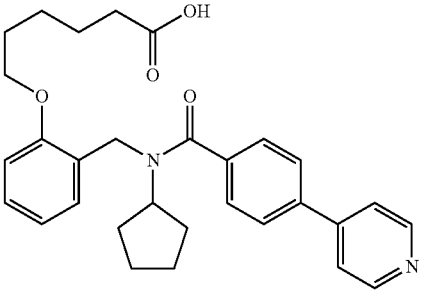 [SMILES: O=C(O)CCCCCOc1ccccc1CN(C(=O)c1ccc(-c2ccncc2)cc1)C1CCCC1] |
| 68 | C$_{28}$H$_{33}$N$_3$O$_4$ | 475.58 | 474.2 [M − H]− | 605 | 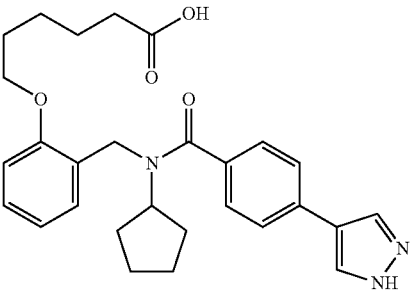 [SMILES: O=C(O)CCCCCOc1ccccc1CN(C(=O)c1ccc(-c2cn[nH]c2)cc1)C1CCCC1] |
| 69 | C$_{29}$H$_{33}$NO$_5$ | 475.58 | 474.2 [M − H]− | 51.4 | 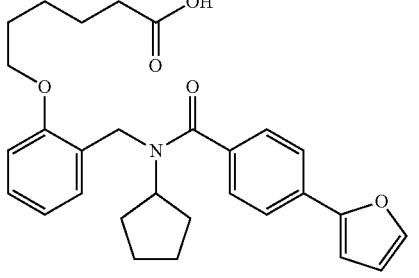 |
| 70 | C$_{29}$H$_{33}$NO$_5$ | 475.58 | 474.2 [M − H]− | 127 | 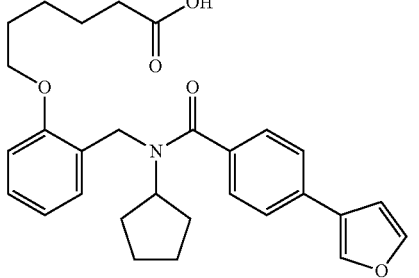 |
| 71 | C$_{29}$H$_{33}$NO$_4$S | 491.64 | 490.2 [M − H]− | 753 | 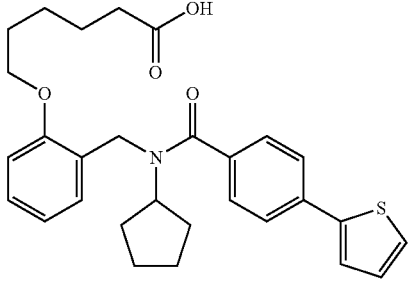 [SMILES: O=C(O)CCCCCOc1ccccc1CN(C(=O)c1ccc(-c2ccco2)cc1)C1CCCC1] |

TABLE 1-continued
| ID | Formula | MW Calc. | MW Obser. | EC$_{50}$ nM | Structure |
|---|---|---|---|---|---|
| 72 | C$_{29}$H$_{33}$NO$_4$S | 491.64 | 490.2 [M − H]− | 29.3 | 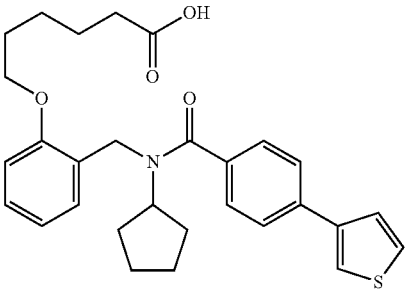 [SMILES: O=C(O)CCCCCOc1ccccc1CN(C(=O)c1ccc(-c2ccoc2)cc1)C1CCCC1] |
| 73 | C$_{33}$H$_{33}$NO$_4$ | 507.62 | 506.2 [M − H]− | ND | 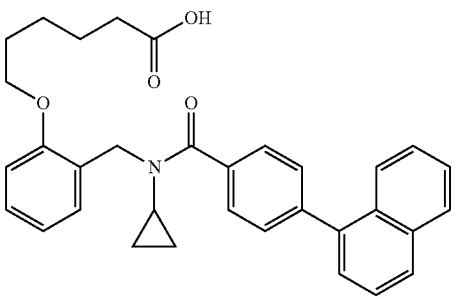 [SMILES: O=C(O)CCCCCOc1ccccc1CN(C(=O)c1ccc(-c2cccc3ccccc23)cc1)C1CC1] |
| 74 | C$_{33}$H$_{33}$NO$_4$ | 507.62 | 506.2 [M − H]− | ND | 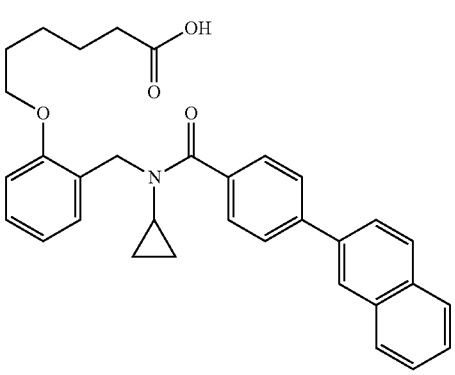 [SMILES: O=C(O)CCCCCOc1ccccc1CN(C(=O)c1ccc(-c2ccc3ccccc3c2)cc1)C1CC1] |
| 75 | C$_{30}$H$_{33}$NO$_4$ | 471.59 | 470.2 [M − H]− | 1190 | 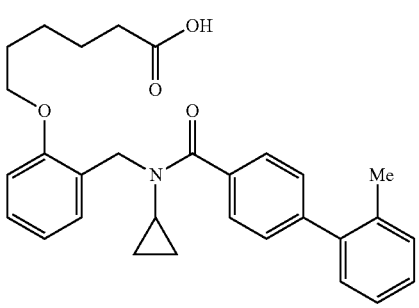 |
| 76 | C$_{30}$H$_{33}$NO$_4$ | 471.59 | 470.2 [M − H]− | 318 | 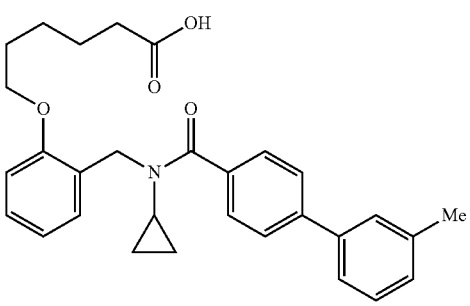 [SMILES: Cc1cccc(-c2ccc(C(=O)N(Cc3ccccc3OCCCCCC(=O)O)C3CC3)cc2)c1] |

TABLE 1-continued
| ID | Formula | MW Calc. | MW Obser. | EC$_{50}$ nM | Structure |
|---|---|---|---|---|---|
| 77 | C$_{30}$H$_{33}$NO$_4$ | 471.59 | 470.2 [M − H]− | 372 | 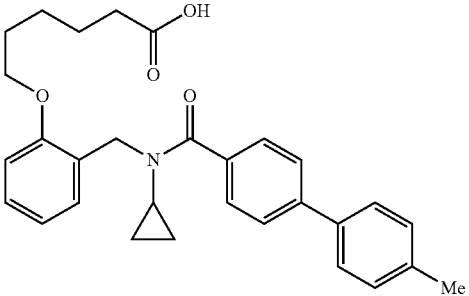 [SMILES: Cc1ccc(-c2ccc(C(=O)N(Cc3ccccc3OCCCCCC(=O)O)C3CC3)cc2)cc1] |
| 78 | C$_{30}$H$_{33}$NO$_5$ | 487.59 | 486.2 [M − H]− | 1870 | 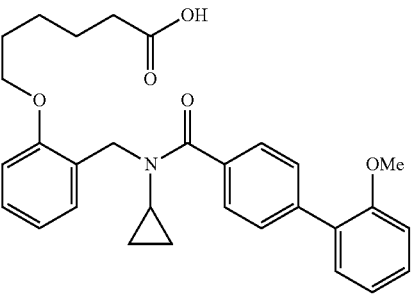 [SMILES: COc1ccccc1-c1ccc(C(=O)N(Cc2ccccc2OCCCCCC(=O)O)C2CC2)cc1] |
| 79 | C$_{30}$H$_{33}$NO$_5$ | 487.59 | 486.2 [M − H]− | 301 | 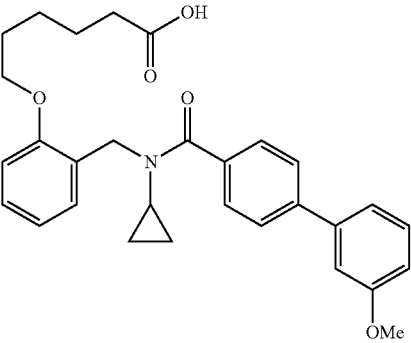 [SMILES: COc1cccc(-c2ccc(C(=O)N(Cc3ccccc3OCCCCCC(=O)O)C3CC3)cc2)c1] |
| 80 | C$_{30}$H$_{33}$NO$_5$ | 487.59 | 486.2 [M − H]− | 439 | 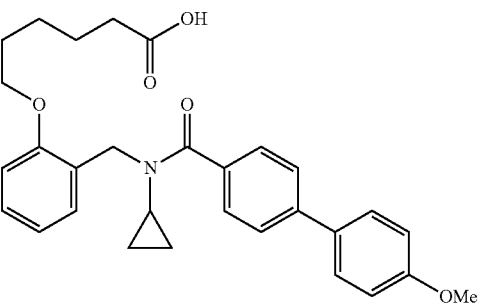 [SMILES: COc1ccc(-c2ccc(C(=O)N(Cc3ccccc3OCCCCCC(=O)O)C3CC3)cc2)cc1] |
| 81 | C$_{29}$H$_{30}$FNO$_4$ | 475.55 | 474.2 [M − H]− | 597 | 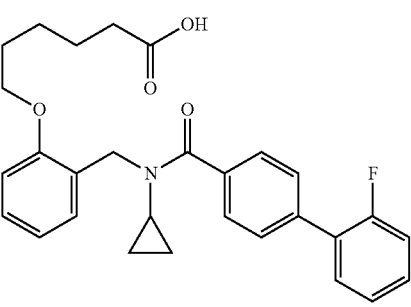 [SMILES: O=C(O)CCCCCOc1ccccc1CN(C(=O)c1ccc(-c2ccccc2F)cc1)C1CC1] |

TABLE 1-continued

| ID | Formula | MW Calc. | MW Obser. | EC$_{50}$ nM | Structure |
|---|---|---|---|---|---|
| 82 | C$_{29}$H$_{30}$FNO$_4$ | 475.55 | 474.2 [M − H]− | 150 | 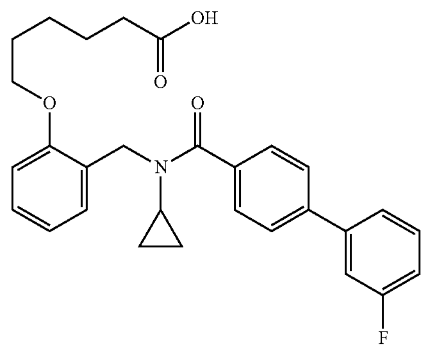 [SMILES: O=C(O)CCCCCOc1ccccc1CN(C(=O)c1ccc(-c2cccc(F)c2)cc1)C1CC1] |
| 83 | C$_{29}$H$_{30}$FNO$_4$ | 475.55 | 474.2 [M − H]− | 364 | 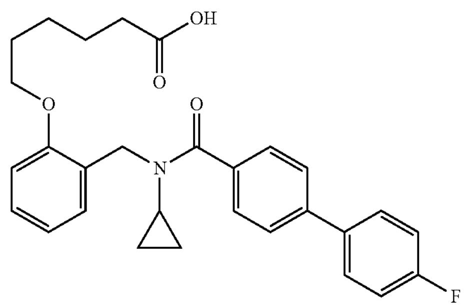 [SMILES: O=C(O)CCCCCOc1ccccc1CN(C(=O)c1ccc(-c2ccc(F)cc2)cc1)C1CC1] |
| 84 | C$_{31}$H$_{35}$NO$_4$ | 485.61 | 484.3 [M − H]− | 2500 | 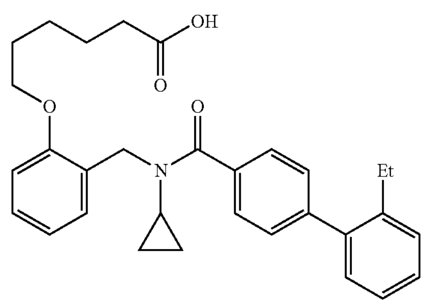 [SMILES: CCc1ccccc1-c1ccc(C(=O)N(Cc2ccccc2OCCCCCC(=O)O)C2CC2)cc1] |
| 85 | C$_{31}$H$_{35}$NO$_4$ | 485.61 | 484.3 [M − H]− | ND | 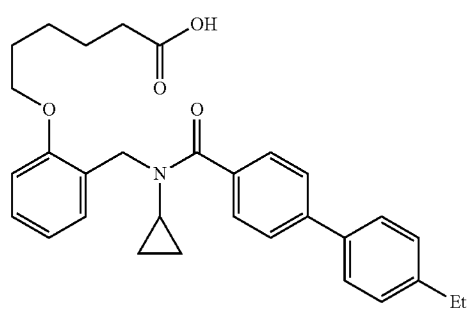 |
| 86 | C$_{31}$H$_{35}$NO$_4$ | 485.61 | 484.3 [M − H]− | 1300 | 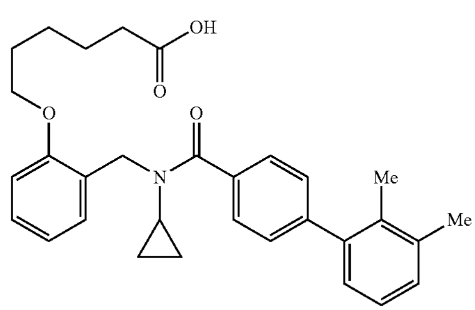 [SMILES: Cc1cccc(-c2ccc(C(=O)N(Cc3ccccc3OCCCCCC(=O)O)C3CC3)cc2)c1C] |

TABLE 1-continued
| ID | Formula | MW Calc. | MW Obser. | EC$_{50}$ nM | Structure |
|----|---------|----------|-----------|--------------|-----------|
| 87 | C$_{31}$H$_{35}$NO$_4$ | 485.61 | 484.3 [M − H]− | 1150 | 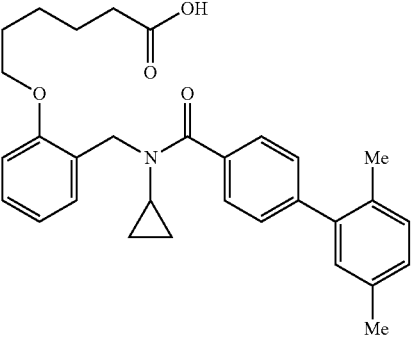 [SMILES: Cc1ccc(C)c(-c2ccc(C(=O)N(Cc3ccccc3OCCCCCC(=O)O)C3CC3)cc2)c1] |
| 88 | C$_{31}$H$_{35}$NO$_4$ | 485.61 | 484.3 [M − H]− | ND | 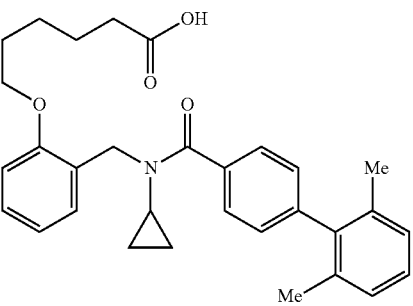 [SMILES: Cc1cccc(C)c1-c1ccc(C(=O)N(Cc2ccccc2OCCCCCC(=O)O)C2CC2)cc1] |
| 89 | C$_{31}$H$_{35}$NO$_4$ | 485.61 | 484.3 [M − H]− | 1760 | 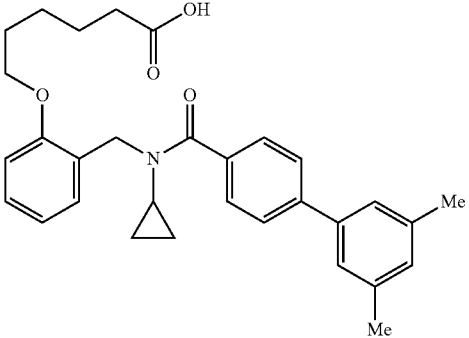 [SMILES: Cc1cc(C)cc(-c2ccc(C(=O)N(Cc3ccccc3OCCCCCC(=O)O)C3CC3)cc2)c1] |
| 90 | C$_{30}$H$_{30}$F$_3$NO$_4$ | 525.56 | 524.2/ 525.2 [M − H]− | 1300 | 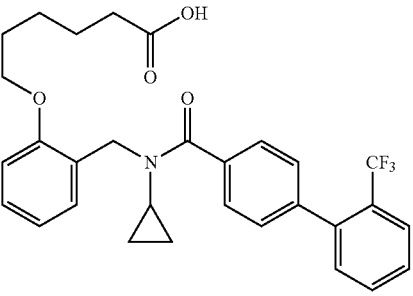 |

TABLE 1-continued

| ID | Formula | MW Calc. | MW Obser. | EC$_{50}$ nM | Structure |
|---|---|---|---|---|---|
| 91 | C$_{30}$H$_{30}$F$_3$NO$_4$ | 525.56 | 524.2/ 525.2 [M − H]− | 1150 | 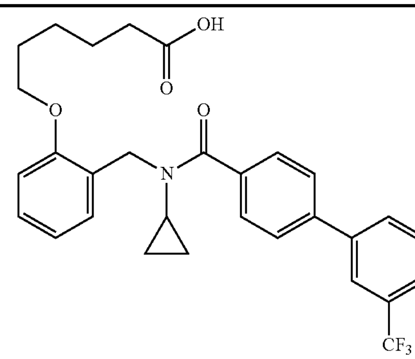 |
| 92 | C$_{30}$H$_{30}$F$_3$NO$_4$ | 525.56 | 524.2/ 525.2 [M − H]− | 1760 | 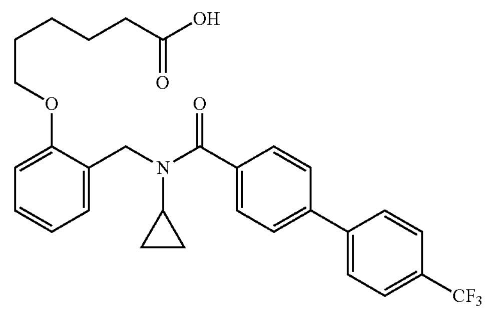 [SMILES: O=C(O)CCCCCOc1ccccc1CN(C(=O)c1ccc(-c2ccc(C(F)(F)F)cc2)cc1)C1CC1] |
| 93 | C$_{32}$H$_{37}$NO$_4$ | 499.64 | 498.3 [M − H]− | 1340 | 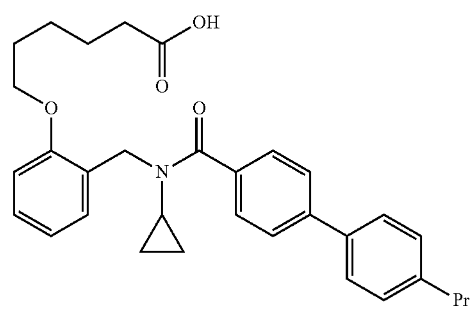 |
| 94 | C$_{33}$H$_{39}$NO$_4$ | 513.67 | 512.3 [M − H]− | ND | 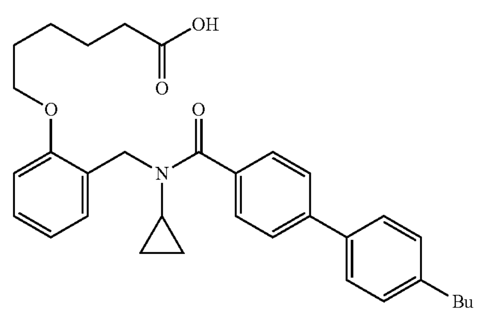 |
| 95 | C$_{35}$H$_{35}$NO$_4$ | 533.66 | 532.3 [M − H]− | ND | 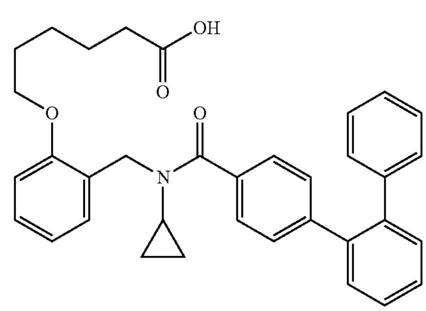 [SMILES: O=C(O)CCCCCOc1ccccc1CN(C(=O)c1ccc(-c2ccccc2-c2ccccc2)cc1)C1CC1] |

Example 1: Synthesis of 6-(2-((6-(Furan-2-yl)-N-isopropylnicotinamido)methyl)phenoxy)hexanoic acid

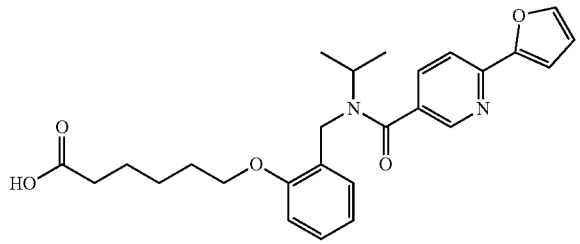 [SMILES: CC(C)N(Cc1ccccc1OCCCCCC(=O)O)C(=O)c1ccc(-c2ccco2)nc1]

a) Synthesis of ethyl 6-(2-formylphenoxy)hexanoate

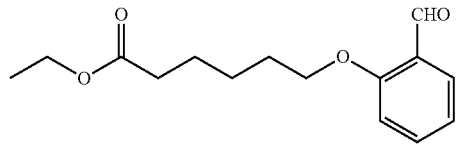 [SMILES: CCOC(=O)CCCCCOc1ccccc1C=O]

A solution of salicylaldehyde (5.0 g, 40.9 mmol) in DMF (50 mL) was treated with potassium carbonate (8.48 g, 61 mmol) and ethyl-6-bromo hexanoate (10.96 g, 49.4 mmol) at rt under nitrogen atmosphere. The resulting reaction mixture was heated at 80° C. with constant stirring for 3 h. The reaction mixture was cooled to rt and filtered and washed with ethyl acetate. The filtrate was concentrated under reduced pressure and residue obtained was diluted with cold water (50 mL), before extracting with ethyl acetate (200 mL). The organic layer was washed with brine, dried over anhydrous $Na_2SO_4$ and concentrated under reduced pressure. The residue obtained was purified by silica gel column chromatography (elution, 10% EtOAc-hexanes) to afford the title compound (10.01 g, 93.4% yield). LCMS (m/z): 265.5 (M+1)$^+$.

b) Synthesis of ethyl 6-(2-((isopropylamino)methyl)phenoxy)hexanoate

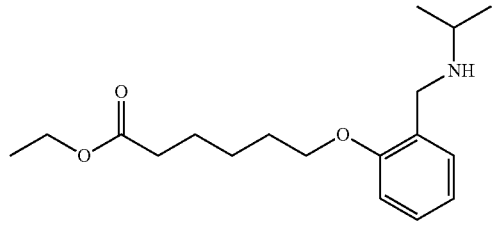 [SMILES: CCOC(=O)CCCCCOc1ccccc1CNC(C)C]

In a 100-mL round bottom flask, isopropyl amine (2.70 g, 45.7 mmol) and ethyl 6-(2-formylphenoxy)hexanoate (10 g, 37.8 mmol) were dissolved in 1,2-dichloroethane (50 mL) at rt. AcOH (14.8 mL) was added carefully to the above mixture (exothermic) followed by portion wise addition of sodium triacetoxyborohydride (17.8 g, 83.9 mmol) at rt. The reaction mixture was stirred at rt under nitrogen atmosphere for 4 h. The reaction mixture was quenched by adding saturated sodium carbonate solution, and was extracted with ethyl acetate. The ethyl acetate extract was washed with brine and dried over anhydrous $Na_2SO_4$. The solution was concentrated under reduced pressure to give title compound (11.1 g, 94%). LCMS (m/z): 308.5 (M+1)$^+$.

c) Synthesis of ethyl 6-(2-((6-chloro-N-isopropylnicotinamido)methyl)phenoxy) hexanoate

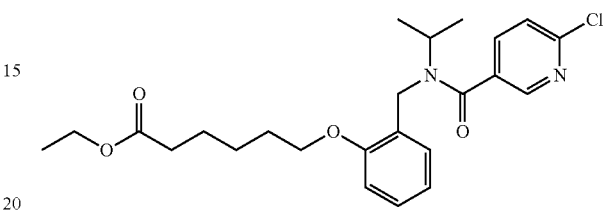

In a 50-mL round bottom flask, EDCI.HCl (0.746 g, 3.89 mmol) and DIPEA (1.3 mL, 7.46 mmol) were added to a solution of ethyl 6-(2-((isopropylamino)methyl)phenoxy) hexanoate (1.0 g, 3.25 mmol), 6-chloronicotinic acid (0.612 g, 3.9 mmol) and HOBt (0.598 g, 3.9 mmol) in dimethylformamide (10 mL) at rt under nitrogen atmosphere. The reaction mixture was stirred at rt for 16 h under nitrogen atmosphere. The reaction mixture was concentrated under reduced pressure and residue obtained was purified by silica gel column chromatography (eluting with 10% EtOAc-hexanes) to furnish the title compound (1.2 g, 75.4%). LCMS (m/z): 469.1 (M+Na)$^+$.

d) Synthesis of ethyl 6-(2-((6-(furan-2-yl)-N-isopropylnicotinamido)methyl)phenoxy) hexanoate

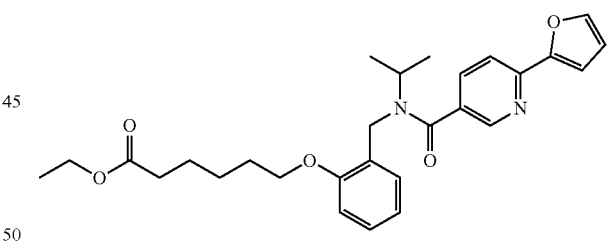

In a 25-mL round bottom flask, a stirred solution of ethyl 6-(2-((6-chloro-N-sopropylnicotinamido)methyl)phenoxy) hexanoate (1.2 g, 2.69 mmol), furan-2-ylboronic acid (0.328 g, 2.93 mmol) and $Na_2CO_3$ (0.647 g, 6.10 mmol) in DME-water (9:1, 10 mL) was degassed by purging argon gas at rt. Pd(dppf)$Cl_2$'DCM (0.099 g, 0.121 mmol) was added to the above mixture under nitrogen atmosphere at rt. The resulting mixture was refluxed for 4 h under nitrogen atmosphere. The reaction mixture was cooled to room temperature and filtered through a celite bed and washed with ethyl acetate. The combined filtrate was concentrated under reduced pressure. The residue obtained was purified by silica gel column chromatography (gradient elution with 10-25% EtOAc-hexanes) to afford title compound (609 mg 47.3%). LCMS (m/z): 479 (M+1)$^+$.

e) Synthesis of 6-(2-((6-(furan-2-yl)-N-isopropylnicotinamido)methyl)phenoxy) hexanoic acid

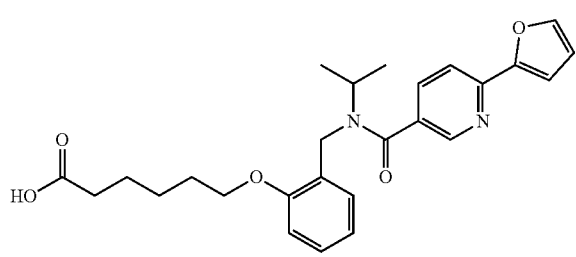 [SMILES: CC(C)N(Cc1ccccc1OCCCCCC(=O)O)C(=O)c1ccc(-c2ccco2)nc1]

25-mL round bottom flask, ethyl 6-(2-((6-(furan-2-yl)-N-isopropylnicotinamido)methyl)phenoxy)hexanoate (0.601 g, 1.25 mmol) was dissolved in THF (4 mL)-water (2 L)-methanol (1 mL) at room temperature. Lithium hydroxide monohydrate (0.131 g, 3.14 mmol) was added to the solution at and reaction mixture was stirred at rt for 3 h. The reaction mixture was concentrated under reduced pressure and residue obtained was dissolved in water and washed with diethyl ether. The aqueous phase was then acidified (HCl) and extracted with ethyl acetate (30 mL×3). The combined extract was washed with brine, dried over anhydrous $Na_2SO_4$ and concentrated under reduced pressure. The residue obtained was purified by silica gel column chromatography to give title compound (0.502 g, 89.2%). $^1$H NMR (400 MHz, DMSO-$d_6$, 60° C.): δ 11.78 (s, 1H), 8.61 (s, 1H), 7.89 (d, J=8.0 Hz, 1H), 7.84 (s, 1H), 7.74 (d, J=8.0 Hz, 1H), 7.27 (d, J=7.2 Hz, 1H), 7.20 (t, J=8.0 Hz, 1H), 7.15 (d, J=3.6 Hz, 1H), 7.00-6.88 (m, 2H), 6.73-6.60 (m, 1H), 4.54 (s, 2H), 4.18 (s, 1H), 3.98 (d, J=6.6 Hz, 2H), 2.23 (t, J=7.2 Hz, 2H), 1.76 (br, 2H), 1.60-1.53 (m, 2H), 1.46 (br, 2H), 1.14 (d, J=6.4 Hz, 6H). LC-MS (m/z): 473.1 (M+Na)$^+$. HPLC: 96.1%. (210 nm).

Example 2: Synthesis of 6-(2-((5-(Furan-2-yl)-N-isopropylpicolinamido)methyl)phenoxy)hexanoic acid

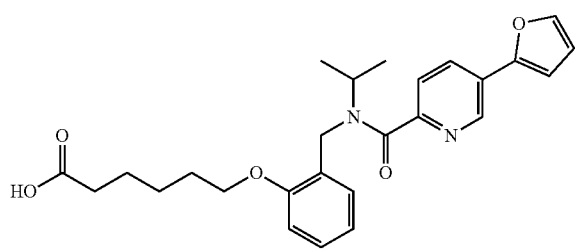 [SMILES: CC(C)N(Cc1ccccc1OCCCCCC(=O)O)C(=O)c1ccc(-c2ccco2)cn1]

a) Synthesis of ethyl 6-(2-((5-bromo-N-isopropylpicolinamido)methyl)phenoxy)hexanoate

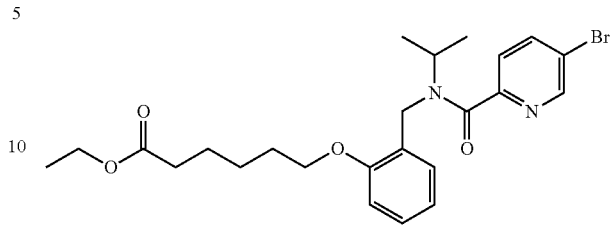

In 50-mL round bottom flask, EDCI.HCl (0.521 g, 2.7 mmol) and triethyl amine (0.76 mL, 5.6 mmol) were sequentially added to a solution of ethyl 6-(2-((isopropylamino)methyl)phenoxy)hexanoate (0.7 g, 2.2 mmol), 5-bromopicolinic acid (0.505 g, 2.5 mmol) and HOBt (0.418 g, 3.09 mmol) in dimethylformamide (7 mL) at rt under nitrogen atmosphere. The resulting reaction mixture was stirred at for 16 h at room temperature under nitrogen atmosphere. The reaction mixture was concentrated under reduced pressure and residue obtained was purified by silica gel column chromatography and eluting with 15% EtOAc-hexanes gave title compound (0.506 g, 46.9%). LCMS (m/z): 491 (M+1)$^+$.

b) Synthesis of ethyl 6-(2-((5-(furan-2-yl)-N-isopropylpicolinamido)methyl) phenoxy)hexanoate

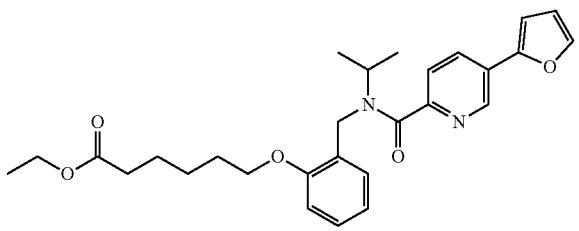 [SMILES: CCOC(=O)CCCCCOc1ccccc1CN(C(=O)c1ccc(-c2ccco2)cn1)C(C)C]

In a 50-mL round bottom flask, a stirred suspension of ethyl 6-(2-((5-bromo-N-isopropylpicolinamido)methyl)phenoxy)hexanoate (0.500 g, 1 02 mmol), furan-2-yl boronic acid (0.125 g, 1.12 mmol) and $Na_2CO_3$ (0.27 g, 2.55 mmol) in DME-water (9:1, 10 mL) was degassed by purging argon gas at rt. Pd(dppf)$Cl_2$'DCM (0.041 mg, 0.05 mmol) was added to the above solution under nitrogen atmosphere. The resulting reaction mixture was refluxed for 4 h under nitrogen atmosphere. The reaction mixture was cooled to room temperature, filtered, and washed with ethyl acetate. The combined filtrate was concentrated under reduced pressure and residue obtained was purified by silica column chromatography (gradient elution, 10% to 25% EtOAc-hexanes) to afford title compound (0.230 g 48.7% yield). LCMS (m/z): 501.3 (M+Na)$^+$.

c) Synthesis of 6-(2-((5-(furan-2-yl)-N-isopropylpicolinamido)methyl)phenoxy)hexanoic acid

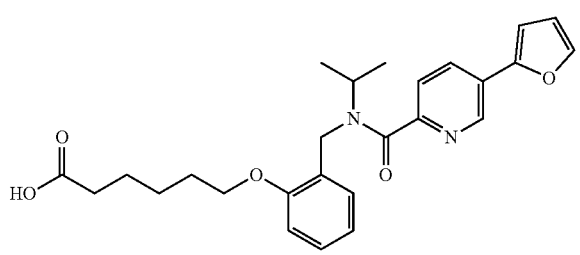 [SMILES: CC(C)N(Cc1ccccc1OCCCCCC(=O)O)C(=O)c1ccc(-c2ccco2)cn1]

In a 25-mL round bottom flask, ethyl 6-(2-((5-(furan-2-yl)-N-isopropylpicolinamido)methyl)phenoxy)hexanoate (0.22 g, 0.4 mmol) was dissolved in THF (4 mL)-H$_2$O (2 mL)-MeOH (1 mL) at room temperature. Lithium hydroxide monohydrate (0.048 g, 1.1 mmol) was added to the solution and resulting mixture was stirred at rt for 3 h. The reaction mixture was concentrated under reduced pressure and residue obtained was dissolved in water and washed with diethyl ether. The aqueous phase was then acidified (HCl) and extracted with ethyl acetate (30 mL×3). The combined extract was washed with brine, dried over anhydrous Na$_2$SO$_4$ and concentrated under reduced pressure. The residue obtained was purified by silica gel column chromatography (elution with 50% EtOAc-hexanes) to give title compound (0.068 g, 32.8%). $^1$H NMR (400 MHz, DMSO-d$_6$, 90° C.): δ 12.17-11.50 (br s, 1H), 8.91 (s, 1H), 8.12 (s, 1H), 7.81 (s, 1H), 7.60 (d, J=8.0 Hz, 1H), 7.30 (d, J=7.2 Hz, 1H), 7.18 (t, J=7.2 Hz, 1H), 7.15-7.06 (m, 1H), 6.93-6.89 (m, 2H), 6.72-6.55 (m, 1H), 4.63 (s, 2H), 4.25 (br, 1H), 4.02 (br s, 2H), 2.25 (t, J=7.2 Hz, 2H), 1.78 (br, 2H), 1.63-0.60 (m, 2H), 1.57-1.42 (m, 2H), 1.13 (br s, 6H). LCMS (m/z): 473.1 (M+Na)$^+$. HPLC=97.49% (210 nm).

Example 3: Synthesis of 6-(2-((3-(Furan-2-yl)-N-isopropylbenzamido)methyl)phenoxy)hexanoic acid

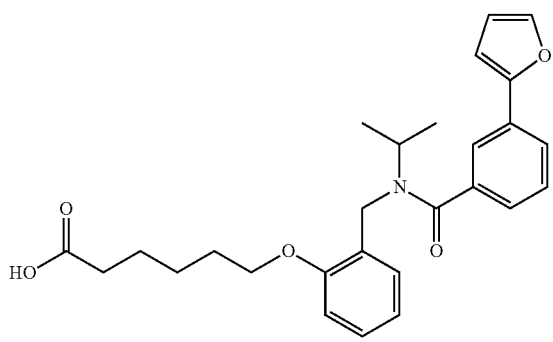 [SMILES: CC(C)N(Cc1ccccc1OCCCCCC(=O)O)C(=O)c1cccc(-c2ccco2)c1]

a) Synthesis of ethyl 6-(2-((3-bromo-N-isopropylbenzamido)methyl)phenoxy)hexanoate

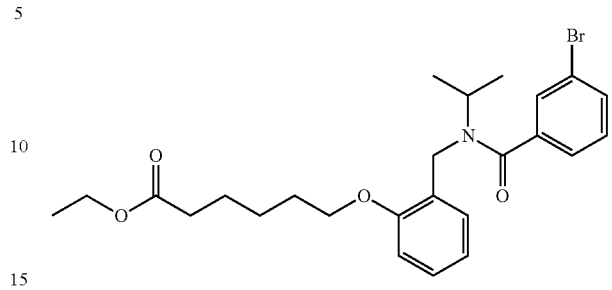

In a 50-mL round bottom flask, a stirred solution of ethyl 6-(2-((isopropylamino)methyl)phenoxy)hexanoate of example 1 (0.500 g, 1.62 mmol) in DMF (5 mL), was treated sequentially with 3-bromo benzoic acid (0.360 g, 1.79 mmol), EDCI.HCl (0.618 g, 3.24 mmol), HOBt (0.440 g, 3.24 mmol), and triethylamine (0.68 mL, 4.8 mmol) at rt under nitrogen atmosphere. The reaction mixture was stirred at rt for 4 h under nitrogen atmosphere. Upon completion of the reaction (TLC), the reaction mixture quenched with cold water and extracted with ethyl acetate (50 mL×3). The combined organic extract was washed with brine, dried over anhydrous Na$_2$SO$_4$ and concentrated under reduced pressure. The residue obtained was purified by silica gel column chromatography (gradient elution, 10-20% EtOAc-hexanes) to afford the title compound as clear oil (406 mg, 53.5%). LCMS (m/z): 491.9 (M+Na)+.

b) Synthesis of methyl 6-(2-((3-(furan-2-yl)-N-isopropylbenzamido)methyl)phenoxy) hexanoate

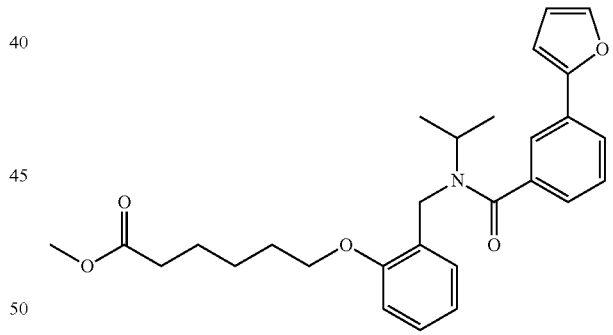

In a resealable reaction tube, ethyl 6-(2-((3-bromo-N-isopropylbenzamido)methyl) phenoxy)hexanoate (0.400 g, 0.81 mmol), 2-furan boronic acid (0.113 g, 0.98 mmol) and Na$_2$CO$_3$ (1.32 g, 12.45 mmol) were dissolved in DME (1.5 mL) and EtOH (1.5 mL) at rt under nitrogen atmosphere. The solution was degassed by purging argon gas at rt for 10 min. Pd(PPh$_3$)$_3$ (28.2 mg, 0.024 mmol) was added to the above solution at rt under nitrogen. The resulting mixture was heated at 90° C. for 4 h. Upon completion of the reaction (TLC), the reaction mixture was cooled to rt and diluted with cold water, before extracting with ethyl acetate (50 mL×3). The combined organic extract was washed with brine, dried over dried over anhydrous Na$_2$SO$_4$ and concentrated under reduced pressure. The residue obtained (0.4 g) was used in the next step without further purification.

c) Synthesis of 6-(2-((3-(furan-2-yl)-N-isopropyl-benzamido)methyl)phenoxy)hexanoic acid)

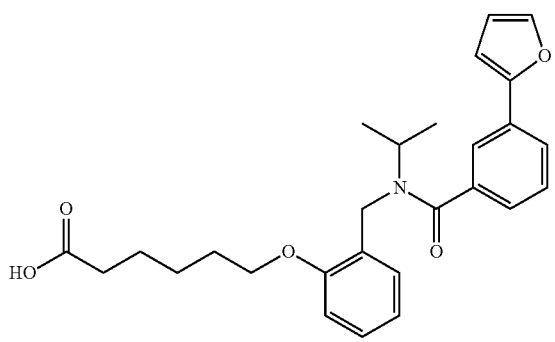 [SMILES: CC(C)N(Cc1ccccc1OCCCCCC(=O)O)C(=O)c1cccc(-c2ccco2)c1]

In a 25-mL round bottom flask, methyl 6-(2-((3-(furan-2-yl)-N-isopropylbenzamido) methyl)phenoxy)hexanoate (0.40 g, 0.83 mmol) was dissolved in THF (10 mL)-water (3 mL)-ethanol (3 mL) mixture at rt. Lithium hydroxide monohydrate (0.105 g, 2.51 mmol) was added to the above solution and the reaction mixture was stirred at 50° C. for 4 h. Upon completion of the reaction (TLC), the reaction mixture was concentrated under reduced pressure. The residue obtained was diluted with cold water and acidified with HCl (2N), before extracting with ethyl acetate (50 mL×3). The combined organic extract was washed with brine, dried over anhydrous Na$_2$SO$_4$ and concentrated under reduced pressure to afford title compound (180 mg, 47.8%) as off-white solid. $^1$H NMR (400 MHz, DMSO-d$_6$, 60° C.): δ 11.82 (s, 1H), 7.75-7.69 (m, 3H), 7.48 (br, 1H), 7.31-7.27 (m, 3H) 7.21 (t, J=7.6 Hz, 1H), 6.96 (t, J=7.2 Hz, 2H), 6.66-6.54 (br, 1H), 4.53 (s, 2H), 4.25-3.89 (m, 1H), 2.26-2.21 (m, 2H), 1.75 (br, 2H), 1.65-1.36 (m, 4H), 1.20-1.02 (br s, 6H). LCMS (m/z): 450.4 (M+1)$^+$. HPLC: 6.65% (210 nm).

Example 4: Synthesis of 6-(2-((N-isopropyl-4-methylbenzamido)methyl)phenoxy)hexanoic acid

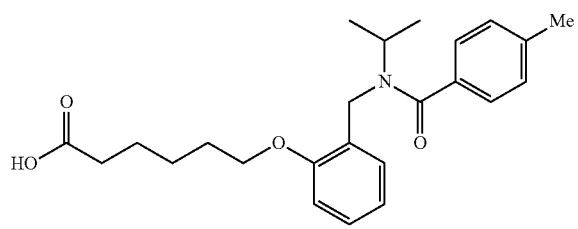 [SMILES: Cc1ccc(C(=O)N(Cc2ccccc2OCCCCCC(=O)O)C(C)C)cc1]

a) Synthesis of ethyl 6-(2-((N-isopropyl-4-methyl-benzamido)methyl)phenoxy)hexanoate

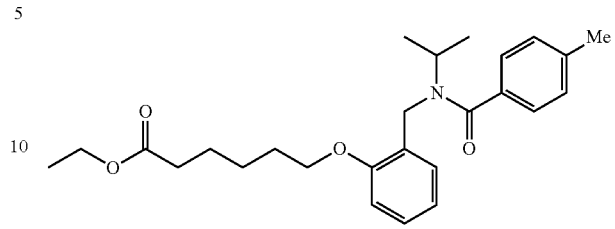

In a 25-mL round bottom flask, a stirred solution of ethyl 6-(2-((isopropylamino)methyl)phenoxy)hexanoate (0.51 g, 1.66 mmol) of example I(b) in DMF (5 mL), was treated sequentially with 4-methylbenzoic acid (0.221 g, 1.54 mmol), HBTU (1.84 g, 4.86 mmol) and triethylamine (0.818 g, 8.10 mmol) at rt under nitrogen atmosphere. The reaction mixture was stirred at rt for 18 h. Upon completion of the reaction (TLC), the reaction mixture was diluted with cold water and extracted with ethyl acetate (25 mL×2). The combined organic layer was washed with brine, dried over anhydrous Na$_2$SO$_4$ and concentrated under reduced pressure. The residue obtained was purified by silica gel column chromatography (elution 15% EtOAc-hexanes) to give title compound (0.450 g, 65%) as a clear oil. LCMS (m/z): 426.3 (M+1)$^+$.

b) Synthesis of 6-(2-((N-isopropyl-4-methylbenzamido)methyl)phenoxy)hexanoic acid

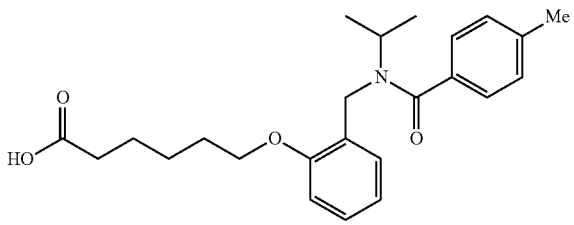 [SMILES: Cc1ccc(C(=O)N(Cc2ccccc2OCCCCCC(=O)O)C(C)C)cc1]

In a 25-mL round bottom flask, ethyl 6-(2-((N-isopropyl-4-ethylbenzamido)methyl)phenoxy)hexanoate (0.400 g, 0.94 mmol) was dissolved in TI-IF (2 mL)-water (1 mL) mixture at rt. Lithium hydroxide monohydrate (0.197 g, 4.7 mmol) was added to the above solution and the reaction mixture was stirred at it for 18 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous Na$_2$SO$_4$ and concentrated under reduced pressure. The crude product was washed with diethyl ether and n-pentane, solvent decanted and residue dried under reduced pressure to afford the title product (0.258 g, 69%) as clear oil. $^1$H NMR (400 MHz, DMSO-d$_6$, 60° C.) δ 11.81 (s, 1H), 7.40-7.12 (m, 6H), 7.07-6.82 (m, 2H), 4.51 (s, 2H), 4.13 (br, 1H), 4.01 (br t, J=6.0 Hz, 2H), 2.34 (s, 3H), 2.24 (t, J=7.2 Hz, 2H), 1.78-1.74 (m, 2H), 1.63-1.57 (m, 2H), 1.49-1.47 (m, 2H), 1.08 (d, J=6.4 Hz, 6H). LCMS (m/z): 398.1 (M+1)$^+$. HPLC: 96.8% (210 nm).

Example 5: Synthesis of 6-(2-((4-fluoro-N-isopropylbenzamido)methyl)phenoxy)hexanoic acid

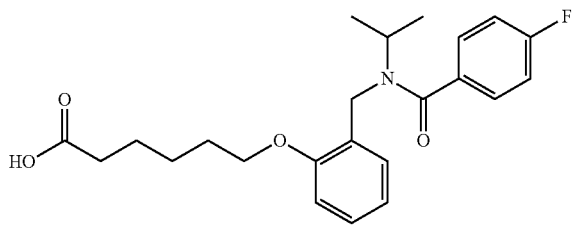 [SMILES: CC(C)N(Cc1ccccc1OCCCCCC(=O)O)C(=O)c1ccc(F)cc1]

a) Synthesis of ethyl 6-(2-((4-fluoro-N-isopropyl-benzamido)methyl)phenoxy)hexanoate

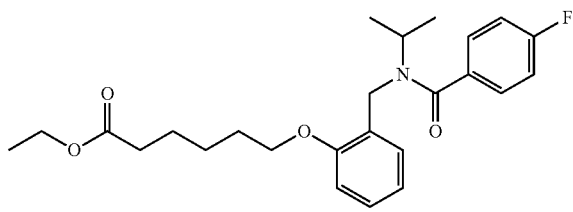 [SMILES: CCOC(=O)CCCCCOc1ccccc1CN(C(=O)c1ccc(F)cc1)C(C)C]

In a 25-mL round bottom flask, a stirred solution of ethyl 6-(2-((isopropylamino)methyl)phenoxy)hexanoate of example I(b) (0.500 g, 1.62 mmol) in DMF (7 mL), was treated sequentially with 4-fluorobenzoic acid (0.272 g, 1.94 mmol), EDCI.HCl (0.370 g, 1.94 mmol), HOBt (0.261 g, 1.94 mmol) and diisopropylethylamine (0.313 g, 2.43 mmol) at rt under nitrogen atmosphere. The reaction mixture was stirred at rt for 18 h under nitrogen atmosphere. Upon completion of the reaction (TLC), the reaction mixture was diluted with cold water and extracted with ethyl acetate (25 mL×2). The combined organic extract was washed with brine, dried over anhydrous $Na_2SO_4$ and concentrated under reduced pressure. The residue obtained was purified by silica gel column chromatography (elution, 15% EtOAc-hexanes) to give the title compound (0.41 g, 58.8%) as clear oil. LCMS (m/z): 430.0 $(M+1)^+$.

b) Synthesis of 6-(2-((4-fluoro-N-isopropylbenzamido)methyl)phenoxy)hexanoic acid

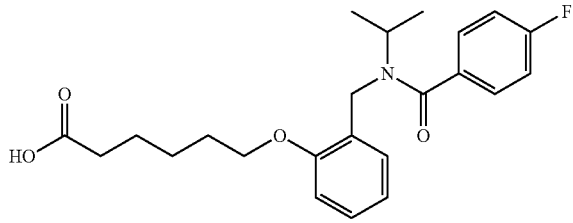 [SMILES: CC(C)N(Cc1ccccc1OCCCCCC(=O)O)C(=O)c1ccc(F)cc1]

In a 25-mL round bottom flask, ethyl 6-(2-((4-fluoro-N-isopropylbenzamido)methyl) phenoxy)hexanoate (0.400 g, 0.93 mmol) was dissolved in THF (2 mL)-water (1 mL) mixture at it Lithium hydroxide monohydrate (0.195 g, 4.6 mmol) was added to the above solution and the reaction mixture was stirred at rt for 18 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous $Na_2SO_4$ and concentrated under reduced pressure. The residue obtained was purified by silica gel column chromatography (elution 30% EtOAc-hexanes) to give the title compound (0.110 g, 29.4%) as clear oil. $^1H$ NMR (400 MHz, DMSO-$d_6$, 60° C.): δ 12.08 (br s, 1H), 7.49 (br, 2H), 7.26-7.18 (m, 4H), 6.96-6.91 (m, 2H), 4.50 (s, 2H), 4.10 (s, 1H), 4.00 (d, J=6.4 Hz, 2H), 2.24 (t, J=7.2 Hz, 2H), 1.86-1.68 (m, 2H), 1.62-1.58 (m, 2H), 1.51-1.48 (m, 2H) 1.09 (d, J=6.4 Hz, 6H). LCMS (m/z): 402.1 $(M+1)^+$. HPLC: 95.32% (210 nm).

Example 6: Synthesis of 6-(2-((N-isopropyl-4-(trifluoromethoxy)benzamido)methyl)phenoxy)hexanoic acid

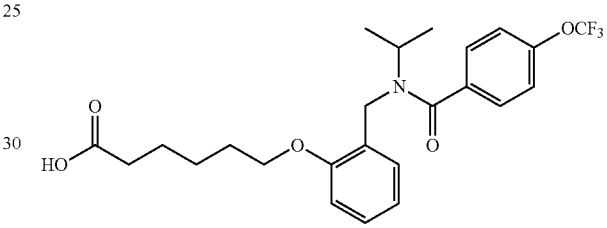

a) Synthesis of ethyl 6-(2-((N-isopropyl-4-(trifluoromethoxy)benzamido)methyl) phenoxy)hexanoate

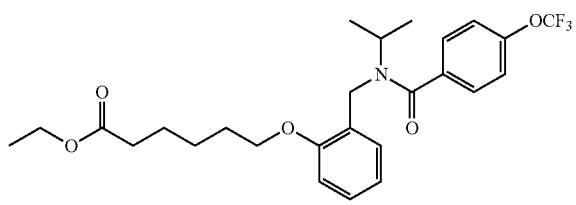 [SMILES: CCOC(=O)CCCCCOc1ccccc1CN(C(=O)c1ccc(OC(F)(F)F)cc1)C(C)C]

In a 50-mL round bottom flask, a stirred solution of methyl 6-(2-((isopropylamino)methyl)phenoxy)hexanoate of example I(b) (0.50 g, 1.63 mmol) in DCM (9 mL)-DMF (1 mL), was treated with 4-trifluoromethoxybenzoic acid (0.32 g, 1.55 mmol), HBTU (1.7 g, 4.65 mmol) and triethylamine (0.7 mL, 5.0 mmol) at rt under nitrogen atmosphere. The reaction mixture was stirred at rt for 3 h under nitrogen atmosphere. Upon completion of the reaction (TLC), the reaction mixture quenched with water and extracted with ethyl acetate (50 mL×3). The combined organic extract was washed with brine, dried over anhydrous $Na_2SO_4$ and concentrated under reduced pressure. The residue obtained was purified by silica gel column chromatography (gradient elution, 10-20% EtOAc-hexanes) to afford the title compound (0.312 g, 38.6%) as a clear oil. LCMS (m/z): 496 $(M+1)^+$.

b) Synthesis of 6-(2-((N-isopropyl-4-(trifluoromethoxy)benzamido)methyl)phenoxy) hexanoic acid

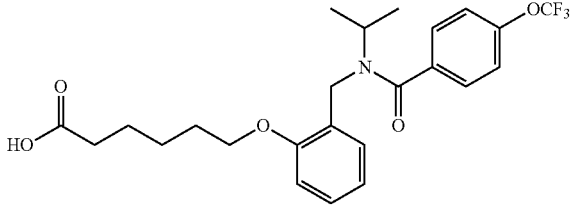 [SMILES: CC(C)N(Cc1ccccc1OCCCCCC(=O)O)C(=O)c1ccc(OC(F)(F)F)cc1]

In a 25-mL round bottom flask, ethyl 6-(2-((N-isopropyl-4-(trifluoromethoxy)benzamido) methyl)phenoxy)hexanoate (0.250 g, 0.50 mmol) was dissolved in THF (10 mL), water (5 mL) and EtOH (5 mL) mixture at it Lithium hydroxide monohydrate (0.636 mg, 1.51 mmol) was added to the above solution and the reaction mixture was stirred at rt for 18 h. Upon completion of the reaction (TLC), the reaction mixture was concentrated under reduced pressure and the residue obtained was diluted with water. The aqueous solution was acidified with 1N HCl and extracted with ethyl acetate (50 mL×3). The combined organic extract was washed with brine, dried over anhydrous $Na_2SO_4$ and concentrated under reduced pressure. The residue obtained was purified by silica gel column chromatography (elution 30% EtOAc-hexanes) to give the title compound (0.230 g, 97.5%) as clear oil. $^1$H NMR (400 MHz, DMSO-$d_6$, 60° C.): δ 11.9 (br, 1H), 7.56 (m, 2H), 7.44-7.35 (m, 2H), 7.28-7.15 (m, 2H), 7.00-6.88 (m, 2H), 4.52 (s, 2H), 4.21-4.04 (m, 1H), 4.00 (t, J=6.4 Hz, 2H), 2.24 (t, J=7.2 Hz, 2H), 1.78-1.75 (m, 2H), 1.63-1.58 (m, 2H), 1.53-1.42 (m, 2H), 1.11 (d, J=6.4 Hz, 6H). LCMS (m/z): 466.6 (M−1)$^+$. HPLC: 97.89% (210 nm).

Example 7: Synthesis of 6-(2-((4-(dimethylamino)-N-isopropylbenzamido)methyl)phenoxy)hexanoic acid

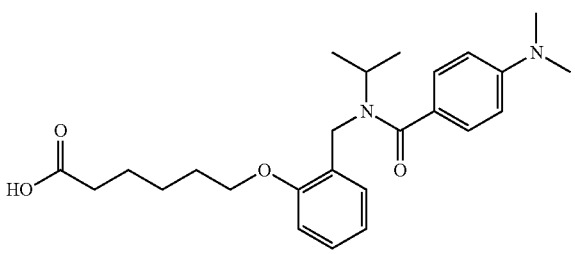 [SMILES: CC(C)N(Cc1ccccc1OCCCCCC(=O)O)C(=O)c1ccc(N(C)C)cc1]

The title compound (0.306 g) was prepared from methyl 6-(2-((isopropylamino)methyl)phenoxy)hexanoate (0.500 g, 1.6 mmol) of Example I(b) and 4-N,N-dimethyl amino benzoic acid (0.26 g, 1.57 mmol) following the procedure of Example-6. $^1$H NMR (400 MHz, DMSO-$d_6$, 60° C.): δ 7.32-7.25 (m, 2H), 7.24-7.14 (m, 2H), 7.00-6.87 (m, 2H), 6.71 (d, J=8.8 Hz, 2H), 4.51 (s, 2H), 4.25-4.21 (m, 1H), 4.02 (t, J=6.3 Hz, 2H), 2.94 (s, 6H), 2.23 (t, J=7.2 Hz, 2H), 1.78-1.73 (m, 2H), 1.62-1.56 (m, 2H), 1.53-1.42 (m, 2H), 1.09 (d, J=6.4 Hz, 6H). LCMS (m/z): 427.25 (M+1)$^+$. HPLC: 96.81% (210 nm).

Example 8: Synthesis of 6-(2-((4-Cyano-N-isopropylbenzamido)methyl)phenoxy)hexanoic acid

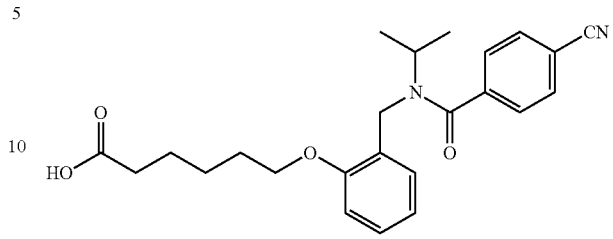

The title compound (0.070 g) was prepared from methyl 6-(2-((isopropylamino) methyl)phenoxy) hexanoate (0.50 g, 1.62 mmol) of Example I(b) and 4-cyanobenzoic acid (0.263 g, 1.79 mmol) following the procedure of Example-6 to afford the product. $^1$H NMR (400 MHz, DMSO-d6, 90° C.) δ 12.0 (br s, 1H), 7.97 (d, J=7.6 Hz, 2H), 7.77 (br, 0.8H), 7.69 (d, J=7.6 Hz, 2H), 7.49 (br, 0.9H), 7.24-1.18 (m, 3H), 6.99-6.91 (m, 3H), 4.55 (s, 2H), 4.42-4.32 (br, 1H), 4.03 (br, 2H), 3.84 (br, 2H), 2.24 (br, 2.8H), 1.79 (br, 2H), 1.65-1.41 (br, 6H), 1.33-1.17 (br, 3.5H), 1.04 (d, J=6 Hz, 6H). (NMR peaks were broad due to presence of rotamers). LCMS (m/z): 431.2 (M+Na)$^+$. HPLC=99.17% (210 nm).

Example 9: Synthesis of 6-(2-((N-isopropyl-4-methoxybenzamido)methyl)phenoxy)hexanoic acid

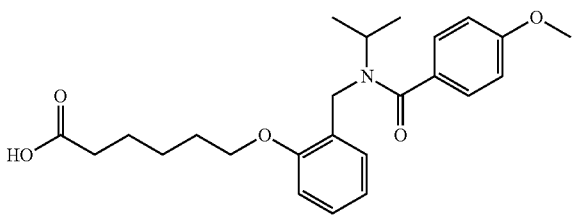 [SMILES: COc1ccc(C(=O)N(Cc2ccccc2OCCCCCC(=O)O)C(C)C)cc1]

The title compound (0.235 g) was prepared from methyl 6-(2-((isopropylamino) methyl)phenoxy)hexanoate (0.500 g, 1.62 mmol) of Example I(b) and 4-methoxybenzoic acid (0.271 g, 1.8 mmol) following the procedure of Example-6. $^1$H NMR (400 MHz, DMSO-$d_6$, 60° C.) δ 11.81 (s, 1H), 7.42-7.34 (m, 2H), 7.26-7.15 (m, 2H), 6.99-6.91 (m, 4H), 4.51 (s, 2H), 4.17-4.14 (m, 1H), 4.01 (t, J=6.0 Hz, 2H), 3.80 (s, 3H), 2.24 (t, J=7.2 Hz, 2H), 1.78-1.74 (m, 2H), 1.64-1.56 (m, 2H), 1.51-1.45 (m, 2H), 1.09 (d, J=6.4 Hz, 6H). LCMS (m/z): 431.2 (M+Na)$^+$. HPLC: 97.61% (210 nm).

Example 10: Synthesis of 6-(2-((4-chloro-N-isopropylbenzamido)methyl)phenoxy)hexanoic acid

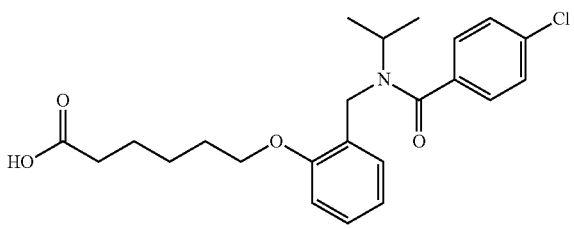 [SMILES: CC(C)N(Cc1ccccc1OCCCCCC(=O)O)C(=O)c1ccc(Cl)cc1]

The title compound (0.275 g) was prepared from methyl 6-(2-((isopropylamino)methyl) phenoxy)hexanoate (0.500 g, 1.62 mmol) of example I(b) and 4-chlorobenzoic acid (0.28 g, 1.8 mmol) following the procedure of Example-6. $^1$H NMR (400 MHz, DMSO-d$_6$, 60° C.): δ 7.47-7.45 (m, 4H), 7.24-7.18 (m, 2H), 6.96-6.91 (m, 2H), 4.50 (s, 2H), 4.18-3.95 (m, 3H), 2.24 (t, J=7.2 Hz, 2H), 1.77-1.72 (m, 2H), 1.64-1.47 (m, 4H), 1.09 (d, J=6.4 Hz, 6H). LCMS (m/z): 440.2 (M+Na)$^+$. HPLC: 97.5% (210 nm).

Example 11: Synthesis of 6-(2-((4-acetyl-N-isopropylbenzamido)methyl)phenoxy)hexanoic acid

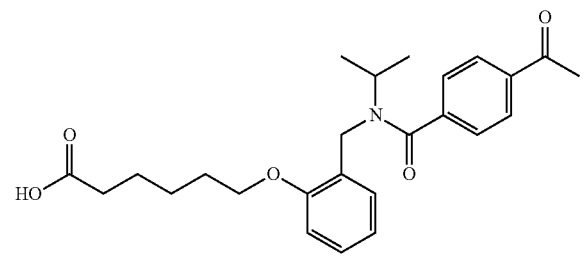 [SMILES: CC(=O)c1ccc(C(=O)N(Cc2ccccc2OCCCCCC(=O)O)C(C)C)cc1]

The title compound (0.150 g) was prepared from methyl 6-(2-((isopropylamino)methyl) phenoxy)hexanoate (0.50 g, 1.62 mmol) of Example I(b) and 4-acetyl benzoic acid (0.32 g, 1.95 mmol) using the procedure of Example-6. $^1$H NMR (400 MHz, DMSO-d$_6$, 60° C.): δ 11.84 (s, 1H), 8.07-7.95 (br, 2H), 7.56 (br, 2H), 7.30-7.18 (m, 2H), 6.95 (t, J=7.2 Hz, 2H), 4.53 (br s, 2H), 4.01 (br, 3H), 2.60 (s, 3H), 2.24 (t, J=7.2 Hz, 2H), 1.78-1.75 (m, 2H), 1.62-0.158 (m, 2H), 1.51-1.46 (m, 2H), 1.01 (br s, 6H). LCMS (m/z): 426.2 (M+1)$^+$. HPLC=95.21% (210 nm).

Example 12: Synthesis of 6-(2-((N-isopropyl-4-(methylsulfonyl)benzamido)methyl)phenoxy) hexanoic acid

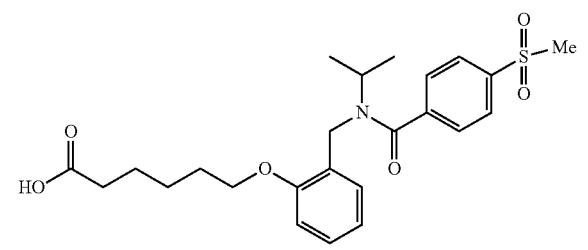 [SMILES: CC(C)N(Cc1ccccc1OCCCCCC(=O)O)C(=O)c1ccc(S(C)(=O)=O)cc1]

The title compound (0.130 g) was prepared from methyl 6-(2-((isopropylamino)methyl)phenoxy)hexanoate (0.5 g, 1.62 mmol) of example I(b) and 4-methane sulfonyl benzoic acid (0.39 g, 1.95 mmol) following the procedure of Example-6. $^1$H NMR (400 MHz, DMSO-d$_6$, 60° C.): δ 12.03 (br s, 1H), 7.94 (br, 2H), 7.63 (br, 2H), 7.23 (d, J=7.2 Hz, 1H), 7.17 (t, J=7.6 Hz, 1H), 6.91 (t, J=7.2 Hz, 2H), 4.54 (br, 2H), 4.01 (br, 3H), 3.18 (s, 3H), 2.21 (t, J=7.3 Hz, 2H), 1.72 (br, 2H), 1.62-1.59 (m, 2H), 1.48 (br, 2H), 1.08 (br s, 6H). LCMS (m/z): 462.2 (M+1)$^+$. HPLC: 98.89 (210 nm).

Example 13: Synthesis of 6-(2-((N-isopropyl-4-(pyrrolidin-1-yl)benzamido)methyl)phenoxy) hexanoic acid

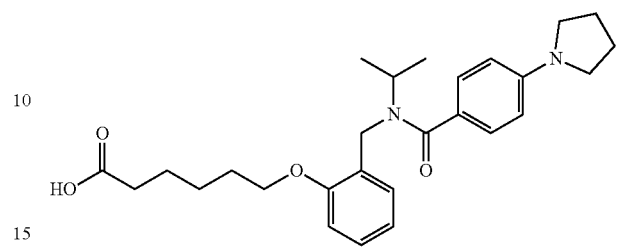

a) Synthesis of ethyl 6-(2-((4-bromo-N-isopropylbenzamido)methyl)phenoxy)hexanoate

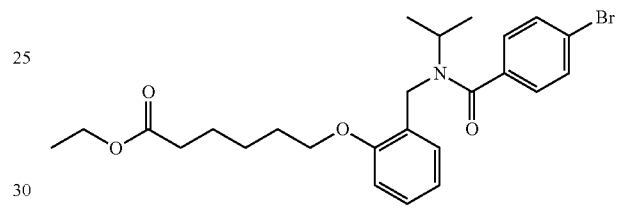

In a 25-mL round bottom flask, a stirred solution of ethyl 6-(2-((isopropylamino)methyl)phenoxy)hexanoate (0.76 g, 2.48 mmol) of example I(b) in DMF (2 mL), was treated sequentially with 4-bromo benzoic acid (0.500 g, 2.48 mmol), HBTU (2.81 g, 7.44 mmol) and triethylamine (0.78 g, 7.44 mmol) at rt under nitrogen atmosphere. The reaction mixture was stirred at rt for 3 h. Upon completion of the reaction (TLC), the reaction mixture was diluted with cold water and extracted with ethyl acetate (25 mL×2). The combined organic layer was washed with brine, dried over anhydrous Na$_2$SO$_4$ and concentrated under reduced pressure. The residue obtained was purified by silica gel column chromatography (elution 15% EtOAc-hexanes) to give title compound (0.660 g, 54.3%) as a clear oil. LCMS (m/z): 490.1 (M+1)$^+$.

b) Synthesis of ethyl 6-(2-((N-isopropyl-4-(pyrrolidin-1-yl)benzamido)methyl) phenoxy)hexanoate

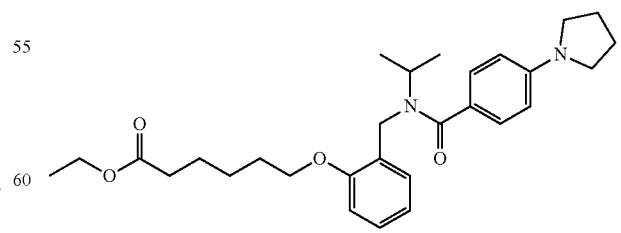

In a resealable reaction tube, the solution of ethyl 6-(2-((4-bromo-N-isopropylbenzamido) methyl)phenoxy) hexanoate (0.40 g, 0.81 mmol) in toluene (40 mL), was treated sequentially with pyrrolidine hydrochloride (0.115 g, 1.06 mmol), rac-BINAP (0.101 g, 0.16 mmol) and Cs$_2$CO$_3$ (1.32 g, 4.05 mmol) at rt under nitrogen atmosphere. The mixture was degassed by purging with argon gas and thereafter treated with Pd$_2$(dba)$_3$ (0.134 mg, 0.14 mmol) under atmosphere. The resulting reaction mixture was heated at 70° C. for 12 h. Upon completion of the reaction (TLC), the reaction mixture was cooled to rt and diluted with cold water before extracting with ethyl acetate (100 mL×3). The combined organic extract was washed with brine and concentrated under reduced pressure. The residue obtained was purified by silica gel column chromatography (gradient elution, 10-20% EtOAc-hexanes) to afford title compound (308 mg, 79.2%). LCMS (m/z): 481.1 (M+1)$^+$.

c) Synthesis of 6-(2-((N-isopropyl-4-(pyrrolidin-1-yl)benzamido)methyl)phenoxy) hexanoic acid

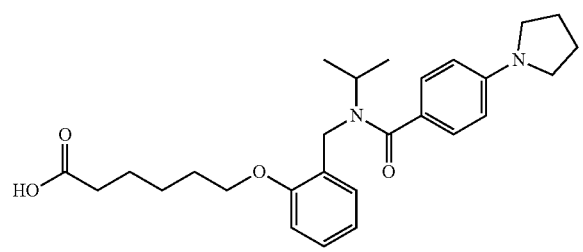 [SMILES: CC(C)N(Cc1ccccc1OCCCCCC(=O)O)C(=O)c1ccc(N2CCCC2)cc1]

In a 25-mL round bottom flask, ethyl 6-(2-((N-isopropyl-4-(pyrrolidin-1-yl)benzamido)methyl)phenoxy)hexanoate (0.30 g, 0.62 mmol) was dissolved in THF (10 mL)-water (3 mL)-EtOH (3 mL) mixture at rt. Lithium hydroxide monohydrate (78.7 mg, 1.87 mmol) was added to the above solution and the reaction mixture was stirred at rt for 12 h. Upon completion of the reaction (TLC), the reaction mixture was concentrated under reduced pressure and the residue obtained was diluted with water. The aqueous solution was acidified with 1N HCl and extracted with ethyl acetate (50 mL×3). The combined organic extract was washed with brine, dried over anhydrous Na$_2$SO$_4$ and concentrated under reduced pressure. The residue obtained was purified by silica gel column chromatography (elution 5% MeOH—CHCl$_3$) to give the title compound (120 mg, 42.5%) as off-white solid. $^1$H NMR (400 MHz, DMSO-d$_6$, 90° C.): δ 7.28 (d, J=8.0 Hz, 2H), 7.25-7.15 (m, 2H), 7.01-6.87 (m, 2H), 6.54 (d, J=8.0 Hz, 2H), 4.51 (s, 2H), 4.26-4.18 (m, 1H), 4.02 (t, J=6.0 Hz, 2H), 3.32-3.22 (m, 4H), 2.24 (t, J=7.2 Hz, 2H), 2.03-1.92 (m, 4H), 1.78-1.74 (m, 2H), 1.62-1.58 (m, 2H), 1.53-1.42 (m, 2H), 1.09 (d, J=6.4 Hz, 6H). LCMS (m/z): 453.4 (M+1)$^+$. HPLC: 97.99% (210 nm).

Example 14: Synthesis of 6-(2-((4-(Cyclopropylethynyl)-N-isopropylbenzamido)methyl)phenoxy) hexanoic acid a) Synthesis of ethyl 6-(2-((4-(cyclopropylethynyl)-N-isopropylbenzamido)methyl) phenoxy)hexanoate

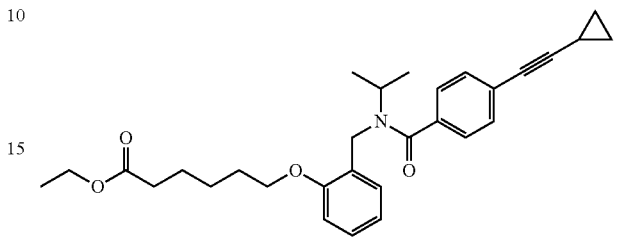

In a resealable tube, ethyl 6-(2-((4-bromo-N-isopropylbenzamido)methyl)phenoxy) hexanoate from example-13 (a) (0.40 g, 0.86 mmol), cyclopropyl acetylene (0.534 g, 8.03 mmol) CuI (0.015 g, 0.08 mmol), were dissolved in dry DMF (1 mL) at rt under nitrogen atmosphere. The solution was degassed and treated with PdCl$_2$(PPh$_3$)$_2$ (28.5 mg, 0.04 mmol) and triethyl amine (0.24 mL, 2.4 mmol) under argon atmosphere. The resulting mixture was heated at 60° C. for 24 h. Upon completion of the reaction (TLC), the reaction mixture was cooled to room temperature, diluted with cold water and extracted with EtOAc (3×50 mL). The combined organic extract was washed with brine and concentrated under reduced pressure. The residue obtained was purified by silica gel column chromatography and gradient elution with 10-20% EtOAc-hexanes gave the title compound (316 mg, 77.5%). LCMS (m/z): 476.3 (M+1)$^+$.

b) Synthesis of 6-(2-((4-(cyclopropylethynyl)-N-isopropylbenzamido)methyl)phenoxy) hexanoic acid

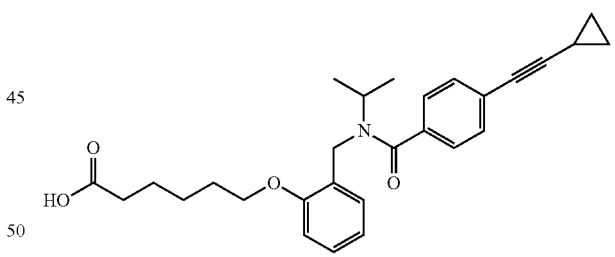 [SMILES: CCOC(=O)CCCCCOc1ccccc1CN(C(=O)c1ccc(C#CC2CC2)cc1)C(C)C]

In a 25-ml round bottom flask, ethyl 6-((4-(cyclopropylethynyl)-N-isopropylbenzamido)methyl)phenoxy)hexanoate (0.250 g, 0.52 mmol) was dissolved in THF (10 mL), water (3 mL) and ethanol (3 mL) mixture at rt. Lithium hydroxide monohydrate (0.066 mg, 1.57 mmol) was added to the above solution and the reaction mixture was stirred at rt for 12 h. Upon completion of the reaction (TLC), the reaction mixture was concentrated under reduced pressure and the residue obtained was diluted with water and acidified with 1N HCl and extracted with ethyl acetate (50 mL×3). The combined organic layer was washed with brine, dried over anhydrous Na$_2$SO$_4$ and concentrated under reduced pressure. The residue obtained was purified by preparative HPLC to give the title compound (170 mg, 72.21%). $^1$H NMR (400 MHz, DMSO-d$_6$, 60° C.): δ 11.88

(br s, 1H), 7.38-7.34 (m, 4H), 7.27-7.15 (m, 2H), 6.99-6.87 (m, 2H), 4.50 (s, 2H), 4.15-4.03 (m, 1H), 4.00 (t, J=6.4 Hz, 2H), 2.24 (t, J=7.2 Hz, 2H), 1.76-1.74 (m, 2H), 1.66-1.41 (m, 4H), 1.08 (d, J=6.4 Hz, 6H), 0.93-0.86 (m, 2H), 0.81-0.69 (m, 2H). LCMS (m/z): 448.1 (M+1)⁺. HPLC: 99.49% (210 nm).

Example 15: Synthesis of 6-(2-((4-Cyclopropoxy-N-isopropylbenzamido)methyl)phenoxy)hexanoic acid

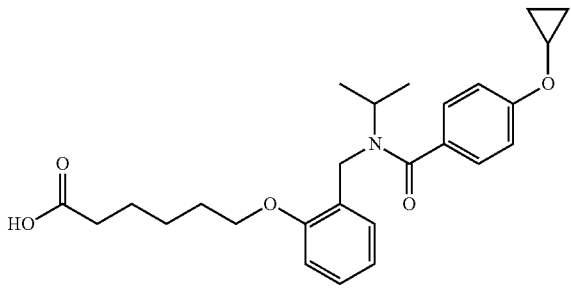 [SMILES: CC(C)N(Cc1ccccc1OCCCCCC(=O)O)C(=O)c1ccc(OC2CC2)cc1]

a) Synthesis of methyl 4-cyclopropoxybenzoate

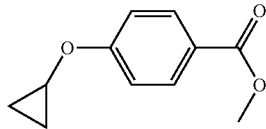

In a resealable reaction tube, methyl 4-hydroxybenzoate (2.0 g, 13.14 mmol) and bromocyclopropane (5.26 g, 43.47 mmol) were dissolved in dry DMF (10 mL) at rt under nitrogen atmosphere. K$_2$CO$_3$ (6.0 g, 43.47 mmol) was added to the above solution and resulting reaction mixture was heated in microwave at 140° C. for 2 h. Upon completion of reaction (TLC), the reaction mixture was cooled to rt and diluted with water, before extracting diethyl ether (3×100 mL). The combined organic extract was washed with brine and concentrated under reduced pressure. The residue obtained was purified by silica gel column chromatography (eluting with 0-10% EtOAc/hexanes) to afford title compound (520 mg). LCMS (m/z): 192.9 (M+1)+.

b) Synthesis of 4-cyclopropoxybenzoic acid

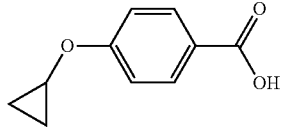 [SMILES: O=C(O)c1ccc(OC2CC2)cc1]

The stirred solution of methyl 4-cyclopropoxybenzoate (0.40 g, 2.08 mmol) in THF (10 mL)-MeOH (2 mL) was treated with 1N NaOH (10 mL) at rt. The reaction mixture was stirred at rt until completion of the reaction (TLC). The reaction mixture was concentrated under reduced pressure; residue obtained was acidified with 1N HCl and extracted with EtOAc (50 mL×3). The combined organic extract washed with brine and concentrated under reduced pressure to afford title compound which was used in next step without any further purifications (178 mg, crude).

c) Synthesis of ethyl 6-(2-((4-cyclopropoxy-N-isopropylbenzamido)methyl)phenoxy) hexanoate

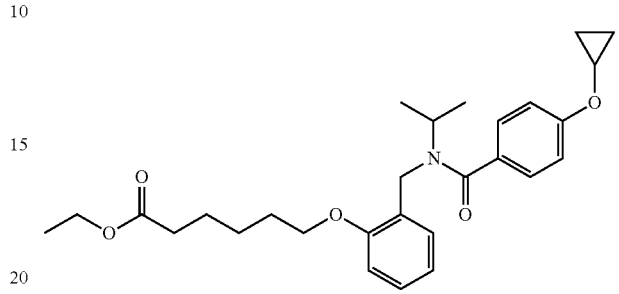

In a 50-mL round bottom flask, a stirred solution of ethyl 6-(2-((isopropylamino)methyl) phenoxy)hexanoate (0.27 g, 0.87 mmol) from example 1(b) in DMF (5 mL) was treated sequentially with 4-cyclopropoxybenzoic acid (0.150 g, 0.87 mmol), EDCI.HCl (0.336 g, 1.75 mmol), HOBt (0.239 g, 1.82 mmol), and triethylamine (0.88 mL, 2.64 mmol) at rt under nitrogen atmosphere. The reaction mixture was stirred at rt for 12 h. Upon completion of the reaction (TLC), the reaction mixture was diluted with cold water and extracted with ethyl acetate (50 mL×3). The combined organic extract was washed with brine, dried over anhydrous Na$_2$SO$_4$ and concentrated under reduced pressure. The residue obtained was purified by silica gel column chromatography (elution 20% EtOAc-hexanes) to afford the title compound (130 mg, 31.7%) as clear oil. LCMS (m/z): 468.2 (M+1)⁺.

d) Synthesis of 6-(2-((4-cyclopropoxy-N-isopropylbenzamido)methyl)phenoxy)hexanoic acid

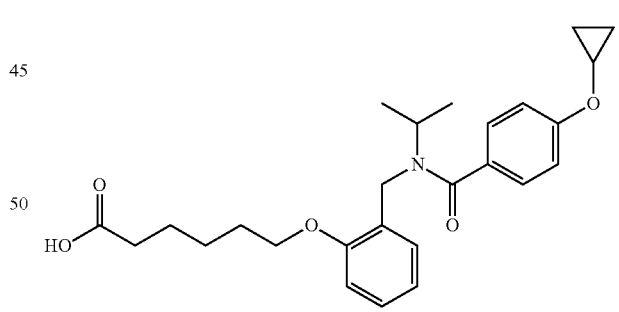

In a 25-mL round bottom flask, methyl 6-(2-((4-cyclopropoxy-N-isopropylbenzamido)methyl)phenoxy)hexanoate (0.10 g, 0.21 mmol) was dissolved in F (3 mL)-water (1 mL)-EtOH (1 mL) mixture at rt. Lithium hydroxide monohydrate (0.027 g, 0.63 mmol) was added to the above solution and the reaction mixture was stirred at it for 12 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous Na$_2$SO$_4$ and concentrated under reduced pressure. The residue obtained was purified by preparative HPLC to give the title compound (56 mg, 60.6%) as off white solid. $^1$H NMR (400 MHz, DMSO-$d_6$, 60° C.) δ 7.42-7.32 (m, 2H), 7.26-7.14 (m, 2H), 7.12-7.03 (m, 2H), 7.03-6.85 (m, 2H), 4.51 (s, 2H), 4.21-4.13 (m, 1H), 4.01 (t, J=6.0 Hz, 2H), 3.88-3.86 (m, 1H), 2.24 (t, J=7.2 Hz, 2H), 1.79-1.74 (m, 2H), 1.62-1.58 (m, 2H), 1.49-1.45 (m, 2H), 1.09 (d, J=6.4 Hz, 6H), 0.87-0.75 (m, 2H), 0.71-0.62 (m, 2H). LCMS (m/z): 440.2 (M+1)$^+$. HPLC=98.85% (210 nm).

Example 16: Synthesis of N-(2-(4-(2H-Tetrazol-5-yl)butoxy)benzyl)-4-(furan-2-yl)-N-isopropylbenzamide

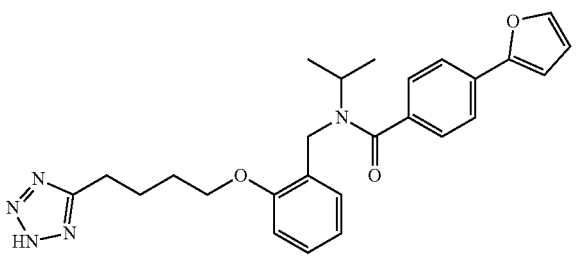 [SMILES: CC(C)N(Cc1ccccc1OCCCCc1nn[nH]n1)C(=O)c1ccc(-c2ccco2)cc1]

a) Synthesis of 2-((isopropylamino)methyl)phenol

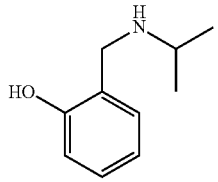

Isopropyl amine (2.65 g, 44.8 mmol) and salicylaldehyde (5.0 g, 40.9 mmol) were dissolved in 1,2-dichloroethane (50 mL) at rt. AcOH (16 mL) was added slowly to the above solution (exothermic). Sodium triacetoxyborohydride (19.0 g, 89.6 mmol) was added in portions to the mixture and resulting reaction mixture was stirred at rt for 4 h under nitrogen atmosphere. The reaction mixture was quenched by adding saturated sodium carbonate solution, and extracted with ethyl acetate. The ethyl acetate extract was washed with brine and dried over anhydrous $Na_2SO_4$ and concentrated under reduced pressure to afford the title compound (6.70 g, 88.7%). LCMS (m/z): 349.9 (M+1)$^+$.

b) Synthesis of 4-bromo-N-(2-hydroxybenzyl)-N-isopropylbenzamide

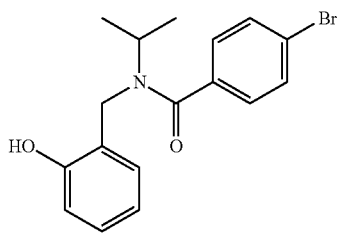 [SMILES: CC(C)N(Cc1ccccc1O)C(=O)c1ccc(Br)cc1]

In 100-mL round bottom flask, EDCI.HCl (9.0 g, 47 mmol) and DIPEA (17 mL, 97.6 mmol) were added sequentially to a solution of 2-((isopropylamino)methyl)phenol (6.50 g, 39.3 mmol), 4-bromobenzoic acid (9.50 g, 47.3 mmol) and HOBt (7.20 g, 53.3 mmol) in dimethylformamide (65 mL) at rt under nitrogen atmosphere. The resulting reaction mixture was stirred at rt for 16 h under nitrogen atmosphere. The mixture was concentrated under reduced pressure and residue obtained was purified by silica gel column chromatography (elution 10% EtOAc-hexanes) to give title compound (6.08 g, 46.1%). LCMS (m/z): 336.1 (M+1)$^+$.

c) Synthesis of 4-(furan-2-yl)-N-(2-hydroxybenzyl)-N-isopropylbenzamide

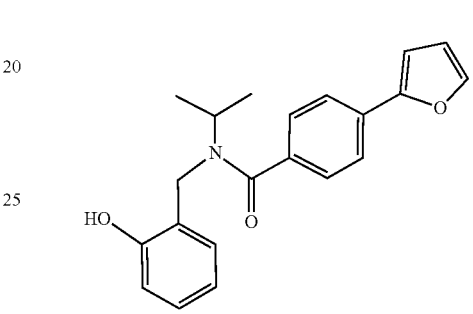

In a 50-mL round bottom flask, a stirred suspension of 4-bromo-N-(2-hydroxybenzyl)-N-isopropylbenzamide (0.70 g, 2 mmol), furan-2-boronic acid (0.269 g, 2.4 mmol) and $Na_2CO_3$ (0.533 g, 5 mmol) in DME (9 mL)-water (1 mL) was degassed with argon gas. Pd(dppf)Cl$_2$.DCM (0.082 g, 0.1 mmol) was added to the above mixture at rt under nitrogen atmosphere. The resulting reaction mixture was refluxed for 4 h under nitrogen atmosphere. The reaction mixture was cooled to rt, filtered and residue washed with ethyl acetate. The combined filtrate was concentrated under reduced pressure. The residue obtained was purified by silica gel column chromatography (gradient elution 10-20% EtOAc-hexanes) to afford title compound (512 mg, 76.4%). LCMS (m/z): 336.1 (M+1)$^+$.

d) Synthesis of N-(2-(4-cyanobutoxy)benzyl)-4-(furan-2-yl)-N-isopropylbenzamide

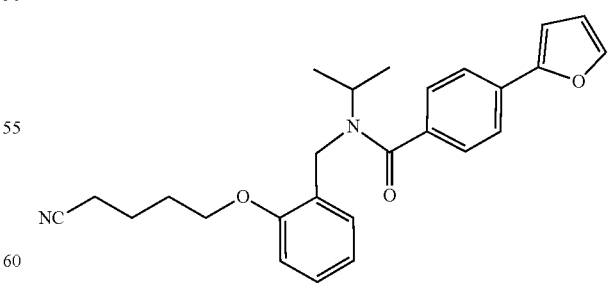

In 25-mL round bottom flask, a solution of 4-(furan-2-yl)-N-(2-hydroxybenzyl)-N-isopropylbenzamide (0.50 g, 1.49 mmol) in DMF (7.5 mL) was treated with potassium carbonate (0.308 g, 2.2 mmol) and 5-bromopentane nitrile (0.289 g, 1.7 mmol) at rt under nitrogen atmosphere. The reaction mixture was heated at 80° C. for 3 h. Upon completion of the reaction (TLC), the reaction mixture was cooled to rt, filtered and washed with EtOAc. The combined filtrate was concentrated under reduced pressure. The residue obtained was diluted water (50 mL) and extracted with EtOAc (200 mL). The organic layer was washed with brine, dried over anhydrous Na$_2$SO$_4$ and concentrated under reduced pressure. The residue obtained was purified by silica gel column chromatography (elution 10% EtOAc-hexanes) to give title compound (0.599 g, 96.7%). LCMS (m/z): 417.1 (M+1)$^+$.

e) Synthesis of N-(2-(4-(2H-tetrazol-5-yl)butoxy) benzyl)-4-(furan-2-yl)-N-isopropyl benzamide

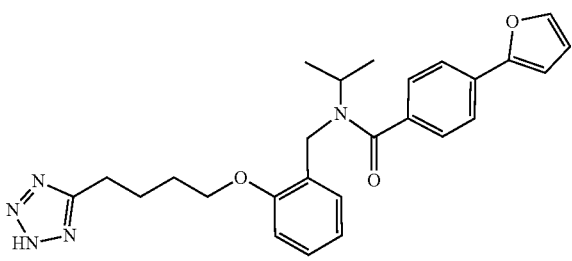 [SMILES: CC(C)N(Cc1ccccc1OCCCCc1nn[nH]n1)C(=O)c1ccc(-c2ccco2)cc1]

In a 25-mL resealable reaction tube, a solution of N-(2-(4-cyanobutoxy)benzyl)-4-(furan-2-yl)-N-isopropylbenzamide (0.50 g, 1.2 mmol) in DMF (7.5 mL) was treated with NaN$_3$ (0.39 g, 6.0 mmol) and triethylamine hydrochloride (0.494 g, 3.58 mmol) at rt under nitrogen atmosphere. The reaction mixture was stirred 135° C. for 24 h. Upon completion of the reaction (TLC), the reaction mixture was cooled to rt and neutralized with saturated Na$_2$CO$_3$, before extracting with EtOAc (25 mL×3). The combined organic extract was washed with water, brine, dried over anhydrous Na$_2$SO$_4$ and concentrated under reduced pressure. The residue obtained was purified by preparative HPLC to give the title compound (120 mg, 21.8%). $^1$H NMR (400 MHz, DMSO-d$_6$, 60° C.): δ 7.76-7.72 (m, 3H), 7.47 (d, J=7.6 Hz, 2H), 7.31-7.15 (m, 2H), 7.00-6.92 (m, 3H), 6.61 (br, 1H), 4.52 (s, 2H), 4.09 (d, J=37.6 Hz, 3H), 2.95 (t, J=7.2 Hz, 2H), 2.00-1.71 (m, 4H), 1.09 (d, J=6.4 Hz, 6H). LCMS (m/z): 482.1 (M+Na)$^+$. HPLC: 99.3% (210 nm).

Example 17: 5-(2-((4-(Furan-2-yl)-N-isopropylbenzamido)methyl)phenoxy)pentanoic acid

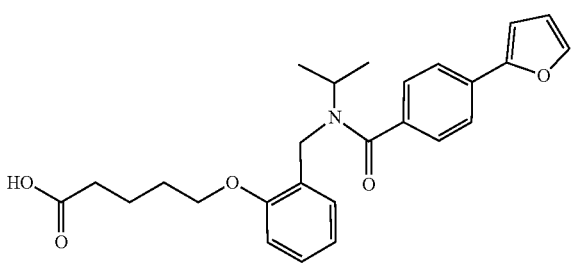 [SMILES: CC(C)N(Cc1ccccc1OCCCCC(=O)O)C(=O)c1ccc(-c2ccco2)cc1]

a) Synthesis of ethyl 5-(2-((4-(furan-2-yl)-N-isopropylbenzamido)methyl)phenoxy) pentanoate

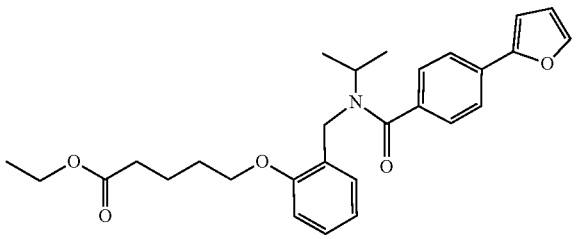 [SMILES: CCOC(=O)CCCCOc1ccccc1CN(C(=O)c1ccc(-c2ccco2)cc1)C(C)C]

In a 25-mL round bottom flask, a stirred solution of 4-(furan-2-yl)-N-(2-hydroxybenzyl)-N-isopropylbenzamide (0.30 g, 0.895 mmol) of example 16(c) in DMF (5 mL) was treated with potassium carbonate (0.148 g, 1.09 mmol) and ethyl 5-bromopentanoate (0.205 g, 0.985 mmol) at rt under nitrogen atmosphere. The reaction mixture was heated at 90° C. for 18 h under nitrogen atmosphere. Upon completion of the reaction (TLC), the reaction mixture was cooled at rt, diluted with cold water and extracted with ethyl acetate (10 mL×2). The combined organic extract was washed with water, brine, dried over anhydrous Na$_2$SO$_4$ and concentrated under reduced pressure. The residue obtained was purified by silica gel column chromatography (elution 30% EtOAc-hexanes) to give title compound (0.31 g, 74.8%) as clear oil. LCMS (m/z): 464.3 (M+1)$^+$.

b) Synthesis of 5-(2-((4-(furan-2-yl)-N-isopropylbenzamido)methyl)phenoxy)pentanoic acid

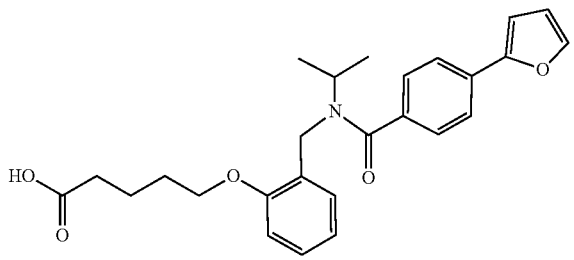 [SMILES: CC(C)N(Cc1ccccc1OCCCCC(=O)O)C(=O)c1ccc(-c2ccco2)cc1]

In a 25-mL round bottom flask, ethyl 5-(2-((4-(furan-2-yl)-N-isopropylbenzamido) methyl)phenoxy)pentanoate (0.30 g, 0.64 mmol) was dissolved in THF (3 mL)-water (3 mL) at rt Lithium hydroxide monohydrate (0.135 g, 3.23 mmol) was added to the above solution and the reaction mixture was stirred at rt for 18 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous Na$_2$SO$_4$ and concentrated under reduced pressure. The residue obtained was purified by preparative HPLC to give the title compound (0.111 g, 39.4%) as sticky liquid. $^1$H NMR (400 MHz, DMSO-d$_6$, 60° C.): δ 11.87 (s, 1H), 7.83-7.74 (m, 3H), 7.51 (d, J=7.6 Hz, 2H), 7.33-7.20 (m, 2H), 7.06-6.93 (m, 3H), 6.65 (dd, J=3.2, 1.6 Hz, 1H), 4.58 (s, 2H), 4.19 (br, 1H), 4.06 (t, J=6.0 Hz, 2H), 2.35 (t, J=6.8 Hz, 2H), 1.92-1.65 (m, 4H), 1.15 (d, J=6.4 Hz, 6H). LCMS (m/z): 436.5 (M+1)⁺. HPLC: 98.85% (210 nm).

Example 18: 7-(2-((4-(Furan-2-yl)-N-isopropylbenzamido)methyl)phenoxy)heptanoic acid

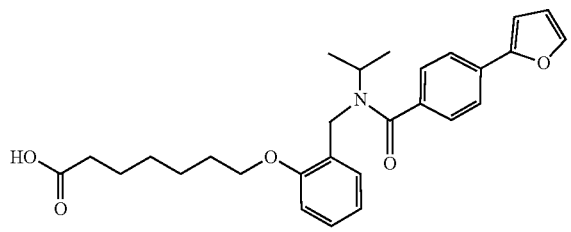 [SMILES: CC(C)N(Cc1ccccc1OCCCCCCC(=O)O)C(=O)c1ccc(-c2ccco2)cc1]

a) Synthesis of ethyl 7-(2-((4-(furan-2-yl)-N-isopropylbenzamido)methyl)phenoxy) heptanoate

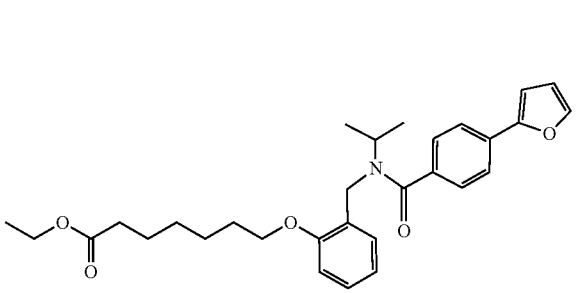 [SMILES: CCOC(=O)CCCCCCOc1ccccc1CN(C(=O)c1ccc(-c2ccco2)cc1)C(C)C]

In a 25-mL round bottom flask, a stirred solution of 4-(furan-2-yl)-N-(2-hydroxybenzyl)-N-isopropylbenzamide (0.450 g, 1.34 mmol) of example 16(c) in DMF (5 mL) at rt under reduced pressure. Potassium carbonate (0.222 g, 1.60 mmol) and ethyl 7-bromoheptanoate (0.35 g, 1.67 mmol) were added at the above solution at rt under nitrogen atmosphere. The reaction mixture was heated at 90° C. for 4 h. Upon completion of the reaction (TLC), the reaction mixture was cooled to rt, diluted with cold water and extracted with ethyl acetate (30 mL×2). The combined organic extract was washed with brine, dried over anhydrous Na₂SO₄ and concentrated under reduced pressure. The residue obtained was purified by silica gel column chromatography (elution 10% EtOAc-hexanes) to give title compound (0.39 g, 63%) as clear oil. LCMS (m/z): 492.1 (M+1)⁺.

b) Synthesis of 7-(2-((4-(furan-2-yl)-N-isopropylbenzamido)methyl)phenoxy)heptanoic acid

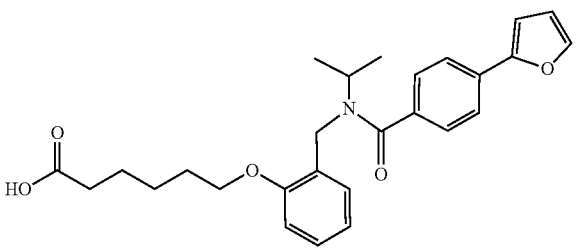 [SMILES: CC(C)N(Cc1ccccc1OCCCCCC(=O)O)C(=O)c1ccc(-c2ccco2)cc1]

In a 25-mL round bottom flask, methyl 7-(2-((4-(furan-2-yl)-N-isopropylbenzamido) methyl)phenoxy)heptanoate (0.39 g, 0.79 mmol) was dissolved in THF (3 mL)-water (3 mL) at rt. Lithium hydroxide monohydrate (0.266 g, 6.35 mmol) was added to the above solution and the reaction mixture was stirred at rt for 18 h. Upon completion of the reaction (TLC), the reaction mixture was concentrated under reduced pressure and the residue obtained was diluted with water. The aqueous solution was washed with diethyl ether (25 mL) and acidified with 1N HCl. The solid precipitated was filtered, washed with n-pentane and dried under reduced pressure to give the title compound (0.209 g, 57.1%). ¹H NMR (400 MHz, DMSO-d₆, 60° C.) δ 7.81-7.67 (m, 3H), 7.46 (d, J=7.6 Hz, 2H), 7.26 (d, J=7.2 Hz, 1H), 7.20 (t, J=7.2 Hz, 1H), 7.05-6.86 (m, 3H), 6.61 (dd, J=3.2, 1.6 Hz, 1H), 4.53 (s, 2H), 4.16 (br, 1H), 4.01 (t, J=6.3 Hz, 2H), 2.21 (t, J=7.2 Hz, 2H), 1.80-1.72 (m, 2H), 1.56-1.51 (m, 2H), 1.49-1.30 (m, 4H), 1.11 (d, J=6.4 Hz, 6H). LCMS (m/z): 486.2 (M+Na)⁺. HPLC: 96.32% (210 nm).

Example 19: 3-(2-(2-((4-(Furan-2-yl)-N-isopropylbenzamido)methyl)phenoxy)ethoxy)propanoic acid

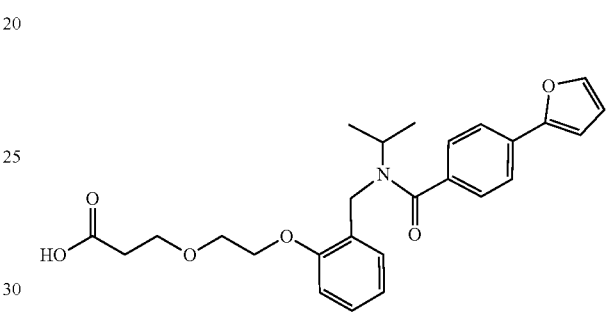

a) Synthesis of ethyl 3-(2-(benzyloxy)ethoxy)propanoate

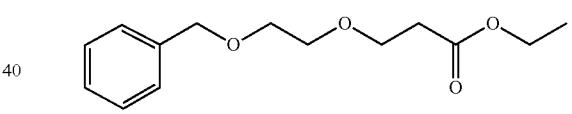

In a 250-mL round bottom flask, a stirred solution of 2-(benzyloxy)ethanol (9.0 g, 59.1 mmol) in of anhydrous THF (100 mL), was treated with ethyl propenoate (5.62 g, 49.2 mmol) and sodium metal (0.0013 g, 0.591 mmol) at rt under nitrogen atmosphere. The reaction mixture was stirred at rt for 18 h. Upon completion of the reaction (TLC), the reaction mixture quenched with cold water and extracted with ethyl acetate (250 mL×2). The combined organic extract was washed with brine, dried over anhydrous Na₂SO₄ and concentrated under reduced pressure. The residue obtained was purified by silica gel column chromatography and eluting with 10% EtOAc-hexanes gave title compound (2.51 g, 16.8%) as a clear oil. LCMS (m/z): 253.1 (M+1)⁺.

b) Synthesis of ethyl 3-(2-hydroxyethoxy)propanoate

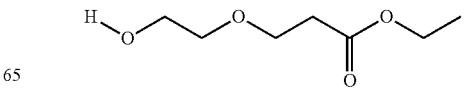

In a 100-mL round bottom flask, a stirred solution of ethyl 3-(2-(benzyloxy) ethoxy)propanoate (2.0 g, 7.93 mmol) in 20 mL of EtOAc, was treated with palladium on carbon (10 wt %, activated carbon support, 0.50 g) under nitrogen atmosphere. The stirred reaction mixture was hydrogenated (balloon pressure) at rt for 4 h. Upon completion of the reaction (TLC), the reaction mixture was filtered over celite bed and washed with ethyl acetate (25 mL×2). The combined filtrate was concentrated under reduced pressure to give title compound as clear oil. The crude product was taken to next step without any purification. (1.203 g). LCMS (ESI, m/z): 163.0 (M+1)$^+$.

c) Synthesis of ethyl 3-(2-bromoethoxy)propanoate

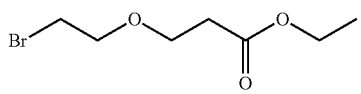

In a 25-mL round bottom flask, a stirred solution of ethyl 3-(2-hydroxyethoxy)propanoate (0.20 g, 1.23 mmol) in of dry THF (5 mL) was treated sequentially with triphenylphosphine (0.386 g, 1.47 mmol) and carbon tetrabromide (0.614 g, 1.85 mmol) at rt under nitrogen atmosphere. The reaction mixture was stirred at rt for 3 h. Upon completion of the reaction (TLC), the reaction mixture quenched with cold water and extracted with ethyl acetate (10 mL×2). The combined organic extract was washed with brine, dried over anhydrous Na$_2$SO$_4$ and concentrated under reduced pressure. The residue obtained was purified by silica gel column chromatography (elution 10% EtOAc-hexanes) to afford the title product as clear oil. (0.150 g, 54.1%). LCMS (m/z): 226.9 (M+2)$^+$.

d) Synthesis of ethyl 3-(2-(2-((4-(furan-2-yl)-N-isopropylbenzamido)methyl)phenoxy) ethoxy)propanoate

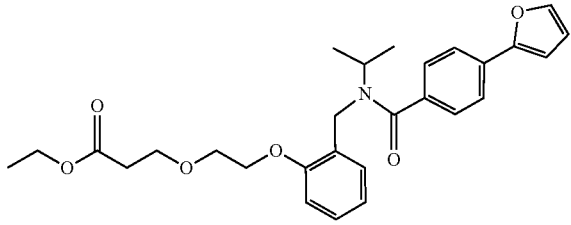 [SMILES: CCOC(=O)CCOCCOc1ccccc1CN(C(=O)c1ccc(-c2ccco2)cc1)C(C)C]

In a 25-mL round bottom flask, a stirred solution of 4-(furan-2-yl)-N-(2-hydroxybenzyl)-N-isopropylbenzamide (0.50 g, 1.49 mmol) of Example 16c in DMF (5 mL) was treated with potassium carbonate (0.247 g, 1.78 mmol) and ethyl 3-(2-bromoethoxy)propanoate (0.369 g, 1.63 mmol) at rt under nitrogen atmosphere. The reaction mixture was heated at 90° C. for 18 h. Upon completion of the reaction (TLC), the reaction mass cooled to rt, diluted with cold water and extracted with ethyl acetate (10 mL×2). The combined organic extract was washed with water, brine, dried over anhydrous Na$_2$SO$_4$ and concentrated under reduced pressure. The residue obtained was purified by silica gel column chromatography (elution 30% EtOAc-hexanes) to afford the title compound (0.421 g, 59%) as a clear oil. LCMS (m/z): 480 (M+1)$^+$.

e) Synthesis of 3-(2-(2-((4-(furan-2-yl)-N-isopropylbenzamido)methyl)phenoxy)ethoxy) propanoic acid

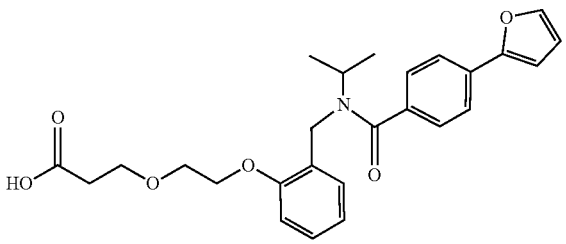 [SMILES: CC(C)N(Cc1ccccc1OCCOCCC(=O)O)C(=O)c1ccc(-c2ccco2)cc1]

In a 25-mL round bottom flask, ethyl 3-(2-((4-(furan-2-yl)-N-isopropylbenzamido)methyl)phenoxy)ethoxy)propanoate (0.40 g, 0.83 mmol) was dissolved in THF (4 mL)-water (4 mL) at rt. Lithium hydroxide monohydrate (0.174 g, 4.1 mmol) was added to the above solution and the reaction mixture was stirred at rt for 18 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous Na$_2$SO$_4$ and concentrated under reduced pressure. The residue obtained was purified by preparative HPLC to give the title compound (0.099 g, 26.5%) as pale yellow solid. $^1$H NMR (400 MHz, DMSO-d$_6$, 60° C.): δ 7.80-7.78 (m, 3H), 7.52 (d, J=8.0 Hz, 2H), 7.36-7.18 (m, 2H), 7.08-6.93 (m, 3H), 6.65 (t, J=2.4 Hz, 1H), 4.59 (s, 2H), 4.16 (br, 3H), 3.74 (m, 4H), 2.28 (t, J=7.2 Hz, 2H), 1.14 (d, J=6.4 Hz, 6H). LCMS (m/z): 452.3 (M+1)$^+$. HPLC: 96.88% (210 nm).

Example 20: 2-(3-(2-((4-(Furan-2-yl)-N-isopropylbenzamido)methyl)phenoxy)propoxy)acetic acid

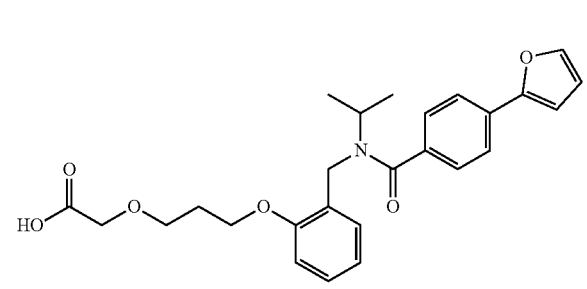 [SMILES: CC(C)N(Cc1ccccc1OCCCOCC(=O)O)C(=O)c1ccc(-c2ccco2)cc1]

a) Synthesis of ethyl 2-(3-hydroxypropoxy) acetate

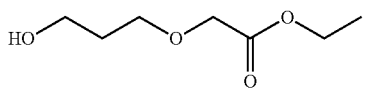

In a 50-mL round bottom flask, a stirred solution of ethyl 3-diazo-2-oxo propanoate (1.08 ml, 7.77 mmol) was treated with catalytic amount of rhodium diacetate (0.02 g) under nitrogen atmosphere. The reaction mixture was cooled to 0° C. and propane-1,3-diol (10 mL) was added drop wise at the same temperature. The reaction mixture was stirred at rt for 3 days. Upon completion of the reaction (TLC), the reaction mixture quenched with water and extracted with ethyl acetate (100 mL×2). The combined organic extract was washed with brine, dried over anhydrous Na$_2$SO$_4$ and concentrated under reduced pressure. The residue obtained was purified by silica gel column chromatography and eluting with 50% EtOAc-hexanes afforded the title product (1.10 g, 88%) as clear oil. LCMS (m/z): 163.2 (M+1)$^+$.

b) Synthesis of ethyl 2-(3-bromopropoxy) acetate

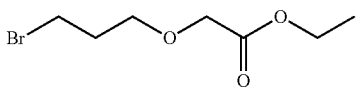

In a 50-mL round bottom flask, a stirred solution of ethyl 2-(3-hydroxypropoxy)acetate (1.0 g, 6.17 mmol) in THF (20 mL) was treated with PPh$_3$ (1.93 g, 7.40 mmol) and CBr$_4$ (3.0 g, 9.25 mmol) at rt under nitrogen atmosphere. The reaction mixture was stirred at rt for 3 h under nitrogen atmosphere. Upon completion of the reaction (TLC), the reaction mixture was quenched with cold water and extracted with ethyl acetate (100 mL×2). The combined organic extract was washed with brine, dried over anhydrous Na$_2$SO$_4$ and concentrated under reduced pressure. The residue obtained was purified by silica gel column chromatography (elution with 10% EtOAc-hexanes) to afford the title product as clear oil (0.688 g, 50%). LCMS (m/z): 224 (M+1)$^+$.

c) Synthesis of ethyl 2-(3-(2-((4-(furan-2-yl)-N-isopropylbenzamido)methyl)phenoxy) propoxy) acetate

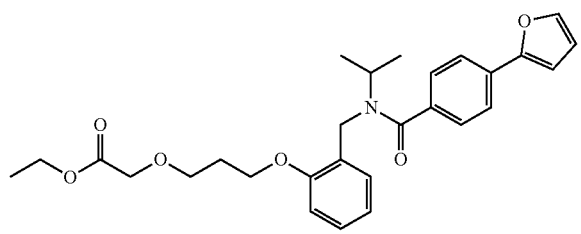 [SMILES: CCOC(=O)COCCCOc1ccccc1CN(C(=O)c1ccc(-c2ccco2)cc1)C(C)C]

A solution of 4-(furan-2-yl)-N-(2-hydroxybenzyl)-N-isopropylbenzamide (0.30 g, 0.88 mmol) of example 16c in DMF (5 mL) was treated with potassium carbonate (0.183 g, 1.3 mmol) and ethyl 2-(3-bromopropoxy)acetate (0.22 g, 0.98 mmol) at rt under nitrogen atmosphere. The reaction mixture was heated at 80° C. for 3 h. Upon completion of the reaction (TLC), the reaction mixture was filtered and washed with EtOAc. The combined filtrate was concentrated under reduced pressure. The residue obtained was diluted with cold water (50 mL) and extracted with EtOAc (200 mL). The organic extract was washed with brine, dried over anhydrous Na$_2$SO$_4$ and concentrated under reduced pressure. The residue obtained was purified by silica gel column chromatography (elution 30% EtOAc-hexanes) to give the title compound (0.295 g, 70%). LCMS (m/z): 480.3 (M+1)$^+$.

d) Synthesis of 2-(3-(2-((4-(furan-2-yl)-N-isopropylbenzamido)methyl)phenoxy)propoxy) acetic acid

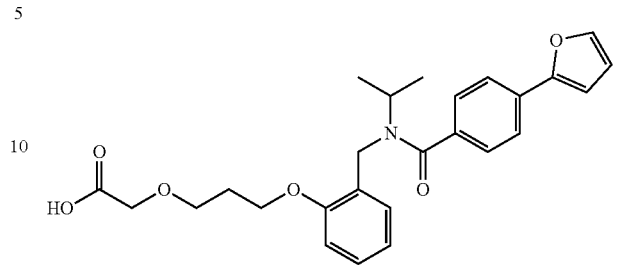

In a 50-mL round bottom flask, ethyl 2-(3-(2-((4-(furan-2-yl)-N-isopropylbenzamido) methyl)phenoxy)ac-etate (0.47 g, 0.98 mmol) was dissolved in THF (5 mL)-water (3 mL) at rt. Lithium hydroxide monohydrate (0.206 g, 4.9 mmol) was added to the above solution and the reaction mixture was stirred at rt for 18 h. Upon completion of the reaction (TLC), the reaction mixture was concentrated under reduced pressure and the residue obtained was diluted with cold water and washed with diethyl ether. The aqueous solution was acidified with 2N HCl and extracted with ethyl acetate (20 mL×3). The combined organic extract was washed with brine, dried over anhydrous Na$_2$SO$_4$ and concentrated under reduced pressure. The residue obtained was purified by silica gel column chromatography (elution 100% EtOAc) to give the title compound (0.205 g, 46.4%). $^1$H NMR (400 MHz, DMSO-d6, 60° C.) δ 12.2 (br s, 1H), 7.75-7.73 (m, 3H), 7.48 (d, J=8.0 Hz, 2H), 6.99-6.95 (m, 3H), 6.61-6.60 (m, 1H), 4.53 (s, 2H), 4.12-4.08 (m, 3H), 4.0 (s, 2H), 3.68 3.61 (m, 2H), 2.05-1.94 (m, 2H), 1.1 (m, J=6.4 Hz, 6H). LCMS (m/z): 452.2 (M+1)$^+$. HPLC=96.27% (210 nm).

Example 21: 6-(2-((4-(Furan-2-yl)-N-(2-methoxyethyl)benzamido)methyl)phenoxy)hexanoic acid

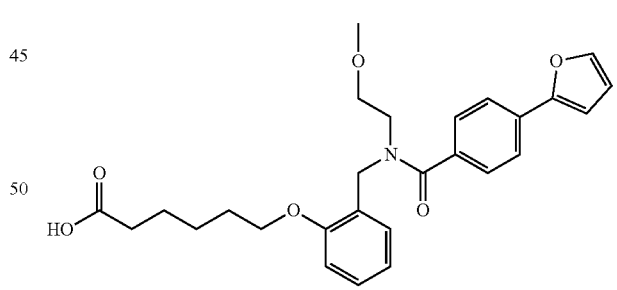

a) Synthesis of 4-(furan-2-yl)benzoic acid

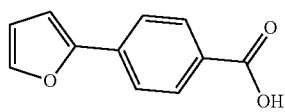

In a 100-mL resealable reaction tube, 4-iodobenzoic acid (10.0 g, 40.03 mmol) and furan-2-ylboronic acid (8.95 g, 80.06 mmol) were dissolved in degassed DMF (250 mL) and water (50 mL) at rt under nitrogen atmosphere. Pd(PPh$_3$)$_4$ (4.65 g, 3.99 mmol), K$_2$CO$_3$ (16.6 g, 120.09 mmol) were sequentially added to the above solution under nitrogen atmosphere. The resulting mixture was degassed by purging argon gas for 15 min, and reaction mixture was heated to 90° C. until completion of the reaction (TLC). The reaction mixture was cooled to rt, diluted with cold water and washed with ethyl acetate (3×30 mL). The aqueous layer was separated and acidified to pH 3 with concentrated HCl, before extracting with EtOAc (100 mL×2). The combined extract was washed with brine and concentrated under reduced pressure to get title compound (6.92 g, 92%) as light yellow solid. LCMS (m/z): 187 (M−1)$^+$.

b) Synthesis of ethyl 6-(2-(((2-methoxyethyl) amino) methyl)phenoxy)hexanoate

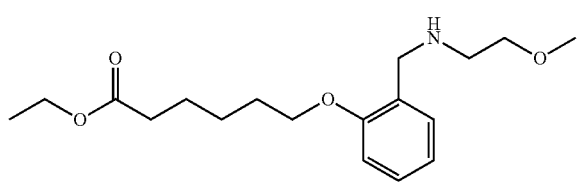 [SMILES: CCOC(=O)CCCCCOc1ccccc1CNCCOC]

In a 100-mL round bottom flask, 2-methoxyethanamine (0.62 g, 8.3 mmol) was added to solution of ethyl 6-(2-formylphenoxy)hexanoate (2.0 g, 7.5 mmol) of example 1(a) in 1,2-dichloroethane (30 mL) at rt under nitrogen atmosphere. AcOH (3 mL) was added dropwise to the above solution at rt (exothermic). The reaction mixture was stirred at rt for 2 h under nitrogen atmosphere. Sodium borohydride (0.54 g, 14.6 mmol) was added in portions to the above reaction mixture at rt under nitrogen atmosphere. The reaction mixture was stirred at rt for further 1 h under nitrogen atmosphere. The reaction mixture was quenched by addition of saturated sodium carbonate solution and extracted with dichloromethane. The dichloromethane layer was washed with brine and dried over anhydrous Na$_2$SO$_4$. The solution was concentrated under reduced pressure to give the title compound (2.58 g) which was used in the next step without further purification. LCMS (m/z): 324.2 (M+1)$^+$.

c) Synthesis of ethyl 6-(2-((4-(furan-2-yl)-N-(2-methoxyethyl)benzamido)methyl) phenoxy)hexanoate

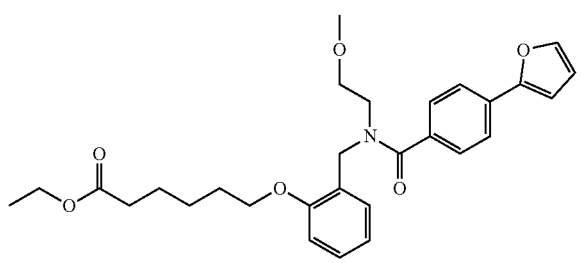 [SMILES: CCOC(=O)CCCCCOc1ccccc1CN(CCOC)C(=O)c1ccc(-c2ccco2)cc1]

In a 50-mL round bottom flask, a stirred solution of ethyl 6-(2-(((2-methoxyethyl)amino)methyl)phenoxy)hexanoate (0.50 g, 1.47 mmol) in DMF (10 mL) was treated sequentially with 4-(furan-2-yl)benzoic acid (0.304 g, 1.62 mmol) EDCI.HCl (0.330 g, 1.56 mmol) Et$_3$N (0.3 mL, 2.15 mmol) and HOBt (0.231 g, 1.7 mmol) at rt under nitrogen atmosphere. The reaction mixture was stirred at rt for 16 h under nitrogen atmosphere. Upon completion of the reaction (TLC), the reaction mixture was diluted with cold water and extracted with ethyl acetate (50 mL×3). The combined organic extract was washed with brine, dried over anhydrous Na$_2$SO$_4$ and concentrated under reduced pressure. The residue obtained was purified by silica gel column chromatography (elution 50% EtOAc-hexanes) to afford the title compound (0.646 g, 89.2%) as clear oil. LCMS (m/z): 494.3 (M+1)$^+$.

d) Synthesis of 6-(2-((4-(furan-2-yl)-N-(2-methoxyethyl)benzamido)methyl)phenoxy) hexanoic acid

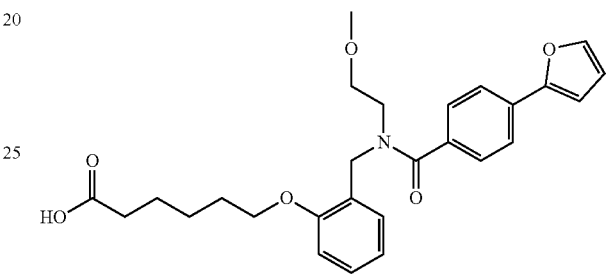

In a 25-mL round bottom flask, ethyl 6-(2-((4-(furan-2-yl)-N-(2-methoxyethyl) benzamido)methyl)phenoxy) hexanoate (0.50 g, 1.01 mmol) was dissolved in THF (5 mL)-water (3 mL) at Lithium hydroxide monohydrate (0.212 g, 5.0 mmol) was added to the above solution and the reaction mixture was stirred at rt for 12 h. Upon completion of the reaction (TLC), the reaction mixture was concentrated under reduced pressure and the residue obtained was diluted with water. The aqueous solution washed with diethyl ether and acidified with 2N HCl. The solid precipitated was filtered, washed with n-pentane and dried under reduced pressure to give title compound (0.179 g, 38.13%). $^1$H NMR (400 MHz, DMSO-d$_6$, 60° C.): δ 12.06-11.32 (br, 1H), 7.81-7.67 (m, 3H), 7.45 (d, J=8.0 Hz, 2H), 7.27-7.23 (m, 2H), 7.06-6.89 (m, 3H), 6.60 (dd, J=3.6, 2.0 Hz, 1H), 4.63 (br s, 2H), 3.98 (br, 2H), 3.46 (s, 3H), 2.21 (t, J=7.2 Hz, 2H), 1.71 (br, 2H), 1.56 (m, 2H), 1.42 (br, 2H). LCMS (m/z): 466.1 (M+1)$^+$. HPLC: 97.81% (210 nm).

Example 22: 6-((3-((4-(Furan-2-yl)-N-isopropylbenzamido)methyl)pyridin-2-yl)oxy)hexanoic acid

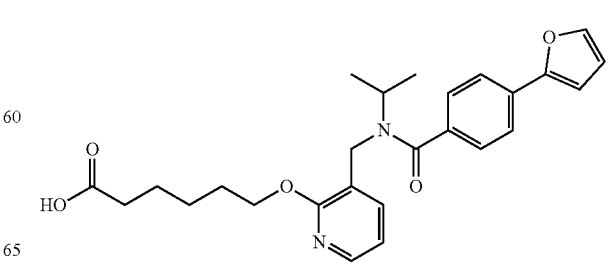

a) Synthesis of ethyl 6-((3-formylpyridin-2-yl)oxy)hexanoate

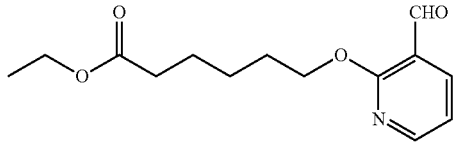

In a 50-mL round bottom flask, a stirred solution of 2-hydroxynicotinaldehyde (1.5 g, 12.19 mmol) in DMF (30 mL), was treated with potassium carbonate (5.0 g, 36.58 mmol) and ethyl 6-bromohexanoate (2.99 g, 13.41 mmol) at rt under nitrogen atmosphere. The reaction mixture was stirred at rt for 4 h. Upon completion of the reaction (TLC), the reaction mixture was diluted with cold water and extracted with ethyl acetate (50 mL×2). The combined organic extract was washed with brine, dried over anhydrous $Na_2SO_4$ and concentrated under reduced pressure. The residue obtained was purified by silica gel column chromatography (elution 10% EtOAc-hexanes) to give title compound (0.297 g, 9.2%) as the clear oil. $^1$H NMR (300 MHz, $CDCl_3$): δ 10.38 (s, 1H), 8.36-8.34 (m, 1H), 8.09 (dd, J=7.5, 2.1 Hz, 1H), 7.00-6.96 (m, 1H), 4.44 (t, J=13.2, 6.6 Hz, 2H), 4.17-4.08 (m, 2H), 2.35 (t, J=13.2, 7.2 Hz, 2H), 1.90-1.85 (m, 2H) 1.77-1.65 (m, 2H), 1.56-1.46 (m, 2H), 1.24 (t, J=7.2 Hz, 3H). LCMS (m/z): Desired mass peak not observed.

b) Synthesis of ethyl 6-((3-((isopropylamino) methyl)pyridin-2-yl)oxy)hexanoate

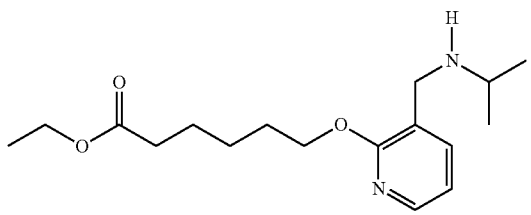 [SMILES: CCOC(=O)CCCCCOc1ncccc1CNC(C)C]

In a 50-mL round bottom flask, a stirred solution of ethyl 6-((3-formylpyridin-2-yl)oxy)hexanoate (300 mg, 1.13 mmol) in ethanol (10 mL) was treated with isopropyl amine (200 mg, 3.39 mmol) and acetic acid (0.3 mL) at rt under nitrogen atmosphere. The mixture stirred at rt for 6 h under nitrogen atmosphere. Sodium borohydride (85.4 mg, 2.26 mmol) was added to the above reaction mixture at rt under nitrogen atmosphere. The resulting mixture was stirred for further 3 h at rt. Upon completion of the reaction (TLC) the reaction mixture was quenched with saturated $NaHCO_3$ and extracted with ethyl acetate (50 mL×2). The combined organic extract was washed with water, brine, dried over anhydrous $Na_2SO_4$. The solution was concentrated under reduced pressure to afford the title compound (310 mg) as yellow oil. The product was used directly in the next step without any further purification. LCMS (m/z): 309.2 $(M+1)^+$.

c) Synthesis of ethyl 6-((3-((4-(furan-2-yl)-N-isopropylbenzamido)methyl)pyridin-2-yl)oxy)hexanoate

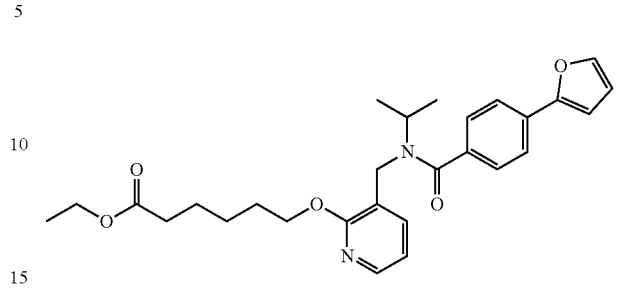

In a 25-mL round bottom flask, a stirred solution of ethyl 6-((3-((isopropylamino)methyl)pyridin-2-yl)oxy)hexanoate (0.301 g, 0.974 mmol) in DMF (10 mL) was treated with 4-(furan-2-yl)benzoic acid (0.210 g, 1.07 mmol), EDCI.HCl (0.372 g, 1.94 mmol), HOBt (0.264 g, 1.94 mmol) and triethylamine (0.412 g, 4.07 mmol) at rt under nitrogen atmosphere. The reaction mixture was stirred at rt for 2 days. Upon completion of the reaction (TLC), the reaction mixture diluted with cold water and extracted with ethyl acetate (25 mL×2). The combined organic extract was washed with brine, dried over anhydrous $Na_2SO_4$ and concentrated under reduced pressure. The residue obtained was purified by silica gel column chromatography (elution 30% EtOAc-hexanes) to give title compound (0.251 g, 53.9%) as off-white solid. LCMS (m/z): 479.2 $(M+1)^+$.

d) Synthesis of 6-((3-((4-(furan-2-yl)-N-isopropylbenzamido)methyl)pyridin-2-yl)oxy)hexanoic acid

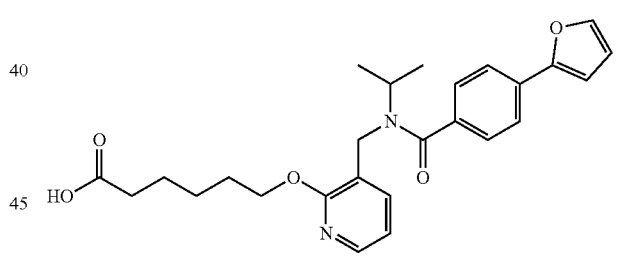

In a 25-mL round bottom flask, ethyl 6-((3-((4-(furan-2-yl)-N-isopropylbenzamido) methyl)pyridin-2-yl)oxy) hexanoate (250 mg, 0.523 mmol) was dissolved in THF (10 mL)-water (10 mL) mixture at it Lithium hydroxide monohydrate (109 mg. 2.61 mmol) was added to the above solution and the reaction mixture was stirred at rt for 18 h. Upon completion of the reaction (TLC), the reaction mixture was concentrated under reduced pressure. The residue obtained was diluted with cold water and acidified with 2N HCl, before extracting with ethyl acetate (10 mL×2). The combined organic extract was washed with brine, dried over anhydrous $Na_2SO_4$ and concentrated under reduced pressure. The residue obtained was purified by silica gel column chromatography (elution, 50% EtOAc-hexanes) to give title compound (129 mg, 55%) a pale yellow gummy liquid. $^1$H NMR (400 MHz, DMSO-$d_6$, 60° C.) δ 12.02 (s, 1H), 8.08-7.96 (m, 1H), 7.80 (br, 2H), 7.60-7.50 (m, 3H), 7.06 (br, 1H), 6.98 (dd, J=7.2, 5.2 Hz, 1H), 6.69-6.57 (m, 1H), 4.44 (s, 2H), 4.33 (m, 2H), 4.05 (br, 1H), 2.25 (br s, 2H), 1.79-1.76 (m, 2H), 1.60-1.55 (m, 2H), 1.49-1.45 (m, 2H), 1.08 (br s, 6H). LCMS (m/z): 451.2 (M+1)⁺. HPLC: 96.87% (210 nm).

Example 23: 6-(2-((4-(Furan-2-yl)-N-isopropylphenylsulfonamido)methyl)phenoxy)hexanoic acid

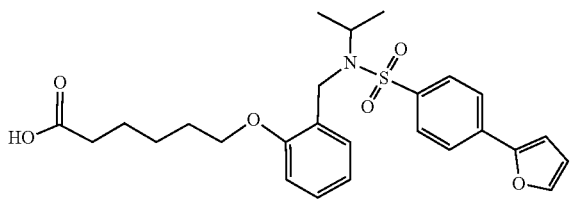 [SMILES: CC(C)N(Cc1ccccc1OCCCCCC(=O)O)S(=O)(=O)c1ccc(-c2ccco2)cc1]

a) Synthesis of ethyl 6-(2-((4-bromo-N-isopropylphenylsulfonamido)methyl)phenoxy) hexanoate

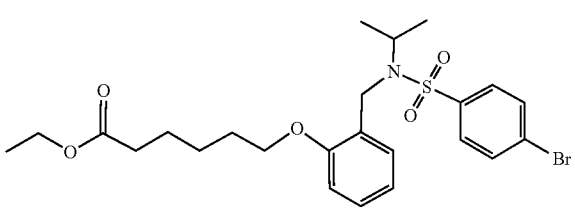 [SMILES: CCOC(=O)CCCCCOc1ccccc1CN(C(C)C)S(=O)(=O)c1ccc(Br)cc1]

In a 25-mL round bottom flask, a stirred solution of ethyl 6-(2-((isopropylamino)methyl)phenoxy)hexanoate (500 mg, 1.62 mmol) in pyridine (10 mL) was treated with 4-bromobenzene-1-sulfonyl chloride (496 mg, 1.95 mmol) at rt under nitrogen atmosphere. The reaction mixture was stirred at rt for 12 h. Upon completion of the reaction (TLC) the reaction mixture was quenched with cold water and extracted with ethyl acetate (25 mL×2). The combined organic extract was washed with brine, dried over anhydrous Na₂SO₄ and concentrated under reduced pressure. The residue obtained was purified by silica gel (60-120 mesh) column chromatography (elution 20% EtOAc-hexanes) to give title compound (301 mg, 35%) as yellow oil. LCMS (m/z): 547.9 (M+Na)⁺.

b) Synthesis of ethyl 6-(2-((4-(furan-2-yl)-N-isopropylphenylsulfonamido)methyl)phenoxy) hexanoate

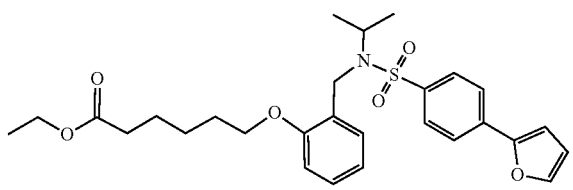 [SMILES: CCOC(=O)CCCCCOc1ccccc1CN(C(C)C)S(=O)(=O)c1ccc(-c2ccco2)cc1]

In a 50-mL resealable reaction tube, ethyl 6-(2-((4-bromo-N-isopropylphenylsulfonamido)methyl) phenoxy)hexanoate (300 mg, 0.57 mmol) was dissolved in degassed solvent mixture of DME (7 mL), water (7 mL) and ethanol (2 mL) at rt under nitrogen atmosphere. Pd(PPh₃)₄ (19.7 mg, 0.017 mmol), furan-2-ylboronic acid (127 mg, 1.14 mmol) and Na₂CO₃ (181 mg, 1.71 mmol) were sequentially added to the above solution under nitrogen atmosphere. The resulting mixture was degassed by purging argon gas for 15 min. The reaction mixture was heated to 90° C. and stirred at same temperature until completion of the reaction (TLC). The reaction mixture was cooled to rt, diluted with cold water and extracted with ethyl acetate (30 mL×3). The combined EtOAc extract was washed with brine and concentrated under reduced pressure. The residue obtained was purified by silica gel column chromatography (elution 30% EtOAc-hexanes) to afford the title product (278 mg, 95%) as clear oil. LCMS (m/z): 514.3 (M+1)⁺.

c) Synthesis of 6-(2-((4-(furan-2-yl)-N-isopropylphenylsulfonamido)methyl)phenoxy) hexanoic acid

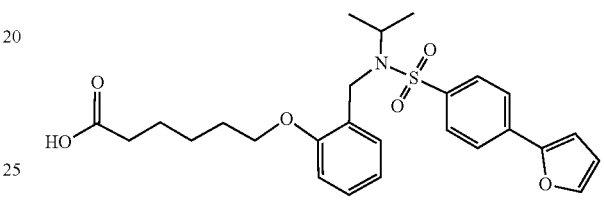

In a 25-mL round bottom flask, ethyl 6-(2-((4-(furan-2-yl)-N-isopropylphenyl sulfonamido)methyl)phenoxy) hexanoate (270 mg, 0.526 mmol) was dissolved in THF (10 mL), water (10 mL) and ethanol (2 mL) mixture at it. Lithium hydroxide monohydrate (122 mg, 2.92 mmol) was added to the above solution and the reaction mixture was stirred at rt for 12 h. Upon completion of the reaction (TLC), the reaction mixture was concentrated under reduced pressure and residue obtained was diluted with cold water. The aqueous solution was acidified with 2N HCl and extracted with ethyl acetate (10 mL×2). The combined organic extract was washed with brine, dried over anhydrous Na₂SO₄ and concentrated under reduced pressure. The residue obtained was washed with n-pentane to afford the title compound (186 mg, 70.1%) as off white solid. ¹H NMR (300 MHz, DMSO-d₆, 60° C.): δ 11.98 (s, 1H), 8.10-7.73 (m, 5H), 7.55-7.32 (m, 1H), 7.32-7.10 (m, 2H), 7.01-6.84 (m, 2H), 6.66 (dd, J=3.6, 1.8 Hz, 1H), 4.33 (s, 2H), 4.12-4.05 (m, 1H), 3.97 (t, J=6.4 Hz, 2H), 2.19 (t, J=7.2 Hz, 2H), 1.74-1.70 (m, 2H), 1.53-1.51 (m, 2H), 1.43-1.41 (m, 2H), 0.83 (d, J=6.6 Hz, 6H). LCMS (m/z): 508.5 (M+1)⁺. HPLC: 94.32% (210 nm).

Example 24: 6-(2-((4-(Furan-2-yl)benzamido)methyl)phenoxy)hexanoic acid

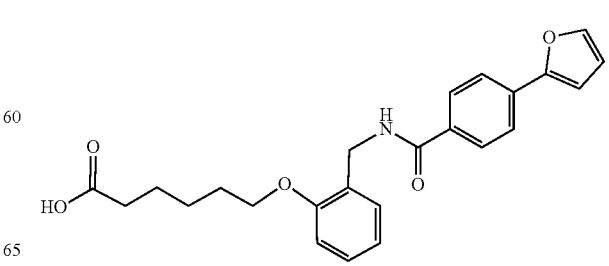

a) Synthesis of (E)-methyl 6-(2-((hydroxyimino)methyl) phenoxy) hexanoate

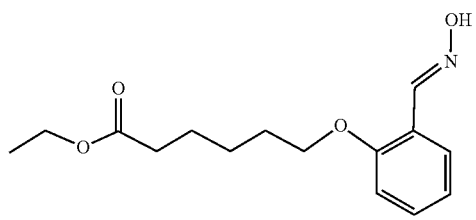 [SMILES: CCOC(=O)CCCCCOc1ccccc1/C=N/O]

In a 100-mL round bottom flask, a stirred solution of ethyl 6-(2-formylphenoxy)hexanoate (2.0 g, 7.5 mmol) in water (40 mL), was treated aqueous hydroxyl amine (1.25 g, 37.8 mmol) at rt. The resulting mixture was heated at 100° C. for 30 min to give an off white suspension. The suspension was allowed to cool to ambient temperature and then further cooled in an ice-bath. The solid formed was filtered, washed with water and dried under reduced pressure to afford the title compound (1.81 g, 86.8%) as white solid. $^1$H-NMR (300 MHz, DMSO-$d_6$): δ 11.18 (s, 1H), 8.27 (s, 1H), 7.65-7.59 (m, 1H), 7.35-7.29 (m, 1H), 7.04-7.00 (d, J=8.1 Hz, 1H), 6.94-6.89 (t, J=7.8 Hz, 1H), 4.06-3.96 (m, 4H), 2.31-2.27 (t, J=14.4 Hz, 2H), 1.76-1.67 (m, 2H), 1.62-1.52 (m, 2H), 1.46-1.38 (m, 2H), 1.17 (t, J=7.2 Hz, 3H). LCMS (m/z): 279.3 (M+1)$^+$.

b) Synthesis of ethyl 6-(2-(aminomethyl)phenoxy)hexanoate

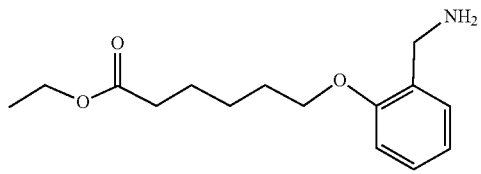 [SMILES: CCOC(=O)CCCCCOc1ccccc1CN]

In a 100-mL round bottom flask, a stirred solution of (E)-methyl 6-(2-((hydroxyimino)methyl)phenoxy)hexanoate (1.30 g, 4.6 mmol) in ethanol (20 mL) was treated with 10% palladium on activated carbon (0.30 g) at rt under nitrogen atmosphere. The resulting suspension was hydrogenated (balloon) at rt for 12 h. Upon completion of the reaction (TLC), reaction mixture was filtered over a celite bed and filtrated was concentrated under reduced pressure to afford the title compound (1.10 g, 89.43%) as clear oil. LCMS (m/z): 266.3 (M+1)$^+$.

c) Synthesis of ethyl 6-(2-((4-(furan-2-yl)benzamido)methyl)phenoxy)hexanoate

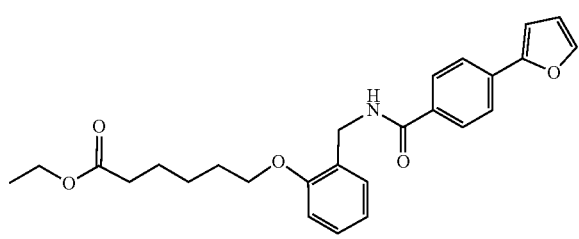 [SMILES: CCOC(=O)CCCCCOc1ccccc1CNC(=O)c1ccc(-c2ccco2)cc1]

In a 50-mL round bottom flask, EDCI.HCl (0.25 g, 1.3 mmol) and triethylamine (2.0 mL, 1.6 mmol) were sequentially to a solution of methyl 6-(2-(amino methyl)phenoxy) hexanoate (0.3 g, 1.1 mmol), 4-(furan-2-yl)benzoic acid (0.21 g, 1.1 mmol) and HOBt (0.180 g, 1.3 mmol) in dimethylformamide (10 mL) at rt under nitrogen atmosphere. The reaction mixture was stirred at rt for 16 h under nitrogen atmosphere. The reaction mixture was concentrated under reduced pressure. The residue obtained was purified by silica gel (60-120 mesh) column chromatography (elution 50% EtOAc-hexanes) to give the title compound (0.243 g, 50.7%). LCMS (m/z): 458.2 (M+Na)$^+$.

d) Synthesis of 6-(2-((4-(furan-2-yl)benzamido) methyl)phenoxy)hexanoic acid

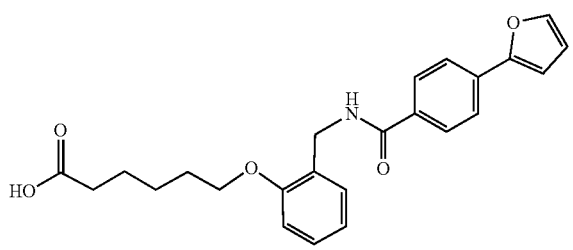 [SMILES: O=C(O)CCCCCOc1ccccc1CNC(=O)c1ccc(-c2ccco2)cc1]

A solution of ethyl 6-(2-((4-(furan-2-yl) benzamido)methyl)phenoxy)hexanoate (0.25 g, 0.57 mmol) in THF (10 mL) and water (5 mL) was treated with lithium hydroxide monohydrate (0.241 g, 5.7 mmol) at rt. The reaction mixture was stirred at rt for 12 h Upon completion of reaction (TLC), the reaction mixture was concentrated under reduced pressure and residue obtained was diluted with water. The aqueous solution was washed with diethyl ether and acidified with 1N HCl, when solid precipitated. The solid was filtered, washed with water, n-pentane and dried under reduced pressure to afford the title compound (0.099 g, 42.7%). $^1$H NMR (300 MHz, DMSO-$d_6$, 60° C.): δ 11.99 (s, 1H), 8.83 (t, J=5.8 Hz, 1H), 8.03-7.87 (m, 2H), 7.86-7.71 (m, 3H), 7.24-7.11 (m, 2H), 7.09 (d, J=3.4 Hz, 1H), 6.96 (d, J=8.1 Hz, 1H), 6.87 (t, J=7.4 Hz, 1H), 6.63 (dd, J=3.4, 1.8 Hz, 1H), 4.45 (d, J=5.8 Hz, 2H), 3.99 (t, J=6.2 Hz, 2H), 2.21 (t, J=7.1 Hz, 2H), 1.76-1.71 (m, 2H), 1.57-1.44 (m, 4H). LCMS (m/z): 430.1 (M+Na)$^+$. HPLC: 95.46% (210 nm).

Example 25: 6-(4-Bromo-2-((4-(furan-2-yl)-N-isopropylbenzamido)methyl)phenoxy)hexanoic acid

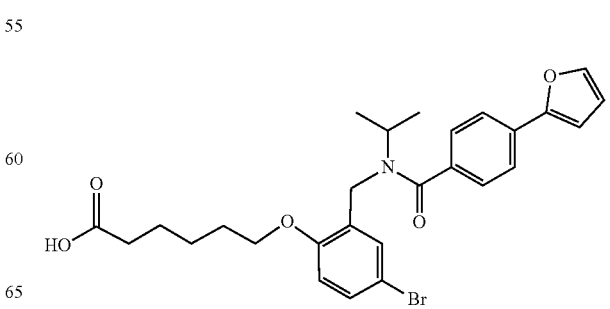

a) Synthesis of ethyl 6-(4-bromo-2-formylphenoxy)hexanoate

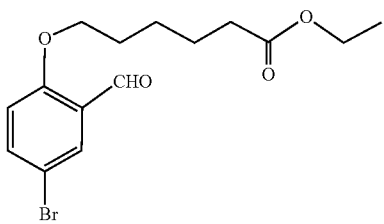 [SMILES: CCOC(=O)CCCCCOc1ccc(Br)cc1C=O]

In a 50-mL round bottom flask, a stirred solution of substituted 5-bromo-2-hydroxybenzaldehyde (5.0 g, 24.8 mmol) in DMF (30 mL), was treated with potassium carbonate (10.26 g, 74.4 mmol) and ethyl 6-bromohexanoate (6.6 g, 29.8 mmol) at rt under nitrogen atmosphere. The reaction mixture was heated at 90° C. for 4 h. Upon completion of the reaction (TLC) the reaction mixture was cooled to rt, diluted with cold water and extracted ethyl acetate (250 mL×2). The combined organic extract was washed with brine and dried over anhydrous $Na_2SO_4$. The solution was concentrated under reduced pressure to give the title compound (7.97 g, 94%) as yellow oil. LCMS (m/z): 343.2 (M+1)$^+$.

b) Synthesis of ethyl 6-(2-(aminomethyl)-4-bromophenoxy)hexanoate

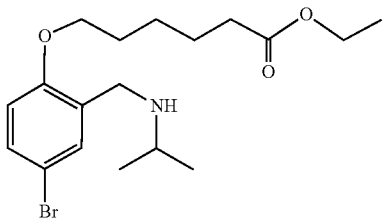 [SMILES: CCOC(=O)CCCCCOc1ccc(Br)cc1CNC(C)C]

In a 100-mL round bottom flask, a stirred solution of substituted ethyl 6-(4-bromo-2-formylphenoxy)hexanoate (2.0 g, 5.84 mmol) in 1,2-dichloroethane (50 mL), was treated with isopropylamine (0.37 g, 6.26 mmol) and acetic acid (2.5 g, 41.6 mmol) at rt. The mixture was stirred at rt for 30 min and treated with $NaBH(OAc)_3$ (2.70 g, 12.73 mmol) at rt under nitrogen atmosphere. The reaction mixture was stirred at rt for 3 h. Upon completion of the reaction (TLC) the reaction mixture was quenched with saturated $NaHCO_3$ and extracted with ethyl acetate (50 mL×2). The combined organic extract was washed with water, brine and dried over anhydrous $Na_2SO_4$. The solution was concentrated under reduced pressure to afford the title compound (1.52 g) as yellow oil, which was used in the next step without further purification. LCMS (m/z): 386.1 (M+1)$^+$.

c) Synthesis of ethyl 6-(4-bromo-2-((4-(furan-2-yl)-N-isopropylbenzamido)methyl) phenoxy)hexanoate

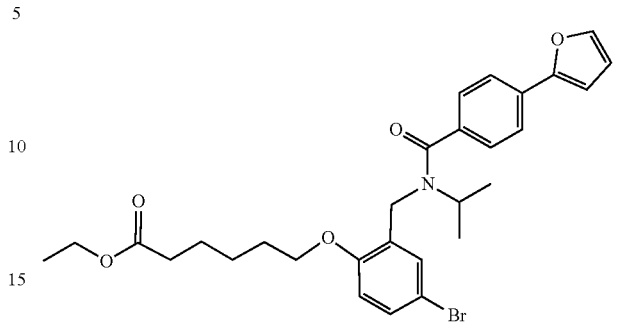

In a 25-mL round bottom flask, a stirred solution of 6-(4-bromo-2-((isopropylamino)methyl)phenoxy)hexanoate (500 mg, 1.29 mmol) in DMF (15 mL), was treated sequentially with 4-(furan-2-yl)benzoic acid (267 mg, 1.42 mmol), EDCI.HCl (492 mg, 2.58 mmol), HOBt (350 mg, 2.58 mmol) and triethylamine (546 mg, 5.6 mmol) at rt under nitrogen atmosphere. The reaction mixture was stirred at rt for 18 h under nitrogen atmosphere. Upon completion of the reaction (TLC), the reaction mixture was diluted with cold water and extracted with ethyl acetate (25 mL×2). The combined organic extract was washed with water, brine, dried over anhydrous $Na_2SO_4$ and concentrated under reduced pressure. The residue obtained was purified by silica gel column chromatography (elution 15% EtOAc-hexanes) to give the title compound (681 mg, 94.7%) as clear oil. LCMS (m/z): 557.2 (M+1)$^+$.

d) Synthesis of 6-(4-bromo-2-((4-(furan-2-yl)-N-isopropylbenzamido)methyl)phenoxy) hexanoic acid

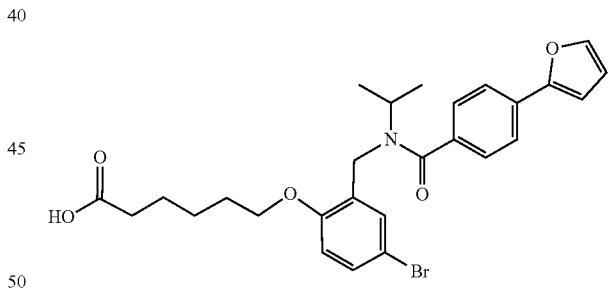

In a 25-mL round bottom flask, a stirred solution ethyl 6-(4-bromo-2-((4-(furan-2-yl)-N-isopropylbenzamido) methyl)phenoxy)hexanoate (500 mg, 0.899 mmol) was dissolved in THF (10 mL)-water (10 mL)-EtOH (2 mL) at rt. Lithium hydroxide monohydrate (188 mg, 4.48 mmol) was added to the above solution and the reaction mixture was stirred at n for 5 h. Upon completion of the reaction (TLC), the reaction mixture was concentrated under reduced pressure and the residue obtained was diluted with water. The aqueous solution was acidified with 2N HCl and extracted with ethyl acetate (10 mL×2). The combined organic extract was washed with brine, dried over anhydrous $Na_2SO_4$ and concentrated under reduced pressure. The residue obtained was washed repeatedly with n-pentane to give the title compound (349 mg, 73.7%) as clear oil. $^1$H NMR (400 MHz, DMSO-d$_6$, 60° C.): δ 11.80 (s, 1H), 7.81-7.75 (m, 3H), 7.44 (d, J=7.6 Hz, 2H), 7.37 (dd, J=8.8, 2.4 Hz, 1H), 7.31 (s, 1H), 7.00 (d, J=3.2 Hz, 1H), 6.95 (d, J=8.8 Hz, 1H), 6.66-6.58 (m, 1H), 4.51 (s, 2H), 4.17 (br, 1H), 4.02 (t, J=6.4 Hz, 2H), 3.62 (d, J=6.4 Hz, 2H), 2.24 (t, J=7.3 Hz, 2H), 1.79-1.75 (m, 4H), 1.61-1.58 (m, 2H), 1.52-1.40 (m, 2H), 1.11 (d, J=6.4 Hz, 6H). LCMS (m/z): 527.9 (M+1)$^+$. HPLC: 95.01% (210 nm).

Example 26: 6-(4-Fluoro-2-((4-(furan-2-yl)-N-isopropylbenzamido)methyl)phenoxy)hexanoic acid

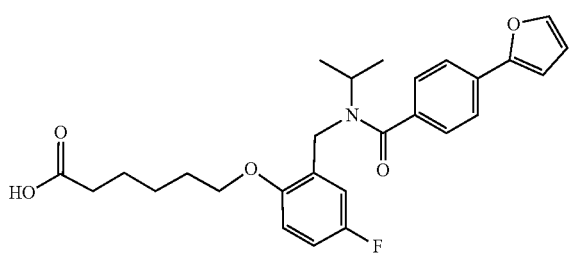 [SMILES: CC(C)N(Cc1cc(F)ccc1OCCCCCC(=O)O)C(=O)c1ccc(-c2ccco2)cc1]

The title compound (190 mg) was prepared starting from 5-fluoro-2-hydroxybenzaldehyde (1.0 g, 7.14 mmol) using the procedure of Example-25. $^1$H NMR (400 MHz, DMSO-d$_6$, 60° C.): δ 7.77-7.74 (m, 3H), 7.48 (d, J=7.6 Hz, 2H), 7.01-6.99 (m, 4H), 6.61 (dd, J=3.2, 1.6 Hz, 1H), 4.52 (s, 2H), 4.15 (br, 1H), 4.00 (t, J=6.4 Hz, 2H), 2.24 (t, J=7.2 Hz, 2H), 1.81-1.70 (m, 2H), 1.62-1.58 (m, 2H), 1.49-1.47 (m, 2H), 1.11 (d, J=6.6 Hz, 6H). LCMS (m/z): 468.2 (M+1)$^+$. HPLC: 96.75% (210 nm).

Example 27: 6-((4-(Furan-2-yl)-N-isopropylbenzamido)methyl)-4-methylphenoxy)hexanoic acid

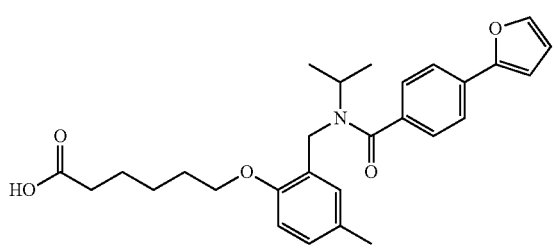 [SMILES: Cc1ccc(OCCCCCC(=O)O)c(CN(C(=O)c2ccc(-c3ccco3)cc2)C(C)C)c1]

The title compound (350 mg) was prepared from 2-hydroxy-5-methylbenzaldehyde (2.5 g, 18.38 mmol) using the procedure of Example-25. $^1$H NMR (400 MHz, DMSO-d$_6$, 60° C.): δ 11.79 (s, 1H), 7.79-7.69 (m, 3H), 7.46 (d, J=7.6 Hz, 2H), 7.08-6.94 (m, 3H), 6.84 (d, J=8.0 Hz, 1H), 6.61 (dd, J=3.2, 1.6 Hz, 1H), 4.50 (s, 2H), 4.15 (br, 1H), 3.96 (t, J=6.4 Hz, 2H), 2.25 (m, 5H), 1.78-1.70 (br, 2H), 1.60-1.55 (m, 2H), 1.47-1.42 (m, 2H), 1.11 (d, J=6.4 Hz, 6H). LCMS (m/z): 464.3 (M+1)$^+$. HPLC: 97.47% (210 nm).

Example 28: 6-((4-(Furan-2-yl)-N-isopropylbenzamido)methyl)-4-methoxyphenoxy)hexanoic acid

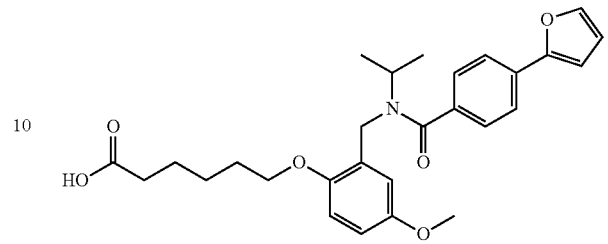

a) Synthesis of 2-hydroxy-5-methoxybenzaldehyde

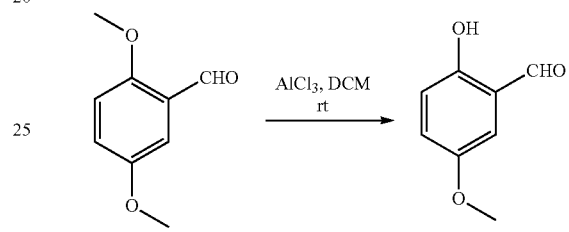

In a 250-mL round bottom flask, a stirred solution of 2,5-dimethoxybenzaldehyde (5.0 g, 30.02 mmol) was dissolved in DCM (50 mL). Aluminum chloride (18.2 g, 136.8 mmol) was added to the above solution at rt under nitrogen atmosphere. The reaction mixture was stirred at rt for 12 h. Upon completion of the reaction (TLC), the reaction mixture was diluted with cold water and extracted with DCM (100 mL×2). The combined organic extract was washed with brine and concentrated under reduced pressure to get title compound (4.51 g, 98%) as yellow oil. LCMS (m/z): 152.1 (M+1)$^+$.

b) Synthesis of 6-((4-(furan-2-yl)-N-isopropylbenzamido)methyl)-4-methoxyphenoxy) hexanoic acid

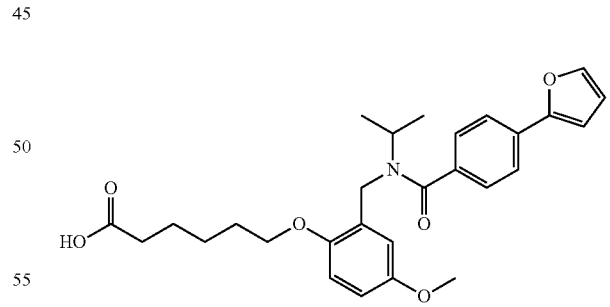

The title compound (230 mg) was prepared from 2-hydroxy-5-methoxybenzaldehyde (2.5 g, 16.44 mmol) using the procedure of Example-25. $^1$H NMR (400 MHz, DMSO-d$_6$, 60° C.): δ 11.81 (s, 1H), 7.75 (d, J=6.4 Hz, 3H), 7.45 (d, J=7.6 Hz, 2H), 6.99 (d, J=3.2 Hz, 1H), 6.89 (d, J=8.8 Hz, 1H), 6.82-6.72 (m, 2H), 6.61 (m, 1H), 4.51 (s, 2H), 4.14 (br, 1H), 3.94 (t, J=6.1 Hz, 2H), 3.72 (s, 3H), 2.23 (t, J=7.2 Hz, 2H), 1.73 (br, 2H), 1.60-1.57 (m, 2H), 1.50-1.38 (m, 2H), 1.11 (d, J=6.4 Hz, 6H). LCMS (m/z): 480.5 (M+1)$^+$. HPLC: 95.33% (210 nm).

Example 29: 6-(4-Cyano-2-((4-(furan-2-yl)-N-isopropylbenzamido)methyl)phenoxy)hexanoic acid

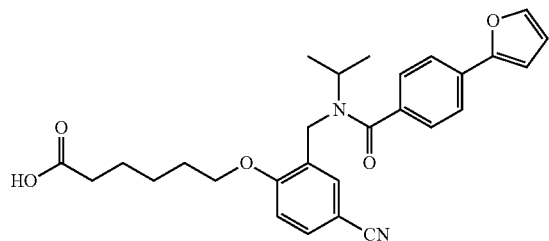 [SMILES: CC(C)N(Cc1cc(C#N)ccc1OCCCCCC(=O)O)C(=O)c1ccc(-c2ccco2)cc1]

a) Synthesis of ethyl 6-(4-cyano-2-((4-(furan-2-yl)-N-isopropylbenzamido)methyl) phenoxy)hexanoate

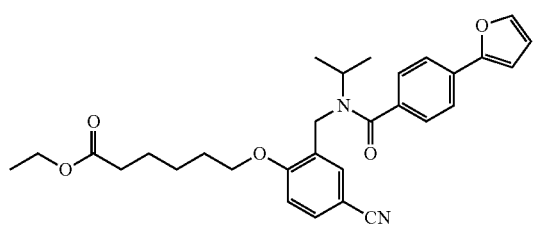 [SMILES: CCOC(=O)CCCCCOc1ccc(C#N)cc1CN(C(=O)c1ccc(-c2ccco2)cc1)C(C)C]

In a 50-mL resealable reaction tube, ethyl 6-(4-bromo-2-((4-(furan-2-yl)-N-isopropylbenzamido)methyl)phenoxy) hexanoate (500 mg, 0.879 mmol) from example 25c was dissolved in degassed DMA (15 mL) at rt under nitrogen atmosphere. $Pd_2(dba)_3$ (21.0 mg, 0.023 mmol), Zn powder (0.126 g, 0.002 mmol) and dppf (14.9 mg, 0.027 mmol) and $Zn(CN)_2$ (62.6 mg, 0.51 mmol) were sequentially added to the above solution under nitrogen atmosphere. The resulting mixture was degassed by purging argon gas for 15 min. The reaction mixture was heated to 100° C. and stirred at same temperature until completion of the reaction (TLC). The reaction mixture was cooled to rt, diluted with cold water and extracted with ethyl acetate (3×30 mL). The combined organic extract was washed with brine and concentrated under reduced pressure. The residue obtained was purified by silica gel column chromatography (gradient elution, 10-15% EtOAc-hexanes) to afford the title compound (361 mg, 81.8%) as pale yellow solid. LCMS (m/z): 503.2 (M+1)⁺.

b) Synthesis of 6-(4-cyano-2-((4-(furan-2-yl)-N-isopropylbenzamido)methyl)phenoxy) hexanoic acid

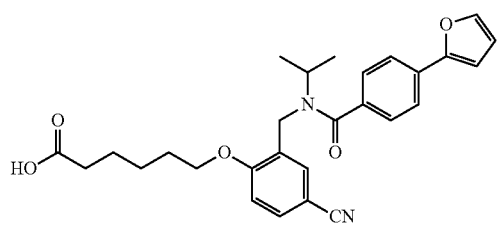 [SMILES: CC(C)N(Cc1cc(C#N)ccc1OCCCCCC(=O)O)C(=O)c1ccc(-c2ccco2)cc1]

In a 25-mL round bottom flask, ethyl 6-(4-cyano-2-((4-(furan-2-yl)-N-isopropylbenzamido)methyl)phenoxy) hexanoate (0.30 g, 0.597 mmol) was dissolved in THF (4 mL)-water (4 mL) mixture at rt. Lithium hydroxide monohydrate (0.125 g, 2.988 mmol) was added to the above solution and the reaction mixture was stirred at rt for 18 h. Upon completion of the reaction (TLC), the reaction mixture was concentrated under reduced pressure; residue obtained was diluted with water and acidified with 2N HCl. The aqueous solution was extracted with ethyl acetate (10 mL×2). The combined organic extract was washed with brine, dried over anhydrous $Na_2SO_4$ and concentrated under reduced pressure. The residue obtained was washed with n-pentane and dried under reduced pressure to give the title compound (0.150 g, 53%) as pale yellow solid. ¹H NMR (400 MHz, DMSO-d6, 60° C.) δ 11.80 (s, 1H), 7.77-7.75 (m, 3H), 7.70 (dd, J=8.4, 2.0 Hz, 1H), 7.55 (d, J=2.0 Hz, 1H), 7.51 (d, J=7.6 Hz, 2H), 7.17 (d, J=8.8 Hz, 1H), 7.00 (d, J=3.2 Hz, 1H), 6.62 (dd, J=3.6, 1.6 Hz, 1H), 4.52 (s, 2H), 4.14 (t, J=6.4 Hz, 2H), 2.24 (t, J=7.2 Hz, 2H), 1.81-178 (m, 2H), 1.62-159 (m, 2H), 1.50-1.47 (m, 2H), 1.12 (d, J=6.4 Hz, 6H). LCMS (m/z): 475.2 (M+1)⁺. HPLC: 95.98% (210 nm).

Example 30: 6-((4-(furan-2-yl)-N-(2,2,2-trifluoroethyl)benzamido)methyl)phenoxy)hexanoic acid

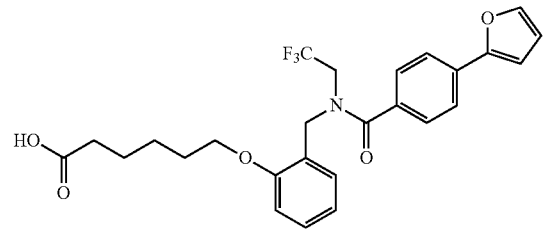 [SMILES: O=C(O)CCCCCOc1ccccc1CN(CC(F)(F)F)C(=O)c1ccc(-c2ccco2)cc1]

a) Synthesis of ethyl 6-(2-(((2,2,2-trifluoroethyl)amino)methyl)phenoxy)hexanoate

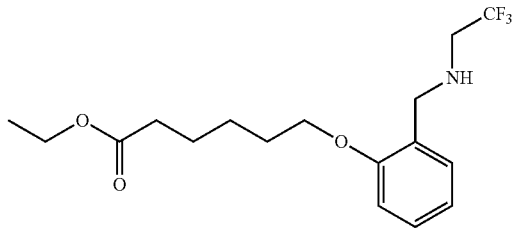 [SMILES: CCOC(=O)CCCCCOc1ccccc1CNCC(F)(F)F]

To a stirred solution of ethyl 6-(2-formylphenoxy)hexanoate (0.50 g, 1.89 mmol) in 1,2-dichloroethane (50 mL), 2,2,2-trifluoroethanamine (0.21 g, 2.12 mmol) and acetic acid (0.85 g, 124.74 mmol) were added at rt under nitrogen atmosphere. The mixture was stirred at rt for 30 min and treated with $NaBH(OAc)_3$ (0.9 g, 12.47 mmol) under nitrogen atmosphere. The reaction mixture was stirred at rt for 3 h. Upon completion of the reaction (TLC), the reaction mixture was quenched with saturated $NaHCO_3$ and extracted with ethyl acetate (50 mL×2). The combined organic extract was washed with water, brine, dried over anhydrous $Na_2SO_4$. The solution was concentrated under b) Synthesis of ethyl 6-(2-((4-(furan-2-yl)-N-(2,2,2-trifluoroethyl)benzamido)methyl) phenoxy)hexanoate

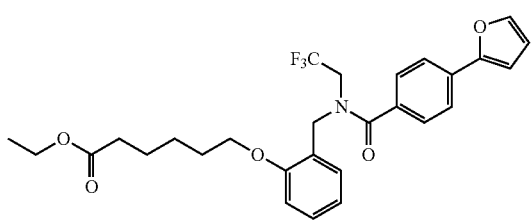 [SMILES: CCOC(=O)CCCCCOc1ccccc1CN(CC(F)(F)F)C(=O)c1ccc(-c2ccco2)cc1]

In a 50-mL round bottom flask, a stirred solution ethyl 6-(2-(((2,2,2-trifluoroethyl) amino)methyl)phenoxy) hexanoate (0.55 g, 1.58 mmol) in DCM (30 mL) was treated with 4-(furan-2-yl)benzoyl chloride (0.3 g, 1.4 mmol) [prepared by reaction of 4-(furan-2-yl)benzoic acid (0.3 g) and thionyl chloride (2 mL) at rt for 12 h] and Et$_3$N (0.431 mL, 3.17 mmol) at rt under nitrogen atmosphere. The reaction mixture was stirred at rt for 2 h under nitrogen atmosphere. Upon completion of the reaction (TLC), the reaction mixture was diluted with cold water (10 mL) and extracted with DCM (30 mL×2). The combined organic extract was washed with aqueous NaHCO$_3$, brine and dried over anhydrous Na$_2$SO$_4$. The solution was concentrated under reduced pressure and residue obtained was purified by silica gel column chromatography (elution 50% EtOAc-hexanes) to give title compound (0.351 g, 42.9%). LCMS (m/z): 540.2 (M+Na)$^+$.

c) Synthesis of 6-(2-((4-(furan-2-yl)-N-(2,2,2-trifluoroethyl)benzamido)methyl)phenoxy) hexanoic acid

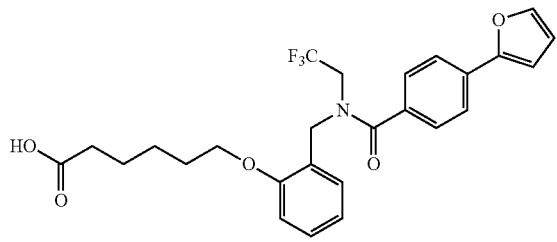 [SMILES: O=C(O)CCCCCOc1ccccc1CN(CC(F)(F)F)C(=O)c1ccc(-c2ccco2)cc1]

A stirred solution of ethyl 6-(2-((4-(furan-2-yl)-N-(2,2,2-trifluoroethyl)benzamido) methyl)phenoxy)hexanoate (0.10 g, 0.193 mmol) in THF (5 mL), EtOH (3 mL) and water (2 mL) was treated with lithium hydroxide monohydrate (0.04 g, 0.96 mmol) at rt. The mixture was stirred at 90° C. for 3 h. Upon completion of the reaction (TLC), the solvent was removed under reduced pressure. The residue obtained was washed with EtOAc and n-pentane. The residue was dissolved in water and the solution acidified with 2 N HCl. The aqueous solution was extracted with EtOAc (25 mL×3). The combined organic extract was dried over anhydrous Na$_2$SO$_4$, and concentrated under reduced pressure to give the title compound (0.025 g, 62.8%). $^1$H NMR (400 MHz, DMSO-d$_6$, 80° C.): δ 7.75 (d, J=8.0 Hz, 3H), 7.46 (d, J=8.0 Hz, 2H), 7.26 (t, J=7.6 Hz, 1H), 7.08 (d, J=7.2 Hz, 1H), 7.02-6.87 (m, 3H), 6.60 (dd, J=3.2, 1.6 Hz, 1H), 4.68 (s, 2H), 4.18 (q, J=9.6 Hz, 2H), 3.95 (t, J=6.4 Hz, 2H), 2.01 (br t, J=7.2 Hz, 2H), 1.69-1.65 (m, 2H), 1.56-1.50 (m, 2H), 1.39-1.34 (m, 2H). LCMS (m/z): 540.2 (M+1)$^+$. HPLC: 95.11% (210 nm).

Example 31: 6-(2-((4-(furan-2-yl)-N-methylbenzamido)methyl)phenoxy)hexanoic acid

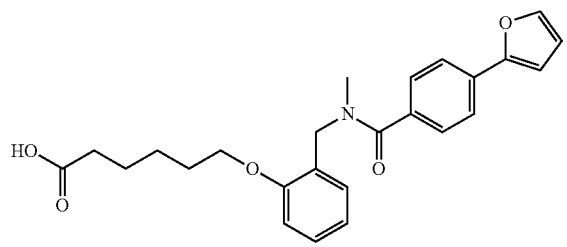 [SMILES: CN(Cc1ccccc1OCCCCCC(=O)O)C(=O)c1ccc(-c2ccco2)cc1]

a) Synthesis of ethyl 6-(2-((methylamino)methyl)phenoxy)hexanoate

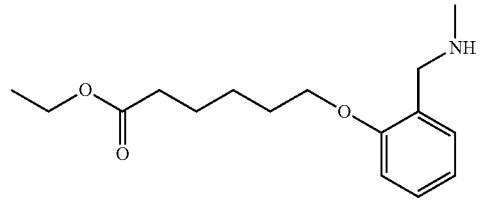 [SMILES: CCOC(=O)CCCCCOc1ccccc1CNC]

In a 50-mL round bottom flask, a solution of methyl amine hydrochloride (0.515 g, 7.62 mmol) in MeOH (15 mL) was treated with Et$_3$N (1.03 mL, 7.5 mmol) at rt. The mixture was stirred at rt for 15 min and treated with a solution ethyl 6-(2-formylphenoxy)hexanoate (0.5 g, 1.89 mmol) in MeOH (15 mL) at rt under nitrogen atmosphere. The resulting mixture was stirred at rt for 1 h. The mixture was cooled to 0° C. and NaBH$_4$ (0.037 g, 0.99 mmol) was added in portions at rt. The reaction mixture was stirred at rt for 1 h. Upon completion of the reaction (TLC), the reaction mixture was concentrated under reduced pressure. The residue obtained was diluted with cold water and extracted with EtOAc (30 mL×2). The combined organic extract was washed with brine and dried over anhydrous Na$_2$SO$_4$. The solution was concentrated under reduced pressure to afford the title compound (0.408 g), which was used in the next step without further purification. LCMS (m/z): 280.1 (M+1)$^+$.

b) Synthesis of ethyl 6-((4-(furan-2-yl)-N-methyl-benzamido)methyl)phenoxy) hexanoate

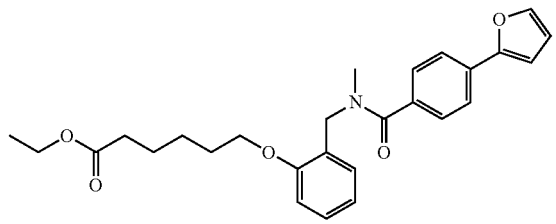 [SMILES: CCOC(=O)CCCCCOc1ccccc1CN(C)C(=O)c1ccc(-c2ccco2)cc1]

In a 50-mL round bottom flask, a stirred solution of ethyl 6-(2-((methylamino)methyl)phenoxy)hexanoate (0.4 g, 1.43 mmol) and 4-(furan-2-yl)benzoic acid (0.323 g, 1.72 mmol) in DMF (20 mL) was treated with EDCI.HCl (0.546 g, 2.86 mmol), HOBt (0.388 g, 2.86 mmol) and Et$_3$N (0.778 mL, 5.72 mol) at rt under nitrogen atmosphere. The reaction mixture was stirred at rt for 12 h under nitrogen atmosphere. Upon completion of reaction (TLC), the reaction mixture was diluted with cold water, and extracted with EtOAc (30 mL×2). The combined organic extract was washed with saturated NaHCO$_3$, brine and dried over anhydrous Na$_2$SO$_4$. The solution was concentrated under reduced pressure and residue obtained was purified by silica gel column chromatography (elution, 20% EtOAc-hexanes) to yield the title compound (0.399 g, 62.1%). LCMS (m/z): 472.1 (M+Na)$^+$.

c) Synthesis of 6-(2-((4-(furan-2-yl)-N-methylbenzamido)methyl)phenoxy)hexanoic acid

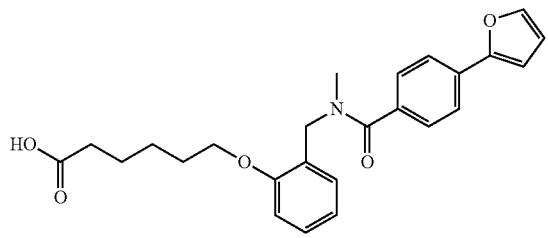 [SMILES: CN(Cc1ccccc1OCCCCCC(=O)O)C(=O)c1ccc(-c2ccco2)cc1]

To a stirred solution of ethyl 6-(2-((4-(furan-2-yl)-N-methylbenzamido)methyl)phenoxy) hexanoate (0.200 g, 0.44 mmol) in THF (10 mL), EtOH (8 mL) and water (5 mL), was treated with lithium hydroxide monohydrate (0.092 g, 2.20 mmol) at rt. The mixture was stirred at 90° C. for 3 h. Upon completion of reaction (TLC), the reaction mixture was concentrated under reduced pressure. The residue was washed with EtOAc, diluted with cold water and acidified with 2N HCl. The aqueous layer was extracted with EtOAc (25 mL×3). The combined organic extract was washed with brine and dried over anhydrous Na$_2$SO$_4$. The solution was concentrated under reduced pressure to give the title compound (0.110 g, 59.5%). $^1$H NMR (400 MHz, DMSO-d$_6$, 60° C.): δ 11.76 (s, 1H), 7.79-7.68 (m, 3H), 7.47 (d, J=8.0 Hz, 2H), 7.26 (t, J=7.6 Hz, 1H), 7.19 (d, J=7.2 Hz, 1H), 7.04-6.93 (m, 3H), 6.60 (br, 1H), 4.58 (br s, 2H), 3.98 (br, 2H), 2.90 (s, 3H), 2.20 (t, J=7.2 Hz, 2H), 1.72-1.63 (m, 2H), 1.62-1.51 (m, 2H), 1.48-1.29 (m, 2H). LCMS (m/z): 422.0 (M+1)$^+$. HPLC: 96.89% (210 nm).

Example 32: Synthesis of 6-(2-((6-(furan-2-yl)-N-isopropylnicotinamido)methyl-d)phenoxy)hexanoic acid

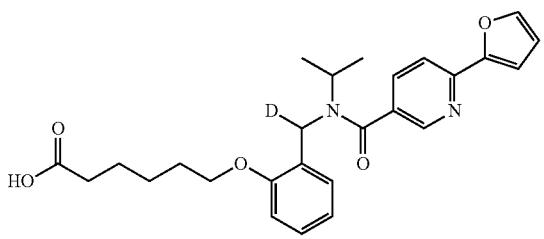 [SMILES: [2H]C(c1ccccc1OCCCCCC(=O)O)N(C(=O)c1ccc(-c2ccco2)nc1)C(C)C]

a) Synthesis of ethyl 6-(2-((isopropylamino)methyl-d)phenoxy)hexanoate

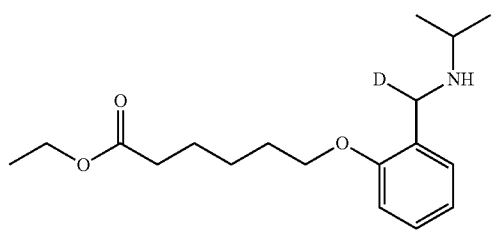 [SMILES: [2H]C(NC(C)C)c1ccccc1OCCCCCC(=O)OCC]

In a 100-mL round bottom flask, isopropyl amine (2.70 g, 45.7 mmol) and ethyl 6-(2-formylphenoxy)hexanoate (10 g, 37.8 mmol) from example 1(b) are dissolved in 1,2-dichloroethane (50 mL) at rt. Sodium cyanoborodeuteride (17.8 g, 83.9 mmol) is added slowly in portions at rt. The reaction mixture is stirred at rt under nitrogen atmosphere. The reaction mixture is quenched by adding saturated sodium carbonate solution, and is extracted with ethyl acetate. The ethyl acetate extract is washed with brine and dried over anhydrous Na$_2$SO$_4$. The solution is concentrated under reduced pressure to give title compound.

b) Synthesis of ethyl 6-(2-((6-chloro-N-isopropylnicotinamido)methyl-d)phenoxy)hexanoate

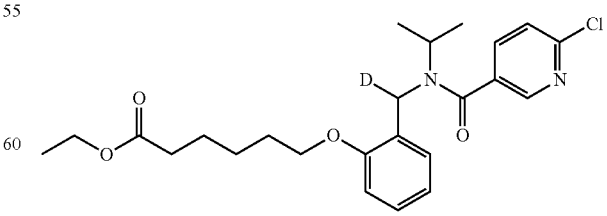

The title compound is prepared from ethyl 6-(2-((isopropylamino)methyl-d)phenoxy)hexanoate using the method of example 1(c).

c) Synthesis of ethyl 6-(2-((6-(furan-2-yl)-N-isopropylnicotinamido)methyl-d)phenoxy) hexanoate a) Synthesis of 2-((propan-2-ylideneamino)methyl)phenol

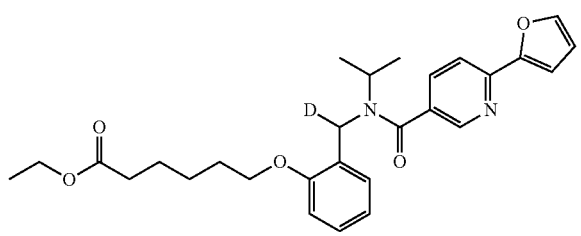 [SMILES: [2H]C(c1ccccc1OCCCCCC(=O)OCC)N(C(=O)c1ccc(-c2ccco2)nc1)C(C)C]

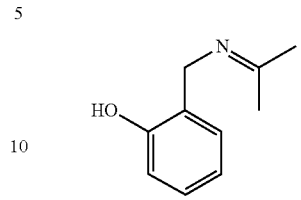

A solution of 2-(aminomethyl)phenol in acetone is heated to reflux for 4 hours. After cooling to room temperature, the solution is dried over $Na_2SO_4$ and concentrated under reduced pressure to leave the title compound.

The title compound is prepared from ethyl 6-(2-((6-chloro-N-sopropylnicotinamido)methyl-d)phenoxy)hexanoate using the method of example 1(d).

b) Synthesis of ethyl 6-(2-((propan-2-ylideneamino)methyl)phenoxy)hexanoate d) Synthesis of 6-(2-((6-(furan-2-yl)-N-isopropylnicotinamido)methyl-d)phenoxy) hexanoic acid

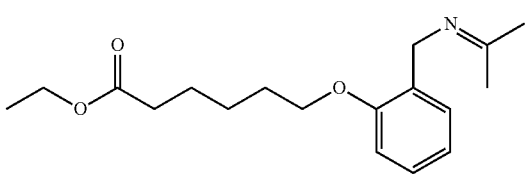

The title compound is prepared from 2-((propan-2-ylideneamino)methyl)phenol using the method of example 1(a).

c) Synthesis of ethyl 6-(2-(((propan-2-yl-2-d)amino)methyl)phenoxy)hexanoate

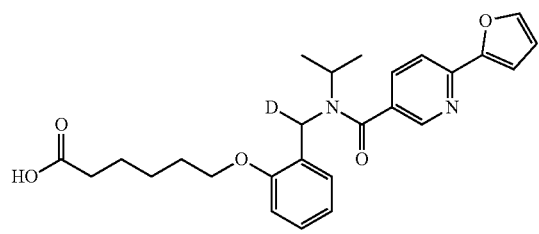 [SMILES: [2H]C(c1ccccc1OCCCCCC(=O)O)N(C(=O)c1ccc(-c2ccco2)nc1)C(C)C]

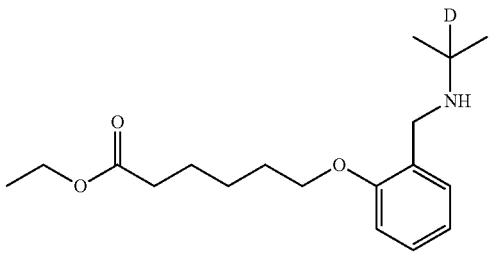

The title compound is prepared from ethyl 6-(2-((6-(furan-2-yl)-N-isopropylnicotinamido)methyl-d)phenoxy) hexanoate using the method of example 1 (e).

Example 33: Synthesis of 6-(2-((6-(furan-2-yl)-N-(propan-2-yl-2-d)nicotinamido)methyl)phenoxy) hexanoic acid In a round bottom flask, ethyl 6-(2-((propan-2-ylideneamino)methyl)phenoxy)hexanoate is dissolved in 1,2-dichloroethane at rt. Sodium cyanoborodeuteride is added slowly in portions at rt. The reaction mixture is stirred at rt under nitrogen atmosphere. The reaction mixture is quenched by adding saturated sodium carbonate solution, and is extracted with ethyl acetate. The ethyl acetate extract is washed with brine and dried over anhydrous $Na_2SO_4$. The solution is concentrated under reduced pressure to give title compound.

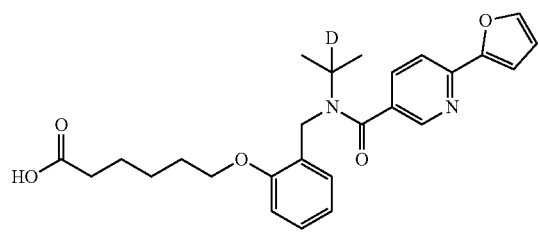 [SMILES: [2H]C(C)(C)N(Cc1ccccc1OCCCCCC(=O)O)C(=O)c1ccc(-c2ccco2)nc1]

d) Synthesis of ethyl 6-(2-((6-chloro-N-(propan-2-yl-2-d)nicotinamido)methyl)phenoxy)hexanoate

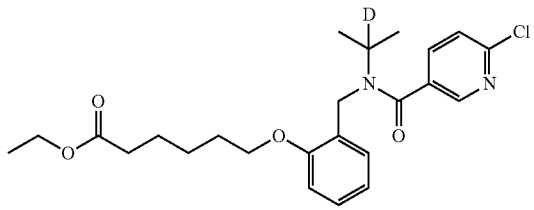 [SMILES: [2H]C(C)(C)N(Cc1ccccc1OCCCCCC(=O)OCC)C(=O)c1ccc(Cl)nc1]

The title compound is prepared from ethyl 6-(2-(((propan-2-yl-2-d)amino)methyl)phenoxy)hexanoate using the method of example 1(c).

e) Synthesis of ethyl 6-(2-((6-(furan-2-yl)-N-(propan-2-yl-2-d)nicotinamido)methyl)phenoxy)hexanoate

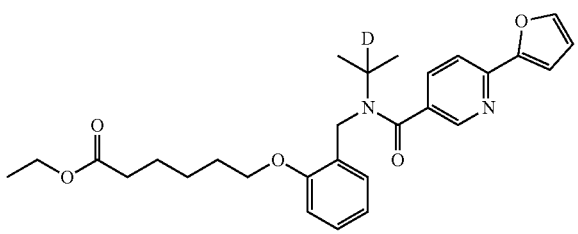 [SMILES: [2H]C(C)(C)N(Cc1ccccc1OCCCCCC(=O)OCC)C(=O)c1ccc(-c2ccco2)nc1]

The title compound is prepared from ethyl 6-(2-((6-chloro-N-(propan-2-yl-2-d)nicotinamido)methyl)phenoxy)hexanoate using the method of example 1(d).

f) Synthesis of 6-(2-((6-(furan-2-yl)-N-(propan-2-yl-2-d)nicotinamido)methyl)phenoxy)hexanoic acid

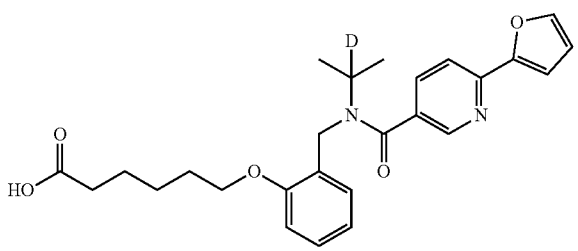 [SMILES: [2H]C(C)(C)N(Cc1ccccc1OCCCCCC(=O)O)C(=O)c1ccc(-c2ccco2)nc1]

The title compound is prepared from ethyl 6-(2-((6-(furan-2-yl)-N-(propan-2-yl-2-d)nicotinamido)methyl)phenoxy)hexanoate using the method of example 1 (e).

Example 13

Pharmacokinetics

In this example, the PK profile of several PPARδ agonists disclosed herein in male CD-1 mice or Wistar rats was determined. Similar methods can be used to analyze other compounds provided herein.

Compounds 12 and 176 were dissolved in 2% dimethylacetamide (DMA) and 20% 2-hydroxypropyl-beta-cyclodextrin (HPβCD) q.s. Compound 245 and GW501516 were dissolved in 5% ethanol and 5% solutol in purified water q.s. (quantity sufficient ie made up to a final volume of 100% with water). All compounds were separately administered to CD-1 mice at 3 mg/kg iv or 10 mg/kg po. GW501516 was administered to Wistar rats at 3 mg/kg (i.v.) or 10 mg/kg (p.o.).

The concentration of the compound in plasma was determined, as illustrated in FIGS. 9A-9E.

Experimental parameters for compound 12 are provided in Tables 2A and 2B, with in vitro parameters and data provided in Table 2C.

TABLE 2A

| | Intravenous PK parameters | | | | | | | |
|---|---|---|---|---|---|---|---|---|
| Parameters | $K_{el}$ (hr−1) | Beta $T_{1/2}$ (hr) | $AUC_{(0-inf)}$ (hr*ng/mL) | $C_0$ (ng/mL) | $V_z$ (L/kg) | $V_{ss}$ (L/kg) | Cl (mL/hr/kg) | MRT (hr) |
| 3 mg/Kg | 3.85 | 0.18 | 256.5 | 1938.2 | 3.03 | 1.58 | 1169.3 | 0.12 |

TABLE 2B

| | Oral PK parameters | | | | |
|---|---|---|---|---|---|
| | Parameters | | | | |
| | $AUC_{(0-inf)}$ (hr*ng/mL) | $T_{max}$ (hr) | $C_{max}$ (ng/mL) | $T_{1/2}$ (hr) | F % |
| 10 mg/Kg | 187.0 | 0.50 | 128.7 | 2.60 | ~22 |

TABLE 2C

| In vitro parameters/data | | |
|---|---|---|
| Solubility (μM) | Kinetic | 6 |
| | Thermodynamic | 253 |
| % Parent remained at 15/60 min | MLM | 59/19 |
| | HLM | 92/64 |
| Potency (cell based) $EC_{50}$ (nM) | PPAR delta NHR ptn interaction assay | 4.8 |

Experimental parameters for compound 176 are provided in Tables 3A and 3B, with in vitro parameters and data provided in Table 3C.

TABLE 3A

| Parameters | $K_{el}$ (hr−1) | Beta $T_{1/2}$ (hr) | $AUC_{(0-inf)}$ (hr*ng/mL) | $C_0$ (ng/mL) | $V_z$ (L/kg) | $V_{ss}$ (L/kg) | Cl (mL/hr/kg) | MRT (hr) |
|---|---|---|---|---|---|---|---|---|
| | | | Intravenous PK parameters | | | | | |
| 3 mg/Kg | 0.41 | 1.68 | 1134.7 | 7056.5 | 6.42 | 1.64 | 2643.8 | 0.47 |

TABLE 3B

Oral PK parameters

| Parameters | $AUC_{(0-inf)}$ (hr*ng/mL) | $T_{max}$ (hr) | $C_{max}$ (ng/mL) | $T_{1/2}$ (hr) | F % |
|---|---|---|---|---|---|
| 10 mg/Kg | 943.8 | 0.25 | 1111.7 | 2.68 | ~25.0 |

TABLE 3C

In vitro parameters/data

| | | |
|---|---|---|
| Solubility (µM) | Kinetic | 191 |
| | Thermodynamic | 506 |
| % Parent remained at 15/60 min | MLM | 78/56 |
| | HLM | 100/73 |
| Potency (cell based) $EC_{50}$ (nM) | PPAR delta NHR ptn interaction assay | 12.6 |

Experimental in vitro parameters and data for compound 237 are provided in Table 4.

TABLE 4

| | | |
|---|---|---|
| Solubility (µM) | Kinetic | 146 |
| | Thermodynamic | 88 |
| % Parent remained at 15/60 min | MLM | 88/60 |
| | HLM | 77/38 |
| Potency (cell based) $EC_{50}$ (nM) | PPAR delta NHR ptn interaction assay | 11 nM |

Experimental parameters for compound GW501516 administered to male Wistar rats are provided in Tables 5A and 5B, with in vitro parameters and data provided in Table 5C.

TABLE 5A

| Parameters | $K_{el}$ (hr−1) | Beta $T_{1/2}$ (hr) | $AUC_{(0-inf)}$ (hr*ng/mL) | $C_0$ (ng/mL) | $V_z$ (L/kg) | $V_{ss}$ (L/kg) | Cl (mL/hr/kg) | MRT (hr) |
|---|---|---|---|---|---|---|---|---|
| | | | Intravenous PK parameters | | | | | |
| 3 mg/Kg | 0.09 | 8.07 | 9960.0 | 5277.8 | 3.58 | 1.99 | 305.9 | 4.30 |

TABLE 5B

Oral PK parameters

| Parameters | $AUC_{(0-inf)}$ (hr*ng/mL) | $T_{max}$ (hr) | $C_{max}$ (ng/mL) | $T_{1/2}$ (hr) | F % |
|---|---|---|---|---|---|
| 10 mg/Kg | 35121.0 | 2.00 | 6920.0 | 6.21 | ~100 |

TABLE 5C

In vitro parameters/data

| | | |
|---|---|---|
| Solubility (µM) | Kinetic | 195 |
| | Thermodynamic | 246 |
| % Parent remained at 15/60 min | MLM | 93/76 |
| Potency (cell based) $EC_{50}$ (nM) | PPAR delta trans activation | 2 nM |

Experimental parameters for compound GW501516 administered to CD-1 mice are provided in Tables 6A and 6B, with in vitro parameters and data provided in Table 6C.

TABLE 6A

| | | | Intravenous PK parameters | | | | | |
|---|---|---|---|---|---|---|---|---|
| Parameters | Kel (hr−1) | Beta T½ (hr) | AUC (0-inf) (hr*ng/mL) | C0 (ng/mL) | Vz (L/kg) | Vss (L/kg) | Cl (mL/hr/kg) | MRT (hr) |
| 3 mg/Kg | 0.11 | 6.44 | 11319.1 | 5560.5 | 2.46 | 1.71 | 265.0 | 4.96 |

TABLE 6B

Oral PK parameters

| | Parameters | | | | |
|---|---|---|---|---|---|
| | $AUC_{(0-inf)}$ (hr*ng/mL) | $T_{max}$ (hr) | $C_{max}$ (ng/mL) | $T_{1/2}$ (hr) | F % |
| 10 mg/Kg | 30990.7 | 2.00 | 3293.3 | 5.98 | 82.1 |

TABLE 6C

| In vitro parameters/data | | |
|---|---|---|
| Solubility (μM) | Kinetic | 195 |
| | Thermodynamic | 246 |
| % Parent remained at 15/60 min | MLM | 93/76 |
| Potency (cell based) $EC_{50}$ (nM) | PPAR delta trans activation | 2 nM |

Example 14

The following examples provide physical and in vitro data for various different exemplary compounds.

Nuclear Hormone Receptor (NHR) Assays

Cell Handling: PathHunter NHR cell lines were expanded from freezer stocks according to standard procedures. Cells were seeded in a total volume of 20 μL into white walled, 384-well microplates and incubated at 37° C. for the appropriate time prior to testing. Assay media contained charcoal-dextran filtered serum to reduce the level of hormones present.

Agonist Format: For agonist determination, cells were incubated with sample to induce response. Intermediate dilution of sample stocks was performed to generate 5× sample in assay buffer. 5 μL of 5× sample was added to cells and incubated at 37° C. or room temperature for 3-16 hours. Final assay vehicle concentration was 1%.

Antagonist Format: For antagonist determination, cells were pre-incubated with antagonist followed by agonist challenge at the $EC_{80}$ concentration. Intermediate dilution of sample stocks was performed to generate 5× sample in assay buffer. 5 μL of 5× sample was added to cells and incubated at 37° C. or room temperature for 60 minutes. Vehicle concentration was 1%. 5 μL of 6×$EC_{80}$ agonist in assay buffer was added to the cells and incubated at 37° C. or room temperature for 3-16 hours.

Signal Detection: Assay signal was generated through a single addition of 12.5 or 15 μL (50% v/v) of PathHunter Detection reagent cocktail, followed by a one hour incubation at room temperature. Microplates were read following signal generation with a PerkinElmer Envision™ instrument for chemiluminescent signal detection.

Data Analysis: Compound activity was analyzed using CBIS data analysis suite (ChemInnovation, CA). For agonist mode assays, percentage activity was calculated using the following formula:

% Activity=100%×(mean RLU of test sample−mean RLU of vehicle control)/(mean MAX control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of $EC_{80}$ control−mean RLU of vehicle control)).

Note that for select assays, the ligand response produces a decrease in receptor activity (inverse agonist with a constitutively active target). For those assays inverse agonist activity was calculated using the following formula:

% Inverse Agonist Activity=100%×((mean RLU of vehicle control−mean RLU of test sample)/ (mean RLU of vehicle control−mean RLU of MAX control)).

TABLE 7

| Compd No | MW | ClogP | NHR protein interaction assay, $EC_{50}$ (nM) for PPARδ |
|---|---|---|---|
| 127 | 467 | 5.57 | 44.6 |
| 176 | 421 | 4.68 | 12.6 |
| 247 | 447 | 5.49 | 10.54 |
| 12 | 447 | 5.27 | 4.8 |
| 247 | 497 | 6.45 | 18.8 |

TABLE 8

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 126 | 413 | 4.47 | 1298.5 |
| 127 | 467 | 5.57 | 44.6 |
| 129 | 425 | 3.96 | 5071.10 |
| 130 | 461 | 3.03 | >10000 |
| 237 | 447 | 5.49 | 10.54 |
| 132 | 401 | 4.47 | 2184.70 |
| 151 | 408 | 3.85 | 894.3 |
| 135 | 449 | 5.31 | 3151.9 |
| 136 | 450 | 4.58 | 351.8 |
| 134 | 437 | 4.80 | 95.5 |
| 133 | 497 | 3.67 | |

TABLE 9

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 152 | 485 | 5.83 | >10000 |
| 153 | 450 | 4.42 | 206.4 |
| 154 | 453 | 5.51 | 21.3 |

TABLE 9-continued

| Compd No | MW | ClogP | NHR protein interaction assay, $EC_{50}$ (nM) for PPARδ |
|---|---|---|---|
| 155 | 450 | 4.63 | 26.1 |
| 156 | 456 | 4.46 | 142.9 |
| 157 | 449 | 5.82 | >10000 |
| 158 | 449 | 5.60 | >10000 |
| 160 | 467 | 5.75 | |
| 159 | 467 | 5.75 | |

TABLE 10

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 176 | 421 | 4.68 | 12.6 |
| 178 | 465 | 5.0 | 79.4 |
| 177 | 489 | 5.48 | 12.1 |
| 179 | 407 | 4.71 | 485.11 |
| 180 | 463 | 5.02 | |

TABLE 11

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 202 | 547 | 6.53 | 7.3 |
| 203 | 463 | 6.02 | 7.1 |
| 204 | 467 | 5.81 | 24.6 |
| 205 | 474 | 5.28 | 223.6 |
| 206 | 479 | 5.61 | 5.1 |
| 207 | 450 | 4.92 | 19.4 |
| 208 | 450 | 4.53 | |

TABLE 12

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 219 | 459 | 5.01 | 338.5 |
| 220 | 463 | 5.98 | 511.8 |
| 221 | 451 | 4.75 | 1295.1 |
| 225 | 451 | 4.43 | 392.3 |
| 226 | 435 | 5.00 | 112.9 |
| 227 | 464 | 3.68 | |
| 231 | 462 | 2.6 | |

TABLE 13

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 248 | 419 | 4.65 | 21.1 |

TABLE 14

| Compd No | MW | ClogP | NHR protein interaction assay, $EC_{50}$ (nM) for PPARδ |
|---|---|---|---|
| 61 | 449 | 5.52 | 5.9 |
| 12 | 447 | 5.04 | 4.8 |
| 125 | 417 | 5.03 | 291.4 |
| 126 | 413 | 4.47 | 1298.5 |
| 127 | 467 | 5.57 | 44.6 |
| 128 | 426 | 4.72 | 5390.50 |
| 129 | 425 | 3.96 | 5071.10 |
| 130 | 461 | 3.03 | >10000 |
| 131 | 397 | 4.75 | 1609.50 |
| 245 | 447 | 5.49 | 10.54 |
| 132 | 401 | 4.47 | 2184.70 |
| 151 | 408 | 3.85 | 894.3 |
| 135 | 449 | 5.31 | 3151.9 |
| 136 | 450 | 4.58 | 351.8 |
| 134 | 437 | 4.80 | >10000 |

TABLE 15

| Compd No | MW | ClogP | PPARd, $EC_{50}$ (nM) (from Salk) | NHR protein interaction assay, $EC_{50}$ (nM) for PPARδ |
|---|---|---|---|---|
| 57 | 459 | 6.14 | 42 | 25.9 |
| 37 | 463 | 6.05 | 41 | 17.5 |
| 61 | 449 | 5.52 | 9 | 5.9 |
| 62 | 449 | 5.3 | 61 | 36.8 |
| 63 | 465 | 6.0 | ND | 8.4 |
| 64 | 465 | 5.81 | 17.2 | 8.02 |
| 12 | 447 | 5.27 | 19.6 | 4.8 |
| 28 | 497 | 6.45 | 290 | 18.8 |
| 267 | 469 | 5.02 | 19.6 | 5.0 |

TABLE 16

| Compd No | MW | ClogP | NHR protein interaction assay, $EC_{50}$ (nM) for PPARδ |
|---|---|---|---|
| 127 | 467 | 5.57 | 44.6 |
| 176 | 421 | 4.68 | 12.6 |
| 245 | 447 | 5.49 | 10.54 |
| 12 | 447 | 5.27 | 4.8 |
| 247 | 497 | 6.45 | 18.8 |

Example 15

GW Treatment Prevents the Accumulation of VLCFAs by Inducing Mitochondrial FA Oxidation in a Mouse Model of ALD As GW treatment dramatically induced mitochondrial fatty acid (FA) oxidation and reduced fat accumulation, GW was evaluated to see if could improve FA metabolism disorders such as ALD. ALD is a rare genetic disorder caused by defects in peroxisomal oxidation of very long-chain fatty acids (VLCFAs), resulting in systemic accumulation of VLCFAs, which causes tissue defects mainly in the central nervous system and the adrenal glands. The majority of VLCFAs in the body are endogenously synthesized from long-chain fatty acids (LCFAs). Therefore, one potential way to prevent VLCFA accumulation in ALD is by inducing mitochondrial LCFA oxidation to reduce the availability of LCFAs for VLCFA biosynthesis. In order to test this, a previously described mouse model of ALD was used, in which the X-linked adrenoleukodystrophy gene abcd1 was systemically ablated and the knockout (AKO) mice faithfully recapitulated the abnormal VLCFA accumulation phenotype seen in ALD patients.

Figure 10A:
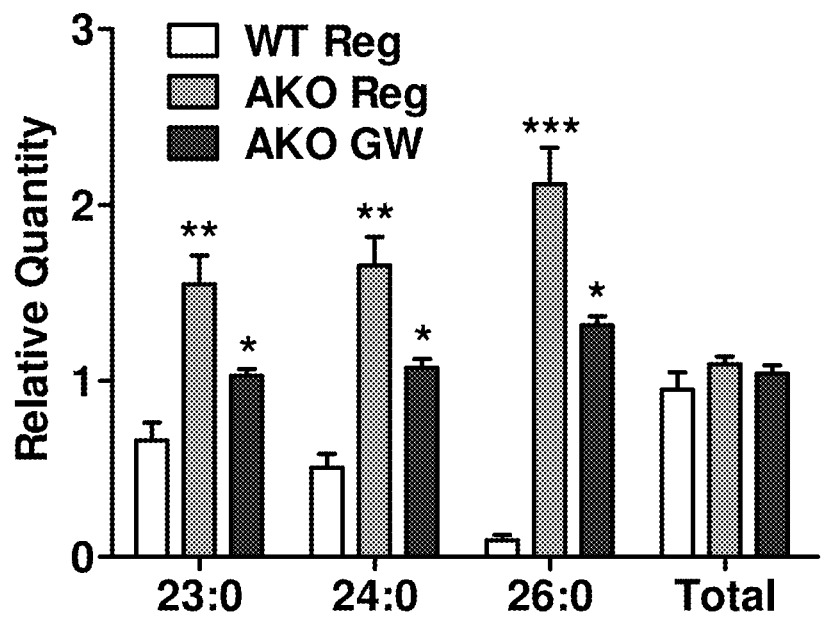
FIGS. 10A and 10B are graphs showing relative guanines of free fatty acids in the brain (A) and liver (B) of AKO mice administered GW, compared to AKO mice not administered GW and wild-type mice.
Figure 10B:
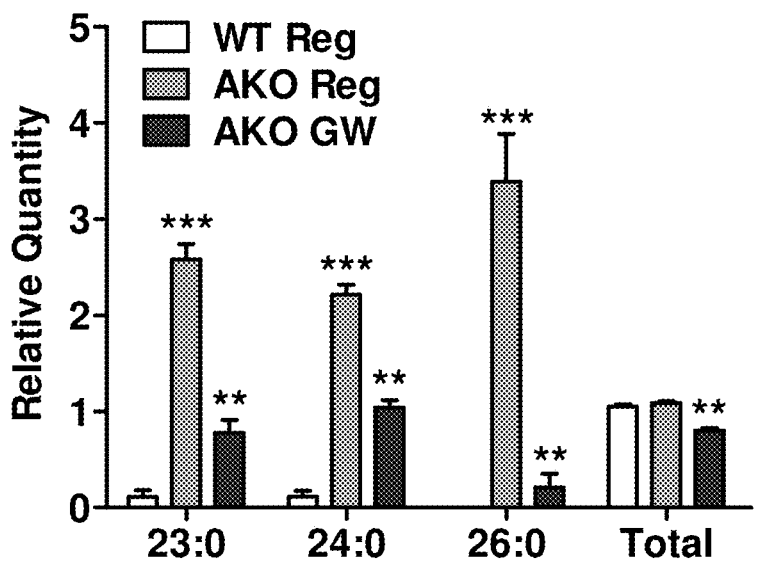
Figure 11A:
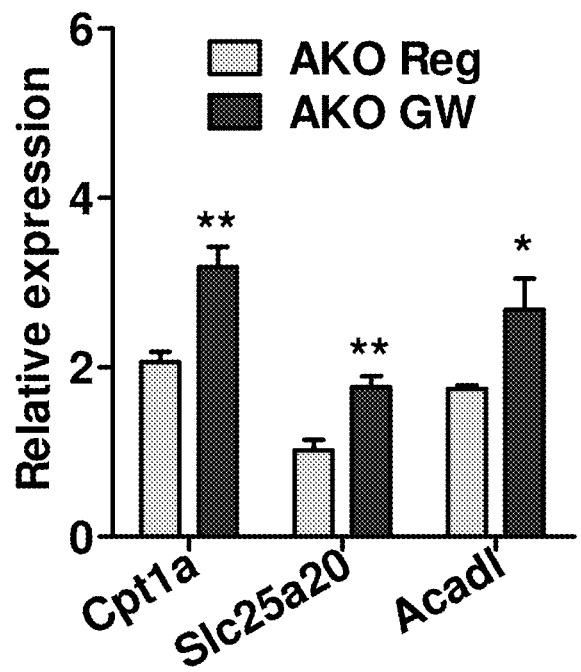
FIG. 11A is a graph showing expression of mitochondrial fatty acid oxidation genes Cpt1a, Slc25a20, and Acadl in the livers of AKO mice administered GW compared to AKO mice not administered GW.
Figure 11B:
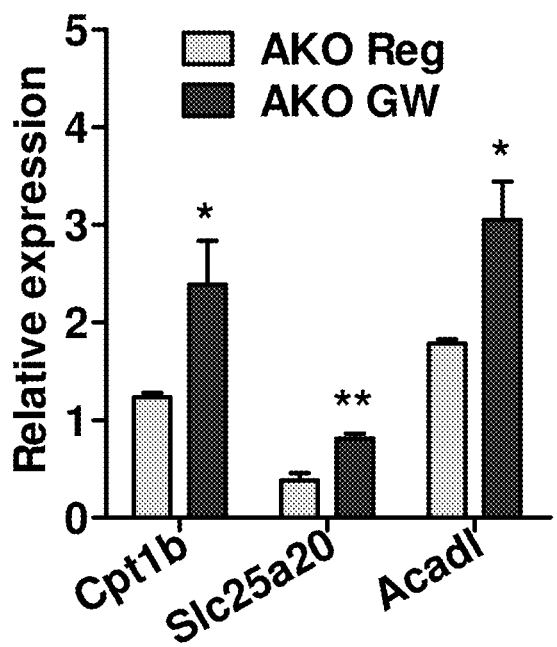
FIG. 11B is a graph showing expression of mitochondrial fatty acid oxidation genes Cpt1b, Slc25a20, and Acadl in the skeletal muscle of AKO mice administered GW compared to AKO mice not administered GW.
Figure 12A:
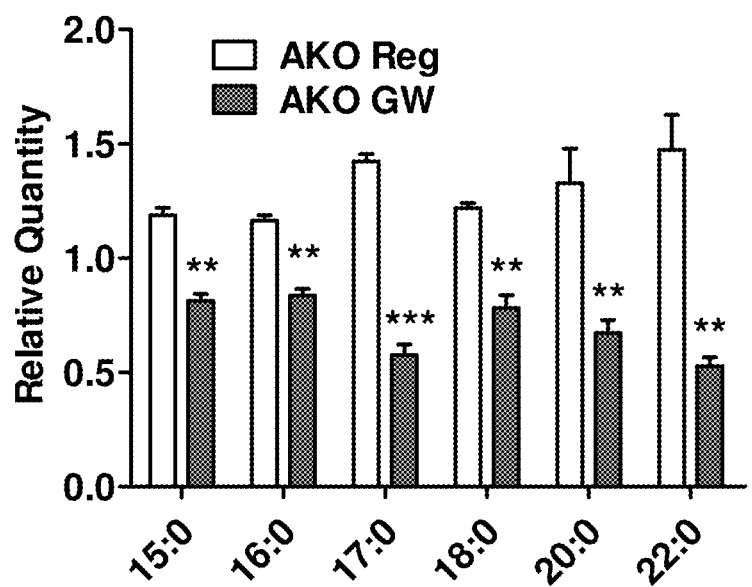
FIGS. 12A and 12B are graphs showing the relative quanitites of total fatty acids in the liver (A) and skeletal muscle (B) of AKO mice administered GW compared to AKO mice not administered GW.
Figure 12B:
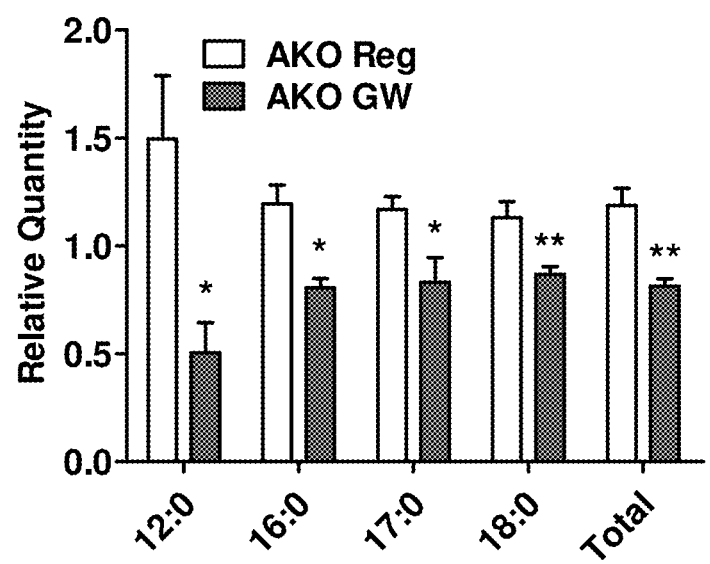

3-month-old AKO mice were treated with or without GW and their tissues collected for free FA analysis using GC/MS. Similar to what was previously reported, both brain and liver from AKO mice had greatly increased levels of VLCFAs including C22:0, C23:0, C24:0, and C26:0, while the levels of total FAs (C12-C26) remained unaffected (FIGS. 10A and 10B). After 8 weeks of GW treatment, the levels of all four VLCFAs in AKO brain and liver were significantly reduced, with all liver C26:0 cleared in most GW-treated animals (FIGS. 10A and 10B). Without being bound to a particular theory, the reduction of VLCFAs may be due to GW-induced mitochondrial FA oxidation in peripheral tissues, since GW treatment dramatically induced the expression of mitochondrial FA oxidation genes including Cpt1a and 1b, Slc25a20, and Acadl in AKO liver and skeletal muscle (FIGS. 11A and 11B), which was further supported by the fact that most saturated LCFAs including C12:0 to C22:0 and the total FAs were significantly reduced by GW treatment in both liver and muscle (FIGS. 12A, 12B and 10B).

While the disclosure has been described and illustrated with reference to certain embodiments thereof, those having ordinary skill in the art will appreciate that various changes, modifications, and substitutions can be made therein without departing from the spirit and scope of the present disclosure. For example, effective dosages other than the dosages as set forth herein may be applicable as a consequence of variations in the responsiveness of the mammal being treated for PPARδ-related disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present disclosure. Accordingly, the disclosure is not to be limited as by the appended claims.

The features disclosed in this description and/or in the claims may both separately and in any combination thereof be material for realizing the disclosure in diverse forms thereof.

In view of the many possible embodiments to which the principles of the disclosure may be applied, it should be recognized that the illustrated embodiments are only examples of the invention and should not be taken as limiting the scope of the invention. Rather, the scope of the disclosure is defined by the following claims. We therefore claim as our invention all that comes within the scope and spirit of these claims.

We claim:

1. A compound having a formula,

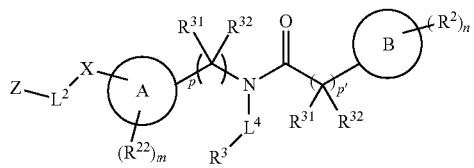

wherein:
ring A is phenyl;
ring B is selected from phenyl, or pyridine;
each $R^2$ independently is selected from deuterium, halogen, aryl, heteroaryl, aliphatic, heteroaliphatic, cycloaliphatic, $NO_2$, OH, amino, amide, aminosulfonyl, carboxyl, carboxyl ester, alkylsulfonyl, $SO_3H$, or acyl;

each $R^{22}$ independently is selected from deuterium, halogen, aryl, heteroaryl, aliphatic, heteroaliphatic, cycloaliphatic, $NO_2$, OH, amino, amide, aminosulfonyl, carboxyl, carboxyl ester, alkylsulfonyl, $SO_3H$, or acyl;
n is from 0 to 5;
m is from 0 to 4;
X is O, $NR^{30}$, sulfonyl, or S;
each $R^{30}$ independently is selected from H or aliphatic, aryl, or cycloaliphatic;
each $L^2$ is selected from a bond, aliphatic, heteroaliphatic, arylene, heteroarylene, cycloalkylene, heterocycloalkylene or —$CR^{23}R^{24}$—;
$R^{23}$ and $R^{24}$ are each independently selected from H, deuterium, halogen, aliphatic, alkyl, —$C(O)OR^{25}$ or —$C(O)NR^{25}R^{26}$;
$R^{25}$ and $R^{26}$ are each independently selected from hydrogen or aliphatic;
Z is R'L'C(O)—;
$L^1$ is a bond or —$NR^{30}$—;
$R^1$ is hydrogen, aliphatic, —$OR^{1A}$, —$NR^{1A}R^{1B}$, —C(O)$R^{1A}$, —$S(O)_2R^{1A}$, —$C(O)OR^{1A}$, —$S(O)_2NR^{1A}R^{1B}$ or —$C(O)NR^{1A}R^{1B}$;
$R^{1A}$, $R^{1B}$ are each independently selected from hydrogen or aliphatic;
p is 0, 1, 2, or 3;
p' is 0;
$L^4$ is selected from a bond, aliphatic, heteroaliphatic, arylene, heteroarylene, cycloalkylene, heterocycloalkylene or —$CR^{23}R^{24}$—;
$R^3$ is selected from —OH, —$OR^{3A}$, —$NR^{3A}R^{3B}$, —C(O)$R^{3A}$, —$S(O)_2R^{3A}$, —$C(O)OR^{3A}$, —$S(O)_2NR^{3A}R^{3B}$, —$C(O)NR^{3A}R^{3B}$, aliphatic, heteroaliphatic, cycloalkyl, heterocycloalkyl, aryl, heteroaryl; and
$R^{3A}$ and $R^{3B}$ are independently selected from hydrogen or aliphatic;
$R^{31}$ and $R^{32}$ are independently H, D, or aliphatic;
with the provisos that
at least one of $L^4$ or $R^3$ comprises at least one deuterium; or
at least one of $R^{31}$ and $R^{32}$ is D.

2. The compound according to claim 1, wherein $L^4R^3$ is isopropyl

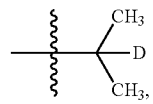

cyclopropyl, of

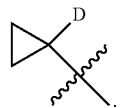

3. The compound of claim 1, wherein ring B is phenyl.
4. The compound of claim 1, wherein $L^2$ is

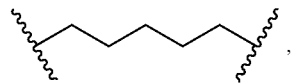

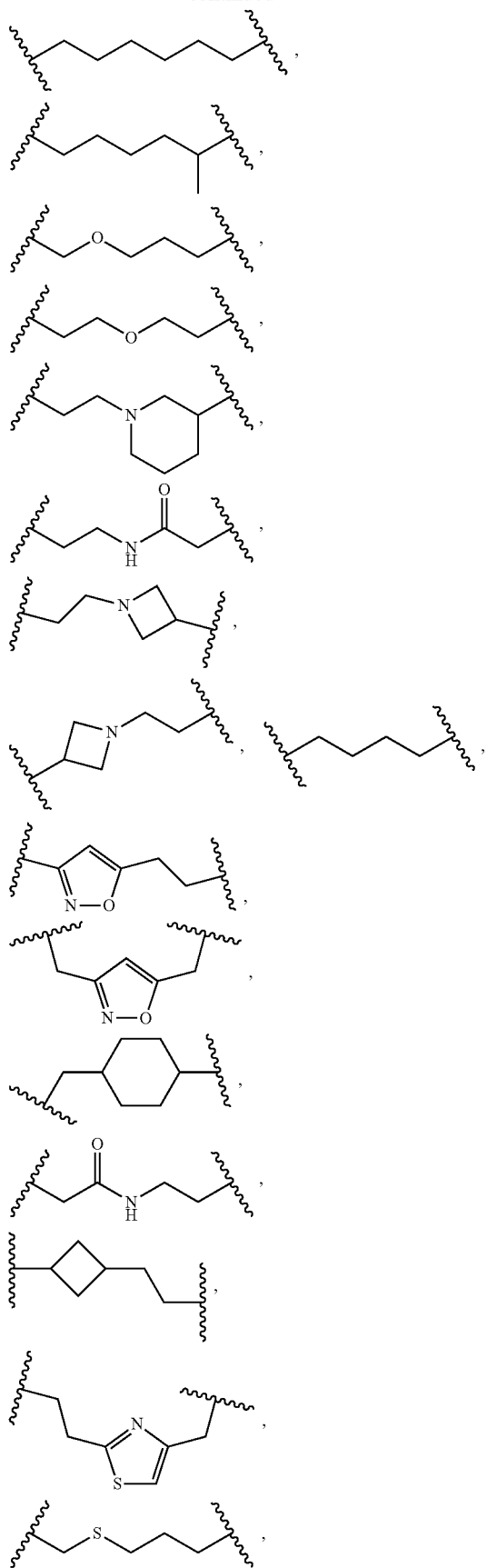

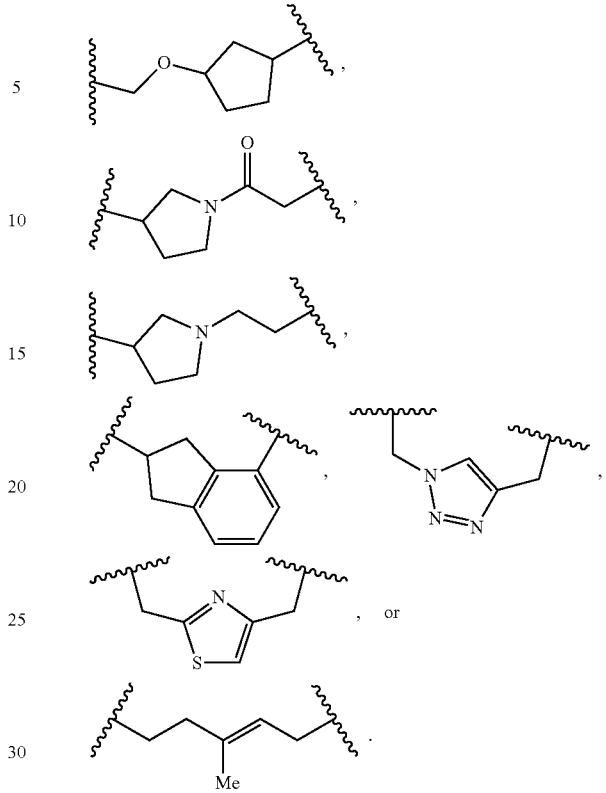

5. The compound of claim 1, wherein p is 1.

6. The compound of claim 5, wherein each of $R^{31}$ and $R^{32}$ is independently H or D.

7. The compound of claim 1, wherein Z is $CO_2H$.

8. The compound of claim 1, wherein at least one of $L^4$ or $R^3$ comprises at least one deuterium.

9. The compound of claim 1 wherein X is O.

10. The compound of claim 1, wherein each $R^2$ independently is selected from methyl, trifluoromethyl, methoxy, trifluoromethoxy, dimethylamino, acetyl, methanesulfonyl, cyano, cyclopropoxy, furan-2-yl, furan-3-yl, thiophen-2-yl, thiophen-3-yl, 3-pyridyl, 4-pyridyl, pyrrolidin-1-yl,

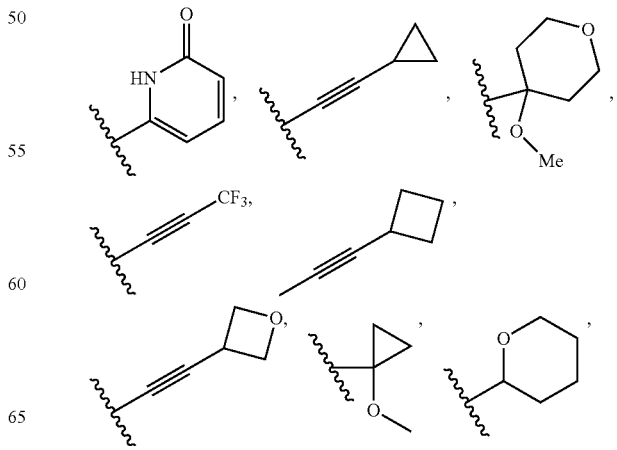

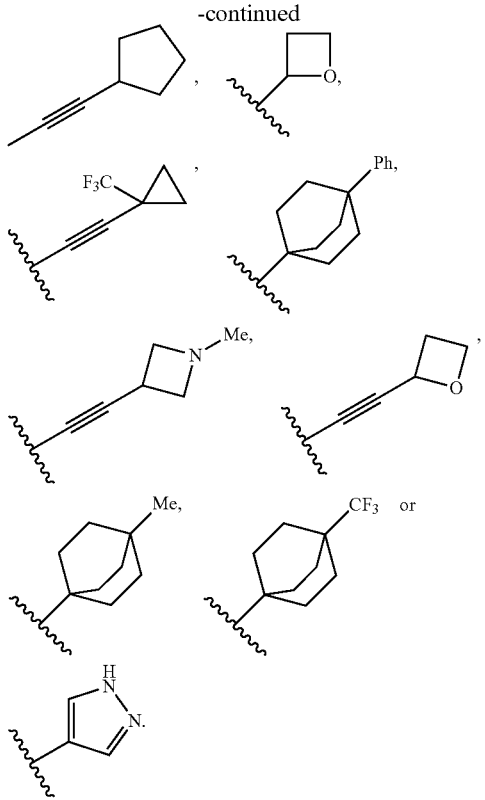

11. The compound of claim 1, wherein n is 1 and R² is heteroaryl.

12. The compound of claim 1, wherein R² is furan-2-yl or furan-3-yl.

13. The compound according to claim 1, wherein the compound has a formula

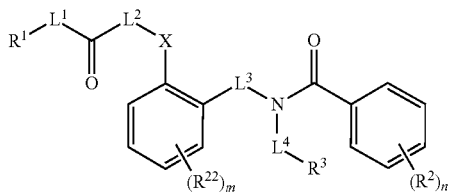

wherein:
  each R² independently is selected from deuterium, halogen, aryl, heteroaryl, aliphatic, heteroaliphatic, cycloaliphatic, NO₂, OH, amino, amide, aminosulfonyl, carboxyl, carboxyl ester, alkylsulfonyl, SO₃H, or acyl;
  each R²² independently is selected from deuterium, halogen, aryl, heteroaryl, aliphatic, heteroaliphatic, cycloaliphatic, NO₂, OH, amino, amide, aminosulfonyl, carboxyl, carboxyl ester, alkylsulfonyl, SO₃H, or acyl;
  n is from 0 to 5;
  m is from 0 to 4;
  X is O, NR³⁰, sulfonyl, or S;
  each R³⁰ independently is selected from H or aliphatic, aryl, or cycloaliphatic;
  each L² is selected from a bond, aliphatic, heteroaliphatic, arylene, heteroarylene, cycloalkylene, heterocycloalkylene or —CR²³R²⁴—;

R²³ and R²⁴ are each independently selected from H, deuterium, halogen, aliphatic, alkyl, —C(O)OR²⁵ or —C(O)NR²⁵R²⁶;
R²⁵ and R²⁶ are each independently selected from hydrogen or alkyl;
L¹ is a bond or —NR³⁰—;
R¹ is hydrogen, aliphatic, —OR¹ᴬ, —NR¹ᴬR¹ᴮ, —C(O)R¹ᴬ, —S(O)₂R¹ᴬ, —C(O)OR¹ᴬ, —S(O)₂NR¹ᴬR¹ᴮ or —C(O)NR¹ᴬR¹ᴮ;
R¹ᴬ, R¹ᴮ are each independently selected from hydrogen or aliphatic;
L³ is selected from a bond or C₁₋₃aliphatic;
L⁴ is selected from a bond, aliphatic, heteroaliphatic, arylene, heteroarylene, cycloalkylene, heterocycloalkylene or —CR²³R²⁴—;
R³ is selected from —OH, —OR³ᴬ, —NR³ᴬR³ᴮ, —C(O)R³ᴬ, —S(O)₂R³ᴬ, —C(O)OR³ᴬ, —S(O)₂NR³ᴬR³ᴮ, —C(O)NR³ᴬR³ᴮ, aliphatic, heteroaliphatic, cycloalkyl, heterocycloalkyl, aryl, heteroaryl; and
R³ᴬ and R³ᴮ are independently selected from hydrogen or aliphatic;

with the provisos that
  at least one of L³, L⁴ or R³ comprises at least one deuterium.

14. The compound of claim 13, wherein at least one of L⁴ or R³ comprises at least one deuterium.

15. The compound of claim 13, wherein L³ is -CHD- or -CD₂-.

16. The compound of claim 15, wherein L³ is -CHD-.

17. The compound of claim 13, wherein each R² independently is selected from methyl, trifluoromethyl, methoxy, trifluoromethoxy, dimethylamino, acetyl, methanesulfonyl, cyano, cyclopropoxy, furan-2-yl, furan-3-yl, thiophen-2-yl, thiophen-3-yl, 3-pyridyl, 4-pyridyl, pyrrolidin-1-yl,

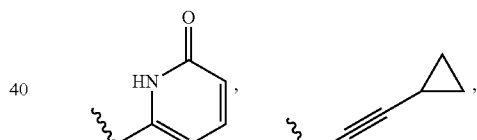

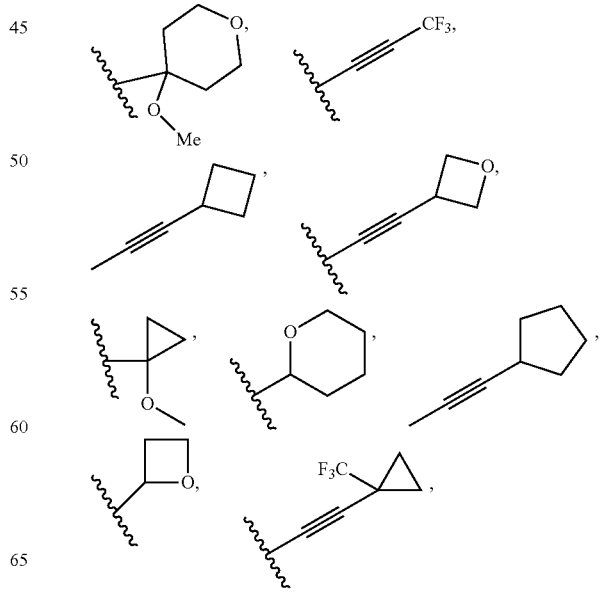

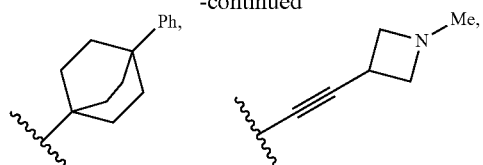
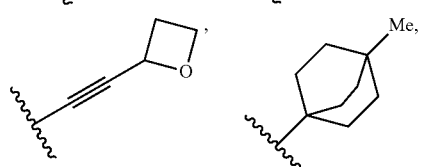
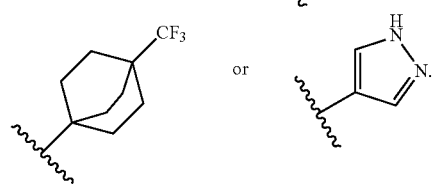
18. The compound of claim 13, wherein n is 1 and $R^2$ is heteroaryl.
19. The compound of claim 13, wherein $R^2$ is furan-2-yl or furan-3-yl.
20. A pharmaceutical composition comprising a pharmaceutically acceptable excipient and a compound according to claim 1.
* * * * *